United States Patent
McKinnell et al.

(10) Patent No.: US 12,384,761 B2
(45) Date of Patent: Aug. 12, 2025

(54) IMIDAZOLO INDAZOLE COMPOUNDS AS JAK INHIBITORS

(71) Applicant: Theravance Biopharma R&D IP, LLC, South San Francisco, CA (US)

(72) Inventors: Robert Murray McKinnell, Millbrae, CA (US); Tom M. Lam, San Francisco, CA (US); Cameron Smith, San Bruno, CA (US); Philip Gerken, San Francisco, CA (US); Paul Allegretti, Mountain View, CA (US); Gabrielle Elaine Dolgonos, San Francisco, CA (US); Christina Owens, Oakland, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 17/848,724

(22) Filed: Jun. 24, 2022

(65) Prior Publication Data

US 2024/0092758 A1    Mar. 21, 2024

Related U.S. Application Data

(60) Provisional application No. 63/202,811, filed on Jun. 25, 2021.

(51) Int. Cl.
| | | |
|---|---|---|
| *C07D 401/14* | (2006.01) | |
| *C07D 403/14* | (2006.01) | |
| *C07D 405/14* | (2006.01) | |
| *C07D 413/14* | (2006.01) | |
| *C07D 498/08* | (2006.01) | |

(52) U.S. Cl.
CPC ......... *C07D 401/14* (2013.01); *C07D 403/14* (2013.01); *C07D 405/14* (2013.01); *C07D 413/14* (2013.01); *C07D 498/08* (2013.01)

(58) Field of Classification Search
CPC .. C07D 401/14; C07D 403/14; C07D 405/14; C07D 413/14; C07D 498/08
See application file for complete search history.

(56) References Cited

U.S. PATENT DOCUMENTS

| | | |
|---|---|---|
| 6,534,524 B1 | 3/2003 | Kania et al. |
| 6,884,890 B2 | 4/2005 | Kania et al. |
| 7,884,109 B2 | 2/2011 | Ohlmeyer et al. |
| 8,193,197 B2 | 6/2012 | Li et al. |
| 8,450,340 B2 | 5/2013 | Hood et al. |
| 8,575,336 B2 | 11/2013 | Coe et al. |
| 8,609,687 B2 | 12/2013 | Zhu et al. |
| 8,648,069 B2 | 2/2014 | Akritopoulou-Zanze et al. |
| 8,895,544 B2 | 11/2014 | Coe et al. |
| 9,012,464 B2 | 4/2015 | Gidwani et al. |
| 9,518,052 B2 | 12/2016 | Coe et al. |
| 9,617,258 B2 | 4/2017 | Thorarensen et al. |
| 10,100,049 B2 | 10/2018 | Fatheree et al. |
| 10,183,942 B2 | 1/2019 | Benjamin et al. |
| 10,196,393 B2 | 2/2019 | Fatheree et al. |
| 10,196,418 B2 | 2/2019 | Fatheree et al. |
| 10,208,040 B2 | 2/2019 | Fatheree et al. |
| 10,251,874 B2 | 4/2019 | Dabros et al. |
| 10,294,207 B2 | 5/2019 | Choi et al. |
| 10,392,386 B2 | 8/2019 | Fatheree et al. |
| 10,406,148 B2 | 9/2019 | Thalladi et al. |
| 10,493,077 B2 | 12/2019 | Fatheree et al. |
| 10,519,153 B2 | 12/2019 | Fatheree et al. |
| 10,526,330 B2 | 1/2020 | Fatheree et al. |

(Continued)

FOREIGN PATENT DOCUMENTS

| | | |
|---|---|---|
| CN | 102695706 A | 9/2012 |
| CN | 112279848 A | 1/2021 |

(Continued)

OTHER PUBLICATIONS

Donal P McLornan, Janet E Pope, Jason Gotlib, Claire N Harrison, Current and future status of JAK inhibitors, The Lancet, vol. 398, Issue 10302, pp. 803-816. (Year: 2021).*
Sailliet et al. Role of JAK inhibitors and immune cells in transplantation, Cytokine & Growth Factor Reviews, vol. 47, pp. 62-73. (Year: 2019).*
Schwartz DM, Kanno Y, Villarino A, Ward M, Gadina M, O'Shea JJ. JAK inhibition as a therapeutic strategy for immune and inflammatory diseases. Nat Rev Drug Discov. (Year: 2017).*
International Search Report and Written Opinion for Application No. PCT/US2022/034838, mailed on Aug. 31, 2022.
Abcouwer, "Angiogenic factors and cytokines in diabetic retinopathy", J Clin Cell Immunol, Supplement 1: 1-12 (2013).

(Continued)

*Primary Examiner* — James H Alstrum-Acevedo
*Assistant Examiner* — Justin Christopher Sanchez
(74) *Attorney, Agent, or Firm* — Sheppard Mullin Richter & Hampton LLP

(57) ABSTRACT

Provided herein are compounds of formula (I):

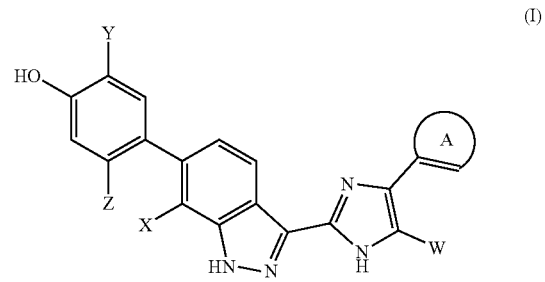

and pharmaceutically-acceptable salts thereof, where A, W, X, Y and Z are defined in the specification. The compounds of formula (I) and pharmaceutically-acceptable salts thereof are Janus kinase (JAK) inhibitors. Also provided herein are pharmaceutical compositions comprising such compounds; and methods of using such compounds to treat, e.g., inflammatory and fibrotic diseases, including respiratory diseases.

21 Claims, No Drawings

(56) References Cited

U.S. PATENT DOCUMENTS

| | | | |
|---|---|---|---|
| 10,548,886 | B2 | 2/2020 | Kleinschek et al. |
| 10,550,118 | B2 | 2/2020 | Fatheree et al. |
| 10,836,763 | B2 | 11/2020 | Long et al. |
| 10,844,057 | B2 | 11/2020 | Colson et al. |
| 10,913,740 | B2 | 2/2021 | Fatheree et al. |
| 10,947,229 | B2 | 3/2021 | Long et al. |
| 10,954,237 | B2 | 3/2021 | Fatheree et al. |
| 10,968,222 | B2 | 4/2021 | Fatheree et al. |
| 11,160,800 | B2 | 11/2021 | Thalladi et al. |
| 11,160,810 | B2 | 11/2021 | McKinnell et al. |
| 11,254,669 | B2 | 2/2022 | Fatheree et al. |
| 11,299,492 | B2 | 4/2022 | Fatheree et al. |
| 11,453,668 | B2 | 9/2022 | Fatheree et al. |
| 11,634,419 | B2 * | 4/2023 | Long .................... C07D 471/04 546/118 |
| 2005/0090529 | A1 | 4/2005 | McAlpine et al. |
| 2013/0029968 | A1 | 1/2013 | Coe et al. |
| 2015/0158864 | A1 | 6/2015 | Thorarensen et al. |
| 2015/0329542 | A1 | 11/2015 | Coe et al. |
| 2016/0289196 | A1 | 10/2016 | Choi et al. |
| 2017/0121327 | A1 * | 5/2017 | Fatheree .............. A61K 31/437 |
| 2018/0258087 | A1 | 9/2018 | Fatheree et al. |
| 2018/0258088 | A1 | 9/2018 | Fatheree et al. |
| 2018/0311223 | A1 | 11/2018 | Dabros et al. |
| 2018/0311226 | A1 | 11/2018 | Thalladi et al. |
| 2018/0311255 | A1 | 11/2018 | Fatheree et al. |
| 2018/0319796 | A1 | 11/2018 | Benjamin et al. |
| 2019/0106420 | A1 | 4/2019 | Fatheree et al. |
| 2019/0119275 | A1 | 4/2019 | Fatheree et al. |
| 2019/0127371 | A1 | 5/2019 | Fatheree et al. |
| 2019/0337945 | A1 | 11/2019 | Fatheree et al. |
| 2019/0350916 | A1 | 11/2019 | Kleinschek et al. |
| 2020/0046719 | A1 | 2/2020 | McKinnell et al. |
| 2020/0071323 | A1 | 3/2020 | Long et al. |
| 2020/0071324 | A1 | 3/2020 | Colson et al. |
| 2020/0071325 | A1 | 3/2020 | Long et al. |
| 2020/0087303 | A1 | 3/2020 | Fatheree et al. |
| 2020/0121669 | A1 | 4/2020 | Thalladi et al. |
| 2020/0131178 | A1 | 4/2020 | Fatheree et al. |
| 2020/0181141 | A1 | 6/2020 | Fatheree et al. |
| 2020/0216447 | A1 | 7/2020 | Fatheree et al. |
| 2021/0024517 | A1 | 1/2021 | Long et al. |
| 2022/0008403 | A1 | 1/2022 | Kleinschek et al. |
| 2022/0008428 | A1 | 1/2022 | Fatheree et al. |
| 2022/0306626 | A1 | 9/2022 | Nzerem et al. |
| 2022/0388992 | A1 * | 12/2022 | Lu ........................ A61P 29/00 |

FOREIGN PATENT DOCUMENTS

| | | |
|---|---|---|
| JP | 2010111624 A | 5/2010 |
| KR | 10-2018-0137057 A | 12/2018 |
| WO | WO 2005/009389 A2 | 2/2005 |
| WO | WO 2009/155551 A1 | 12/2009 |
| WO | WO 2009/155565 A1 | 12/2009 |
| WO | WO 2010/039825 A1 | 4/2010 |
| WO | WO 2010/039939 A1 | 4/2010 |
| WO | WO 2010/114971 A1 | 10/2010 |
| WO | WO 2011/017178 A1 | 2/2011 |
| WO | WO 2011/076419 A1 | 6/2011 |
| WO | WO 2012/121764 A1 | 9/2012 |
| WO | WO 2013/014567 A1 | 1/2013 |
| WO | WO 2013/060636 A1 | 5/2013 |
| WO | WO 2013/151708 A1 | 10/2013 |
| WO | WO 2014/111380 A1 | 7/2014 |
| WO | WO 2015/061665 A1 | 4/2015 |
| WO | WO 2015/173683 A1 | 11/2015 |
| WO | WO 2016/026078 A1 | 2/2016 |
| WO | WO 2017/077283 A1 | 5/2017 |
| WO | WO 2017/077288 A1 | 5/2017 |
| WO | WO 2017/079205 A1 | 5/2017 |
| WO | WO 2018/011681 A1 | 1/2018 |
| WO | WO 2018/165392 A1 | 9/2018 |
| WO | WO 2018/204238 A1 | 11/2018 |
| WO | WO 2008/157208 A2 | 12/2018 |
| WO | WO 2020/051105 A1 | 3/2020 |
| WO | WO 2020/092019 A1 | 5/2020 |
| WO | WO 2020/173400 A1 | 9/2020 |
| WO | WO 2020/181034 A1 | 9/2020 |
| WO | WO 2021/136345 A1 | 7/2021 |

OTHER PUBLICATIONS

Abelson et al., "Sorting out the stats from the Jaks", Review of Ophthalmology, pp. 84-88 (Apr. 2013).

Bao et al., "The involvement of the JAK-STAT signaling pathway in chronic inflammatory skin disease atopic dermatitis", JAK-STAT, 2(3): e24137-1-e24137-8 (2013).

Barnes et al., "Kinases as Novel Therapeutic Targets in Asthma and Chronic Obstructive Pulmonary Disease", Pharmacological Review, 68:788-815, Jul. 2016.

Berastegui et al., "BALF cytokines in different phenotypes of chronic lung allograft dysfunction in lung transplant patients", Clinical Transplantation, 31: e12898 (2017).

Chander et al., "Lung lamellar bodies maintain an acidic internal pH", The Journal of Biological Chemistry, 261 (13):6126-6131 (1986).

Coghill et al., "Effector CD4+ T cells, the cytokines they generate, and GVHD: something old and something new", Blood, 117(12): 3268-3276 (Mar. 24, 2011).

Cottin, "Eosinophilic lung diseases", Clin Chest Med, 37: 535-556 (2016).

Craiglow et al., "Tofacitinib citrate for the treatment of vitiligo: A pathogenesis-directed therapy", JAMA Dermatology, 151: 1110-1112(2015).

De La Torre et al., "Salbutamol metabolism how to differentiate oral vs. inhaled administrations: looking outside the box", World Anti-doping Agency (Nov. 20, 2015).

De Nitto et al., "Involvement of interleukin-15 and interleukin-21, two gamma-chain-related cytokines, in celiac disease". World J Gastroenterol, 15(37): 4609-4614 (Oct. 7, 2009).

De Savi et al., "Efficacious inhaled PDE4 inhibitors with low emetic potential and long duration of action for the treatment of COPD", Journal of Medicinal Chemistry, 57:4661-4676 (2014).

Deobhakta et al., "Inflammation in retinal vein occlusion", International Journal of Inflammation, vol. 2013, 6 pages (2013).

Down et al., "Optimization of novel indazoles as highly potent and selective inhibitors of phosphoinositide 3-kinase delta for the treatment of respiratory disease" Journal of Medicinal Chemistry, 58:7381-7399 (2015).

Duffel et al., "On the mechanism of aryl sulfotransferase", J Biological Chemistry, 256(21):11123-11127 (1981).

Eaton et al., "Stereoselective sulphate conjugation of salbutamol by human lung and bronchial epithelial cells", Br J Clin Pharmacol, 41:201-206 (1996).

El-Hashemite et al., "Interferon-gamma-Jak-Stat signaling in pulmonary lymphangioleiomyomatosis and renal angiomyolipoma", Am J Respir Cell Mol Biol, 33: 227-230 (2005).

El-Hashemite et al., "Perturbed IFN-gamma-Jak-signal transducers and activators of transcription signaling in tuberous sclerosis mouse models: Synergistic effects of rapamycin-IFN-gamma treatment", Cancer Research, 64: 3436-3443 (May 15, 2004).

Fang et al., "Interleukin-6—572C/G polymorphism is associated with serum interleukin-6 levels and risk of idiopathic pulmonary arterial hypertension", Journal of the American Society of Hypertension, 11(3): 171-177 (2017).

Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).

Fenwick et al., "Effect of JAK inhibitors on release of CXCL9, CXCL10 and CXCL11 from human airway epithelial cells", PLOS One, 10(6):e0128757 (2015).

Foloppe et al., "Identification of a buried pocket for potent and selective inhibition of Chk1: Prediction and verification", Bioorganic & Medicinal Chemistry, 14:1792-1804 (2006).

(56) References Cited

OTHER PUBLICATIONS

Fowler et al., "Carbon-11 labeled aliphatic amines in lung uptake and metabolism studies: potential for dynamic measurements in vivo", The Journal of Pharmacology and Experimental Therapeutics, 198(1):133-145 (1976).
Funatsu et al., "Association of vitreous inflammatory factors with diabetic macular edema", Ophthalmology, 116: 73-79 (2009).
Gauthier et al., "Update on chronic lung allograft dysfunction", Curr Transplant Rep, 3(3): 185-191 (Sep. 2016).
Gontcharov et al., "Development of a scalable synthesis for an inhaled pan-JAK inhibitor", Organic Process Research & Development, Jul. 2019, vol. 23, Issue 9, pp. 1990-2000.
Gonzales, A. J. et al., "Oclacitinib (APOQUEL(®)) is a novel Janus kinase inhibitor with activity against cytokines invoived in allergy", Journal of veterinary pharmacology and therapeutics, vol. 37, No., 4, pp. 3'17-324 (2014).
Horai et al., "Cytokines in autoimmune uveitis", Journal of Interferon & Cytokine Research, 31(10): 733-744 (2011).
Hori et al., "Binding of basic drugs to rat lung mitochondria", Pharmaceutical Research, 4(2):142-146 (1987).
Horig et al., "From bench to clinic and back: Perspective on the 1st IQPC Translational Research conference", Journal of Translational Medicine, 2(44), (2004).
Huang et al., "Glycoprotein 130 inhibitor ameliorates monocrotalline-induced pulmonary hypertension in rats", Canadian Journal of Cardiology, 32: 1356.e1-1356.e10 (2016).
Jones et al., "Design and synthesis of a Pan-Janus kinase inhibitor clinical candidate (PF-06263276) suitable for inhaled and topical delivery for the treatment of inflammatory diseases of the lungs and skin", J. Med. Chern., 60: 767-786 (Jan. 2017).
Knickelbein et al., "Inflammatory mechanisms of age-related macular degeneration", International Ophthalmology Clinics, 55(3): 63-78 (2015).
Krejcie et al., "A recirculatory model of the pulmonary uptake and pharmacokinetics of lidocaine based on analysis of arterial and mixed venous data from dogs", Journal of Pharmacokinetics and Biopharmaceutics, 25(2):169-190 (1997).
Kudlacz et al., "The JAK-3 inhibitor CP-690550 is a potent anti-inflammatory agent in a murine model of pulmonary eosinophilia", European Journal of Pharmacology, 582: 154-161 (2008).
Kumawat et al., "Microscopic colitis patients demonstrate a mixed Th17/Tc17 and Th1/Tc1 mucosal cytokine profile", Molecular Immunology, 55: 355-364 (2013).
Lu et al., "Role of a janus kinase 2-dependent signaling pathway in platelet activation", Thromb. Res., 133(6), 1088-1096 (2014).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
McBride et al., "3-Benzimidazol-2-yl-1H-indazoles as potent c-ABL inhibitors", Bioorganic & Medicinal Chemistry Letters, 16:3789-3792 (2006).
McBride et al., "Design and structure-activity relationship of 3-benzimidazol-2-yl-1H-indazoles as inhibitors of receptor tyrosine kinases", Bioorganic & Medicinal Chemistry Letters, 16:3595-3599 (2006).
Minchin et al., "Effect of desmethylimipramine on the kinetics of chlorphentermine accumulation in isolated perfused rat lung", The Journal of Pharmacology and Experimental Therapeutics, 211(3):514-518 (1979).
Miniati et al., "Mitochondria act as a reservoir for the basic amine HIPDM in the lung", European Respiratory Journal, 9:2306-2312 (1996).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).

Okiyama et al., "Reversal of CD8 T-cell-mediated mucocutaneous graft-vershost-like disease by the JAK inhibitor tofacitinib", Journal of Investigative Dermatology, 134: 992-1000 (2014).
Orton et al., "Xenobiotic accumulation and metabolism by isolated perfused rabbit lungs", The Journal of Pharmacology and Experimental Therapeutics, 186(3):482-497 (1973).
Owen et al., "Soluble mediators of diabetic macular edema: The diagnostic role of aqueous VEGF and cytokine levels in diabetic macular edema", Curr Diab Rep, 13(4): 476-480 (Aug. 2013).
Paci et al., "Lung tissue binding of iodobenzyl-propanediamine: involvement of beta-adrenergic receptors", 7 (12):1467-1472 (1989).
Reimund et al., "Mucosal inflammatory cytokine production by intestinal biopsies in patients with ulcerative colitis and Crohn's disease", Journal of Clinical Immunology, 16(3): 144-150 (1996).
Roerig et al., "Effect of plasma protein binding on the uptake of methadone and diazepam in the isolated perfused rat lung", Drug Metabolism and Disposition, 12(5):536-542 (1984).
Roerig et al., "First-pass uptake of verapamil, diazepam, and thiopental in the human lung", Anesth Analg, 69:461-466 (1989).
Roth et al., "Action by the lungs on circulating xenobiotic agents, with a case study of physiologically based pharmacokinetic modeling of benzo(A)pyrene disposition", Pharmaceutical Therapy, 48:143-155 (1990).
Schafer et al., "Failure is an option: learning from unsuccessful proof-of-concept trials", Drug Discovery Today, 13 (21): 913-916 (Nov. 2008).
Sharan et al., "Pulmonary metabolism of resveratrol: in vitro and in vivo evidence", Drug Metab Dispos, 41 :1163-1169 (May 2013).
Shaw et al., "Optimization of platelet-derived growth factor receptor (PDGFR) inhibitors for duration of action, as an inhaled therapy for lung remodeling in pulmonary arterial hypertension", Journal of Medicinal Chemistry, 59:7901-7914 (2016).
Shchuko et al., "Intraocular cytokines in retinal vein occlusion and its relation to the efficiency of anti-vascular endothelial growth factor therapy", Indian Journal of Ophthalmology, 63: 905-911 (2015).
Shino et al., "The prognostic importance of CXCR3 chemokine during organizing pneumonia on the risk of chronic lung allograft dysfunction after lung transplantation", PLOS One, 12(7): e0180281 (2017).
Simov et al., "Structure-based design and development of (benz)imidazole pyridones as JAK1-selective kinase inhibitors", Bioorganic & Medicinal Chemistry Letters, 26:1803-1808 (2016).
Slosman et al., "Evaluation of [iodine-125]N,N, N'-trimethyl-N'-[2-hydroxy-3-methyl-5-iodobenzyl]-1,3-pro- panediamine lung uptake using an isolated-perfused lung model", Journal of Nuclear Medicine, 28(2):203-208 (1987).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Stallmach et al., "Cytokine/chemokine transcript profiles reflect mucosal inflammation in Crohn's disease", Int J Colorectal Dis, 19: 308-315 (2004).
Stevenson et al., "Dry eye disease: an immune-mediated ocular surface disorder", Arch Ophthalmol, 130(1): 90-100 (Jan. 2012).
Tanaka et al., "New insight into mechanisms of pruritus from molecular studies on familial primary localized cutaneous amyloidosis", British Journal of Dermatology, 161: 1217-1224 (2009).
Trujillo et al., "2-(6-Phenyl-1H-indazol-3-yl)-1H-benzo[d]imidazoles: Design and synthesis of a potent and isoform selective PKC-zeta inhibitor", Bioorganic & Medicinal Chemistry Letters, 19:908-911 (2009).
Vestal et al., "Active uptake of propranolol by isolated rabbit alveolar macrophages and its inhibition by other basic amines", The Journal of Pharmacology and Experimental Therapeutics, 214(1):106-111 (1980).
Vincenti et al., "Randomized phase 2b trial of tofacitinib (CP-690,550) in de novo kidney transplant patients: Efficacy, renal function and safety at 1 year", American Journal of Transplantation, 12: 2446-2456 (2012).

(56) References Cited

OTHER PUBLICATIONS

Ward et al., "Enantiomeric disposition of inhaled, intravenous and oral racemic-salbutamol in man—no evidence of enantioselective lung metabolish", J Clin Pharmacol, 49:15-22 (2000).
Waters et al., "Uptake of fentanyl in pulmonary endothelium", The Journal of Pharmacology and Experimental Therapeutics, 288(1):157-163 (1999).
Waters et al., Facilitated uptake of fentanyl, but not alfentanyl, by human pulmonary endothelial cells, Anesthesiology, 93(3):825-831 (2000).
Weinbrand-Goichberg et al., "Eosinophilic esophagitis: an immune-mediated esophageal disease", Immunol Res, 56: 249-260 (2013).
Welz-Kubiak et al., "IL-31 is overexpressed in lichen planus but its level does not correlate with pruritus severity", Journal of Immunology Research, Article 854747, 6 pages (2015).
Wilcken et al., "Principles and applications of halogen bonding in medicinal chemistry and chemical bioloav", Journal of Medicinal Chemistry, 56: 1363-1388 (2013).
Wilson et al., "Studies on the persistence of basic amines in the rabbit lung", Drug Metabolism and Disposition, 7(6):420-424 (1979).
Woywodt et al., "Mucosal cytokine expression, cellular markers and adhesion molecules in inflammatory bowel disease", European Journal of Gastroenterology & Hepatology, 11: 267-276 (1999).
Xing et al., "Alopecia areata is driven by cytotoxic T lymphocytes and is reversed by JAK inhibition", Nature Medicine, 20(9): 1043-1049 (Sep. 2014).
Yamamoto et al., "Mucosal inflammation in the terminal ileum of ulcerative colitis patients: Endoscopic findings and cytokine profiles", Digestive and Liver Disease, 40: 253-259 (2008).
Yan et al., "Discovery of 3-(5'-Substituted)-benzimidazol-5-(1-(3,5-dichloropyridin-4-yl)ethoxy)-1H-indazoles as potent fibroblast growth factor receptor inhibitors: Design, synthesis, and biological evaluation", J. Med. Chern., 59: 6690-6708(2016).
Yano et al., "Ipilimumab augments antitumor activity of bispecific antibody-armed T cells", Journal of Translational Medicine, 12: 191 (2014).
Yoshida et al., "Contribution of monoamine oxidase (MAO) to the binding of tertiary basic drugs in lung mitochondria", Pharmaceutical Research, 6(10):877-882 (1989).
Zeiser et al., "Ruxolitinib in corticosteroid-refractory graft-vershost disease after allogeneic stem cell transplantation: a multi-center survey", Leukemia, 29(10): 2062-2068 (Oct. 2015).
Zhou et al., "Cytokines and Behcet's Disease", Autoimmunity Reviews, 11: 699-704 (2012).
Zhou et al., "Tertiary amine mediated targeted therapy against metastatic lung cancer", Journal of Controlled Release, 241:81-93 (2016).

\* cited by examiner

IMIDAZOLO INDAZOLE COMPOUNDS AS JAK INHIBITORS

CROSS REFERENCE TO RELATED APPLICATIONS

This application claims the benefit under 35 U.S.C. § 119(e) of U.S. Provisional Application No. 63/202,811, filed Jun. 25, 2021, which application is incorporated by reference in its entirety.

FIELD

Provided herein are compounds useful as Janus kinase (JAK) inhibitors. Also provided herein are pharmaceutical compositions comprising such compounds and methods of using such compounds to treat, e.g., inflammatory and fibrotic diseases, including respiratory diseases.

BACKGROUND

Asthma is a chronic disease of the airways for which there are no preventions or cures. The disease is characterized by inflammation, fibrosis, hyper-responsiveness, and remodeling of the airways, all of which contribute to airflow limitation. An estimated 300 million people worldwide suffer from asthma and it is estimated that the number of people with asthma will grow by more than 100 million by 2025. In the United States, asthma afflicts about 6% to 8% of the population, making it one of the most common chronic diseases in the country. Although most patients can achieve control of asthma symptoms with the use of inhaled corticosteroids that may be combined with a leukotriene modifier and/or a long acting beta agonist, there remains a subset of patients with severe asthma whose disease is not controlled by conventional therapies. Severe persistent asthma is defined as disease that remains uncontrolled on high doses of inhaled corticosteroids. While severe asthmatics are estimated to account for approximately 5% of all asthma sufferers, they have a high risk of morbidity and mortality and are responsible for a disproportionate share of health care resource utilization among asthmatics. There remains a need for novel therapies to treat these patients.

Cytokines are intercellular signaling molecules which include chemokines, interferons, interleukins, lymphokines, and tumor necrosis factor. Cytokines are critical for normal cell growth and immunoregulation but also drive immune-mediated diseases and contribute to the growth of malignant cells. Elevated levels of many cytokines have been implicated in the pathology of asthma inflammation. For example, antibody-based therapies targeted at interleukins (IL)-5, and 13 have been shown to provide clinical benefit in subsets of severe asthma patients. Among the cytokines implicated in asthma inflammation, many act through signaling pathways dependent upon the Janus family of tyrosine kinases (JAKs), which signal through the Signal Transducer and Activator of Transcription (STAT) family of transcription factors. Cytokines implicated in asthma inflammation which signal through the JAK-STAT pathway include IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF).

The JAK family comprises four members, JAK1, JAK2, JAK3, and tyrosine kinase 2 (TYK2). Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. The JAKs usually associate with cytokine receptors in pairs as homodimers or heterodimers. Specific cytokines are associated with specific JAK pairings. Each of the four members of the JAK family is implicated in the signaling of at least one of the cytokines associated with asthma inflammation. Consequently, a chemical inhibitor with pan-activity against all members of the JAK family could modulate a broad range of pro-inflammatory pathways that contribute to severe asthma.

However, the broad anti-inflammatory effect of such inhibitors could suppress normal immune cell function, potentially leading to increased risk of infection. Evidence of increased infection risk has been observed with the JAK inhibitor tofacitinib, which is dosed orally for the treatment of rheumatoid arthritis. In asthma, inflammation is localized to the respiratory tract. Inflammation of the airways is characteristic of other respiratory diseases in addition to asthma. Chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and sarcoidosis are also respiratory tract diseases in which the pathophysiology is believed to be related to JAK-signaling cytokines. Local administration of a JAK inhibitor to the lungs by inhalation offers the potential to be therapeutically efficacious by delivering a potent anti-cytokine agent directly to the site of action, limiting systemic exposure and therefore limiting the potential for adverse systemic immunosuppression. The need remains for a potent JAK inhibitor suitable for local administration to the lungs for treatment of respiratory disease.

JAK-signaling cytokines also play a major role in the activation of T cells, a sub-type of immune cells that is central to many immune processes. Pathological T cell activation is critical in the etiology of multiple respiratory diseases. Autoreactive T cells play a role in bronchiolitis obliterans organizing pneumonia (also termed COS). Similar to COS the etiology of lung transplant rejections is linked to an aberrant T cell activation of the recipient's T cells by the transplanted donor lung. Lung transplant rejections may occur early as Primary Graft Dysfunction (PGD), organizing pneumonia (OP), acute rejection (AR) or lymphocytic bronchiolitis (LB) or they may occur years after lung transplantation as Chronic Lung Allograft Dysfunction (CLAD). CLAD was previously known as bronchiolitis obliterans (BO) but now is considered a syndrome that can have different pathological manifestations including BO, restrictive CLAD (rCLAD or RAS) and neutrophilic allograft dysfunction. Chronic lung allograft dysfunction (CLAD) is a major challenge in long-term management of lung transplant recipients as it causes a transplanted lung to progressively lose functionality (Gauthier et al., *Curr. Transplant. Rep.*, 2016, 3(3), 185-191). CLAD is poorly responsive to treatment and therefore, there remains a need for effective compounds capable of preventing or treating this condition. Several JAK-dependent cytokines such as IFNγ and IL-5 are up-regulated in CLAD and lung transplant rejection (Berastegui et al, *Clin. Transplant.* 2017, 31, e12898). Moreover, high lung levels of CXCR3 chemokines such as CXCL9 and CXCL10 which are downstream of JAK-dependent IFN signaling, are linked to worse outcomes in lung transplant patients (Shino et al, *PLOS One*, 2017, 12 (7), e0180281).

Systemic JAK inhibition has been shown to be effective in kidney transplant rejection (Vicenti et al., *American Journal of Transplantation*, 2012, 12, 2446-56). Therefore, JAK inhibitors have the potential to be effective in treating or preventing lung transplant rejection and CLAD. Similar T cell activation events as described as the basis for lung transplant rejection also are considered the main driver of lung graft-versus-host disease (GVHD) which can occur post hematopoietic stem cell transplants. Similar to CLAD, lung GVHD is a chronic progressive condition with extremely poor outcomes and no treatments are currently approved. A retrospective, multicenter survey study of 95 patients with steroid-refractory acute or chronic GVHD who received the systemic JAK inhibitor ruxolitinib as salvage therapy demonstrated complete or partial response to ruxolitinib in the majority of patients including those with lung GVHD (Zeiser et al, *Leukemia*, 2015, 29, 10, 2062-68). As systemic JAK inhibition is associated with serious adverse events and a small therapeutic index, the need remains for an inhaled lung-directed, non-systemic JAK inhibitor to prevent and/or treat lung transplant rejection or lung GVHD.

SUMMARY

Provided herein are compounds of formula (I):

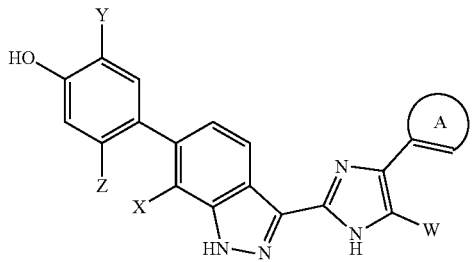

(I)

or a pharmaceutically-acceptable salt thereof,
wherein:
W is H, —$C_{1-6}$ alkyl or halogen;
X is H or F;
Y is H, —$CH_3$, or F;
Z is —$CH_2CH_3$, —$CF_2CH_3$, or —$CH_2CF_3$;
A is a 4 to 7 membered monocyclic heterocyclic group having a double bond and optionally substituted with 1 to 8 substituents independently selected from the group consisting of —$C_{1-6}$ alkyl, —$COR^1$, —$SO_2R^1$, —$CO_2R^2$, —$CONR^2R^3$, —$SO_2NR^2R^3$, aryl, heteroaryl, a 3 to 7 membered cycloalkyl group, and a 4 to 7 membered heterocyclic group,
wherein the —$C_{1-6}$ alkyl is optionally substituted with 1 to 5 substituents independently selected from the group consisting of —$C_{1-6}$ alkyl, —$NR^2R^3$, —CN, —$CO_2R^2$, —$CONR^2R^3$, —OH, —$SO_2NR^2R^3$, —$SO_2$—$C_{1-6}$ alkyl, —SH, —O—$C_{1-6}$ alkyl, —S—$C_{1-6}$ alkyl, —$OC(O)NR^2R^3$, —$NR^2C(O)$—$R^1$, —$NR^2C(O)_2R^3$, —$NR^2$—$C(O)NR^3R^4$, —$OCO_2R^3$, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —$C_{1-6}$ alkyl, —CN, —$CO_2R^5$, —$CONR^5R^6$, —OH, —SH, —O—$C_{1-6}$ alkyl, —S—$C_{1-6}$ alkyl, —$NR^5R^6$, —OC(O)$NR^5R^6$, —$NR^5C(O)$—$C_{1-6}$ alkyl, —$NR^5C(O)_2R^6$, —$NR^5$—$C(O)NR^6R^7$, —$C_{1-6}$ alkyl-OR—, —$C_{1-6}$ alkyl-$NR^5R^6$, and —$C_{1-6}$ alkyl-$CO_2R^5$, and wherein the aryl and heteroaryl are optionally substituted with 1 to 5 substituents independently selected from the group consisting of halogen, —CN, —$CO_2R^8$, —$CONR^8R^9$, —OH, —SH, —$C_{1-6}$ alkyl, —O—$C_{1-6}$ alkyl, —S—$C_{1-6}$ alkyl, —$NR^8R^9$, —OC(O)$NR^8R^9$, —$OCO_2R^8$, —$NR^8C(O)$—$C_{1-6}$ alkyl, —$NR^8C(O)_2R^9$, —$NR^B$—$C(O)NR^9R^{10}$, —$C_{1-6}$ alkyl-$OR^8$, —$C_{1-6}$ alkyl-$NR^8R^9$, and —$C_{1-6}$ alkyl-$CO_2R^8$,
wherein A is optionally fused or bridged with a 3 to 7 membered cycloalkyl group or a 4 to 7 membered heterocyclic group,
wherein each 3 to 7 membered cycloalkyl group and each 4 to 7 membered heterocyclic group is optionally substituted with 1 to 5 substituents independently selected from the group consisting of a spiro 3 to 7 membered cycloalkyl group, a spiro 4 to 7 membered heterocyclic group, a 3 to 7 membered cycloalkyl group, a 4 to 7 membered heterocyclic group, —$C_{1-6}$ alkyl, —$CF_3$, oxo, —CN, —$CO_2R^{11}$, —$CONR^{11}R^{12}$, —OH, —SH, —O—$C_{1-6}$ alkyl, —S—$C_{1-6}$ alkyl, —$NR^{11}R^{12}$, —OC(O)$NR^{11}R^{12}$, —$NR^{11}C(O)$—$C_{1-6}$ alkyl, —$NR^{11}C(O)_2R^{12}$, —$NR^{11}$—$C(O)NR^{12}R^{13}$, —$OCO_2R^{12}$, —$NR^{11}$—$SO_2$—$C_{1-6}$ alkyl, —$C_{1-6}$ alkyl-$OR^{11}$, —$C_{1-6}$ alkyl-$NR^{11}R^{12}$, and —$C_{1-6}$ alkyl-$CO_2R^{11}$;
each $R^1$ is independently selected from the group consisting of aryl, a 3 to 7 membered cycloalkyl group, a 4 to 7 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, —O—$C_{1-6}$ alkyl, —O—$C_{1-6}$ alkyl-$NR^aR^b$, aryl, heteroaryl, and a 4 to 7 membered heterocyclic group, wherein the aryl, 3 to 7 membered cycloalkyl group, 4 to 7 membered heterocyclic group and heteroaryl are each optionally substituted with 1 to 5 substituents independently selected from the group consisting of halogen, —$NR^{14}R^{15}$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —OC(O)$NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$OCO_2R^{14}$ and —$NR^{14}SO_2$—$C_{1-6}$ alkyl;
each $R^2$, $R^3$, $R^4$, $R^5$, $R^6$, $R^7$, $R^8$, $R^9$, $R^{10}$, $R^{11}$, $R^{12}$, $R^{13}$, $R^a$, and $R^b$ is independently selected from the group consisting of H, $C_{1-6}$ alkyl, and —$C_{1-6}$ alkyl-$OR^{14}$;
wherein in —$CONR^2R^3$ and —$SO_2NR^2R^3$, $R^2$ and $R^3$ are optionally joined to form a 4 to 7 membered heterocyclic group optionally substituted with 1 to 5 substituents independently selected from the group consisting of —$NR^cR^d$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —OC(O)$NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$OCO_2R^{14}$, and —$NR^{14}SO_2$—$C_{1-6}$ alkyl, and
each $R^c$, $R^d$, $R^{14}$, $R^{15}$, and $R^{16}$ is independently selected from the group consisting of H and $C_{1-6}$ alkyl.

In some embodiments, the compound of formula (I) is a compound of formula (II):

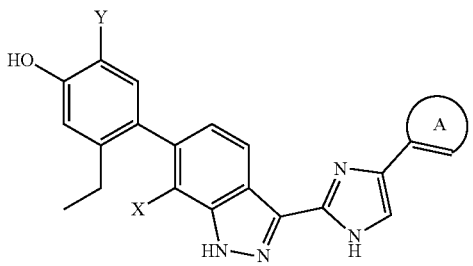

(II)

or a pharmaceutically-acceptable salt thereof,
wherein:
X is H or F;
Y is H or F;
A is a 4 to 7 membered monocyclic heterocyclic group having a double bond and optionally substituted with 1 to 8 substituents independently selected from the group consisting of —$C_{1-6}$ alkyl, —$COR^1$, —$SO_2R^1$, —$CO_2R^2$, —$CONR^2R^3$, —$SO_2NR^2R^3$, a 3 to 7 membered cycloalkyl group, and a 4 to 7 membered heterocyclic group,
  wherein the —$C_{1-6}$ alkyl is optionally substituted with 1 to 5 substituents independently selected from the group consisting of —$C_{1-6}$ alkyl, —$NR^2R^3$, —CN, —$CO_2R^2$, —$CONR^2R^3$, —OH, —$SO_2NR^2R^3$, —$SO_2$—$C_{1-6}$ alkyl, —SH, —O—$C_{1-6}$ alkyl, —S—$C_{1-6}$ alkyl, —$OC(O)NR^2R^3$, —$NR^2C(O)$—$C_{1-6}$ alkyl, —$NR^2C(O)_2R^3$, —$NR^2$—$C(O)NR^3R^4$, —$OCO_2R^3$, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —$C_{1-6}$ alkyl, —CN, —$CO_2R^5$, —$CONR^5R^6$, —OH, —SH, —O—$C_{1-6}$ alkyl, —S—$C_{1-6}$ alkyl, —$NR^5R^6$, —$OC(O)NR^5R^6$, —$NR^5C(O)$—$C_{1-6}$ alkyl, —$NR^5C(O)_2R^6$, —$NR^5$—$C(O)NR^6R^7$, —$C_{1-6}$ alkyl-$OR^5$, —$C_{1-6}$ alkyl-$NR^5R^6$, and —$C_{1-6}$ alkyl-$CO_2R^5$, and wherein the aryl and heteroaryl are optionally substituted with 1 to 5 substituents independently selected from the group consisting of halogen, —CN, —$CO_2R^8$, —$CONR^8R^9$, —OH, —SH, —$C_{1-6}$ alkyl, —O—$C_{1-6}$ alkyl, —S—$C_{1-6}$ alkyl, —$NR^8R^9$, —$OC(O)NR^8R^9$, —$OCO_2R^8$, —$NR^8C(O)$—$C_{1-6}$ alkyl, —$NR^8C(O)_2R^9$, —$NR^8$—$C(O)NR^9R^{10}$, —$C_{1-6}$ alkyl-$OR^8$, —$C_{1-6}$ alkyl-$NR^8R^9$, and —$C_{1-6}$ alkyl-$CO_2R^8$,
  wherein A is optionally fused or bridged with a 3 to 7 membered cycloalkyl group or a 4 to 7 membered heterocyclic group,
  wherein each 3 to 7 membered cycloalkyl group and each 4 to 7 membered heterocyclic group is optionally substituted with 1 to 5 substituents independently selected from the group consisting of a spiro 3 to 7 membered cycloalkyl group, a spiro 4 to 7 membered heterocyclic group, a 3 to 7 membered cycloalkyl group, a 4 to 7 membered heterocyclic group, —$C_{1-6}$ alkyl, oxo, —CN, —$CO_2R^{11}$, —$CONR^{11}R^{12}$, —OH, —SH, —O—$C_{1-6}$ alkyl, —S—$C_{1-6}$ alkyl, —$NR^{11}R^{12}$, —$OC(O)NR^{11}R^{12}$, —$NR^{11}C(O)$—$C_{1-6}$alkyl, —$NR^{11}C(O)_2R^{12}$, —$NR^{11}$—$C(O)NR^{12}R^{13}$, —$OCO_2R^{12}$, —$NR^{11}$—$SO_2$—$C_{1-6}$ alkyl, —$C_{1-6}$ alkyl-$OR^{11}$, —$C_{1-6}$ alkyl-$NR^{11}R^{12}$, and —$C_{1-6}$ alkyl-$CO_2R^{11}$;

each $R^1$ is independently selected from the group consisting of aryl, a 3 to 7 membered cycloalkyl group, a 4 to 7 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, —O—$C_{1-6}$ alkyl, aryl, and heteroaryl, wherein the aryl, 3 to 7 membered cycloalkyl group, 4 to 7 membered heterocyclic group and heteroaryl are each optionally substituted with 1 to 5 substituents independently selected from the group consisting of halogen, —$NR^{14}R^{15}$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —$OC(O)NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$OCO_2R^{14}$ and —$NR^{14}SO_2$—$C_{1-6}$ alkyl;

each $R^2$, $R^3$, $R^4$, $R^5$, $R^6$, $R^7$, $R^8$, $R^9$, $R^{10}$, $R^{11}$, $R^{12}$, $R^{13}$, $R^a$, and $R^b$ is independently selected from the group consisting of H and $C_{1-6}$ alkyl;

wherein in —$CONR^2R^3$ and —$SO_2NR^2R^3$, $R^2$ and $R^3$ are optionally joined to form a 4 to 7 membered heterocyclic group optionally substituted with 1 to 5 substituents independently selected from the group consisting of —$NR^cR^d$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —$OC(O)NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$OCO_2R^{14}$, and —$NR^{14}SO_2$—$C_{1-6}$ alkyl, and each $R^c$, $R^d$, $R^{14}$, $R^{15}$, and $R^{16}$ is independently selected from the group consisting of H and $C_{1-6}$ alkyl.

Also provided herein are pharmaceutical compositions comprising a compound of formula (I) or formula (II), or a pharmaceutically acceptable salt thereof, and a pharmaceutically-acceptable carrier.

Also provided herein are methods of treating respiratory disease, in particular, asthma and lung rejection, in a mammal (e.g. a human), the method comprising administering to the mammal (or human) a compound of formula (I) or formula (II), or a pharmaceutically acceptable salt thereof.

The present disclosure also provides a compound of formula (I) or formula (II), or a pharmaceutically acceptable salt thereof, for use in medical therapy, as well as the use of such compound in the manufacture of a formulation or medicament for treating a respiratory disease in a mammal (e.g. a human).

DETAILED DESCRIPTION

Provided herein are compounds of formula (I):

(I)

or a pharmaceutically-acceptable salt thereof, wherein A, W, X, Y and Z are as defined herein.

In some embodiments, W is H. In some embodiments, W is —$C_{1-6}$ alkyl (including, e.g., methyl, ethyl, n-propyl, and isopropyl). In some embodiments, W is halogen (including, e.g., fluoro, chloro and bromo). In some embodiments, W is H, —$CH_3$ or bromo.

In some embodiments, X is H. In some embodiments, X is F.

In some embodiments, Y is H. In some embodiments, Y is F. In some embodiments, Y is —$CH_3$. In some embodiments, Y is H or F.

In some embodiments, Z is —$CH_2CH_3$. In some embodiments, Z is —$CF_2CH_3$. In some embodiments, Z is —$CH_2CF_3$.

In some embodiments, the compound of formula (I) is a compound of formula (II):

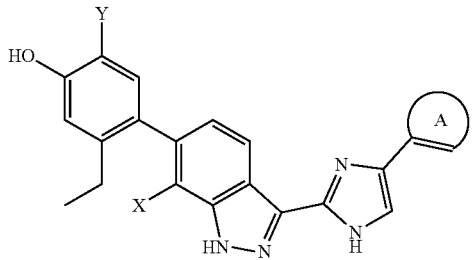

(II)

or a pharmaceutically-acceptable salt thereof,
wherein:
X is H or F;
Y is H or F;
A is a 4 to 7 membered monocyclic heterocyclic group having a double bond and optionally substituted with 1 to 8 substituents independently selected from the group consisting of —$C_{1-6}$ alkyl, —$COR^1$, —$SO_2R^1$, —$CO_2R^2$, —$CONR^2R^3$, —$SO_2NR^2R^3$, a 3 to 7 membered cycloalkyl group, and a 4 to 7 membered heterocyclic group,
wherein the —$C_{1-6}$ alkyl is optionally substituted with 1 to 5 substituents independently selected from the group consisting of —$C_{1-6}$ alkyl, —$NR^2R^3$, —CN, —$CO_2R^2$, —$CONR^2R^3$, —OH, —$SO_2NR^2R^3$, —$SO_2$—$C_{1-6}$ alkyl, —SH, —O—$C_{1-6}$ alkyl, —S—$C_{1-6}$ alkyl, —$OC(O)NR^2R^3$, —$NR^2C(O)$—$C_{1-6}$ alkyl, —$NR^2C(O)_2R^3$, —$NR^2$—$C(O)NR^3R^4$, —$OCO_2R^3$, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —$C_{1-6}$ alkyl, —CN, —$CO_2R^5$, —$CONR^5R^6$, —OH, —SH, —O—$C_{1-6}$ alkyl, —S—$C_{1-6}$alkyl, —$NR^5R^6$, —$OC(O)NR^5R^6$, —$NR^5C(O)$—$C_{1-6}$ alkyl, —$NR^5C(O)_2R^6$, —$NR^5$—$C(O)NR^6R^7$, —$C_{1-6}$ alkyl-$OR^5$, —$C_{1-6}$ alkyl-$NR^5R^6$, and —$C_{1-6}$ alkyl-$CO_2R^5$, and wherein the aryl and heteroaryl are optionally substituted with 1 to 5 substituents independently selected from the group consisting of halogen, —CN, —$CO_2R^8$, —$CONR^8R^9$, —OH, —SH, —$C_{1-6}$ alkyl, —O—$C_{1-6}$ alkyl, —S—$C_{1-6}$ alkyl, —$NR^8R^9$, —$OC(O)NR^8R^9$, —$OCO_2R^8$, —$NR^8C(O)$—$C_{1-6}$ alkyl, —$NR^8C(O)_2R^9$, —$NR^8$—$C(O)NR^9R^{10}$, —$C_{1-6}$ alkyl-$OR^8$, —$C_{1-6}$ alkyl-$NR^8R^9$, and —$C_{1-6}$alkyl-$CO_2R^8$,
wherein A is optionally fused or bridged with a 3 to 7 membered cycloalkyl group or a 4 to 7 membered heterocyclic group,
wherein each 3 to 7 membered cycloalkyl group and each 4 to 7 membered heterocyclic group is optionally substituted with 1 to 5 substituents independently selected from the group consisting of a spiro 3 to 7 membered cycloalkyl group, a spiro 4 to 7 membered heterocyclic group, a 3 to 7 membered cycloalkyl group, a 4 to 7 membered heterocyclic group, —$C_{1-6}$ alkyl, oxo, —CN, —$CO_2R^{11}$, —$CONR^{11}R^{12}$, —OH, —SH, —O—$C_{1-6}$ alkyl, —S—$C_{1-6}$ alkyl, —$NR^{11}R^{12}$, —$OC(O)NR^{11}R^{12}$, —$NR^{11}C(O)$—$C_{1-6}$alkyl, —$NR^{11}C(O)_2R^2$, —$NR^{11}$—$C(O)NR^{12}R^{13}$, —$OCO_2R^2$, —$NR^{11}$—$SO_2$—$C_{1-6}$ alkyl, —$C_{1-6}$ alkyl-$OR^{11}$, —$C_{1-6}$ alkyl-$NR^{11}R^{12}$, and —$C_{1-6}$ alkyl-$CO_2R^{11}$;
each $R^1$ is independently selected from the group consisting of aryl, a 3 to 7 membered cycloalkyl group, a 4 to 7 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, —O—$C_{1-6}$ alkyl, aryl, and heteroaryl, wherein the aryl, 3 to 7 membered cycloalkyl group, 4 to 7 membered heterocyclic group and heteroaryl are each optionally substituted with 1 to 5 substituents independently selected from the group consisting of halogen, —$NR^{14}R^{15}$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —$OC(O)NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$OCO_2R^{14}$ and —$NR^{14}SO_2$—$C_{1-6}$ alkyl;
each $R^2$, $R^3$, $R^4$, $R^5$, $R^6$, $R^7$, $R^8$, $R^9$, $R^{10}$, $R^{11}$, $R^{12}$, $R^{13}$, $R^a$, and $R^b$ is independently selected from the group consisting of H and $C_{1-6}$ alkyl;
wherein in —$CONR^2R^3$ and —$SO_2NR^2R^3$, $R^2$ and $R^3$ are optionally joined to form a 4 to 7 membered heterocyclic group optionally substituted with 1 to 5 substituents independently selected from the group consisting of —$NR^cR^d$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —$OC(O)NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$OCO_2R^{14}$, and —$NR^{14}SO_2$—$C_{1-6}$ alkyl, and
each $R^c$, $R^d$, $R^{14}$, $R^{15}$, and $R^{16}$ is independently selected from the group consisting of H and $C_{1-6}$ alkyl.

In some embodiments, X is H or F; Y is H or F;
A is a piperidine or a pyrrolidine having a double bond and optionally substituted with 1 to 6 substituents independently selected from the group consisting of $C_{1-6}$ alkyl, —$COR^1$, $SO_2R^1$, —$CO_2R^2$, —$CONR^2R^3$, $SO_2NR^2R^3$, a 3 to 7 membered cycloalkyl group, and a 4 to 7 membered heterocyclic group,
wherein the —$C_{1-6}$ alkyl is optionally substituted with 1 to 5 substituents independently selected from the group consisting of —$C_{1-6}$ alkyl, —$NR^2R^3$, —$CONR^2R^3$, —OH, —$SO_2NR^2R^3$, —$SO_2$—$C_{1-6}$ alkyl, —O—$C_{1-6}$ alkyl, —S—$C_{1-6}$ alkyl, —$NR^2C(O)$—$C_{1-6}$ alkyl, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —C$_{1-6}$ alkyl, and —OH, and wherein the aryl and heteroaryl are optionally substituted with 1 to 3 substituents independently selected from the group consisting of halogen, —CN, —CO$_2$R$^8$, —CONR$^8$R$^9$, OH, SH, C$_{1-6}$alkyl, —O—C$_{1-6}$ alkyl, —S—C$_{1-6}$ alkyl, —NR$^8$R$^9$, —OC(O)NR$^8$R$^9$, —NR$^8$C(O)—C$_{1-6}$ alkyl, —NR$^8$C(O)$_2$R$^9$, —NR$^8$—C(O)NR$^9$R$^{10}$, —OCO$_2$R$^8$, —C$_{1-6}$ alkyl-OR$^8$, —C$_{1-6}$ alkyl-NR$^8$R$^9$, and —C$_{1-6}$ alkyl-CO$_2$R$^8$, wherein A is optionally bridged with a 3 to 7 membered cycloalkyl group or a 4 to 7 membered heterocyclic group, wherein each 3 to 7 membered cycloalkyl group and each 4 to 7 membered heterocyclic group is optionally substituted with 1 to 5 substituents independently selected from the group consisting of —C$_{1-6}$ alkyl, oxo, and —OH;

each R$^1$ is independently selected from the group consisting of phenyl, a 4 to 6 membered heterocyclic group, and —C$_{1-6}$ alkyl wherein the —C$_{1-6}$ alkyl is optionally substituted with 1 to 5 substituents independently selected from the group consisting of —NR$^a$R$^b$, —OH, and phenyl;

each R$^2$, R$^3$, R$^8$, R$^9$, R$^{10}$, R$^a$, and R$^b$ is independently selected from the group consisting of H and C$_{1-6}$ alkyl;

wherein in —CONR$^2$R$^3$ and —SO$_2$NR$^2$R$^3$, R$^2$ and R$^3$ are optionally joined to form a 4 to 7 membered heterocyclic group optionally substituted with NR$^c$R$^d$, and each R$^c$ and R$^d$ is independently selected from the group consisting of H and C$_{1-6}$ alkyl.

In some embodiments, A is selected from the group consisting of:

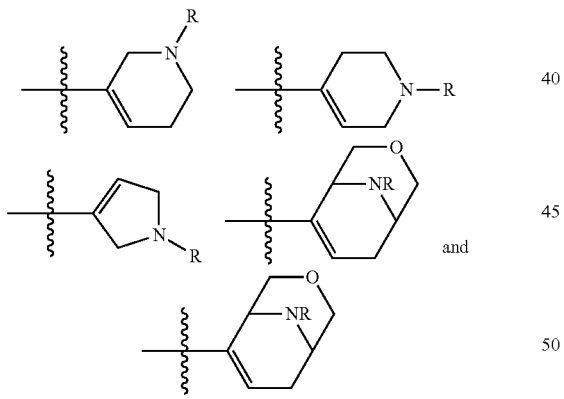

each of which is optionally substituted with 1 to 3 R$^x$ independently selected from the group consisting of —CO$_2$R$^y$, —CONR$^y$R$^z$, and —C$_{1-6}$ alkyl, wherein the —C$_{1-6}$ alkyl is optionally substituted with 1 to 5 substituents independently selected from the group consisting of —CN, —OH, —O—C$_{1-6}$alkyl, —CO$_2$R$^y$, and —CONR$^y$R$^z$;

R is selected from the group consisting of H, —C$_{1-6}$ alkyl, —COR$^1$, —SO$_2$R$^1$, —CO$_2$R$^2$, —CONR$^2$R$^3$, —SO$_2$NR$^2$R$^3$, a 3 to 7 membered cycloalkyl group, and a 4 to 7 membered heterocyclic group, wherein the C$_{1-6}$ alkyl is optionally substituted with 1 to 5 substituents independently selected from the group consisting of —C$_{1-6}$ alkyl, —NR$^2$R$^3$, —CN, —CO$_2$R$^2$, —CONR$^2$R$^3$, OH, —SO$_2$NR$^2$R$^3$, SO$_2$—C$_{1-6}$ alkyl, SH, —O—C$_{1-6}$ alkyl, —S—C$_{1-6}$ alkyl, —OC(O)NR$^2$R$^3$, —NR$^2$C(O)—C$_{1-6}$ alkyl, —NR$^2$C(O)$_2$R$^3$, —NR$^2$—C(O)NR$^3$R$^4$, —OCO$_2$R$^2$, —NR$^2$SO$_2$—C$_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —C$_{1-6}$ alkyl, —CN, —CO$_2$R$^5$, —CONR$^5$R$^6$, —OH, —SH, —O—C$_{1-6}$ alkyl, —S—C$_{1-6}$ alkyl, —NR$^5$R$^6$, —OC(O)NR$^5$R$^6$, —NR$^5$C(O)—C$_{1-6}$ alkyl, —NR$^5$C(O)$_2$R$^6$, —NR$^5$—C(O)NR$^6$R$^7$, —OCO$_2$R$^5$, —C$_{1-6}$ alkyl-OR$^5$, —C$_{1-6}$ alkyl-NR$^5$R$^6$, and —C$_{1-6}$ alkyl-CO$_2$R$^5$, and wherein the aryl and heteroaryl are optionally substituted with 1 to 5 substituents independently selected from the group consisting of halogen, —CN, —CO$_2$R$^8$, —CONR$^8$R$^9$, —OH, —SH, —C$_{1-6}$ alkyl, —O—C$_{1-6}$ alkyl, —S—C$_{1-6}$ alkyl, —NR$^8$R$^9$, —OC(O)NR$^8$R$^9$, —NR$^8$C(O)—C$_{1-6}$ alkyl, —NR$^8$C(O)$_2$R$^9$, —NR$^8$—C(O)NR$^9$R$^{10}$, —OCO$_2$R$^8$, —C$_{1-6}$ alkyl-OR$^8$, —C$_{1-6}$ alkyl-NR$^8$R$^9$, and —C$_{1-6}$ alkyl-CO$_2$R$^8$, wherein each 3 to 7 membered cycloalkyl group and each 4 to 7 membered heterocyclic group is optionally substituted with 1 to 5 substituents independently selected from the group consisting of a spiro 3 to 7 membered cycloalkyl group, a spiro 4 to 7 membered heterocyclic group, a 3 to 7 membered cycloalkyl group, a 4 to 7 membered heterocyclic group, —C$_{1-6}$ alkyl, oxo, —CN, —CO$_2$R$^{11}$, —CONR$^{11}$R$^{12}$, —OH, —SH, —O—C$_{1-6}$ alkyl, —S—C$_{1-6}$ alkyl, —NR$^{11}$R$^{12}$, —OC(O)NR$^{11}$R$^{12}$, —NR$^{11}$C(O)—C$_{1-6}$ alkyl, —NR$^{11}$C(O)$_2$R$^{12}$, —NR$^{11}$—C(O)NR$^{12}$R$^{13}$, —OCO$_2$R$^{11}$, —NR$^{11}$—SO$_2$—C$_{1-6}$ alkyl, —C$_{1-6}$ alkyl-OR$^{11}$, —C$_{1-6}$ alkyl-NR$^{11}$R$^{12}$, and —C$_{1-6}$ alkyl-CO$_2$R$^{11}$;

each R$^1$ is independently selected from the group consisting of aryl, a 3 to 7 membered cycloalkyl group, a 4 to 7 membered heterocyclic group, and —C$_{1-6}$ alkyl wherein the —C$_{1-6}$ alkyl is optionally substituted with 1 to 5 substituents independently selected from the group consisting of —NR$^a$R$^b$, —OH, —O—C$_{1-6}$ alkyl, aryl, and heteroaryl, wherein the aryl, 3 to 7 membered cycloalkyl group, 4 to 7 membered heterocyclic group and heteroaryl are each optionally substituted with 1 to 5 substituents independently selected from the group consisting of —NR$^{14}$R$^{15}$, —OH, —C$_{1-6}$ alkyl, —CN, —CO$_2$R$^{14}$, —CONR$^{14}$R$^{15}$, —SO$_2$NR$^{14}$R$^{15}$, —SO$_2$—C$_{1-6}$ alkyl, —SH, —O—C$_{1-6}$ alkyl, —S—C$_{1-6}$ alkyl, —OC(O)NR$^{14}$R$^{15}$, —NR$^{14}$C(O)—C$_{1-6}$ alkyl, —NR$^{14}$C(O)$_2$R$^{15}$, —NR$^{14}$—C(O)NR$^{15}$R$^{16}$, —OCO$_2$R$^{14}$, and —NR$^{14}$SO$_2$—C$_{1-6}$ alkyl;

each R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^a$, R$^b$, R$^c$, R$^d$, R$^y$, and R$^z$ is independently selected from the group consisting of H and C$_{1-6}$ alkyl; and wherein in —CONR$^y$R$^z$, R$^y$ and R$^z$ are optionally joined to form a 4 to 7 membered heterocyclic group optionally substituted with 1 to 5 substituents independently selected from the group consisting of NR$^c$R$^d$, OH, —C$_{1-6}$ alkyl, CN, —CO$_2$R$^{14}$, —CONR$^{14}$R$^{15}$, —SO$_2$NR$^{14}$R$^{15}$, SO$_2$—C$_{1-6}$ alkyl, SH, —O—C$_{1-6}$ alkyl, —S—C$_{1-6}$ alkyl, —OC(O)NR$^{14}$R$^{15}$, —NR$^{14}$C (O)—C$_{1-6}$ alkyl, —NR$^{14}$C(O)$_2$R$^{15}$, —NR$^{14}$—C(O) NR$^{15}$R$^{16}$, —OCO$_2$R$^{14}$, and —NR$^{14}$SO$_2$—C$_{1-6}$ alkyl.

In some embodiments, A is selected from the group consisting of:

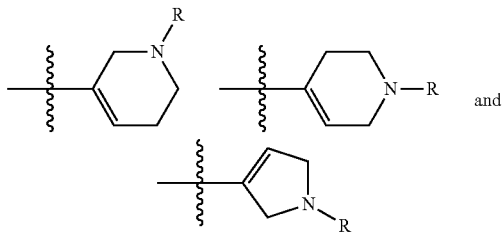

each of which is optionally substituted with 1 to 3 R$^x$ wherein each R$^x$ is independently —C$_{1-3}$ alkyl optionally substituted with —OH, —OC$_{1-3}$ alkyl, —CN, —CO$_2$—C$_{1-3}$ alkyl, and —CONR$^y$R$^z$ wherein R$^y$ and R$^z$ are each independently selected from C$_{1-3}$ alkyl and wherein R$^y$ and R$^z$ are optionally joined to form a 4 to 6 membered heterocyclic group optionally substituted with NR$^c$R$^d$, wherein R$^c$ and R$^d$ are each independently selected from the group consisting of H and C$_{1-3}$ alkyl.

In some embodiments, each R$^x$ is independently selected from the group consisting of Me, —CH$_2$OH, —CH$_2$OMe, —CH$_2$CN, —CH$_2$CONMe$_2$, —CH$_2$CO$_2$Me, —CO$_2$Me, and

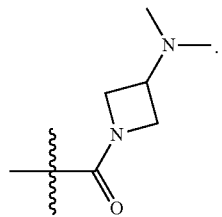

In some embodiments, R is selected from the group consisting of H, —C$_{1-6}$ alkyl, —COR$^1$, —SO$_2$R$^1$, —CO$_2$R$^2$, —CONR$^2$R$^3$, —SO$_2$NR$^2$R$^3$, a 3 to 7 membered cycloalkyl group, and a 4 to 7 membered heterocyclic group,
  wherein the —C$_{1-6}$ alkyl is optionally substituted with 1 to 5 substituents independently selected from the group consisting of —C$_{1-6}$ alkyl, —NR$^2$R$^3$, —CONR$^2$R$^3$, —OH, —SO$_2$NR$^2$R$^3$, —SO$_2$—C$_{1-6}$ alkyl, —O—C$_{1-6}$ alkyl, —S—C$_{1-6}$ alkyl, —NR$^2$C(O)—C$_{1-6}$ alkyl, —NR$^2$SO$_2$—C$_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —C$_{1-6}$ alkyl, and —OH, and wherein the aryl and heteroaryl are optionally substituted with 1 to 5 substituents independently selected from the group consisting of halogen, —CN, —CO$_2$R$^8$, —CONR$^8$R$^9$, OH, SH, C$_{1-6}$ alkyl, —O—C$_{1-6}$ alkyl, —S—C$_{1-6}$ alkyl, —NR$^8$R$^9$, —OC(O)NR$^8$R$^9$, —NR$^8$C(O)—C$_{1-6}$ alkyl, —NR$^8$C(O)$_2$—C$_{1-6}$ alkyl, —NR$^8$—C(O)NR$^9$R$^{10}$, —OCO$_2$R$^8$, —C$_{1-6}$ alkyl-OR$^8$, —C$_{1-6}$ alkyl-NR$^8$R$^9$, and —C$_{1-6}$ alkyl-CO$_2$R$^8$,
  wherein each 3 to 7 membered cycloalkyl group and each 4 to 7 membered heterocyclic group is optionally substituted with 1 to 5 substituents independently selected from the group consisting of —C$_{1-6}$ alkyl, oxo, and —OH;
  each R$^1$ is independently selected from the group consisting of aryl, a 4 to 7 membered heterocyclic group, and —C$_{1-6}$ alkyl wherein the —C$_{1-6}$ alkyl is optionally substituted with 1 to 5 substituents independently selected from the group consisting of —NR$^a$R$^b$, —OH, and aryl; and
  each R$^2$, R$^3$, R$^8$, R$^9$, R$^{10}$, R$^a$, and R$^b$ is independently selected from the group consisting of H and C$_{1-6}$ alkyl.

In some embodiments, R is selected from the group consisting of H, —C$_{1-6}$ alkyl, —COR$^1$, —SO$_2$R$^1$, —CO$_2$R$^2$, —CONR$^2$R$^3$, —SO$_2$NR$^2$R$^3$, a 4 to 6 membered cycloalkyl group, and a 4 to 6 membered heterocyclic group,
  wherein the —C$_{1-6}$ alkyl is optionally substituted with 1 to 5 substituents independently selected from the group consisting of —NR$^2$R$^3$, —CONR$^2$R$^3$, —OH, —SO$_2$NR$^2$R$^3$, —SO$_2$—C$_{1-6}$ alkyl, —O—C$_{1-6}$ alkyl, —S—C$_{1-6}$ alkyl, —NR$^2$C(O)—C$_{1-6}$ alkyl, —NR$^2$SO$_2$—C$_{1-6}$ alkyl, phenyl, a 5 membered heteroaryl, a 4 to 6 membered cycloalkyl group, and a 4 to 6 membered heterocyclic group, wherein the 4 to 6 membered cycloalkyl group and the 4 to 6 membered heterocyclic group are optionally substituted with 1 to 5 substituents independently selected from the group consisting of oxo, and —OH,
  wherein the 4 to 6 membered cycloalkyl group and the 4 to 6 membered heterocyclic group are optionally substituted with 1 to 5 substituents independently selected from the group consisting of —C$_{1-6}$ alkyl, oxo, and —OH;
  each R$^1$ is independently selected from the group consisting of phenyl, a 4 to 6 membered heterocyclic group, and —C$_{1-6}$ alkyl wherein the —C$_{1-6}$ alkyl is optionally substituted with 1 to 5 substituents independently selected from the group consisting of —NR$^a$R$^b$, —OH, and phenyl; and
  each R$^2$, R$^3$, R$^a$, and R$^b$ is independently selected from the group consisting of H and C$_{1-6}$ alkyl.

In some embodiments, Y is H, A is selected from the group consisting of:

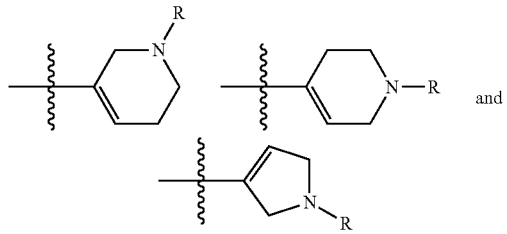

each of which is optionally substituted with 1 to 3 R$^x$ wherein each R$^x$ is independently —C$_{1-3}$ alkyl optionally substituted with —OH, —OC$_{1-3}$ alkyl, —CN, —CO$_2$—C$_{1-3}$ alkyl, and —CONR$^y$R$^z$ wherein R$^y$ and R$^z$ are each independently selected from C$_{1-3}$ alkyl and wherein R$^y$ and R$^z$ are optionally joined to form a 4 to 6 membered heterocyclic group optionally substituted with NR$^c$R$^d$, wherein R$^c$ and R$^d$ are each independently selected from the group consisting of H and C$_{1-3}$ alkyl;
R is selected from the group consisting of H, —C$_{1-6}$ alkyl, —COR$^1$, —SO$_2$R$^1$, —CO$_2$R$^2$, —CONR$^2$R$^3$, —SO$_2$NR$^2$R$^3$, a 3 to 7 membered cycloalkyl group, and a 4 to 7 membered heterocyclic group, wherein the —C$_{1-6}$ alkyl is optionally substituted with 1 to 5 substituents independently selected from the group consisting of —C$_{1-6}$ alkyl, —NR$^2$R$^3$, —CONR$^2$R$^3$, —OH, —SO$_2$NR$^2$R$^3$, —SO$_2$—C$_{1-6}$ alkyl, —O—C$_{1-6}$ alkyl, —S—C$_{1-6}$ alkyl, —NR$^2$C(O)—C$_{1-6}$ alkyl, —NR$^2$SO$_2$—C$_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —C$_{1-6}$ alkyl, and —OH, and wherein the aryl and heteroaryl are optionally substituted with 1 to 5 substituents independently selected from the group consisting of halogen, —CN, —CO$_2$R$^8$, —CONR$^8$R$^9$, OH, SH, C$_{1-6}$ alkyl, —O—C$_{1-6}$alkyl, —S—C$_{1-6}$alkyl, —NR$^8$R$^9$, —OC(O)NR$^8$R$^9$, —NR$^8$C(O)—C$_{1-6}$ alkyl, —NR$^8$C(O)$_2$—C$_{1-6}$ alkyl, —NR$^8$—C(O) NR$^9$R$^{10}$, —OCO$_2$R$^8$, —C$_{1-6}$ alkyl-OR$^8$, —C$_{1-6}$ alkyl-NR$^8$R$^9$, and —C$_{1-6}$ alkyl-CO$_2$R$^8$, wherein the 3 to 7 membered cycloalkyl group and the 4 to 7 membered heterocyclic group are optionally substituted with 1 to 5 substituents independently selected from the group consisting of —C$_{1-6}$ alkyl, oxo, and —OH;

each R$^1$ is independently selected from the group consisting of aryl, a 4 to 7 membered heterocyclic group, and —C$_{1-6}$ alkyl wherein the —C$_{1-6}$ alkyl is optionally substituted with 1 to 5 substituents independently selected from the group consisting of —NR$^a$R$^b$, —OH, and aryl; and each R$^2$, R$^3$, R$^8$, R$^9$, R$^{10}$, R$^a$, and R$^b$ is independently selected from the group consisting of H and C$_{1-6}$ alkyl.

In some embodiments, Y is H, A is selected from the group consisting of:

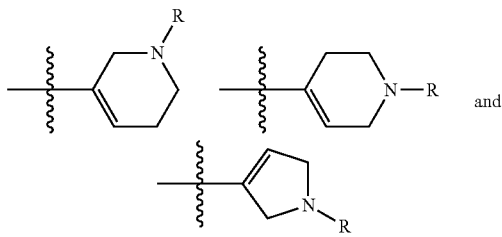

each of which is optionally substituted with 1 to 3 R$^x$ independently selected from the group consisting of Me, —CH$_2$OH, —CH$_2$OMe, —CH$_2$CN, —CH$_2$CONMe$_2$, —CH$_2$CO$_2$Me, CO$_2$Me and

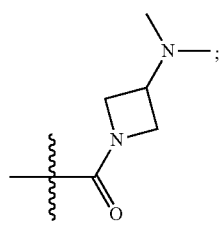 [SMILES: *C(=O)N1CC(N(C)C)C1]

R is selected from the group consisting of H, —C$_{1-6}$ alkyl, —COR$^1$, —SO$_2$R$^1$, —CO$_2$R$^2$, —CONR$^2$R$^3$, —SO$_2$NR$^2$R$^3$, a 4 to 6 membered cycloalkyl group, and a 4 to 6 membered heterocyclic group, wherein the —C$_{1-6}$ alkyl is optionally substituted with 1 to 5 substituents independently selected from the group consisting of —NR$^2$R$^3$, —CONR$^2$R$^3$, —OH, —SO$_2$NR$^2$R$^3$, —SO$_2$—C$_{1-6}$alkyl, —O—C$_{1-6}$ alkyl, —S—C$_{1-6}$ alkyl, —NR$^2$C(O)—C$_{1-6}$ alkyl, —NR$^2$SO$_2$—C$_{1-6}$ alkyl, phenyl, a 5 membered heteroaryl, a 4 to 6 membered cycloalkyl group, and a 4 to 6 membered heterocyclic group, wherein the 4 to 6 membered cycloalkyl group and the 4 to 6 membered heterocyclic group are optionally substituted with 1 to 5 substituents independently selected from the group consisting of oxo, and —OH, wherein the 4 to 6 membered cycloalkyl group and the 4 to 6 membered heterocyclic group are optionally substituted with 1 to 5 substituents independently selected from the group consisting of —C$_{1-6}$ alkyl, oxo, and —OH;

each R$^1$ is independently selected from the group consisting of phenyl, a 4 to 6 membered heterocyclic group, and —C$_{1-6}$ alkyl wherein the —C$_{1-6}$ alkyl is optionally substituted with 1 to 5 substituents independently selected from the group consisting of —NR$^a$R$^b$, —OH, and phenyl; and each R$^2$, R$^3$, R$^a$, and R$^b$ is independently selected from the group consisting of H and C$_{1-6}$ alkyl.

In some embodiments, X is H. In some embodiments, X is F.

In some embodiments, Y is H. In some embodiments, Y is F.

Also provided herein is a compound of formula 1:

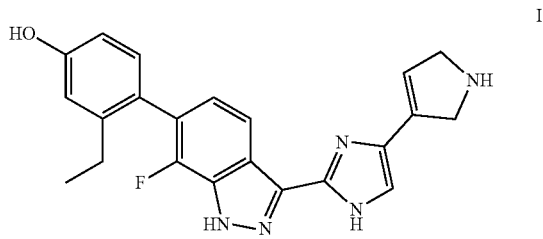 [SMILES: CCc1cc(O)ccc1-c1ccc2c(-c3nc(C4=CCNC4)c[nH]3)n[nH]c2c1F]

or a pharmaceutically-acceptable salt thereof.

Also provided herein is a compound of formula 2:

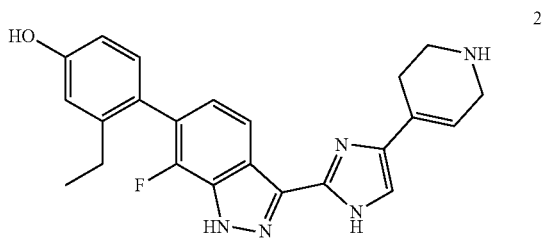 [SMILES: CCc1cc(O)ccc1-c1ccc2c(-c3nc(C4=CCNCC4)c[nH]3)n[nH]c2c1F]

or a pharmaceutically-acceptable salt thereof.

Also provided herein is a compound of formula 3:

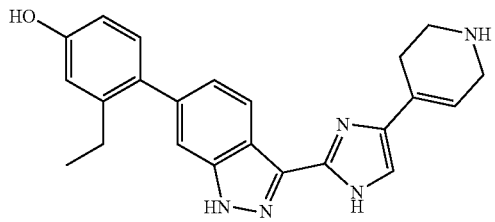

or a pharmaceutically-acceptable salt thereof.

In some embodiments, the compound of formula I is selected from a compound having the chemical structure of any one of Examples 1 to 393, or a pharmaceutically acceptable salt thereof. In some embodiments, the compound of formula I is a compound having a chemical structure of any one of compounds in Table 4 of the Examples section, or a pharmaceutically acceptable salt thereof.

Chemical structures are named herein according to IUPAC conventions as implemented in ChemDraw software (PerkinElmer, Inc., Cambridge, MA).

Furthermore, the imidazole portion of the compounds of the present disclosure exists in tautomeric forms. It will be understood that although structures are shown, or named, in a particular form, the invention and present disclosure also include the tautomer thereof.

The compounds of the present disclosure may contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

The compounds of the present disclosure may also contain several basic groups (e.g., amino groups) and therefore, such compounds can exist as the free base or in various salt forms, such a mono-protonated salt form, a di-protonated salt form, a tri-protonated salt form, etc or mixtures thereof. All such forms are included within the scope of this invention and disclosure, unless otherwise indicated.

This invention and disclosure also include isotopically-labeled compounds of formula (I) or formula (II), i.e., compounds of formula (I) or formula (II) where one or more atom has been replaced or enriched with an atom having the same atomic number but an atomic mass different from the atomic mass that predominates in nature. Examples of isotopes that may be incorporated into a compound of formula (I) include, but are not limited to, $^{2}H$, $^{3}H$, $^{11}C$, $^{13}C$, $^{14}C$, $^{13}N$, $^{15}N$, $^{15}O$, $^{17}O$, and $^{18}O$. Of particular interest are compounds of formula (I) or formula (II) enriched in tritium or carbon-14, which compounds can be used, for example, in tissue distribution studies. Also of particular interest are compounds of formula (I) or formula (II) enriched in deuterium especially at a site of metabolism, which compounds are expected to have greater metabolic stability. Additionally, of particular interest, are compounds of formula (I) or formula (II) enriched in a positron emitting isotope, such as $^{11}C$, $^{15}O$ and $^{13}N$, which compounds can be used, for example, in Positron Emission Tomography (PET) studies.

Definitions

When describing this invention and disclosure including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "aryl" means an aromatic hydrocarbon group having a single ring (i.e., phenyl) or fused rings (i.e., naphthalene). Unless otherwise defined, such aryl groups typically contain from 6 to 10 carbon ring atoms. Representative aryl groups include, by way of example, phenyl (i.e., a benzene ring), naphthyl (i.e., a naphthalene ring), and the like. As used herein, the term aryl includes monovalent, divalent or multivalent aryl groups.

The term "cycloalkyl" means a monovalent saturated or partially unsaturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl (cBu), cyclopentyl, cyclohexyl, cycloheptyl, cyclooctyl, adamantyl, and the like.

The term "halo" or "halogen" means fluoro, chloro, bromo or iodo.

The term "heteroaryl" means an aromatic group having a single ring or two fused rings and containing in a ring at least one heteroatom (typically 1 to 3 heteroatoms) selected from nitrogen, oxygen or sulfur (i.e., a heteroaromatic group). Unless otherwise defined, such heteroaryl groups typically contain from 1 to 9 carbon atoms and from 3 to 10 total ring atoms. Representative heteroaryl groups include, by way of example, mono-, di- or multivalent species of benzimidazole, benzofuran, benzothiazole, benzothiophene, furan, imidazole, indole, isoquinoline, isothiazole, isoxazole, oxazole, pyrazine, pyrazole, pyridazine, pyridine, pyrimidine, pyrrole, quinazoline, quinoline, quinoxaline, tetrazole, thiazole, thiophene, triazole, triazine and the like, where the point or points of attachment are at any available carbon or nitrogen ring atom. As used herein, the term heteroaryl includes monovalent, divalent or multivalent heteroaryl groups.

The term "heterocyclyl", "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclyl groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbomanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "therapeutically effective amount" means an amount sufficient to effect treatment when administered to a patient in need of treatment.

The term "treating" or "treatment" means ameliorating or suppressing the medical condition, disease or disorder being treated (e.g., a respiratory disease) in a patient (particularly a human); or alleviating the symptoms of the medical condition, disease or disorder.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

General Synthetic Procedures

Compounds of the present disclosure, and intermediates thereof, can be prepared according to the following general methods and procedures using commercially-available or routinely-prepared starting materials and reagents. The substituents and variables (e.g., X, Y, A, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present disclosure may be shown or described in the following procedures, those skilled in the art will recognize that other embodiments or aspects of the present disclosure can also be prepared using such procedures or by using other methods, reagents, and starting materials known to those skilled in the art. In particular, it will be appreciated that compounds of the present disclosure may be prepared by a variety of process routes in which reactants are combined in different orders to provide different intermediates en route to producing final products.

General methods for preparing final compounds of the present disclosure are illustrated in the following schemes.

Compounds I-17, I-27, I-54 can be prepared as shown in the Example section. The 7-des-fluoro analog of I-54 can be prepared using similar chemistry with the appropriate reagents and starting materials.

Suzuki Coupling

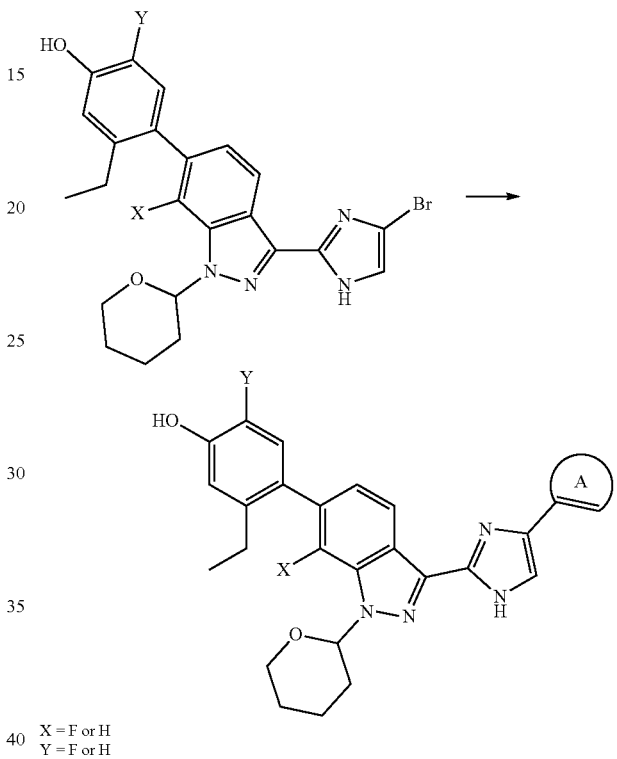

X = F or H
Y = F or H

The starting material (I-17, I-27, I-54, or its 7-des-fluoro analog) (1 equivalent) can be reacted with a boronic acid or ester of A (1-5 equivalents) by dissolving them in a solvent, such as 1,4-dioxane to achieve a concentration of 0.05 to 1 mmol, or about 0.15 mmol of the starting material. A base such as sodium carbonate is dissolved in a solvent such as water (volume equal to between $\frac{1}{10}$ and 2 volumes of 1,4-dioxane used or about $\frac{1}{3}$ the volume of 1,4-dioxane used), and the resulting solution is added to the above solvent solution, for example 1,4-dioxane. The reaction flask is then purged with nitrogen, and a palladium catalyst such as methanesulfonato(2-dicyclohexylphosphino-2',4',6'-tri-i-propyl-1,1'-biphenyl)(2'-methylamino-1,1'-biphenyl-2-yl) palladium(II) (between 0.01 and 0.2 equivalents, or about 0.05 equivalents) is added, and the reaction mixture is stirred and heated at between 8° and 130° C., or at about 110° C. until the reaction is complete, or between 2 to 24 hours, or between 8 and 24 hours. The reaction mixture is then worked up, for example by partitioning between dichloromethane and a saturated sodium bicarbonate solution, and the solvent layer (e.g. dichloromethane) is collected, dried (for example by using sodium sulfate), then concentrated (for example by rotary evaporation). The resulting crude product is then purified, for example by silica gel chromatography (0-10% methanol/dichloromethane gradient).

Deprotection

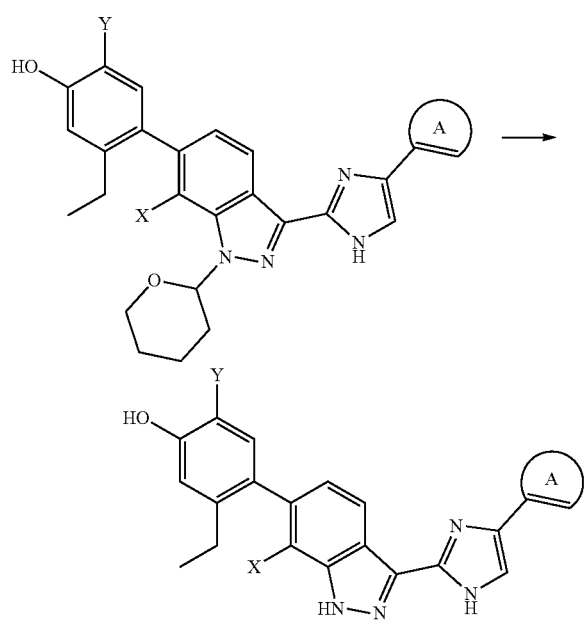

Method A

The product of the Suzuki reaction described above can be dissolved in a sufficient volume of solvent such as methanol to achieve a solution concentration of 0.05-1 mmol, or 0.1-0.2 mmol, then concentrated HCl equal to about ½ the volume of solvent used (for example methanol) is added and the reaction mixture is stirred and heated at between 35 and 65° C., or about 50° C. until complete, or between 1 and 24 hours, or between 4 and 24 hours. The products can be obtained using standard isolation techniques including the methods described below. For small scale reactions (solution volume <5 mL) the reaction mixtures are then partially concentrated to remove the bulk of the solvent (for example methanol) and the resulting solutions are diluted with a solvent/water mixture, for example acetonitrile/water mixtures and purified, for example by reverse phase chromatography (for example with 5-70% acetonitrile/water gradient with 0.05% TFA). For larger scale reactions the reaction mixture is dripped into a solution of aqueous ammonia (for example in concentrated ammonia solution diluted 1:5 in water) to precipitate out the product, which is then collected by filtration. The resulting solid is then purified by reverse phase chromatography (5-70% acetonitrile/water gradient with 0.05% TFA).

Method B

The product of the Suzuki reaction can be dissolved in a mixture of 4 M HCl in 1,4-dioxane (30-40 equivalents) and water (about 5-50% or 20% of the volume of the HCl/dioxane solution), then the reaction mixture is stirred and heated at 40-80° C. or 60° C. until complete or for 1-48 hours or for 8-48 hours). The reaction mixture is then frozen and lyophilized, and the resulting solid purified, for example by reverse phase chromatography (for example with 0-70% acetonitrile/water gradient with 0.05% TFA).

Method C

The product of the Suzuki reaction is dissolved in TFA (30-50 equivalents) and the reaction mixture is stirred at room temperature until complete, or for 1-24 hours. The reaction mixture is then concentrated by rotary evaporation and the crude product purified, for example by preparative HPLC (for example with 5-70% acetontrile/water gradient with 0.05% TFA).

Ring A may be further substituted using conventional chemistry as illustrated in the Examples section.

Pharmaceutical Compositions

The compounds of the invention and present disclosure and pharmaceutically-acceptable salts thereof are typically used in the form of a pharmaceutical composition or formulation. Such pharmaceutical compositions may advantageously be administered to a patient by inhalation. In addition, pharmaceutical compositions may be administered by any acceptable route of administration including, but not limited to, oral, rectal, nasal, topical (including transdermal) and parenteral modes of administration.

Accordingly, in one of its compositions aspects, the invention is directed to a pharmaceutical composition comprising a pharmaceutically-acceptable carrier or excipient and a compound of formula (I) or formula (II) where, as defined above, "compound of formula (I)" means a compound of formula (I) or a pharmaceutically-acceptable salt thereof; and "compound of formula (II)" means a compound of formula (II) or a pharmaceutically-acceptable salt thereof. Optionally, such pharmaceutical compositions may contain other therapeutic and/or formulating agents if desired. In some embodiments, such pharmaceutical compositions further comprise one or more other therapeutic agents. In some embodiments, the one or more other therapeutic agents are useful for treating a respiratory disease in a mammal (e.g. a human).

When discussing compositions and uses thereof, the "compound of the invention" or "compound of the present disclosure" may also be referred to herein as the "active agent". As used herein, the term "compound of the invention" or "compound of the present disclosure" is intended to include all compounds encompassed by formula (I) or formula (II) as well as the species embodied in formula (I) or formula (II), and pharmaceutically-acceptable salts thereof.

The pharmaceutical compositions of the present disclosure typically contain a therapeutically effective amount of a compound of the present disclosure. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.01 to about 95% by weight of the active agent; including, for example, from about 0.05 to about 30% by weight; and from about 0.1% to about 10% by weight of the active agent. In some embodiments, pharmaceutical compositions contain from 0.1 mg to 100 mg of the active agent; including, for example, from 1 mg to 20 mg of the active agent including, for example, from 1 mg to 10 mg of the active agent.

Any conventional carrier or excipient may be used in the pharmaceutical compositions of the present disclosure. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of the present disclosure are commercially-available. By way of further illustration, conventional formulation techniques are described in Remington: The Science and Practice of Pharmacy, 20th Edition, Lippincott Williams & White, Baltimore, Maryland (2000); and H. C. Ansel et al., Pharmaceutical Dosage Forms and Drug Delivery Systems, 7th Edition, Lippincott Williams & White, Baltimore, Maryland (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

In some embodiments, the pharmaceutical composition is suitable for inhaled administration. Pharmaceutical compositions for inhaled administration are typically in the form of an aerosol or a powder. Such compositions are generally administered using inhaler delivery devices, such as a dry powder inhaler (DPI), a metered-dose inhaler (MDI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a composition suitable for inhalation.

A representative pharmaceutical composition for use in a dry powder inhaler comprises lactose and a compound of the present disclosure in micronized form. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Ellipta (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

In another particular embodiment, the pharmaceutical composition is administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is hydrofluoroalkanes. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a compound of the present disclosure; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In some embodiments, the pharmaceutical composition is administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized or nanomilled and combined with a suitable carrier to form a suspension.

A representative pharmaceutical composition for use in a nebulizer inhaler comprises a solution or suspension comprising from about 0.05 μg/mL to about 20 mg/mL of a compound of the present disclosure and excipients compatible with nebulized formulations. In one embodiment, the solution has a pH of about 3 to about 8.

Nebulizer devices suitable for administering therapeutic agents by inhalation are described in the art and examples of such devices are commercially available. For example, representative nebulizer devices or products include the Respimat Softmist Inhalaler (Boehringer Ingelheim); the AERx Pulmonary Delivery System (Aradigm Corp.); the PARI LC Plus Reusable Nebulizer (Pari GmbH); and the like.

In yet another aspect, the pharmaceutical compositions of the present disclosure may alternatively be prepared in a dosage form intended for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form, the pharmaceutical compositions of the present disclosure will typically comprise the active agent and one or more pharmaceutically-acceptable carriers, such as sodium citrate or dicalcium phosphate. Optionally or alternatively, such solid dosage forms may also comprise: fillers or extenders, binders, humectants, solution retarding agents, absorption accelerators, wetting agents, absorbents, lubricants, coloring agents, and buffering agents. Release agents, wetting agents, coating agents, sweetening, flavoring and perfuming agents, preservatives and antioxidants can also be present in the pharmaceutical compositions of the present disclosure.

Alternative formulations may also include controlled release formulations, liquid dosage forms for oral administration, transdermal patches, and parenteral formulations. Conventional excipients and methods of preparation of such alternative formulations are described, for example, in the reference by Remington, supra.

The following non-limiting examples illustrate representative pharmaceutical compositions of the present disclosure.

Dry Powder Composition

A micronized compound of formula (I) or formula (II) (1 g) is blended with milled lactose (25 g). This blended mixture is then loaded into individual blisters of a peelable blister pack in an amount sufficient to provide between about 0.1 mg to about 4 mg of the compound of formula (I) or formula (II) per dose. The contents of the blisters are administered using a dry powder inhaler.

Dry Powder Composition

A micronized compound of formula (I) or formula (II) (1 g) is blended with milled lactose (20 g) to form a bulk composition having a weight ratio of compound to milled lactose of 1:20. The blended composition is packed into a dry powder inhalation device capable of delivering between about 0.1 mg to about 4 mg of the compound of formula (I) or formula (II) per dose.

Metered-Dose Inhaler Composition

A micronized compound of formula (I) or formula (II) (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 m. The micronized composition is then loaded into metered-dose inhaler cartridges containing pressurized 1,1,1,2-tetrafluoroethane in an amount sufficient to provide about 0.1 mg to about 4 mg of the compound of formula (I) or formula (II) per dose when administered by the metered dose inhaler.

Nebulizer Composition

A compound of formula (I) or formula (II) (25 mg) is dissolved in a solution containing 1.5-2.5 equivalents of hydrochloric acid, followed by addition of sodium hydroxide to adjust the pH to 3.5 to 5.5 and 3% by weight of glycerol. The solution is stirred well until all the components are dissolved. The solution is administered using a nebulizer device that provides about 0.1 mg to about 4 mg of the compound of formula (I) or formula (II) per dose.

Utility

The compounds of the present dislcosure are Janus kinase (JAK) inhibitors. The JAK inhibitors of the present disclosure have been designed for the treatment of inflammatory and fibrotic diseases, including inflammatory and fibrotic diseases of the respiratory tract. In particular, the compounds have been designed to enable delivery of a potent anti-cytokine agent directly to the site of action of respiratory disease in the lung while limiting systemic exposure.

As shown in Assays 1-2 and Table 1, the compounds of the present disclosure have been shown to be potent inhibitors of the JAK family of enzymes: JAK1, JAK2, JAK3, and TYK2.

It has been recognized that the broad anti-inflammatory effect of JAK inhibitors could suppress normal immune cell function, potentially leading to increased risk of infection. The present compounds have therefore been optimized to limit absorption from the lung into the plasma, thus minimizing the risk of immunosuppression. As described in the experimental section below, the absorption and distribution of select compounds have been profiled in preclinical assays. Several compounds were tested in mice, in Assay 4, and showed post-dosing high concentration in lung tissue and low absorption into plasma.

Compounds 1-3 have been shown to inhibit an effect of the pro-inflammatory cytokine IL-13 in mouse lung tissue. Specifically, the compounds have demonstrated inhibition of IL-13-induced phosphorylation of STAT6 in lung tissue which provides evidence of local lung JAK target engagement in vivo. This effect has been observed when the pro-inflammatory cytokine IL-13 is administered 8 hours after administration of the test compound, providing further evidence of significant retention in the lung.

The anti-inflammatory activity of JAK inhibitors has been robustly demonstrated in preclinical models of asthma (Malaviya et al., *Int. Immunopharmacol.,* 2010, 10, 829,-836; Matsunaga et al., *Biochem. and Biophys. Res. Commun.,* 2011, 404, 261-267; Kudlacz et al., *Eur. J. Pharmacol,* 2008, 582, 154-161). Cytokines implicated in asthma inflammation which signal through the JAK-STAT pathway include IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF). Accordingly, the compounds of the present disclosure are expected to be useful for the treatment of inflammatory respiratory disorders, in particular, asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, and sarcoidosis. The present compounds, therefore, are also expected to be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema, bronchiolitis obliterans, and sarcoidosis. Further, Asthma endotypes may be broadly regarded as type 2 (T2) high or T2-low (Kuruvilla et al, Clin Rev Allergy Immunol, 2019, 56(2), 219-233). Based on their mechanism of action, the compounds of the disclosure have the potential to treat both endotypes, T2-high and T2-low.

The compounds of the present disclosure possess biological activity involved in the inhibition of cytokines associated with inflammation. Therefore, the compounds of the present disclosure are expected to be useful for the treatment of certain specific respiratory diseases, as detailed below.

Eosinophilic airway inflammation is a characteristic feature of diseases collectively termed eosinophilic lung diseases (Cottin et al., Clin. Chest. Med., 2016, 37(3), 535-56). Eosinophilic diseases have been associated with IL-4, IL-13 and IL-5 signaling. Eosinophilic lung diseases include infections (especially helminthic infections), drug-induced pneumonitis (induced for example by therapeutic drugs such as antibiotics, phenytoin, or 1-tryptophan), fungal-induced pneumonitis (e.g. allergic bronchopulmonary aspergillosis), hypersensitivity pneumonitis and eosinophilic granulomatosis with polyangiitis (formerly known as Churg-Strauss syndrome). Eosinophilic lung diseases of unknown etiology include idiopathic acute eosinophilic pneumoni, idiopathic chronic eosinophilic pneumonia, hypereosinophilic syndrome, and Löffler syndrome.

A polymorphism in the IL-6 gene has been associated with elevated IL-6 levels and an increased risk of developing pulmonary arterial hypertension (PAH) (Fang et al., J. Am. Soc. Hypertens., 2017, 11(3), 171-177). Corroborating the role of IL-6 in PAH, inhibition of the IL-6 receptor chain gp130 ameliorated the disease in a rat model of PAH (Huang et al., Can. J. Cardiol., 2016, 32(11), 1356.e1-1356.e10).

Cytokines such as IFNγ, IL-12 and IL-6 have been implicated in a range of non-allergic lung diseases such as sarcoidosis, and lymphangioleiomyomatosis (El-Hashemite et al., Am. J. Respir. Cell. Mol. Biol., 2005, 33, 227-230, and El-Hashemite et al., Cancer Res., 2004, 64, 3436-3443).

Bronchiectasis and infiltrative pulmonary diseases are diseases associated with chronic neutrophilic inflammation.

Pathological T cell activation is critical in the etiology of multiple respiratory diseases. Autoreactive T cells play a role in bronchiolitis obliterans organizing pneumonia (also termed COS). Similar to COS the etiology of lung transplant rejections is linked to an aberrant T cell activation of the recipients T cells by the transplanted donor lung. Lung transplant rejections may occur early as Primary Graft Dysfunction (PGD), organizing pneumonia (OP), acute rejection (AR) or lymphocytic bronchiolitis (LB) or they may occur years after lung transplantation as Chronic Lung Allograft Dysfunction (CLAD). CLAD was previously known as bronchiolitis obliterans (BO) but now is considered a syndrome that can have different pathological manifestations including BO, restrictive CLAD (rCLAD or RAS) and neutrophilic allograft dysfunction. Chronic lung allograft dysfunction (CLAD) is a major challenge in long-term management of lung transplant recipients as it causes a transplanted lung to progressively lose functionality (Gauthier et al., Curr Transplant Rep., 2016, 3(3), 185-191). CLAD is poorly responsive to treatment and therefore, there remains a need for effective compounds capable of preventing or treating this condition. Several JAK-dependent cytokines such as IFNγ and IL-5 are up-regulated in CLAD and lung transplant rejection (Berastegui et al, Clin. Transplant. 2017, 31, e12898). Moreover, high lung levels of CXCR3 chemokines such as CXCL9 and CXCL10 which are downstream of JAK-dependent IFN signaling, are linked to worse outcomes in lung transplant patients (Shino et al, PLOS One, 2017, 12 (7), e0180281). Systemic JAK inhibition has been shown to be effective in kidney transplant rejection (Vicenti et al., American Journal of Transplantation, 2012, 12, 2446-56). Therefore, JAK inhibitors have the potential to be effective in treating or preventing lung transplant rejection and CLAD. Similar T cell activation events as described as the basis for lung transplant rejection also are considered the main driver of lung graft-versus-host disease (GVHD) which can occur post hematopoietic stem cell transplants. Similar to CLAD, lung GVHD is a chronic progressive condition with extremely poor outcomes and no treatments are currently approved. A retrospective, multicenter survey study of 95 patients with steroid-refractory acute or chronic GVHD who received the systemic JAK inhibitor ruxolitinib as salvage therapy demonstrated complete or partial response to ruxolitinib in the majority of patients including those with lung GVHD (Zeiser et al, Leukemia, 2015, 29, 10, 2062-68). As systemic JAK inhibition is associated with serious adverse events and a small therapeutic index, the need remains for an inhaled lung-directed, non-systemic JAK inhibitor to prevent and/or treat lung transplant rejection or lung GVHD. The compounds of the present disclosure have the characteristics required to meet this need.

Therefore, provided herein is a method of treating or preventing lung transplant rejection in a human in need thereof comprising administering to the human a compound of formula (I) or formula (II), or a pharmaceutically-acceptable salt thereof. In some embodiments, the lung transplant rejection is selected from the group consisting of primary graft dysfunction, organizing pneumonia, acute rejection, lymphocytic bronchiolitis, and chronic lung allograft dysfunction. In some embodiments, the lung transplant rejection is acute lung transplant rejection. In some embodiments, the lung transplant rejection is chronic lung allograft dysfunction. In some embodiments, the lung transplant rejection is selected from the group consisting of bronchiolitis obliterans, restrictive chronic lung allograft dysfunction, and neutrophilic allograft dysfunction.

More recently, immune-checkpoint inhibitor induced pneumonitis, another T cell mediated lung disease emerged with the increased use of immune-checkpoint inhibitors. In cancer patients treated with these T cell stimulating agents, fatal pneumonitis can develop. The compounds of the disclosure possess biological activity allowing inhibition of IFNγ secretion.

In one embodiment, therefore, the present disclosure provides a method of treating a respiratory disease in a mammal (e.g., a human), the method comprising administering to the mammal (or human) a compound of the present disclosure, or a pharmaceutically acceptable salt thereof, or of a pharmaceutical composition comprising a pharmaceutically-acceptable carrier and a compound of the present disclosure, or a pharmaceutically acceptable salt thereof.

In some embodiments, the respiratory disease is asthma, chronic obstructive pulmonary disease (COPD), cystic fibrosis, pneumonitis, cystic fibrosis (CF), pneumonitis, interstitial lung diseases (including idiopathic pulmonary fibrosis), acute lung injury, acute respiratory distress syndrome, bronchitis, emphysema, bronchiolitis obliterans, or sarcoidosis. In some embodiments, the respiratory disease is asthma or chronic obstructive pulmonary disease. In some embodiments, the Asthma is T2-high Asthma. In some embodiments, the Asthma is T2-low Asthma.

In some embodiments, the respiratory disease is a lung infection, an eosinophilic disease, a helminthic infection, pulmonary arterial hypertension, lymphangioleiomyomatosis, bronchiectasis, an infiltrative pulmonary disease, drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Löffler syndrome, bronchiolitis obliterans organizing pneumonia, acute and chronic lung transplant rejections (including PGD, OP, LB, AR and CLAD, BO, restrictive CLAD and neutrophilic allograft dysfunction), lung graft-versus-host disease, or immune-checkpoint-inhibitor induced pneumonitis.

The present disclosure further provides a method of treating asthma in a mammal (e.g. a human), the method comprising administering to the mammal (or human) a compound of the present disclosure, or a pharmaceutically acceptable salt thereof, or of a pharmaceutical composition comprising a pharmaceutically-acceptable carrier and a compound of the present disclosure, or a pharmaceutically acceptable salt thereof.

When used to treat asthma, the compounds of the present disclosure will typically be administered in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

The present disclosure further provides a method of treating a respiratory disease (including but not limited to the disease described herein) in a mammal (e.g. a human), the method comprising administering to the mammal (or human), a compound of the present disclosure, or a pharmaceutically acceptable salt thereof, or of a pharmaceutical composition comprising a pharmaceutically-acceptable carrier and a compound of the present disclosure, or a pharmaceutically acceptable salt thereof.

When used to treat a respiratory disease (including but not limited to the disease described herein), the compounds of the present disclosure will typically be administered in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Human coronavirus is a common respiratory pathogen and typically induces mild upper respiratory disease. The two highly pathogenic viruses, Severe Acute Respiratory Syndrome associated-Coronavirus (SARS-CoV-1) and Middle East Respiratory Syndrome-associated Coronavirus (MERS-CoV), caused severe respiratory syndromes resulting in more than 10% and 35% mortality, respectively (Assiri et al., *N Engl J Med.,* 2013, 369, 407-1). The recent emergence of Coronavirus Disease 2019 (COVID-19 and subsequent pandemic has created a global health care emergency. Similar to SARS-CoV-1 and MERS-CoV, a subset of patients (about 16%) can develop a severe respiratory illness manifested by acute lung injury (ALI) leading to ICU admission (about 5%), respiratory failure (about 6.1%) and death (Wang et al., *JAMA,* 2020, 323, 11, 1061-1069; Guan et al., *N Engl J Med.,* 2020, 382, 1708-1720; Huang et al., *The Lancet,* 2020. 395 (10223), 497-506; Chen et al., *The Lancet,* 2020, 395(10223), 507-13). A subgroup of patients with COVID-19 appears to have a hyperinflammatory "cytokine storm" resulting in acute lung injury and acute respiratory distress syndrome (ARDS). This cytokine storm may also spill over into the systemic circulation and produce sepsis and ultimately, multi-organ dysfunction syndrome. The dysregulated cytokine signaling that appears in COVID-19 is characterized by increased expression of interferons (IFNs), interleukins (ILs), and chemokines, resulting in ALI and associated mortality. This hyperinflammatory response can potentially be modulated and treated by a lung-selective pan-Janus Kinase (JAK) inhibitor. Monoclonal antibodies directed against IL-6 (tocilizumab) appear to be effective in treating patients with ALI from COVID-19 (Xu X, Han M, Li T, Sun W, Wang D, Fu B, et al. Effective Treatment of Severe COVID-19 Patients with Tocilizumab, 2020, *PNAS.* Infection with mouse adapted strains of the 2003 SARS-CoV-1 and 2012 MERS-CoV, as well as a transgenic mouse expressing the human SARS-CoV-1 receptor hACE2 infected with human SARS-CoV-1, demonstrate elevations of JAK-dependent cytokines, such as IFNγ, IL-6, and IL-12, and downstream chemokines, such as chemokine (C—C motif) ligand 10 (CCL10), CCL2, and CCL7 (McCray et al., *J Virol.,* 2007, 81(2), 813-21; Gretebeck et al., *Curr Opin Virol.* 2015, 13, 123-9; Day et al., *Virology.* 2009, 395(2), 210-22. JAK inhibitors have also been shown to be beneficial in mouse models of lipopolysaccharide-or ganciclovir-induced ALI (Severgnini et al., *Am J Respir Crit Care Med.,* 2005, 171(8), 858-67; Jin et al., *Am J Physiol-Lung Cell Mol Physiol.,* 2018, 314(5), L882-92). Finally, based on the results of clinical trials, baricitinib, a JAK inhibitor, has received an emergency use authorization (EUA) in combination with remdesivir, for the treatment of COVID-19 in patients requiring supplemental oxygen, invasive mechanical ventilation, or extracorporeal membrane oxygenation. In a clinical trial of hospitalized patients with COVID-19, baricitinib, in combination with remdesivir, was shown to reduce time to recovery within 29 days after initiating treatment compared to patients who received a placebo with remdesivir.

Therefore, compounds of formula (I) or formula (II), which are lung-selective inhaled pan-JAK inhibitors, could be uniquely suited to dampen the cytokine storm associated with COVID-19. By delivering to the lung and avoiding systemic immunosuppression, additional infections that lead to worsened mortality may also be avoided. This is particularly true in those patients requiring ventilatory support. As major causes of death in subjects with COVID-19 appear to be comorbidities and superinfection, an inhaled medication may be a way to avoid systemic immunosuppression that would pre-dispose patients to these risks.

Therefore, the present disclosure provides a method of treating a mammal (or patient) infected with a coronavirus such as SARS-CoV-1, SARS-CoV-2, and MERS-CoV, or the symptoms thereof, the method comprising administering to the mammal (or patient) a compound of the present disclosure, or a pharmaceutically acceptable salt thereof, or of a pharmaceutical composition comprising a pharmaceutically-acceptable carrier and a compound of the present disclosure, or a pharmaceutically acceptable salt thereof. The present disclosure also provides a method of treating ALI and/or ARDS in a mammal (or a patient) caused by a coronavirus infection (such as SARS-CoV-1, SARS-CoV-2, and MERS-CoV), the method comprising administering to the mammal (or patient) a compound of the present disclosure, or a pharmaceutically acceptable salt thereof, or of a pharmaceutical composition comprising a pharmaceutically-acceptable carrier and a compound of the present disclosure, or a pharmaceutically acceptable salt thereof.

The mechanism of action of JAK inhibitors has been linked to the treatment of nasal inflammatory diseases (Therapeutic Effects of Intranasal Tofacitinib on Chronic Rhinosinusitis with Nasal Polyps in Mice, Joo et al., The Laryngoscope, 2020. Further, Dupilumab, which acts by blocking the IL-4 and IL-13 signaling pathways, has been approved for the treatment of chronic rhinosinusitis with nasal polyps. Nasal Polyps in Mice, Joo et al., *The Laiyngoscope,* 2020, https://doi.org/10.1002/lary.29129). Further, Dupilumab, which acts by blocking the IL-4 and IL-13 signaling pathways, has been approved for the treatment of chronic rhinosinusitis with nasal polyps.

Therefore, also provided herein is a method of treating nasal inflammatory diseases in a mammal (e.g. a human), the method comprising administering to the mammal (or human) a compound of the present disclosure, or a pharmaceutically acceptable salt thereof, or of a pharmaceutical composition comprising a pharmaceutically-acceptable carrier and a compound of the present disclosure, or a pharmaceutically acceptable salt thereof. In some embodiments, the nasal inflammatory disease is selected from the group consisting of chronic rhinosinusitis with or without nasal polyps, nasal polyposis, sinusitis with nasal polyps, and rhinitis (non-allergic, allergic, perenial, and vasomotor rhinitis).

As JAK inhibitors, the compounds of the present disclosure may also be useful for a variety of other diseases. The compounds of the present disclosure may be useful for a variety of gastrointestinal inflammatory indications that include, but are not limited to, inflammatory bowel disease, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J. Clin. Immunology,* 1996, 16, 144-150), Crohn's disease (Woywodt et al., *Eur. J. Gastroenterology Hepatology,* 1999, 11, 267-276), collagenous colitis (Kumawat et al., *Mol. Immunology,* 2013, 55, 355-364), lymphocytic colitis (Kumawat et al., 2013), eosinophilic esophagitis (Weinbrand-Goichberg et al., *Immunol. Res.,* 2013, 56, 249-260), graft versus host disease-related colitis (Coghill et al., *Blood,* 2001, 117, 3268-3276), infectious colitis (Stallmach et al., *Int. J. Colorectal Dis.,* 2004, 19, 308-315), Behcet's disease (Zhou et al., *Autoimmun. Rev.,* 2012, 11, 699-704), celiac disease (de Nitto et al., *World J. Gastroenterol.,* 2009, 15, 4609-4614), immune checkpoint inhibitor induced colitis (e.g., CTLA-4 inhibitor-induced colitis; (Yano et al., *J. Translation. Med.,* 2014, 12, 191), PD-1- or PD-L1-inhibitor-induced colitis), and ileitis (Yamamoto et al., *Dig. Liver Dis.,* 2008, 40, 253-259) are characterized by elevation of certain pro-inflammatory cytokine levels. As many pro-inflammatory cytokines signal via JAK activation, compounds described in this application may be able to alleviate the inflammation and provide symptom relief. In particular, the compounds of the present disclosure may be useful for the induction and maintenance of remission of ulcerative colitis, and for the treatment of Crohn's disease, immune checkpoint inhibitor induced colitis, and the gastrointestinal adverse effects in graft versus host disease. In one embodiment, therefore, the present disclosure provides a method of treating a gastrointestinal inflammatory disease in a mammal (e.g., a human), the method comprising administering to the mammal a compound of the present disclosure, or a pharmaceutically acceptable salt thereof, or a pharmaceutical composition comprising a pharmaceutically-acceptable carrier and a compound of the present disclosure, or a pharmaceutically acceptable salt thereof.

Atopic dermatitis and other inflammatory skin diseases have been associated with elevation of proinflammatory cytokines that rely on the JAK-STAT pathway. Therefore, the compounds of the present disclosure, or a pharmaceutically acceptable salt thereof, may be beneficial in a number of dermal inflammatory or pruritic conditions that include, but are not limited to atopic dermatitis, alopecia areata, vitiligo, psoriasis, dermatomyositis, cutaneous T cell lymphoma (Netchiporouk et al., *Cell Cycle* 2014; 13, 3331-3335) and subtypes (Sezary syndrome, mycosis fungoides, pagetoid reticulosis, granulomatous slack skin, lymphomatoid papulosis, *pityriasis* lichenoides chronica, *pityriasis* lichenoides et varioliformis *acuta,* CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma, angiocentric lymphoma, blastic NK-cell lymphoma), prurigo nodularis, lichen planus, primary localized cutaneous amyloidosis, bullous pemphigoid, skin manifestations of graft versus host disease, pemphigoid, discoid lupus, granuloma annulare, lichen simplex chronicus, vulvar/scrotal/perianal pruritus, lichen sclerosus, post herpetic neuralgia itch, lichen planopilaris, and foliculitis decalvans. In particular, atopic dermatitis (Bao et al., *JAK-STAT,* 2013, 2, e24137), alopecia areata (Xing et al., *Nat. Med.* 2014, 20, 1043-1049), vitiligo (Craiglow et al, *JAMA Dermatol.* 2015, 151, 1110-1112), prurigo nodularis (Sonkoly et al., *J. Allergy Clin. Immunol.* 2006, 117, 411-417), lichen planus (Welz-Kubiak et al., *J. Immunol. Res.* 2015, ID:854747), primary localized cutaneous amyloidosis (Tanaka et al., *Br. J. Dermatol.* 2009, 161, 1217-1224), bullous pemphigoid (Feliciani et al., *Int. J. Immunopathol. Pharmacol.* 1999, 12, 55-61), and dermal manifestations of graft versus host disease (Okiyama et al., *J. Invest. Dermatol.* 2014, 134, 992-1000) are characterized by elevation of certain cytokines that signal via JAK activation. Accordingly, compounds of the present disclosure, or a pharmaceutically acceptable salt thereof, may be able to alleviate associated dermal inflammation or pruritus driven by these cytokines. In particular, compounds of the present disclosure, or a pharmaceutically acceptable salt thereof, may be expected to be useful for the treatment of atopic dermatitis and other inflammatory skin diseases. In one embodiment, therefore, the present disclosure provides a method of treating an inflammatory skin disease in a mammal (e.g., a human), the method comprising applying a pharmaceutical composition comprising a compound of the present disclosure, or a pharmaceutically acceptable salt thereof and a pharmaceutical carrier to the skin of the mammal. In some embodiments, the inflammatory skin disease is atopic dermatitis.

Many ocular diseases have been shown to be associated with elevations of proinflammatory cytokines that rely on the JAK-STAT pathway. The compounds of the present disclosure, or a pharmaceutically acceptable salt thereof, therefore, may be useful for the treatment of a number of ocular diseases that include, but are not limited to, uveitis, diabetic retinopathy, diabetic macular edema, dry eye disease, age-related macular degeneration, and atopic keratoconjunctivitis. In particular, uveitis (Horai and Caspi, *J. Interferon Cytokine Res.*, 2011, 31, 733-744), diabetic retinopathy (Abcouwer, *J. Clin. Cell. Immunol.*, 2013, Suppl 1, 1-12), diabetic macular edema (Sohn et al., *American Journal of Opthamology*, 2011, 152, 686-694), dry eye disease (Stevenson et al, *Arch. Ophthalmol.*, 2012, 130, 90-100), and age-related macular degeneration (Knickelbein et al, *Int. Ophthalmol. Clin.*, 2015, 55(3), 63-78) are characterized by elevation of certain pro-inflammatory cytokines that signal via the JAK-STAT pathway. Accordingly, compounds of the present disclosure, or a pharmaceutically acceptable salt thereof, may be able to alleviate the associated ocular inflammation and reverse disease progression or provide symptom relief. In one embodiment, therefore, the present disclosure provides a method of treating an ocular disease in a mammal (e.g. a human), the method comprising administering a pharmaceutical composition comprising a compound of the present disclosure or a pharmaceutically-acceptable salt thereof and a pharmaceutical carrier to the eye of the mammal (or human). In some embodiments, the ocular disease is uveitis, diabetic retinopathy, diabetic macular edema, dry eye disease, age-related macular degeneration, or atopic keratoconjunctivitis. In some embodiments, the method comprises administering the compound of the present disclosure, or a pharmaceutically acceptable salt thereof by intravitreal injection. Compounds of the present disclosure, or a pharmaceutically acceptable salt thereof, may also be used in combination with one or more compound useful to ocular diseases.

The compounds of the present disclosure, or a pharmaceutically acceptable salt thereof, may also be useful to treat other diseases such as other inflammatory diseases, autoimmune diseases or cancers. The compounds of the present disclosure, or a pharmaceutically acceptable salt thereof, may be useful to treat one or more of cytokine release syndrome (CRS), arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

Combination Therapy

Compounds of the present disclosure or a pharmaceutically acceptable salt thereof may be used in combination with one or more agents which act by the same mechanism or by different mechanisms to treat a disease. The different agents may be administered sequentially or simultaneously, in separate compositions or in the same composition. Useful classes of agents for combination therapy include, but are not limited to, a beta 2 adrenoceptor agonist, a muscarinic receptor antagonist, a glucocorticoid agonist, a G-protein coupled receptor-44 antagonist, a leukotriene D4 antagonist, a muscarinic M3 receptor antagonist, a histamine H1 receptor antagonist, an immunoglobulin E antagonist, a PDE 4 inhibitor, an IL-4 antagonist, a muscarinic M1 receptor antagonist, a histamine receptor antagonist, an IL-13 antagonist, an IL-5 antagonist, a 5-Lipoxygenase inhibitor, a beta adrenoceptor agonist, a CCR3 chemokine antagonist, a CFTR stimulator, an immunoglobulin modulator, an interleukin 33 ligand inhibitor, a PDE 3 inhibitor, a phosphoinositide-3 kinase delta inhibitor, a thromboxane A2 antagonist, an elastase inhibitor, a Kit tyrosine kinase inhibitor, a leukotriene E4 antagonist, a leukotriene antagonist, a PGD2 antagonist, a TNF alpha ligand inhibitor, a TNF binding agent, a complement cascade inhibitor, an eotaxin ligand inhibitor, a glutathione reductase inhibitor, an histamine H4 receptor antagonist, an IL-6 antagonist, an IL2 gene stimulator, an immunoglobulin gamma Fc receptor IIB modulator, an interferon gamma ligand, an interleukin 13 ligand inhibitor, an interleukin 17 ligand inhibitor, a L-Selectin antagonist, a leukocyte elastase inhibitor, a leukotriene C4 antagonist, a Leukotriene C4 synthase inhibitor, a membrane copper amine oxidase inhibitor, a metalloprotease-12 inhibitor, a metalloprotease-9 inhibitor, a mite allergen modulator, a muscarinic receptor modulator, a nicotinic acetylcholine receptor agonist, a nuclear factor kappa B inhibitor, a p-Selectin antagonist, a PDE 5 inhibitor, a PDGF receptor antagonist, a phosphoinositide-3 kinase gamma inhibitor, a TLR-7 agonist, a TNF antagonist, an Abl tyrosine kinase inhibitor, an acetylcholine receptor antagonist, an acidic mammalian chitinase inhibitor, an ACTH receptor agonist, an actin polymerization modulator, an adenosine A1 receptor antagonist, an adenylate cyclase stimulator, an adrenoceptor antagonist, an adrenocorticotrophic hormone ligand, an alcohol dehydrogenase 5 inhibitor, an alpha 1 antitrypsin stimulator, an alpha 1 proteinase inhibitor, an androgen receptor modulator, an angiotensin converting enzyme 2 stimulator, an ANP agonist, a Bcr protein inhibitor, a beta 1 adrenoceptor antagonist, a beta 2 adrenoceptor antagonist, a beta 2 adrenoceptor modulator, a beta amyloid modulator, a BMP10 gene inhibitor, a BMP15 gene inhibitor, a calcium channel inhibitor, a cathepsin G inhibitor, a CCL26 gene inhibitor, a CCR3 chemokine modulator, a CCR4 chemokine antagonist, a cell adhesion molecule inhibitor, a chaperonin stimulator, a chitinase inhibitor, a collagen I antagonist, a complement C3 inhibitor, a CSF-1 antagonist, a CXCR2 chemokine antagonist, a cytokine receptor common beta chain modulator, a cytotoxic T-lymphocyte protein-4 stimulator, a deoxyribonuclease I stimulator, a deoxyribonuclease stimulator, a dipeptidyl peptidase I inhibitor, a DNA gyrase inhibitor, a DP prostanoid receptor modulator, an E-Selectin antagonist, an EGFR family tyrosine kinase receptor inhibitor, an elastin modulator, an Endothelin ET-A antagonist, an Endothelin ET-B antagonist, an epoxide hydrolase inhibitor, a FGF3 receptor antagonist, a Fyn tyrosine kinase inhibitor, a GATA 3 transcription factor inhibitor, a Glucosylceramidase modulator, a Glutamate receptor modulator, a GM-CSF ligand inhibitor, a Guanylate cyclase stimulator, a H+K+ ATPase inhibitor, an hemoglobin modulator, an Heparin agonist, an Histone deacetylase inhibitor, an Histone deacetylase-2 stimulator, an HMG CoA reductase inhibitor, an I-kappa B kinase beta inhibitor, an ICAM1 gene inhibitor, an IL-17 antagonist, an IL-17 receptor modulator, an IL-23 antagonist, an IL-4 receptor modulator, an Immunoglobulin G modulator, an Immunoglobulin G1 agonist, an Immunoglobulin G1 modulator, an Immunoglobulin epsilon Fc receptor IA antagonist, an Immunoglobulin gamma Fc receptor IIB antagonist, an Immunoglobulin kappa modulator, an Insulin sensitizer, an Interferon beta ligand, an Interleukin 1 like receptor antagonist, an Interleukin 18 ligand inhibitor, an Interleukin receptor 17A antagonist, an Interleukin-1 beta ligand inhibitor, an Interleukin-5 ligand inhibitor, an Interleukin-6 ligand inhibitor, a KCNA voltage-gated potassium channel-3 inhibitor, a Kit ligand inhibitor, a Laminin-5 agonist, a Leukotriene CysLT1 receptor antagonist, a Leukotriene CysLT2 receptor antagonist, a LOXL2 gene inhibitor, a Lyn tyrosine kinase inhibitor, a MARCKS protein inhibitor, a MDR associated protein 4 inhibitor, a Metalloprotease-2 modulator, a Metalloprotease-9 modulator, a Mineralocorticoid receptor antagonist, a Muscarinic M2 receptor antagonist, a Muscarinic M4 receptor antagonist, a Muscarinic M5 receptor antagonist, a Natriuretic peptide receptor A agonist, a Natural killer cell receptor modulator, a Nicotinic ACh receptor alpha 7 subunit stimulator, a NK cell receptor modulator, a Nuclear factor kappa B modulator, an opioid growth factor receptor agonist, a P-Glycoprotein inhibitor, a P2X3 purinoceptor antagonist, a p38 MAP kinase inhibitor, a Peptidase 1 modulator, a phospholipase A2 inhibitor, a phospholipase C inhibitor, a plasminogen activator inhibitor 1 inhibitor, a platelet activating factor receptor antagonist, a PPAR gamma agonist, a prostacyclin agonist, a protein tyrosine kinase inhibitor, a SH2 domain inositol phosphatase 1 stimulator, a signal transduction inhibitor, a sodium channel inhibitor, a STAT-3 modulator, a Stem cell antigen-1 inhibitor, a superoxide dismutase modulator, a T cell surface glycoprotein CD28 inhibitor, a T-cell surface glycoprotein CD8 inhibitor, a TGF beta agonist, a TGF beta antagonist, a thromboxane synthetase inhibitor, a thymic stromal lymphoprotein ligand inhibitor, a thymosin agonist, a thymosin beta 4 ligand, a TLR-8 agonist, a TLR-9 agonist, a TLR9 gene stimulator, a Topoisomerase IV inhibitor, a Troponin I fast skeletal muscle stimulator, a Troponin T fast skeletal muscle stimulator, a Type I IL-1 receptor antagonist, a Type II TNF receptor modulator, an ion channel modulator, a uteroglobin stimulator, and a VIP agonist.

Specific agents that may be used in combination with the present JAK inhibitor compounds include, but are not limited to rositor acetate, umeclidinium bromide, secukinumab, metenkefalin acetate, tridecactide acetate, fluticasone propionate, alpha-cyclodextrin-stabilized sulforaphane, tezepelumab, mometasone furoate, BI-1467335, dupilumab, aclidinium, formoterol, AZD-1419, HI-1640V, rivipansel, CMP-001, mannitol, ANB-020, omalizumab, tregalizumab, Mitizax, benralizumab, golimumab, roflumilast, imatinib, REGN-3500, masitinib, apremilast, RPL-554, Actimmune, adalimumab, rupatadine, parogrelil, MK-1029, beclometasone dipropionate, formoterol fumarate, mogamulizumab, seratrodast, UCB-4144, nemiralisib, CK-2127107, fevipiprant, danirixin, bosentan, abatacept, EC-18, duvelisib, dociparstat, ciprofloxacin, salbutamol HFA, erdosteine, PrEP-001, nedocromil, CDX-0158, salbutamol, enobosarm, R-TPR-022, lenzilumab, fluticasone furoate, vilanterol trifenatate, fluticasone propionate, salmeterol, PT-007, PRS-060, remestemcel-L, citrulline, RPC-4046, nitric oxide, DS-102, gerilimzumab, Actair, fluticasone furoate, umeclidinium, vilanterol, AG-NPP709, Gamunex, infliximab, Ampion, acumapimod, canakinumab, INS-1007, CYP-001, sirukumab, fluticasone propionate, mepolizumab, pitavastatin, solithromycin, etanercept, ivacaftor, anakinra, MPC-300-IV, glycopyrronium bromide, aclidinium bromide, FP-025, risankizumab, glycopyrronium, formoterol fumarate, Adipocell, YPL-001, tiotropium bromide, glycopyrronium bromide, indacaterol maleate, andecaliximab, olodaterol, esomeprazole, dust mite vaccine, mugwort pollen allergen vaccine, vamorolone, gefapixant, revefenacin, gefitinib, ReJoin, tipelukast, bedoradrine, SCM-CGH, SHP-652, RNS-60, brodalumab, BIO-11006, umeclidinium bromide, vilanterol trifenatate, ipratropium bromide, tralokinumab, PUR-1800, VX-561, VX-371, olopatadine, tulobuterol, formoterol fumarate, triamcinolone acetonide, reslizumab, salmeterol xinafoate, fluticasone propionate, beclometasone dipropionate, formoterol fumarate, tiotropium bromide, ligelizumab, RUT1, bertilimumab, omalizumab, glycopyrronium bromide, SENS-111, beclomethasone dipropionate, CHF-5992, LT-4001, indacaterol, glycopyrronium bromide, mometasone furoate, fexofenadine, glycopyrronium bromide, azithromycin, AZD-7594, formoterol, CHF-6001, batefenterol, OATD-01, olodaterol, CJM-112, rosiglitazone, salmeterol, setipiprant, inhaled interferon beta, AZD-8871, plecanatide, fluticasone, salmeterol, eicosapentaenoic acid monoglycerides, lebrikizumab, RG-6149, QBKPN, Mometasone, indacaterol, AZD-9898, sodium pyruvate, zileuton, CG-201, imidafenacin, CNTO-6785, CLBS-03, mometasone, RGN-137, procaterol, formoterol, CCI-15106, POL-6014, indacaterol, beclomethasone, MV-130, GC-1112, Allergovac depot, MEDI-3506, QBW-251, ZPL-389, udenafil, GSK-3772847, levocetirizine, AXP-1275, ADC-3680, timapiprant, abediterol, AZD-7594, ipratropium bromide, salbutamol sulfate, tadekinig alfa, ACT-774312, dornase alfa, iloprost, batefenterol, fluticasone furoate, alicaforsen, ciclesonide, emeramide, arformoterol, SB-010, Ozagrel, BTT-1023, Dectrekumab, levalbuterol, pranlukast, hyaluronic acid, GSK-2292767, Formoterol, NOV-14, Lucinactant, salbutamol, prednisolone, ebastine, dexamethasone cipecilate, GSK-2586881, BI-443651, GSK-2256294, VR-179, VR-096, hdm-ASIT+, budesonide, GSK-2245035, VTX-1463, Emedastine, dexpramipexole, levalbuterol, N-6022, dexamethasone sodium phosphate, PIN-201104, OPK-0018, TEV-48107, suplatast, BI-1060469, Gemilukast, interferon gamma, dalazatide, bilastine, fluticasone propionate, salmeterol xinafoate, RP-3128, bencycloquidium bromide, reslizumab, PBF-680, CRTH2 antagonist, Pranlukast, salmeterol xinafoate, fluticasone propionate, tiotropium bromide monohydrate, masilukast, RG-7990, Doxofylline, abediterol, glycopyrronium bromide, TEV-46017, ASM-024, fluticasone propionate, glycopyrronium bromide, salmeterol xinafoate, salbutamol, TA-270, Flunisolide, sodium chromoglycate, Epsi-gam, ZPL-521, salbutamol, aviptadil, TRN-157, Zafirlukast, Stempeucel, pemirolast sodium, nadolol, fluticasone propionate+salmeterol xinafoate, RV-1729, salbutamol sulfate, carbon dioxide+perfluorooctyl bromide, APL-1, dectrekumab+VAK-694, lysine acetylsalicylate, zileuton, TR-4, human allogenic adipose-derived mesenchymal progenitor cell therapy, MEDI-9314, PL-3994, HMP-301, TD-5471, NKTT-120, pemirolast, beclomethasone dipropionate, trantinterol, monosodium alpha luminol, IMD-1041, AM-211, TBS-5, ARRY-502, seratrodast, recombinant midismase, ASM-8, deflazacort, bambuterol, RBx-10017609, ipratropium+fenoterol, fluticasone+formoterol, epinastine, WIN-901X, VALERGEN-DS,OligoG-COPD-5/20, tulobuterol, oxis Turbuhaler, DSP-3025, ASM-024, mizolastine, budesonide+salmeterol, LH-011, AXP-E, histamine human immunoglobulin, YHD-001, theophylline, ambroxol+erdosteine, ramatroban, montelukast, pranlukast, AG-1321001, tulobuterol, ipratropium+salbutamol, tranilast, methylprednisolone suleptanate, colforsin daropate, repirinast, and doxofylline.

Also provided, herein, is a pharmaceutical composition comprising a compound of the present disclosure, or a pharmaceutically acceptable salt thereof, and one or more other therapeutic agents. The therapeutic agent may be selected from the class of agents specified above and from the list of specific agents described above. In some embodiments, the pharmaceutical composition is suitable for delivery to the lungs. In some embodiments, the pharmaceutical composition is suitable for inhaled or nebulized administration. In some embodiments, the pharmaceutical composition is a dry powder or a liquid composition.

Further, the present disclosure provides a method of treating a disease or disorder in a mammal (e.g. a human) comprising administering to the mammal (or human) a compound of the present disclosure, or a pharmaceutically acceptable salt thereof, and one or more other therapeutic agents.

When used in combination therapy, the agents may be formulated in a single pharmaceutical composition, or the agents may be provided in separate compositions that are administered simultaneously or at separate times, by the same or by different routes of administration. Such compositions can be packaged separately or may be packaged together as a kit. The two or more therapeutic agents in the kit may be administered by the same route of administration or by different routes of administration.

EXAMPLES

The following synthetic and biological examples are offered to illustrate the invention and are not to be construed in any way as limiting the scope of the invention. In the examples below, the following abbreviations have the following meanings unless otherwise indicated. Abbreviations not defined below have their generally accepted meanings.

ABBREVIATIONS

ACN=acetonitrile
bis(pinacolato)diboron=,4,5,5,4',4',5',5'-octamethyl [2,2'] bi[[1,3,2]dioxaborolanyl]
Calcd=calculated
DCM=dichloromethane
DIPEA=N,N-diisopropylethylamine
DMA=dimethylacetamide
DMSO=dimethyl sulfoxide
DMF=N,N-dimethylformamide
$PdCl_2$(dppf)=[1,1'-Bis(diphenylphosphino)ferrocene]dichloropalladium(II)
Eq=equivalent
EtOAc=ethyl acetate
h=hour(s)
HATU=N,N,N',N'-tetramethyl-O-(7-azabenzotriazol-1-yl)uronium hexafluorophosphate
HBTU=N,N,N',N'-Tetramethyl-O-(1H-benzotriazol-1-yl) uronium hexafluorophosphate, O-(Benzotriazol-1-yl)-N,N,N',N'-tetramethyluronium hexafluorophosphate
IPA=isopropyl alcohol
MeOH=methanol
min=minute(s)
NaHMDS=sodium bis(trimethylsilyl)amide
NBS=N-Bromosuccinimide
Pd(PPh$_3$)$_4$=tetrakis(triphenylphosphine)palladium(0)
RT=room temperature
SEM=2-(Trimethylsilyl)ethoxymethyl
SEMCl=2-(Trimethylsilyl)ethoxymethyl chloride
TBAF=tetra-N-butylammonium fluoride
TBDPSCl=tert-Butyl(chloro)diphenylsilane
TEA=triethylamine
TFA=trifluoroacetic acid
THF=tetrahydrofuran
THP=tetrahydropyran Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as $CD_3OD$, $CDCl_3$, or $d_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, CA) model API 150 EX instrument or a Waters (Milford, MA) 3100 instrument, coupled to autopurification systems.

Preparative HPLC Conditions

Column: C18, 5 µm. 21.2×150 mm or C18, 5 µm 21×250 or
C14, 5 µm 21×150 mm
Column temperature: Room Temperature
Flow rate: 20.0 mL/min
Mobile Phases: A=Water+0.05% TFA
B=ACN+0.05% TFA,
Injection volume: (100-1500 µL)
Detector wavelength: 214 nm
Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 µL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Preparation of (2-((3-ethyl-4-(4,4,5,5-tetramethyl-1,3,2-dioxaborolan-2-yl)phenoxy)methoxy)ethyl)trimethylsilane (I-7)

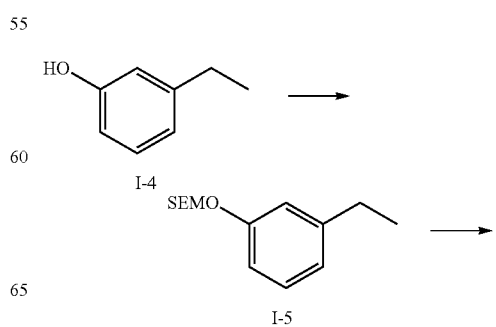

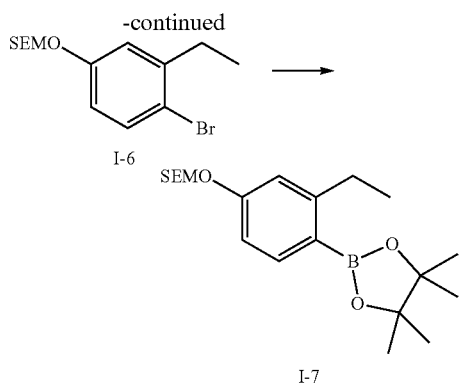

(a) (2-((3-ethylphenoxy)methoxy)ethyl)trimethylsilane (I-5)

To a stirred solution of I-4, 3-ethylphenol (200 g, 1.64 mol) in DMF (1.50 L) cooled to 0° C. was added NaH (78.6 g, 1.96 mol) portion wise. The reaction mixture was then stirred at 0° C. for 1 h. SEMCl (300 g, 1.80 mol) was then added drop-wise at 0° C., and the reaction mixture was allowed to stir at room temperature for 2 h. TLC showed complete consumption of starting material. The reaction mixture was quenched with ice-water (2.0 L) and extracted with ethyl acetate (2×1.0 L). The combined organic layers were washed with brine solution (1.0 L), dried over $Na_2SO_4$, and concentrated under reduced pressure. The crude compound was purified by silica gel column chromatography (5-10% EtOAc in heptane) to afford the desired product as a clear liquid (305 g, 74% yield). $^1$H NMR (400 MHz, DMSO-$d_6$) δ 7.17 (t, J=7.8 Hz, 1H), 6.88-6.77 (m, 3H), 5.20 (s, 2H), 3.69 (t, J=8.0 Hz, 2H), 2.56 (q, J=7.6 Hz, 2H), 1.16 (t, J=7.6 Hz, 3H), 0.88 (t, J=8.1 Hz, 2H), 0.00 (s, 9H).

(b) (2-((4-bromo-3-ethylphenoxy)methoxy)ethyl)trimethylsilane (I-6)

To a stirred solution of I-5 (200 g, 792 mmol) in ACN (1.40 L) cooled to 0° C. was added NBS (141 g, 792 mmol) portion wise over a period of 30 minutes. The resulting reaction mixture was stirred at room temperature for 2 h. TLC showed complete consumption of starting material. The reaction mixture was poured into ice cold water (1 L) and extracted with EtOAc (2×1 L). The combined organic layers were washed with water (1 L), dried over $Na_2SO_4$, filtered and concentrated under reduced pressure. The crude mixture was purified by silica gel column chromatography (100% heptane) to afford the desired product (230 g, 88% yield). $^1$H NMR (400 MHz, DMSO-$d_6$) δ 7.44 (dd, J=8.8, 1.9 Hz, 1H), 6.99 (d, J=2.9 Hz, 1H), 6.81 (dt, J=8.8, 2.6 Hz, 1H), 5.21 (d, J=2.0 Hz, 2H), 3.73-3.64 (m, 2H), 2.63 (qd, J=7.5, 2.0 Hz, 2H), 1.14 (td, J=7.6, 1.9 Hz, 3H), 0.95-0.79 (m, 2H), 0.00 (s, 9H).

(c) (2-((3-ethyl-4-(4,4,5,5-tetramethyl-1,3,2-dioxaborolan-2-yl)phenoxy)methoxy)ethyl)trimethylsilane (I-7)

To a stirred solution of I-6 (100 g, 302 mmol) in 1,4-dioxane (1.00 L) were added bis(pinacolato)diboron (76.6 g, 302 mmol) and potassium acetate (59.2 g, 604 mmol). The reaction mixture was degassed with nitrogen for 15 minutes after which $PdCl_2$(dppf)·DCM (24.6 g, 30.2 mmol) was added. The reaction mixture was stirred and heated at 110° C. for 16 hours under nitrogen. TLC indicated the complete consumption of the starting material. The reaction mixture was diluted with EtOAc (1 L) and washed with water (1 L). The combined organic layers were separated, dried over $Na_2SO_4$, and concentrated. The crude mixture was purified by silica gel column chromatography (0-10% EtOAc in heptane) to afford the desired product as a yellow liquid (75.0 g, 66% yield). $^1$H NMR (400 MHz, DMSO-$d_6$) δ 7.57 (d, J=8.1 Hz, 1H), 6.87-6.77 (m, 2H), 5.21 (d, J=13.2 Hz, 2H), 3.69 (t, J=8.0 Hz, 2H), 2.80 (q, J=7.5 Hz, 2H), 1.27 (s, 12H), 1.11 (t, J=7.5 Hz, 3H), 0.91-0.84 (m, 2H), 0.00 (s, 9H).

Preparation of 3-(1-benzyl-1H-imidazol-2-yl)-6-bromo-1-(tetrahydro-2H-pyran-2-yl)-1H-indazole (I-12)

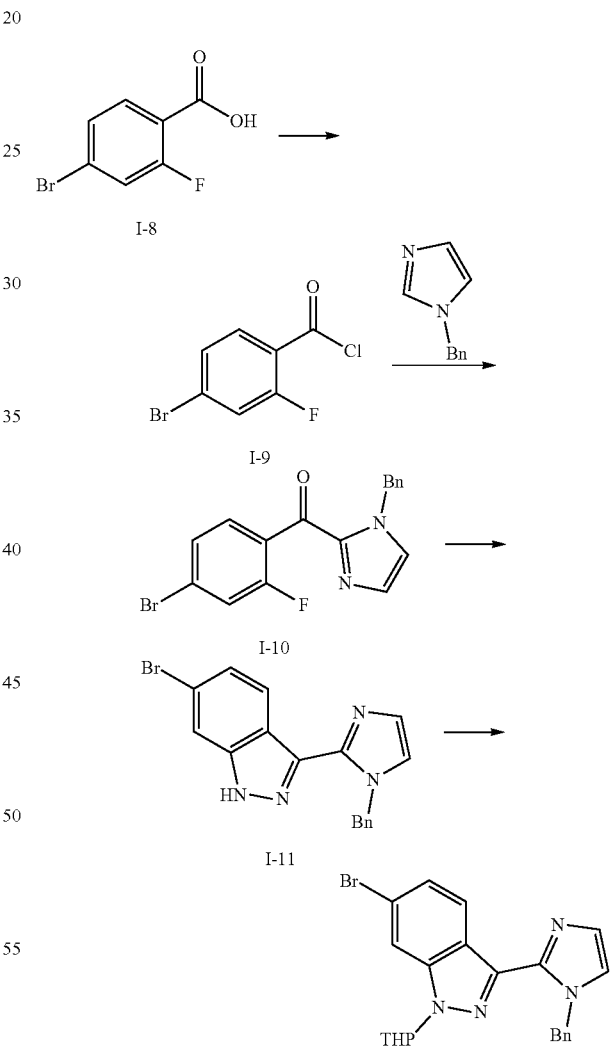

(a) 4-bromo-2-fluorobenzoyl chloride (1-9)

To a stirred solution of I-8, 4-bromo-2, -fluorobenzoic acid (50.0 g, 228 mmol), in DCM (300 mL) and DMF (4.0 mL) was added oxalyl chloride (96.57 mL, 913 mmol) drop wise at 0° C. The resulting reaction mixture was stirred at room temperature for 1 h. After completion of reaction (TLC monitoring, checked by quenching in MeOH), the reaction was concentrated under reduced pressure (under nitrogen) to afford an off-white solid (54.2 g) which was used in the next step without further purification.

(b) (1-benzyl-1H-imidazol-2-yl)(4-bromo-2-fluorophenyl)methanone (I-10)

To a stirred solution of 1-benzyl-1H-imidazole (30.0 g, 190 mmol) in acetonitrile (165 mL) was added triethylamine (133.4 mL, 949 mmol) at room temperature. Compound I-9 (54.2 g, 228 mmol) was taken up separately in acetonitrile (165 ml) and added to the reaction mixture. The reaction was allowed to stir at room temperature for 2 h. TLC showed consumption of starting material. The reaction was quenched with cold water (500 mL) and extracted with ethyl acetate (2×600 mL). The combined organic layers were dried over $Na_2SO_4$, filtered and concentrated under reduced pressure to get crude product which was purified by silica gel column chromatography (10% EtOAc in Heptane) to obtain the desired product as an off-white solid (79.0 g, 58% yield). $^1$H NMR (400 MHz, DMSO-$d_6$) δ 7.80 (s, 1H), 7.68 (dd, J=9.7, 1.8 Hz, 1H), 7.61 (t, J=7.8 Hz, 1H), 7.54 (dd, J=8.3, 1.8 Hz, 1H), 7.36 (dd, J=8.1, 6.5 Hz, 2H), 7.32-7.26 (m, 1H), 7.25 (s, 1H), 7.22 (dd, J=6.9, 1.8 Hz, 2H), 5.70 (s, 2H). (m/z): [M+H]$^+$ calcd for $C_{17}H_{13}BrFN_2O$ 359.02 found 358.97

(c) 3-(1-benzyl-1H-imidazol-2-yl)-6-bromo-1H-indazole (I-11)

To a stirred solution of I-10 (53.0 g, 147.5 mmol) in DMSO (105 mL) was added drop wise hydrazine hydrate (72.5 mL, 1475.5 mmol) at room temperature. The reaction mixture was allowed to stired at 90° C. for 3 h. After 3 h, TLC showed complete consumption of starting material. The reaction mixture was diluted with ice cold water (800 mL) and precipitation was observed. The reaction was filtered, washed with ice cold water (500 mL) to afford the desired product as an off-white solid (47.0 g, 90% yield). $^1$H NMR (400 MHz, DMSO-$d_6$) δ 8.36 (d, J=8.6 Hz, 1H), 7.79 (d, J=1.6 Hz, 1H), 7.40 (s, 1H), 7.35 (dd, J=8.6, 1.7 Hz, 1H), 7.29 (dd, J=8.1, 6.5 Hz, 2H), 7.26-7.22 (m, 1H), 7.21-7.17 (m, 2H), 7.16 (s, 1H), 5.84 (s, 2H). (m/z): [M+H]$^+$ calcd for $C_{17}H_{14}BrN_4$ 353.04 found 353.03.

(d) 3-(1-benzyl-1H-imidazol-2-yl)-6-bromo-1-(tetrahydro-2H-pyran-2-yl)-1H-indazole (1-12)

To a stirred solution of 1-11 (47.0 g, 133.1 mmol) in ethyl acetate (350 mL) at 0° C. was added TFA (30.5 mL, 399.1 mmol). Dihydropyran (60.8 mL, 665.3 mmol) was added drop wise. The reaction mixture was then heated to 80° C. and stirred for 2 days. After 2 days, TLC showed complete consumption of starting material. The reaction mixture was diluted with water (400 mL) and extracted with ethyl acetate (2×900 mL). The combined organic layers were further washed with saturated aq. $NaHCO_3$ solution (800 mL), dried over anhydrous $Na_2SO_4$, filtered and concentrated. The crude product was purified by silica gel column chromatography (5% EtOAc in Heptane) to afford the desired product as an off white solid (40 g, 69% yield). $^1$H NMR (400 MHz, DMSO-$d_6$) δ 8.37 (d, J=8.6 Hz, 1H), 8.07 (d, J=1.6 Hz, 1H), 7.48 (d, J=1.2 Hz, 1H), 7.42 (dd, J=8.6, 1.6 Hz, 1H), 7.33-7.25 (m, 2H), 7.25-7.19 (m, 3H), 7.19 (d, J=1.2 Hz, 1H), 5.94 (dd, J=8.9, 2.5 Hz, 1H), 5.86 (d, J=15.3 Hz, 1H), 5.77 (d, J=15.3 Hz, 1H), 3.78 (tp, J=11.6, 3.8 Hz, 2H), 2.38-2.25 (m, 1H), 2.04-1.89 (m, 2H), 1.70 (dtt, J=11.5, 8.5, 4.0 Hz, 1H), 1.62-1.45 (in, 2H). (m/z): [M+H]$^+$ calcd for $C_{22}H_{22}BrN_4O$ 437.10 found 437.11.

Preparation of 6-(2-ethyl-4-((2-(trimethylsilyl)ethoxy)methoxy)phenyl)-1-(tetrahydro-2H-pyran-2-yl)-3-(1-((2-(trimethylsilyl)ethoxy)methyl)-1H-imidazol-2-yl)-1H-indazole (1-15)

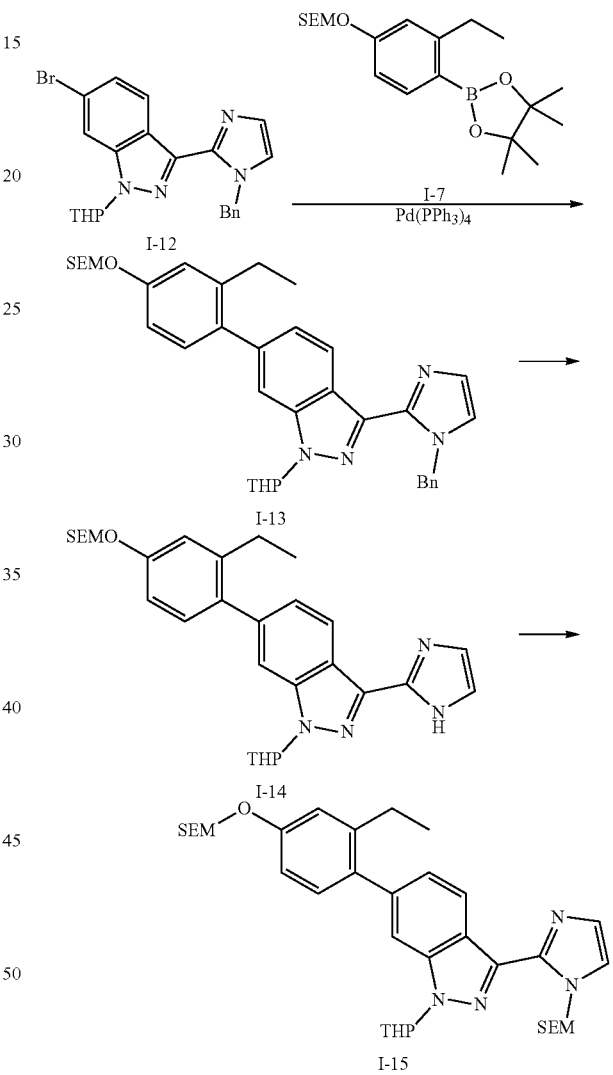

(a) 3-(1-benzyl-1H-imidazol-2-yl)-6-(2-ethyl-4-((2-(trimethylsilyl)ethoxy)methoxy)phenyl)-1-(tetrahydro-2H-pyran-2-yl)-1H-indazole (I-13)

To a stirred solution of I-12 (60.0 g, 137 mmol) and 1-7 (62.3 g, 165 mmol) in dioxane (360 mL) and water (90.0 mL) was added $K_3PO_4$ (87.4 g, 412 mmol). The reaction mixture was purged with argon for 15 minutes, and Pd(PPh$_3$)$_4$ (15.9 g, 13.7 mmol) was then added to it. The reaction was then heated to 110° C. and stirred for 3 h. TLC showed consumption of the starting material. The reaction mixture was diluted with water (600 mL) and extracted with ethyl acetate (2×500 mL). The combined organics were then washed with brine (600 mL), dried over anhydrous Na$_2$SO$_4$ and concentrated under reduced pressure to afford the crude product which was purified by silica gel column chromatography (10% EtOAC in heptane). The desired product was isolated as a clear liquid (65 g, 78% yield). $^1$H NMR (400 MHz, DMSO-d$_6$) δ 8.43 (d, J=8.4 Hz, 1H), 7.61 (s, 1H), 7.47 (s, 1H), 7.34-7.27 (m, 2H), 7.27-7.20 (m, 3H), 7.20-7.14 (m, 3H), 7.01 (d, J=2.6 Hz, 1H), 6.94 (dd, J=8.4, 2.6 Hz, 1H), 5.98-5.87 (m, 2H), 5.85-5.74 (m, 1H), 5.27 (s, 2H), 3.82 (d, J=11.4 Hz, 1H), 3.72 (q, J=10.1, 9.0 Hz, 3H), 2.55 (t, J=7.5 Hz, 2H), 2.35 (s, 1H), 1.98 (s, 2H), 1.79-1.64 (m, 1H), 1.55 (s, 2H), 1.04 (t, J=7.5 Hz, 3H), 0.92 (t, J=8.1 Hz, 2H), 0.00 (s, 9H). (m/z): [M+H]$^+$ calcd for C$_{36}$H$_{45}$N$_4$O$_3$Si 609.33 found 609.38.

(b) 6-(2-ethyl-4-((2-(trimethylsilyl)ethoxy)methoxy)phenyl)-3-(1H-imidazol-2-yl)-1-(tetrahydro-2H-pyran-2-yl)-1H-indazole (I-14)

To a stirred solution of I-13 (65.0 g, 107 mmol) in isopropanol (450 mL) and THF (150.0 mL) was added 20% Pd(OH)$_2$/C (60.0 g, 84.5 mmol). The reaction mixture was subjected to hydrogenation using a H$_2$ balloon and was allowed to stir a room temperature for 16 h. TLC showed complete consumption of starting material. The reaction mixture was filtered through a pad of Celite, washed with EtOAc (500 mL), and the filtrate was concentrated under reduced pressure to afford the crude desired product (53.0 g, 96% yield) as a colorless liquid that was used directly in the next step without further purification. $^1$H NMR (400 MHz, DMSO-d$_6$) δ 12.68 (s, 1H), 8.38 (d, J=8.3 Hz, 1H), 7.65 (s, 1H), 7.23 (s, 1H), 7.19 (dd, J=8.3, 3.7 Hz, 2H), 7.14 (s, 1H), 7.01 (s, 1H), 6.95 (d, J=9.4 Hz, 1H), 5.95 (d, J=9.8 Hz, 1H), 5.27 (s, 2H), 3.93 (d, J=12.0 Hz, 1H), 3.74 (t, J=8.1 Hz, 3H), 2.56 (d, J=7.6 Hz, 2H), 2.03 (s, 2H), 1.76 (s, 1H), 1.58 (s, 2H), 1.05 (t, J=7.5 Hz, 3H), 0.92 (t, J=8.1 Hz, 2H), 0.00 (s, 9H). (m/z): [M+H]$'^0$ calcd for C$_{29}$H$_{39}$N$_4$O$_3$Si 519.28 found 519.28.

(c) 6-(2-ethyl-4-((2-(trimethylsilyl)ethoxy)methoxy)phenyl)-1-(tetrahydro-2H-pyran-2-yl)-3-(1-((2-(trimethylsilyl)ethoxy)methyl)-1H-imidazol-2-yl)-1H-indazole (I-15)

To the stirred solution of I-14 (43.0 g, 82.9 mmol) in DMF (400 mL) was added sodium hydride 60% w/w (4.97 g, 124 mmol) at 0° C. The reaction mixture was then allowed to stir at 0° C. for 20 min, after which SEMCl (17.6 mL, 99.5 mmol) was then added dropwise at 0° C. The reaction mixture was allowed to warm to room temperature and stirred for 1 h. TLC showed complete consumption of the starting material. The reaction mixture was quenched with ice-water (1 L) and extracted ethyl acetate (3×500 mL). The combined organic layers were washed with water (800 mL) and brine (800 mL), dried over Na$_2$SO$_4$, and concentrated under reduced pressure to afford the crude compound which was purified by silica gel column chromatography (15% EtOAc in heptane). The desired product was isolated as an off white solid (42.0 g, 66% yield). $^1$H NMR (400 MHz, Chloroform-d) δ 8.50 (d, J=8.4 Hz, 1H), 7.50 (s, 1H), 7.26 (s, 2H), 7.25-7.19 (m, 2H), 7.02 (s, 1H), 6.96 (d, J=8.5 Hz, 1H), 6.09 (d, J=10.5 Hz, 1H), 5.93 (d, J=10.5 Hz, 1H), 5.75 (d, J=9.0 Hz, 1H), 5.28 (s, 2H), 4.03 (d, J=11.5 Hz, 1H), 3.81 (t, J=8.4 Hz, 2H), 3.74 (t, J=10.0 Hz, 2H), 3.63 (d, J=8.5 Hz, 1H), 3.58 (t, J=8.2 Hz, 2H), 2.59 (q, J=7.5 Hz, 3H), 2.13 (d, J=16.5 Hz, 2H), 1.83-1.70 (m, 2H), 1.10 (t, J=7.5 Hz, 2H), 1.00 (t, J=8.3 Hz, 2H), 0.88 (q, J=7.3, 6.5 Hz, 2H), 0.00 (s, 9H), −0.09 (s, 9H). (m/z): [M+H]$^+$ calcd for C$_{35}$H$_{53}$N$_4$O$_4$Si$_2$ 649.36 found 649.49.

Preparation of 4-(3-(4-bromo-1H-imidazol-2-yl)-1-(tetrahydro-2H-pyran-2-yl)-1H-indazol-6-yl)-3-ethylphenol (I-17)

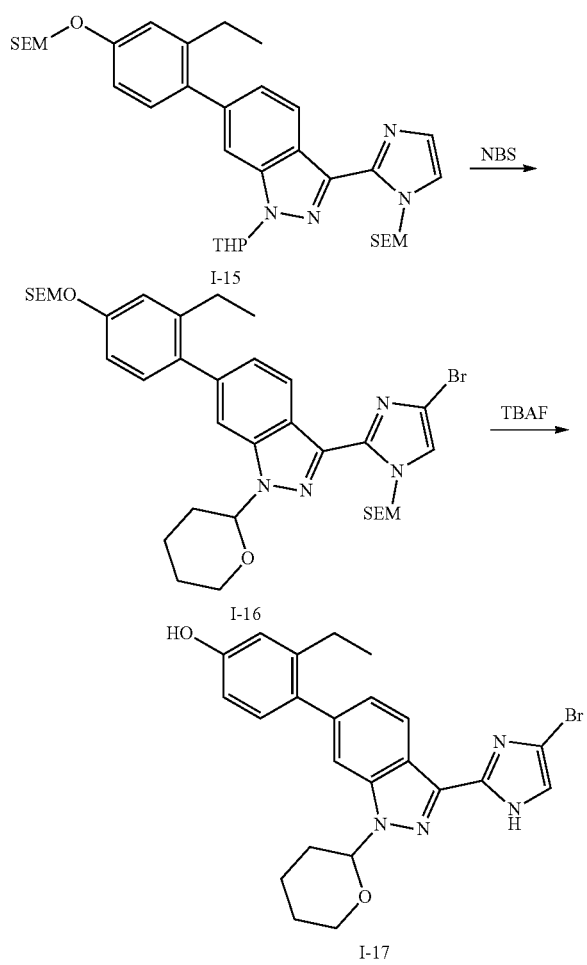

(a) 3-(4-bromo-1-((2-(trimethylsilyl)ethoxy)methyl)-1H-imidazol-2-yl)-6-(2-ethyl-4-((2-(trimethylsilyl)ethoxy)methoxy)phenyl)-1-(tetrahydro-2H-pyran-2-yl)-1H-indazole (1-16)

NBS (2.74 g, 15.4 mmol) was taken up in DCM (100 mL) and added dropwise to a stirred solution of I-15 (10.0 g, 15.4 mmol) in DCM (400 mL) at 0° C. The reaction mixture was stirred at 0° C. for 5 minutes. TLC showed complete consumption of the starting material. The reaction mixture was quenched with ice water (300 mL) and extracted with DCM (2×250 mL). The combined organic layers were dried over anhydrous Na$_2$SO$_4$, filtered and evaporated to afford crude product which was purified by silica gel column chromatography (8-10% EtOAc in heptane). The desired product was isolated as a colorless amorphous solid (9.10 g, 81% yield). $^1$H NMR (400 MHz, DMSO-d$_6$) δ 8.31 (d, J=8.3 Hz, 1H), 7.68 (s, 1H), 7.32 (s, 1H), 7.19 (dd, J=13.4, 8.4 Hz, 2H), 7.01 (d, J=2.5 Hz, 1H), 6.95 (dd, J=8.4, 2.5 Hz, 1H), 6.09-5.94 (m, 3H), 5.27 (s, 2H), 3.89 (d, J=11.4 Hz, 1H), 3.78 (d, J=5.7 Hz, 1H), 3.74 (t, J=8.1 Hz, 2H), 3.52 (dt, J=16.0, 8.0 Hz, 2H), 2.55 (t, J=7.5 Hz, 2H), 2.44 (s, 1H), 2.05 (d, J=11.1 Hz, 2H), 1.77 (s, 1H), 1.59 (s, 2H), 1.23 (s, 1H), 1.03 (t, J=7.5 Hz, 2H), 0.92 (t, J=8.1 Hz, 2H), 0.84 (td, J=10.5, 9.0, 5.4 Hz, 2H), 0.00 (m, 9H), −0.19 (s, 9H). (m/z): [M+H]$^+$ calcd for $C_{35}H_{52}BrN_4O_4Si_2$ 727.27 found 727.58.

(b) 4-(3-(4-bromo-1H-imidazol-2-yl)-1-(tetrahydro-2H-pyran-2-yl)-1H-indazol-6-yl)-3-ethylphenol (I-17)

To a stirred solution of I-16 (32.0 g, 44.0 mmol) in THF (100 mL) was added TBAF (1M in THF) (448 mL, 448 mmol) at room temperature. The reaction mixture was then heated to 80° C. and stirred for 2 days. TLC indicated complete consumption of the starting material. The reaction mixture was diluted with ethyl acetate (500 mL) and washed with water (3×300 mL) and brine (300 mL). The organic layer was dried over Na$_2$SO$_4$, filtered and concentrated under reduced pressure. The crude product was purified by silica gel column chromatography (20% EtOAc in heptane) to afford the desired product as an off-white solid (13.7 g, 66% yield). $^1$H NMR (400 MHz, DMSO-d$_6$) δ 13.10 (s, 1H), 9.43 (s, 1H), 8.26 (d, J=8.3 Hz, 1H), 7.64 (s, 1H), 7.39 (d, J=1.9 Hz, 1H), 7.20 (dd, J=8.4, 1.3 Hz, 1H), 7.07 (d, J=8.2 Hz, 1H), 6.76 (d, J=2.5 Hz, 1H), 6.69 (dd, J=8.2, 2.5 Hz, 1H), 5.96 (dd, J=10.0, 2.4 Hz, 1H), 3.92 (d, J=11.4 Hz, 1H), 3.77 (dt, J=11.5, 6.9 Hz, 1H), 2.07 (s, 2H), 2.03 (s, 1H), 1.76 (s, 1H), 1.58 (p, J=5.0 Hz, 2H), 1.04 (t, J=7.5 Hz, 3H). (m/z): [M+H]$^+$ calcd for $C_{23}H_{24}BrN_4O_2$ 469.11 found 469.36.

Preparation of 3-(1-benzyl-1H-imidazol-2-yl)-6-bromo-7-fluoro-1-(tetrahydro-2H-pyran-2-yl)-1H-indazole (I-22)

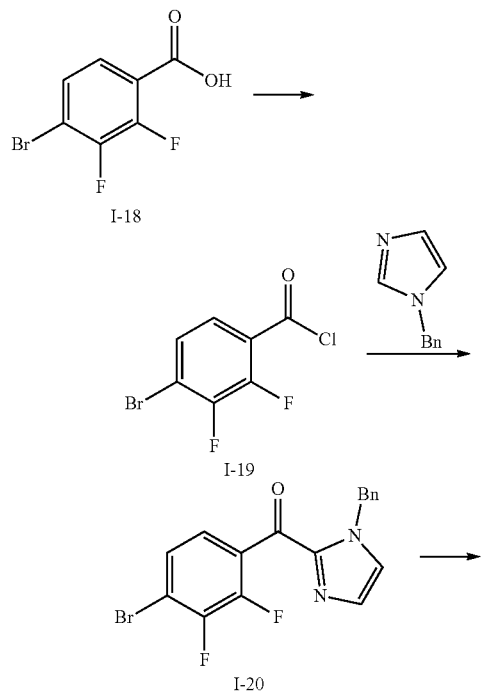

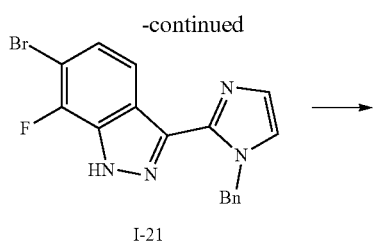

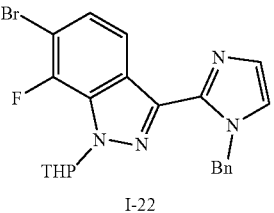

(a) 4-bromo-2,3-difluorobenzoyl chloride (I-19)

To a stirred solution of I-18 4-bromo-2,3-difluorobenzoic acid (28.0 g, 118 mmol), in DCM (300 mL) and DMF (915 μL, 0.1 eq., 11.8 mmol) was added oxalyl chloride (40.5 mL, 473 mmol) drop wise at room temperature. The resulting reaction mixture was stirred at room temperature for 2 h. After completion of reaction (TLC monitoring, checked by quenching in MeOH), the reaction was concentrated under reduced pressure (under nitrogen) to afford an off-white solid (31.0 g) which was used in the next step without further purification.

(b) (1-benzyl-1H-imidazol-2-yl)(4-bromo-2,3-difluorophenyl)methanone (I-20)

To a stirred solution of compound I-19 (16.0 g, 101 mmol) in acetonitrile (100 ml) was added triethylamine (51.2 g, 506 mmol). 1-benzyl-1H-imidazole (31.0 g, 121 mmol) was dissolved in acetonitrile (100 mL) separately and added to the reaction mixture at room temperature. The reaction was allowed to stir at room temperature for 2 h. TLC showed consumption of starting material. The reaction was quenched with cold water (500 mL) and extracted with ethyl acetate (2×600 mL). The combined organic layers were dried over Na$_2$SO$_4$, filtered and concentrated under reduced pressure to get crude product which was purified by silica gel column chromatography (10-15% EtOAc in Heptane) to obtain a the desired product as a light yellow solid (28.0 g, 73% yield). $^1$H NMR (400 MHz, DMSO-d$_6$) δ 7.83 (s, 1H), 7.66 (ddd, J=8.1, 5.9, 1.8 Hz, 1H), 7.46 (ddd, J=8.4, 6.4, 2.0 Hz, 1H), 7.36 (t, J=7.4 Hz, 2H), 7.30 (t, J=7.0 Hz, 1H), 7.28 (s, 2H), 7.23 (d, J=6.9 Hz, 2H), 5.70 (s, 2H). (m/z): [M+H]$^+$ calcd for $C_{17}H_{12}BrF_2N_2O$ 377.01 found 374.94.

(c) 3-(1-benzyl-1H-imidazol-2-yl)-6-bromo-7-fluoro-1H-indazole (I-21)

To a stirred solution of I-20 (21.7 g, 57.5 mmol) in DMSO (120 mL) was added drop wise hydrazine hydrate (28.0 mL, 575 mmol) at room temperature. The reaction mixture was allowed to stirred at 90° C. for 3 h. After 3 h, TLC showed complete consumption of SM. The reaction mixture was diluted with ice cold water (2×500 mL) and precipitation was observed. The reaction was filtered, washed with ice cold water (500 mL) to afford the desired product as an off-white solid (20.0 g, 87% yield). $^1$H NMR (400 MHz, DMSO-d$_6$) δ 8.19 (d, J=8.7 Hz, 1H), 7.43 (s, 1H), 7.40 (dd, J=8.6, 5.8 Hz, 1H), 7.30 (t, J=7.3 Hz, 2H), 7.24 (d, J=7.1 Hz, 1H), 7.20 (d, J=1.7 Hz, 1H), 7.18 (s, 2H), 5.84 (s, 2H). (m/z): [M+H]$^+$ calcd for C$_{17}$H$_{13}$BrFN$_4$ 373.03 found 372.94.

(d) 3-(1-benzyl-1H-imidazol-2-yl)-6-bromo-7-fluoro-1-(tetrahydro-2H-pyran-2-yl)-1H-indazole (I-22)

To a stirred solution of I-21 (20.0 g, 53.9 mmol) in ethyl acetate (350 mL) was added TFA (12.4 mL, 162 mmol). Dihydropyran (23.6 mL, 269 mmol) was added drop wise at 0° C. The reaction mixture was then heated to 80° C. and stirred for 2 days. After 2 days, TLC showed complete consumption of starting material. The reaction mixture was diluted with water (400 mL) and extracted with ethyl acetate (2×300 mL). The combined organic layers were further washed with saturated aq. NaHCO$_3$ solution (800 mL), dried over anhydrous Na$_2$SO$_4$, filtered and concentrated. The crude product was purified by silica gel column chromatography (8-10% EtOAc in Heptane) to afford the desired product as an off white solid (19.5 g, 78% yield). $^1$H NMR (400 MHz, DMSO-d$_6$) δ 8.23 (d, J=8.6 Hz, 1H), 7.52 (s, 1H), 7.49 (dd, J=8.6, 5.6 Hz, 1H), 7.30 (dd, J=8.0, 6.5 Hz, 2H), 7.24 (d, J=6.6 Hz, 1H), 7.21 (d, J=2.9 Hz, 2H), 7.19 (s, 1H), 5.87 (dd, J=6.9, 2.4 Hz, 1H), 5.86 (d, J=15.3 Hz, 1H), 5.77 (d, J=15.3 Hz, 1H), 3.87-3.80 (m, 1H), 3.65 (td, J=11.1, 3.3 Hz, 1H), 2.36-2.27 (m, 1H), 2.01 (s, 1H), 1.75-1.67 (m, 1H), 1.61-1.42 (m, 1H). (m/z): [M+H]$^+$ calcd for C$_{22}$H$_{21}$BrFN$_4$O 455.09 found 455.06.

Preparation of 6-(2-ethyl-4-((2-(trimethylsilyl)ethoxy)methoxy)phenyl)-7-fluoro-1-(tetrahydro-2H-pyran-2-yl)-3-(1-((2-(trimethylsilyl)ethoxy)methyl)-1H-imidazol-2-yl)-1H-indazole (I-25)

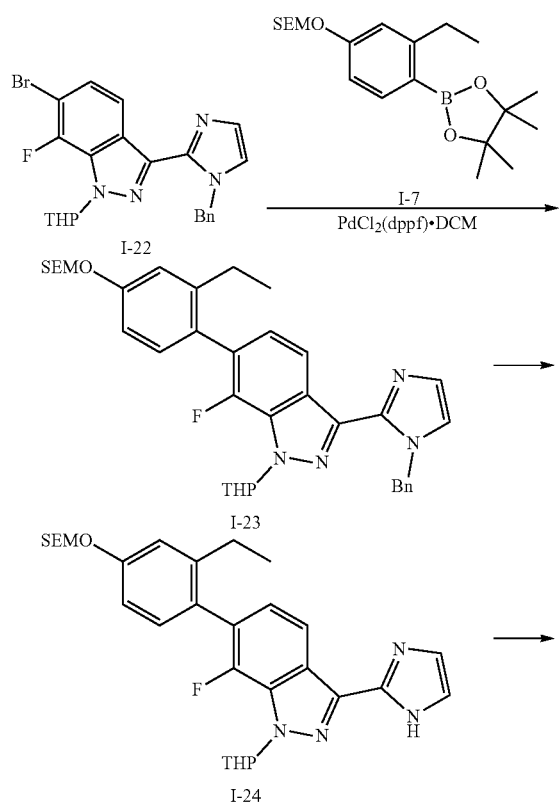

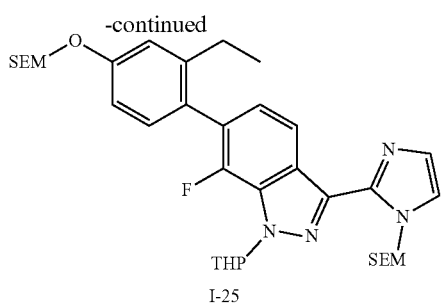

(a) 3-(1-benzyl-1H-imidazol-2-yl)-6-(2-ethyl-4-((2-(trimethylsilyl)ethoxy)methoxy)phenyl)-7-fluoro-1-(tetrahydro-2H-pyran-2-yl)-1H-indazole (I-23)

To a stirred solution of 1-22 (19.5 g, 42.8 mmol) and I-7 (17.8 g, 47.1 mmol) in dioxane (200 mL) and water (20.0 mL) was added K$_3$PO$_4$ (27.3 g, 128 mmol). The reaction mixture was purged with argon for 5 minutes, and PdCl$_2$(dppf).DCM (3.49 g, 4.28 mmol) was then added to it. The reaction was then heated to 100° C. and stirred for 16 h. TLC showed consumption of the starting material. The reaction mixture was then filtered through a pad of Celite and the residue washed with ethyl acetate (2×200 mL). The combined organics were then washed with cold water (300 mL) and brine (300 mL), dried over anhydrous Na$_2$SO$_4$ and concentrated under reduced pressure to afford the crude product which was purified by silica gel column chromatography (12% EtOAC in heptane). The desired product was isolated as a clear amorphous solid (20.0 g, 73% yield). $^1$H NMR (400 MHz, DMSO-d$_6$) δ 8.29 (d, J=8.4 Hz, 1H), 7.52 (s, 1H), 7.30 (d, J=7.2 Hz, 2H), 7.25 (d, J=6.3 Hz, 2H), 7.22 (d, J=3.6 Hz, 2H), 7.16 (d, J=8.4 Hz, 1H), 7.11 (t, J=7.2 Hz, 1H), 7.03 (d, J=2.6 Hz, 1H), 6.95 (dd, J=8.5, 2.6 Hz, 1H), 5.94-5.84 (m, 2H), 5.80 (d, J=15.4 Hz, 1H), 5.28 (s, 2H), 3.84 (s, 1H), 3.74 (t, J=8.1 Hz, 2H), 3.58 (d, J=11.9 Hz, 1H), 2.04 (d, J=14.0 Hz, 2H), 1.69 (s, 1H), 1.53 (s, 2H), 1.44 (s, 1H), 1.24 (s, 1H), 0.99 (t, J=7.5 Hz, 3H), 0.92 (t, J=8.1 Hz, 2H), 0.88-0.79 (m, 2H), 0.00 (s, 9H). (m/z): [M+H]$^+$ calcd for C$_{36}$H$_{44}$FN$_4$O$_3$Si 627.32 found 627.54.

(b) 6-(2-ethyl-4-((2-(trimethylsilyl)ethoxy)methoxy)phenyl)-7-fluoro-3-(1H-imidazol-2-yl)-1-(tetrahydro-2H-pyran-2-yl)-1H-indazole (I-24)

To a stirred solution of I-23 (20.0 g, 31.9 mmol) in isopropanol (200 mL) and THF (50.0 mL) was added 20% Pd(OH)$_2$/C (20.0 g, 163 mmol). The reaction mixture was subjected to hydrogenation using a H$_2$ balloon and was allowed to stir a room temperature for 5 h. TLC showed complete consumption of starting material. The reaction mixture was filtered through a pad of Celite and the filtrate was concentrated under reduced pressure to afford the crude desired product (18.0 g, 71% yield) as a transparent amorphous solid that was used directly in the next step without further purification. $^1$H NMR (400 MHz, DMSO-d$_6$) δ 8.23 (d, J=8.2 Hz, 1H), 7.25 (s, 2H), 7.18 (d, J=8.3 Hz, 1H), 7.12 (dd, J=8.3, 5.9 Hz, 1H), 7.04 (d, J=2.6 Hz, 1H), 6.96 (dd, J=8.4, 2.6 Hz, 1H), 5.90 (d, J=9.4 Hz, 1H), 5.76 (s, 1H), 5.29 (s, 2H), 3.95 (d, J=11.6 Hz, 1H), 3.75 (t, J=8.1 Hz, 2H), 3.65 (s, 1H), 2.44 (s, 2H), 2.09 (d, J=13.8 Hz, 2H), 1.75 (s, 1H), 1.57 (s, 2H), 1.44 (s, 1H), 1.01 (t, J=7.5 Hz, 3H), 0.91 (d, J=8.1 Hz, 2H), 0.00 (s, 9H). (m/z): [M+H]+ calcd for C29H38FN4O3Si 537.27 found 537.36.

(c) 6-(2-ethyl-4-((2-(trimethylsilyl)ethoxy)methoxy)phenyl)-7-fluoro-1-(tetrahydro-2H-pyran-2-yl)-3-(1-((2-(trimethylsilyl)ethoxy)methyl)-1H-imidazol-2-yl)-1H-indazole (I-25)

To the stirred solution of I-24 (18.0 g, 33.5 mmol) in DMF (180 mL) was added sodium hydride (2.81 g, 70.3 mmol) at 0° C. The reaction mixture was then allowed to stir at 0° C. for 30 min, after which SEMCl (8.39 g, 50.3 mmol) was then added dropwise at 0° C. The reaction mixture was allowed to warm to room temperature and stirred for 2 h. TLC showed complete consumption of the starting material. The reaction mixture was quenched with ice-water (300 mL) and extracted with ethyl acetate (2×300 mL). The combined organic layers were washed with water (400 mL) and brine (400 mL), dried over Na2SO4, and concentrated under reduced pressure to afford the crude compound which was purified by silica gel column chromatography (20-25% EtOAc in heptane). The desired product was isolated as an off white solid (18.0 g, 71% yield). 1H NMR (400 MHz, DMSO-d6) δ 8.22 (d, J=8.3 Hz, 1H), 7.53 (s, 1H), 7.21 (s, 1H), 7.17 (d, J=8.3 Hz, 1H), 7.12 (dd, J=8.3, 5.9 Hz, 1H), 7.04 (d, J=2.6 Hz, 1H), 6.96 (dd, J=8.4, 2.6 Hz, 1H), 5.99-5.88 (m, 3H), 5.29 (s, 2H), 3.92 (d, J=11.4 Hz, 1H), 3.75 (t, J=8.1 Hz, 2H), 3.67 (d, J=12.9 Hz, 1H), 3.51 (t, J=8.0 Hz, 2H), 2.43 (s, 3H), 2.19-2.11 (m, 1H), 2.06 (s, 1H), 1.76 (d, J=13.7 Hz, 2H), 1.57 (s, 2H), 1.00 (t, J=7.5 Hz, 3H), 0.92 (t, J=8.1 Hz, 2H), 0.80 (t, J=8.0 Hz, 2H), 0.00, (s, 9H),−0.15 (s, 9H). (m/z): [M+H]+ calcd for C35H52FN4O4Si2 667.35 found 667.47.

Preparation of 3-ethyl-4-(3-(4,5,6,7-tetrahydro-1H-imidazo[4,5-c]pyridin-2-yl)-1H-indazol-6-yl)phenol (I-27)

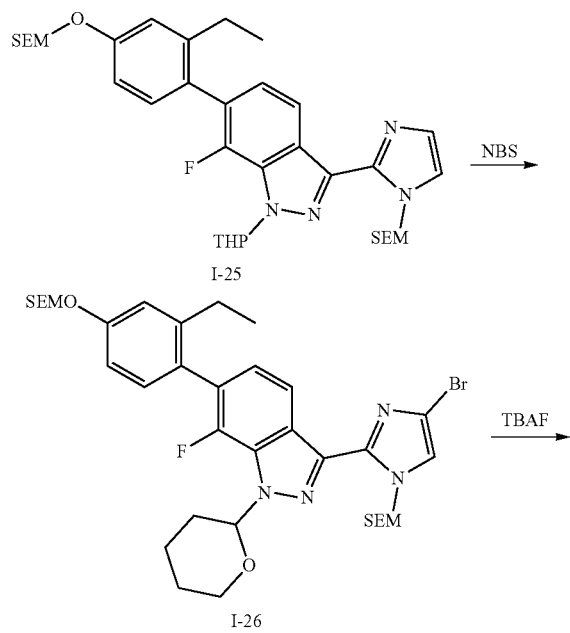

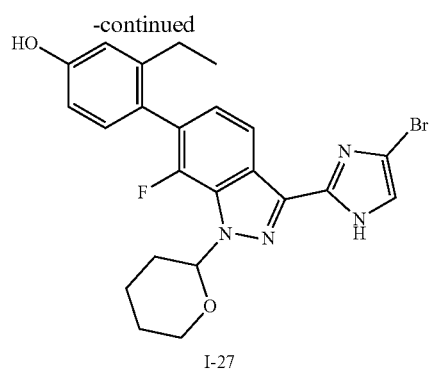

(a) 3-(4-bromo-1-((2-(trimethylsilyl)ethoxy)methyl)-1H-imidazol-2-yl)-6-(2-ethyl-4-((2-(trimethylsilyl)ethoxy)methoxy)phenyl)-7-fluoro-1-(tetrahydro-2H-pyran-2-yl)-1H-indazole (I-26)

NBS (1.60 g, 9.0 mmol) was taken up in DCM (60 mL) and added dropwise to a stirred solution of I-25 (6.0 g, 9.0 mmol) in DCM (240 mL) at 0° C. The reaction mixture was stirred at 0° C. for 5 minutes. TLC showed complete consumption of the starting material. The reaction mixture was quenched with water (100 mL) and extracted with DCM (2×300 mL). The combined organic layers were dried over anhydrous Na2SO4, filtered and evaporated to afford crude product which was purified by silica gel column chromatography (8-10% EtOAc in heptane). The desired product was isolated as a colorless amorphous solid (5.0 g, 60% yield). 1H NMR (400 MHz, DMSO-d6) δ 8.17 (d, J=8.4 Hz, 1H), 7.35 (s, 1H), 7.14 (q, J=7.6, 6.7 Hz, 2H), 7.03 (d, J=2.4 Hz, 1H), 6.96 (d, J=7.9 Hz, 1H), 5.98 (s, 1H), 5.92 (d, J=9.6 Hz, 2H), 5.28 (s, 2H), 3.92 (d, J=11.1 Hz, 1H), 3.74 (t, J=8.0 Hz, 2H), 3.66 (s, 1H), 3.51 (t, J=8.1 Hz, 2H), 2.44 (d, J=8.1 Hz, 3H), 2.15 (d, J=12.9 Hz, 1H), 2.06 (s, 1H), 1.77 (s, 1H), 1.57 (s, 2H), 0.99 (t, J=7.5 Hz, 3H), 0.92 (t, J=8.0 Hz, 2H), 0.78 (t, J=8.0 Hz, 3H), 0.00 (s, 9H), −0.17 (d, J=1.9 Hz, 9H). (m/z): [M+H]+ calcd for C35H51BrFN4O4Si2 747.26 found 747.26.

(b) 4-(3-(4-bromo-1H-imidazol-2-yl)-7-fluoro-1-(tetrahydro-2H-pyran-2-yl)-1H-indazol-6-yl)-3-ethylphenol (I-27)

To a stirred solution of 1-26 (15.0 g, 20.1 mmol) in THF (30 mL) was added TBAF (1M in THF) (52.0 mL, 18.5 mmol) at 0° C. The reaction mixture was then heated to 80° C. and stirred for 2 days. TLC indicated complete consumption of the starting material. The reaction mixture was diluted with water (500 mL) and extracted with ethyl acetate (2×500 mL). The combined organic layers were dried over Na2SO4, filtered and concentrated under reduced pressure. The crude product was purified by silica gel column chromatography (20-25% EtOAc in heptane) to afford the desired product as an off-white solid (5.25 g, 53% yield). 1H NMR (400 MHz, DMSO-d6) 9.53 (s, 1H), 8.12 (d, J=8.2 Hz, 1H), 7.44 (s, 1H), 7.13 (dd, J=8.3, 6.0 Hz, 1H), 7.04 (d, J=8.2 Hz, 1H), 6.78 (d, J=2.6 Hz, 1H), 6.70 (dd, J=8.2, 2.6 Hz, 1H), 5.93-5.86 (m, 1H), 3.95 (d, J=11.3 Hz, 1H), 3.65 (dt, J=11.8, 6.6 Hz, 1H), 2.39 (d, J=7.7 Hz, 3H), 2.09 (q, J=10.0, 7.3 Hz, 3H), 1.75 (s, 1H), 1.57 (d, J=8.6 Hz, 2H), 0.99 (t, J=7.5 Hz, 3H). (m/z): [M+H]+ calcd for C23H23BrFN4O2 487.10 found 487.35.

Preparation of tert-butyl (R)-2-(((tert-butyldiphenyl-silyl)oxy)methyl)-4-(4,4,5,5-tetramethyl-1,3,2-di-oxaborolan-2-yl)-2,5-dihydro-1H-pyrrole-1-carboxylate (I-33)

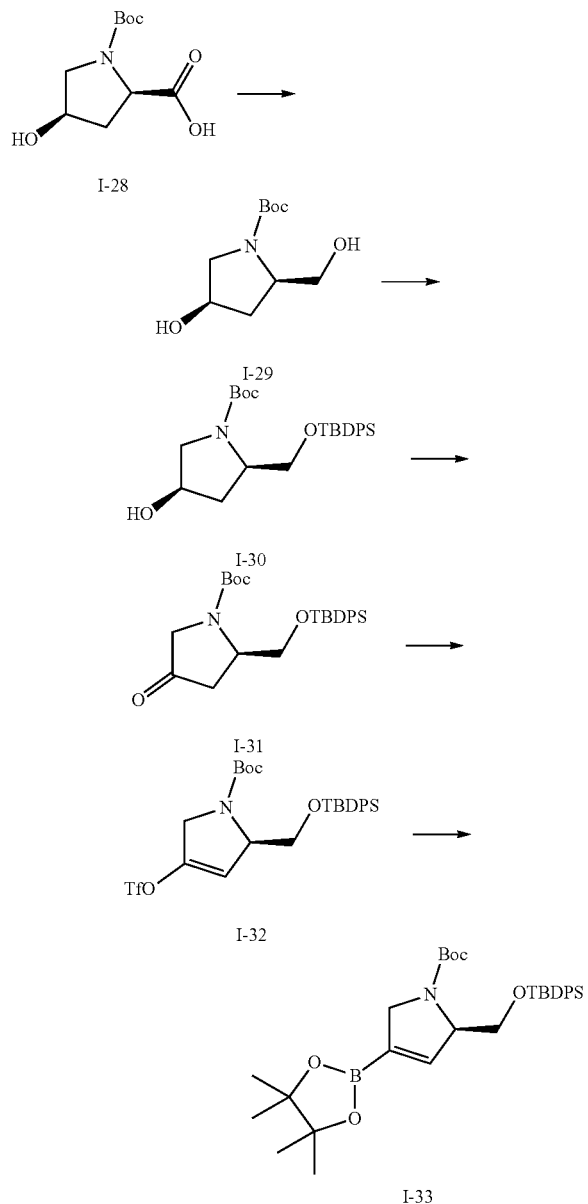

(a) tert-butyl (2R,4R)-4-hydroxy-2-(hydroxymethyl)pyrrolidine-1-carboxylate (I-29)

To a solution of (2R,4R)-1-(tert-butoxycarbonyl)-4-hydroxypyrrolidine-2-carboxylic acid (10.0 g, 43.2 mmol) (I-28) in THF (150 mL) at −10° C. was added 4-methylmorpholine (5.23 mL, 47.6 mmol), then isobutyl chloroformate (6.18 mL, 47.6 mmol) was added dropwise. The reaction mixture was then stirred at −10° C. for 1 h. The reaction mixture was filtered and the filtrate was used directly in the next step. A solution of NaBH$_4$ (8.18 g, 216 mmol) in water (30.0 mL) was added a dropwise to the reaction mixture at 0° C. The reaction mixture was then allowed to stir at room temperature overnight. After 16 h the reaction mixture was quenched by addition of saturated ammonium chloride solution (100 ml), after which the solution was extracted with EtOAc (3×200 ml). The organic layer was then dried over sodium sulfate and concentrated under reduced pressure. The crude product was then purified by silica gel chromatography, eluting with 60-70% EtOAc/heptane to provide the product (I-29) as a white solid (8.0 g, 85% yield)

(b) tert-butyl (2R,4R)-2-(((tert-butyldiphenylsilyl)oxy)methyl)-4-hydroxypyrrolidine-1-carboxylate (I-30)

To a stirred solution of tert-butyl (2R,4R)-4-hydroxy-2-(hydroxymethyl)pyrrolidine-1-carboxylate (10.0 g, 46.0 mmol) in DMF (50.0 mL) (I-29) was added 1H-imidazole (9.40 g, 138 mmol). A solution of TBDPSCl (12.5 mL, 46.0 mmol) in DMF (30.0 mL) was then added and the reaction mixture was stirred at room temperature for 16 h. The reaction mixture was then diluted with ice-cooled water and extracted with EtOAc (3×80 mL). The combined organic layers were then washed with brine, dried over sodium sulfate, and concentrated under reduced pressure. The crude product was then purified by silica gel chromatography, eluting in 20-30% EtOAc/heptane to provide the product (I-30) as a colorless liquid (6.0 g, 25% yield).

(c) tert-butyl (R)-2-(((tert-butyldiphenylsilyl)oxy)methyl)-4-oxopyrrolidine-1-carboxylate (I-31)

To a solution of tert-butyl (2R,4R)-2-(((tert-butyldiphenylsilyl)oxy)methyl)-4-hydroxypyrrolidine-1-carboxylate (6.00 g, 13.2 mmol) (I-30) in DCM (70.0 mL) at 0° C., trichloro-1,3,5-triazinane-2,4,6-trione (3.37 g, 14.5 mmol) was added and the reaction mixture was stirred at 0° C. for 2 mins. To this solution TEMPO (206 mg, 1.32 mmol) was added and the reaction mixture was stirred at 0° C. for 30 min. The reaction mixture was then filtered through celite and the pad was washed with DCM. The resulting organic filtrate was then washed with aqueous sodium carbonate solution and extracted with DCM (3×100 ml). The combined organic layers were then dried over sodium sulfate and concentrated under reduced pressure. The crude product was then purified by silica gel chromatography, eluting in 20-25% EtOAc/heptane to the product (I-31) as a white solid (5.0 g, 84% yield).

(d) tert-butyl (R)-2-(((tert-butyldiphenylsilyl)oxy)methyl)-4-(((trifluoromethyl)sulfonyl)oxy)-2,5-dihydro-1H-pyrrole-1-carboxylate (I-32)

To a stirred solution of tert-butyl (R)-2-(((tert-butyldiphenylsilyl)oxy)methyl)-4-oxopyrrolidine-1-carboxylate (5.0 g, 11.0 mmol) (I-31) in dry THF (50.0 mL) at −78° C. under a nitrogen atmosphere, NaHMDS (1M in THF) (14.3 mL, 14.3 mmol) was added dropwise and the reaction mixture was allowed to stirred at −78° C. for 45 min. Then, a solution of N-(5-chloropyridin-2-yl)-N-(methanesulfonyl)methanesulfonamide (5.63 g, 14.3 mmol) in dry THF (20.0 mL) was added dropwise at −78° C. The reaction mixture was allowed to slowly warm to room temperature and stirred for 16 h, after which TLC showed consumption of starting material. The reaction mixture was then quenched by addition of ice-cold water and the resulting solution was extracted with EtOAc (3×120 ml). The combined organic layers were then dried over sodium sulfate and concentrated under reduced pressure. The crude product was then purified by silica gel chromatography, eluting in 12-15% EtOAc/heptane to provide the product (1-32) as a colorless liquid (4.9 g, 73% yield).

(e) tert-butyl (R)-2-(((tert-butyldiphenylsilyl)oxy)methyl)-4-(4,4,5,5-tetramethyl-1,3,2-dioxaborolan-2-yl)-2,5-dihydro-1H-pyrrole-1-carboxylate (I-33)

To a stirred solution of tert-butyl (R)-2-(((tert-butyldiphenylsilyl)oxy)methyl)-4-(((trifluoromethyl)sulfonyl)oxy)-2,5-dihydro-1H-pyrrole-1-carboxylate (4.90 g, 8.37 mmol) (1-32) and bis(pinacolato)diboron (1.70 g, 6.69 mmol) in 1,4-dioxane (50.0 mL) was added potassium acetate (2.46 g, 25.1 mmol). The reaction mixture was purged with nitrogen for 10 min, then [1,1'-bis(diphenylphosphino)ferrocene]dichloropalladium(II) (612 mg, 0.1 eq., 837 µmol) was added and the reaction mixture was stirred at 110° C. for 5 h. The reaction mixture was then filtered through a pad of celite, the pad was washed with EtOAc (60 ml), and the resulting filtrate was concentrated under reduced pressure. The crude product was then purified by silica gel chromatography, eluting with 5% EtOAc/heptane to provide the product (I-33) as a pale yellow liquid (1.95 g, 40% yield). 1H NMR (400 MHz, DMSO-d6) δ 7.61-7.51 (m, 4H), 7.50-7.34 (m, 6H), 6.40 (d, J=9.5 Hz, 1H), 4.55 (d, J=19.0 Hz, 1H), 4.22-3.81 (m, 3H), 3.73 (dd, J=26.8, 8.9 Hz, 1H), 1.43 (s, 5H), 1.30 (s, 4H), 1.23 (s, 12H), 0.93 (d, J=4.9 Hz, 9H).

Preparation of tert-butyl (R)-2-(methoxymethyl)-4-(4,4,5,5-tetramethyl-1,3,2-dioxaborolan-2-yl)-2,5-dihydro-1H-pyrrole-1-carboxylate (I-42)

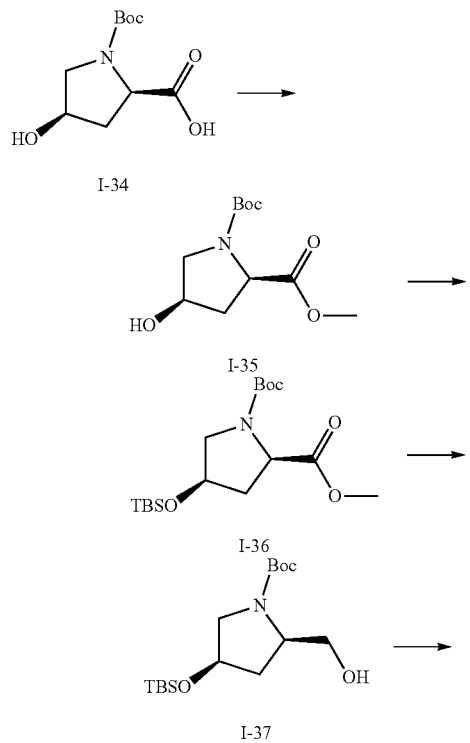

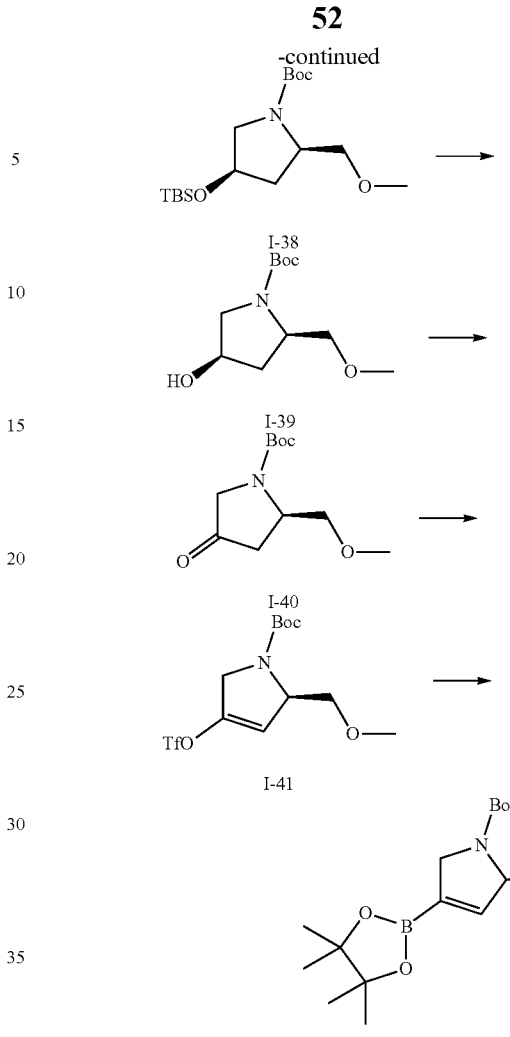

(a) 1-(tert-butyl) 2-methyl (2R,4R)-4-hydroxypyrrolidine-1,2-dicarboxylate (I-35)

To a stirred solution of (2R,4R)-1-(tert-butoxycarbonyl)-4-hydroxypyrrolidine-2-carboxylic acid (20.0 g, 86.5 mmol) (I-34) in acetonitrile (200 mL), potassium carbonate (23.9 g, 173 mmol) was added slowly at 0° C., followed by the addition of methyl iodide (24.6 g, 173 mmol). The reaction mixture was heated at 80° C. until disappearance of starting material by TLC (16 h). The reaction mixture was diluted with ice-cold water and extracted with EtOAc (3 times). The combined organic layers were then washed with brine, dried over sodium sulfate, and concentrated under reduced pressure. The crude product was then purified by silica gel chromatography, eluting with 60-70% EtOAc/heptane to provide the product (I-35) as an off white solid (21.1 g, 99% yield).

(b) 1-(tert-butyl) 2-methyl (2R,4R)-4-((tert-butyldimethylsilyl)oxy)pyrrolidine-1,2-dicarboxylate (I-36)

To an ice cold solution of 1-(tert-butyl) 2-methyl (2R,4R)-4-hydroxypyrrolidine-1,2-dicarboxylate (10.0 g, 40.8 mmol) (I-35) in dichloromethane (100 mL) was added imidazole (8.33 g, 122 mmol) and the resulting solution was stirred for 10 min. tert-butyldimethylsilyl chloride (6.76 g, 44.8 mmol) was then added slowly and the reaction mixture was stirred at room temperature until disappearance of starting material by TLC (16 h). The reaction mixture was then diluted with ice cold water (50 mL) and extracted with dichloromethane (2×100 mL). The combined organic layers were then washed with brine, dried over sodium sulfate, and concentrated under reduced pressure. The crude product was then purified by silica gel chromatography, eluting with 25% EtOAc/heptane to provide the product (I-36) (12.1 g, 77% yield).

(c) tert-butyl (2R,4R)-4-((tert-butyldimethylsilyl) oxy)-2-(hydroxymethyl)pyrrolidine-1-carboxylate (I-37)

To a stirred solution of 1-(tert-butyl) 2-methyl (2R,4R)-4-((tert-butyldimethylsilyl)oxy)pyrrolidine-1,2-dicarboxylate (12.0 g, 33.4 mmol) (I-36) in THF (120 mL) lithium borohydride (2M in THF) (41.7 mL, 2.5 eq., 83.4 mmol) was added at 0° C. The reaction mixture was then stirred at room temperature until disappearance of starting material was observed by TLC (16 h), the reaction mixture was then quenched by addition of saturated ammonium chloride solution and extracted with EtOAc (200 mL). The organic layer was then washed with brine, dried over sodium sulfate, and concentrated under vacuum. The crude product was then purified by silica gel chromatography, eluting with 20-30% EtOAc/heptane to provide the product (I-37) (11.1 g, 92% yield).

(d) tert-butyl (2R,4R)-4-((tert-butyldimethylsilyl) oxy)-2-(methoxymethyl)pyrrolidine-1-carboxylate (I-38)

To a stirred solution of tert-butyl (2R,4R)-4-((tert-butyldimethylsilyl)oxy)-2-(hydroxymethyl)pyrrolidine-1-carboxylate (5.00 g, 15.1 mmol) (1-37) in DMF (50.0 mL), sodium hydride (905 mg, 22.6 mmol) was added slowly at 0° C. and the reaction mixture was stirred for 30 min. Methyl iodide (4.28 g, 30.2 mmol) was then added dropwise and the reaction mixture was allowed to stir at room temperature until disappearance of starting material was observed by TLC (2 h). The reaction mixture was then diluted with ice-cold water and extracted with EtOAc (3 times). The combined organic layers were then washed with brine, dried over sodium sulfate, and concentrated under vacuum. The crude product was then purified by silica gel chromatography, eluting with 25% EtOAc/heptane to provide the product (I-38) (4.1 g, 69% yield).

(e) tert-butyl (2R,4R)-4-hydroxy-2-(methoxymethyl)pyrrolidine-1-carboxylate (I-39)

To a stirred solution of tert-butyl (2R,4R)-4-((tert-butyldimethylsilyl)oxy)-2-(methoxymethyl)pyrrolidine-1-carboxylate (4.00 g, 11.6 mmol) (I-38) in THF (40.0 mL), tetra-N-butylammonium fluoride (1M in THF) (23.2 mL, 23.2 mmol) was added at 0° C. The reaction mixture was then stirred at room temperature until disappearance of starting material was observed by TLC (16 h). The reaction mixture was then diluted with cold water and extracted with EtOAc. The organic layer was then washed with brine, dried over sodium sulfate, and concentrated under reduced pressure. The crude product was then purified by silica gel chromatography, eluting at 25-30% EtOAc/hexane to provide the product (I-39) (2.6 g, 86% yield).

(f) tert-butyl (R)-2-(methoxymethyl)-4-oxopyrrolidine-1-carboxylate (I-40)

To a stirred solution of tert-butyl (2R,4R)-4-hydroxy-2-(methoxymethyl)pyrrolidine-1-carboxylate (7.90 g, 34.2 mmol) (I-39) in dichloromethane (80.0 mL) was added Dess-Martin periodinane (29.0 g, 68.3 mmol) and the reaction mixture was stirred at room temperature until disappearance of starting material was observed by TLC (16 h). The reaction mixture was then filtered through a pad of celite, rinsing with dichloromethane. The filtrate was then washed with ice cold water, after which the organic layer was dried over sodium sulfate and concentrated under reduced pressure. The crude product was then purified by silica gel chromatography, eluting at 15% EtOAc/heptane to provide the product (I-40) (6.6 g, 62% yield).

(g) tert-butyl (R)-2-(methoxymethyl)-4-(((trifluoromethyl)sulfonyl)oxy)-2,5-dihydro-1H-pyrrole-1-carboxylate (I-41)

To a stirred solution of tert-butyl (R)-(methoxymethyl)-4-oxopyrrolidine-1-carboxylate (6.50 g, 28.4 mmol) (I-40) in THF (70.0 mL) sodium bis(trimethylsilyl)amide (1 M in THF) (31.2 mL, 31.2 mmol) was added at −78° C. under a nitrogen atmosphere and the reaction mixture was stirred for 30 min. A solution of N-(5-chloropyridin-2-yl)-N-(methanesulfonyl)methanesulfonamide (12.3 g, 31.2 mmol) in THF (5.0 ml) was then added drop-wise at −78° C. The reaction mixture was stirred for 30 min at −78° C., then allowed to warm to room temperature and stirred until disappearance of starting material was observed by TLC (16 h). The reaction mixture was then quenched by addition of ice-cold water and extracted with EtOAc. The organic layer was then washed with brine, dried over sodium sulfate, and concentrated under reduced pressure. The crude product was then purified by silica gel chromatography, eluting at 15% EtOAc/heptane to provide the product (1-41) (5.8 g, 48% yield).

(h) tert-butyl (R)-2-(methoxymethyl)-4-(4,4,5,5-tetramethyl-1,3,2-dioxaborolan-2-yl)-2,5-dihydro-1H-pyrrole-1-carboxylate (I-42)

To a stirred solution of tert-butyl (R)-2-(methoxymethyl)-4-(((trifluoromethyl)sulfonyl)oxy)-2,5-dihydro-1H-pyrrole-1-carboxylate (5.80 g, 16.1 mmol) (I-41) in 1,4-dioxane (58.0 mL) was added bis(pinacolato)diboron (4.08 g, 16.1 mmol) and potassium acetate (3.15 g, 32.1 mmol). The reaction mixture was then purged with argon for 10 minutes followed by the addition of 1,1'-bis(diphenylphosphino) ferrocene-palladium(II)dichloride dichloromethane (1.31 g, 1.61 mmol). The reaction mixture was then stirred at 110° C. until judged complete by TLC and LCMS (4 h). The reaction mixture was then filtered through a pad of celite, which was then rinsed with EtOAc. The filtrate was then concentrated under reduced pressure and the resulting crude product was purified by silica gel chromatography, eluting at 5% EtOAc/heptane to provide the product (I-42) (1.9 g, 34% yield). 1H NMR (400 MHz, DMSO-d6) δ 6.35 (s, 1H), 4.53 (s, 1H), 4.10 (d, J=15.2 Hz, 1H), 4.01-3.85 (m, 1H), 3.61-3.51 (m, 1H), 3.47-3.36 (m, 1H), 3.23 (d, J=7.3 Hz, 3H), 1.41 (s, 9H), 1.22 (s, 12H).

Preparation of 2-(4-(benzyloxy)-2-ethyl-5-fluorophenyl)-4,4,5,5-tetramethyl-1,3,2-dioxaborolane (I-49)

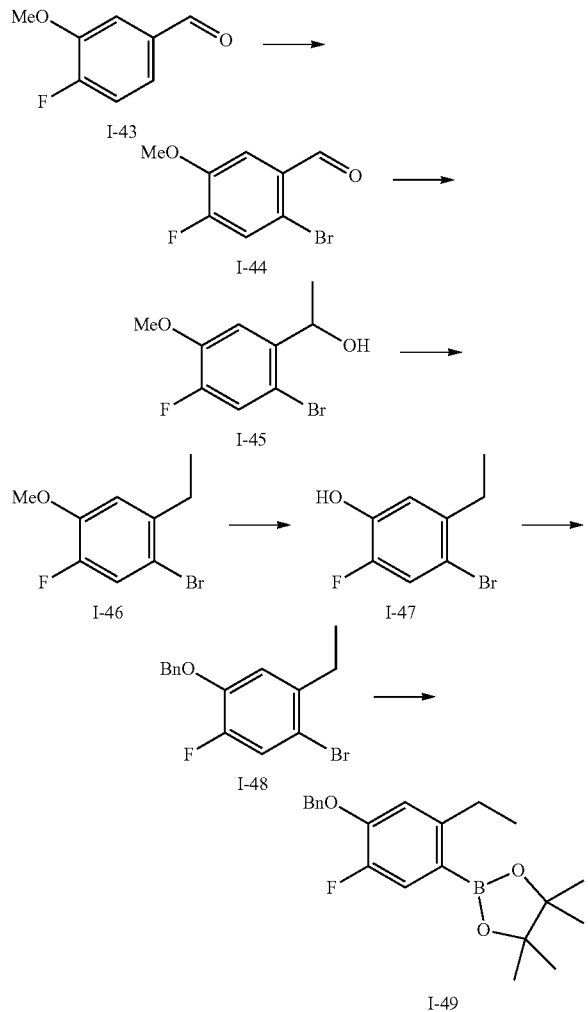

(a) 2-bromo-4-fluoro-5-methoxybenzaldehyde (I-44)

To a stirred solution of 4-fluoro-3-methoxybenzaldehyde (100 g, 648 mmol) (I-43) in water (800 mL) was added KBr (231 g, 1946 mmol). The suspension was stirred at room temperature for 30 min, after which Br$_2$ (66.9 mL, 1297 mmol) was added drop wise at room temperature. The resulting solution was allowed to stir at room temperature for 1 h. TLC showed complete consumption of the starting material. The product precipitated out of solution and was collected by filtration and washed with water (2×300 mL), dried under reduced pressure to afford the desired product as a pale yellow solid (135 g, 89% yield). $^1$H NMR (400 MHz, Chloroform-d) δ 10.24 (s, 1H), 7.53 (d, J=8.9 Hz, 1H), 7.37 (d, J=10.0 Hz, 1H), 3.93 (s, 3H).

(b) 1-(2-bromo-4-fluoro-5-methoxyphenyl)ethan-1-ol (I-45)

To a solution of compound of I-44 (90.0 g, 386 mmol) in dry THF (600 mL) was added 3.0 M MeMgCl (386 mL, 1158 mmol) drop wise at 0° C. The resulting reaction mixture was allowed to warm to room temperature and stirred for 16 h. TLC showed complete consumption of the starting material. The reaction mixture was carefully quenched with saturated NH$_4$Cl solution (800 mL), and further diluted with water (300 mL). The mixture was extracted with ethyl acetate (3×500 mL), dried over Na$_2$SO$_4$, and concentrated under reduced pressure to afford the desired product as a colorless liquid (80 g, 83% yield). The reaction was used directly in the subsequent step without further purification. $^1$H NMR (400 MHz, DMSO-d$_6$) δ 7.47 (d, J=10.8 Hz, 1H), 7.33 (d, J=9.3 Hz, 1H), 5.50 (s, 1H), 4.88 (d, J=6.5 Hz, 1H), 3.85 (s, 3H), 1.28 (d, J=6.3 Hz, 3H).

(c) 1-bromo-2-ethyl-5-fluoro-4-methoxybenzene (I-46)

To a stirred solution of compound I-45 (72.0 g, 289 mmol) in DCM (800 mL) was added Et$_3$SiH (116 mL, 723 mmol) at 0° C. followed by TFA (178 mL, 2312 mmol). The resulting reaction mixture was stirred at room temperature for 16 h. TLC indicated complete consumption of the starting material. The reaction mixture was concentrated under reduced pressure and the crude was dissolved in EtOAc (400 mL) and washed with water (400 mL), sat. NaHCO$_3$ solution (400 mL) and brine (400 mL). The organic layer was dried over Na$_2$SO$_4$, concentrated under reduced pressure and purified by silica gel column chromatography (1-2% EtOAc in hexanes) to afford the desired product (42.0 g, 65% yield). $^1$H NMR (400 MHz, Chloroform-d) δ 7.25 (d, J=10.9 Hz, 1H), 6.82 (d, J=8.8 Hz, 1H), 3.88 (s, 3H), 2.70 (q, J=7.6 Hz, 2H), 1.22 (q, J=7.6 Hz, 3H).

(d) 4-bromo-5-ethyl-2-fluorophenol (I-47)

To stirred a solution of compound I-46 (42.0 g, 180 mmol) in DCM (150 mL) was added BBr$_3$ (26.0 mL, 270.38 mmol) at 0° C. The reaction mixture was allowed to stir at room temperature for 16 h. The reaction mixture was carefully quenched with drop wise addition of MeOH at 0° C. The reaction mixture was then diluted with water (200 mL) and extracted with DCM (2×300 mL). The combined organic layers were dried over anhydrous Na$_2$SO$_4$ and concentrated under reduced pressure to afford the crude product as a green liquid (30.0 g, 76% yield) which was used directly in the next step without further purification. $^1$H NMR (400 MHz, Chloroform-d) δ 7.25 (d, J=10.1 Hz, 1H), 6.89 (d, J=9.2 Hz, 1H), 5.15 (s, 1H), 2.65 (q, J=7.6 Hz, 2H), 1.18 (t, J=7.6 Hz, 3H). (m/z): [M+H]$^+$ calcd for C$_8$H$_9$BrFO 218.98 found 218.91.

(e) 1-(benzyloxy)-4-bromo-5-ethyl-2-fluorobenzene (I-48)

To a solution of compound of I-47 (22 g, 100.4 mmol) in ACN (200 mL) was added K$_2$CO$_3$ (27.7 g, 200.9 mmol) followed by BnBr (13.9 mL, 120.5 mmol) at room temperature. The resulting reaction mixture was heated to 80° C. and stirred for 2 It. TLC indicated the complete consumption of the starting material. The reaction mixture was diluted with water (300 mL) and extracted with EtOAc (3×200 mL). The combined organic layers were dried over Na$_2$SO$_4$, concentrated under reduced pressure, and purified by silica gel flash column chromatography (3-5% EtOAc in heptane) to afford the desired product (20.0 g, 65% yield). $^1$H NMR (400 MHz, Chloroform-d) δ 7.38 (m, 5H), 7.27 (d, J=10.4 Hz, 1H), 6.88 (d, J=8.7 Hz, 1H), 5.12 (s, 2H), 2.67 (q, J=7.5 Hz, 2H), 1.17 (t, J=7.6 Hz, 3H).

(f) 2-(4-(benzyloxy)-2-ethyl-5-fluorophenyl)-4,4,5,5-tetramethyl-1,3,2-dioxaborolane (I-49)

To a solution of I-48 (15.0 g, 48.5 mmol) in dioxane (150 mL) were added bis(pinacolato)diboron (12.32 g, 48.5 mmol) and KOAc (14.3 g, 145.6 mmol). The reaction mixture was sparged with argon for 5 min, then PdCl$_2$(dppf)·DCM (3.9 g, 4.84 mmol) was added. The reaction mixture was heated to 110° C. and stirred for 16 h under an argon atmosphere. TLC showed complete consumption of the starting material. The reaction mixture was filtered through a pad of Celite and washed with ethyl acetate. The filtrate was then diluted with ethyl acetate (100 mL) and washed with water (50 mL) and brine (50 mL), then dried over Na$_2$SO$_4$ and concentrated under reduced pressure. The crude was then purified by silica gel column chromatography (3-5% EtOAc in heptane) to afford the desired product as an off-white solid (12.0 g, 69% yield). $^1$H NMR (400 MHz, Chloroform-d) δ 7.48 (d, J=12.1 Hz, 1H), 7.45 (d, J=7.3 Hz, 2H), 7.38 (t, J=7.3 Hz, 2H), 7.35-7.28 (m, 1H), 6.82 (d, J=7.9 Hz, 1H), 5.16 (s, 2H), 2.84 (q, J=7.5 Hz, 2H), 1.32 (s, 12H), 1.14 (t, J=7.5 Hz, 3H).

Preparation of 4-(3-(4-bromo-1H-imidazol-2-yl)-7-fluoro-1-(tetrahydro-2H-pyran-2-yl)-1H-indazol-6-yl)-5-ethyl-2-fluorophenol (I-54)

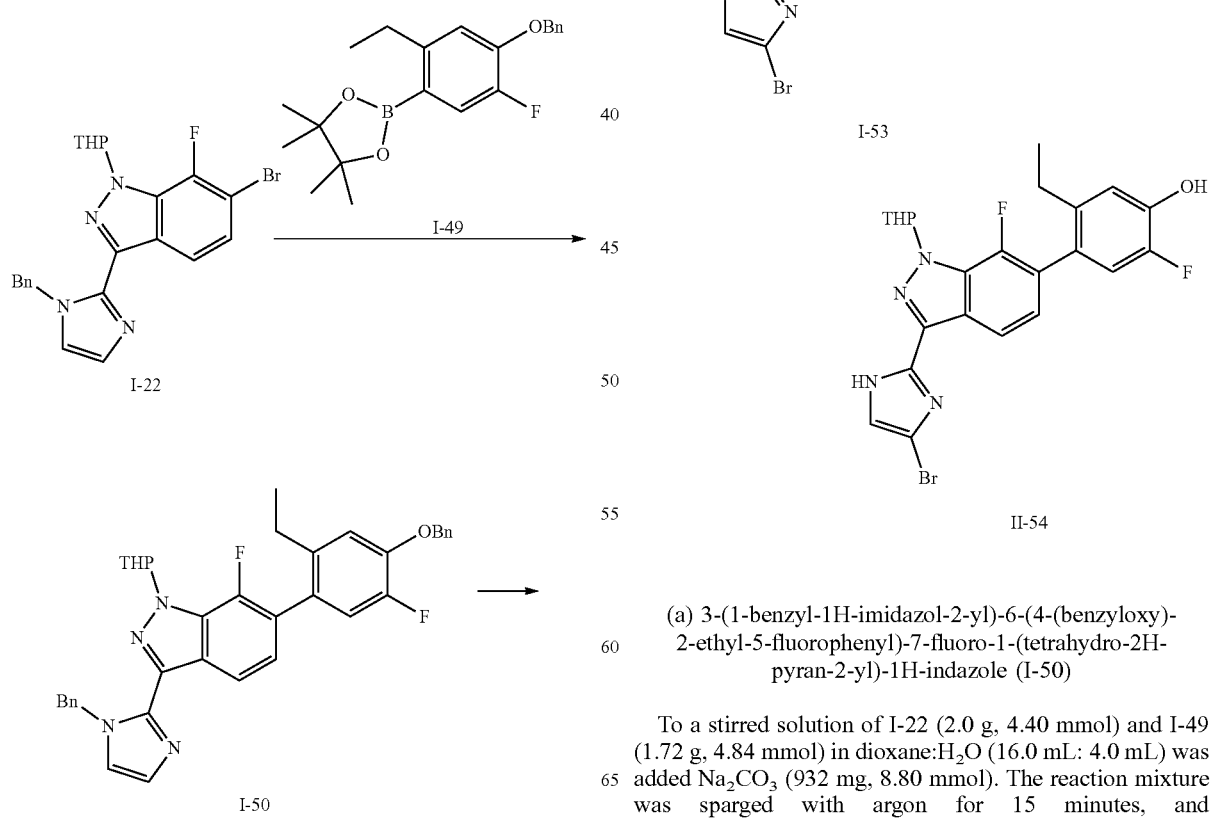

(a) 3-(1-benzyl-1H-imidazol-2-yl)-6-(4-(benzyloxy)-2-ethyl-5-fluorophenyl)-7-fluoro-1-(tetrahydro-2H-pyran-2-yl)-1H-indazole (I-50)

To a stirred solution of I-22 (2.0 g, 4.40 mmol) and I-49 (1.72 g, 4.84 mmol) in dioxane:H$_2$O (16.0 mL: 4.0 mL) was added Na$_2$CO$_3$ (932 mg, 8.80 mmol). The reaction mixture was sparged with argon for 15 minutes, and PdCl$_2$(dppf)·DCM (360 mg, 0.44 mmol) was then added to the reaction mixture. The reaction mixture was then heated to 100° C. and stirred for 5 h under an argon atmosphere. LCMS and TLC showed complete consumption of starting material. The reaction mixture was then filtered through a pad of Celite and the residue washed with ethyl acetate. The filtrate was diluted with ethyl acetate (200 mL) and washed with cold water (200 mL) and brine (200 mL). The organic layer was dried over anhydrous $Na_2SO_4$, concentrated under reduced pressure and purified by silica gel column chromatography (11% EtOAc in heptane) to afford the product as an off-white solid (2.0 g, 76% yield). $^1$H NMR (400 MHz, DMSO-$d_6$) δ 8.30 (d, J=8.5 Hz, 1H), 7.55-7.48 (m, 3H), 7.44 (t, J=7.4 Hz, 2H), 7.40-7.33 (m, 1H), 7.30 (d, J=6.6 Hz, 2H), 7.26 (d, J=5.4 Hz, 1H), 7.23 (d, J=8.6 Hz, 4H), 7.18-7.09 (m, 2H), 5.90 (d, J=15.4 Hz, 1H), 5.88 (s, 2H), 5.80 (d, J=15.4 Hz, 1H), 5.26 (s, 2H), 3.84 (s, 1H), 3.61 (t, J=10.6 Hz, 1H), 3.31 (d, J=9.4 Hz, 1H), 2.42 (d, J=7.4 Hz, 2H), 2.36 (s, 1H), 2.02 (s, 1H), 1.69 (s, 1H), 1.53 (s, 1H), 0.99 (t, J=7.5 Hz, 3H). (m/z): [M+H]$^+$ calcd for $C_{37}H_{35}F_2N_4O_2$ 605.27 found 605.94.

(b) 5-ethyl-2-fluoro-4-(7-fluoro-3-(1H-imidazol-2-yl)-1-(tetrahydro-2H-pyran-2-yl)-1H-indazol-6-yl)phenol (I-51)

To a stirred solution of I-50 (2.0 g, 3.31 mmol) in IPA:THF (15 mL:5 mL) was added 20% Pd(OH)$_2$/C (1.5 g). The reaction mixture was subjected to hydrogenation using a $H_2$ balloon and was allowed to stir at room temperature for 16 h. TLC showed complete consumption of starting material. The reaction mixture was filtered through a pad of Celite and the filtrate was concentrated under reduced pressure to afford the desired product as an off-white solid (1.4 g, 99% yield). The product was used directly in the next step without further purification. $^1$H NMR (400 MHz, DMSO-$d_6$) δ 8.22 (d, J=8.3 Hz, 1H), 7.21 (s, 1H), 7.11 (dd, J=8.2, 5.9 Hz, 1H), 7.02 (d, J=11.8 Hz, 1H), 6.94 (d, J=9.1 Hz, 1H), 5.89 (d, J=9.4 Hz, 1H), 3.95 (d, J=11.3 Hz, 1H), 3.66 (dt, J=11.5, 6.5 Hz, 1H), 3.38 (q, J=7.0 Hz, 1H), 2.56 (d, J=11.7 Hz, 1H), 2.36 (q, J=7.6 Hz, 2H), 2.11 (d, J=11.9 Hz, 2H), 1.76 (s, 1H), 1.57 (s, 2H), 1.09 (t, J=7.1 Hz, 1H), 0.98 (t, J=7.5 Hz, 3H). (m/z): [M+H]$^+$ calcd for $C_{23}H_{23}F_2N_4O_2$ 425.18 found 425.10.

(c) 6-(2-ethyl-5-fluoro-4-((2-(trimethylsilyl)ethoxy)methoxy)phenyl)-7-fluoro-1-(tetrahydro-2H-pyran-2-yl)-3-(1-((2-(trimethylsilyl)ethoxy)methyl)-1H-imidazol-2-yl)-1H-indazole (I-52)

To the stirred solution of I-51 (1.4 g, 3.30 mmol) in DMF (20.0 mL) was added NaH (528 mg, 13.2 mmol) at 0° C. The reaction mixture was then allowed to stir at 0° C. for 30 min, and SEMCl (1.76 mL, 9.90 mmol) was then added drop wise. The reaction mixture was then warmed to room temperature and stirred for 2 h. TLC indicated the complete consumption of the starting material. The reaction mixture was quenched with ice cold water and extracted with ethyl acetate (200 mL). The organic layer was washed with sat. brine (200 mL), dried over $Na_2SO_4$, concentrated under reduced pressure and purified by silica gel column chromatography (10% EtOAc in heptane) to afford the desired product as a clear amorphous solid (1.5 g, 66% yield). $^1$H NMR (400 MHz, DMSO-$d_6$) δ 8.24 (d, J=8.2 Hz, 1H), 7.52 (d, J=1.3 Hz, 1H), 7.27 (d, J=8.5 Hz, 1H), 7.22-7.10 (m, 3H), 5.93 (t, J=8.7 Hz, 4H), 5.36 (s, 2H), 3.92 (d, J=11.3 Hz, 1H), 3.79 (t, J=8.0 Hz, 2H), 3.66 (s, 1H), 3.52 (t, J=8.0 Hz, 2H), 3.28 (d, J=7.5 Hz, 2H), 2.42 (d, J=7.8 Hz, 2H), 2.15 (d, J=14.1 Hz, 1H), 2.08 (d, J=13.2 Hz, 1H), 1.77 (s, 1H), 1.58 (s, 2H), 0.99 (t, J=7.5 Hz, 3H), 0.93 (t, J=8.0 Hz, 2H), 0.80 (t, J=8.0 Hz, 2H), 0.00 (s, 9H), −0.14 (s, 9H). (m/z): [M+H]$^+$ calcd for $C_{35}H_{52}F_2N_4O_4Si_2$ 685.34 found 685.18.

(d) 3-(4-bromo-1-((2-(trimethylsilyl)ethoxy)methyl)-1H-imidazol-2-yl)-6-(2-ethyl-5-fluoro-4-((2-(trimethylsilyl)ethoxy)methoxy)phenyl)-7-fluoro-1-(tetrahydro-2H-pyran-2-yl)-1H-indazole (I-53)

A stirred solution of I-52 (1.5 g, 2.19 mmol) in DCM (60 mL) was cooled to 0° C. In a separate vial, recrystallized NBS (390 mg, 2.19 mmol) was dissolved in DCM (15.0 mL) and was added to the reaction mixture dropwise. The reaction mixture was stirred at 0° C. for 5 min. TLC indicated conversion of the starting material. The reaction mixture was quenched with water and extracted with DCM (200 mL). The organic layer was dried over $Na_2SO_4$, concentrated under reduced pressure, and purified by silica gel column chromatography (8.5% EtOAc in heptane) to obtain the desired product as a clear amorphous solid (1.3 g, 77% yield). $^1$H NMR (400 MHz, DMSO-$d_6$) δ 8.19 (d, J=8.3 Hz, 1H), 7.35 (s, 1H), 7.27 (d, J=8.6 Hz, 1H), 7.15 (d, J=10.5 Hz, 2H), 5.98 (s, 1H), 5.93 (d, J=9.8 Hz, 2H), 5.36 (s, 2H), 3.93 (d, J=11.3 Hz, 1H), 3.79 (t, J=8.0 Hz, 2H), 3.66 (s, 1H), 3.52 (t, J=8.0 Hz, 2H), 3.30 (d, J=7.5 Hz, 2H), 2.41 (d, J=7.9 Hz, 2H), 2.15 (d, J=12.9 Hz, 1H), 2.06 (s, 1H), 1.78 (s, 1H), 1.58 (s, 2H), 0.99 (t, J=7.5 Hz, 3H), 0.93 (t, J=8.0 Hz, 2H), 0.78 (t, J=8.1 Hz, 2H), 0.00 (s, 9H), −0.17 (s, 9H). (m/z): [M+H]$^+$ calcd for $C_{35}H_{50}BrF_2N_4O_4Si_2$ 765.25 found 765.88.

(e) 4-(3-(4-bromo-1H-imidazol-2-yl)-7-fluoro-1-(tetrahydro-2H-pyran-2-yl)-1H-indazol-6-yl)-5-ethyl-2-fluorophenol (I-54)

To a stirred solution of I-53 (1.3 g, 1.70 mmol) in THF (10 mL) was added 1.0 M TBAF (13 mL) at room temperature. The reaction mixture was heated to 80° C. and stirred for 16 h. TLC indicated the complete consumption of starting material. The reaction mixture was diluted with water (200 mL) and extracted with ethyl acetate (2×100 mL). The combined organic layers were dried over $Na_2SO_4$, concentrated under reduced pressure and purified by silica gel column chromatography (18% EtOAc in heptane) to afford the desired product as an off-white solid (625 mg, 72% yield). $^1$H NMR (400 MHz, DMSO-$d_6$) δ 13.20 (s, 1H), 9.98 (s, 1H), 8.13 (d, J=8.2 Hz, 1H), 7.44 (s, 1H), 7.15 (dd, J=8.3, 6.0 Hz, 1H), 7.06 (d, J=11.6 Hz, 1H), 6.96 (dd, J=9.1, 2.2 Hz, 1H), 5.90 (dd, J=9.9, 2.3 Hz, 1H), 3.95 (d, J=11.6 Hz, 1H), 3.71-3.60 (m, 1H), 3.30 (d, J=7.5 Hz, 2H), 2.37 (q, J=7.8 Hz, 2H), 2.11 (d, J=12.3 Hz, 2H), 1.74 (s, 1H), 1.60-1.54 (m, 2H), 0.98 (t, J=7.5 Hz, 3H). (m/z): [M+H]$^+$ calcd for $C_{23}H_{22}BrF_2N_4O_2$ 503.09 found 502.94.

General Procedures for the Preparation of Compounds

Suzuki Coupling Reactions

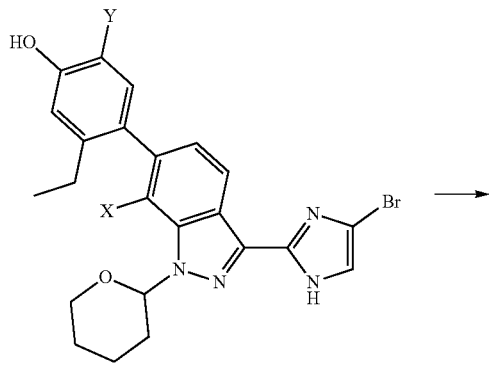

X = H, F
Y = H, F

The starting material, 4-(3-(4-bromo-1H-imidazol-2-yl)-1-(tetrahydro-2H-pyran-2-yl)-1H-indazol-6-yl)-3-ethylphenol (I-17), 4-(3-(4-bromo-1H-imidazol-2-yl)-7-fluoro-1-(tetrahydro-2H-pyran-2-yl)-1H-indazol-6-yl)-3-ethylphenol (I-27), or 4-(3-(4-bromo-1H-imidazol-2-yl)-7-fluoro-1-(tetrahydro-2H-pyran-2-yl)-1H-indazol-6-yl)-5-ethyl-2-fluorophenol (I-54) (1 eq) and a boronic acid or ester (1.5 eq) were dissolved in sufficient 1,4-dioxane to achieve a concentration of approximately 0.15 mmol of I-17/I-27. Sodium carbonate was then dissolved in water (volume equal to about ⅓ the volume of 1,4-dioxane used), and the resulting solution was added to the 1,4-dioxane solution. The reaction flask was then purged with nitrogen. Methanesulfonato(2-dicyclohexylphosphino-2',4',6'-tri-i-propyl-1,1'-biphenyl)(2'-methylamino-1,1'-biphenyl-2-yl)palladium(II) (0.05 eq) was added, and the reaction mixture was stirred and heated at 110° C. until the reaction was judged complete by LCMS (8-24 hours). The reaction mixture was then partitioned between dichloromethane and saturated sodium bicarbonate solution, and the dichloromethane layer was collected, dried over sodium sulfate, then concentrated by rotary evaporation. The resulting crude product was then purified by silica gel chromatography (0-10% methanol/dichloromethane gradient).

Deprotection Reactions

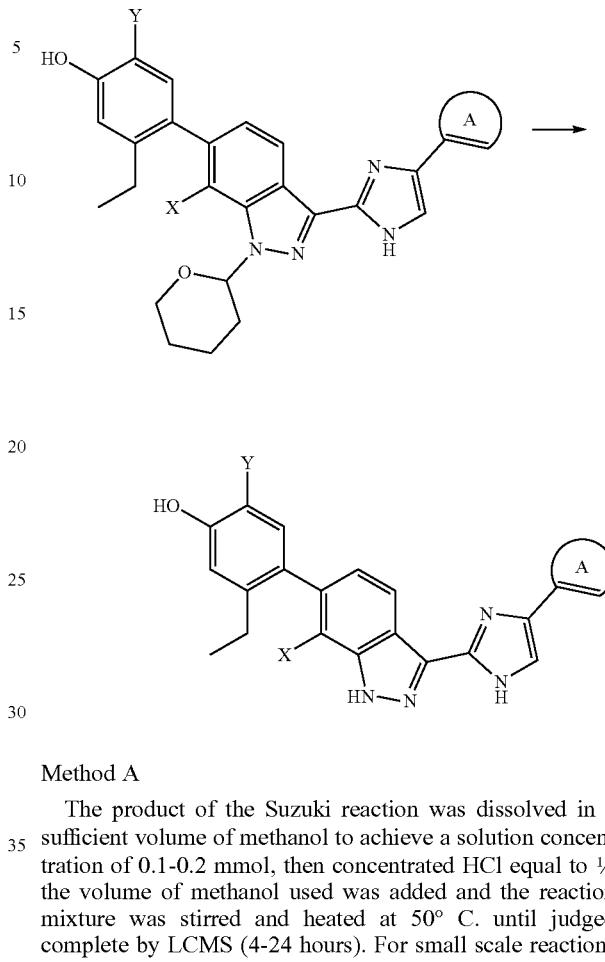

Method A

The product of the Suzuki reaction was dissolved in a sufficient volume of methanol to achieve a solution concentration of 0.1-0.2 mmol, then concentrated HCl equal to ½ the volume of methanol used was added and the reaction mixture was stirred and heated at 50° C. until judged complete by LCMS (4-24 hours). For small scale reactions (solution volume <5 mL) the reaction mixtures were then partially concentrated to remove the bulk of the methanol, and the resulting solutions were diluted with acetonitrile/water mixtures and purified by reverse phase chromatography (5-70% acetonitrile/water gradient with 0.05% TFA). For larger scale reactions the reaction mixture was dripped into a solution of aqueous ammonia (concentrated ammonia solution diluted 1:5 in water) to precipitate out the product, which was then collected by filtration. The resulting solid was then purified by reverse phase chromatography (5-70% acetonitrile/water gradient with 0.05% TFA).

Method B

The product of the Suzuki reaction was dissolved in a mixture of of 4 M HCl in 1,4-dioxane (30-40 eq) and water (20% of the volume of the HCl/dioxane solution), then the reaction mixture was stirred and heated at 60° C. until judged complete by LCMS (8-48 hours). The reaction mixture was then frozen and lyophilized, and the resulting solid was purified by reverse phase chromatography (0-70% acetonitrile/water gradient with 0.05% TFA).

Method C

The product of the Suzuki reaction was dissolved in TFA (30-50 eq) and the reaction mixture was stirred at room temperature until judged complete by LCMS (1-24 hours). The reaction mixture was then concentrated by rotary evaporation and the crude product was purified by preparative HPLC (5-70% acetonitrile/water gradient with 0.05% TFA).

Example 1: 4-(3-(4-(2,5-dihydro-1H-pyrrol-3-yl)-1H-imidazol-2-yl)-7-fluoro-1H-indazol-6-yl)-3-ethylphenol (1)

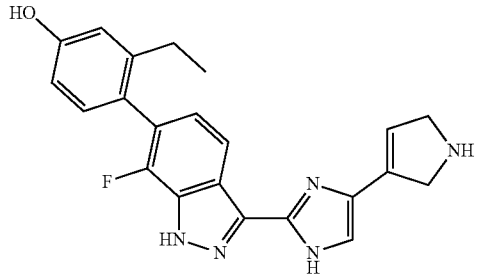 [SMILES: CCc1cc(O)ccc1-c1ccc2c(-c3nc(C4=CCNC4)c[nH]3)n[nH]c2c1F]

The general procedure was followed using 1.20 mmol of I-27, using tert-butyl 3-(4,4,5,5-tetramethyl-1,3,2-dioxaborolan-2-yl)-2,5-dihydro-1H-pyrrole-1-carboxylate as the boronic ester and Method B for deprotection to provide the TFA salt of the title compound (341 mg, 57% yield). (m/z): [M+H]$^+$ calcd for $C_{22}H_{20}FN_5O$ 390.17 found 390.2. $^1$H NMR (601 MHz, Methanol-d$_4$) δ 7.94 (d, J=8.3 Hz, 1H), 7.54 (s, 1H), 7.05 (t, J=6.3 Hz, 1H), 6.96 (d, J=8.2 Hz, 1H), 6.72 (s, 1H), 6.62 (d, J=8.2 Hz, 1H), 6.38 (s, 1H), 4.39 (s, 2H), 4.22 (s, 2H), 2.38 (q, J=7.6 Hz, 2H), 0.95 (t, J=7.5 Hz, 3H).

Example 2: 3-ethyl-4-(7-fluoro-3-(4-(1,2,3,6-tetrahydropyridin-4-yl)-1H-imidazol-2-yl)-1H-indazol-6-yl)phenol (2)

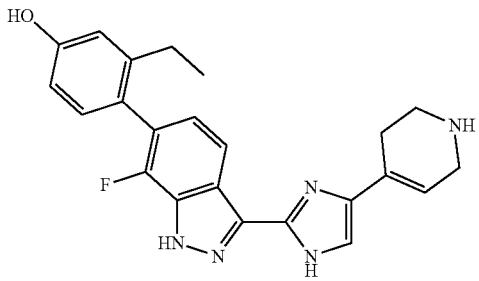 [SMILES: CCc1cc(O)ccc1-c1ccc2c(-c3nc(C4=CCNCC4)c[nH]3)n[nH]c2c1F]

The general procedure was followed using 4.12 mmol of I-27, using tert-butyl 4-(4,4,5,5-tetramethyl-1,3,2-dioxaborolan-2-yl)-3,6-dihydropyridine-1(2H)-carboxylate as the boronic ester and Method A for deprotection to provide the TFA salt of the title compound (1.39 g, 62% yield). (m/z): [M+H]$^+$ calcd for $C_{23}H_{22}FN_5O$ 404.18 found 404.1. $^1$H NMR (601 MHz, Methanol-d$_4$) δ 7.89 (d, J=8.3 Hz, 1H), 7.59 (s, 1H), 7.08 (dd, J=8.3, 6.1 Hz, 1H), 6.96 (d, J=8.2 Hz, 1H), 6.71 (s, 1H), 6.63 (d, J=8.2 Hz, 1H), 6.45 (s, 1H), 3.85 (s, 2H), 3.42 (t, J=6.1 Hz, 2H), 2.76 (s, 2H), 2.38 (q, J=7.5 Hz, 2H), 0.94 (t, J=7.6 Hz, 3H).

Example 3: 3-ethyl-4-(3-(4-(1,2,3,6-tetrahydropyridin-4-yl)-1H-imidazol-2-yl)-1H-indazol-6-yl)phenol (3)

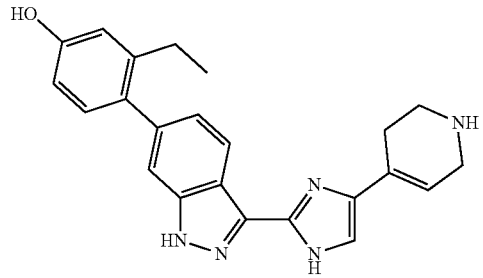 [SMILES: CCc1cc(O)ccc1-c1ccc2c(-c3nc(C4=CCNCC4)c[nH]3)n[nH]c2c1]

The general procedure was followed using 4.28 mmol of 1-17, using tert-butyl 4-(4,4,5,5-tetramethyl-1,3,2-dioxaborolan-2-yl)-3,6-dihydropyridine-1(2H)-carboxylate as the boronic ester and Method A for deprotection to provide the TFA salt of the title compound (1.17 g, 55% yield). (m/z): [M+H]$^+$ calcd for $C_{23}H_{23}N_5O$ 386.19 found 386.1. $^1$H NMR (601 MHz, Methanol-d$_4$) δ 8.06 (d, J=8.4 Hz, 1H), 7.63 (s, 1H), 7.43 (s, 1H), 7.20 (dd, J=8.4, 1.4 Hz, 1H), 6.97 (d, J=8.2 Hz, 1H), 6.69 (s, 1H), 6.60 (d, J=8.3 Hz, 1H), 6.47 (s, 1H), 3.86 (s, 2H), 3.43 (t, J=6.1 Hz, 2H), 2.76 (s, 2H), 2.47 (q, J=7.6 Hz, 2H), 0.97 (t, J=7.5 Hz, 3H).

Example 4: 3-ethyl-4-(3-(4-(1,2,5,6-tetrahydropyridin-3-yl)-1H-imidazol-2-yl)-1H-indazol-6-yl)phenol (4)

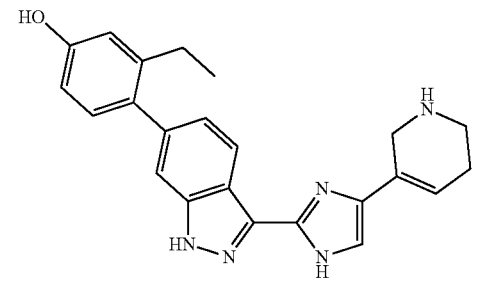 [SMILES: CCc1cc(O)ccc1-c1ccc2c(-c3nc(C4=CCCNC4)c[nH]3)n[nH]c2c1]

The general procedure was followed using 0.096 mmol of I-17, using tert-butyl 5-(4,4,5,5-tetramethyl-1,3,2-dioxaborolan-2-yl)-3,6-dihydropyridine-1(2H)-carboxylate as the boronic ester and Method C for deprotection to provide the TFA salt of the title compound (10 mg, 40% yield). (m/z): [M+H]$^+$ calcd for $C_{23}H_{23}N_5O$ 386.19 found 386.2.

Example 5: 4-(3-(4-(2,5-dihydro-1H-pyrrol-3-yl)-1H-imidazol-2-yl)-1H-indazol-6-yl)-3-ethylphenol (5)

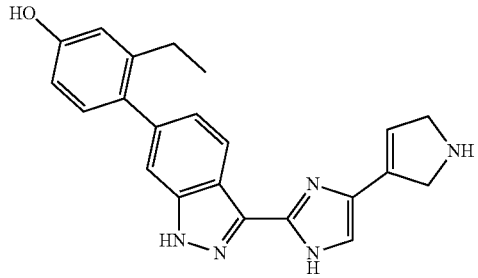 [SMILES: CCc1cc(O)ccc1-c1ccc2c(-c3nc(C4=CCNC4)c[nH]3)n[nH]c2c1]

The general procedure was followed using 0.214 mmol of I-17, using tert-butyl 3-(4,4,5,5-tetramethyl-1,3,2-dioxaborolan-2-yl)-2,5-dihydro-1H-pyrrole-1-carboxylate as the boronic ester and Method B for deprotection to provide the TFA salt of the title compound (29 mg, 28% yield). (m/z): [M+H]$^+$ calcd for $C_{22}H_{21}N_5O$ 372.18 found 372.2. $^1$H NMR (601 MHz, Methanol-$d_4$) δ 8.11 (d, J=8.4 Hz, 1H), 7.71 (s, 1H), 7.44 (s, 1H), 7.22 (d, J=8.4 Hz, 1H), 6.99 (d, J=8.2 Hz, 1H), 6.71 (s, 1H), 6.62 (d, J=8.3 Hz, 1H), 6.51 (s, 1H), 4.43 (s, 2H), 4.27 (s, 2H), 2.48 (q, J=7.5 Hz, 2H), 0.98 (t, J=7.5 Hz, 3H).

Example 6: 3-ethyl-4-(7-fluoro-3-(4-(1,2,5,6-tetrahydropyridin-3-yl)-1H-imidazol-2-yl)-1H-indazol-6-yl)phenol (6)

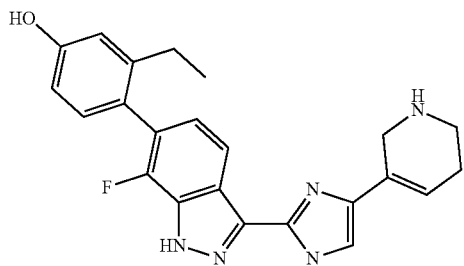

The general procedure was followed using 2.06 mmol of I-27, using tert-butyl 5-(4,4,5,5-tetramethyl-1,3,2-dioxaborolan-2-yl)-3,6-dihydropyridine-1(2H)-carboxylate as the boronic ester and Method B for deprotection to provide the TFA salt of the title compound (0.65 g, 61% yield). (m/z): [M+H]$^+$ calcd for $C_{23}H_{22}FN_5O$ 404.18 found 404.1. $^1$H NMR (601 MHz, Methanol-$d_4$) δ 7.91 (d, J=8.4 Hz, 1H), 7.51 (s, 1H), 7.06 (dd, J=8.2, 6.1 Hz, 1H), 6.96 (d, J=8.2 Hz, 1H), 6.71 (s, 1H), 6.62 (d, J=5.8 Hz, 2H), 4.04 (s, 2H), 3.34 (t, J=6.2 Hz, 2H), 2.57 (s, 2H), 2.38 (q, J=7.6 Hz, 2H), 0.94 (t, J=7.6 Hz, 3H).

Example 7: 4-(3-(4-(3-oxa-9-azabicyclo[3.3.1]non-6-en-7-yl)-1H-imidazol-2-yl)-1H-indazol-6-yl)-3-ethylphenol (7)

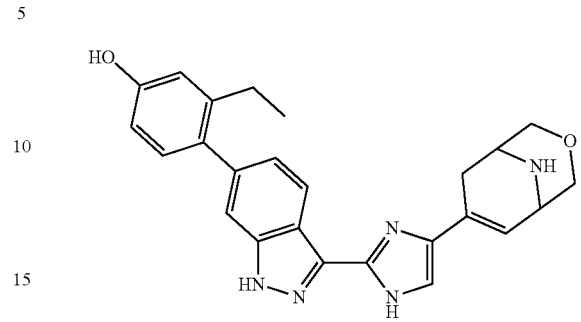

The general procedure was followed using 0.214 mmol of I-17, using 7-(4,4,5,5-tetramethyl-[1,3,2]dioxaborolan-2-yl)-3-oxa-9-aza-bicyclo[3.3.1]non-6-ene-9-carboxylic acid tert-butyl ester as the boronic ester and Method B for deprotection to provide the TFA salt of the title compound (14 mg, 12% yield). (m/z): [M+H]$^+$ calcd for $C_{25}H_{25}N_5O_2$ 428.20 found 428.0.

Example 8: (R)-3-ethyl-4-(7-fluoro-3-(4-(5-(hydroxymethyl)-2,5-dihydro-1H-pyrrol-3-yl)-1H-imidazol-2-yl)-1H-indazol-6-yl)phenol (8)

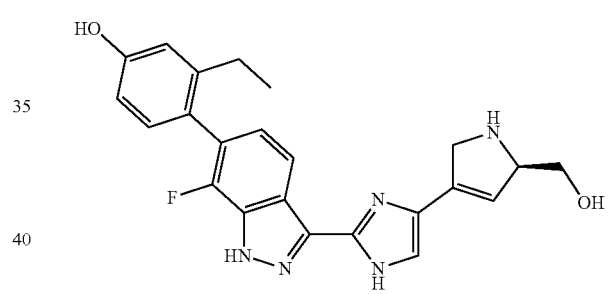

The general procedure was followed using 1.24 mmol of I-27, using I-33 as the boronic ester and Method B for deprotection to provide the TFA salt of the title compound (306 mg, 42% yield). (m/z): [M+H]$^+$ calcd for $C_{23}H_{22}FN_5O_2$ 420.18 found 420.1.

Example 9: (R)-3-ethyl-4-(7-fluoro-3-(4-(5-(methoxymethyl)-2,5-dihydro-1H-pyrrol-3-yl)-1H-imidazol-2-yl)-1H-indazol-6-yl)phenol (9)

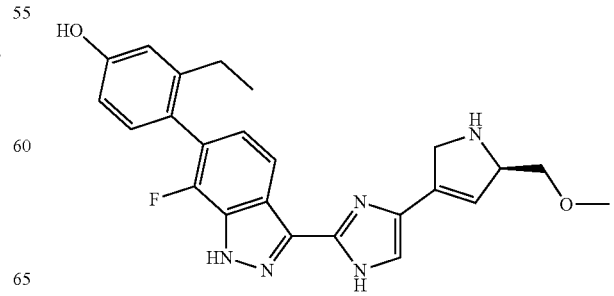

The general procedure was followed using 0.103 mmol of I-27, using I-42 as the boronic ester and Method B for deprotection to provide the TFA salt of the title compound (29 mg, 51% yield). (m/z): [M+H]$^+$ calcd for $C_{24}H_{24}FN_5O_2$ 434.19 found 434.2.

Example 10: 3-ethyl-4-(7-fluoro-3-(4-(1-(3-hydroxycyclobutyl)-1,2,5,6-tetrahydropyridin-3-yl)-1H-imidazol-2-yl)-1H-indazol-6-yl)phenol (10)

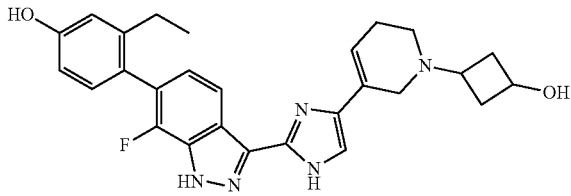 [SMILES: CCc1cc(O)ccc1-c1ccc2c(-c3nc(C4=CCCN(C5CC(O)C5)C4)c[nH]3)n[nH]c2c1F]

3-ethyl-4-(7-fluoro-3-(4-(1,2,5,6-tetrahydropyridin-3-yl)-1H-imidazol-2-yl)-1H-indazol-6-yl)phenol, TFA (20 mg, 0.039 mmol) and 3-hydroxycyclobutanone (7 mg, 0.077 mmol) were dissolved in methanol (1 mL). Sodium cyanoborohydride (12 mg, 0.193 mmol) was then added and the reaction mixture was stirred at room temperature until judged complete by LCMS (24 h). The reaction mixture was then concentrated and the crude product was purified by preparative HPLC (5-75% acetonitrile/water gradient with 0.05% TFA) to provide the TFA salt of the title compound (17.3 mg, 75% yield). (m/z): [M+H]$^+$ calcd for $C_{27}H_{28}FN_5O_2$ 474.23 found 474.1.

Example 11: 4-(3-(4-(1-((1H-pyrazol-4-yl)methyl)-1,2,3,6-tetrahydropyridin-4-yl)-1H-imidazol-2-yl)-7-fluoro-1H-indazol-6-yl)-3-ethylphenol (11)

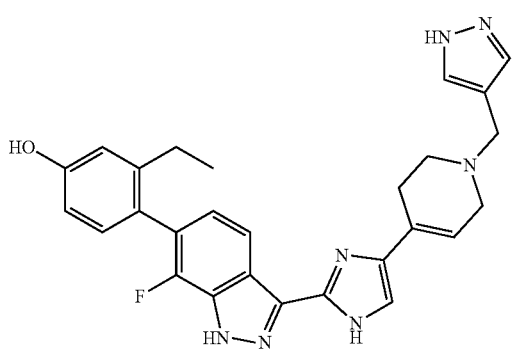 [SMILES: CCc1cc(O)ccc1-c1ccc2c(-c3nc(C4=CCN(Cc5cn[nH]c5)CC4)c[nH]3)n[nH]c2c1F]

3-ethyl-4-(7-fluoro-3-(4-(1,2,3,6-tetrahydropyridin-4-yl)-1H-imidazol-2-yl)-1H-indazol-6-yl)phenol, TFA (20 mg, 0.039 mmol) and 1H-pyrazole-4-carboxaldehyde (7 mg, 0.077 mmol) were dissolved in methanol (1 mL). Sodium cyanoborohydride (12.14 mg, 0.193 mmol) was then added and the reaction mixture was stirred at room temperature until judged complete by LCMS (24 h). The reaction mixture was then concentrated and the crude product was purified by preparative HPLC (5-75% acetonitrile/water gradient with 0.05% TFA) to provide the TFA salt of the title compound (15.1 mg, 65% yield). (m/z): [M+H]$^+$ calcd for $C_{27}H_{26}FN_7O$ 484.22 found 484.1.

Example 12: 2-(4-(2-(6-(2-ethyl-4-hydroxyphenyl)-7-fluoro-1H-indazol-3-yl)-1H-imidazol-4-yl)-3,6-dihydropyridin-1(2H)-yl)-N-methylacetamide (12)

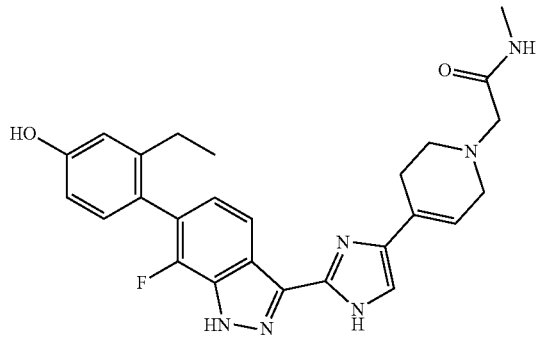 [SMILES: CCc1cc(O)ccc1-c1ccc2c(-c3nc(C4=CCN(CC(=O)NC)CC4)c[nH]3)n[nH]c2c1F]

3-ethyl-4-(7-fluoro-3-(4-(1,2,3,6-tetrahydropyridin-4-yl)-1H-imidazol-2-yl)-1H-indazol-6-yl)phenol, TFA (20 mg, 0.039 mmol), 2-bromo-N-methyl-acetamide (7 mg, 0.046 mmol), and N,N-diisopropylethylamine (0.027 ml, 0.155 mmol) were dissolved in DMF (1 mL). The reaction mixture was then stirred at 50° C. until judged complete by LCMS (24 hours). The reaction mixture was then concentrated and the crude product was purified by preparative HPLC (5-75% acetonitrile/water gradient with 0.05% TFA) to provide the TFA salt of the title compound (8.8 mg, 38% yield). (m/z): [M+H]$^+$ calcd for $C_{26}H_{27}FN_6O_2$ 475.22 found 475.1.

Example 13: 3-ethyl-4-(7-fluoro-3-(4-(1-(1-hydroxypropan-2-yl)-1,2,3,6-tetrahydropyridin-4-yl)-1H-imidazol-2-yl)-1H-indazol-6-yl)phenol (13)

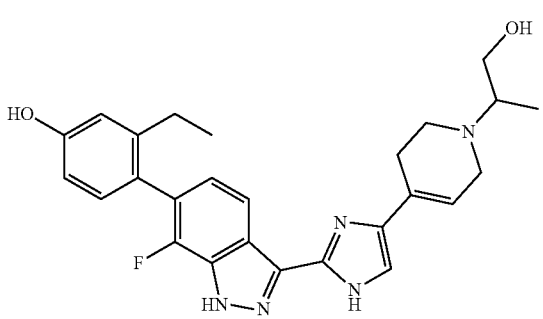 [SMILES: CCc1cc(O)ccc1-c1ccc2c(-c3nc(C4=CCN(C(C)CO)CC4)c[nH]3)n[nH]c2c1F]

3-ethyl-4-(7-fluoro-3-(4-(1,2,3,6-tetrahydropyridin-4-yl)-1H-imidazol-2-yl)-1H-indazol-6-yl)phenol, TFA (30 mg, 0.058 mmol) and hydroxyacetone (21 mg, 0.290 mmol) were dissolved in methanol (1.0 ml), then sodium cyanoborohydride (22 mg, 0.348 mmol) was added and the reaction mixture was stirred at 50° C. until judged complete by LCMS (24 hours). The reaction mixture was then concentrated and the crude product was purified by preparative HPLC (5-70% acetonitrile/water gradient with 0.05% TFA) to provide the TFA salt of the title compound (28.4 mg, 85% yield). (m/z): [M+H]$^+$ calcd for $C_{26}H_{28}FN_5O_2$ 462.23 found 462.1.

Example 14: 3-ethyl-4-(7-fluoro-3-(4-(1-(3-hydroxypropyl)-1,2,3,6-tetrahydropyridin-4-yl)-1H-imidazol-2-yl)-1H-indazol-6-yl)phenol (14)

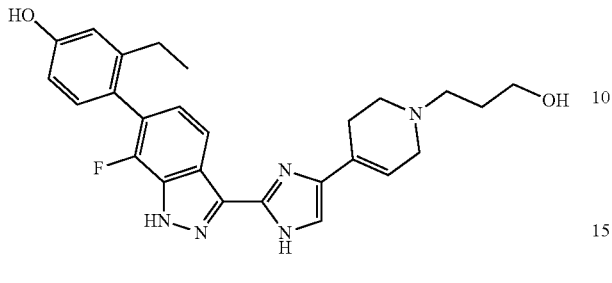

3-ethyl-4-(7-fluoro-3-(4-(1,2,3,6-tetrahydropyridin-4-yl)-1H-imidazol-2-yl)-1H-indazol-6-yl)phenol, TFA (30.0 mg, 0.058 mmol) and 3-(tert-butyldimethylsilyloxy)propanol (22 mg, 0.116 mmol) were dissolved in methanol (1.0 ml), then sodium cyanoborohydride (18 mg, 0.290 mmol) was added and the reaction mixture was stirred at room temperature until judged complete by LCMS (24 hours). The reaction mixture was then concentrated and the silyl-protected intermediate was dissolved in 3 mL of 1:1 acetonitrile water. 0.5 mL of TFA was then added, and the solution was allowed to stand at room temperature until LCMS showed the silyl group was fully removed (30 minutes). The solution was then filtered and purified by preparative HPLC (5-70% acetonitrile/water gradient with 0.05% TFA) to provide the TFA salt of the title compound (17.1 mg, 51% yield). (m/z): [M+H]+ calcd for $C_{26}H_{28}FN_5O_2$ 462.23 found 462.2.

Example 15: 3-ethyl-4-(3-(4-(1-(1-methylazetidin-3-yl)-1,2,3,6-tetrahydropyridin-4-yl)-1H-imidazol-2-yl)-1H-indazol-6-yl)phenol (15)

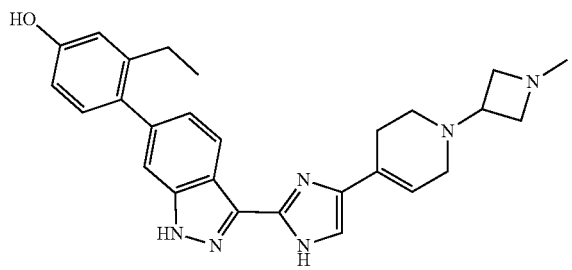 [SMILES: CCc1cc(O)ccc1-c1ccc2c(-c3nc(C4=CCN(C5CN(C)C5)CC4)c[nH]3)n[nH]c2c1]

3-ethyl-4-(3-(4-(1,2,3,6-tetrahydropyridin-4-yl)-1H-imidazol-2-yl)-1H-indazol-6-yl)phenol, TFA (20 mg, 0.040 mmol) and 1-methylazetidin-3-one hydrochloride (15 mg, 0.120 mmol) were dissolved in methanol (1 ml), then sodium cyanoborohydride (13 mg, 0.200 mmol) was added and the reaction mixture was stirred at 50° C. until judged complete by LCMS (24 hours). The reaction mixture was then concentrated and the crude product was purified by preparative HPLC (5-70% acetonitrile/water gradient with 0.05% TFA) to provide the TFA salt of the title compound (14.1 mg, 52% yield). (m/z): [M+H]+ calcd for $C_{27}H_{30}N_6O$ 455.25 found 455.2.

Example 16: (S)-6-(2-ethyl-4-hydroxyphenyl)-7-fluoro-3-(4-(1-prolyl-1,2,3,6-tetrahydropyridin-4-yl)-1H-imidazol-2-yl)-1H-indazole (16)

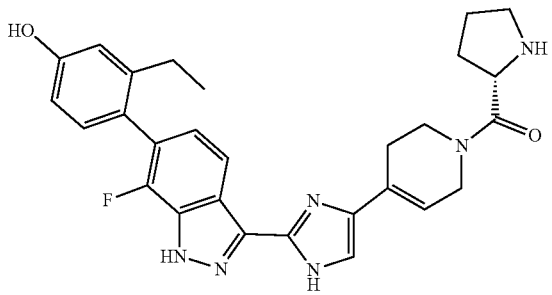 [SMILES: CCc1cc(O)ccc1-c1ccc2c(-c3nc(C4=CCN(C(=O)[C@@H]5CCCN5)CC4)c[nH]3)n[nH]c2c1F]

3-ethyl-4-(7-fluoro-1-(tetrahydro-2H-pyran-2-yl)-3-(4-(1,2,3,6-tetrahydropyridin-4-yl)-1H-imidazol-2-yl)-1H-indazol-6-yl)phenol, TFA (20 mg, 0.033 mmol), N-Boc-L-proline (11 mg, 0.050 mmol), and N,N-diisopropylethylamine (17 µL, 0.10 mmol) were dissolved in DMF (1 mL). HATU (19 mg, 0.050 mmol) was then added and the reaction mixture was stirred at room temperature until judged complete by LCMS (24 hours). Hydrazine (5 µl, 0.166 mmol) was then added to cleave undesired byproducts and the reaction mixture was concentrated. The residue was then dissolved in TFA (1 mL) and stirred at room temperature until LCMS showed complete removal of the Boc protecting group (30 minutes). The reaction mixture was then concentrated and the crude product was purified by preparative HPLC (5-70% acetonitrile/water gradient with 0.05% TFA) to provide the TFA salt of the title compound (12.9 mg, 63% yield). (m/z): [M+H]+ calcd for $C_{28}H_{29}FN_6O_2$ 501.24 found 501.3.

Example 17: (R)-3-ethyl-4-(3-(4-(1-(morpholin-3-ylmethyl)-1,2,3,6-tetrahydropyridin-4-yl)-1H-imidazol-2-yl)-1H-indazol-6-yl)phenol (17)

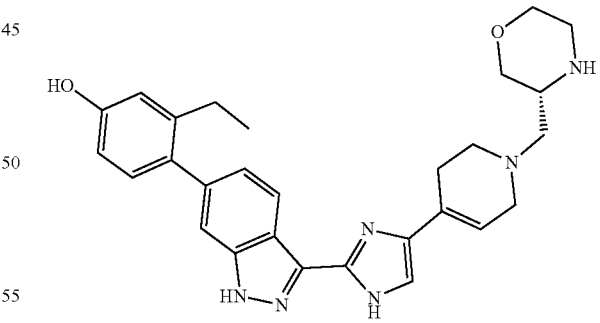

3-ethyl-4-(3-(4-(1,2,3,6-tetrahydropyridin-4-yl)-1H-imidazol-2-yl)-1H-indazol-6-yl)phenol, TFA (20 mg, 0.040 mmol) and (S)—N-Boc-3-morpholinecarbaldehyde (13 mg, 0.060 mmol) were dissolved in methanol (1.0 ml), then sodium cyanoborohydride (10 mg, 0.160 mmol) was added and the reaction mixture was stirred at room temperature until judged complete by LCMS (48 hours). The reaction mixture was then concentrated, and the resulting residue was dissolved in TFA (1 mL) and stirred at room temperature until full removal of the Boc group was observed by LCMS (10 minutes). The reaction mixture was then concentrated and the crude product was purified by preparative HPLC (5-70% acetonitrile/water gradient with 0.05% TFA) to provide the TFA salt of the title compound (7.8 mg, 27% yield). (m/z): [M+H]+ calcd for $C_{28}H_{32}N_6O_2$ 485.26 found 485.2.

Example 18: 4-(3-(4-(2,5-dihydro-1H-pyrrol-3-yl)-1H-imidazol-2-yl)-7-fluoro-1H-indazol-6-yl)-5-ethyl-2-fluorophenol (18)

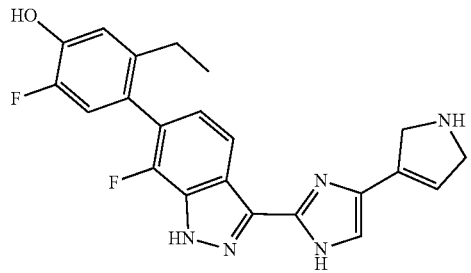 [SMILES: CCc1cc(O)c(F)cc1-c1ccc2c(-c3nc(C4=CCNC4)c[nH]3)n[nH]c2c1F]

4-(3-(4-bromo-1H-imidazol-2-yl)-7-fluoro-1-(tetrahydro-2H-pyran-2-yl)-1H-indazol-6-yl)-5-ethyl-2-fluorophenol (200 mg, 0.397 mmol) (I-54) and tert-butyl 3-(4,4,5,5-tetramethyl-1,3,2-dioxaborolan-2-yl)-2,5-dihydro-1H-pyrrole-1-carboxylate (176 mg, 0.596 mmol) were dissolved in dioxane (4.0 ml), then sodium carbonate (126 mg, 1.192 mmol) in water (2.0 ml) was added. The reaction vial was purged with nitrogen, then methanesulfonato(2-dicyclohexylphosphino-2',4',6'-tri-i-propyl-1,1'-biphenyl)(2'-methylamino-1,1'-biphenyl-2-yl)palladium(II) (17.10 mg, 0.020 mmol) was added and the reaction mixture was stirred at 110° C. until judged complete by LCMS (16 h). The reaction mixture was then partitioned between dichloromethane and saturated sodium bicarbonate solution, after which the dichloromethane layer was dried over sodium sulfate and concentrated. The crude product was then purified by silica gel chromatography (0-10% methanol/dichloromethane gradient) to provide protected intermediate tert-butyl 3-(2-(6-(2-ethyl-5-fluoro-4-hydroxyphenyl)-7-fluoro-1-(tetrahydro-2H-pyran-2-yl)-1H-indazol-3-yl)-1H-imidazol-4-yl)-2,5-dihydro-1H-pyrrole-1-carboxylate (183 mg, 78% yield). This intermediate was then deprotected using Method B from the general procedures to provide the TFA salt of the title compound (107 mg, 54% yield). (m/z): [M+H]+ calcd for $C_{22}H_{19}F_2N_5O$ 408.16 found 408.2.

The compounds in the following Table 4 were prepared using the procedures described in the examples above or similar synthetic methods and the appropriate reactants.

TABLE 4

| Ex. No. | Structure | Calc. [M + H]+ | Found [M + H]+ |
|---|---|---|---|
| 1 | 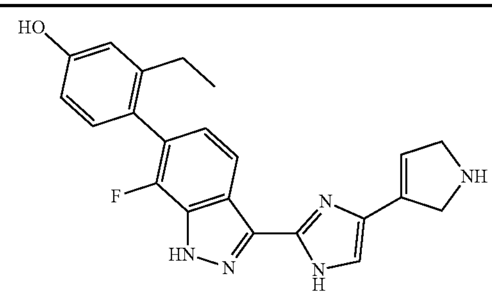 | 390.2 | 390.2 |
| 2 | 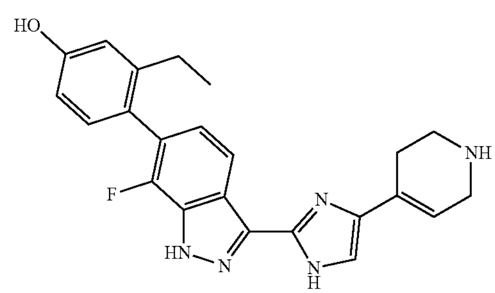 [SMILES: CCc1cc(O)ccc1-c1ccc2c(-c3nc(C4=CCNCC4)c[nH]3)n[nH]c2c1F] | 404.2 | 404.2 |
| 3 | 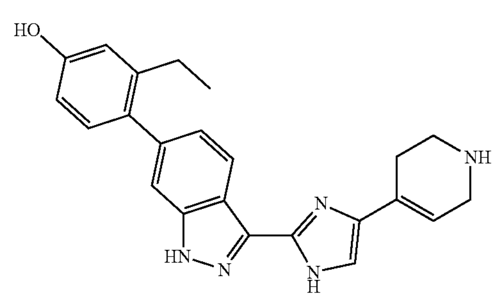 [SMILES: CCc1cc(O)ccc1-c1ccc2c(-c3nc(C4=CCNCC4)c[nH]3)n[nH]c2c1] | 386.2 | 386.1 |

TABLE 4-continued

| Ex. No. | Structure | Calc. [M + H]⁺ | Found [M + H]⁺ |
|---|---|---|---|
| 4 | 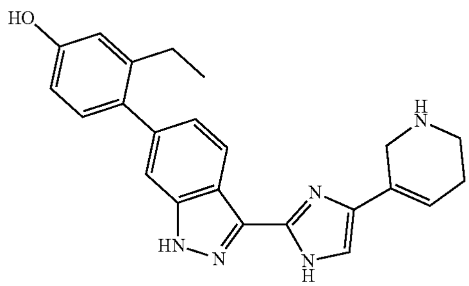 [SMILES: CCc1cc(O)ccc1-c1ccc2c(-c3nc(C4=CCCNC4)c[nH]3)n[nH]c2c1] | 386.2 | 386.2 |
| 5 | 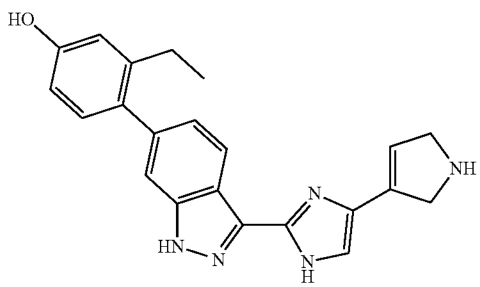 [SMILES: CCc1cc(O)ccc1-c1ccc2c(-c3nc(C4=CCNC4)c[nH]3)n[nH]c2c1] | 372.2 | 373.2 |
| 6 | 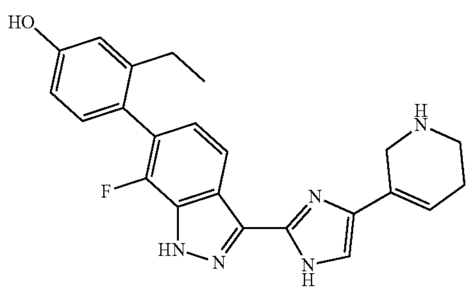 [SMILES: CCc1cc(O)ccc1-c1ccc2c(-c3nc(C4=CCCNC4)c[nH]3)n[nH]c2c1F] | 404.2 | 404.1 |
| 7 | 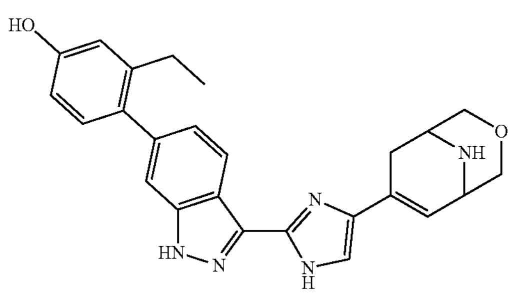 [SMILES: CCc1cc(O)ccc1-c1ccc2c(-c3nc(C4=CC5COCC(C4)N5)c[nH]3)n[nH]c2c1] | 428.2 | 428.0 |
| 8 | 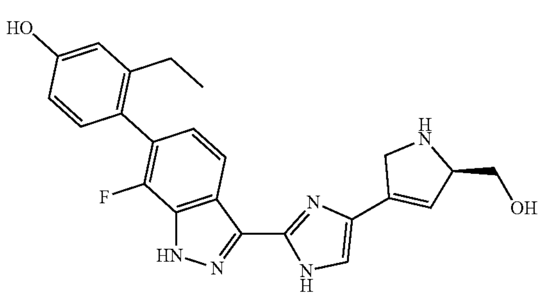 [SMILES: CCc1cc(O)ccc1-c1ccc2c(-c3nc(C4=C[C@H](CO)NC4)c[nH]3)n[nH]c2c1F] | 420.2 | 420.1 |

TABLE 4-continued

| Ex. No. | Structure | Calc. [M + H]⁺ | Found [M + H]⁺ |
|---|---|---|---|
| 9 | 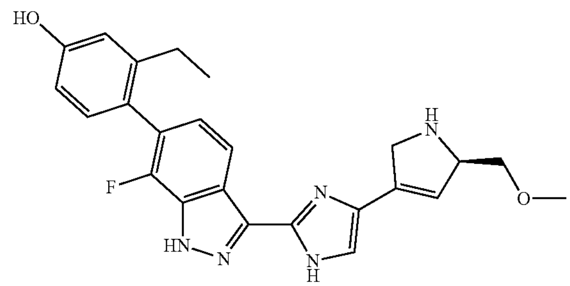 [SMILES: CCc1cc(O)ccc1-c1ccc2c(-c3nc(C4=C[C@H](COC)NC4)c[nH]3)n[nH]c2c1F] | 434.2 | 434.2 |
| 10 | 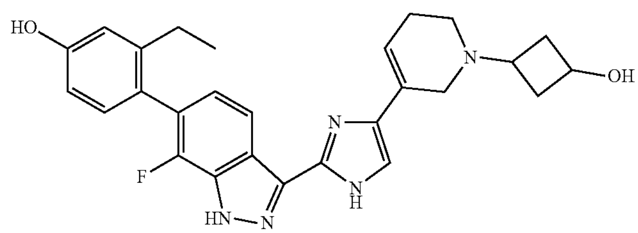 [SMILES: CCc1cc(O)ccc1-c1ccc2c(-c3nc(C4=CCCN(C5CC(O)C5)C4)c[nH]3)n[nH]c2c1F] | 474.2 | 474.1 |
| 11 | 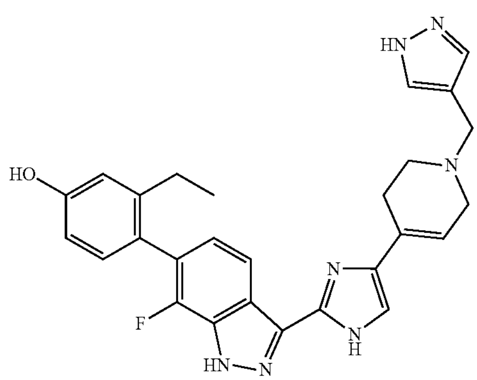 [SMILES: CCc1cc(O)ccc1-c1ccc2c(-c3nc(C4=CCN(Cc5cn[nH]c5)CC4)c[nH]3)n[nH]c2c1F] | 484.2 | 484.1 |
| 12 | 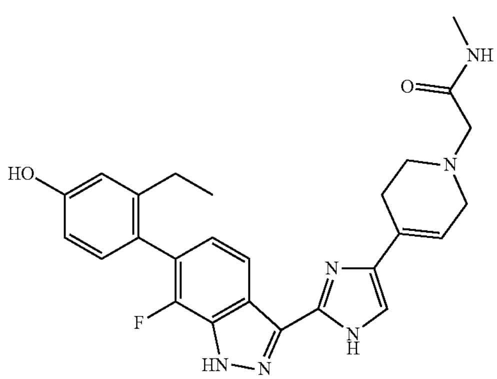 [SMILES: CCc1cc(O)ccc1-c1ccc2c(-c3nc(C4=CCN(CC(=O)NC)CC4)c[nH]3)n[nH]c2c1F] | 475.2 | 474.1 |

TABLE 4-continued
| Ex. No. | Structure | Calc. [M + H]+ | Found [M + H]+ |
|---|---|---|---|
| 13 | 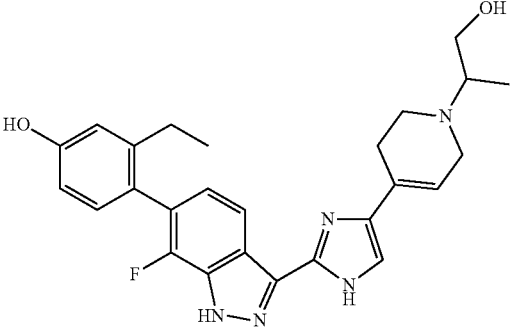 [SMILES: CCc1cc(O)ccc1-c1ccc2c(-c3nc(C4=CCN(C(C)CO)CC4)c[nH]3)n[nH]c2c1F] | 464.2 | 464.1 |
| 14 | 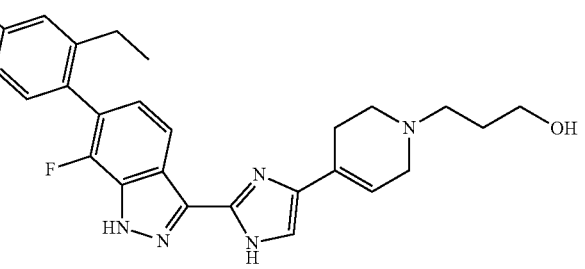 | 464.2 | 464.2 |
| 15 | 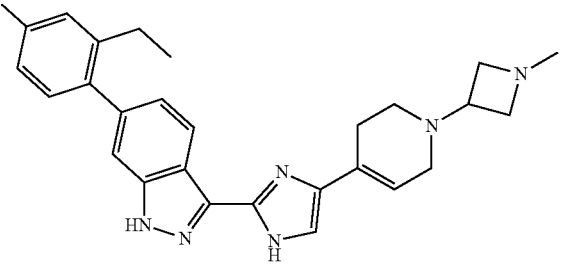 | 455.3 | 455.2 |
| 16 | 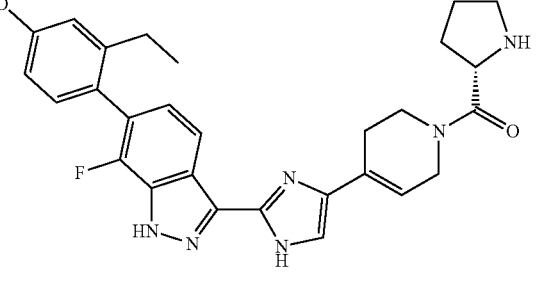 | 501.2 | 501.3 |
| 17 | 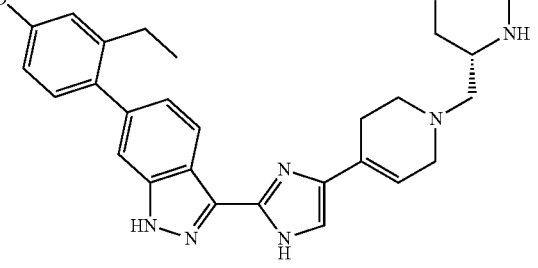 | 485.3 | 484.2 |

TABLE 4-continued

| Ex. No. | Structure | Calc. [M + H]+ | Found [M + H]+ |
|---|---|---|---|
| 18 | 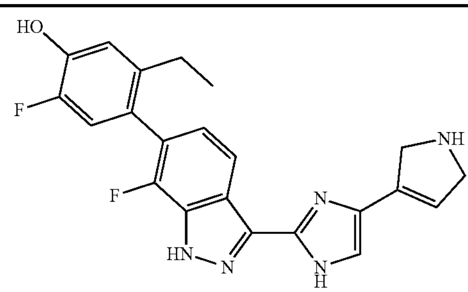 | 408.2 | 408.2 |
| 19 | 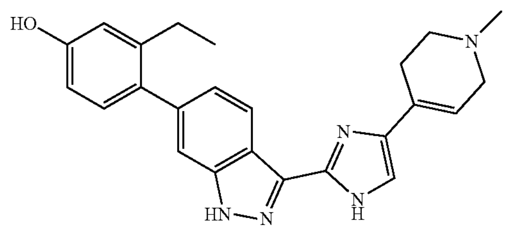 [SMILES: CCc1cc(O)ccc1-c1ccc2c(-c3nc(C4=CCN(C)CC4)c[nH]3)n[nH]c2c1] | 400.2 | 400.2 |
| 20 | 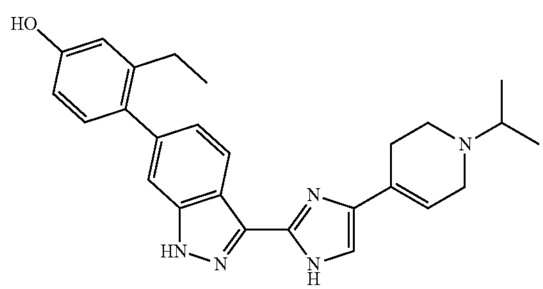 [SMILES: CCc1cc(O)ccc1-c1ccc2c(-c3nc(C4=CCN(C(C)C)CC4)c[nH]3)n[nH]c2c1] | 428.2 | 428.2 |
| 21 | 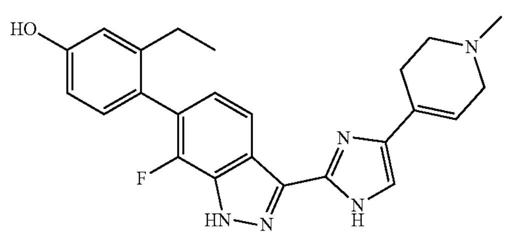 [SMILES: CCc1cc(O)ccc1-c1ccc2c(-c3nc(C4=CCN(C)CC4)c[nH]3)n[nH]c2c1F] | 418.2 | 418.2 |
| 22 | 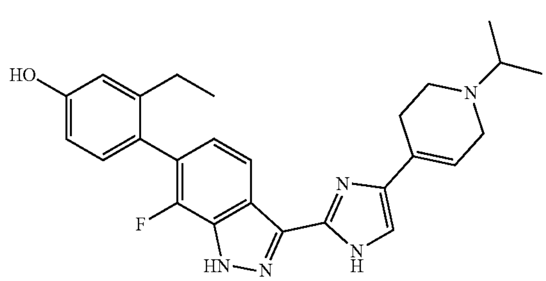 [SMILES: CCc1cc(O)ccc1-c1ccc2c(-c3nc(C4=CCN(C(C)C)CC4)c[nH]3)n[nH]c2c1F] | 446.2 | 446.1 |
| 23 | 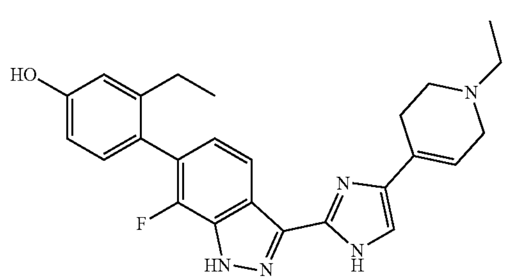 [SMILES: CCc1cc(O)ccc1-c1ccc2c(-c3nc(C4=CCN(CC)CC4)c[nH]3)n[nH]c2c1F] | 432.2 | 432.3 |

TABLE 4-continued

| Ex. No. | Structure | Calc. [M + H]+ | Found [M + H]+ |
|---|---|---|---|
| 24 | 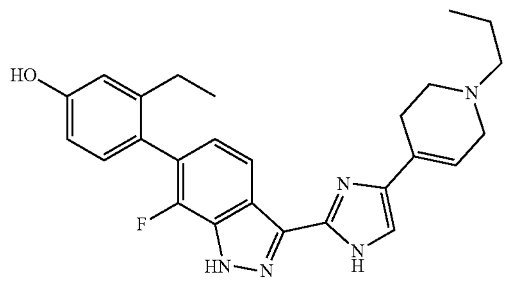 [SMILES: CCCN1CC=C(c2c[nH]c(-c3n[nH]c4c(F)c(-c5ccc(O)cc5CC)ccc34)n2)CC1] | 446.2 | 446.2 |
| 25 | 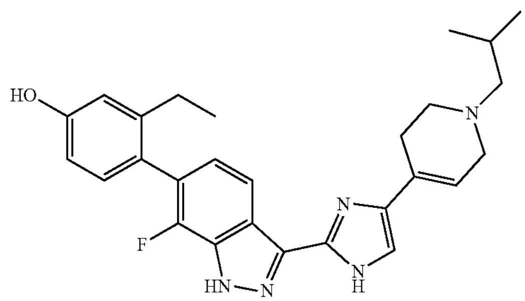 [SMILES: CCc1cc(O)ccc1-c1ccc2c(-c3nc(C4=CCN(CC(C)C)CC4)c[nH]3)n[nH]c2c1F] | 460.2 | 460.3 |
| 26 | 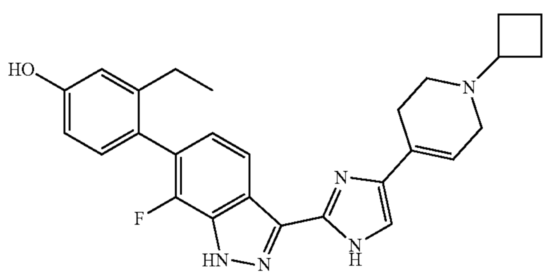 [SMILES: CCc1cc(O)ccc1-c1ccc2c(-c3nc(C4=CCN(C5CCC5)CC4)c[nH]3)n[nH]c2c1F] | 458.2 | 458.2 |
| 27 | 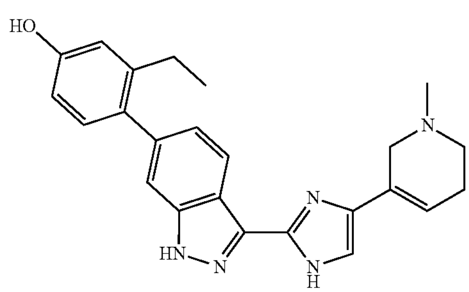 [SMILES: CCc1cc(O)ccc1-c1ccc2c(-c3nc(C4=CCCN(C)C4)c[nH]3)n[nH]c2c1] | 400.2 | 400.2 |
| 28 | 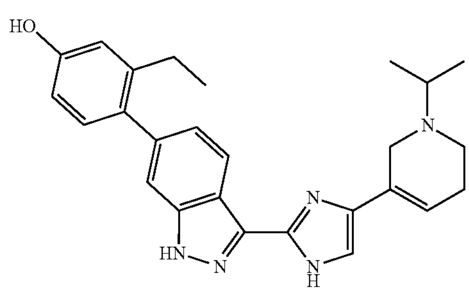 [SMILES: CCc1cc(O)ccc1-c1ccc2c(-c3nc(C4=CCCN(C(C)C)C4)c[nH]3)n[nH]c2c1] | 428.2 | 428.2 |

TABLE 4-continued

| Ex. No. | Structure | Calc. [M + H]+ | Found [M + H]+ |
|---|---|---|---|
| 29 | 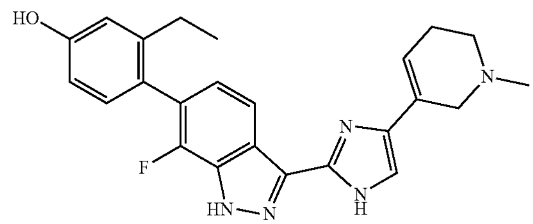 [SMILES: CCc1cc(O)ccc1-c1ccc2c(-c3nc(C4=CCCN(C)C4)c[nH]3)n[nH]c2c1F] | 418.2 | 418.2 |
| 30 | 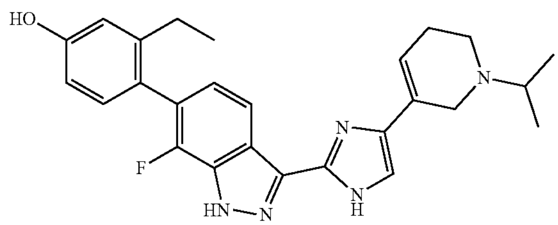 [SMILES: CCc1cc(O)ccc1-c1ccc2c(-c3nc(C4=CCCN(C(C)C)C4)c[nH]3)n[nH]c2c1F] | 446.2 | 446.2 |
| 31 | 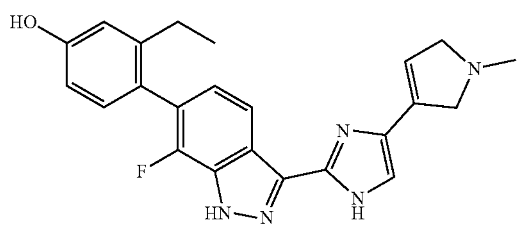 [SMILES: CCc1cc(O)ccc1-c1ccc2c(-c3nc(C4=CCN(C)C4)c[nH]3)n[nH]c2c1F] | 404.2 | 404.1 |
| 32 | 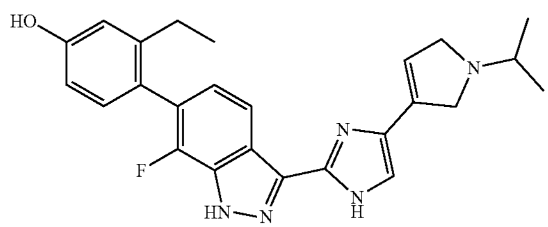 [SMILES: CCc1cc(O)ccc1-c1ccc2c(-c3nc(C4=CCN(C(C)C)C4)c[nH]3)n[nH]c2c1F] | 432.2 | 432.2 |
| 33 | 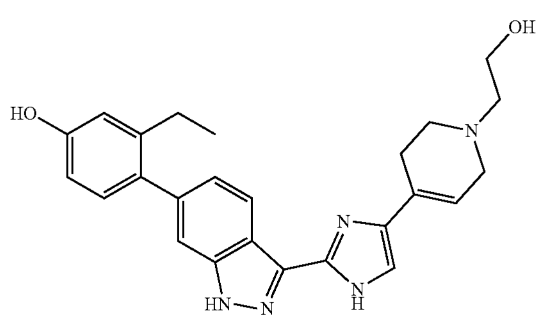 [SMILES: CCc1cc(O)ccc1-c1ccc2c(-c3nc(C4=CCN(CCO)CC4)c[nH]3)n[nH]c2c1] | 430.2 | 430.2 |
| 34 | 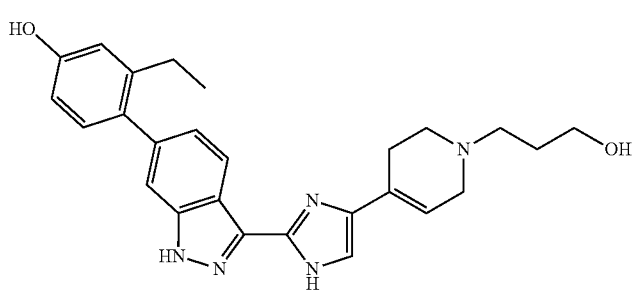 [SMILES: CCc1cc(O)ccc1-c1ccc2c(-c3nc(C4=CCN(CCCO)CC4)c[nH]3)n[nH]c2c1] | 444.2 | 444.3 |

TABLE 4-continued
| Ex. No. | Structure | Calc. [M + H]+ | Found [M + H]+ |
|---|---|---|---|
| 35 | 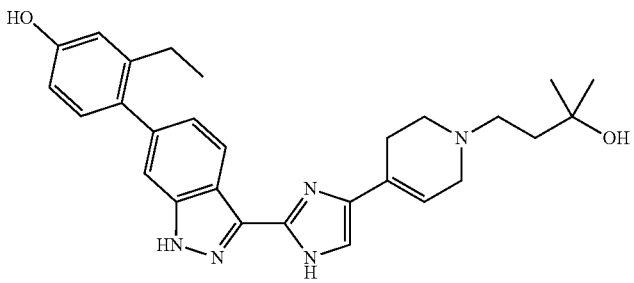 [SMILES: CCc1cc(O)ccc1-c1ccc2c(-c3nc(C4=CCN(CCC(C)(C)O)CC4)c[nH]3)n[nH]c2c1] | 472.3 | 472.1 |
| 36 | 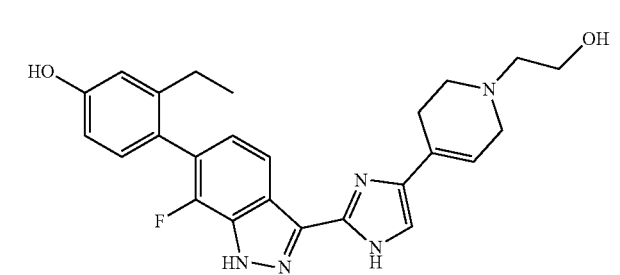 [SMILES: CCc1cc(O)ccc1-c1ccc2c(-c3nc(C4=CCN(CCO)CC4)c[nH]3)n[nH]c2c1F] | 448.2 | 448.2 |
| 37 | 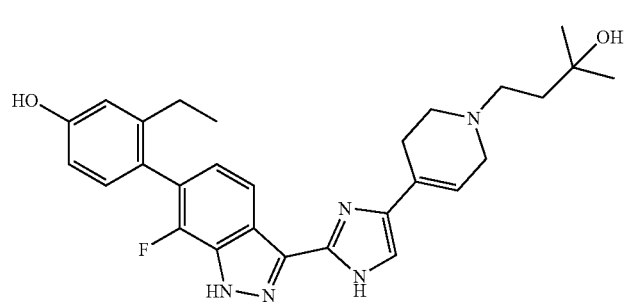 [SMILES: CCc1cc(O)ccc1-c1ccc2c(-c3nc(C4=CCN(CCC(C)(C)O)CC4)c[nH]3)n[nH]c2c1F] | 490.3 | 490.2 |
| 38 | 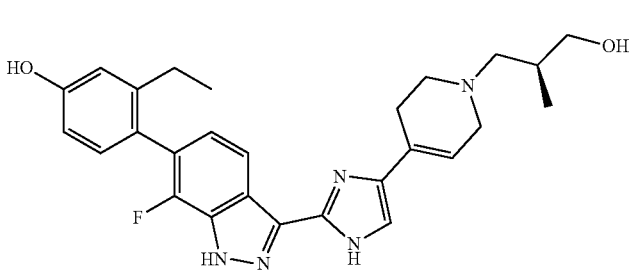 [SMILES: CCc1cc(O)ccc1-c1ccc2c(-c3nc(C4=CCN(C[C@H](C)CO)CC4)c[nH]3)n[nH]c2c1F] | 476.2 | 476.2 |
| 39 | 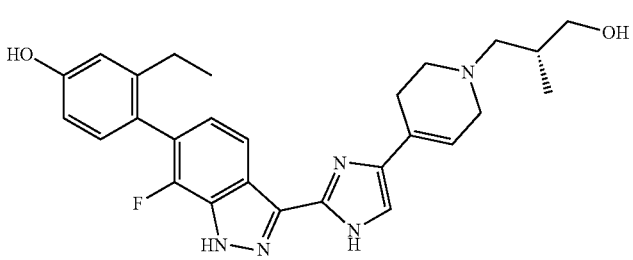 [SMILES: CCc1cc(O)ccc1-c1ccc2c(-c3nc(C4=CCN(C[C@@H](C)CO)CC4)c[nH]3)n[nH]c2c1F] | 476.2 | 476.2 |

TABLE 4-continued

| Ex. No. | Structure | Calc. [M + H]+ | Found [M + H]+ |
|---|---|---|---|
| 40 | 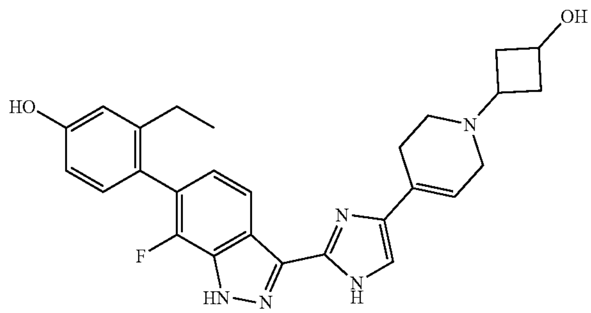 [SMILES: CCc1cc(O)ccc1-c1ccc2c(-c3nc(C4=CCN(C5CC(O)C5)CC4)c[nH]3)n[nH]c2c1F] | 474.2 | 474.1 |
| 41 | 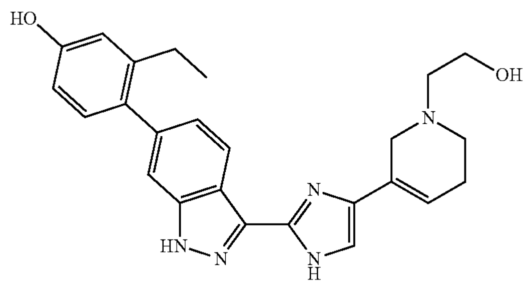 [SMILES: CCc1cc(O)ccc1-c1ccc2c(-c3nc(C4=CCCN(CCO)C4)c[nH]3)n[nH]c2c1] | 430.2 | 430.2 |
| 42 | 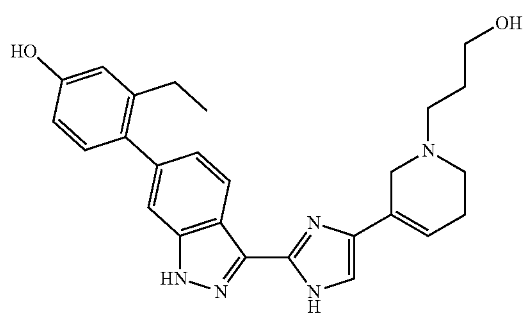 [SMILES: CCc1cc(O)ccc1-c1ccc2c(-c3nc(C4=CCCN(CCCO)C4)c[nH]3)n[nH]c2c1] | 444.2 | 444.2 |
| 43 | 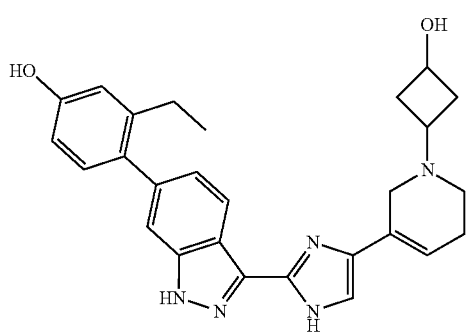 [SMILES: CCc1cc(O)ccc1-c1ccc2c(-c3nc(C4=CCCN(C5CC(O)C5)C4)c[nH]3)n[nH]c2c1] | 456.2 | 456.2 |
| 44 | 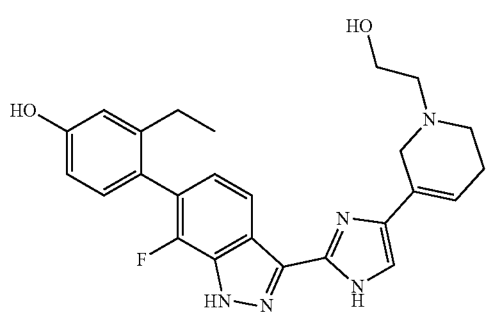 [SMILES: CCc1cc(O)ccc1-c1ccc2c(-c3nc(C4=CCCN(CCO)C4)c[nH]3)n[nH]c2c1F] | 448.2 | 448.2 |

TABLE 4-continued

| Ex. No. | Structure | Calc. [M + H]+ | Found [M + H]+ |
|---|---|---|---|
| 45 | 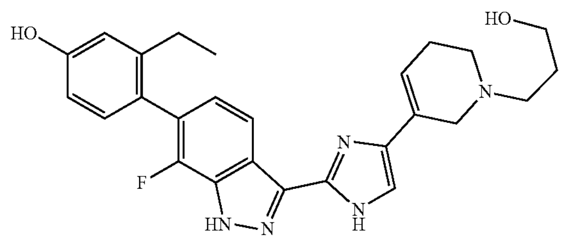 [SMILES: CCc1cc(O)ccc1-c1ccc2c(-c3nc(C4=CCCN(CCCO)C4)c[nH]3)n[nH]c2c1F] | 462.2 | 462.2 |
| 46 | 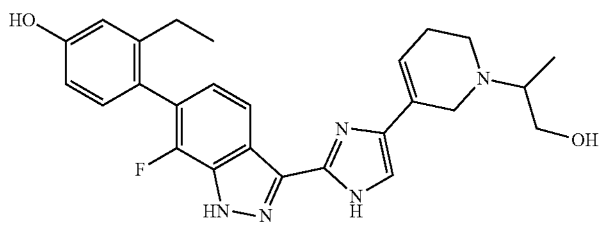 [SMILES: CCc1cc(O)ccc1-c1ccc2c(-c3nc(C4=CCCN(C(C)CO)C4)c[nH]3)n[nH]c2c1F] | 462.2 | 462.2 |
| 47 | 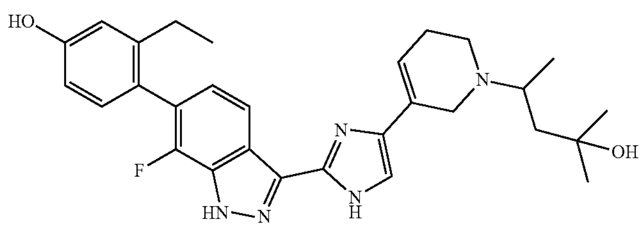 [SMILES: CCc1cc(O)ccc1-c1ccc2c(-c3nc(C4=CCCN(C(C)CC(C)(C)O)C4)c[nH]3)n[nH]c2c1F] | 490.3 | 490.2 |
| 48 | 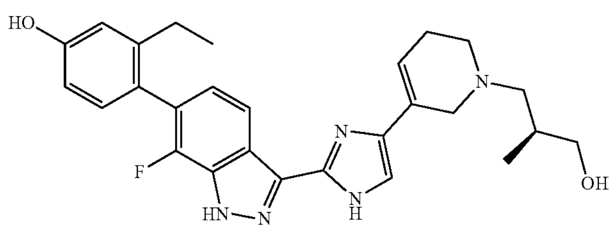 [SMILES: CCc1cc(O)ccc1-c1ccc2c(-c3nc(C4=CCCN(C[C@H](C)CO)C4)c[nH]3)n[nH]c2c1F] | 476.2 | 476.2 |
| 49 | 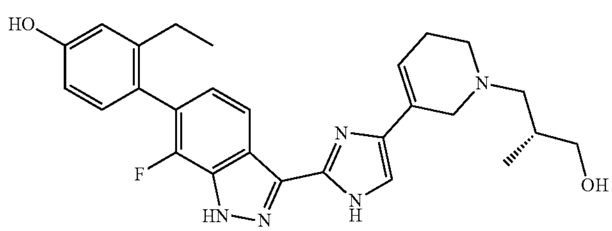 [SMILES: CCc1cc(O)ccc1-c1ccc2c(-c3nc(C4=CCCN(C[C@@H](C)CO)C4)c[nH]3)n[nH]c2c1F] | 476.2 | 476.3 |
| 50 | 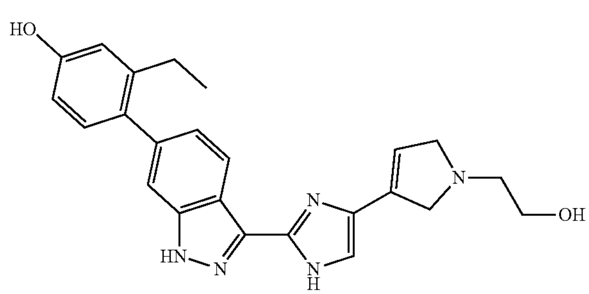 [SMILES: CCc1cc(O)ccc1-c1ccc2c(-c3nc(C4=CCN(CCO)C4)c[nH]3)n[nH]c2c1] | 416.2 | 416.2 |

TABLE 4-continued
| Ex. No. | Structure | Calc. [M + H]+ | Found [M + H]+ |
|---|---|---|---|
| 51 | 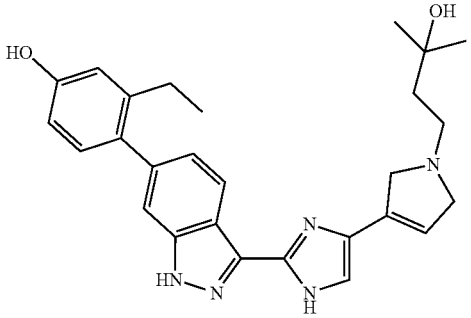 [SMILES: CCc1cc(O)ccc1-c1ccc2c(-c3nc(C4=CCN(CCC(C)(C)O)C4)c[nH]3)n[nH]c2c1] | 458.2 | 458.2 |
| 52 | 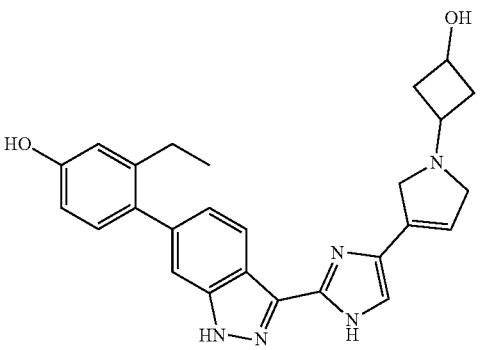 [SMILES: CCc1cc(O)ccc1-c1ccc2c(-c3nc(C4=CCN(C5CC(O)C5)C4)c[nH]3)n[nH]c2c1] | 442.2 | 442.2 |
| 53 | 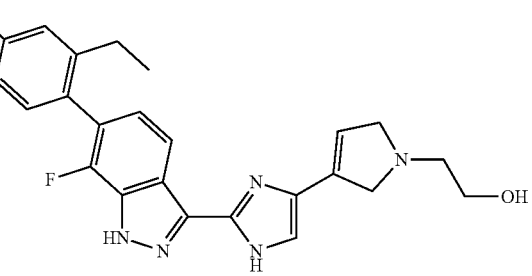 | 434.2 | 434.2 |
| 54 | 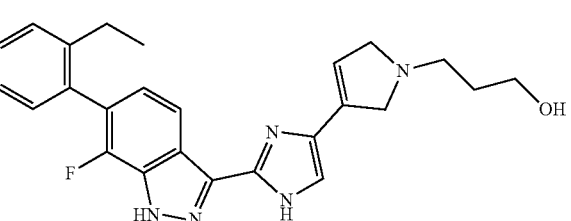 | 448.2 | 448.2 |
| 55 | 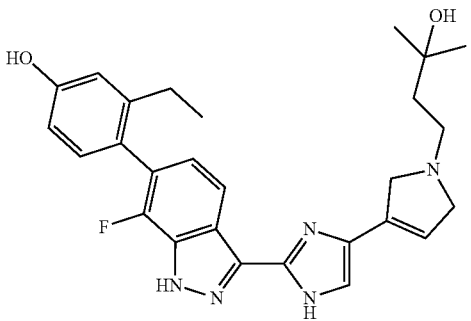 [SMILES: CCc1cc(O)ccc1-c1ccc2c(-c3nc(C4=CCN(CCC(C)(C)O)C4)c[nH]3)n[nH]c2c1F] | 476.2 | 476.2 |

TABLE 4-continued

| Ex. No. | Structure | Calc. [M + H]+ | Found [M + H]+ |
|---|---|---|---|
| 56 | 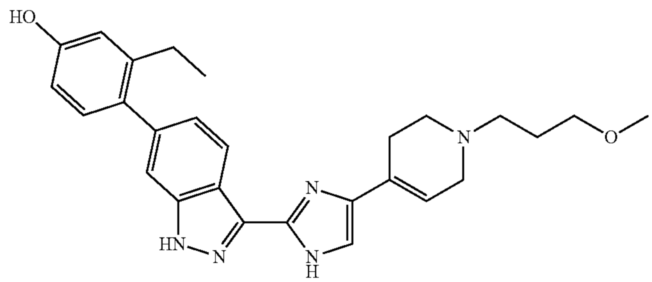 [SMILES: CCc1cc(O)ccc1-c1ccc2c(-c3nc(C4=CCN(CCCOC)CC4)c[nH]3)n[nH]c2c1] | 458.2 | 458.1 |
| 57 | 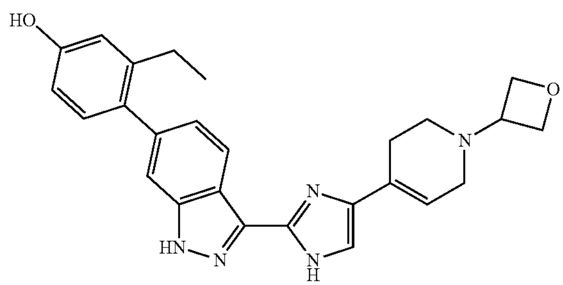 [SMILES: CCc1cc(O)ccc1-c1ccc2c(-c3nc(C4=CCN(C5COC5)CC4)c[nH]3)n[nH]c2c1] | 442.2 | 442.2 |
| 58 | 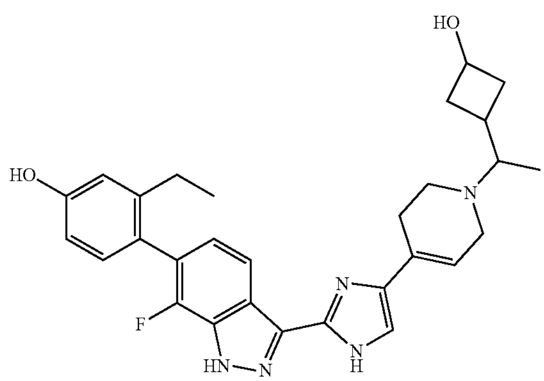 [SMILES: CCc1cc(O)ccc1-c1ccc2c(-c3nc(C4=CCN(C(C)C5CC(O)C5)CC4)c[nH]3)n[nH]c2c1F] | 502.3 | 502.1 |
| 59 | 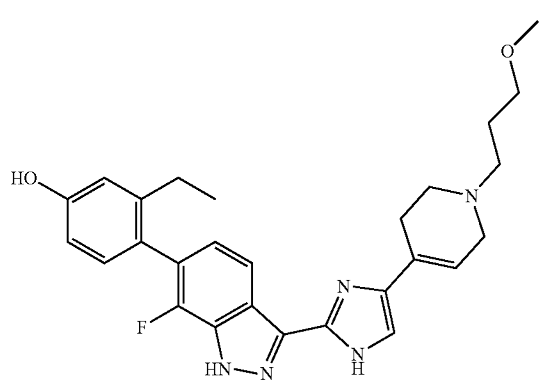 [SMILES: CCc1cc(O)ccc1-c1ccc2c(-c3nc(C4=CCN(CCCOC)CC4)c[nH]3)n[nH]c2c1F] | 476.2 | 476.2 |

TABLE 4-continued
| Ex. No. | Structure | Calc. [M + H]+ | Found [M + H]+ |
|---|---|---|---|
| 60 | 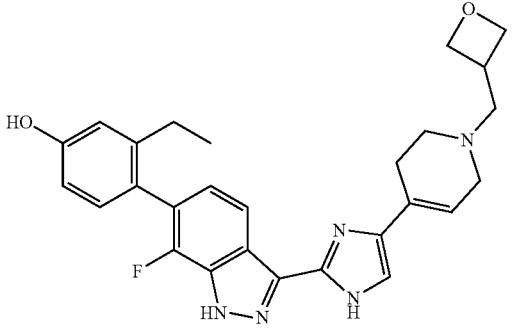 | 474.2 | 474.2 |
| 61 | 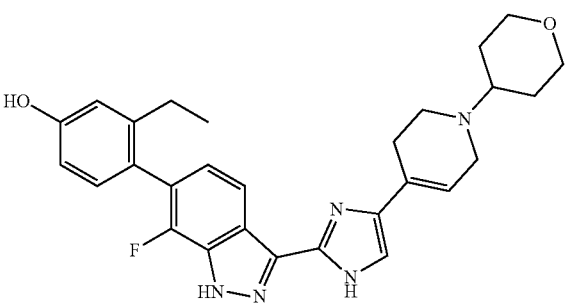 [SMILES: CCc1cc(O)ccc1-c1ccc2c(-c3nc(C4=CCN(C5CCOCC5)CC4)c[nH]3)n[nH]c2c1F] | 488.2 | 488.2 |
| 62 | 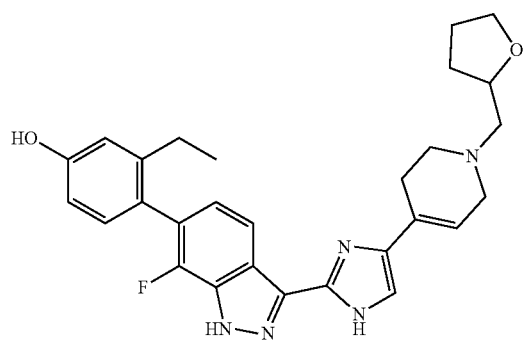 [SMILES: CCc1cc(O)ccc1-c1ccc2c(-c3nc(C4=CCN(CC5CCCO5)CC4)c[nH]3)n[nH]c2c1F] | 488.2 | 488.2 |
| 63 | 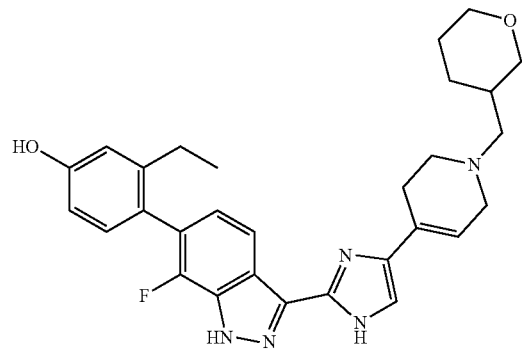 [SMILES: CCc1cc(O)ccc1-c1ccc2c(-c3nc(C4=CCN(CC5CCCOC5)CC4)c[nH]3)n[nH]c2c1F] | 502.3 | 502.2 |

TABLE 4-continued
| Ex. No. | Structure | Calc. [M + H]+ | Found [M + H]+ |
|---|---|---|---|
| 64 | 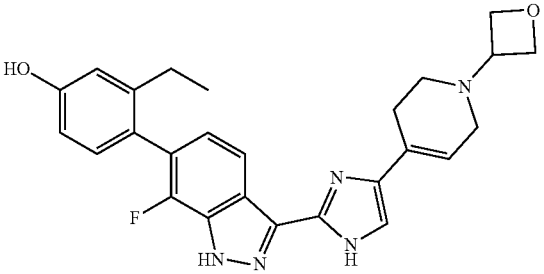 [SMILES: CCc1cc(O)ccc1-c1ccc2c(-c3nc(C4=CCN(C5COC5)CC4)c[nH]3)n[nH]c2c1F] | 460.2 | 460.2 |
| 65 | 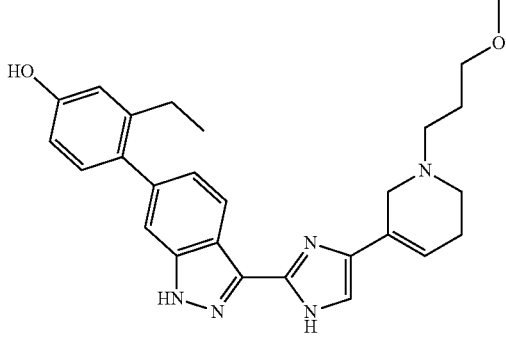 [SMILES: CCc1cc(O)ccc1-c1ccc2c(-c3nc(C4=CCCN(CCCOC)C4)c[nH]3)n[nH]c2c1] | 458.2 | 458.3 |
| 66 | 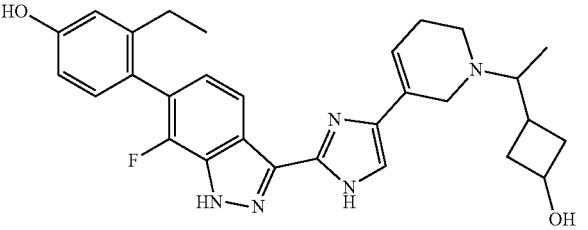 [SMILES: CCc1cc(O)ccc1-c1ccc2c(-c3nc(C4=CCCN(C(C)C5CC(O)C5)C4)c[nH]3)n[nH]c2c1F] | 502.3 | 502.2 |
| 67 | 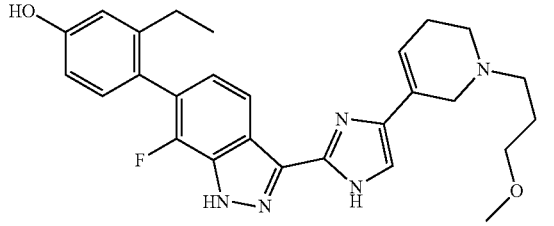 [SMILES: CCc1cc(O)ccc1-c1ccc2c(-c3nc(C4=CCCN(CCCOC)C4)c[nH]3)n[nH]c2c1F] | 476.2 | 476.2 |
| 68 | 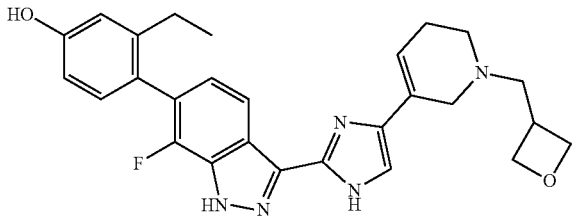 [SMILES: CCc1cc(O)ccc1-c1ccc2c(-c3nc(C4=CCCN(CC5COC5)C4)c[nH]3)n[nH]c2c1F] | 474.2 | 474.2 |
| 69 | 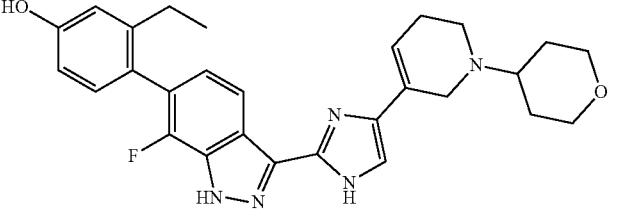 [SMILES: CCc1cc(O)ccc1-c1ccc2c(-c3nc(C4=CCCN(C5CCOCC5)C4)c[nH]3)n[nH]c2c1F] | 488.2 | 488.2 |

TABLE 4-continued
| Ex. No. | Structure | Calc. [M + H]+ | Found [M + H]+ |
|---|---|---|---|
| 70 | 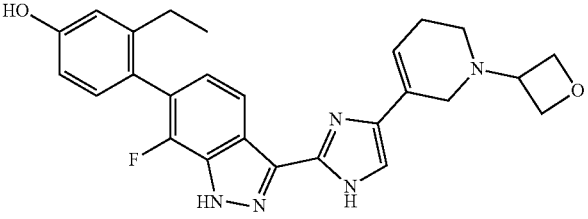 [SMILES: CCc1cc(O)ccc1-c1ccc2c(-c3nc(C4=CCCN(C5COC5)C4)c[nH]3)n[nH]c2c1F] | 460.2 | 460.2 |
| 71 | 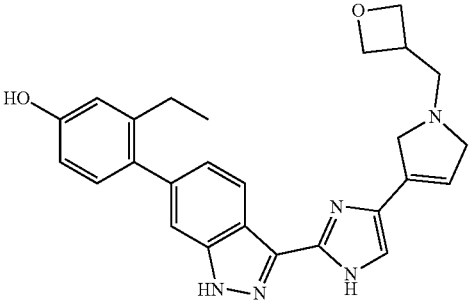 [SMILES: CCc1cc(O)ccc1-c1ccc2c(-c3nc(C4=CCN(CC5COC5)C4)c[nH]3)n[nH]c2c1] | 442.2 | 442.2 |
| 72 | 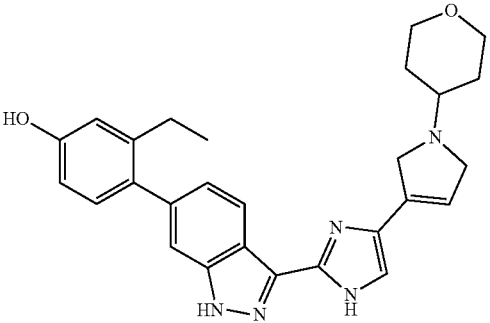 [SMILES: CCc1cc(O)ccc1-c1ccc2c(-c3nc(C4=CCN(C5CCOCC5)C4)c[nH]3)n[nH]c2c1] | 456.2 | 456.2 |
| 73 | 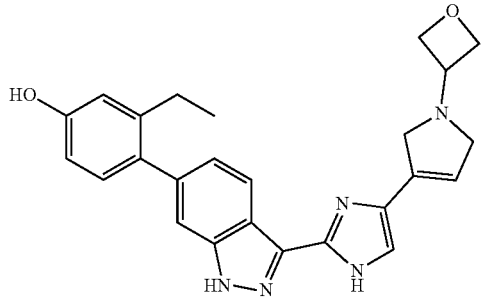 [SMILES: CCc1cc(O)ccc1-c1ccc2c(-c3nc(C4=CCN(C5COC5)C4)c[nH]3)n[nH]c2c1] | 428.2 | 428.1 |
| 74 | 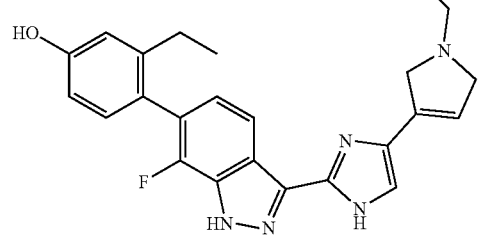 | 460.2 | 460.2 |

TABLE 4-continued

| Ex. No. | Structure | Calc. [M + H]+ | Found [M + H]+ |
|---|---|---|---|
| 75 | 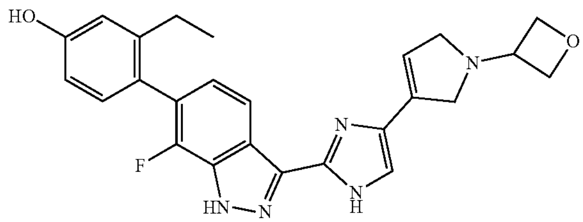 [SMILES: CCc1cc(O)ccc1-c1ccc2c(-c3nc(C4=CCN(C5COC5)C4)c[nH]3)n[nH]c2c1F] | 446.2 | 446.1 |
| 76 | 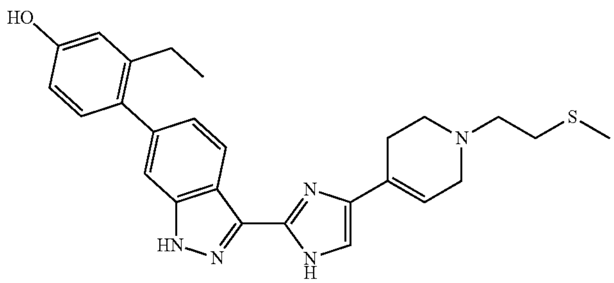 [SMILES: CCc1cc(O)ccc1-c1ccc2c(-c3nc(C4=CCN(CCSC)CC4)c[nH]3)n[nH]c2c1] | 460.2 | 460.1 |
| 77 | 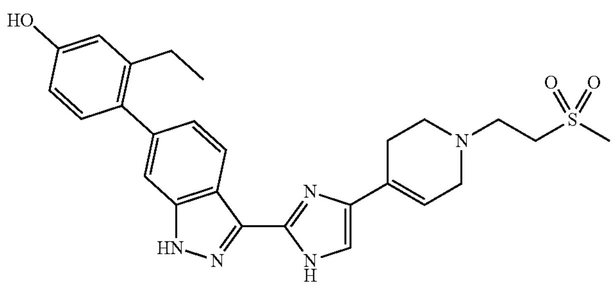 [SMILES: CCc1cc(O)ccc1-c1ccc2c(-c3nc(C4=CCN(CCS(C)(=O)=O)CC4)c[nH]3)n[nH]c2c1] | 492.2 | 492.1 |
| 78 | 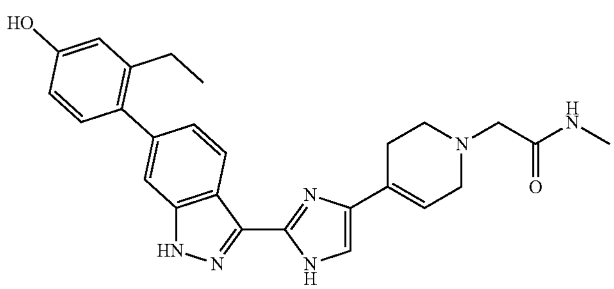 [SMILES: CCc1cc(O)ccc1-c1ccc2c(-c3nc(C4=CCN(CC(=O)NC)CC4)c[nH]3)n[nH]c2c1] | 457.2 | 457.1 |
| 79 | 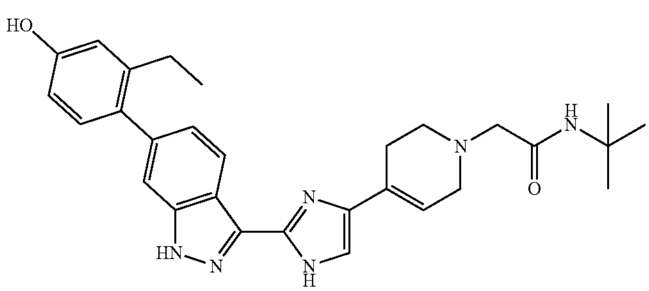 [SMILES: CCc1cc(O)ccc1-c1ccc2c(-c3nc(C4=CCN(CC(=O)NC(C)(C)C)CC4)c[nH]3)n[nH]c2c1] | 499.3 | 499.1 |

TABLE 4-continued

| Ex. No. | Structure | Calc. [M + H]+ | Found [M + H]+ |
|---|---|---|---|
| 80 | 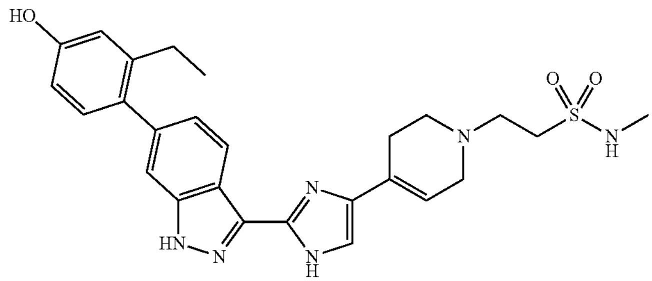 [SMILES: CCc1cc(O)ccc1-c1ccc2c(-c3nc(C4=CCN(CCS(=O)(=O)NC)CC4)c[nH]3)n[nH]c2c1] | 507.2 | 507.0 |
| 81 | 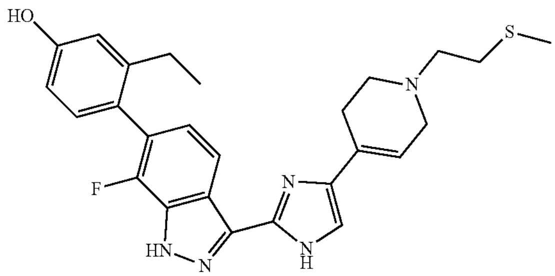 [SMILES: CCc1cc(O)ccc1-c1ccc2c(-c3nc(C4=CCN(CCSC)CC4)c[nH]3)n[nH]c2c1F] | 478.2 | 478.2 |
| 82 | 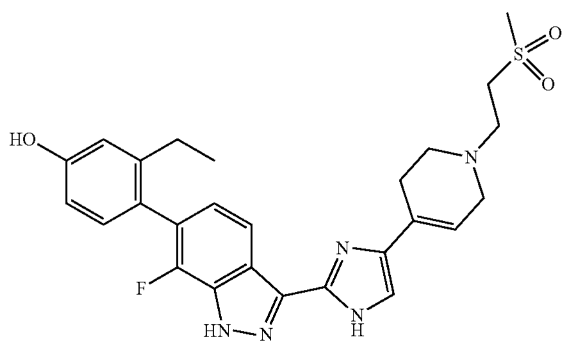 [SMILES: CCc1cc(O)ccc1-c1ccc2c(-c3nc(C4=CCN(CCS(C)(=O)=O)CC4)c[nH]3)n[nH]c2c1F] | 510.2 | 510.0 |
| 83 | 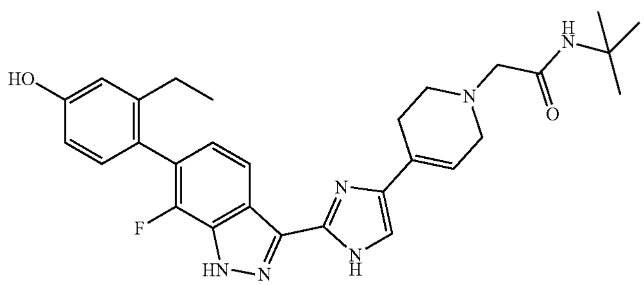 [SMILES: CCc1cc(O)ccc1-c1ccc2c(-c3nc(C4=CCN(CC(=O)NC(C)(C)C)CC4)c[nH]3)n[nH]c2c1F] | 517.3 | 517.2 |
| 84 | 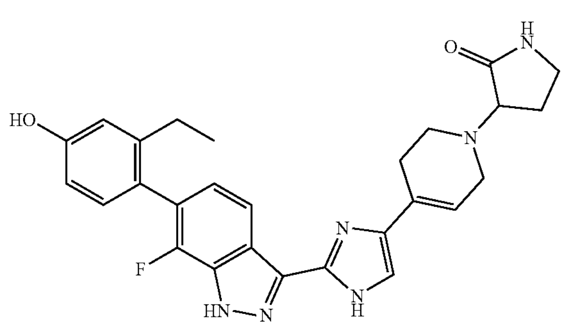 [SMILES: CCc1cc(O)ccc1-c1ccc2c(-c3nc(C4=CCN(C5CCNC5=O)CC4)c[nH]3)n[nH]c2c1F] | 487.2 | 487.2 |

TABLE 4-continued
| Ex. No. | Structure | Calc. [M + H]+ | Found [M + H]+ |
|---|---|---|---|
| 85 | 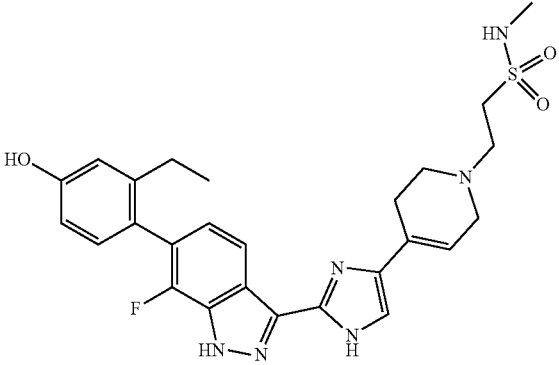 [SMILES: CCc1cc(O)ccc1-c1ccc2c(-c3nc(C4=CCN(CCS(=O)(=O)NC)CC4)c[nH]3)n[nH]c2c1F] | 525.2 | 525.1 |
| 86 | 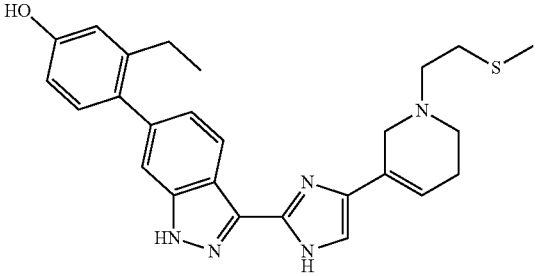 [SMILES: CCc1cc(O)ccc1-c1ccc2c(-c3nc(C4=CCCN(CCSC)C4)c[nH]3)n[nH]c2c1] | 460.2 | 460.2 |
| 87 | 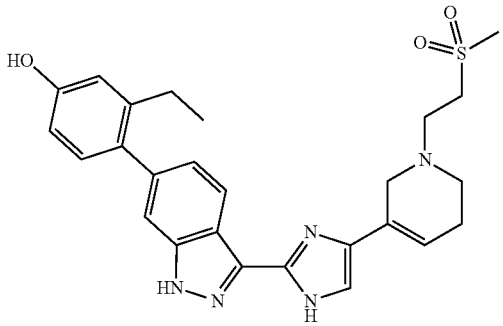 [SMILES: CCc1cc(O)ccc1-c1ccc2c(-c3nc(C4=CCCN(CCS(C)(=O)=O)C4)c[nH]3)n[nH]c2c1] | 492.2 | 492.0 |
| 88 | 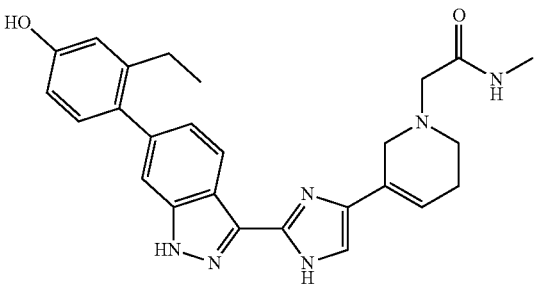 [SMILES: CCc1cc(O)ccc1-c1ccc2c(-c3nc(C4=CCCN(CC(=O)NC)C4)c[nH]3)n[nH]c2c1] | 457.2 | 457.1 |

TABLE 4-continued

| Ex. No. | Structure | Calc. [M + H]+ | Found [M + H]+ |
|---|---|---|---|
| 89 | 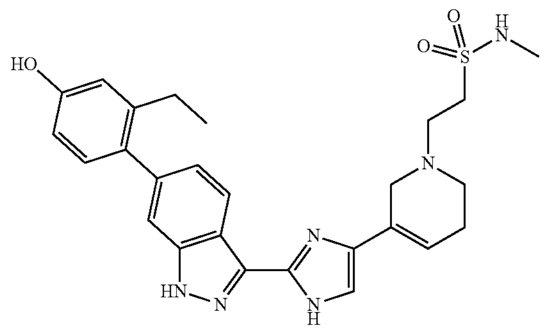 [SMILES: CCc1cc(O)ccc1-c1ccc2c(-c3nc(C4=CCCN(CCS(=O)(=O)NC)C4)c[nH]3)n[nH]c2c1] | 507.2 | 507.0 |
| 90 | 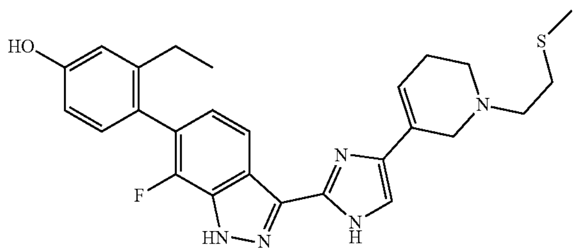 [SMILES: CCc1cc(O)ccc1-c1ccc2c(-c3nc(C4=CCCN(CCSC)C4)c[nH]3)n[nH]c2c1F] | 478.2 | 478.2 |
| 91 | 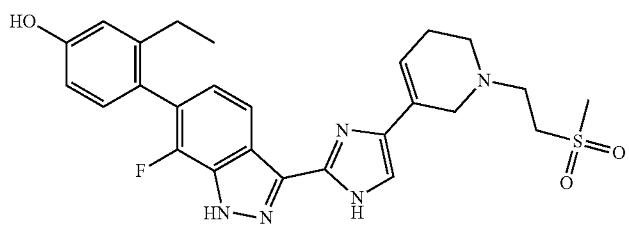 [SMILES: CCc1cc(O)ccc1-c1ccc2c(-c3nc(C4=CCCN(CCS(C)(=O)=O)C4)c[nH]3)n[nH]c2c1F] | 510.2 | 510.0 |
| 92 | 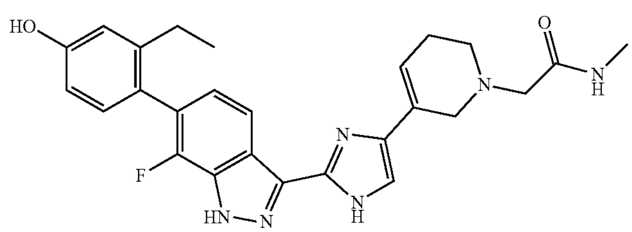 [SMILES: CCc1cc(O)ccc1-c1ccc2c(-c3nc(C4=CCCN(CC(=O)NC)C4)c[nH]3)n[nH]c2c1F] | 475.2 | 475.2 |
| 93 | 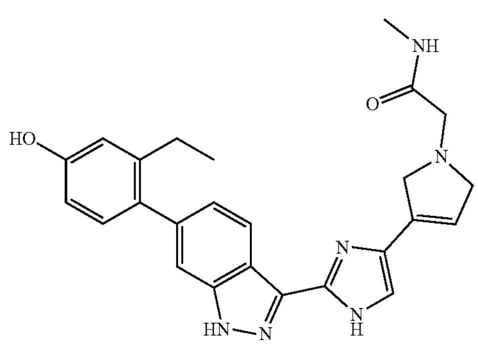 [SMILES: CCc1cc(O)ccc1-c1ccc2c(-c3nc(C4=CCN(CC(=O)NC)C4)c[nH]3)n[nH]c2c1] | 443.2 | 443.0 |

TABLE 4-continued
| Ex. No. | Structure | Calc. [M + H]+ | Found [M + H]+ |
|---|---|---|---|
| 94 | 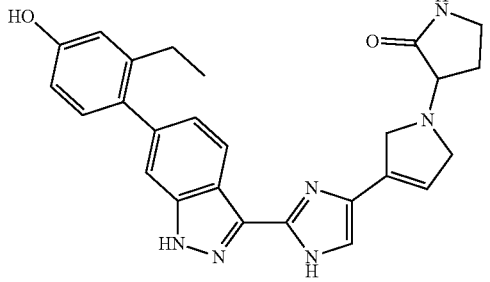 | 455.2 | 455.2 |
| 95 | 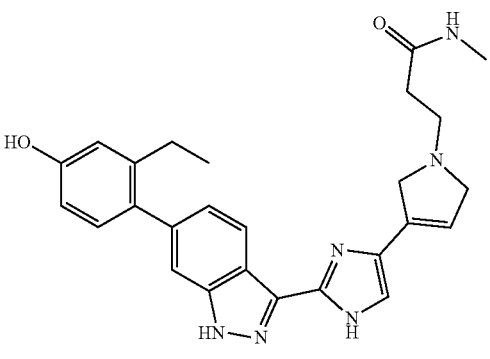 [SMILES: CCc1cc(O)ccc1-c1ccc2c(-c3nc(C4=CCN(CCC(=O)NC)C4)c[nH]3)n[nH]c2c1] | 457.2 | 457.2 |
| 96 | 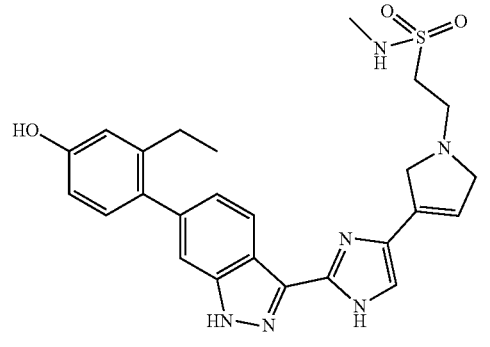 [SMILES: CCc1cc(O)ccc1-c1ccc2c(-c3nc(C4=CCN(CCS(=O)(=O)NC)C4)c[nH]3)n[nH]c2c1] | 493.2 | 493.2 |
| 97 | 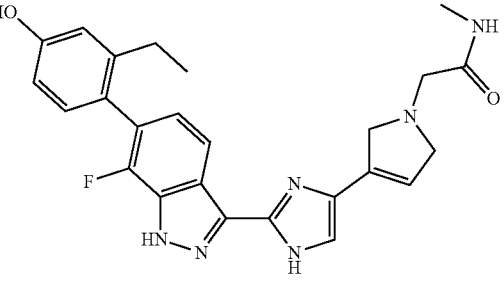 | 461.2 | 461.2 |
| 98 | 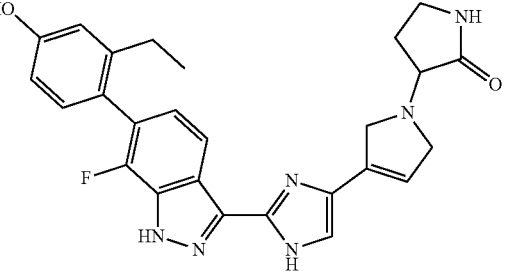 | 473.2 | 473.2 |

TABLE 4-continued

| Ex. No. | Structure | Calc. [M + H]+ | Found [M + H]+ |
|---|---|---|---|
| 99 | 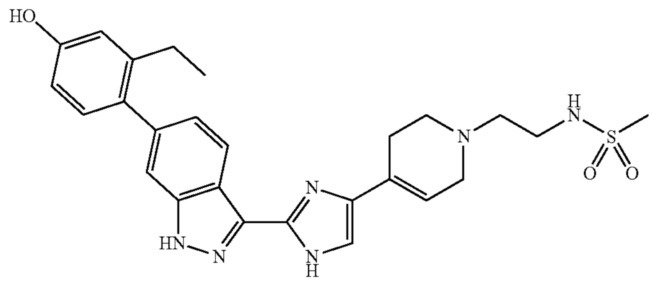 [SMILES: CCc1cc(O)ccc1-c1ccc2c(-c3nc(C4=CCN(CCNS(C)(=O)=O)CC4)c[nH]3)n[nH]c2c1] | 507.2 | 507.0 |
| 100 | 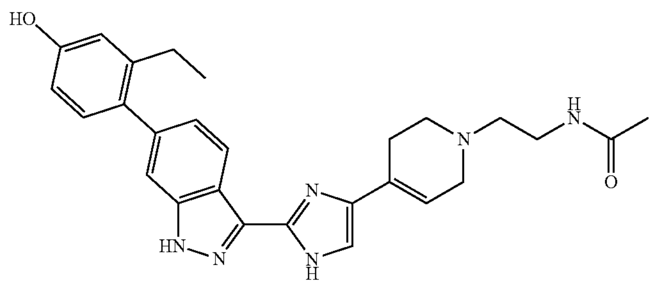 [SMILES: CCc1cc(O)ccc1-c1ccc2c(-c3nc(C4=CCN(CCNC(C)=O)CC4)c[nH]3)n[nH]c2c1] | 471.2 | 471.1 |
| 101 | 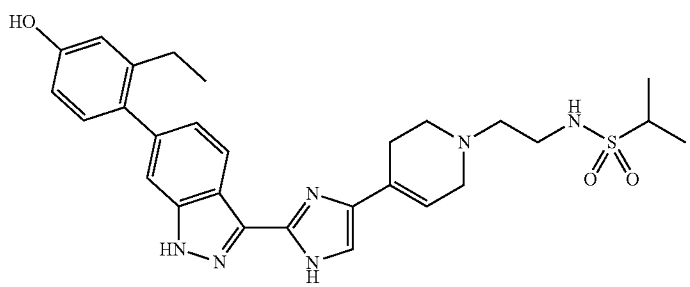 [SMILES: CCc1cc(O)ccc1-c1ccc2c(-c3nc(C4=CCN(CCNS(=O)(=O)C(C)C)CC4)c[nH]3)n[nH]c2c1] | 535.2 | 535.1 |
| 102 | 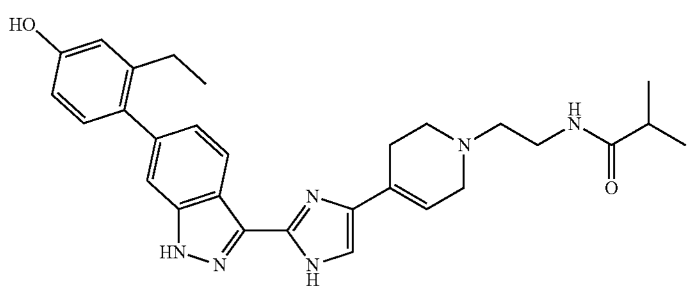 [SMILES: CCc1cc(O)ccc1-c1ccc2c(-c3nc(C4=CCN(CCNC(=O)C(C)C)CC4)c[nH]3)n[nH]c2c1] | 499.3 | 499.1 |
| 103 | 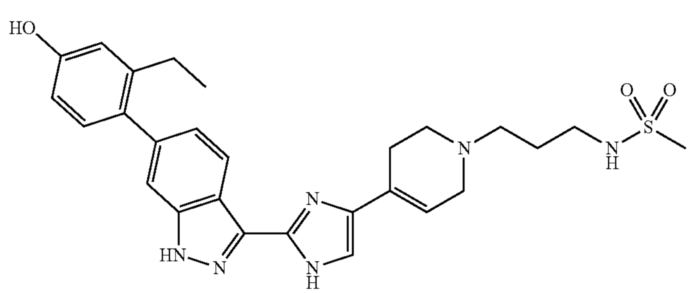 [SMILES: CCc1cc(O)ccc1-c1ccc2c(-c3nc(C4=CCN(CCCNS(C)(=O)=O)CC4)c[nH]3)n[nH]c2c1] | 521.2 | 521.1 |

TABLE 4-continued
| Ex. No. | Structure | Calc. [M + H]+ | Found [M + H]+ |
|---|---|---|---|
| 104 | 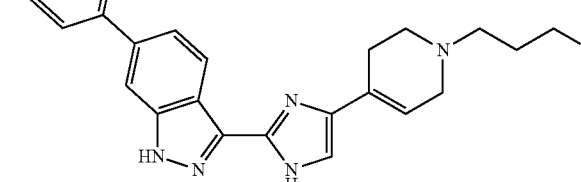 | 485.3 | 485.1 |
| 105 | 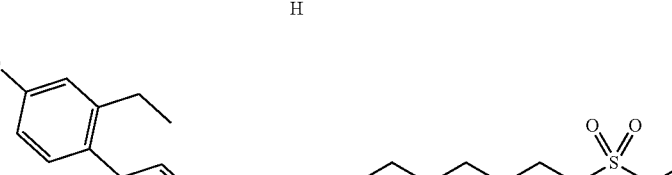 | 549.3 | 549.1 |
| 106 | 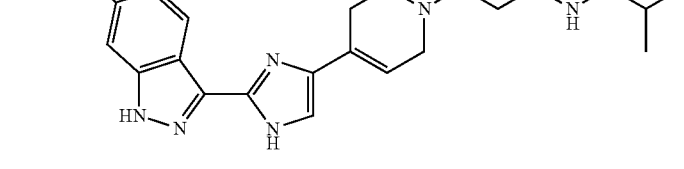 | 525.2 | 525.1 |
| 107 | 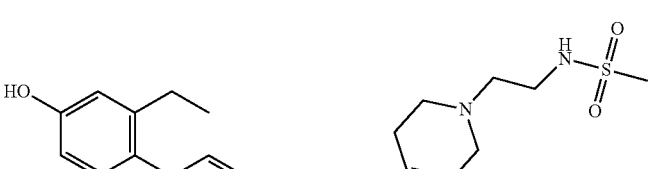 | 489.2 | 489.1 |
| 108 | 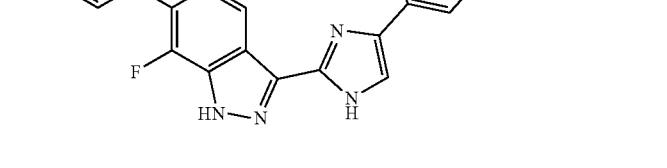 | 507.2 | 507.1 |

TABLE 4-continued

| Ex. No. | Structure | Calc. [M + H]+ | Found [M + H]+ |
|---|---|---|---|
| 109 | 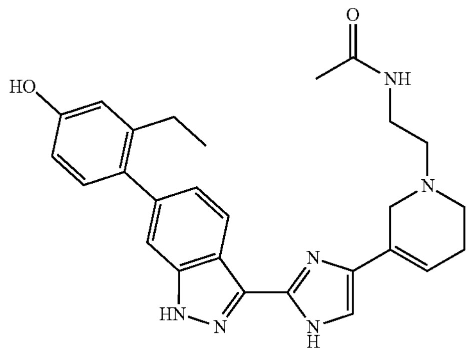 [SMILES: CCc1cc(O)ccc1-c1ccc2c(-c3nc(C4=CCCN(CCNC(C)=O)C4)c[nH]3)n[nH]c2c1] | 471.2 | 471.1 |
| 110 | 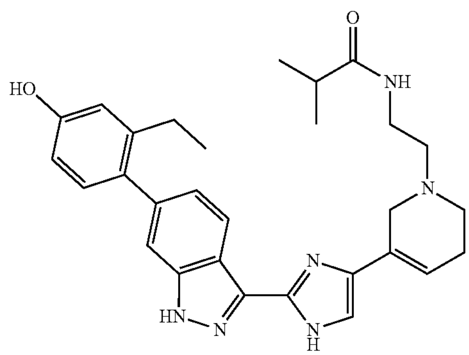 [SMILES: CCc1cc(O)ccc1-c1ccc2c(-c3nc(C4=CCCN(CCNC(=O)C(C)C)C4)c[nH]3)n[nH]c2c1] | 499.3 | 499.2 |
| 111 | 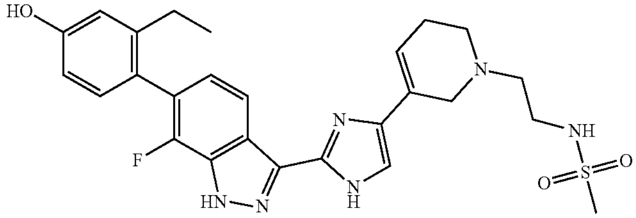 [SMILES: CCc1cc(O)ccc1-c1ccc2c(-c3nc(C4=CCCN(CCNS(C)(=O)=O)C4)c[nH]3)n[nH]c2c1F] | 525.2 | 525.2 |
| 112 | 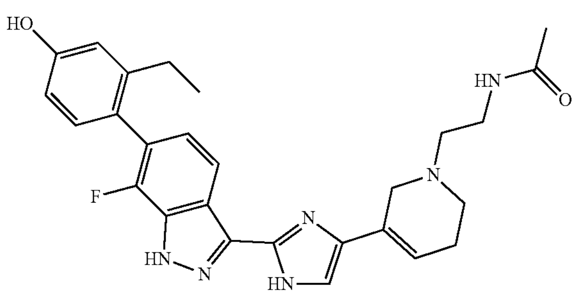 [SMILES: CCc1cc(O)ccc1-c1ccc2c(-c3nc(C4=CCCN(CCNC(C)=O)C4)c[nH]3)n[nH]c2c1F] | 489.2 | 489.1 |
| 113 | 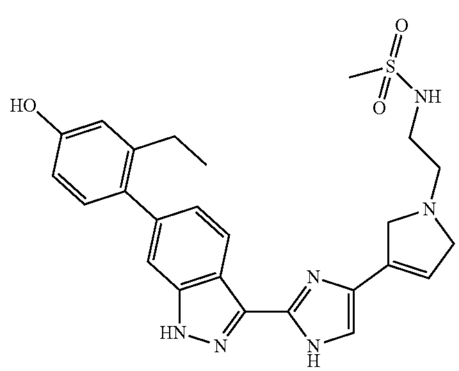 [SMILES: CCc1cc(O)ccc1-c1ccc2c(-c3nc(C4=CCN(CCNS(C)(=O)=O)C4)c[nH]3)n[nH]c2c1] | 493.2 | 493.2 |

TABLE 4-continued

| Ex. No. | Structure | Calc. [M + H]+ | Found [M + H]+ |
|---|---|---|---|
| 114 | 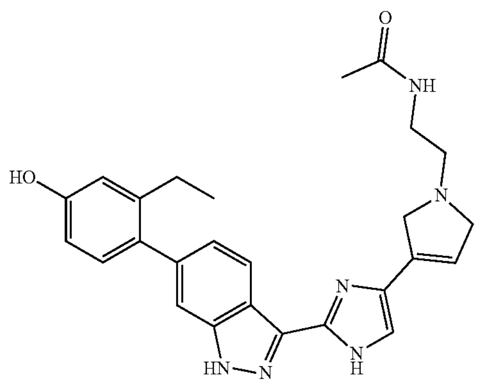 [SMILES: CCc1cc(O)ccc1-c1ccc2c(-c3nc(C4=CCN(CCNC(C)=O)C4)c[nH]3)n[nH]c2c1] | 457.2 | 457.2 |
| 115 | 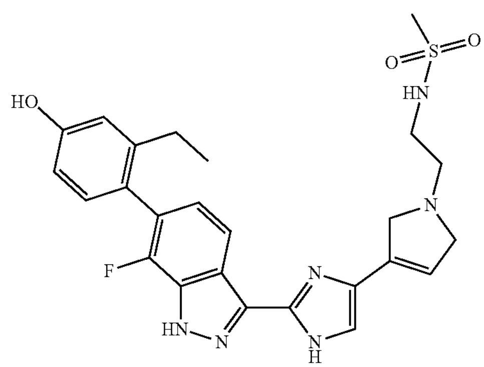 [SMILES: CCc1cc(O)ccc1-c1ccc2c(-c3nc(C4=CCN(CCNS(C)(=O)=O)C4)c[nH]3)n[nH]c2c1F] | 511.2 | 511.2 |
| 116 | 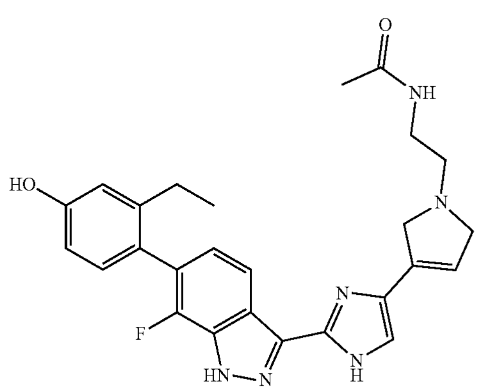 [SMILES: CCc1cc(O)ccc1-c1ccc2c(-c3nc(C4=CCN(CCNC(C)=O)C4)c[nH]3)n[nH]c2c1F] | 475.2 | 475.2 |
| 117 | 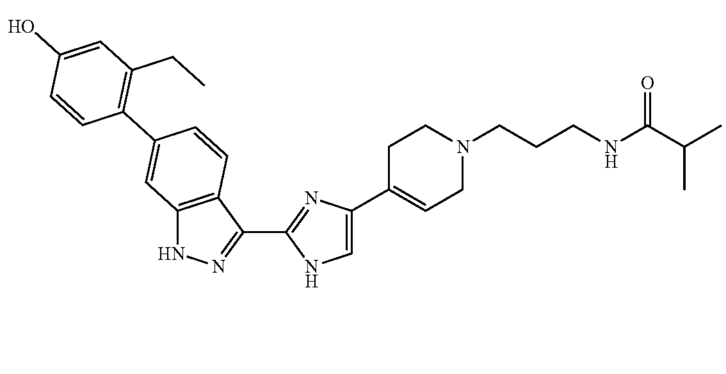 [SMILES: CCc1cc(O)ccc1-c1ccc2c(-c3nc(C4=CCN(CCCNC(=O)C(C)C)CC4)c[nH]3)n[nH]c2c1] | 513.3 | 513.1 |

TABLE 4-continued

| Ex. No. | Structure | Calc. [M + H]+ | Found [M + H]+ |
|---|---|---|---|
| 118 | 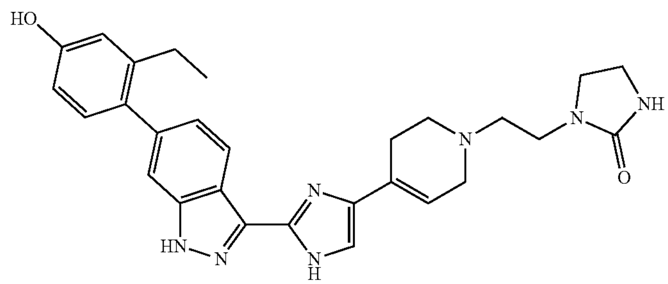 [SMILES: CCc1cc(O)ccc1-c1ccc2c(-c3nc(C4=CCN(CCN5CCNC5=O)CC4)c[nH]3)n[nH]c2c1] | 498.3 | 498.1 |
| 119 | 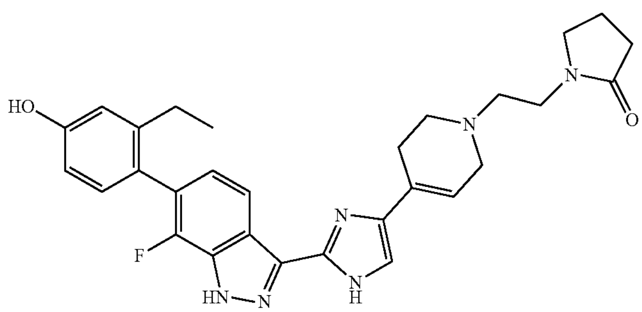 [SMILES: CCc1cc(O)ccc1-c1ccc2c(-c3nc(C4=CCN(CCN5CCCC5=O)CC4)c[nH]3)n[nH]c2c1F] | 515.2 | 515.2 |
| 120 | 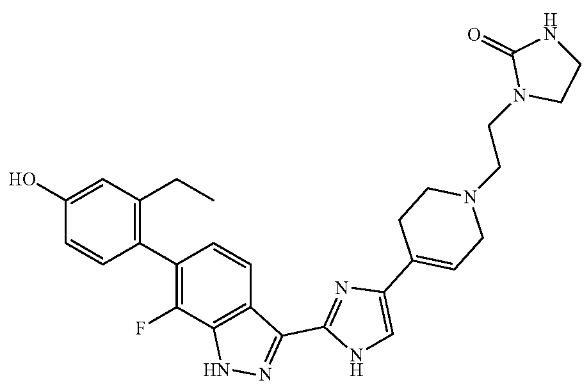 [SMILES: CCc1cc(O)ccc1-c1ccc2c(-c3nc(C4=CCN(CCN5CCNC5=O)CC4)c[nH]3)n[nH]c2c1F] | 516.2 | 516.2 |
| 121 | 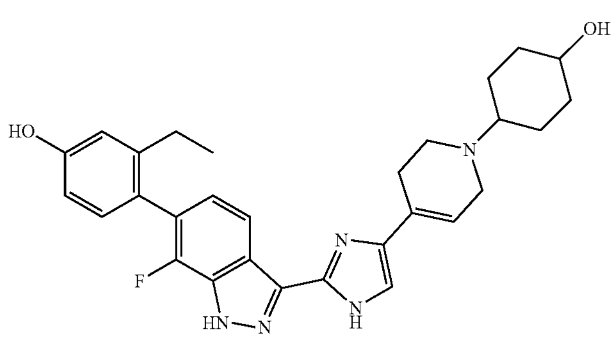 [SMILES: CCc1cc(O)ccc1-c1ccc2c(-c3nc(C4=CCN(C5CCC(O)CC5)CC4)c[nH]3)n[nH]c2c1F] | 502.3 | 502.2 |

TABLE 4-continued

| Ex. No. | Structure | Calc. [M + H]+ | Found [M + H]+ |
|---|---|---|---|
| 122 | 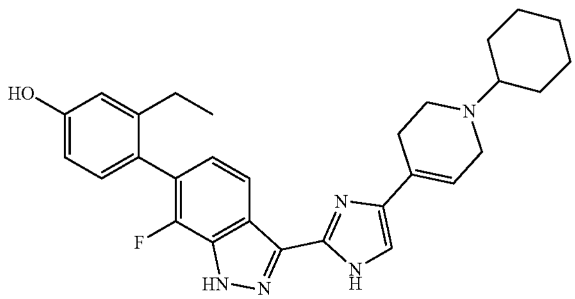 [SMILES: CCc1cc(O)ccc1-c1ccc2c(-c3nc(C4=CCN(C5CCCCC5)CC4)c[nH]3)n[nH]c2c1F] | 486.3 | 486.3 |
| 123 | 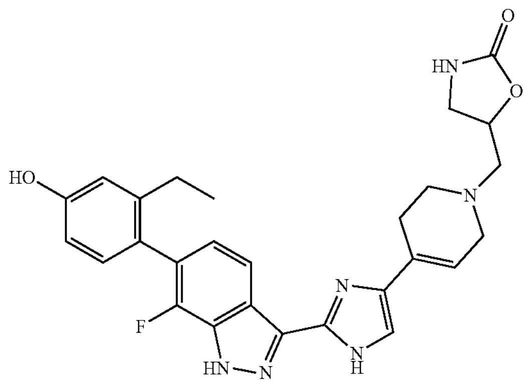 [SMILES: CCc1cc(O)ccc1-c1ccc2c(-c3nc(C4=CCN(CC5CNC(=O)O5)CC4)c[nH]3)n[nH]c2c1F] | 503.2 | 503.2 |
| 124 | 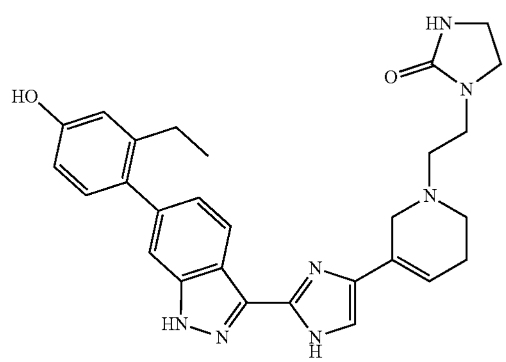 [SMILES: CCc1cc(O)ccc1-c1ccc2c(-c3nc(C4=CCCN(CCN5CCNC5=O)C4)c[nH]3)n[nH]c2c1] | 498.3 | 498.1 |
| 125 | 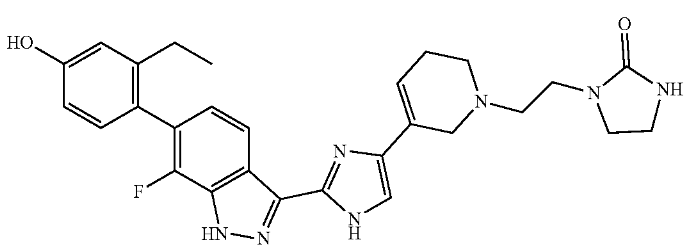 [SMILES: CCc1cc(O)ccc1-c1ccc2c(-c3nc(C4=CCCN(CCN5CCNC5=O)C4)c[nH]3)n[nH]c2c1F] | 516.2 | 516.2 |
| 126 | 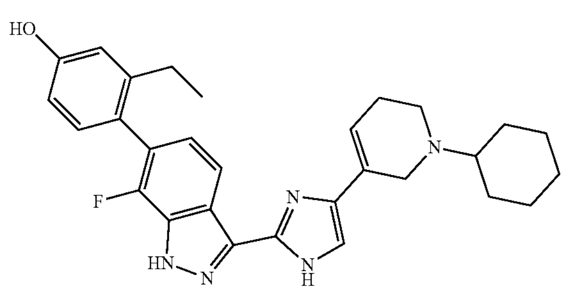 [SMILES: CCc1cc(O)ccc1-c1ccc2c(-c3nc(C4=CCCN(C5CCCCC5)C4)c[nH]3)n[nH]c2c1F] | 486.3 | 486.3 |

TABLE 4-continued
| Ex. No. | Structure | Calc. [M + H]+ | Found [M + H]+ |
|---|---|---|---|
| 127 | 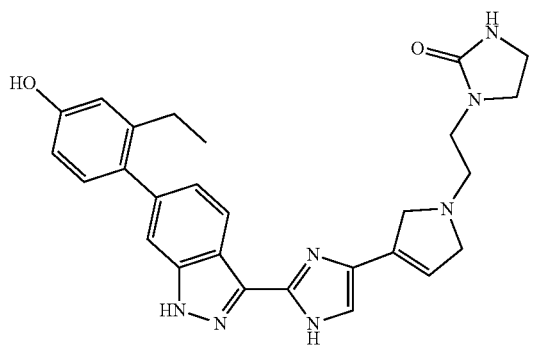 [SMILES: CCc1cc(O)ccc1-c1ccc2c(-c3nc(C4=CCN(CCN5CCNC5=O)C4)c[nH]3)n[nH]c2c1] | 484.2 | 484.4 |
| 128 | 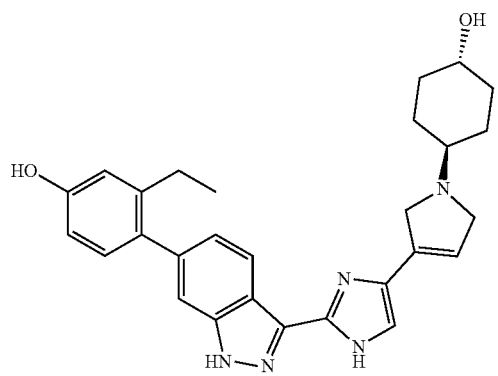 [SMILES: CCc1cc(O)ccc1-c1ccc2c(-c3nc(C4=CCN([C@H]5CC[C@H](O)CC5)C4)c[nH]3)n[nH]c2c1] | 470.2 | 470.2 |
| 129 | 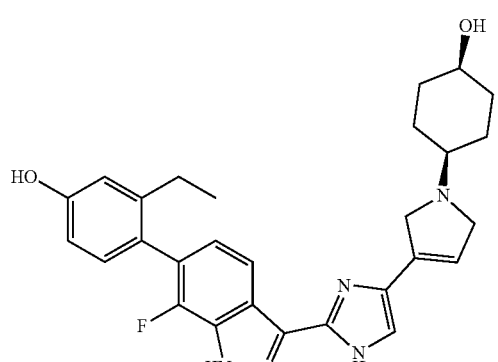 | 488.2 | 488.3 |
| 130 | 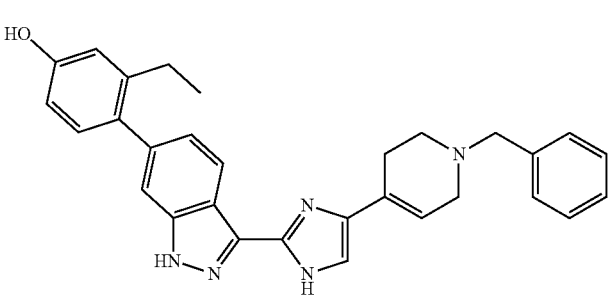 [SMILES: CCc1cc(O)ccc1-c1ccc2c(-c3nc(C4=CCN(Cc5ccccc5)CC4)c[nH]3)n[nH]c2c1] | 476.2 | 476.1 |

TABLE 4-continued

| Ex. No. | Structure | Calc. [M + H]+ | Found [M + H]+ |
|---|---|---|---|
| 131 | 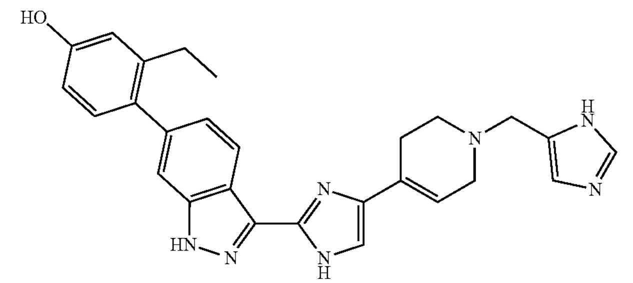 [SMILES: CCc1cc(O)ccc1-c1ccc2c(-c3nc(C4=CCN(Cc5cnc[nH]5)CC4)c[nH]3)n[nH]c2c1] | 466.2 | 466.1 |
| 132 | 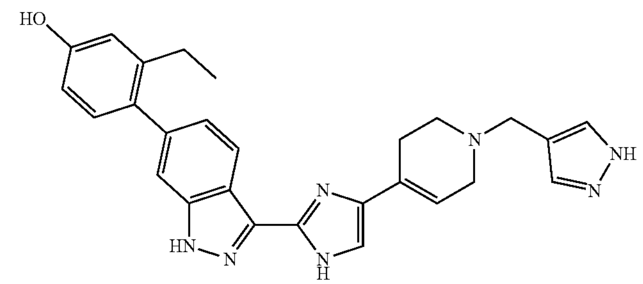 [SMILES: CCc1cc(O)ccc1-c1ccc2c(-c3nc(C4=CCN(Cc5cn[nH]c5)CC4)c[nH]3)n[nH]c2c1] | 466.2 | 466.1 |
| 133 | 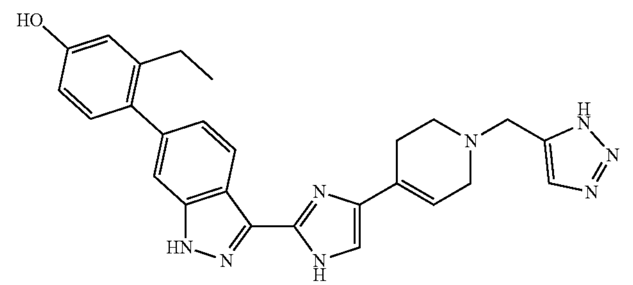 [SMILES: CCc1cc(O)ccc1-c1ccc2c(-c3nc(C4=CCN(Cc5cnn[nH]5)CC4)c[nH]3)n[nH]c2c1] | 467.2 | 467.1 |
| 134 | 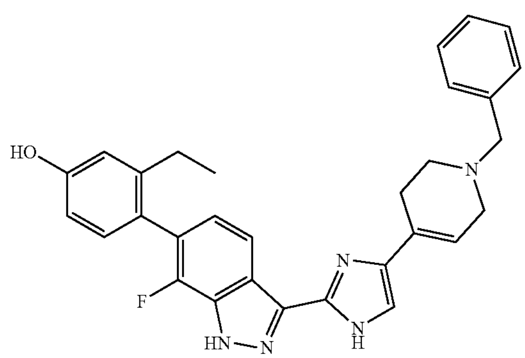 [SMILES: CCc1cc(O)ccc1-c1ccc2c(-c3nc(C4=CCN(Cc5ccccc5)CC4)c[nH]3)n[nH]c2c1F] | 494.2 | 494.1 |
| 135 | 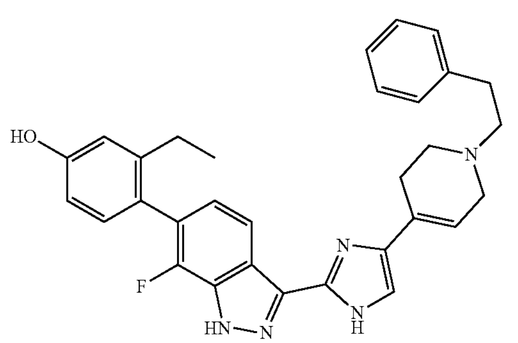 [SMILES: CCc1cc(O)ccc1-c1ccc2c(-c3nc(C4=CCN(CCc5ccccc5)CC4)c[nH]3)n[nH]c2c1F] | 508.2 | 508.2 |

TABLE 4-continued

| Ex. No. | Structure | Calc. [M + H]+ | Found [M + H]+ |
|---|---|---|---|
| 136 | 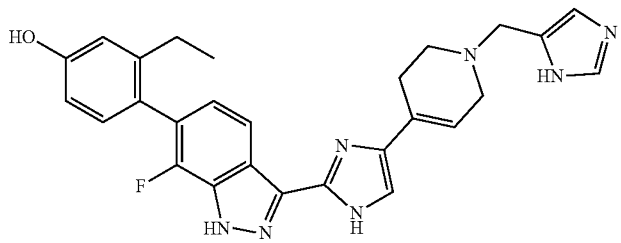 [SMILES: CCc1cc(O)ccc1-c1ccc2c(-c3nc(C4=CCN(Cc5cnc[nH]5)CC4)c[nH]3)n[nH]c2c1F] | 484.2 | 484.2 |
| 137 | 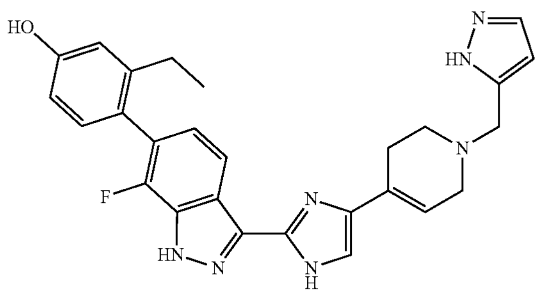 [SMILES: CCc1cc(O)ccc1-c1ccc2c(-c3nc(C4=CCN(Cc5ccn[nH]5)CC4)c[nH]3)n[nH]c2c1F] | 484.2 | 484.2 |
| 138 | 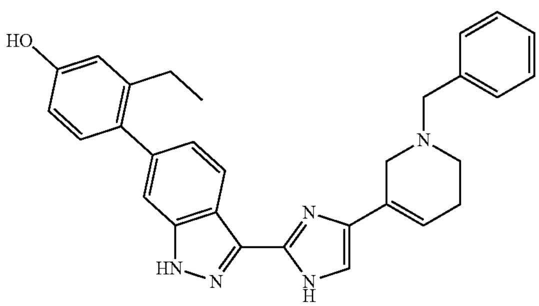 [SMILES: CCc1cc(O)ccc1-c1ccc2c(-c3nc(C4=CCCN(Cc5ccccc5)C4)c[nH]3)n[nH]c2c1] | 476.2 | 476.2 |
| 139 | 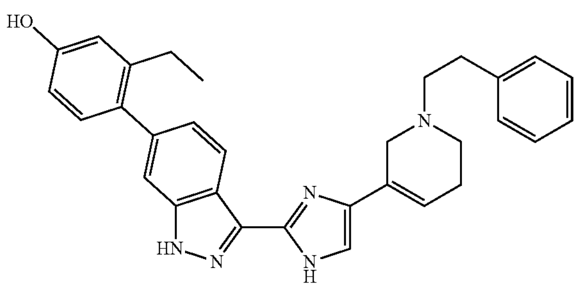 [SMILES: CCc1cc(O)ccc1-c1ccc2c(-c3nc(C4=CCCN(CCc5ccccc5)C4)c[nH]3)n[nH]c2c1] | 490.3 | 490.3 |
| 140 | 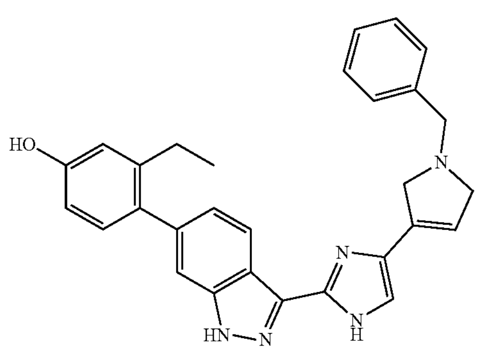 [SMILES: CCc1cc(O)ccc1-c1ccc2c(-c3nc(C4=CCN(Cc5ccccc5)C4)c[nH]3)n[nH]c2c1] | 462.2 | 462.1 |

TABLE 4-continued
| Ex. No. | Structure | Calc. [M + H]+ | Found [M + H]+ |
|---|---|---|---|
| 141 | 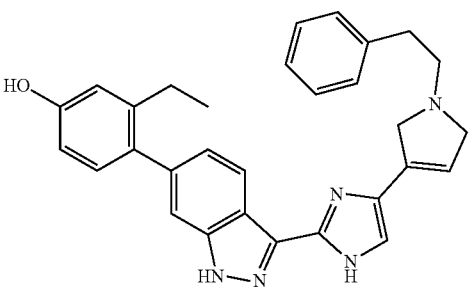 [SMILES: CCc1cc(O)ccc1-c1ccc2c(-c3nc(C4=CCN(CCc5ccccc5)C4)c[nH]3)n[nH]c2c1] | 476.2 | 476.1 |
| 142 | 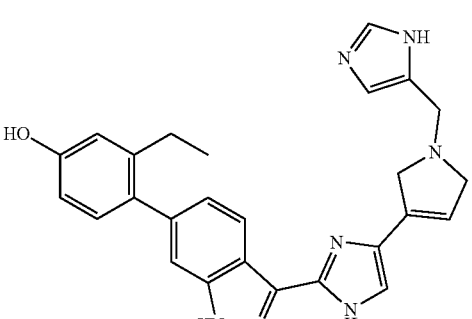 | 452.2 | 452.2 |
| 143 | 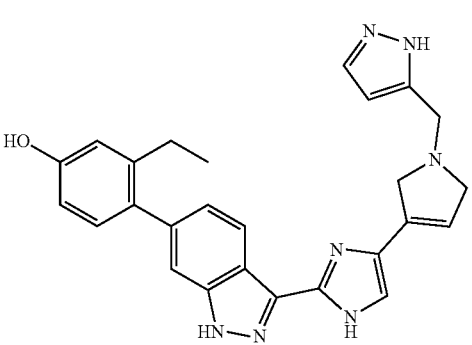 [SMILES: CCc1cc(O)ccc1-c1ccc2c(-c3nc(C4=CCN(Cc5ccn[nH]5)C4)c[nH]3)n[nH]c2c1] | 452.2 | 452.1 |
| 144 | 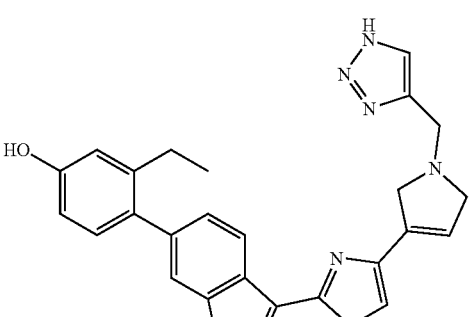 | 453.2 | 453.2 |

TABLE 4-continued
| Ex. No. | Structure | Calc. [M + H]+ | Found [M + H]+ |
|---|---|---|---|
| 145 | 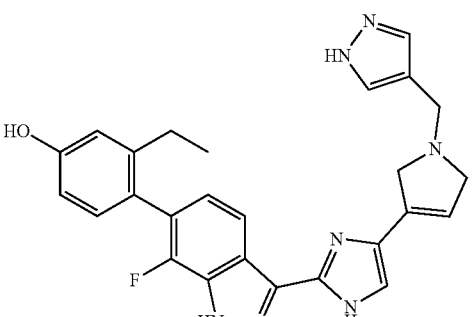 | 470.2 | 470.2 |
| 146 | 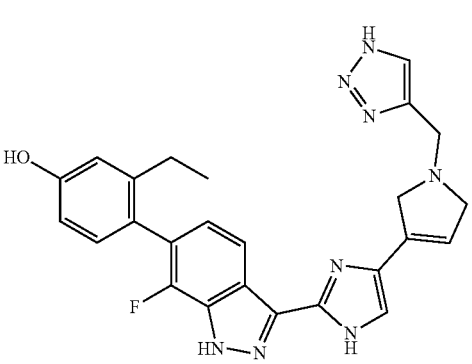 [SMILES: CCc1cc(O)ccc1-c1ccc2c(-c3nc(C4=CCN(Cc5c[nH]nn5)C4)c[nH]3)n[nH]c2c1F] | 471.2 | 471.2 |
| 147 | 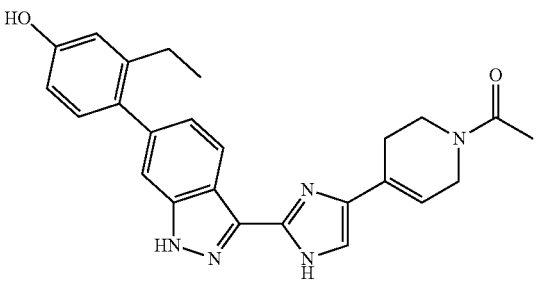 [SMILES: CCc1cc(O)ccc1-c1ccc2c(-c3nc(C4=CCN(C(C)=O)CC4)c[nH]3)n[nH]c2c1] | 428.2 | 428.1 |
| 148 | 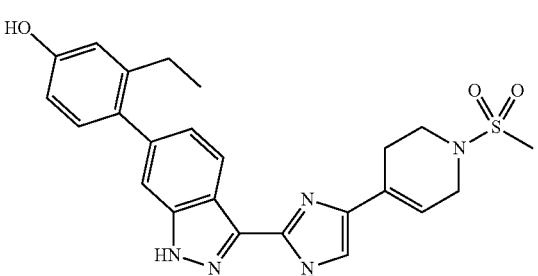 | 464.2 | 464.1 |
| 149 | 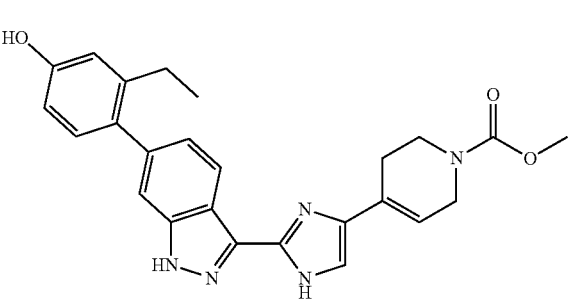 [SMILES: CCc1cc(O)ccc1-c1ccc2c(-c3nc(C4=CCN(C(=O)OC)CC4)c[nH]3)n[nH]c2c1] | 444.2 | 444.1 |

TABLE 4-continued

| Ex. No. | Structure | Calc. [M + H]+ | Found [M + H]+ |
|---|---|---|---|
| 150 | 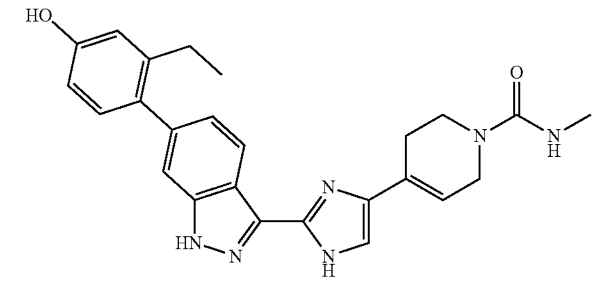 [SMILES: CCc1cc(O)ccc1-c1ccc2c(-c3nc(C4=CCN(C(=O)NC)CC4)c[nH]3)n[nH]c2c1] | 443.2 | 443.1 |
| 151 | 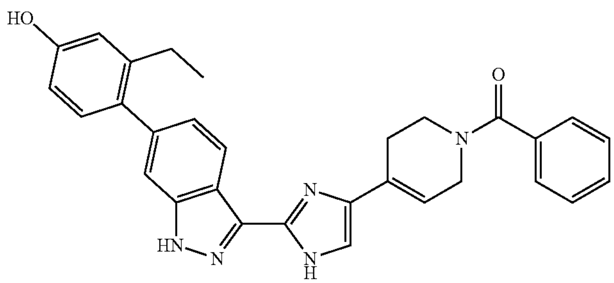 [SMILES: CCc1cc(O)ccc1-c1ccc2c(-c3nc(C4=CCN(C(=O)c5ccccc5)CC4)c[nH]3)n[nH]c2c1] | 490.2 | 490.1 |
| 152 | 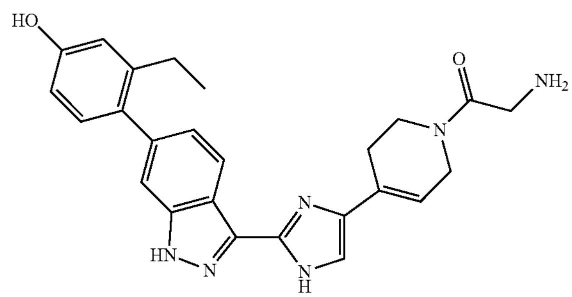 [SMILES: CCc1cc(O)ccc1-c1ccc2c(-c3nc(C4=CCN(C(=O)CN)CC4)c[nH]3)n[nH]c2c1] | 443.2 | 443.2 |
| 153 | 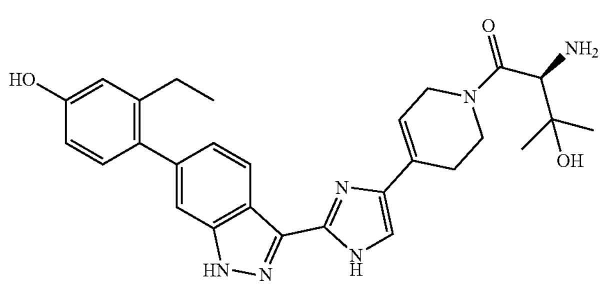 [SMILES: CCc1cc(O)ccc1-c1ccc2c(-c3nc(C4=CCN(C(=O)[C@@H](N)C(C)(C)O)CC4)c[nH]3)n[nH]c2c1] | 501.3 | 501.3 |
| 154 | 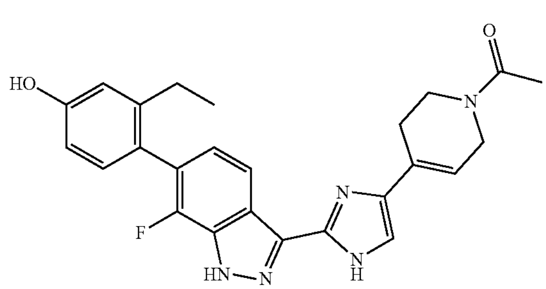 [SMILES: CCc1cc(O)ccc1-c1ccc2c(-c3nc(C4=CCN(C(C)=O)CC4)c[nH]3)n[nH]c2c1F] | 446.2 | 446.2 |

TABLE 4-continued

| Ex. No. | Structure | Calc. [M + H]+ | Found [M + H]+ |
|---|---|---|---|
| 155 | 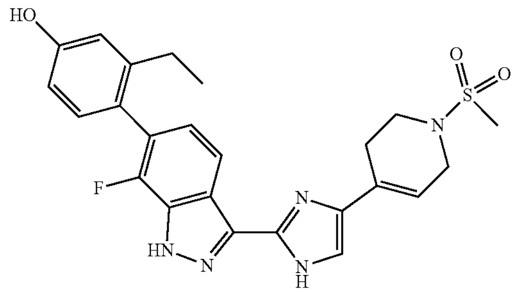 [SMILES: CCc1cc(O)ccc1-c1ccc2c(-c3nc(C4=CCN(S(C)(=O)=O)CC4)c[nH]3)n[nH]c2c1F] | 482.2 | 482.0 |
| 156 | 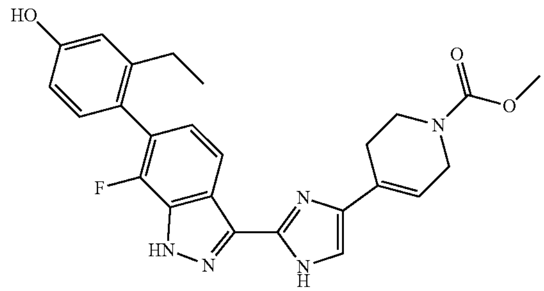 [SMILES: CCc1cc(O)ccc1-c1ccc2c(-c3nc(C4=CCN(C(=O)OC)CC4)c[nH]3)n[nH]c2c1F] | 462.2 | 462.1 |
| 157 | 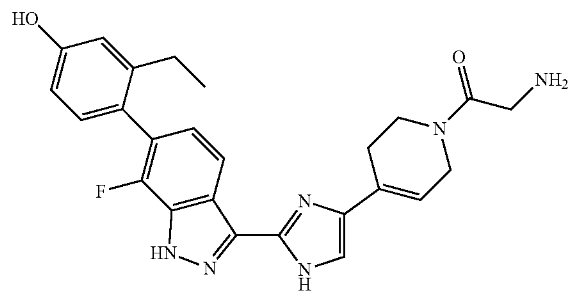 [SMILES: CCc1cc(O)ccc1-c1ccc2c(-c3nc(C4=CCN(C(=O)CN)CC4)c[nH]3)n[nH]c2c1F] | 461.2 | 461.2 |
| 158 | 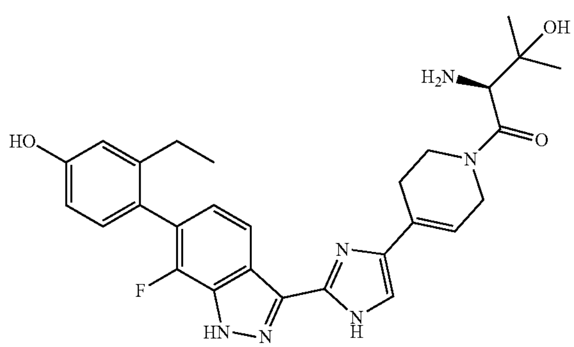 [SMILES: CCc1cc(O)ccc1-c1ccc2c(-c3nc(C4=CCN(C(=O)[C@@H](N)C(C)(C)O)CC4)c[nH]3)n[nH]c2c1F] | 519.2 | 519.2 |
| 159 | 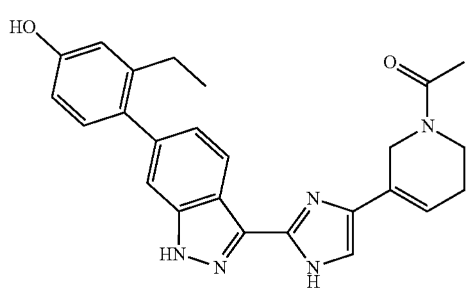 [SMILES: CCc1cc(O)ccc1-c1ccc2c(-c3nc(C4=CCCN(C(C)=O)C4)c[nH]3)n[nH]c2c1] | 428.2 | 428.2 |

TABLE 4-continued

| Ex. No. | Structure | Calc. [M + H]+ | Found [M + H]+ |
|---|---|---|---|
| 160 | 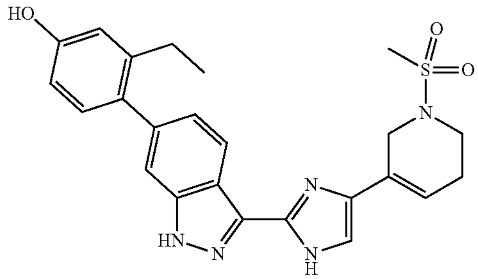 [SMILES: CCc1cc(O)ccc1-c1ccc2c(-c3nc(C4=CCCN(S(C)(=O)=O)C4)c[nH]3)n[nH]c2c1] | 464.2 | 464.1 |
| 161 | 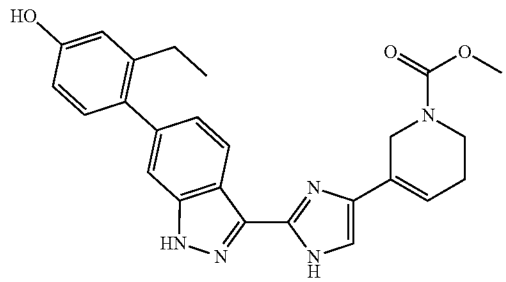 [SMILES: CCc1cc(O)ccc1-c1ccc2c(-c3nc(C4=CCCN(C(=O)OC)C4)c[nH]3)n[nH]c2c1] | 444.2 | 444.3 |
| 162 | 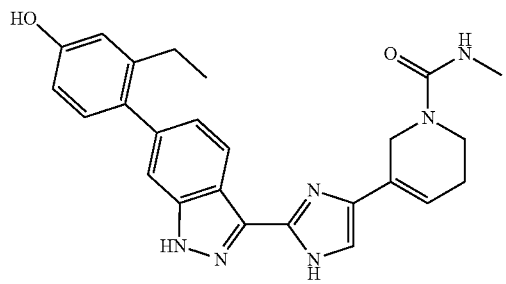 [SMILES: CCc1cc(O)ccc1-c1ccc2c(-c3nc(C4=CCCN(C(=O)NC)C4)c[nH]3)n[nH]c2c1] | 443.2 | 443.0 |
| 163 | 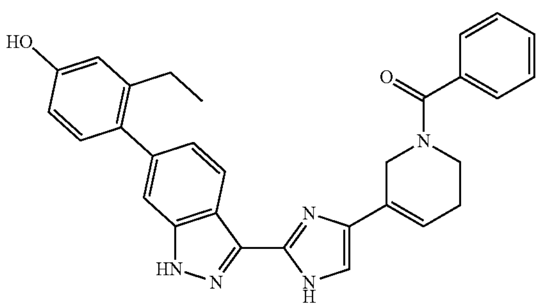 [SMILES: CCc1cc(O)ccc1-c1ccc2c(-c3nc(C4=CCCN(C(=O)c5ccccc5)C4)c[nH]3)n[nH]c2c1] | 490.2 | 490.2 |
| 164 | 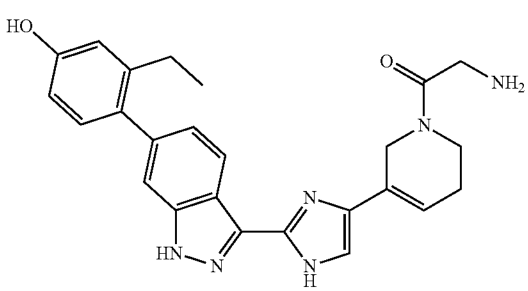 [SMILES: CCc1cc(O)ccc1-c1ccc2c(-c3nc(C4=CCCN(C(=O)CN)C4)c[nH]3)n[nH]c2c1] | 443.2 | 443.1 |

TABLE 4-continued
| Ex. No. | Structure | Calc. [M + H]+ | Found [M + H]+ |
|---|---|---|---|
| 165 | 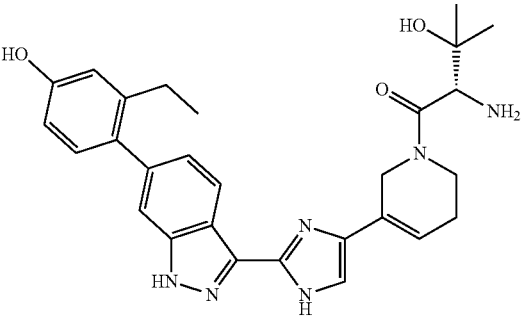 [SMILES: CCc1cc(O)ccc1-c1ccc2c(-c3nc(C4=CCCN(C(=O)[C@@H](N)C(C)(C)O)C4)c[nH]3)n[nH]c2c1] | 501.3 | 501.1 |
| 166 | 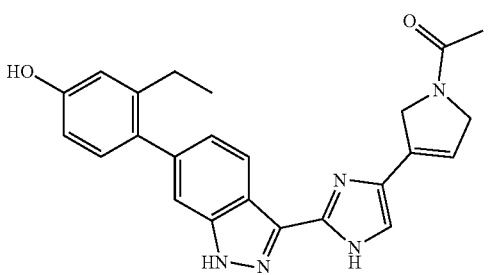 [SMILES: CCc1cc(O)ccc1-c1ccc2c(-c3nc(C4=CCN(C(C)=O)C4)c[nH]3)n[nH]c2c1] | 414.2 | 414.2 |
| 167 | 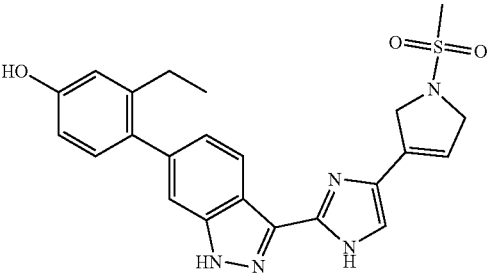 [SMILES: CCc1cc(O)ccc1-c1ccc2c(-c3nc(C4=CCN(S(C)(=O)=O)C4)c[nH]3)n[nH]c2c1] | 450.2 | 450.2 |
| 168 | 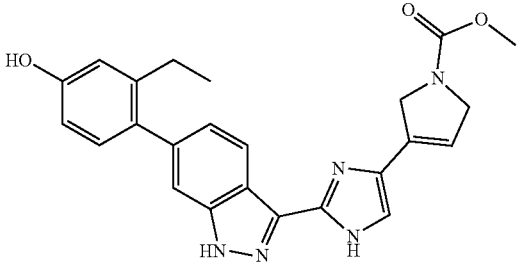 [SMILES: CCc1cc(O)ccc1-c1ccc2c(-c3nc(C4=CCN(C(=O)OC)C4)c[nH]3)n[nH]c2c1] | 430.2 | 430.0 |
| 169 | 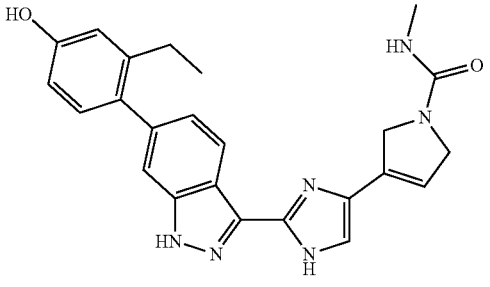 [SMILES: CCc1cc(O)ccc1-c1ccc2c(-c3nc(C4=CCN(C(=O)NC)C4)c[nH]3)n[nH]c2c1] | 429.2 | 429.2 |

TABLE 4-continued

| Ex. No. | Structure | Calc. [M + H]⁺ | Found [M + H]⁺ |
|---|---|---|---|
| 170 | 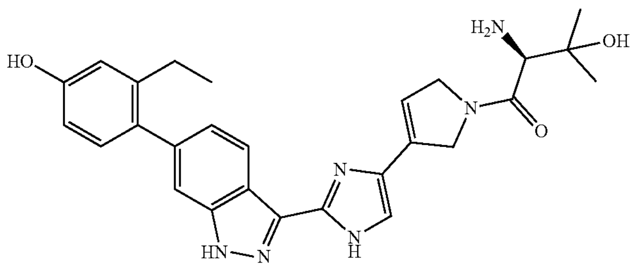 [SMILES: CCc1cc(O)ccc1-c1ccc2c(-c3nc(C4=CCN(C(=O)[C@@H](N)C(C)(C)O)C4)c[nH]3)n[nH]c2c1] | 487.2 | 487.3 |
| 171 | 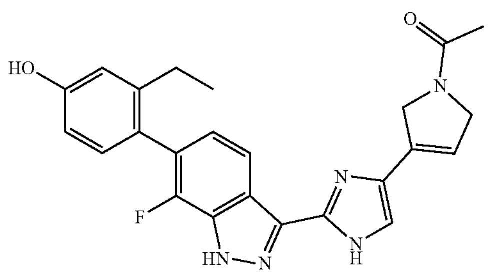 | 432.2 | 432.1 |
| 172 | 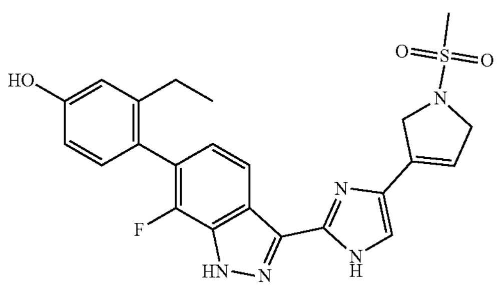 [SMILES: CCc1cc(O)ccc1-c1ccc2c(-c3nc(C4=CCN(S(C)(=O)=O)C4)c[nH]3)n[nH]c2c1F] | 468.1 | 468.1 |
| 173 | 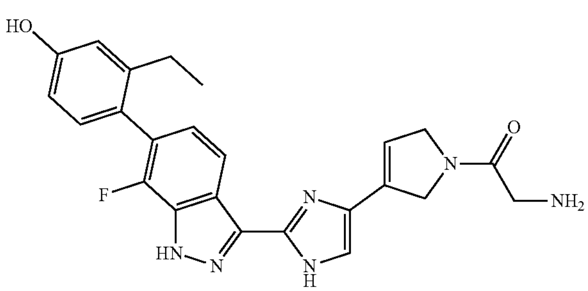 [SMILES: CCc1cc(O)ccc1-c1ccc2c(-c3nc(C4=CCN(C(=O)CN)C4)c[nH]3)n[nH]c2c1F] | 447.2 | 447.2 |
| 174 | 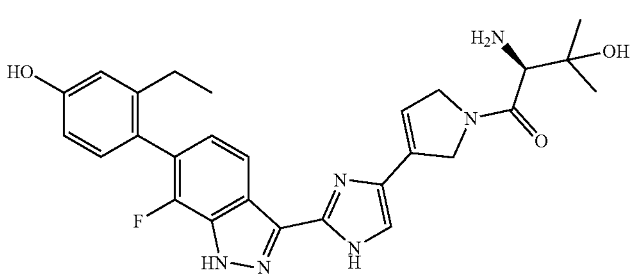 [SMILES: CCc1cc(O)ccc1-c1ccc2c(-c3nc(C4=CCN(C(=O)[C@@H](N)C(C)(C)O)C4)c[nH]3)n[nH]c2c1F] | 505.2 | 505.2 |

TABLE 4-continued

| Ex. No. | Structure | Calc. [M + H]+ | Found [M + H]+ |
|---|---|---|---|
| 175 | 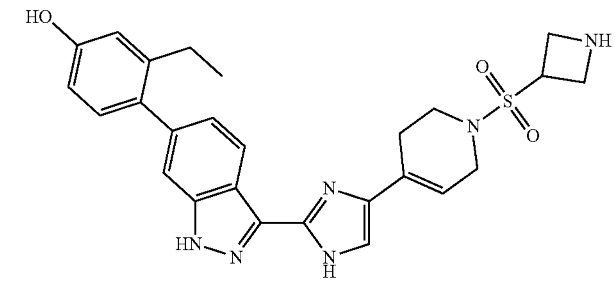 [SMILES: CCc1cc(O)ccc1-c1ccc2c(-c3nc(C4=CCN(S(=O)(=O)C5CNC5)CC4)c[nH]3)n[nH]c2c1] | 505.2 | 505.2 |
| 176 | 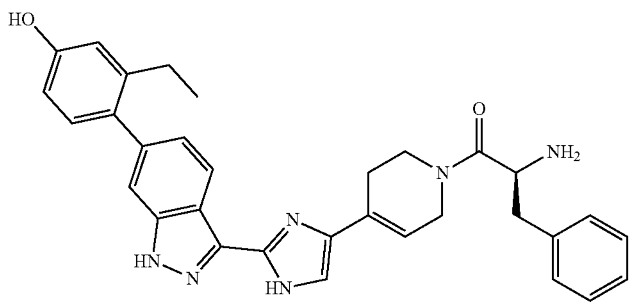 [SMILES: CCc1cc(O)ccc1-c1ccc2c(-c3nc(C4=CCN(C(=O)[C@@H](N)Cc5ccccc5)CC4)c[nH]3)n[nH]c2c1] | 533.3 | 533.3 |
| 177 | 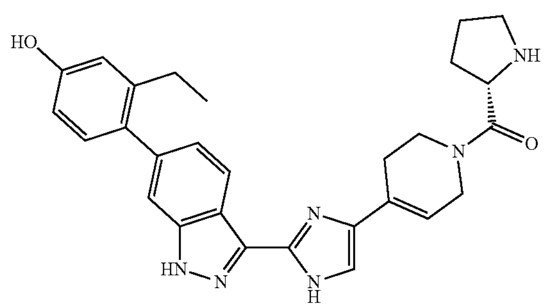 [SMILES: CCc1cc(O)ccc1-c1ccc2c(-c3nc(C4=CCN(C(=O)[C@@H]5CCCN5)CC4)c[nH]3)n[nH]c2c1] | 483.2 | 483.2 |
| 178 | 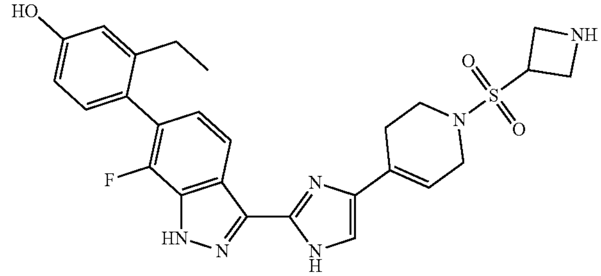 [SMILES: CCc1cc(O)ccc1-c1ccc2c(-c3nc(C4=CCN(S(=O)(=O)C5CNC5)CC4)c[nH]3)n[nH]c2c1F] | 523.2 | 523.2 |
| 179 | 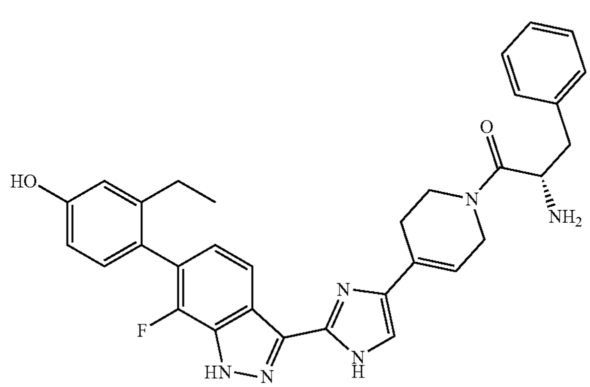 [SMILES: CCc1cc(O)ccc1-c1ccc2c(-c3nc(C4=CCN(C(=O)[C@@H](N)Cc5ccccc5)CC4)c[nH]3)n[nH]c2c1F] | 551.2 | 551.2 |

TABLE 4-continued

| Ex. No. | Structure | Calc. [M + H]+ | Found [M + H]+ |
|---|---|---|---|
| 180 | 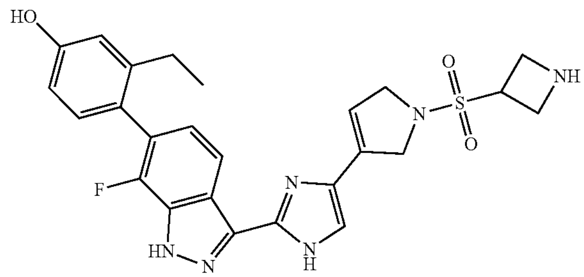 [SMILES: CCc1cc(O)ccc1-c1ccc2c(-c3nc(C4=CCN(S(=O)(=O)C5CNC5)C4)c[nH]3)n[nH]c2c1F] | 509.2 | 509.2 |
| 181 | 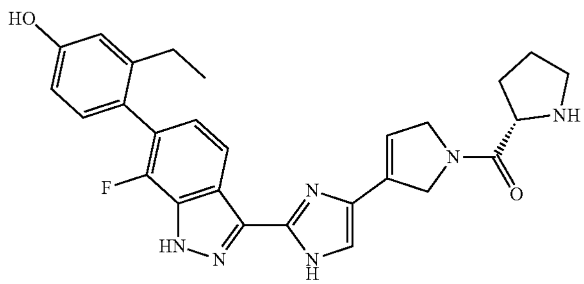 [SMILES: CCc1cc(O)ccc1-c1ccc2c(-c3nc(C4=CCN(C(=O)[C@@H]5CCCN5)C4)c[nH]3)n[nH]c2c1F] | 487.2 | 487.2 |
| 182 | 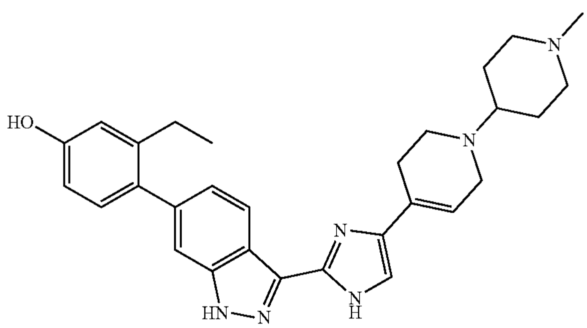 [SMILES: CCc1cc(O)ccc1-c1ccc2c(-c3nc(C4=CCN(C5CCN(C)CC5)CC4)c[nH]3)n[nH]c2c1] | 483.3 | 483.3 |
| 183 | 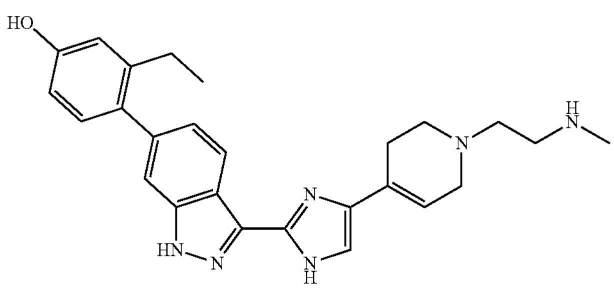 [SMILES: CCc1cc(O)ccc1-c1ccc2c(-c3nc(C4=CCN(CCNC)CC4)c[nH]3)n[nH]c2c1] | 443.2 | 443.2 |
| 184 | 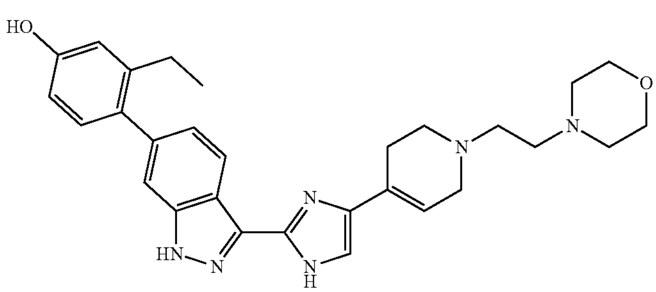 [SMILES: CCc1cc(O)ccc1-c1ccc2c(-c3nc(C4=CCN(CCN5CCOCC5)CC4)c[nH]3)n[nH]c2c1] | 499.3 | 499.3 |

TABLE 4-continued

| Ex. No. | Structure | Calc. [M + H]+ | Found [M + H]+ |
|---|---|---|---|
| 185 | 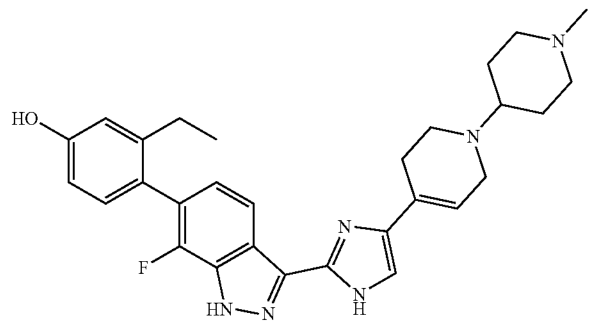 [SMILES: CCc1cc(O)ccc1-c1ccc2c(-c3nc(C4=CCN(C5CCN(C)CC5)CC4)c[nH]3)n[nH]c2c1F] | 501.3 | 501.3 |
| 186 | 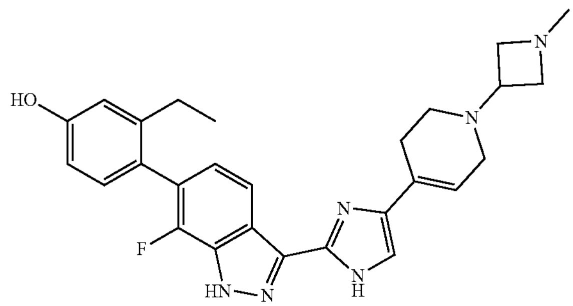 [SMILES: CCc1cc(O)ccc1-c1ccc2c(-c3nc(C4=CCN(C5CN(C)C5)CC4)c[nH]3)n[nH]c2c1F] | 473.2 | 473.2 |
| 187 | 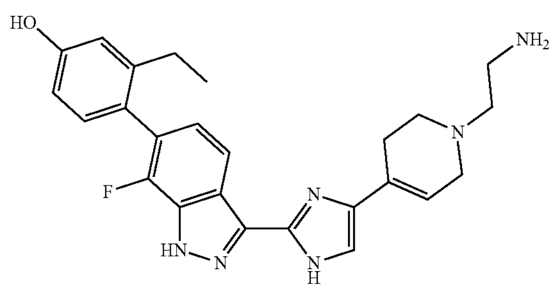 [SMILES: CCc1cc(O)ccc1-c1ccc2c(-c3nc(C4=CCN(CCN)CC4)c[nH]3)n[nH]c2c1F] | 447.2 | 447.3 |
| 188 | 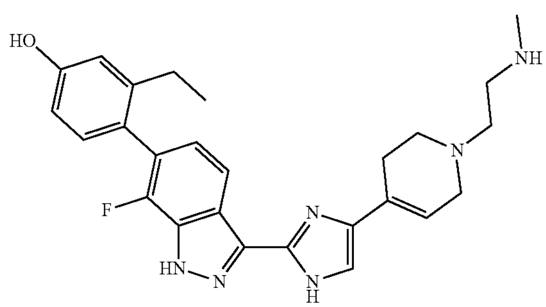 [SMILES: CCc1cc(O)ccc1-c1ccc2c(-c3nc(C4=CCN(CCNC)CC4)c[nH]3)n[nH]c2c1F] | 461.2 | 461.3 |
| 189 | 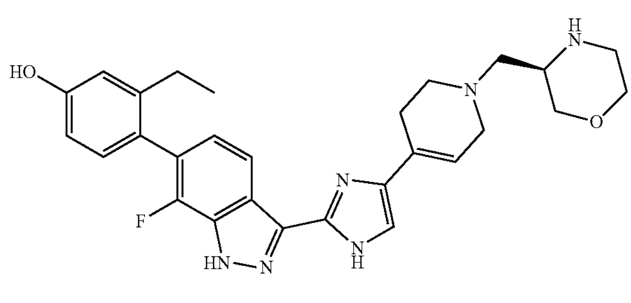 [SMILES: CCc1cc(O)ccc1-c1ccc2c(-c3nc(C4=CCN(C[C@@H]5COCCN5)CC4)c[nH]3)n[nH]c2c1F] | 503.2 | 503.2 |

TABLE 4-continued

| Ex. No. | Structure | Calc. [M + H]+ | Found [M + H]+ |
|---|---|---|---|
| 190 | 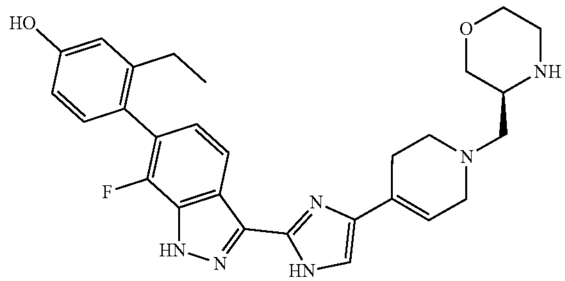 [SMILES: CCc1cc(O)ccc1-c1ccc2c(-c3nc(C4=CCN(C[C@H]5COCCN5)CC4)c[nH]3)n[nH]c2c1F] | 503.2 | 503.3 |
| 191 | 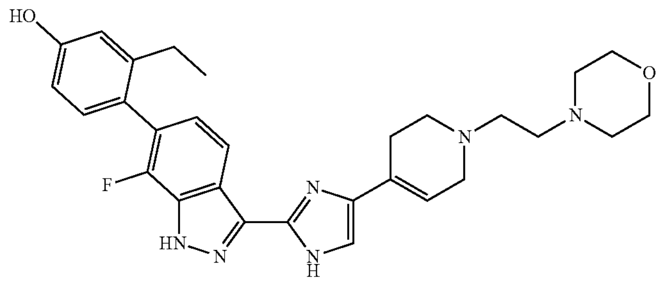 [SMILES: CCc1cc(O)ccc1-c1ccc2c(-c3nc(C4=CCN(CCN5CCOCC5)CC4)c[nH]3)n[nH]c2c1F] | 517.3 | 517.3 |
| 192 | 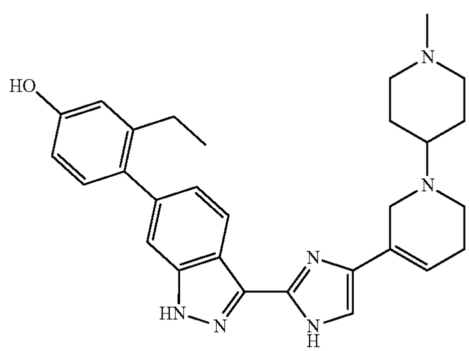 [SMILES: CCc1cc(O)ccc1-c1ccc2c(-c3nc(C4=CCCN(C5CCN(C)CC5)C4)c[nH]3)n[nH]c2c1] | 483.3 | 483.3 |
| 193 | 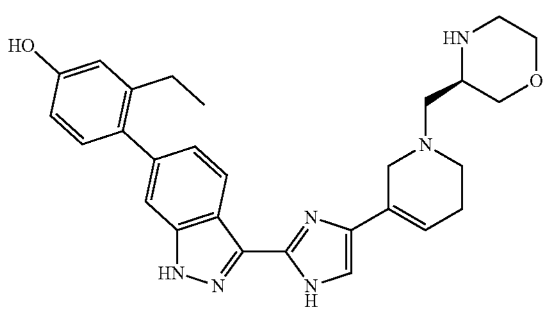 [SMILES: CCc1cc(O)ccc1-c1ccc2c(-c3nc(C4=CCCN(C[C@@H]5COCCN5)C4)c[nH]3)n[nH]c2c1] | 485.3 | 485.3 |
| 194 | 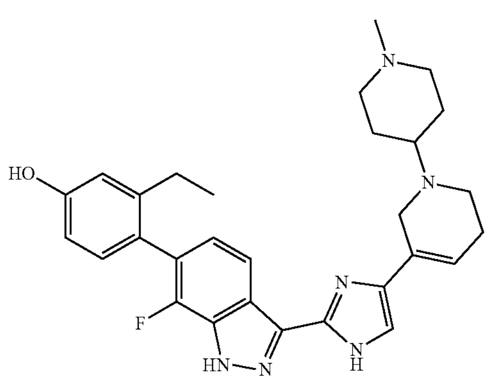 [SMILES: CCc1cc(O)ccc1-c1ccc2c(-c3nc(C4=CCCN(C5CCN(C)CC5)C4)c[nH]3)n[nH]c2c1F] | 501.3 | 501.3 |

TABLE 4-continued
| Ex. No. | Structure | Calc. [M + H]+ | Found [M + H]+ |
|---|---|---|---|
| 195 | 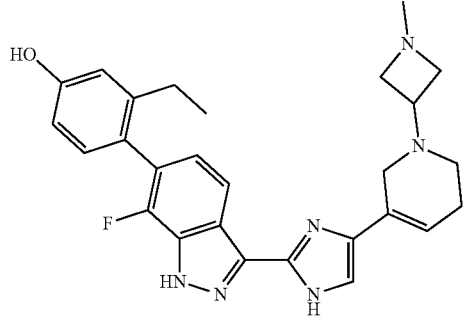 [SMILES: CCc1cc(O)ccc1-c1ccc2c(-c3nc(C4=CCCN(C5CN(C)C5)C4)c[nH]3)n[nH]c2c1F] | 473.2 | 473.3 |
| 196 | 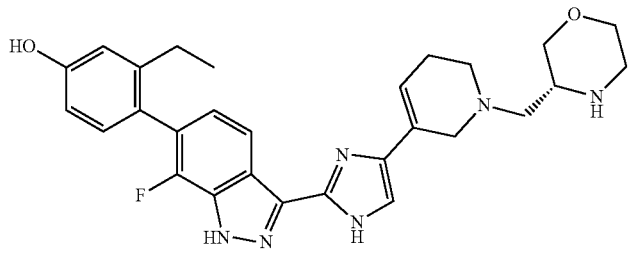 [SMILES: CCc1cc(O)ccc1-c1ccc2c(-c3nc(C4=CCCN(C[C@@H]5COCCN5)C4)c[nH]3)n[nH]c2c1F] | 503.2 | 503.2 |
| 197 | 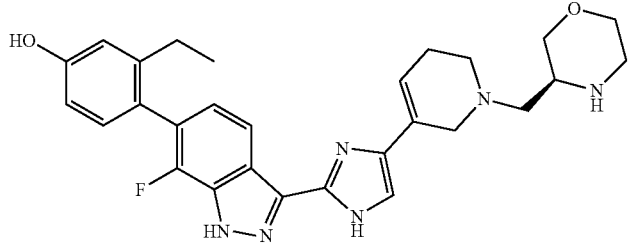 [SMILES: CCc1cc(O)ccc1-c1ccc2c(-c3nc(C4=CCCN(C[C@H]5COCCN5)C4)c[nH]3)n[nH]c2c1F] | 503.2 | 503.3 |
| 198 | 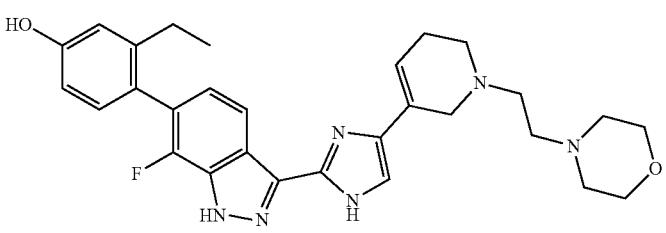 [SMILES: CCc1cc(O)ccc1-c1ccc2c(-c3nc(C4=CCCN(CCN5CCOCC5)C4)c[nH]3)n[nH]c2c1F] | 517.3 | 517.3 |
| 199 | 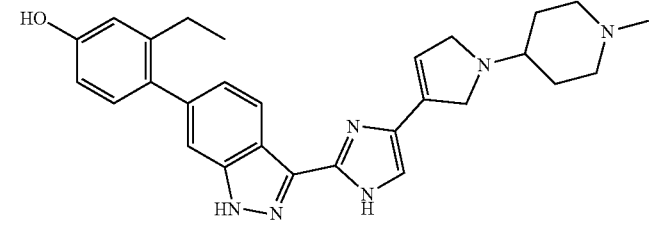 [SMILES: CCc1cc(O)ccc1-c1ccc2c(-c3nc(C4=CCN(C5CCN(C)CC5)C4)c[nH]3)n[nH]c2c1] | 469.3 | 469.3 |

TABLE 4-continued

| Ex. No. | Structure | Calc. [M + H]+ | Found [M + H]+ |
|---|---|---|---|
| 200 | 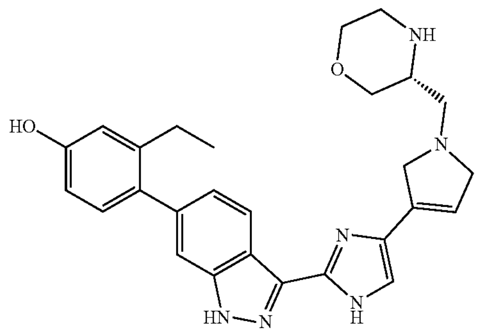 [SMILES: CCc1cc(O)ccc1-c1ccc2c(-c3nc(C4=CCN(C[C@@H]5COCCN5)C4)c[nH]3)n[nH]c2c1] | 471.2 | 471.1 |
| 201 | 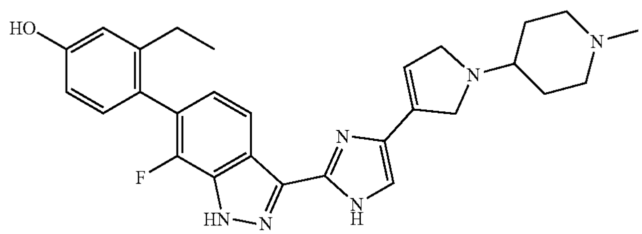 [SMILES: CCc1cc(O)ccc1-c1ccc2c(-c3nc(C4=CCN(C5CCN(C)CC5)C4)c[nH]3)n[nH]c2c1F] | 487.3 | 487.2 |
| 202 | 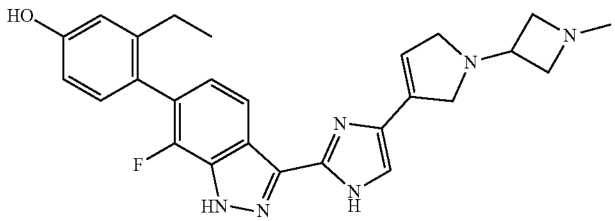 [SMILES: CCc1cc(O)ccc1-c1ccc2c(-c3nc(C4=CCN(C5CN(C)C5)C4)c[nH]3)n[nH]c2c1F] | 459.2 | 459.2 |
| 203 | 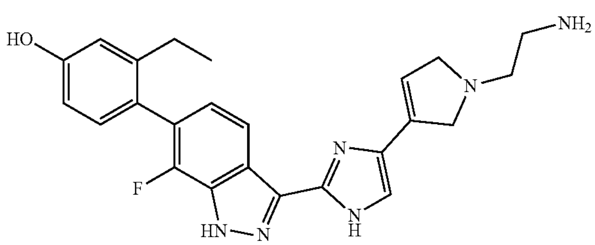 [SMILES: CCc1cc(O)ccc1-c1ccc2c(-c3nc(C4=CCN(CCN)C4)c[nH]3)n[nH]c2c1F] | 433.2 | 433.2 |
| 204 | 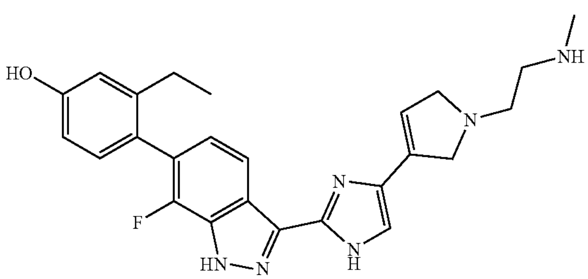 [SMILES: CCc1cc(O)ccc1-c1ccc2c(-c3nc(C4=CCN(CCNC)C4)c[nH]3)n[nH]c2c1F] | 447.2 | 447.2 |
| 205 | 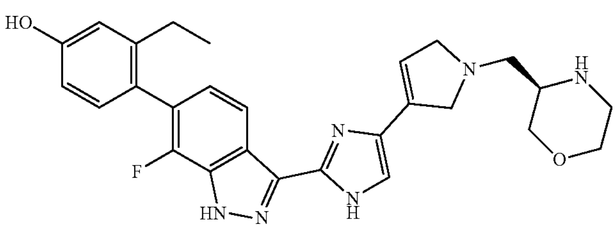 [SMILES: CCc1cc(O)ccc1-c1ccc2c(-c3nc(C4=CCN(C[C@@H]5COCCN5)C4)c[nH]3)n[nH]c2c1F] | 489.2 | 489.2 |

TABLE 4-continued

| Ex. No. | Structure | Calc. [M + H]+ | Found [M + H]+ |
|---|---|---|---|
| 206 | 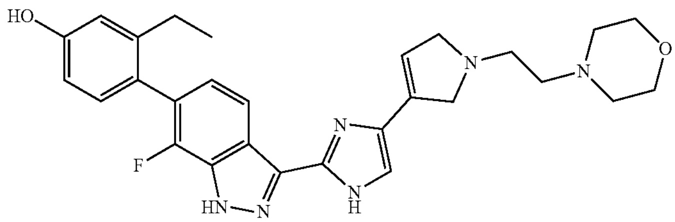 [SMILES: CCc1cc(O)ccc1-c1ccc2c(-c3nc(C4=CCN(CCN5CCOCC5)C4)c[nH]3)n[nH]c2c1F] | 503.2 | 503.2 |
| 207 | 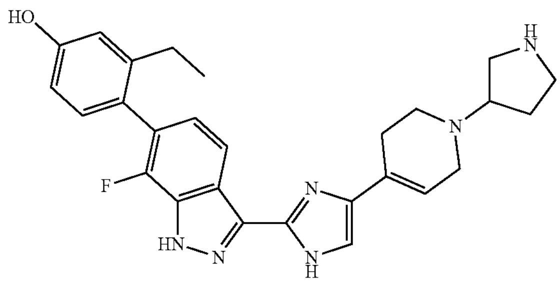 [SMILES: CCc1cc(O)ccc1-c1ccc2c(-c3nc(C4=CCN(C5CCNC5)CC4)c[nH]3)n[nH]c2c1F] | 473.2 | 473.3 |
| 208 | 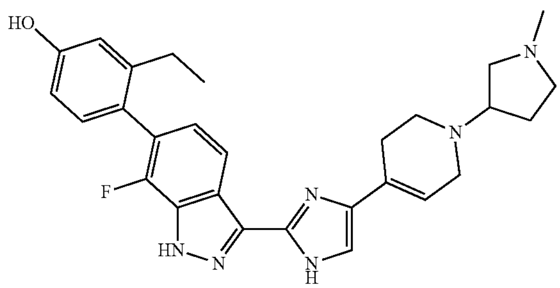 [SMILES: CCc1cc(O)ccc1-c1ccc2c(-c3nc(C4=CCN(C5CCN(C)C5)CC4)c[nH]3)n[nH]c2c1F] | 487.3 | 487.3 |
| 209 | 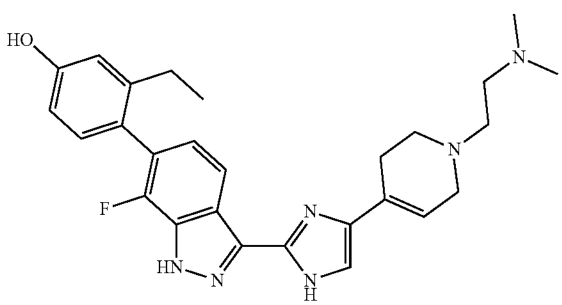 [SMILES: CCc1cc(O)ccc1-c1ccc2c(-c3nc(C4=CCN(CCN(C)C)CC4)c[nH]3)n[nH]c2c1F] | 475.3 | 475.3 |
| 210 | 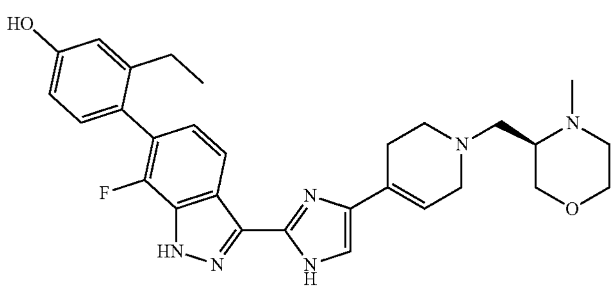 [SMILES: CCc1cc(O)ccc1-c1ccc2c(-c3nc(C4=CCN(C[C@@H]5COCCN5C)CC4)c[nH]3)n[nH]c2c1F] | 517.3 | 517.3 |

TABLE 4-continued

| Ex. No. | Structure | Calc. [M + H]+ | Found [M + H]+ |
|---|---|---|---|
| 211 | 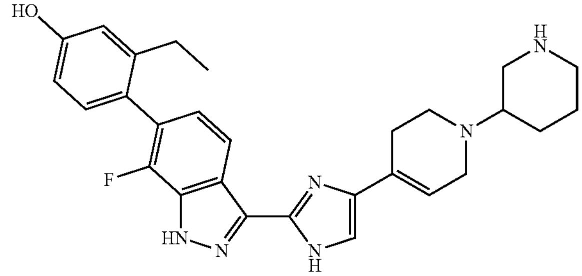 [SMILES: CCc1cc(O)ccc1-c1ccc2c(-c3nc(C4=CCN(C5CCCNC5)CC4)c[nH]3)n[nH]c2c1F] | 487.3 | 487.3 |
| 212 | 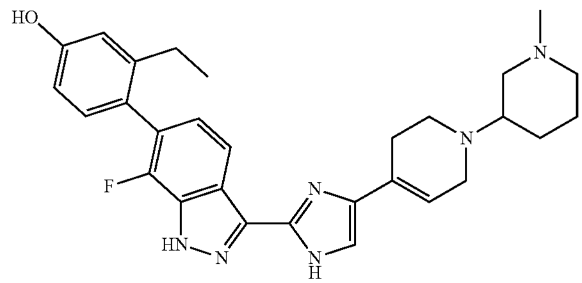 [SMILES: CCc1cc(O)ccc1-c1ccc2c(-c3nc(C4=CCN(C5CCCN(C)C5)CC4)c[nH]3)n[nH]c2c1F] | 501.3 | 501.3 |
| 213 | 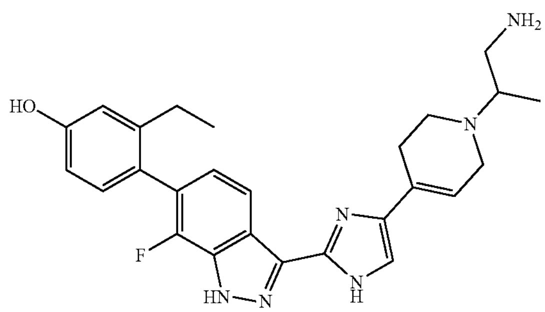 [SMILES: CCc1cc(O)ccc1-c1ccc2c(-c3nc(C4=CCN(C(C)CN)CC4)c[nH]3)n[nH]c2c1F] | 461.2 | 461.3 |
| 214 | 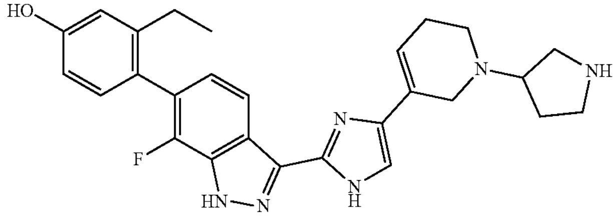 [SMILES: CCc1cc(O)ccc1-c1ccc2c(-c3nc(C4=CCCN(C5CCNC5)C4)c[nH]3)n[nH]c2c1F] | 473.2 | 473.3 |
| 215 | 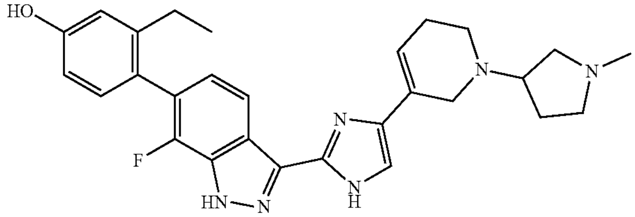 [SMILES: CCc1cc(O)ccc1-c1ccc2c(-c3nc(C4=CCCN(C5CCN(C)C5)C4)c[nH]3)n[nH]c2c1F] | 487.3 | 487.2 |
| 216 | 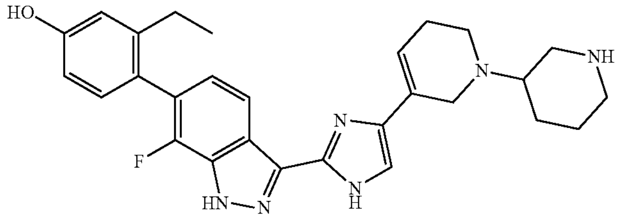 [SMILES: CCc1cc(O)ccc1-c1ccc2c(-c3nc(C4=CCCN(C5CCCNC5)C4)c[nH]3)n[nH]c2c1F] | 487.3 | 487.3 |

TABLE 4-continued
| Ex. No. | Structure | Calc. [M + H]+ | Found [M + H]+ |
|---|---|---|---|
| 217 | 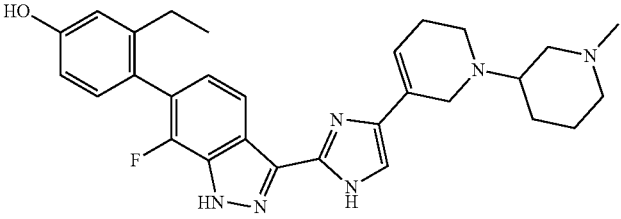 [SMILES: CCc1cc(O)ccc1-c1ccc2c(-c3nc(C4=CCCN(C5CCCN(C)C5)C4)c[nH]3)n[nH]c2c1F] | 501.3 | 501.2 |
| 218 | 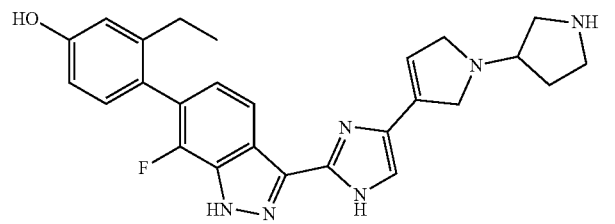 [SMILES: CCc1cc(O)ccc1-c1ccc2c(-c3nc(C4=CCN(C5CCNC5)C4)c[nH]3)n[nH]c2c1F] | 459.2 | 459.2 |
| 219 | 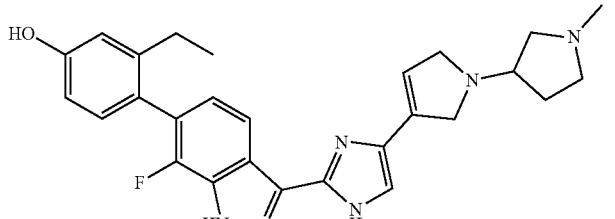 | 473.2 | 473.2 |
| 220 | 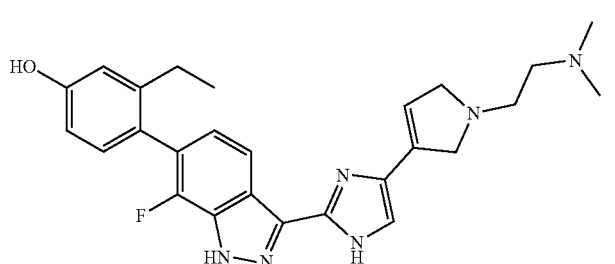 | 461.2 | 461.3 |
| 221 | 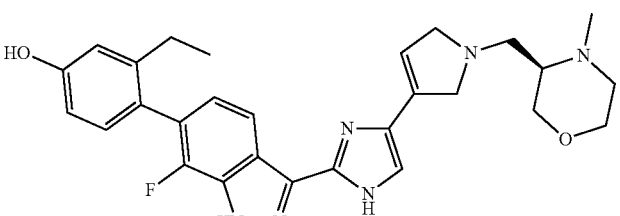 | 503.2 | 503.3 |
| 222 | 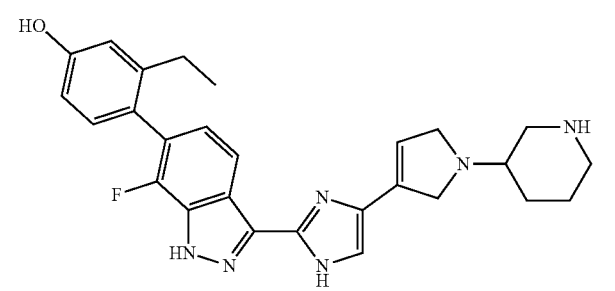 [SMILES: CCc1cc(O)ccc1-c1ccc2c(-c3nc(C4=CCN(C5CCCNC5)C4)c[nH]3)n[nH]c2c1F] | 473.2 | 473.2 |

TABLE 4-continued

| Ex. No. | Structure | Calc. [M + H]+ | Found [M + H]+ |
|---|---|---|---|
| 223 | 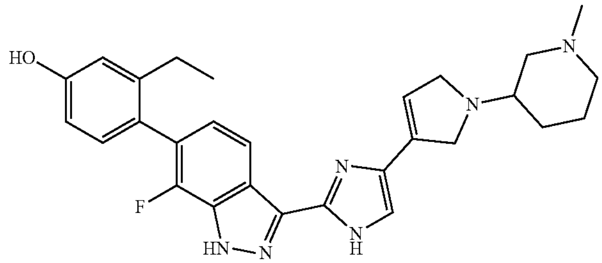 [SMILES: CCc1cc(O)ccc1-c1ccc2c(-c3nc(C4=CCN(C5CCCN(C)C5)C4)c[nH]3)n[nH]c2c1F] | 487.3 | 487.2 |
| 224 | 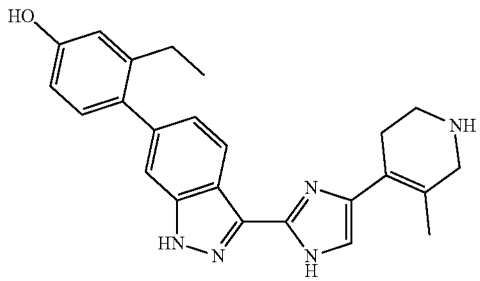 [SMILES: CCc1cc(O)ccc1-c1ccc2c(-c3nc(C4=C(C)CNCC4)c[nH]3)n[nH]c2c1] | 400.2 | 400.2 |
| 225 | 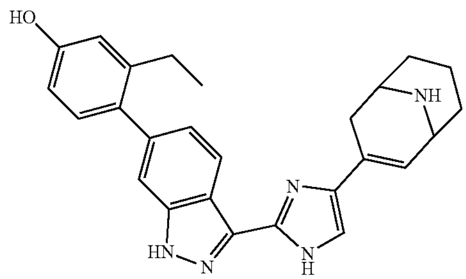 [SMILES: CCc1cc(O)ccc1-c1ccc2c(-c3nc(C4=CC5CCCC(C4)N5)c[nH]3)n[nH]c2c1] | 426.2 | 426.2 |
| 226 | 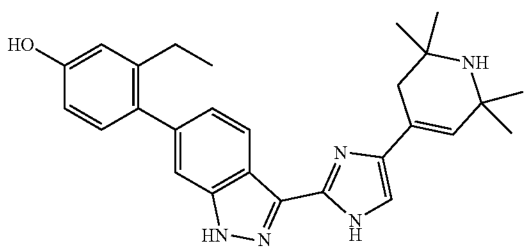 [SMILES: CCc1cc(O)ccc1-c1ccc2c(-c3nc(C4=CC(C)(C)NC(C)(C)C4)c[nH]3)n[nH]c2c1] | 442.3 | 442.2 |
| 227 | 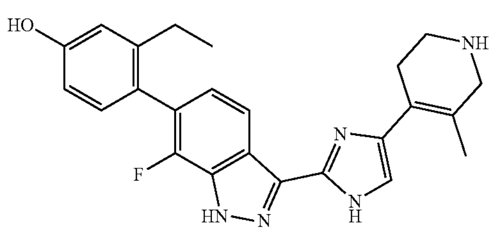 [SMILES: CCc1cc(O)ccc1-c1ccc2c(-c3nc(C4=C(C)CNCC4)c[nH]3)n[nH]c2c1F] | 418.2 | 418.2 |
| 228 | 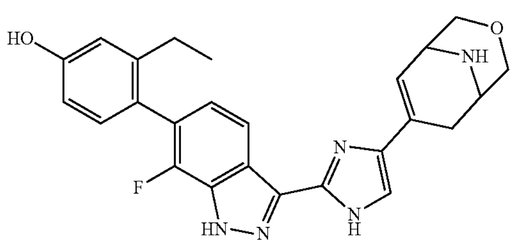 [SMILES: CCc1cc(O)ccc1-c1ccc2c(-c3nc(C4=CC5COCC(C4)N5)c[nH]3)n[nH]c2c1F] | 446.2 | 446.2 |

TABLE 4-continued

| Ex. No. | Structure | Calc. [M + H]+ | Found [M + H]+ |
|---|---|---|---|
| 229 | 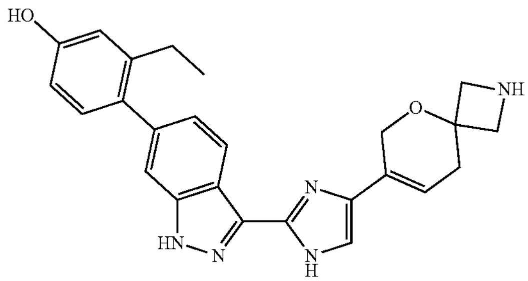 [SMILES: CCc1cc(O)ccc1-c1ccc2c(-c3nc(C4=CCC5(CNC5)OC4)c[nH]3)n[nH]c2c1] | 428.2 | 428.2 |
| 230 | 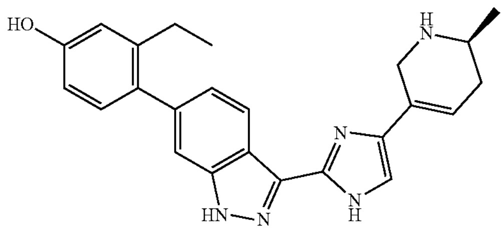 [SMILES: CCc1cc(O)ccc1-c1ccc2c(-c3nc(C4=CC[C@H](C)NC4)c[nH]3)n[nH]c2c1] | 400.2 | 400.2 |
| 231 | 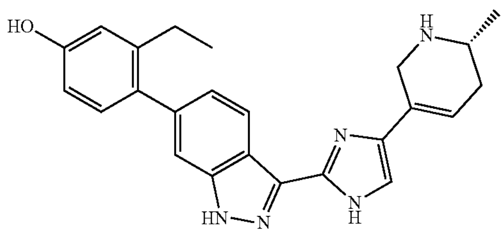 [SMILES: CCc1cc(O)ccc1-c1ccc2c(-c3nc(C4=CC[C@@H](C)NC4)c[nH]3)n[nH]c2c1] | 400.2 | 400.2 |
| 232 | 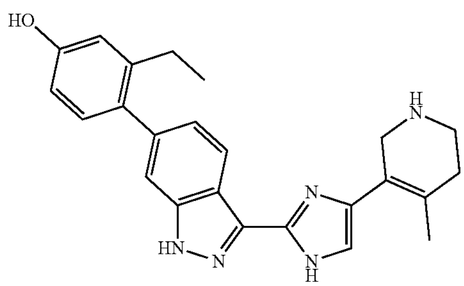 [SMILES: CCc1cc(O)ccc1-c1ccc2c(-c3nc(C4=C(C)CCNC4)c[nH]3)n[nH]c2c1] | 400.2 | 400.1 |
| 233 | 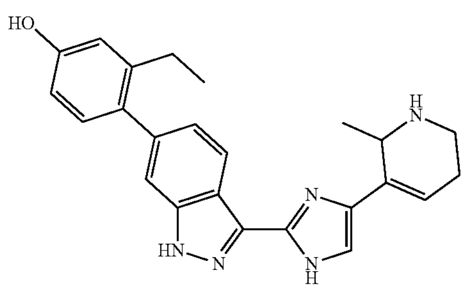 [SMILES: CCc1cc(O)ccc1-c1ccc2c(-c3nc(C4=CCCNC4C)c[nH]3)n[nH]c2c1] | 400.2 | 400.1 |
| 234 | 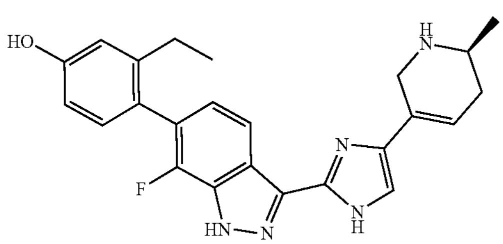 [SMILES: CCc1cc(O)ccc1-c1ccc2c(-c3nc(C4=CC[C@H](C)NC4)c[nH]3)n[nH]c2c1F] | 418.2 | 418.2 |

TABLE 4-continued

| Ex. No. | Structure | Calc. [M + H]+ | Found [M + H]+ |
|---|---|---|---|
| 235 | 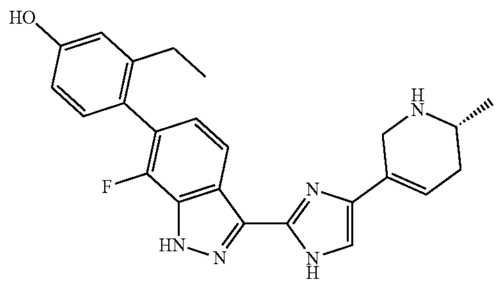 [SMILES: CCc1cc(O)ccc1-c1ccc2c(-c3nc(C4=CC[C@@H](C)NC4)c[nH]3)n[nH]c2c1F] | 418.2 | 418.2 |
| 236 | 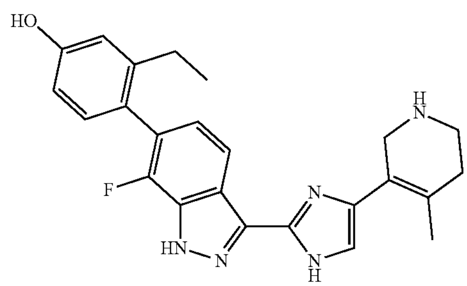 [SMILES: CCc1cc(O)ccc1-c1ccc2c(-c3nc(C4=C(C)CCNC4)c[nH]3)n[nH]c2c1F] | 418.2 | 418.1 |
| 237 | 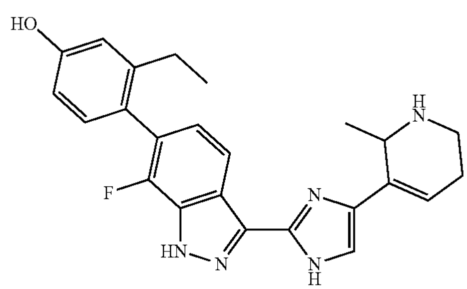 [SMILES: CCc1cc(O)ccc1-c1ccc2c(-c3nc(C4=CCCNC4C)c[nH]3)n[nH]c2c1F] | 418.2 | 418.1 |
| 238 | 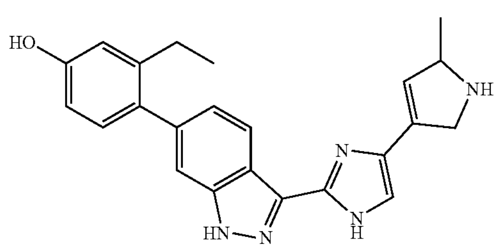 [SMILES: CCc1cc(O)ccc1-c1ccc2c(-c3nc(C4=CC(C)NC4)c[nH]3)n[nH]c2c1] | 386.2 | 386.2 |
| 239 | 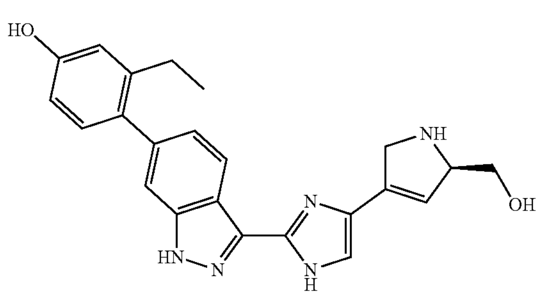 [SMILES: CCc1cc(O)ccc1-c1ccc2c(-c3nc(C4=C[C@H](CO)NC4)c[nH]3)n[nH]c2c1] | 402.2 | 402.3 |

TABLE 4-continued

| Ex. No. | Structure | Calc. [M + H]+ | Found [M + H]+ |
|---|---|---|---|
| 240 | 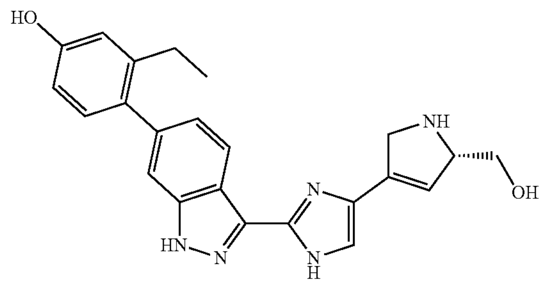 [SMILES: CCc1cc(O)ccc1-c1ccc2c(-c3nc(C4=C[C@@H](CO)NC4)c[nH]3)n[nH]c2c1] | 402.2 | 402.2 |
| 241 | 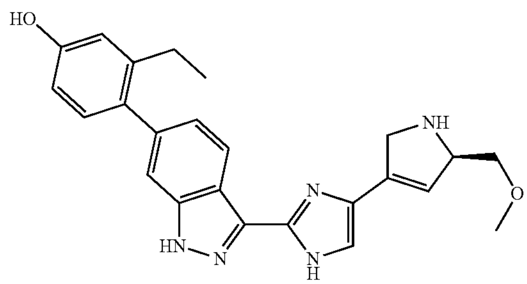 [SMILES: CCc1cc(O)ccc1-c1ccc2c(-c3nc(C4=C[C@H](COC)NC4)c[nH]3)n[nH]c2c1] | 416.2 | 416.3 |
| 242 | 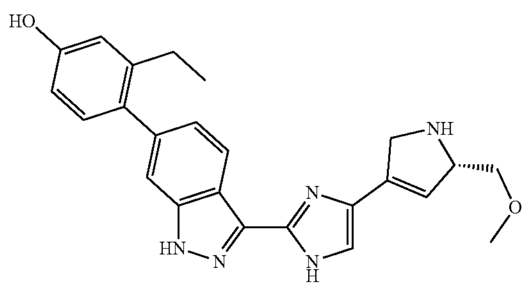 [SMILES: CCc1cc(O)ccc1-c1ccc2c(-c3nc(C4=C[C@@H](COC)NC4)c[nH]3)n[nH]c2c1] | 416.2 | 416.2 |
| 243 | 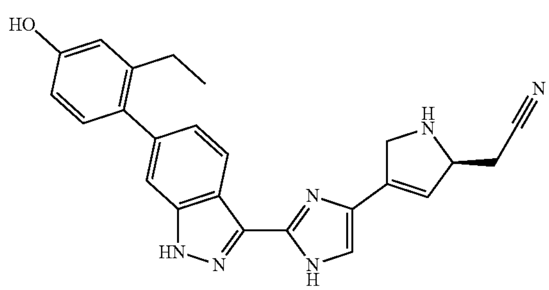 [SMILES: CCc1cc(O)ccc1-c1ccc2c(-c3nc(C4=C[C@H](CC#N)NC4)c[nH]3)n[nH]c2c1] | 411.2 | 411.1 |
| 244 | 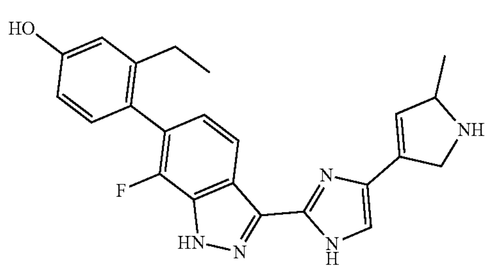 [SMILES: CCc1cc(O)ccc1-c1ccc2c(-c3nc(C4=CC(C)NC4)c[nH]3)n[nH]c2c1F] | 404.2 | 404.2 |

TABLE 4-continued

| Ex. No. | Structure | Calc. [M + H]+ | Found [M + H]+ |
|---|---|---|---|
| 245 | 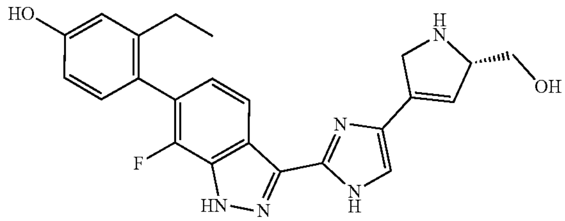 [SMILES: CCc1cc(O)ccc1-c1ccc2c(-c3nc(C4=C[C@@H](CO)NC4)c[nH]3)n[nH]c2c1F] | 420.2 | 420.2 |
| 246 | 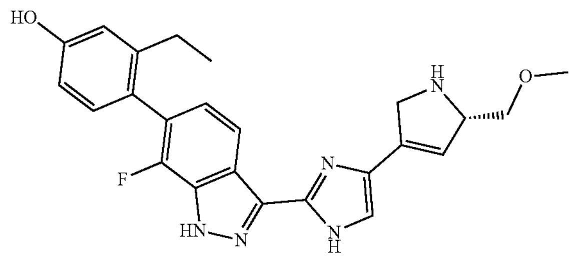 [SMILES: CCc1cc(O)ccc1-c1ccc2c(-c3nc(C4=C[C@@H](COC)NC4)c[nH]3)n[nH]c2c1F] | 434.2 | 434.2 |
| 247 | 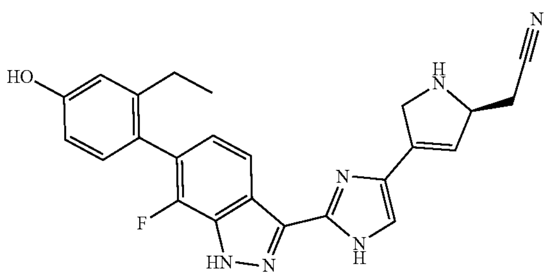 [SMILES: CCc1cc(O)ccc1-c1ccc2c(-c3nc(C4=C[C@H](CC#N)NC4)c[nH]3)n[nH]c2c1F] | 429.2 | 429.0 |
| 248 | 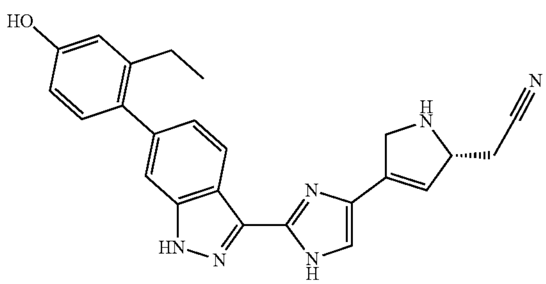 [SMILES: CCc1cc(O)ccc1-c1ccc2c(-c3nc(C4=C[C@@H](CC#N)NC4)c[nH]3)n[nH]c2c1] | 411.2 | 411.1 |
| 249 | 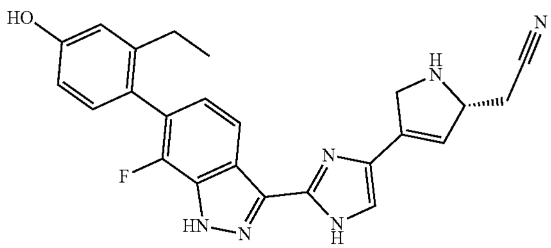 [SMILES: CCc1cc(O)ccc1-c1ccc2c(-c3nc(C4=C[C@@H](CC#N)NC4)c[nH]3)n[nH]c2c1F] | 429.2 | 429.0 |
| 250 | 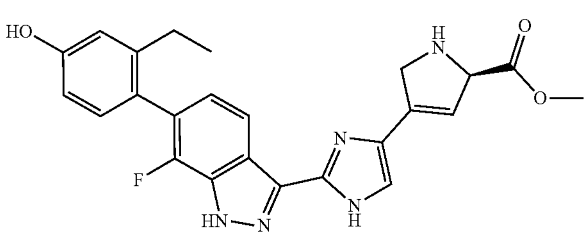 [SMILES: CCc1cc(O)ccc1-c1ccc2c(-c3nc(C4=C[C@H](C(=O)OC)NC4)c[nH]3)n[nH]c2c1F] | 448.2 | 448.1 |

TABLE 4-continued

| Ex. No. | Structure | Calc. [M + H]+ | Found [M + H]+ |
|---|---|---|---|
| 251 | 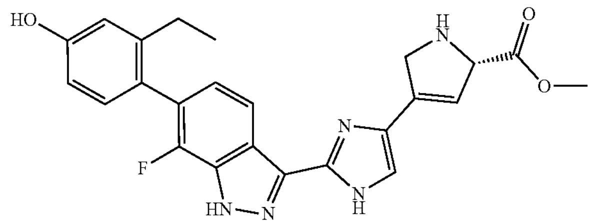 [SMILES: CCc1cc(O)ccc1-c1ccc2c(-c3nc(C4=C[C@@H](C(=O)OC)NC4)c[nH]3)n[nH]c2c1F] | 448.2 | 448.0 |
| 252 | 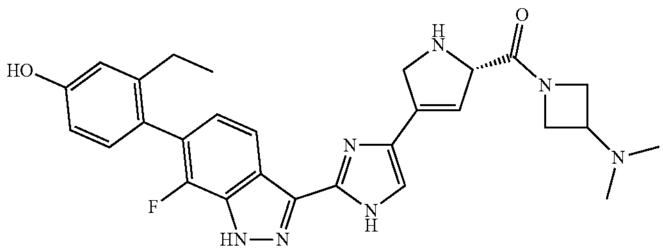 [SMILES: CCc1cc(O)ccc1-c1ccc2c(-c3nc(C4=C[C@@H](C(=O)N5CC(N(C)C)C5)NC4)c[nH]3)n[nH]c2c1F] | 516.2 | 516.1 |
| 253 | 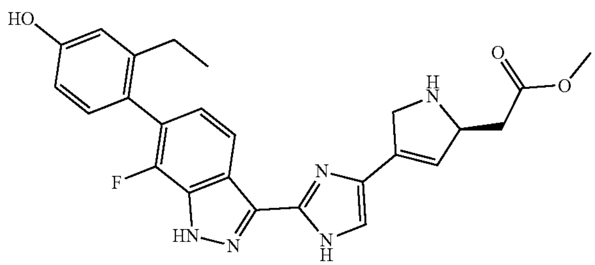 [SMILES: CCc1cc(O)ccc1-c1ccc2c(-c3nc(C4=C[C@H](CC(=O)OC)NC4)c[nH]3)n[nH]c2c1F] | 462.2 | 462.1 |
| 254 | 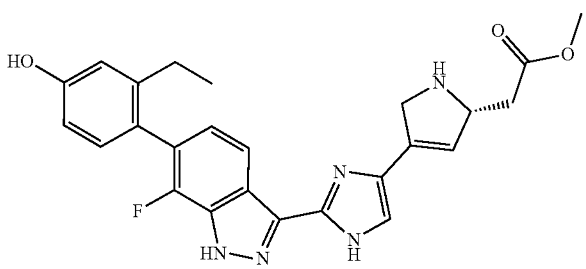 [SMILES: CCc1cc(O)ccc1-c1ccc2c(-c3nc(C4=C[C@@H](CC(=O)OC)NC4)c[nH]3)n[nH]c2c1F] | 462.2 | 462.0 |
| 255 | 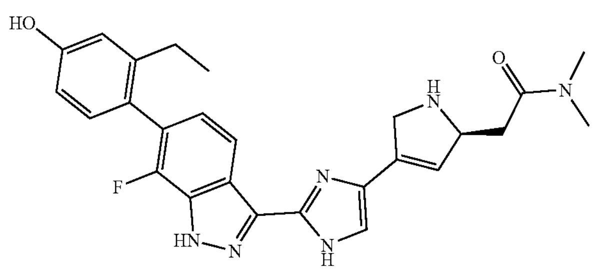 [SMILES: CCc1cc(O)ccc1-c1ccc2c(-c3nc(C4=C[C@H](CC(=O)N(C)C)NC4)c[nH]3)n[nH]c2c1F] | 475.2 | 475.1 |
| 256 | 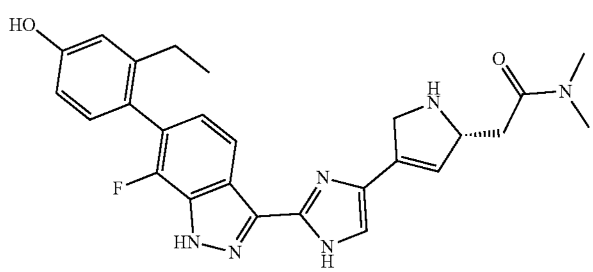 [SMILES: CCc1cc(O)ccc1-c1ccc2c(-c3nc(C4=C[C@@H](CC(=O)N(C)C)NC4)c[nH]3)n[nH]c2c1F] | 475.2 | 475.1 |

US 12,384,761 B2
TABLE 4-continued
| Ex. No. | Structure | Calc. [M + H]+ | Found [M + H]+ |
|---|---|---|---|
| 257 | 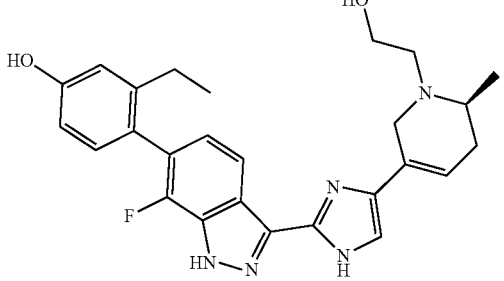 | 462.2 | 462.1 |
| 258 | 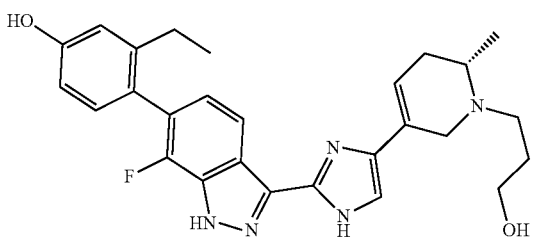 [SMILES: CCc1cc(O)ccc1-c1ccc2c(-c3nc(C4=CC[C@H](C)N(CCCO)C4)c[nH]3)n[nH]c2c1F] | 476.2 | 476.1 |
| 259 | 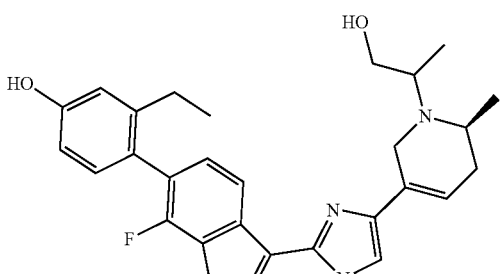 | 476.2 | 476.1 |
| 260 | 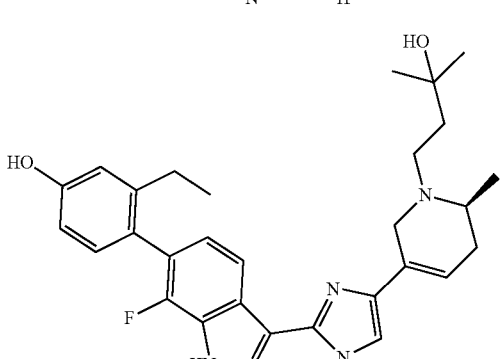 | 504.3 | 504.2 |
| 261 | 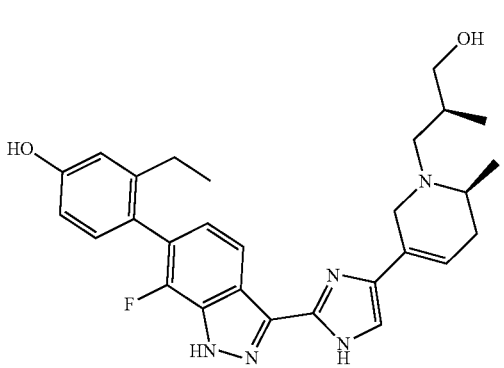 [SMILES: CCc1cc(O)ccc1-c1ccc2c(-c3nc(C4=CC[C@H](C)N(C[C@H](C)CO)C4)c[nH]3)n[nH]c2c1F] | 490.3 | 490.2 |

TABLE 4-continued

| Ex. No. | Structure | Calc. [M + H]⁺ | Found [M + H]⁺ |
|---|---|---|---|
| 262 | 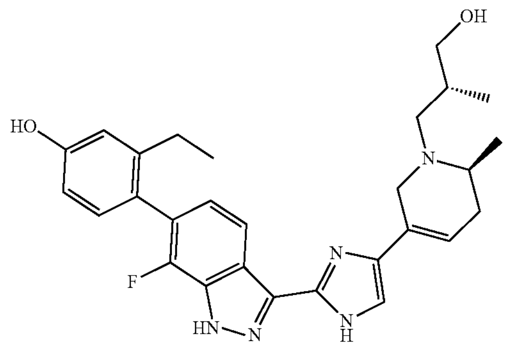 [SMILES: CCc1cc(O)ccc1-c1ccc2c(-c3nc(C4=CC[C@H](C)N(C[C@@H](C)CO)C4)c[nH]3)n[nH]c2c1F] | 490.3 | 490.2 |
| 263 | 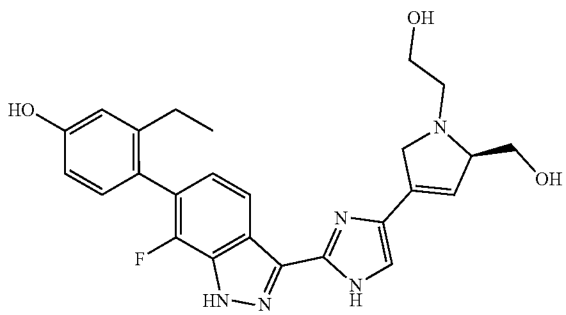 [SMILES: CCc1cc(O)ccc1-c1ccc2c(-c3nc(C4=C[C@H](CO)N(CCO)C4)c[nH]3)n[nH]c2c1F] | 464.2 | 464.1 |
| 264 | 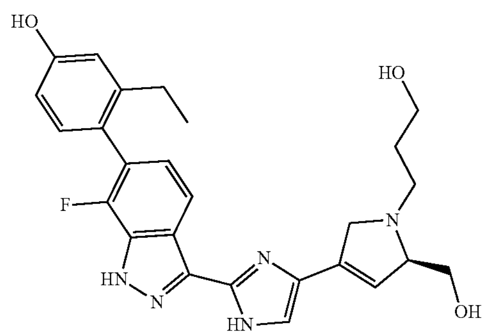 [SMILES: CCc1cc(O)ccc1-c1ccc2c(-c3nc(C4=C[C@H](CO)N(CCCO)C4)c[nH]3)n[nH]c2c1F] | 478.2 | 478.1 |
| 265 | 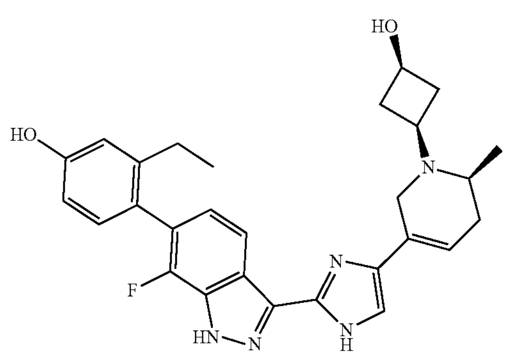 [SMILES: CCc1cc(O)ccc1-c1ccc2c(-c3nc(C4=CC[C@H](C)N([C@H]5C[C@@H](O)C5)C4)c[nH]3)n[nH]c2c1F] | 488.2 | 488.1 |

TABLE 4-continued
| Ex. No. | Structure | Calc. [M + H]⁺ | Found [M + H]⁺ |
|---|---|---|---|
| 266 | 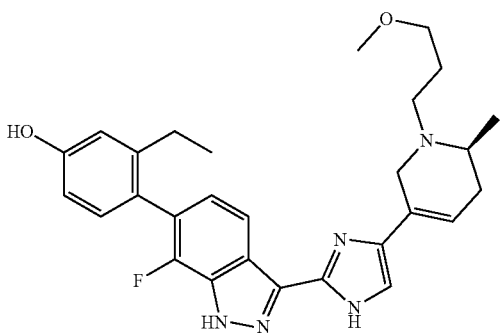 [SMILES: CCc1cc(O)ccc1-c1ccc2c(-c3nc(C4=CC[C@H](C)N(CCCOC)C4)c[nH]3)n[nH]c2c1F] | 490.3 | 490.1 |
| 267 | 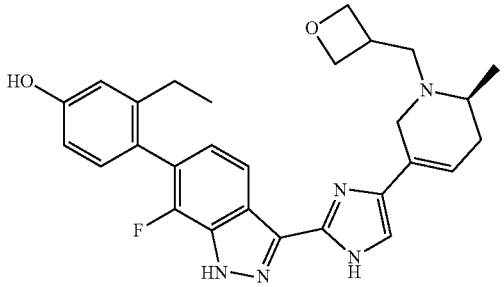 [SMILES: CCc1cc(O)ccc1-c1ccc2c(-c3nc(C4=CC[C@H](C)N(CC5COC5)C4)c[nH]3)n[nH]c2c1F] | 488.2 | 488.1 |
| 268 | 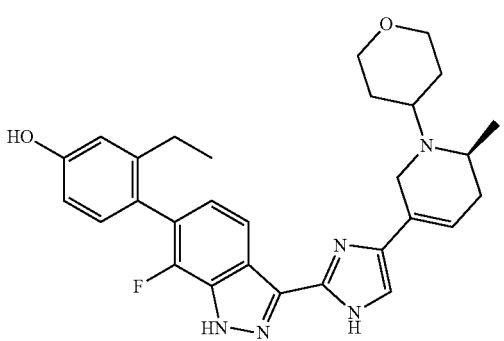 [SMILES: CCc1cc(O)ccc1-c1ccc2c(-c3nc(C4=CC[C@H](C)N(C5CCOCC5)C4)c[nH]3)n[nH]c2c1F] | 502.3 | 502.1 |
| 269 | 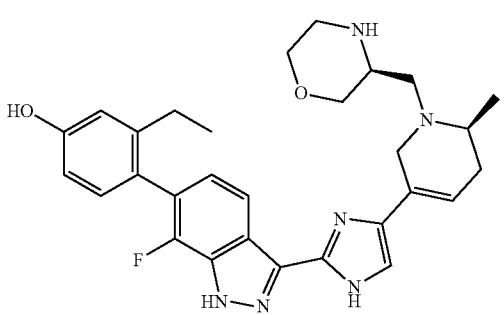 [SMILES: CCc1cc(O)ccc1-c1ccc2c(-c3nc(C4=CC[C@H](C)N(C[C@H]5COCCN5)C4)c[nH]3)n[nH]c2c1F] | 517.3 | 517.1 |

TABLE 4-continued

| Ex. No. | Structure | Calc. [M + H]+ | Found [M + H]+ |
|---|---|---|---|
| 270 | 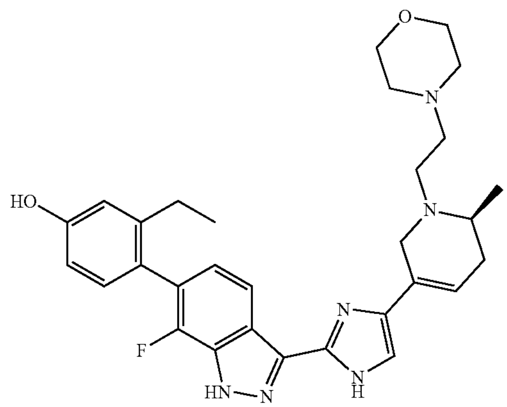 [SMILES: CCc1cc(O)ccc1-c1ccc2c(-c3nc(C4=CC[C@H](C)N(CCN5CCOCC5)C4)c[nH]3)n[nH]c2c1F] | 531.3 | 531.2 |
| 271 | 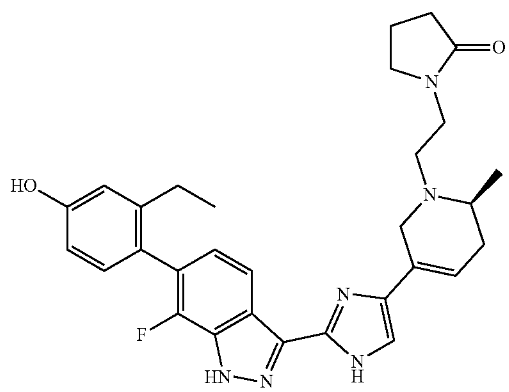 [SMILES: CCc1cc(O)ccc1-c1ccc2c(-c3nc(C4=CC[C@H](C)N(CCN5CCCC5=O)C4)c[nH]3)n[nH]c2c1F] | 529.3 | 529.2 |
| 272 | 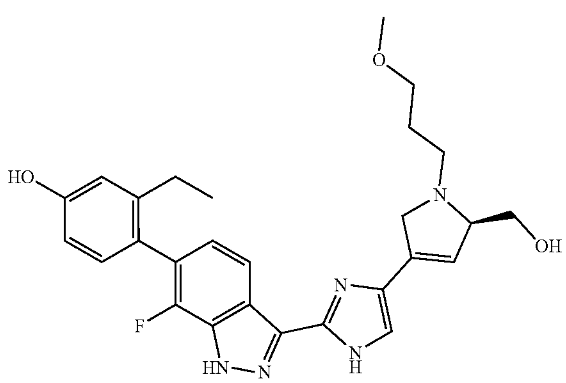 [SMILES: CCc1cc(O)ccc1-c1ccc2c(-c3nc(C4=C[C@H](CO)N(CCCOC)C4)c[nH]3)n[nH]c2c1F] | 492.2 | 492.1 |
| 273 | 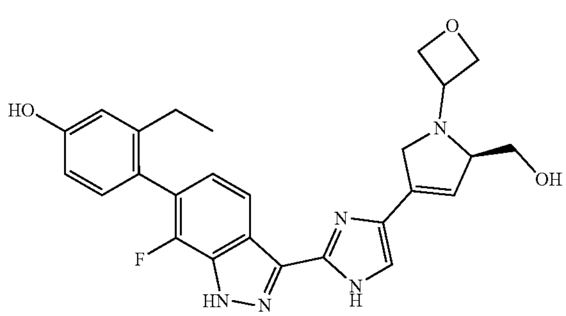 [SMILES: CCc1cc(O)ccc1-c1ccc2c(-c3nc(C4=C[C@H](CO)N(C5COC5)C4)c[nH]3)n[nH]c2c1F] | 476.2 | 476.1 |

TABLE 4-continued

| Ex. No. | Structure | Calc. [M + H]+ | Found [M + H]+ |
|---|---|---|---|
| 274 | 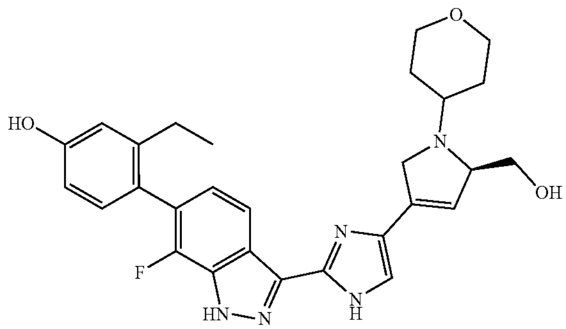 [SMILES: CCc1cc(O)ccc1-c1ccc2c(-c3nc(C4=C[C@H](CO)N(C5CCOCC5)C4)c[nH]3)n[nH]c2c1F] | 504.2 | 504.1 |
| 275 | 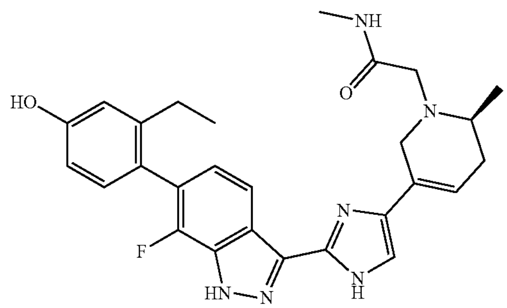 [SMILES: CCc1cc(O)ccc1-c1ccc2c(-c3nc(C4=CC[C@H](C)N(CC(=O)NC)C4)c[nH]3)n[nH]c2c1F] | 489.2 | 489.2 |
| 276 | 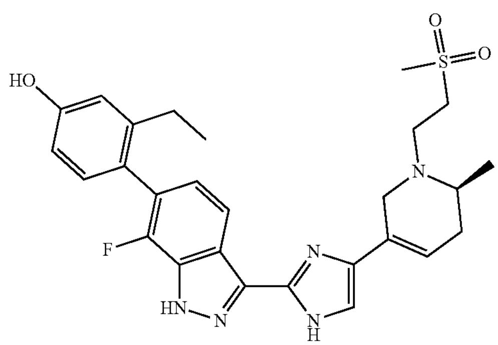 [SMILES: CCc1cc(O)ccc1-c1ccc2c(-c3nc(C4=CC[C@H](C)N(CCS(C)(=O)=O)C4)c[nH]3)n[nH]c2c1F] | 524.2 | 524.0 |
| 277 | 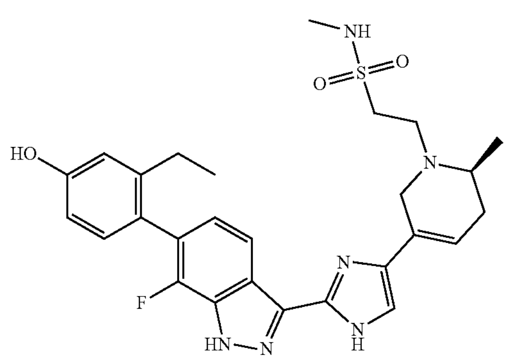 [SMILES: CCc1cc(O)ccc1-c1ccc2c(-c3nc(C4=CC[C@H](C)N(CCS(=O)(=O)NC)C4)c[nH]3)n[nH]c2c1F] | 539.2 | 539.1 |

TABLE 4-continued

| Ex. No. | Structure | Calc. [M + H]+ | Found [M + H]+ |
|---|---|---|---|
| 278 | 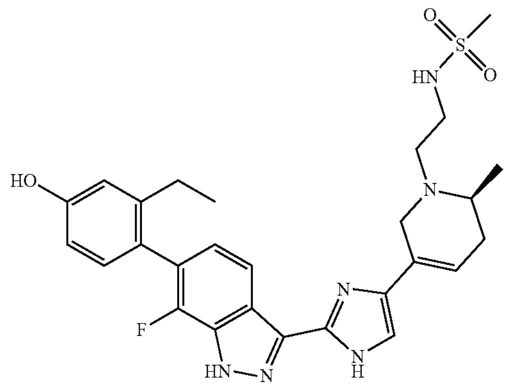 [SMILES: CCc1cc(O)ccc1-c1ccc2c(-c3nc(C4=CC[C@H](C)N(CCNS(C)(=O)=O)C4)c[nH]3)n[nH]c2c1F] | 539.2 | 539.1 |
| 279 | 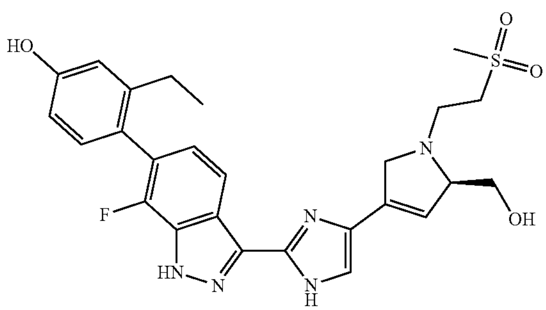 [SMILES: CCc1cc(O)ccc1-c1ccc2c(-c3nc(C4=C[C@H](CO)N(CCS(C)(=O)=O)C4)c[nH]3)n[nH]c2c1F] | 526.2 | 526.0 |
| 280 | 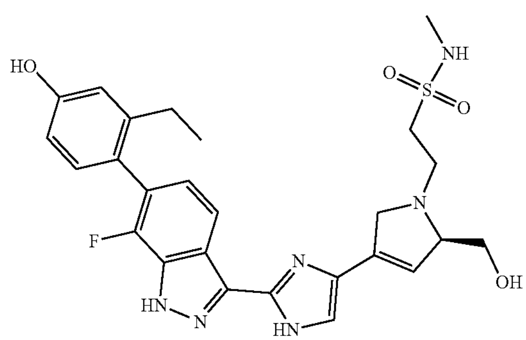 [SMILES: CCc1cc(O)ccc1-c1ccc2c(-c3nc(C4=C[C@H](CO)N(CCS(=O)(=O)NC)C4)c[nH]3)n[nH]c2c1F] | 541.2 | 541.0 |
| 281 | 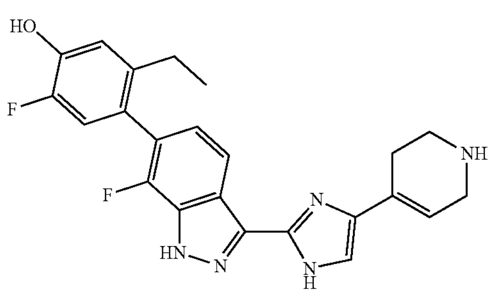 | 422.2 | 422.2 |

TABLE 4-continued

| Ex. No. | Structure | Calc. [M + H]+ | Found [M + H]+ |
|---|---|---|---|
| 282 | 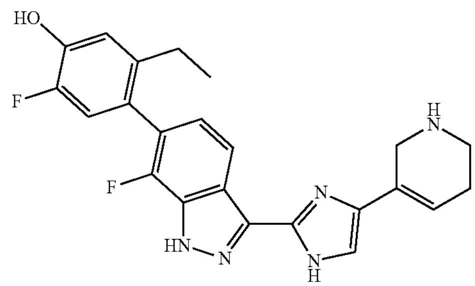 [SMILES: CCc1cc(O)c(F)cc1-c1ccc2c(-c3nc(C4=CCCNC4)c[nH]3)n[nH]c2c1F] | 422.2 | 422.2 |
| 283 | 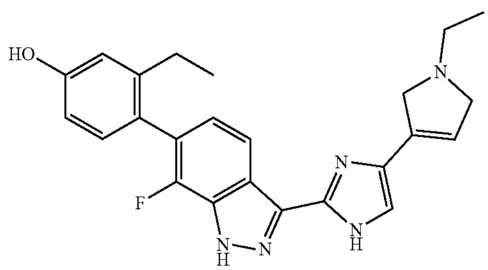 [SMILES: CCc1cc(O)ccc1-c1ccc2c(-c3nc(C4=CCN(CC)C4)c[nH]3)n[nH]c2c1F] | 418.2 | 418.3 |
| 284 | 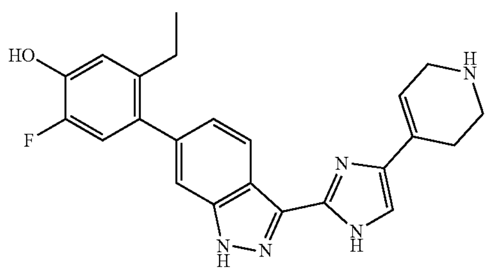 [SMILES: CCc1cc(O)c(F)cc1-c1ccc2c(-c3nc(C4=CCNCC4)c[nH]3)n[nH]c2c1] | 404.2 | 404.3 |
| 285 | 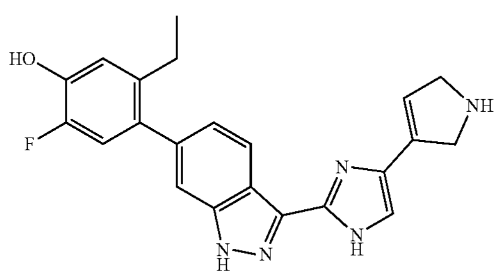 [SMILES: CCc1cc(O)c(F)cc1-c1ccc2c(-c3nc(C4=CCNC4)c[nH]3)n[nH]c2c1] | 390.2 | 390.2 |
| 286 | 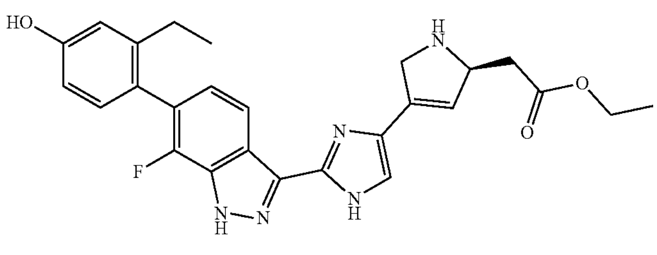 [SMILES: CCOC(=O)C[C@H]1C=C(c2c[nH]c(-c3n[nH]c4c(F)c(-c5ccc(O)cc5CC)ccc34)n2)CN1] | 476.2 | 476.3 |

TABLE 4-continued

| Ex. No. | Structure | Calc. [M + H]+ | Found [M + H]+ |
|---|---|---|---|
| 287 | 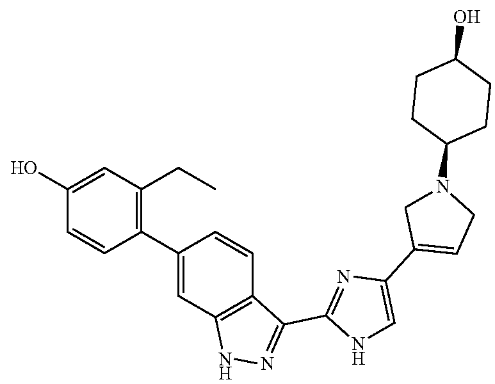 [SMILES: CCc1cc(O)ccc1-c1ccc2c(-c3nc(C4=CCN([C@H]5CC[C@@H](O)CC5)C4)c[nH]3)n[nH]c2c1] | 470.3 | 470.2 |
| 288 | 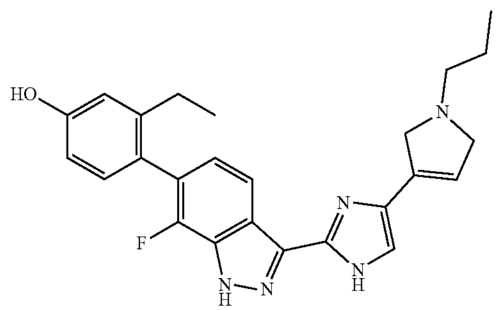 [SMILES: CCCN1CC=C(c2c[nH]c(-c3n[nH]c4c(F)c(-c5ccc(O)cc5CC)ccc34)n2)C1] | 432.2 | 432.3 |
| 289 | 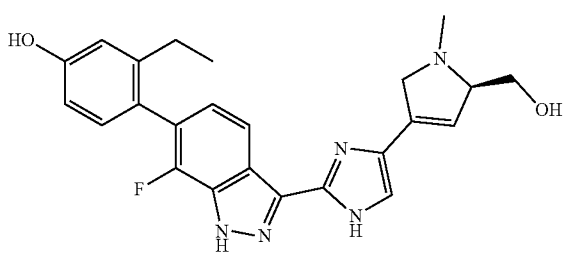 [SMILES: CCc1cc(O)ccc1-c1ccc2c(-c3nc(C4=C[C@H](CO)N(C)C4)c[nH]3)n[nH]c2c1F] | 434.2 | 434.2 |
| 290 | 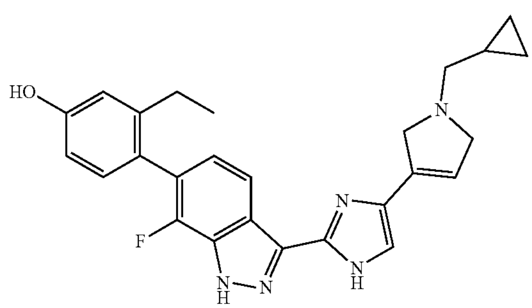 [SMILES: CCc1cc(O)ccc1-c1ccc2c(-c3nc(C4=CCN(CC5CC5)C4)c[nH]3)n[nH]c2c1F] | 444.2 | 444.3 |
| 291 | 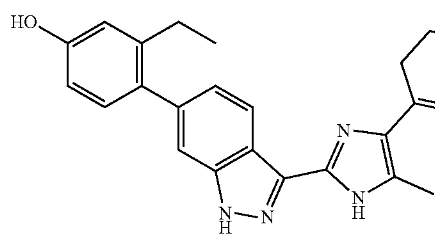 | 400.2 | 400.3 |

TABLE 4-continued
| Ex. No. | Structure | Calc. [M + H]+ | Found [M + H]+ |
|---|---|---|---|
| 292 | 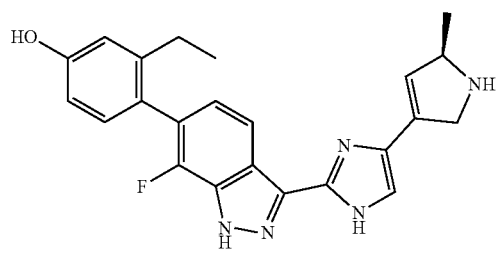 [SMILES: CCc1cc(O)ccc1-c1ccc2c(-c3nc(C4=C[C@@H](C)NC4)c[nH]3)n[nH]c2c1F] | 404.2 | 404.1 |
| 293 | 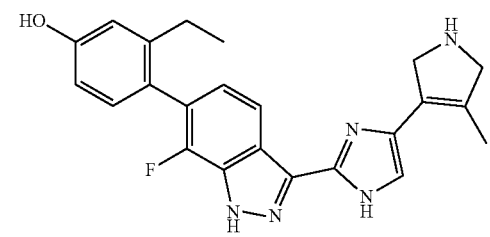 [SMILES: CCc1cc(O)ccc1-c1ccc2c(-c3nc(C4=C(C)CNC4)c[nH]3)n[nH]c2c1F] | 404.2 | 404.2 |
| 294 | 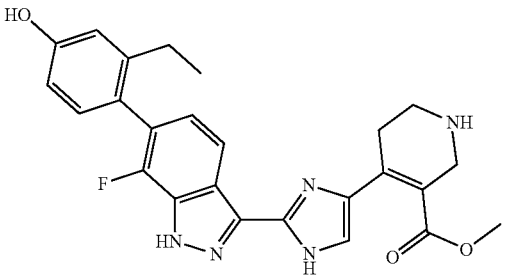 [SMILES: CCc1cc(O)ccc1-c1ccc2c(-c3nc(C4=C(C(=O)OC)CNCC4)c[nH]3)n[nH]c2c1F] | 462.2 | 462.1 |
| 295 | 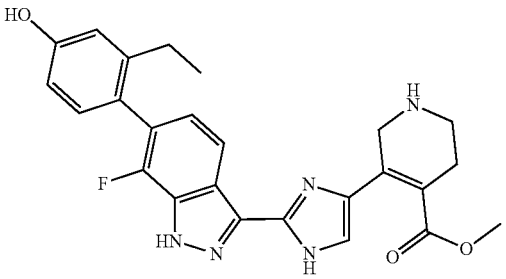 [SMILES: CCc1cc(O)ccc1-c1ccc2c(-c3nc(C4=C(C(=O)OC)CCNC4)c[nH]3)n[nH]c2c1F] | 462.2 | 462.2 |
| 296 | 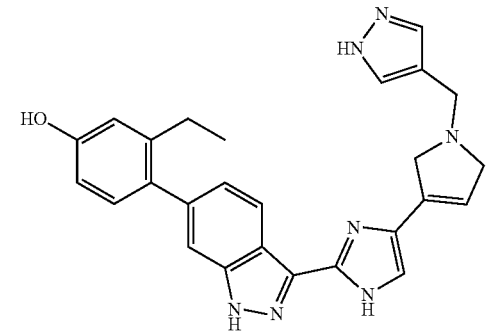 [SMILES: CCc1cc(O)ccc1-c1ccc2c(-c3nc(C4=CCN(Cc5cn[nH]c5)C4)c[nH]3)n[nH]c2c1] | 452.2 | 452.1 |

TABLE 4-continued
| Ex. No. | Structure | Calc. [M + H]+ | Found [M + H]+ |
|---|---|---|---|
| 297 | 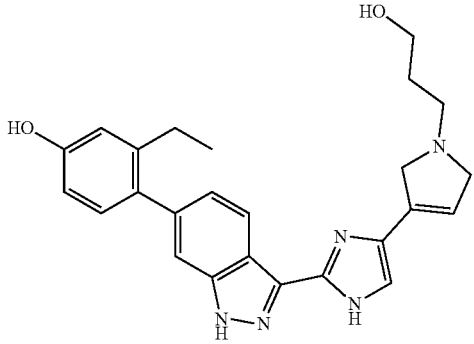 [SMILES: CCc1cc(O)ccc1-c1ccc2c(-c3nc(C4=CCN(CCCO)C4)c[nH]3)n[nH]c2c1] | 430.2 | 430.3 |
| 298 | 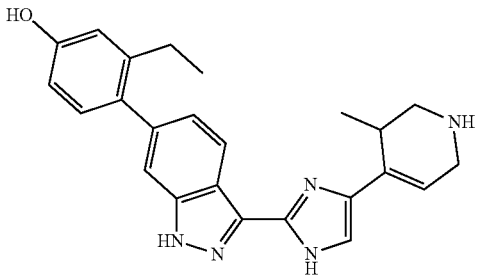 [SMILES: CCc1cc(O)ccc1-c1ccc2c(-c3nc(C4=CCNCC4C)c[nH]3)n[nH]c2c1] | 400.2 | 400.3 |
| 299 | 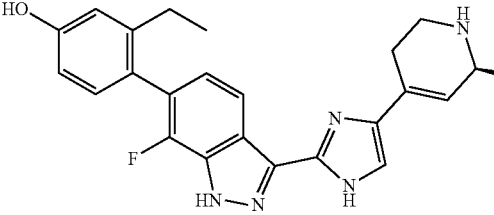 | 418.2 | 418.1 |
| 300 | 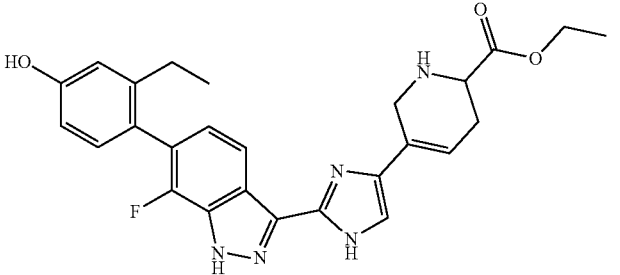 [SMILES: CCOC(=O)C1CC=C(c2c[nH]c(-c3n[nH]c4c(F)c(-c5ccc(O)cc5CC)ccc34)n2)CN1] | 476.2 | 476.1 |
| 301 | 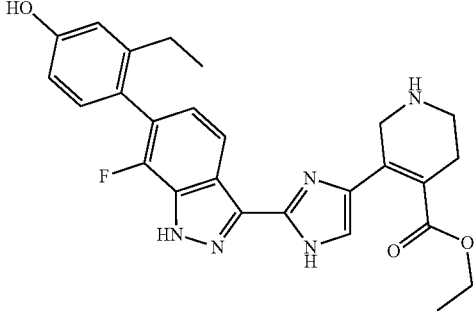 | 476.2 | 476.1 |

TABLE 4-continued

| Ex. No. | Structure | Calc. [M + H]⁺ | Found [M + H]⁺ |
|---|---|---|---|
| 302 | 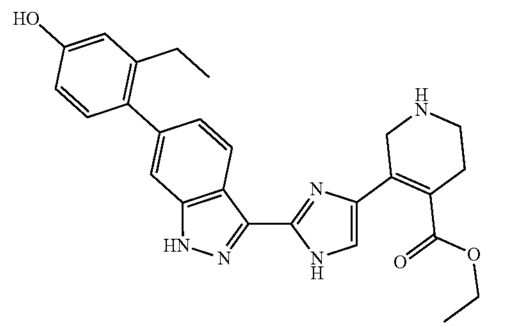 [SMILES: CCOC(=O)C1=C(c2c[nH]c(-c3n[nH]c4cc(-c5ccc(O)cc5CC)ccc34)n2)CNCC1] | 458.2 | 458.3 |
| 303 | 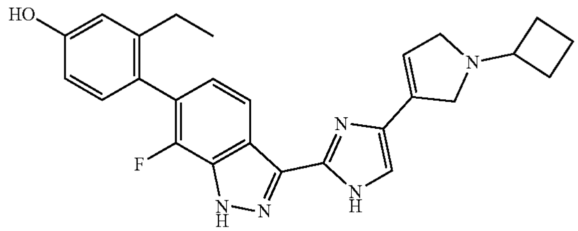 [SMILES: CCc1cc(O)ccc1-c1ccc2c(-c3nc(C4=CCN(C5CCC5)C4)c[nH]3)n[nH]c2c1F] | 444.2 | 444.4 |
| 304 | 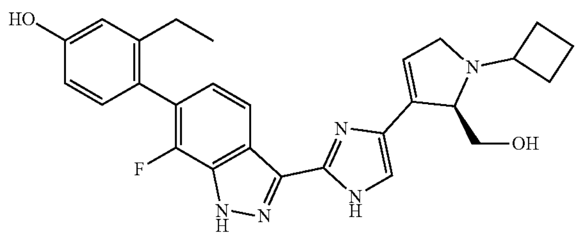 [SMILES: CCc1cc(O)ccc1-c1ccc2c(-c3nc(C4=CCN(C5CCC5)[C@H]4CO)c[nH]3)n[nH]c2c1F] | 474.2 | 474.4 |
| 305 | 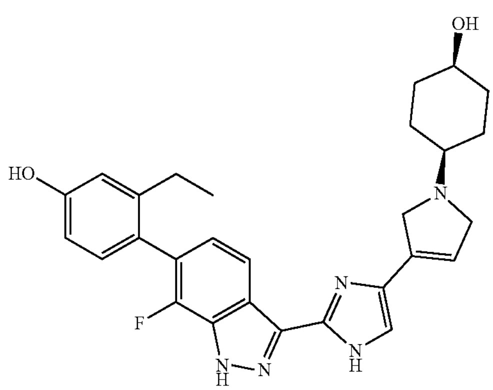 [SMILES: CCc1cc(O)ccc1-c1ccc2c(-c3nc(C4=CCN([C@H]5CC[C@@H](O)CC5)C4)c[nH]3)n[nH]c2c1F] | 488.2 | 488.3 |
| 306 | 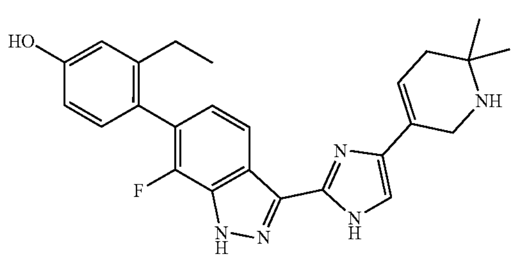 [SMILES: CCc1cc(O)ccc1-c1ccc2c(-c3nc(C4=CCC(C)(C)NC4)c[nH]3)n[nH]c2c1F] | 432.2 | 432.1 |

TABLE 4-continued
| Ex. No. | Structure | Calc. [M + H]+ | Found [M + H]+ |
|---|---|---|---|
| 307 | 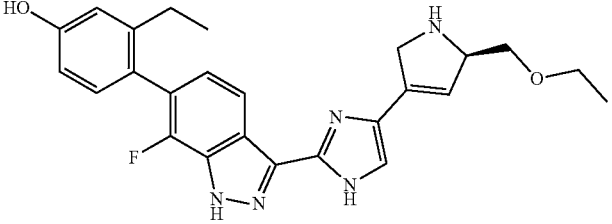 [SMILES: CCOC[C@H]1C=C(c2c[nH]c(-c3n[nH]c4c(F)c(-c5ccc(O)cc5CC)ccc34)n2)CN1] | 448.2 | 448.1 |
| 308 | 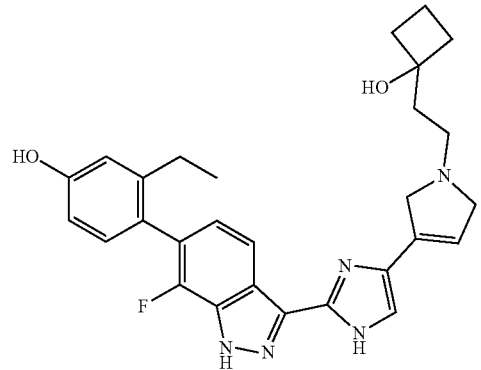 [SMILES: CCc1cc(O)ccc1-c1ccc2c(-c3nc(C4=CCN(CCC5(O)CCC5)C4)c[nH]3)n[nH]c2c1F] | 488.2 | 488.2 |
| 309 | 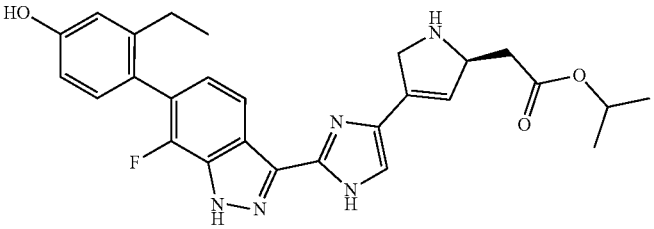 [SMILES: CCc1cc(O)ccc1-c1ccc2c(-c3nc(C4=C[C@H](CC(=O)OC(C)C)NC4)c[nH]3)n[nH]c2c1F] | 490.2 | 490.3 |
| 310 | 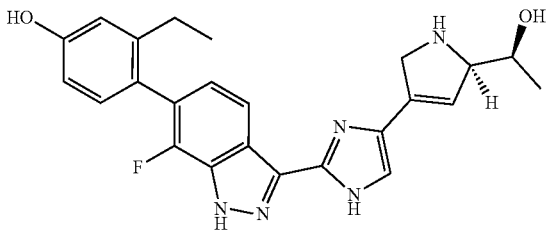 [SMILES: CCc1cc(O)ccc1-c1ccc2c(-c3nc(C4=C[C@H]([C@H](C)O)NC4)c[nH]3)n[nH]c2c1F] | 434.2 | 434.2 |
| 311 | 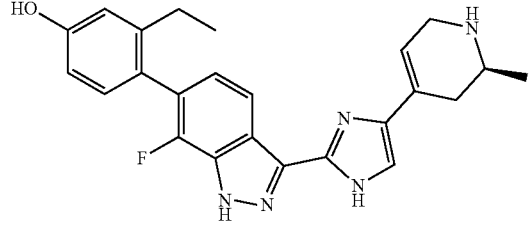 [SMILES: CCc1cc(O)ccc1-c1ccc2c(-c3nc(C4=CCN[C@@H](C)C4)c[nH]3)n[nH]c2c1F] | 418.2 | 418.1 |

TABLE 4-continued

| Ex. No. | Structure | Calc. [M + H]+ | Found [M + H]+ |
|---|---|---|---|
| 312 | 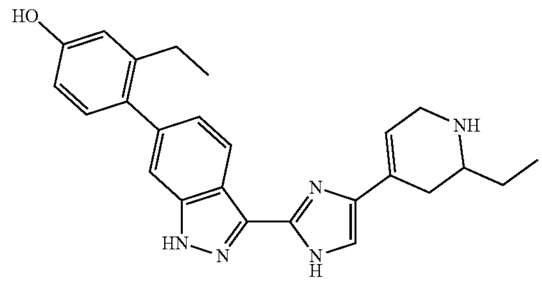 [SMILES: CCc1cc(O)ccc1-c1ccc2c(-c3nc(C4=CCNC(CC)C4)c[nH]3)n[nH]c2c1] | 414.2 | 414.2 |
| 313 | 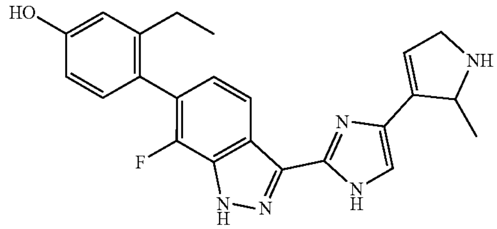 | 404.2 | 404.2 |
| 314 | 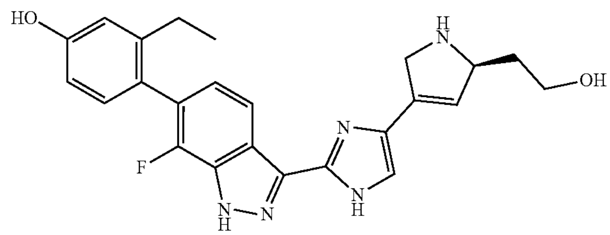 [SMILES: CCc1cc(O)ccc1-c1ccc2c(-c3nc(C4=C[C@H](CCO)NC4)c[nH]3)n[nH]c2c1F] | 434.2 | 434.2 |
| 315 | 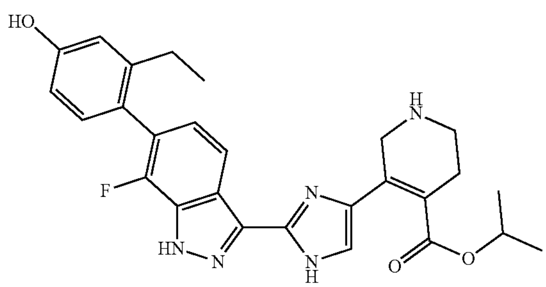 [SMILES: CCc1cc(O)ccc1-c1ccc2c(-c3nc(C4=C(C(=O)OC(C)C)CCNC4)c[nH]3)n[nH]c2c1F] | 490.2 | 490.1 |
| 316 | 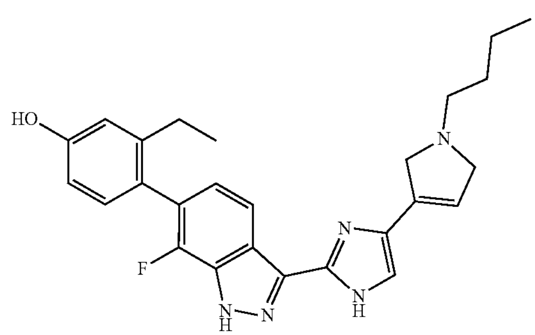 [SMILES: CCCCN1CC=C(c2c[nH]c(-c3n[nH]c4c(F)c(-c5ccc(O)cc5CC)ccc34)n2)C1] | 446.2 | 446.3 |

TABLE 4-continued
| Ex. No. | Structure | Calc. [M + H]+ | Found [M + H]+ |
|---|---|---|---|
| 317 | 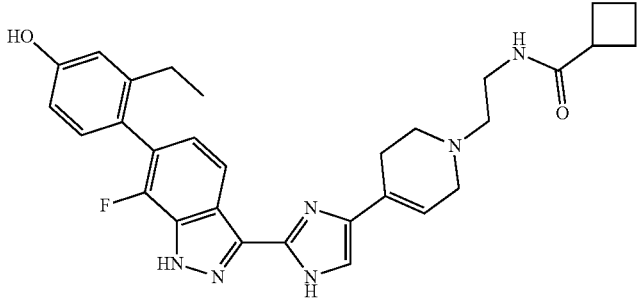 [SMILES: CCc1cc(O)ccc1-c1ccc2c(-c3nc(C4=CCN(CCNC(=O)C5CCC5)CC4)c[nH]3)n[nH]c2c1F] | 529.3 | 529.1 |
| 318 | 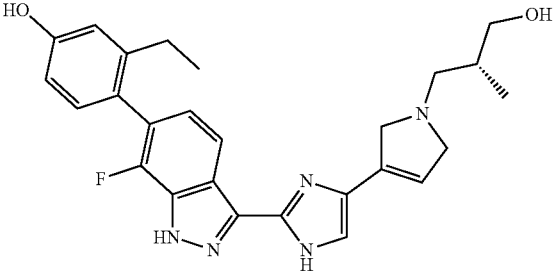 [SMILES: CCc1cc(O)ccc1-c1ccc2c(-c3nc(C4=CCN(C[C@@H](C)CO)C4)c[nH]3)n[nH]c2c1F] | 462.2 | 462.2 |
| 319 | 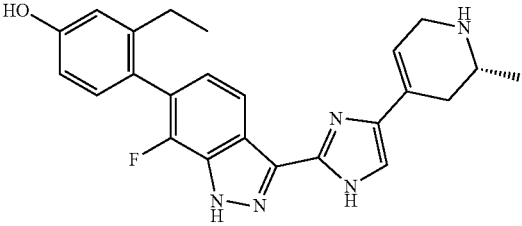 [SMILES: CCc1cc(O)ccc1-c1ccc2c(-c3nc(C4=CCN[C@H](C)C4)c[nH]3)n[nH]c2c1F] | 418.2 | 418.1 |
| 320 | 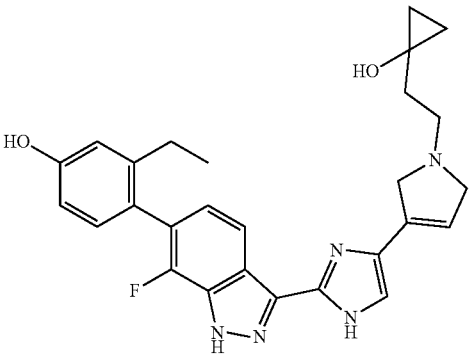 [SMILES: CCc1cc(O)ccc1-c1ccc2c(-c3nc(C4=CCN(CCC5(O)CC5)C4)c[nH]3)n[nH]c2c1F] | 474.2 | 474.2 |
| 321 | 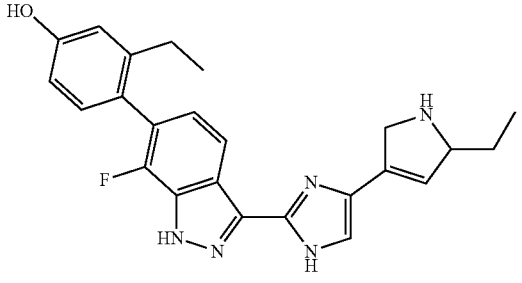 [SMILES: CCc1cc(O)ccc1-c1ccc2c(-c3nc(C4=CC(CC)NC4)c[nH]3)n[nH]c2c1F] | 418.2 | 418.3 |

TABLE 4-continued
| Ex. No. | Structure | Calc. [M + H]+ | Found [M + H]+ |
|---|---|---|---|
| 322 | 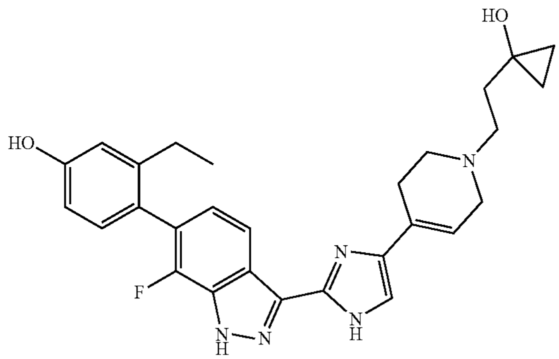 [SMILES: CCc1cc(O)ccc1-c1ccc2c(-c3nc(C4=CCN(CCC5(O)CC5)CC4)c[nH]3)n[nH]c2c1F] | 488.2 | 488.2 |
| 323 | 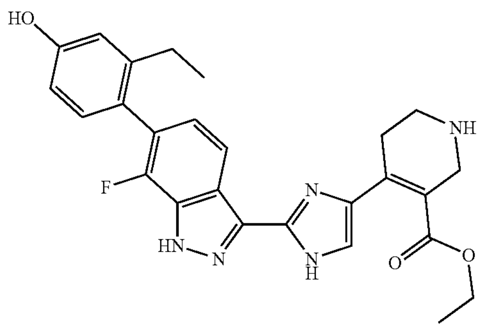 [SMILES: CCOC(=O)C1=C(c2c[nH]c(-c3n[nH]c4c(F)c(-c5ccc(O)cc5CC)ccc34)n2)CCNC1] | 476.2 | 476.2 |
| 324 | 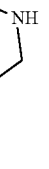 | 418.2 | 418.1 |
| 325 | 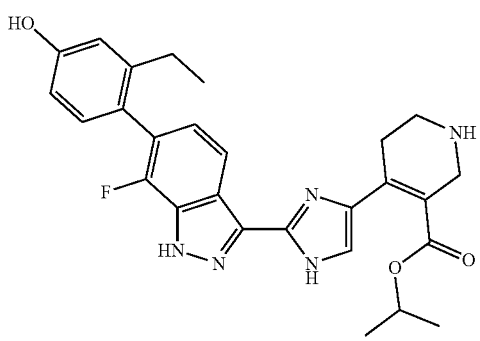 [SMILES: CCc1cc(O)ccc1-c1ccc2c(-c3nc(C4=C(C(=O)OC(C)C)CNCC4)c[nH]3)n[nH]c2c1F] | 490.2 | 490.2 |
| 326 | 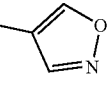 | 485.2 | 485.2 |

TABLE 4-continued

| Ex. No. | Structure | Calc. [M + H]+ | Found [M + H]+ |
|---|---|---|---|
| 327 | 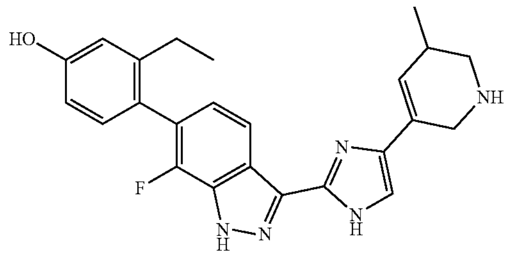 [SMILES: CCc1cc(O)ccc1-c1ccc2c(-c3nc(C4=CC(C)CNC4)c[nH]3)n[nH]c2c1F] | 418.2 | 418.2 |
| 328 | 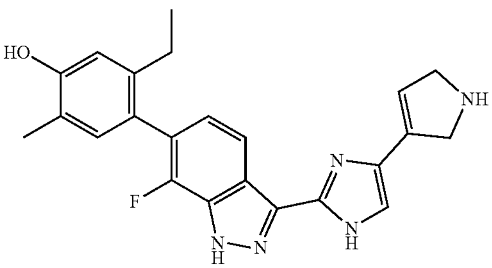 [SMILES: CCc1cc(O)c(C)cc1-c1ccc2c(-c3nc(C4=CCNC4)c[nH]3)n[nH]c2c1F] | 404.2 | 404.2 |
| 329 | 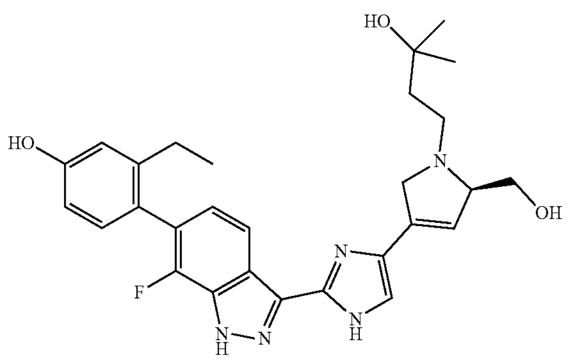 [SMILES: CCc1cc(O)ccc1-c1ccc2c(-c3nc(C4=C[C@H](CO)N(CCC(C)(C)O)C4)c[nH]3)n[nH]c2c1F] | 506.3 | 506.1 |
| 330 | 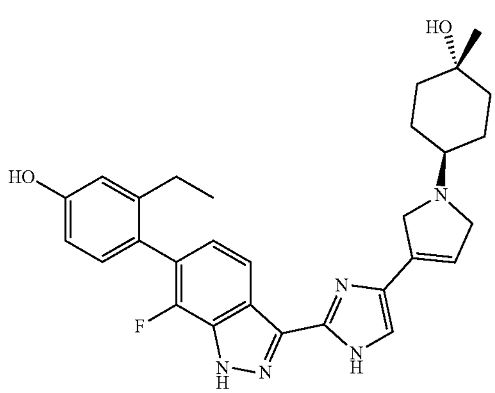 [SMILES: CCc1cc(O)ccc1-c1ccc2c(-c3nc(C4=CCN([C@H]5CC[C@](C)(O)CC5)C4)c[nH]3)n[nH]c2c1F] | 502.3 | 502.2 |

TABLE 4-continued

| Ex. No. | Structure | Calc. [M + H]+ | Found [M + H]+ |
|---|---|---|---|
| 331 | 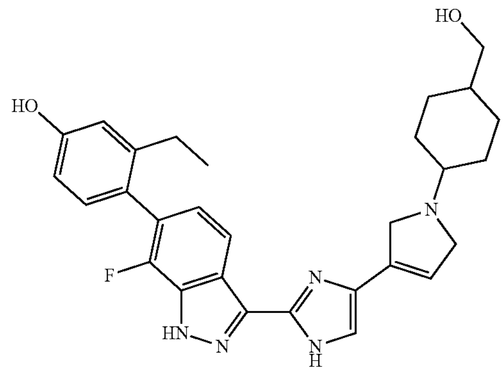 [SMILES: CCc1cc(O)ccc1-c1ccc2c(-c3nc(C4=CCN(C5CCC(CO)CC5)C4)c[nH]3)n[nH]c2c1F] | 502.3 | 502.2 |
| 332 | 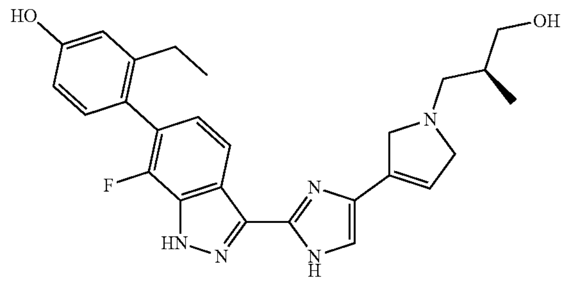 [SMILES: CCc1cc(O)ccc1-c1ccc2c(-c3nc(C4=CCN(C[C@H](C)CO)C4)c[nH]3)n[nH]c2c1F] | 462.2 | 462.2 |
| 333 | 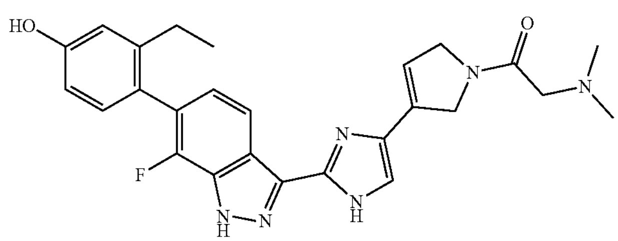 [SMILES: CCc1cc(O)ccc1-c1ccc2c(-c3nc(C4=CCN(C(=O)CN(C)C)C4)c[nH]3)n[nH]c2c1F] | 475.2 | 475.3 |
| 334 | 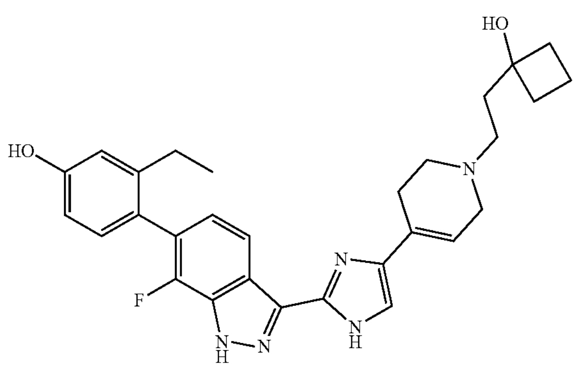 [SMILES: CCc1cc(O)ccc1-c1ccc2c(-c3nc(C4=CCN(CCC5(O)CCC5)CC4)c[nH]3)n[nH]c2c1F] | 502.3 | 502.2 |
| 335 | 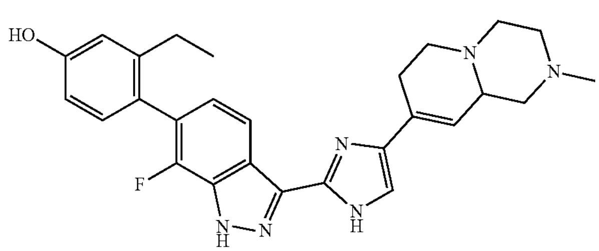 [SMILES: CCc1cc(O)ccc1-c1ccc2c(-c3nc(C4=CC5CN(C)CCN5CC4)c[nH]3)n[nH]c2c1F] | 473.2 | 473.3 |

TABLE 4-continued
| Ex. No. | Structure | Calc. [M + H]+ | Found [M + H]+ |
|---|---|---|---|
| 336 | 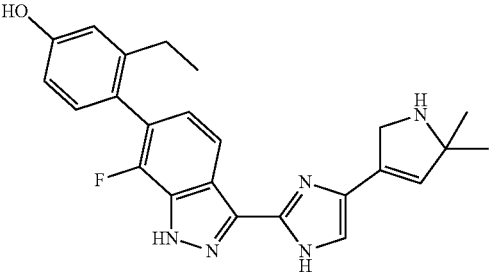 | 418.2 | 418.2 |
| 337 | 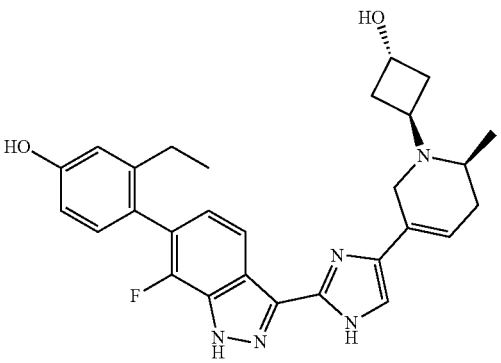 [SMILES: CCc1cc(O)ccc1-c1ccc2c(-c3nc(C4=CC[C@H](C)N([C@H]5C[C@H](O)C5)C4)c[nH]3)n[nH]c2c1F] | 488.2 | 488.1 |
| 338 | 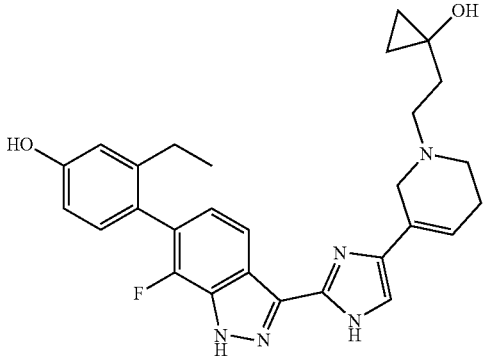 [SMILES: CCc1cc(O)ccc1-c1ccc2c(-c3nc(C4=CCCN(CCC5(O)CC5)C4)c[nH]3)n[nH]c2c1F] | 488.2 | 488.3 |
| 339 | 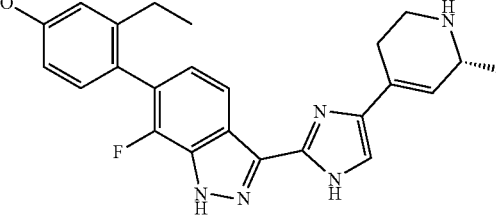 | 418.2 | 418.1 |
| 340 | 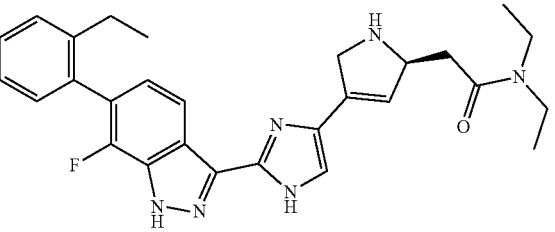 | 503.3 | 503.4 |

TABLE 4-continued
| Ex. No. | Structure | Calc. [M + H]+ | Found [M + H]+ |
|---|---|---|---|
| 341 | 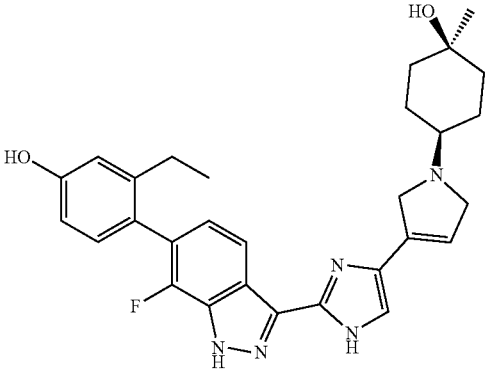 [SMILES: CCc1cc(O)ccc1-c1ccc2c(-c3nc(C4=CCN([C@H]5CC[C@@](C)(O)CC5)C4)c[nH]3)n[nH]c2c1F] | 502.3 | 502.2 |
| 342 | 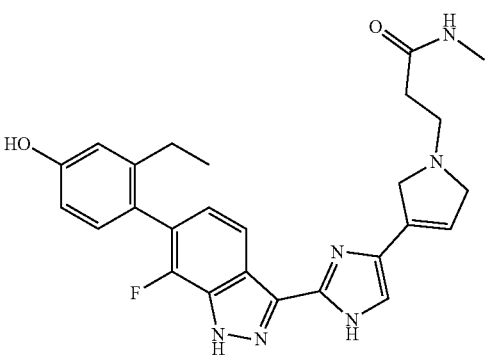 [SMILES: CCc1cc(O)ccc1-c1ccc2c(-c3nc(C4=CCN(CCC(=O)NC)C4)c[nH]3)n[nH]c2c1F] | 475.2 | 475.2 |
| 343 | 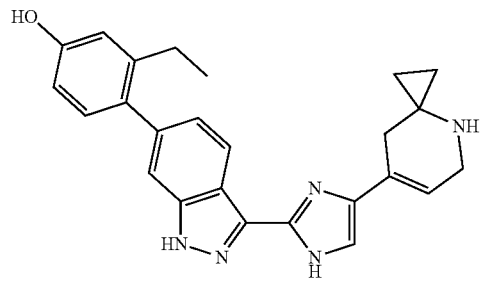 [SMILES: CCc1cc(O)ccc1-c1ccc2c(-c3nc(C4=CCNC5(CC5)C4)c[nH]3)n[nH]c2c1] | 412.2 | 412.1 |
| 344 | 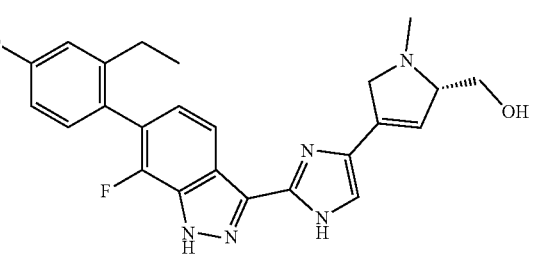 | 434.2 | 434.2 |
| 345 | 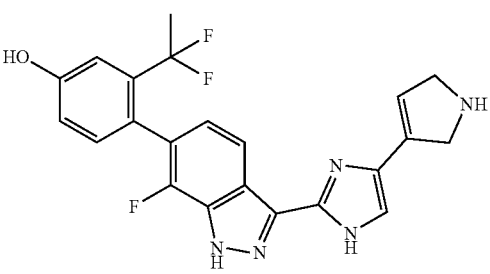 [SMILES: CC(F)(F)c1cc(O)ccc1-c1ccc2c(-c3nc(C4=CCNC4)c[nH]3)n[nH]c2c1F] | 408.2 | 408.2 |

TABLE 4-continued

| Ex. No. | Structure | Calc. [M + H]+ | Found [M + H]+ |
|---|---|---|---|
| 346 | 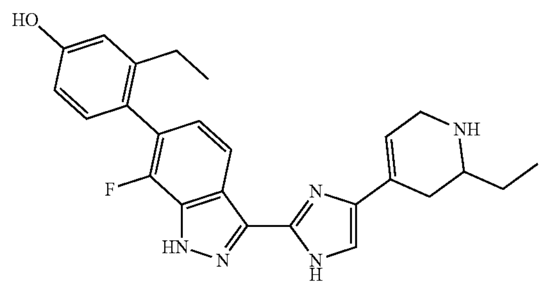 | 432.2 | 432.3 |
| 347 | 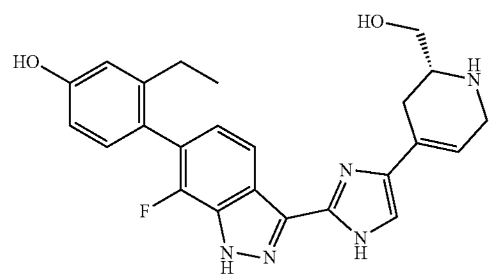 [SMILES: CCc1cc(O)ccc1-c1ccc2c(-c3nc(C4=CCN[C@@H](CO)C4)c[nH]3)n[nH]c2c1F] | 434.2 | 434.1 |
| 348 | 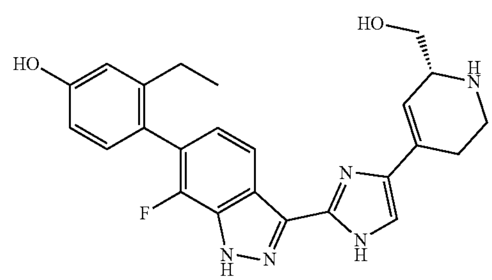 [SMILES: CCc1cc(O)ccc1-c1ccc2c(-c3nc(C4=C[C@H](CO)NCC4)c[nH]3)n[nH]c2c1F] | 434.2 | 434.1 |
| 349 | 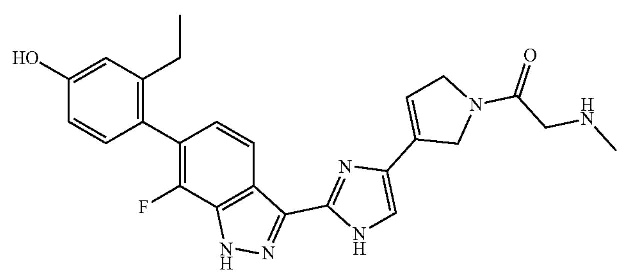 [SMILES: CCc1cc(O)ccc1-c1ccc2c(-c3nc(C4=CCN(C(=O)CNC)C4)c[nH]3)n[nH]c2c1F] | 461.2 | 461.3 |
| 350 | 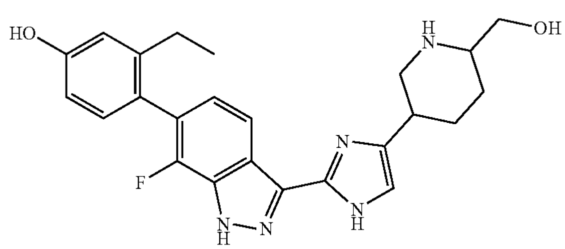 [SMILES: CCc1cc(O)ccc1-c1ccc2c(-c3nc(C4CCC(CO)NC4)c[nH]3)n[nH]c2c1F] | 434.2 | 434.1 |

TABLE 4-continued
| Ex. No. | Structure | Calc. [M + H]+ | Found [M + H]+ |
|---|---|---|---|
| 351 | 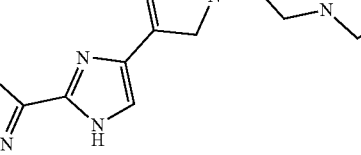 | 501.2 | 501.3 |
| 352 | 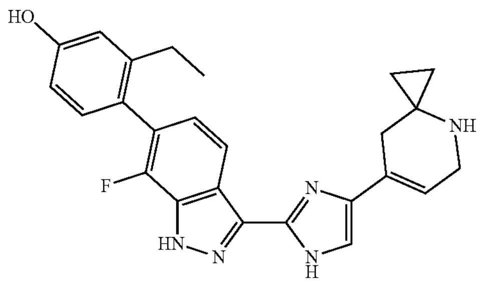 [SMILES: CCc1cc(O)ccc1-c1ccc2c(-c3nc(C4=CCNC5(CC5)C4)c[nH]3)n[nH]c2c1F] | 430.2 | 430.1 |
| 353 | 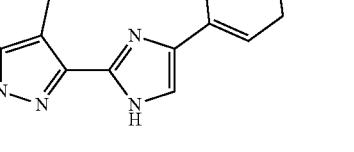  Mixture of enantiomers | 414.2 | 414.2 |
| 354 | 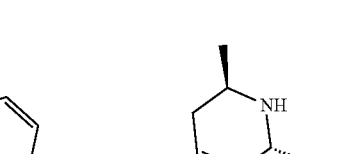 | 458.2 | 458.2 |
| 355 | 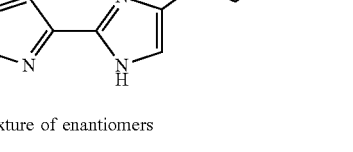 | 501.2 | 501.1 |

TABLE 4-continued
| Ex. No. | Structure | Calc. [M + H]+ | Found [M + H]+ |
|---|---|---|---|
| 356 | 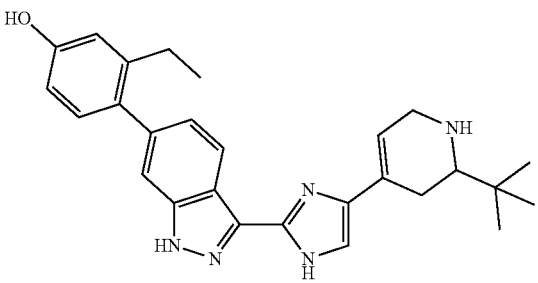 [SMILES: CCc1cc(O)ccc1-c1ccc2c(-c3nc(C4=CCNC(C(C)(C)C)C4)c[nH]3)n[nH]c2c1] | 442.3 | 442.2 |
| 357 | 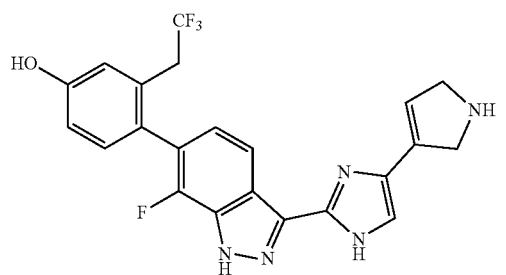 | 444.1 | 444.2 |
| 358 | 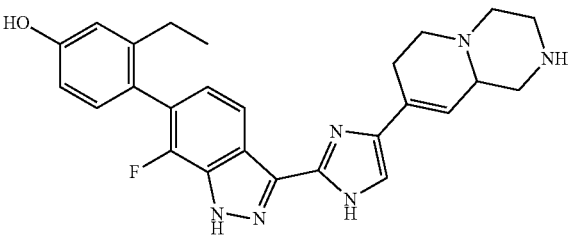 [SMILES: CCc1cc(O)ccc1-c1ccc2c(-c3nc(C4=CC5CNCCN5CC4)c[nH]3)n[nH]c2c1F] | 459.2 | 459.2 |
| 359 | 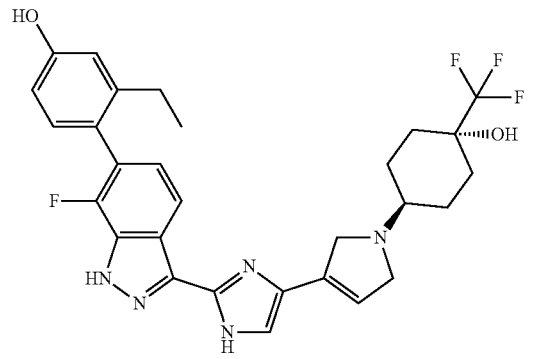 [SMILES: CCc1cc(O)ccc1-c1ccc2c(-c3nc(C4=CCN([C@H]5CC[C@@](O)(C(F)(F)F)CC5)C4)c[nH]3)n[nH]c2c1F] | 556.2 | 556.2 |
| 360 | 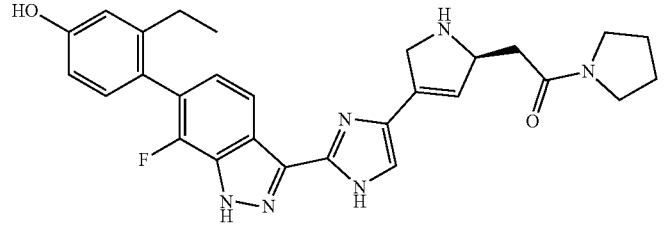 [SMILES: CCc1cc(O)ccc1-c1ccc2c(-c3nc(C4=C[C@H](CC(=O)N5CCCC5)NC4)c[nH]3)n[nH]c2c1F] | 501.2 | 501.3 |

TABLE 4-continued
| Ex. No. | Structure | Calc. [M + H]+ | Found [M + H]+ |
|---|---|---|---|
| 361 | 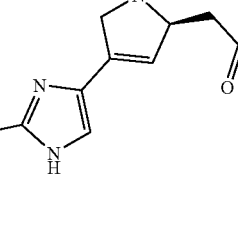 | 517.2 | 517.3 |
| 362 | 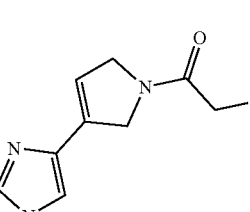 | 505.2 | 505.4 |
| 363 | 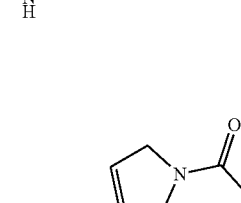 | 489.2 | 489.4 |
| 364 | 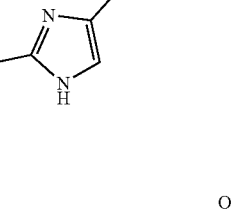 | 535.2 | 535.4 |
| 365 | 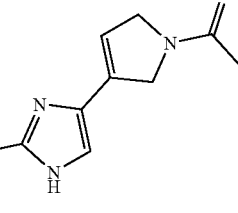 | 530.3 | 530.3 |

TABLE 4-continued

| Ex. No. | Structure | Calc. [M + H]+ | Found [M + H]+ |
|---|---|---|---|
| 366 | Mixture of enantiomers | 414.2 | 414.2 |
| 367 | Mixture of enantiomers | 432.2 | 432.3 |
| 368 | 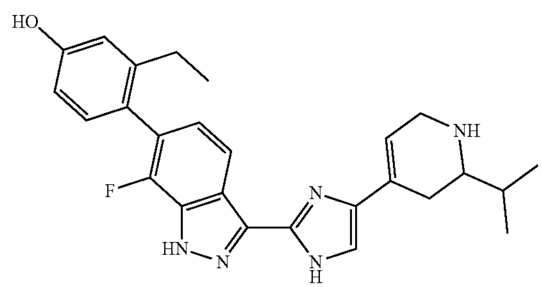 [SMILES: CCc1cc(O)ccc1-c1ccc2c(-c3nc(C4=CCNC(C(C)C)C4)c[nH]3)n[nH]c2c1F] | 446.2 | 446.3 |
| 369 | 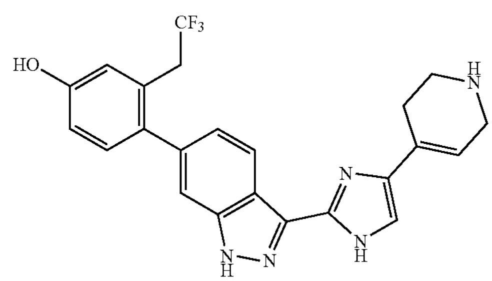 [SMILES: Oc1ccc(-c2ccc3c(-c4nc(C5=CCNCC5)c[nH]4)n[nH]c3c2)c(CC(F)(F)F)c1] | 440.2 | 440.2 |
| 370 | 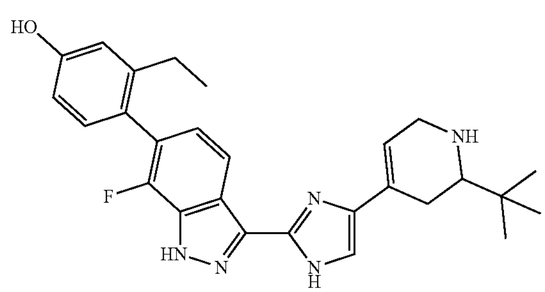 [SMILES: CCc1cc(O)ccc1-c1ccc2c(-c3nc(C4=CCNC(C(C)(C)C)C4)c[nH]3)n[nH]c2c1F] | 460.2 | 460.3 |

TABLE 4-continued

| Ex. No. | Structure | Calc. [M + H]+ | Found [M + H]+ |
|---|---|---|---|
| 371 | 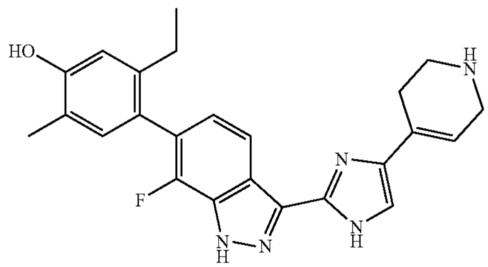 [SMILES: CCc1cc(O)c(C)cc1-c1ccc2c(-c3nc(C4=CCNCC4)c[nH]3)n[nH]c2c1F] | 418.2 | 418.2 |
| 372 | 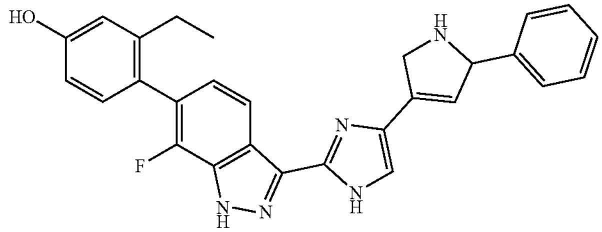 [SMILES: CCc1cc(O)ccc1-c1ccc2c(-c3nc(C4=CC(c5ccccc5)NC4)c[nH]3)n[nH]c2c1F] | 466.2 | 466.2 |
| 373 | 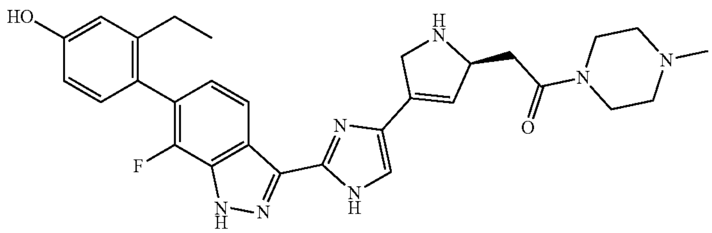 [SMILES: CCc1cc(O)ccc1-c1ccc2c(-c3nc(C4=C[C@H](CC(=O)N5CCN(C)CC5)NC4)c[nH]3)n[nH]c2c1F] | 530.3 | 530.4 |
| 374 | 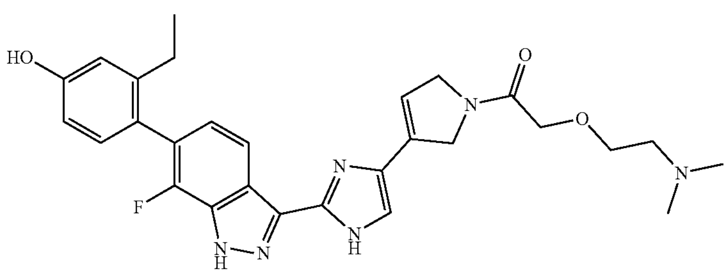 [SMILES: CCc1cc(O)ccc1-c1ccc2c(-c3nc(C4=CCN(C(=O)COCCN(C)C)C4)c[nH]3)n[nH]c2c1F] | 519.2 | 519.4 |
| 375 | 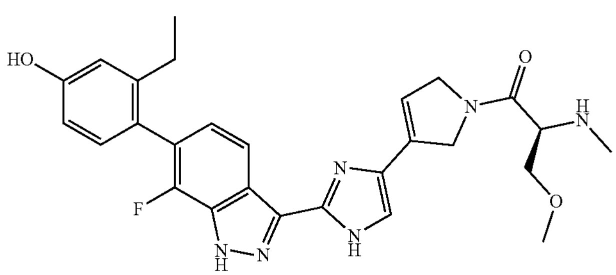 [SMILES: CCc1cc(O)ccc1-c1ccc2c(-c3nc(C4=CCN(C(=O)[C@H](COC)NC)C4)c[nH]3)n[nH]c2c1F] | 505.2 | 505.4 |
| 376 | 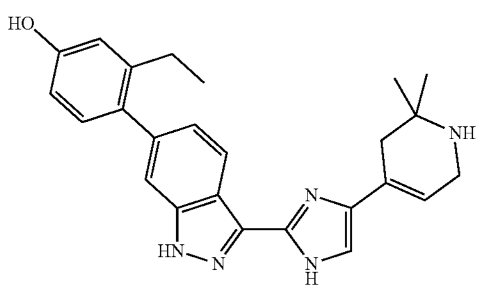 [SMILES: CCc1cc(O)ccc1-c1ccc2c(-c3nc(C4=CCNC(C)(C)C4)c[nH]3)n[nH]c2c1] | 414.2 | 414.2 |

TABLE 4-continued

| Ex. No. | Structure | Calc. [M + H]+ | Found [M + H]+ |
|---|---|---|---|
| 377 | 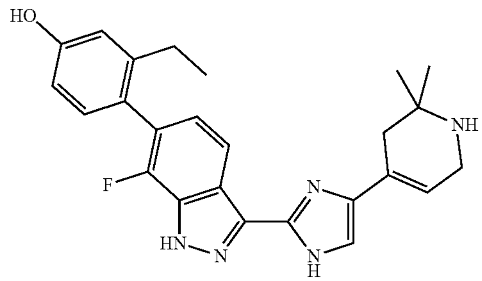 [SMILES: CCc1cc(O)ccc1-c1ccc2c(-c3nc(C4=CCNC(C)(C)C4)c[nH]3)n[nH]c2c1F] | 432.2 | 432.2 |
| 378 | 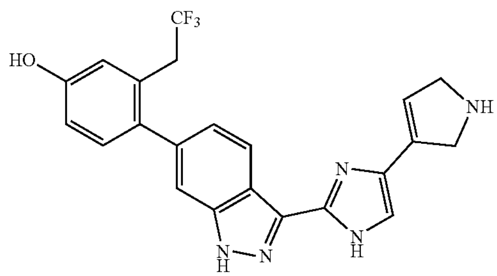 [SMILES: Oc1ccc(-c2ccc3c(-c4nc(C5=CCNC5)c[nH]4)n[nH]c3c2)c(CC(F)(F)F)c1] | 426.2 | 426.3 |
| 379 | 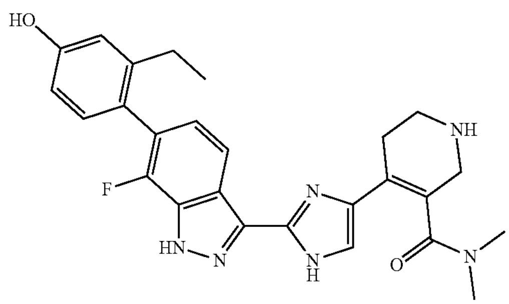 [SMILES: CCc1cc(O)ccc1-c1ccc2c(-c3nc(C4=C(C(=O)N(C)C)CNCC4)c[nH]3)n[nH]c2c1F] | 475.2 | 475.1 |
| 380 | 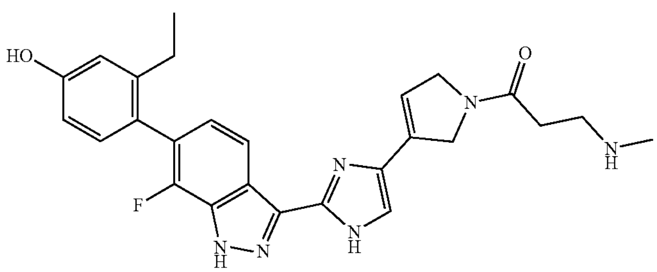 | 475.2 | 475.3 |
| 381 | 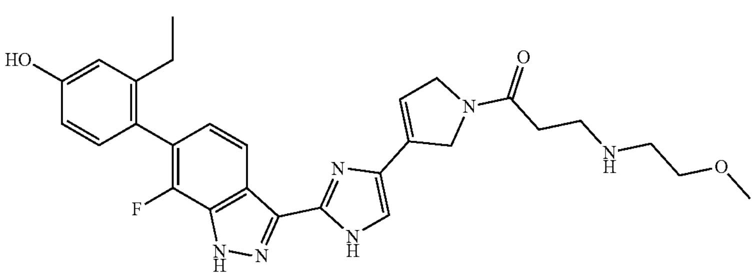 | 519.2 | 519.4 |

TABLE 4-continued

| Ex. No. | Structure | Calc. [M + H]+ | Found [M + H]+ |
|---|---|---|---|
| 382 | Mixture of enantiomers | 432.2 | 432.2 |
| 383 | 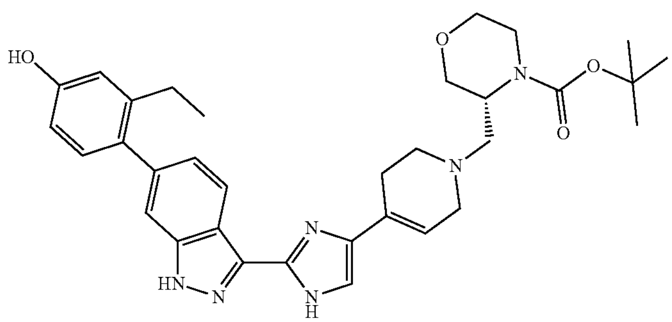 [SMILES: CCc1cc(O)ccc1-c1ccc2c(-c3nc(C4=CCN(C[C@@H]5COCCN5C(=O)OC(C)(C)C)CC4)c[nH]3)n[nH]c2c1] | 585.3 | 585.3 |
| 384 | 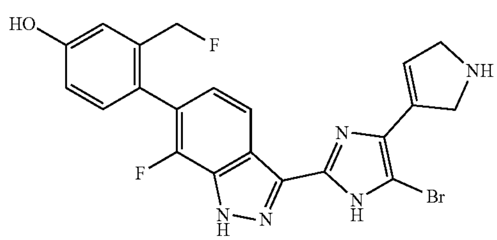 [SMILES: Oc1ccc(-c2ccc3c(-c4nc(C5=CCNC5)c(Br)[nH]4)n[nH]c3c2F)c(CF)c1] | 468.1 | 468.2 |
| 385 | 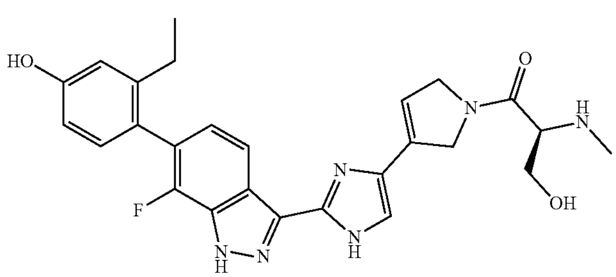 [SMILES: CCc1cc(O)ccc1-c1ccc2c(-c3nc(C4=CCN(C(=O)[C@H](CO)NC)C4)c[nH]3)n[nH]c2c1F] | 491.2 | 491.4 |
| 386 | 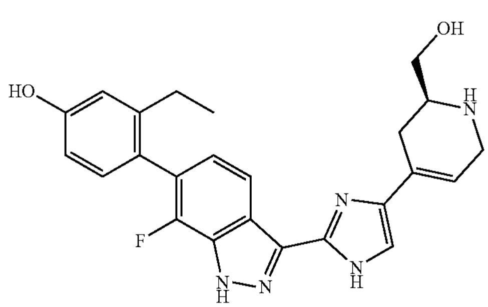 [SMILES: CCc1cc(O)ccc1-c1ccc2c(-c3nc(C4=CCN[C@H](CO)C4)c[nH]3)n[nH]c2c1F] | 434.2 | 434.1 |

TABLE 4-continued
| Ex. No. | Structure | Calc. [M + H]+ | Found [M + H]+ |
|---|---|---|---|
| 387 | 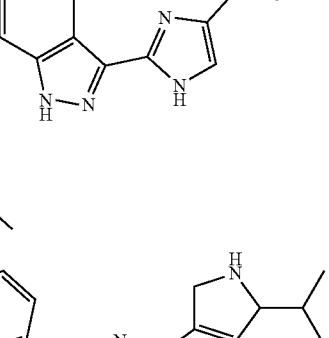 | 458.2 | 458.2 |
| 388 | 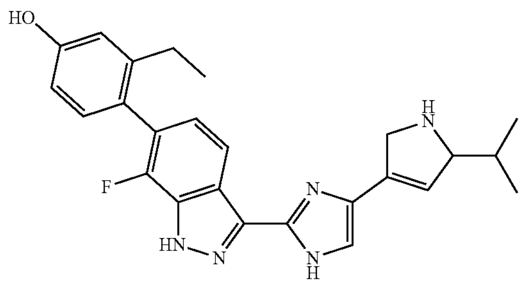 [SMILES: CCc1cc(O)ccc1-c1ccc2c(-c3nc(C4=CC(C(C)C)NC4)c[nH]3)n[nH]c2c1F] | 432.2 | 432.2 |
| 389 | 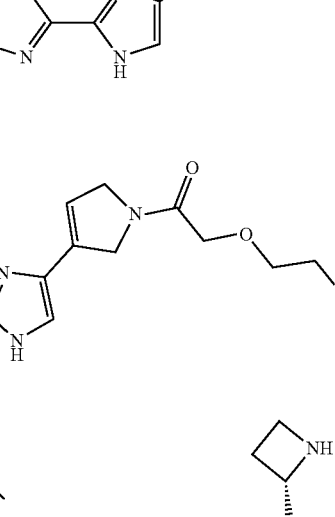 | 549.3 | 549.4 |
| 390 | 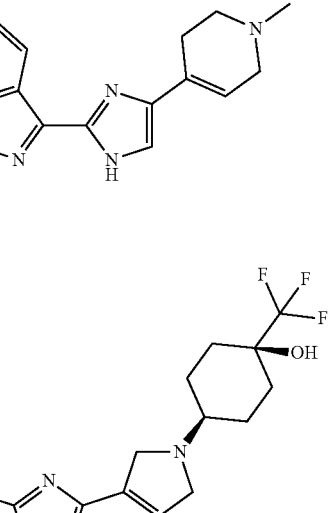 | 473.2 | 473.2 |
| 391 | 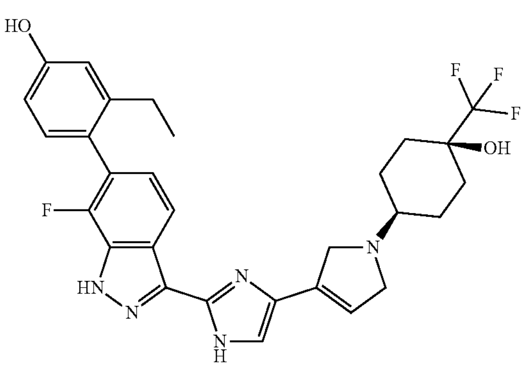 [SMILES: CCc1cc(O)ccc1-c1ccc2c(-c3nc(C4=CCN([C@H]5CC[C@](O)(C(F)(F)F)CC5)C4)c[nH]3)n[nH]c2c1F] | 556.2 | 556.2 |

TABLE 4-continued

| Ex. No. | Structure | Calc. [M + H]+ | Found [M + H]+ |
|---|---|---|---|
| 392 | 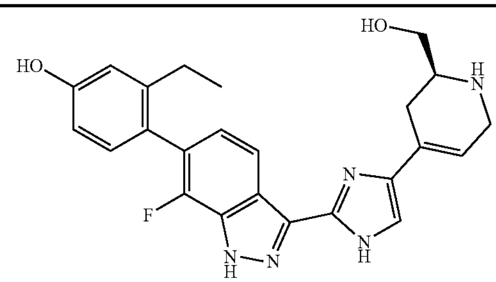 | 434.2 | 434.1 |
| 393 | 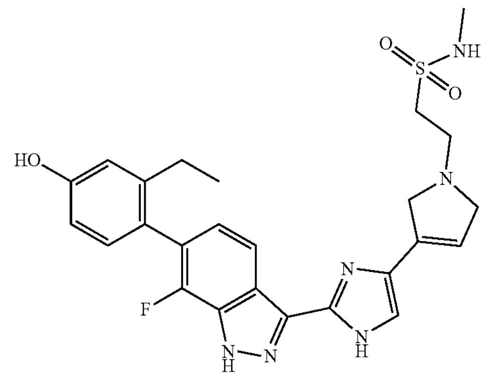 [SMILES: CCc1cc(O)ccc1-c1ccc2c(-c3nc(C4=CCN(CCS(=O)(=O)NC)C4)c[nH]3)n[nH]c2c1F] | 511.2 | 511.2 |

Biological Assays

The compounds of the invention and present disclosure have been characterized in one or more of the following biological assays.

Assay 1: Biochemical JAK Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

Serially diluted compounds were pre-incubated with each of the four JAK enzymes and the substrate in white 384-well microplates (Corning) at ambient temperature for 1 h. ATP was subsequently added to initiate the kinase reactions in 10 μL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 μM, 3 μM, 1.6 μM, and 10 μM; while the substrate concentration is 200 nM for all four assays. Kinase reactions were allowed to proceed for 1 hour at ambient temperature before a 10 μL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to $pK_i$ (negative logarithm of dissociation constant, Ki) using the Cheng-Prusoff equation.

Test compounds having a lower $K_i$ value or higher $pK_i$ value in the four JAK assays show greater inhibition of JAK activity.

Assay 2: Cellular JAKI Potency Assay

The JAKI cellular potency assay was carried out by measuring inhibition of interleukin-13 (IL-13, R&D Systems) induced STAT6 phosphorylation in BEAS-2B human lung epithelial cells (ATCC). BEAS-2B cells were grown at 37° C. in a 5% $CO_2$ humidified incubator in 50% DMEM/50% F-12 medium (Life Technologies) supplemented with 10% FBS (Hyclone), 100 U/mL penicillin, 100 g/mL streptomycin (Life Technologies), and 2 mM GlutaMAX (Life Technologies). On day 1 of the assay, cells were seeded at a 7,500 cells/well density in white poly-D-lysine-coated 384-well plates (Corning) with 25 μL medium and were allowed to adhere overnight in the incubator. On day 2 of the assay, the medium was removed and replaced with 12 μL of assay buffer (Hank's Balanced Salt Solution/HBSS, 25 mM HEPES, and 1 mg/ml bovine serum albumin/BSA) containing dose-responses of test compounds. Compounds were serially diluted in DMSO and then diluted another 1000-fold in media to bring the final DMSO concentration to 0.1%. Cells were incubated with test compounds at 37° C. for 1 h and followed by the addition of 12 μl of pre-warmed IL-13 (80 ng/mL in assay buffer) for stimulation. After incubating at 37° C. for 30 min, the assay buffer (containing compound and IL-13) was removed, and 10 μL of cell lysis buffer (25 mM HEPES, 0.1% SDS, 1% NP-40, 5 mM $MgCl_2$, 1.3 mM EDTA, 1 mM EGTA, supplemented with Complete Ultra mini protease inhibitors and PhosSTOP from Roche Diagnostics). The plates were shaken at ambient temperature for 30 min before the addition of detection reagents. Levels of pSTAT6 were measured using the AlphaLISA SureFire Ultra pSTAT6 (Tyr641) assay kit from PerkinElmer. For dose-response analysis, percent inhibition data were plotted vs. compound concentrations, and $IC_{50}$ values were determined from a 4-parameter robust fit model with the Graphpad Prism software. Results are expressed as the negative logarithm of the $IC_{50}$ value, $pIC_{50}$.

Test compounds having a lower $IC_{50}$ value or higher $pIC_{50}$ value in this assay show greater inhibition of IL-13 induced STAT6 phosphorylation.

In Vitro Assay Results

The compounds were tested in the BEAS-2B cellular potency assay and at least two of the four JAK enzyme assays; JAK1, JAK2, JAK3, and TYK2 described above.

In the Table below, for the JAK1, JAK2, JAK3, and TYK2 enzyme assays, A represents a $pK_i$ value ≥10 ($K_i$≤0.1 nM), B represents a $pK_i$ value between 9 (included) and 10 ($K_i$ between 1 nM and 0.1 nM), C represents a $pK_i$ value between 8 (included) and 9 ($K_i$ between 10 nM and 1 nM), D represents a $pK_i$ value between 7 (included) and 8 ($K_i$ between 100 nM and 10 nM), and E represents a $pK_i$ value of 7 or below ($K_i$ of 100 nM or above). For the BEAS2B Potency assay, A represents a $pIC_{50}$ value between 8 (included) and 8.5, B represents a $pIC_{50}$ value between 7.5 (included) and 8, C represents a $pIC_{50}$ value between 7 (included) and 7.5, D represents a $pIC_{50}$ value between 6.5 (included) and 7, and E represents a $pIC_{50}$ value between 6.0 and 6.5. A blank in Table 1 means not tested.

TABLE 1

| Example Number | JAK1 $pK_i$ | JAK2 $pK_i$ | JAK3 $pK_i$ | Tyk2 $pK_i$ | BEAS2B pIC50 |
|---|---|---|---|---|---|
| 1 | B | B | B | C | A |
| 2 | B | B | C | C | A |
| 3 | B | B | C | B | A |
| 4 | B | B | B | C | A |
| 5 | A | B | B | B | A |
| 6 | B | B | C | C | A |
| 7 | B | A | B | C | B |
| 8 | B | A | B | C | B |
| 9 | A | B | B | D | A |
| 10 | B | B | | | B |
| 11 | B | A | | | B |
| 12 | B | B | | | B |
| 13 | B | A | | | A |
| 14 | B | A | B | C | B |
| 15 | B | A | B | C | B |
| 16 | C | | | C | C |
| 17 | B | B | B | C | A |
| 18 | A | | | C | A |
| 19 | A | A | B | B | A |
| 20 | A | A | B | C | A |
| 21 | A | A | B | B | A |
| 22 | B | A | B | C | A |
| 23 | B | B | B | C | A |
| 24 | B | A | B | C | A |
| 25 | B | B | B | D | B |
| 26 | B | B | B | C | B |
| 27 | A | A | B | C | A |
| 28 | B | B | | | A |
| 29 | B | B | B | C | A |
| 30 | B | B | B | C | B |
| 31 | B | B | B | C | A |
| 32 | B | B | B | C | A |
| 33 | A | A | B | B | A |
| 34 | A | A | B | C | A |
| 35 | A | A | | | A |
| 36 | A | B | B | C | A |
| 37 | B | B | | | B |
| 38 | A | B | | | B |
| 39 | B | B | | | B |
| 40 | A | A | | | B |
| 41 | B | A | | | A |
| 42 | A | A | B | C | A |
| 43 | B | A | | | A |
| 44 | B | B | B | C | A |
| 45 | B | A | B | C | A |
| 46 | B | B | | | B |
| 47 | B | B | | | B |
| 48 | B | B | | | B |
| 49 | B | B | | | B |
| 50 | A | A | B | B | A |
| 51 | A | A | | | A |
| 52 | A | A | | | A |
| 53 | A | A | B | C | A |
| 54 | A | A | B | C | A |
| 55 | A | A | | | A |
| 56 | A | A | | | A |
| 57 | B | B | B | C | B |
| 58 | A | A | | | A |
| 59 | B | B | | | B |
| 60 | B | A | | | B |
| 61 | B | A | | | B |
| 62 | B | A | | | B |
| 63 | B | B | | | B |
| 64 | B | B | B | C | B |
| 65 | B | B | | | A |
| 66 | B | A | | | B |
| 67 | B | B | | | B |
| 68 | B | B | | | B |
| 69 | B | B | | C | B |
| 70 | C | B | B | D | C |
| 71 | A | A | | | A |
| 72 | A | A | | | A |
| 73 | B | A | | | B |
| 74 | B | A | | | B |
| 75 | B | B | B | C | B |
| 76 | B | B | | | B |
| 77 | B | A | | | B |
| 78 | B | A | | | B |
| 79 | B | B | | | B |
| 80 | B | A | | | B |
| 81 | B | A | B | C | C |
| 82 | B | B | | | B |
| 83 | C | B | | | C |
| 84 | B | B | | | C |
| 85 | B | B | | | C |
| 86 | B | B | | | B |
| 87 | B | A | | | B |
| 88 | B | A | | | B |
| 89 | B | A | | | B |
| 90 | B | B | B | D | C |
| 91 | B | B | | | B |
| 92 | C | B | | | B |
| 93 | B | A | | | A |
| 94 | B | A | | | B |
| 95 | A | A | | | B |
| 96 | B | A | | | B |
| 97 | B | A | | | A |
| 98 | B | A | | | C |
| 99 | A | A | | | B |
| 100 | A | A | | | A |
| 101 | B | A | | | B |
| 102 | A | A | | | A |
| 103 | A | A | | | B |
| 104 | A | A | | | A |
| 105 | A | A | | | B |
| 106 | B | A | | | B |
| 107 | A | A | | | B |
| 108 | B | A | | | B |
| 109 | B | B | | | B |
| 110 | B | B | | | B |

TABLE 1-continued

| Example Number | JAK1 pK$_i$ | JAK2 pK$_i$ | JAK3 pK$_i$ | Tyk2 pK$_i$ | BEAS2B pIC50 |
|---|---|---|---|---|---|
| 111 | B | B |  |  | B |
| 112 | B | B |  |  | B |
| 113 | B | A |  |  | B |
| 114 | A | A |  |  | A |
| 115 | B | A |  |  | B |
| 116 | B | A |  |  | B |
| 117 | A | A |  |  | A |
| 118 | A | A |  |  | C |
| 119 | B | B |  |  | B |
| 120 | B | B |  |  | B |
| 121 | B | A |  |  | B |
| 122 | B |  |  | C | C |
| 123 | B | B |  |  | C |
| 124 | A | A |  |  | A |
| 125 | B | B |  |  | C |
| 126 | B |  |  | C | C |
| 127 | B | B |  |  | B |
| 128 | A | A |  |  | A |
| 129 | A | A |  |  | A |
| 130 | B | C |  |  | C |
| 131 | A | A |  |  | B |
| 132 | A | A |  |  | A |
| 133 | B | A |  |  | B |
| 134 | C | C |  |  | D |
| 135 | C | C |  |  | D |
| 136 | B | B |  |  | C |
| 137 | B | B |  |  | B |
| 138 | B | B |  |  | D |
| 139 | C | B |  |  | D |
| 140 | B | B |  |  | C |
| 141 | B | B |  |  | D |
| 142 | A | A |  |  | B |
| 143 | A | A |  |  | B |
| 144 | A | A |  |  | B |
| 145 | A | A |  |  | B |
| 146 | B | B |  |  | B |
| 147 | B | B |  |  | B |
| 148 | B | B |  |  | B |
| 149 | C | C |  |  | C |
| 150 | B | B |  |  | B |
| 151 | C | C |  |  | C |
| 152 | B | A | B | C | B |
| 153 | B | A | B | C | C |
| 154 | B | B |  |  | B |
| 155 | C | B |  |  | B |
| 156 | C | B |  |  | C |
| 157 | B | A | B | C | C |
| 158 | C | B | B | D | C |
| 159 | B | B |  |  | B |
| 160 | B | B |  |  | B |
| 161 | B | C |  |  | C |
| 162 | B | B |  |  | C |
| 163 | C | C |  |  | C |
| 164 | B | B |  |  | B |
| 165 | B |  |  |  | B |
| 166 | A | A |  |  | A |
| 167 | B | C |  |  | A |
| 168 | B | B |  |  | B |
| 169 | B | A |  |  | C |
| 170 | B | A | B | B | B |
| 171 | B | B |  |  | B |
| 172 | C | B |  |  | B |
| 173 | B | A | B | C | C |
| 174 | B | B | B | C | B |
| 175 | B | B | B | C | C |
| 176 | B |  |  | C | C |
| 177 | B |  |  | C | C |
| 178 | C | B | C | D | D |
| 179 | C |  |  | D | D |
| 180 | C |  |  | D | C |
| 181 | B |  |  | C | C |
| 182 | A | B |  | C | B |
| 183 | B |  |  | C | C |
| 184 | A | A | B | C | A |
| 185 | B | B | B | C | B |
| 186 | B | B | B | C | A |
| 187 | B | B |  | C | C |
| 188 | B |  |  | C | C |
| 189 | B | B | B | C | B |
| 190 | B | B |  |  | C |
| 191 | A | A | B | C | B |
| 192 | B | A | B | C | B |
| 193 | B | B |  | C | C |
| 194 | B | B | B | C | B |
| 195 | B | B | B | C | C |
| 196 | C | B | B | D | C |
| 197 | B |  |  | C | C |
| 198 | B | B |  | C | B |
| 199 | A | A | B | B | A |
| 200 | B | A |  |  | B |
| 201 | B | A | B | C | A |
| 202 | B | A | B | C | B |
| 203 | B |  |  | C | C |
| 204 | B |  |  | C | C |
| 205 | B | B | B | C | B |
| 206 | B | A | B | C | B |
| 207 | B | A | B | C | D |
| 208 | B | A | B | C | B |
| 209 | B | A | B | C | B |
| 210 | B | A |  | C | B |
| 211 | B |  |  | C | C |
| 212 | B | A | B | C | B |
| 213 | B | B | B | D | D |
| 214 | B | A | B | D | E |
| 215 | C | B | B | C | C |
| 216 | C | B |  | C | D |
| 217 | C | B | B | C | C |
| 218 | A | A | B | C | C |
| 219 | B | A | B | B | B |
| 220 | B | A | B | C | B |
| 221 | B |  |  | B | B |
| 222 | B |  |  | C | B |
| 223 | B | A | B | C | B |
| 224 | B | B | B | C | A |
| 225 | B | B | B | C | C |
| 226 | B |  |  | C | B |
| 227 | B | B | C | C | B |
| 228 | B | B |  |  | B |
| 229 | B | A |  |  | C |
| 230 | A | A |  | B | A |
| 231 | B | A | B | C | A |
| 232 | B | B |  |  | A |
| 233 | B | B |  |  | B |
| 234 | A | B |  | C | A |
| 235 | B | A | B | C | B |
| 236 | B | B |  |  | B |
| 237 | B | A |  |  | B |
| 238 | B | B | B | D | A |
| 239 | B | B |  |  | C |
| 240 | B | B |  |  | C |
| 241 | B | B |  |  | A |
| 242 | A | B |  |  | A |
| 243 | A | A |  |  | A |
| 244 | B | B | B | C | A |
| 245 | B | B | B | D | C |
| 246 | B | B | C | D | B |
| 247 | B | B |  |  | B |
| 248 | B | B |  |  | B |
| 249 | B | B |  |  | B |
| 250 | B | B |  |  | C |
| 251 | B | B |  |  | B |
| 252 | B | B |  |  | D |
| 253 | A | A |  |  | A |
| 254 | B | B |  |  | B |
| 255 | A | A |  |  | B |
| 256 | A | A |  |  | C |
| 257 | B | B |  |  | B |
| 258 | B | B |  |  | B |
| 259 | B | B |  |  | B |
| 260 | B | B |  |  | B |
| 261 | B | B |  |  | B |
| 262 | B | B |  |  | B |
| 263 | A | A |  |  | B |
| 264 | B | A |  |  | B |

TABLE 1-continued

| Example Number | JAK1 pK$_i$ | JAK2 pK$_i$ | JAK3 pK$_i$ | Tyk2 pK$_i$ | BEAS2B pIC50 |
|---|---|---|---|---|---|
| 265 | B | B | | | A |
| 266 | B | B | | | B |
| 267 | B | B | | | B |
| 268 | B | B | | | B |
| 269 | B | B | | | C |
| 270 | B | B | | | B |
| 271 | B | B | | | B |
| 272 | A | A | | | A |
| 273 | B | A | | | B |
| 274 | A | A | | | B |
| 275 | B | B | | | B |
| 276 | C | B | | | C |
| 277 | C | B | | | C |
| 278 | B | B | | | B |
| 279 | B | | | | C |
| 280 | | A | | | D |
| 281 | A | | | B | A |
| 282 | B | | | C | A |
| 283 | A | A | | | A |
| 284 | A | A | | | A |
| 285 | A | A | | | A |
| 286 | B | B | | | A |
| 287 | A | A | | | A |
| 288 | A | A | | | A |
| 289 | A | A | | | A |
| 290 | A | A | | | A |
| 291 | A | | | B | A |
| 292 | B | B | | | A |
| 293 | B | B | B | B | A |
| 294 | B | A | | | A |
| 295 | B | A | | | A |
| 296 | A | A | | | B |
| 297 | B | B | | | B |
| 298 | B | B | B | B | B |
| 299 | B | B | B | B | B |
| 300 | B | B | B | C | B |
| 301 | A | B | | | B |
| 302 | A | B | | | B |
| 303 | A | A | | | B |
| 304 | A | A | | | B |
| 305 | B | A | B | B | B |
| 306 | B | B | | | B |
| 307 | B | B | B | C | B |
| 308 | B | A | | | B |
| 309 | B | B | | | B |
| 310 | B | A | | | B |
| 311 | B | B | | | B |
| 312 | B | B | | | B |
| 313 | B | B | | | B |
| 314 | B | B | | | B |
| 315 | B | B | | | B |
| 316 | A | A | | | B |
| 317 | B | B | | | B |
| 318 | B | B | | | B |
| 319 | B | B | | | B |
| 320 | B | A | | | B |
| 321 | B | B | B | C | B |
| 322 | B | B | | | B |
| 323 | B | B | | | B |
| 324 | B | B | | | B |
| 325 | B | B | | | B |
| 326 | B | B | | | B |
| 327 | B | B | | | B |
| 328 | B | C | | | B |
| 329 | A | A | | | B |
| 330 | A | B | | | B |
| 331 | A | B | | | B |
| 332 | B | B | | | B |
| 333 | B | A | | | B |
| 334 | B | B | | | B |
| 335 | B | B | | | B |
| 336 | B | B | | | B |
| 337 | B | B | | | B |
| 338 | B | B | | | B |
| 339 | B | B | | | B |
| 340 | A | A | | | B |
| 341 | A | A | | | B |
| 342 | B | B | | | B |
| 343 | B | B | | | B |
| 344 | B | B | | | B |
| 345 | B | B | | | B |
| 346 | C | B | | | B |
| 347 | A | A | | | C |
| 348 | B | A | | | C |
| 349 | B | A | | | C |
| 350 | B | B | | | C |
| 351 | B | A | | | C |
| 352 | B | B | | | C |
| 353 | B | B | | | C |
| 354 | B | B | | | C |
| 355 | B | B | | | C |
| 356 | B | B | | | C |
| 357 | B | B | | | C |
| 358 | B | B | | | C |
| 359 | C | B | | | C |
| 360 | A | A | | | C |
| 361 | B | A | | | C |
| 362 | B | A | | | C |
| 363 | B | A | | | C |
| 364 | B | A | | | C |
| 365 | B | A | | | C |
| 366 | B | B | | | C |
| 367 | B | B | | | C |
| 368 | B | B | | | C |
| 369 | B | B | | | C |
| 370 | C | B | | | C |
| 371 | C | C | | | C |
| 372 | C | C | | | C |
| 373 | B | A | | | C |
| 374 | B | A | | | C |
| 375 | B | A | | | C |
| 376 | B | B | | | C |
| 377 | B | B | | | C |
| 378 | B | B | | | C |
| 379 | B | A | | | C |
| 380 | B | A | | | C |
| 381 | B | A | | | C |
| 382 | B | B | | | C |
| 383 | B | | | D | C |
| 384 | C | B | | | C |
| 385 | B | A | | | C |
| 386 | B | B | | | C |
| 387 | C | B | | | C |
| 388 | C | C | | | C |
| 389 | B | A | | | D |
| 390 | B | A | B | C | D |
| 391 | B | B | | | D |
| 392 | B | B | | | D |
| 393 | B | B | | | D |

Assay 3: Murine (Mouse) Model of IL-13 Induced pSTAT6 Induction in Lung Tissue

IL-13 binds to cell surface receptors activating members of the Janus family of kinases (JAK) which then phosphorylate STAT6 and subsequently activate further transcription pathways. In the described model, a dose of IL-13 was delivered locally into the lungs of mice to induce the phosphorylation of STAT6 (pSTAT6) which is then measured as the endpoint.

Adult balb/c mice from Harlan were used in the assay. On the day of study, animals were lightly anesthetized with isoflurane and administered either vehicle or test compound (0.5 mg/mL, 50 μL total volume over several breaths) via oral aspiration.

Animals were placed in lateral recumbency post dose and monitored for full recovery from anesthesia before being returned to their home cage. Eight hours later, animals were once again briefly anesthetized and challenged with either vehicle or IL-13 (0.03 µg total dose delivered, 50 µL total volume) via oral aspiration before being monitored for recovery from anesthesia and returned to their home cage. One hour after vehicle or IL-13 administration, lungs were collected for both pSTAT6 detection using an AlphaLISA Immunoassay (PerkinElmer) and analyzed for total drug concentration.

Selected compounds of the present disclosure were tested in the assay. Activity in the model is evidenced by a decrease in the level of pSTAT6 present in the lungs of treated animals at 9 hours compared to the vehicle treated, IL-13 challenged control animals. The difference between the control animals which were vehicle-treated, IL-13 challenged and the control animals which were vehicle-treated, vehicle challenged dictated the 0% and 100% inhibitory effect, respectively, in any given experiment. Exemplary compounds were tested in the assay and exhibited inhibition of STAT6 phosphorylation at 9 hours after IL-13 challenge as documented below.

In the following table, A represents between 80% and 100% inhibition, B represents between 60% and 80% inhibition and C represents between 40% and 60% inhibition.

TABLE 2 pSTAT6 Inhibition

| Compound | % pSTAT6 inhibition at 8 hours |
|---|---|
| 1 | A |
| 2 | A |
| 3 | A |

Assay 4: Pharmacokinetics in Plasma and Lung in Mouse after Oral Aspiration Administration of Test Compounds Plasma and lung concentrations of test compounds were quantified and pharmacokinetic parameters were calculated in the following manner. Male CD1 mice from Charles River Laboratories were used in the pharmacokinetic studies. Test compounds were individually formulated in 20% propylene glycol in pH 4 citrate buffer at a concentration of 0.2 mg/mL. Test compounds were administered in two, 25 µL increments introduced into the trachea of each mouse by oral aspiration using a calibrated pipette once the animal was anesthetized using isoflurane. Blood samples were collected as terminal collections via cardiac puncture at 0.167, 1, 4, 8, and 24 hr post-dosing. Following inhalation with $CO_2$, a direct cardiac puncture was performed while avoiding puncturing the lung and blood was immediately transferred into $K_2$EDTA tubes and placed on wet ice. Blood samples were centrifuged (Eppendorf centrifuge, 5804R) for 4 minutes at approximately 12,000 rpm at 4° C. to collect plasma. Intact lungs were also excised from these mice using the same timepoints (0.167, 1, 4, 8, and 24 hr). Lungs were washed with sterile water to remove any blood residue and were patted dry, weighed, and homogenized in 0.1% formic acid in water at a dilution of 1:3 (lung:water, weight/volume). Plasma and lung concentrations of test compounds were determined by LC-MS/MS analysis against analytical standards constructed into a standard curve in the test matrix. The pharmacokinetic parameters of test compounds were determined by non-compartmental analysis. For concentrations below the limit of quantification, zero was used for mean calculations. Mean values were not reported if more than 50% of the samples were below the limit of quantification at a timepoint, or if more than 50% of a calculated pharmacokinetic parameter was not reportable. The area under the concentration-time curve extrapolated to infinity ($AUC_{(0-inf)}$) was calculated as follows: $AUC_{(0-inf)} = AUC_{(0-t)} + C_{last}/k$, where $AUC_{(0-t)}$ is the area under the concentration-time curve from the time of dosing to the last measurable concentration calculated by the linear trapezoidal rule, $C_{last}$ is the last measurable concentration, and k is the first order rate constant associated with the terminal elimination phase, estimated by linear regression of time versus log concentration. The lung-to-plasma AUC ratio was determined as the ratio of the lung $AUC_{(0-inf)}$ in µg*hr/g to the plasma $AUC_{(0-inf)}$ in µg*hr/mL.

In the following table, for Plasma $AUC_{(0-24)}$, A denotes a value below 0.5, B denotes a value between 0.5 and 1, and C denotes a value between 1 and 1.5. For the Lung Tissue $AUC_{(0-24)}$, A denotes a value between 100 and 200, B denotes a value between 50 and 100, and C denotes a value between 9 and 50. For the ratio of lung exposure to plasma exposure, A denotes a ratio 300-410, B denotes a ratio between 200 and 300, C denotes a ratio between 100 and 200, D denotes a ratio between 50 and 100, and E denotes a ratio between 30 and 50.

TABLE 3

Plasma and Lung Exposure in Mice Following Oral Aspiration Administration of Test Compounds

| Compound | Plasma $AUC_{(0-24)}$ (µg hr/mL) | Lung Tissue $AUC_{(0-24)}$ (µg hr/mL) | Lung Tissue:Plasma AUC ratio |
|---|---|---|---|
| 1 | B | B | C |
| 2 | B | B | C |
| 3 | B | A | C |
| 4 | B | B | C |
| 5 | A | C | D |
| 6 | B | B | D |
| 7 | A | B | C |
| 8 | B | B | C |
| 9 | A | C | C |
| 13 | B | B | C |
| 14 | A | C | C |
| 15 | A | B | C |
| 17 | B | B | C |
| 21 | A | C | D |
| 22 | A | C | D |
| 26 | A | C | E |
| 32 | A | C | D |
| 38 | A | C | D |
| 44 | B | B | D |
| 45 | A | C | C |
| 51 | A | C | C |
| 94 | A | C | E |
| 106 | A | C | C |
| 170 | A | B | C |
| 185 | B | A | B |
| 192 | A | A | A |
| 201 | B | A | B |
| 202 | B | B | D |
| 227 | B | A | C |
| 234 | A | B | C |
| 235 | A | C | C |
| 236 | B | B | C |
| 241 | B | C | D |
| 246 | A | C | D |
| 255 | C | A | D |

While the present invention has been described with reference to specific aspects or embodiments thereof, it will be understood by those of ordinary skill in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A compound of formula (I):

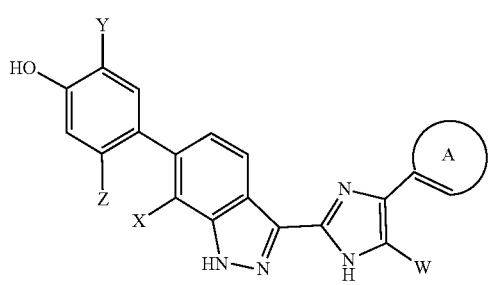

or a pharmaceutically acceptable salt thereof,
wherein:

W is H, —$C_{1-6}$ alkyl or halogen;

X is H or F;

Y is H, —$CH_3$, or F;

Z is —$CH_2CH_3$, —$CF_2CH_3$, or —$CH_2CF_3$;

A is a 4 to 7 membered monocyclic heterocyclic group having a double bond and optionally substituted with 1 to 8 substituents independently selected from the group consisting of —$C_{1-6}$ alkyl, —$COR^1$, —$SO_2R^1$, —$CO_2R^2$, —$CONR^2R^3$, —$SO_2NR^2R^3$, aryl, heteroaryl, a 3 to 7 membered cycloalkyl group, and a 4 to 7 membered heterocyclic group, wherein the —$C_{1-6}$ alkyl is optionally substituted with 1 to 5 substituents independently selected from the group consisting of —$C_{1-6}$ alkyl, —$NR^2R^3$, —CN, —$CO_2R^2$, —$CONR^2R^3$, —OH, —$SO_2NR^2R^3$, —$SO_2$—$C_{1-6}$ alkyl, —SH, —O—$C_{1-6}$ alkyl, —S—$C_{1-6}$ alkyl, —OC(O)$NR^2R^3$, —$NR^2C(O)$—$R^1$, —$NR^2C(O)_2R^3$, —$NR^2$—C(O)$NR^3R^4$, —$OCO_2R^3$, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —$C_{1-6}$ alkyl, —CN, —$CO_2R^5$, —$CONR^5R^6$, —OH, —SH, —O—$C_{1-6}$ alkyl, —S—$C_{1-6}$ alkyl, —$NR^5R^6$, —OC(O)$NR^5R^6$, —$NR^5C(O)$—$C_{1-6}$ alkyl, —$NR^5C(O)_2R^6$, —$NR^5$—C(O)$NR^6R^7$, —$C_{1-6}$ alkyl-$OR^5$, —$C_{1-6}$ alkyl-$NR^5R^6$, and —$C_{1-6}$ alkyl-$CO_2R^5$, and wherein the aryl and heteroaryl are optionally substituted with 1 to 5 substituents independently selected from the group consisting of halogen, —CN, —$CO_2R^8$, —$CONR^8R^9$, —OH, —SH, —$C_{1-6}$ alkyl, —O—$C_{1-6}$ alkyl, —S—$C_{1-6}$ alkyl, —$NR^8R^9$, —OC(O)$NR^8R^9$, —$OCO_2R^8$, —$NR^8C(O)$—$C_{1-6}$ alkyl, —$NR^8C(O)_2R^9$, —$NR^8$—C(O)$NR^9R^{10}$, —$C_{1-6}$ alkyl-$OR^8$, —$C_{1-6}$ alkyl-$NR^8R^9$, and —$C_{1-6}$ alkyl-$CO_2R^8$, wherein A is optionally fused or bridged with a 3 to 7 membered cycloalkyl group or a 4 to 7 membered heterocyclic group, wherein each 3 to 7 membered cycloalkyl group and each 4 to 7 membered heterocyclic group is optionally substituted with 1 to 5 substituents independently selected from the group consisting of a spiro 3 to 7 membered cycloalkyl group, a spiro 4 to 7 membered heterocyclic group, a 3 to 7 membered cycloalkyl group, a 4 to 7 membered heterocyclic group, —$C_{1-6}$ alkyl, —$CF_3$, oxo, —CN, —$CO_2R^{11}$, —$CONR^{11}R^{12}$, —OH, —SH, —O—$C_{1-6}$ alkyl, —S—$C_{1-6}$ alkyl, —$NR^{11}R^{12}$, —OC(O)$NR^{11}R^{12}$, —$NR^{11}C(O)$—$C_{1-6}$ alkyl, —$NR^{11}C(O)_2R^{12}$, —$NR^{11}$—C(O)$NR^{12}R^{13}$, —$OCO_2R^{12}$, —$NR^{11}$—$SO_2$—$C_{1-6}$ alkyl, —$C_{1-6}$ alkyl-$OR^{11}$, —$C_{1-6}$ alkyl-$NR^{11}R^{12}$, and —$C_{1-6}$ alkyl-$CO_2R^{11}$;

each $R^1$ is independently selected from the group consisting of aryl, a 3 to 7 membered cycloalkyl group, a 4 to 7 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, —O—$C_{1-6}$ alkyl, —O—$C_{1-6}$ alkyl-$NR^aR^b$, aryl, heteroaryl, and a 4 to 7 membered heterocyclic group, wherein the aryl, 3 to 7 membered cycloalkyl group, 4 to 7 membered heterocyclic group and heteroaryl are each optionally substituted with 1 to 5 substituents independently selected from the group consisting of halogen, —$NR^{14}R^{15}$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —OC(O)$NR^{14}R^{15}$, —$NR^{14}C(O)$—$C_{1-6}$ alkyl, —$NR^{14}C(O)_2R^{15}$, —$NR^{14}$—C(O)$NR^{15}R^{16}$, —$OCO_2R^{14}$ and —$NR^{14}SO_2$—$C_{1-6}$ alkyl;

each $R^2$, $R^3$, $R^4$, $R^5$, $R^6$, $R^7$, $R^8$, $R^9$, $R^{10}$, $R^{11}$, $R^{12}$, $R^{13}$, $R^a$, and $R^b$ is independently selected from the group consisting of H, $C_{1-6}$ alkyl, and —$C_{1-6}$ alkyl-$OR^{14}$;

wherein in —$CONR^2R^3$ and —$SO_2NR^2R^3$, $R^2$ and $R^3$ are optionally joined to form a 4 to 7 membered heterocyclic group optionally substituted with 1 to 5 substituents independently selected from the group consisting of —$NR^cR^d$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —OC(O)$NR^{14}R^{15}$, —$NR^{14}C(O)$—$C_{1-6}$ alkyl, —$NR^{14}C(O)_2R^{15}$, —$NR^{14}$—C(O)$NR^{15}R^{16}$, —$OCO_2R^{14}$, and —$NR^{14}SO_2$—$C_{1-6}$ alkyl, and each $R^c$, $R^d$, $R^{14}$, $R^{15}$, and $R^{16}$ is independently selected from the group consisting of H and $C_{1-6}$ alkyl.

2. The compound of claim 1, or a pharmaceutically acceptable salt thereof, wherein W is H, —$CH_3$ or bromo.

3. The compound of claim 1, or a pharmaceutically acceptable salt thereof, wherein Y is H or F.

4. The compound of claim 1, or a pharmaceutically acceptable salt thereof, wherein Z is —$CH_2CH_3$.

5. The compound of claim 1, or a pharmaceutically acceptable salt thereof, wherein the compound is a compound of formula (II):

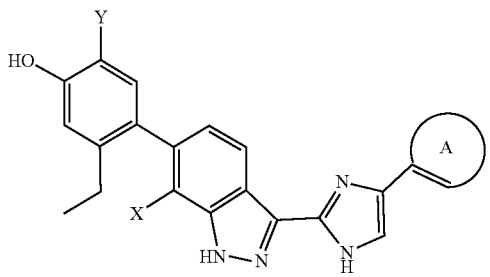

(II)

or a pharmaceutically acceptable salt thereof,
wherein:
X is H or F;
Y is H or F;
A is a 4 to 7 membered monocyclic heterocyclic group having a double bond and optionally substituted with 1 to 8 substituents independently selected from the group consisting of —$C_{1-6}$ alkyl, —$COR^1$, —$SO_2R^1$, —$CO_2R^2$, —$CONR^2R^3$, —$SO_2NR^2R^3$, a 3 to 7 membered cycloalkyl group, and a 4 to 7 membered heterocyclic group,
wherein the —$C_{1-6}$ alkyl is optionally substituted with 1 to 5 substituents independently selected from the group consisting of —$C_{1-6}$ alkyl, —$NR^2R^3$, —CN, —$CO_2R^2$, —$CONR^2R^3$, —OH, —$SO_2NR^2R^3$, —$SO_2$—$C_{1-6}$ alkyl, —SH, —O—$C_{1-6}$ alkyl, —S—$C_{1-6}$ alkyl, —OC(O)$NR^2R^3$, —$NR^2C(O)$—$C_{1-6}$ alkyl, —$NR^2C(O)_2R^3$, —$NR^2$—$C(O)NR^3R^4$, —$OCO_2R^3$, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —$C_{1-6}$ alkyl, —CN, —$CO_2R^5$, —$CONR^5R^6$, —OH, —SH, —O—$C_{1-6}$ alkyl, —S—$C_{1-6}$ alkyl, —$NR^5R^6$, —OC(O)$NR^5R^6$, —$NR^5C(O)$—$C_{1-6}$ alkyl, —$NR^5C(O)_2R^6$, —$NR^5$—$C(O)NR^6R^7$, —$C_{1-6}$ alkyl-$OR^5$, —$C_{1-6}$ alkyl-$NR^5R^6$, and —$C_{1-6}$ alkyl-$CO_2R^5$, and
wherein the aryl and heteroaryl are optionally substituted with 1 to 5 substituents independently selected from the group consisting of halogen, —CN, —$CO_2R^8$, —$CONR^8R^9$, —OH, —SH, —$C_{1-6}$ alkyl, —O—$C_{1-6}$ alkyl, —S—$C_{1-6}$ alkyl, —$NR^8R^9$, —OC(O)$NR^8R^9$, —$OCO_2R^8$, —$NR^8C(O)$—$C_{1-6}$ alkyl, —$NR^8C(O)_2R^9$, —$NR^8$—$C(O)NR^9R^{10}$, —$C_{1-6}$ alkyl-$OR^8$, —$C_{1-6}$ alkyl-$NR^8R^9$, and —$C_{1-6}$ alkyl-$CO_2R^8$,
wherein A is optionally fused or bridged with a 3 to 7 membered cycloalkyl group or a 4 to 7 membered heterocyclic group,
wherein each 3 to 7 membered cycloalkyl group and each 4 to 7 membered heterocyclic group is optionally substituted with 1 to 5 substituents independently selected from the group consisting of a spiro 3 to 7 membered cycloalkyl group, a spiro 4 to 7 membered heterocyclic group, a 3 to 7 membered cycloalkyl group, a 4 to 7 membered heterocyclic group, —$C_{1-6}$ alkyl, oxo, —CN, —$CO_2R^{11}$, —$CONR^{11}R^{12}$, —OH, —SH, —O—$C_{1-6}$ alkyl, —S—$C_{1-6}$ alkyl, —$NR^{11}R^{12}$, —OC(O)$NR^{11}R^{12}$, —$NR^{11}C(O)$—$C_{1-6}$ alkyl, —$NR^{11}C(O)_2R^{12}$, —$NR^{11}$—$C(O)NR^{12}R^{13}$, —$OCO_2R^2$, —$NR^{11}$—$SO_2$—$C_{1-6}$ alkyl, —$C_{1-6}$ alkyl-$OR^{11}$, —$C_{1-6}$ alkyl-$NR^{11}R^{12}$, and —$C_{1-6}$ alkyl-$CO_2R^{11}$;

each $R^1$ is independently selected from the group consisting of aryl, a 3 to 7 membered cycloalkyl group, a 4 to 7 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, —O—$C_{1-6}$ alkyl, aryl, and heteroaryl, wherein the aryl, 3 to 7 membered cycloalkyl group, 4 to 7 membered heterocyclic group and heteroaryl are each optionally substituted with 1 to 5 substituents independently selected from the group consisting of halogen, —$NR^{14}R^{15}$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —OC(O)$NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$OCO_2R^{14}$ and —$NR^{14}SO_2$—$C_{1-6}$ alkyl;

each $R^2$, $R^3$, $R^4$, $R^5$, $R^6$, $R^7$, $R^8$, $R^9$, $R^{10}$, $R^{11}$, $R^{12}$, $R^{13}$, $R^a$, and $R^b$ is independently selected from the group consisting of H and $C_{1-6}$ alkyl;

wherein in —$CONR^2R^3$ and —$SO_2NR^2R^3$, $R^2$ and $R^3$ are optionally joined to form a 4 to 7 membered heterocyclic group optionally substituted with 1 to 5 substituents independently selected from the group consisting of —$NR^cR^d$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —OC(O)$NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$OCO_2R^{14}$, and —$NR^{14}SO_2$—$C_{1-6}$ alkyl, and each $R^c$, $R^d$, $R^{14}$, $R^{15}$, and $R^{16}$ is independently selected from the group consisting of H and $C_{1-6}$ alkyl.

6. The compound of claim 5, or a pharmaceutically acceptable salt thereof, wherein:
X is H or F;
Y is H or F;
A is a piperidine or a pyrrolidine having a double bond and optionally substituted with 1 to 6 substituents independently selected from the group consisting of $C_{1-6}$ alkyl, —$COR^1$, $SO_2R^1$, —$CO_2R^2$, —$CONR^2R^3$, $SO_2NR^2R^3$, a 3 to 7 membered cycloalkyl group, and a 4 to 7 membered heterocyclic group,
wherein the —$C_{1-6}$ alkyl is optionally substituted with 1 to 5 substituents independently selected from the group consisting of —$C_{1-6}$ alkyl, —$NR^2R^3$, —$CONR^2R^3$, —OH, —$SO_2NR^2R^3$, —$SO_2$—$C_{1-6}$ alkyl, —O—$C_{1-6}$ alkyl, —S—$C_{1-6}$ alkyl, —$NR^2C(O)$—$C_{1-6}$ alkyl, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —$C_{1-6}$ alkyl, and —OH, and wherein the aryl and heteroaryl are optionally substituted with 1 to 3 substituents independently selected from the group consisting of halogen, —CN, —$CO_2R^8$, —$CONR^8R^9$, OH, SH, $C_{1-6}$ alkyl, —O—$C_{1-6}$ alkyl, —S—$C_{1-6}$ alkyl, —$NR^8R^9$, —OC(O)$NR^8R^9$, —$NR^8C(O)$—$C_{1-6}$ alkyl, —$NR^8C(O)_2R^9$, —$NR^8$—$C(O)NR^9R^{10}$, —$OCO_2R^8$, —$C_{1-6}$ alkyl-$OR^8$, —$C_{1-6}$ alkyl-$NR^8R^9$, and —$C_{1-6}$ alkyl-$CO_2R^8$,
wherein A is optionally bridged with a 3 to 7 membered cycloalkyl group or a 4 to 7 membered heterocyclic group, wherein each 3 to 7 membered cycloalkyl group and each 4 to 7 membered heterocyclic group is optionally substituted with 1 to 5 substituents independently selected from the group consisting of —$C_{1-6}$ alkyl, oxo, and —OH;

each $R^1$ is independently selected from the group consisting of phenyl, a 4 to 6 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, and phenyl;

each $R^2$, $R^3$, $R^8$, $R^9$, $R^{10}$, $R^a$, and $R^b$ is independently selected from the group consisting of H and $C_{1-6}$ alkyl;

wherein in —$CONR^2R^3$ and —$SO_2NR^2R^3$, $R^2$ and $R^3$ are optionally joined to form a 4 to 7 membered heterocyclic group optionally substituted with $NR^cR^d$, and each $R^c$ and $R^d$ is independently selected from the group consisting of H and $C_{1-6}$ alkyl.

7. The compound of claim 5, or a pharmaceutically acceptable salt thereof, wherein A is selected from the group consisting of:

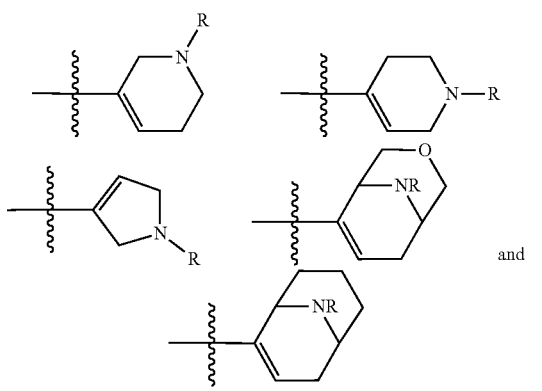

each of which is optionally substituted with 1 to 3 $R^x$ independently selected from the group consisting of —$CO_2R^y$, —$CONR^yR^z$, and —$C_{1-6}$ alkyl, wherein the —$C_{1-6}$ alkyl is optionally substituted with 1 to 5 substituents independently selected from the group consisting of —CN, —OH, —O—$C_{1-6}$ alkyl, —$CO_2R^y$, and —$CONR^yR^z$;

R is selected from the group consisting of H, —$C_{1-6}$ alkyl, —$COR^1$, —$SO_2R^1$, —$CO_2R^2$, —$CONR^2R^3$, —$SO_2NR^2R^3$, a 3 to 7 membered cycloalkyl group, and a 4 to 7 membered heterocyclic group, wherein the $C_{1-6}$ alkyl is optionally substituted with 1 to 5 substituents independently selected from the group consisting of —$C_{1-6}$ alkyl, —$NR^2R^3$, —CN, —$CO_2R^2$, —$CONR^2R^3$, OH, —$SO_2NR^2R^3$, $SO_2$—$C_{1-6}$ alkyl, SH, —O—$C_{1-6}$ alkyl, —S—$C_{1-6}$ alkyl, —OC(O)$NR^2R^3$, —$NR^2C(O)$—$C_{1-6}$ alkyl, —$NR^2C(O)_2R^3$, —$NR^2$—$C(O)NR^3R^4$, —$OCO_2R^2$, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —$C_{1-6}$ alkyl, —CN, —$CO_2R^5$, —$CONR^5R^6$, —OH, —SH, —O—$C_{1-6}$ alkyl, —S—$C_{1-6}$ alkyl, —$NR^5R^6$, —OC(O)$NR^5R^6$, —$NR^5C(O)$—$C_{1-6}$ alkyl, —$NR^5C(O)_2R^6$, —$NR^5$—$C(O)NR^6R^7$, —$OCO_2R^5$, —$C_{1-6}$ alkyl-$OR^5$, —$C_{1-6}$ alkyl-$NR^5R^6$, and —$C_{1-6}$ alkyl-$CO_2R^5$, and wherein the aryl and heteroaryl are optionally substituted with 1 to 5 substituents independently selected from the group consisting of halogen, —CN, —$CO_2R^8$, —$CONR^8R^9$, —OH, —SH, —$C_{1-6}$ alkyl, —O—$C_{1-6}$ alkyl, —S—$C_{1-6}$ alkyl, —$NR^8R^9$, —OC(O)$NR^8R^9$, —$NR^8C(O)$—$C_{1-6}$alkyl, —$NR^8C(O)_2R^9$, —$NR^8$—$C(O)NR^9R^{10}$, —$OCO_2R^8$, —$C_{1-6}$ alkyl-$OR^8$, —$C_{1-6}$ alkyl-$NR^8R^9$, and —$C_{1-6}$ alkyl-$CO_2R^8$, wherein each 3 to 7 membered cycloalkyl group and each 4 to 7 membered heterocyclic group is optionally substituted with 1 to 5 substituents independently selected from the group consisting of a spiro 3 to 7 membered cycloalkyl group, a spiro 4 to 7 membered heterocyclic group, a 3 to 7 membered cycloalkyl group, a 4 to 7 membered heterocyclic group, —$C_{1-6}$ alkyl, oxo, —CN, —$CO_2R^{11}$, —$CONR^{11}R^{12}$, —OH, —SH, —O—$C_{1-6}$ alkyl, —S—$C_{1-6}$ alkyl, —$NR^{11}R^{12}$, —OC(O)$NR^{11}R^{12}$, —$NR^{11}C(O)$—$C_{1-6}$ alkyl, —$NR^{11}C(O)_2R^{12}$, —$NR^{11}$—$C(O)NR^{12}R^{13}$, —$OCO_2R^{11}$, —$NR^{11}$—$SO_2$—$C_{1-6}$ alkyl, —$C_{1-6}$ alkyl-$OR^{11}$, —$C_{1-6}$ alkyl-$NR^{11}R^{12}$, and —$C_{1-6}$ alkyl-$CO_2R^{11}$;

each $R^1$ is independently selected from the group consisting of aryl, a 3 to 7 membered cycloalkyl group, a 4 to 7 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, —O—$C_{1-6}$ alkyl, aryl, and heteroaryl, wherein the aryl, 3 to 7 membered cycloalkyl group, 4 to 7 membered heterocyclic group and heteroaryl are each optionally substituted with 1 to 5 substituents independently selected from the group consisting of —$NR^{14}R^{15}$, —OH, —$C_{1-6}$ alkyl, —CN, —$CO_2R^{14}$, —$CONR^{14}R^{15}$, —$SO_2NR^{14}R^{15}$, —$SO_2$—$C_{1-6}$ alkyl, —SH, —O—$C_{1-6}$ alkyl, —S—$C_{1-6}$ alkyl, —OC(O)$NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$OCO_2R^{14}$, and —$NR^{14}SO_2$—$C_{1-6}$ alkyl;

each $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^a$, $R^b$, $R^c$, $R^d$, $R^y$, and $R^z$ is independently selected from the group consisting of H and $C_{1-6}$ alkyl; and wherein in —$CONR^yR^z$, $R^y$ and $R^z$ are optionally joined to form a 4 to 7 membered heterocyclic group optionally substituted with 1 to 5 substituents independently selected from the group consisting of $NR^cR^d$, OH, —$C_{1-6}$ alkyl, CN, —$CO_2R^{14}$, —$CONR^{14}R^{15}$, —$SO_2NR^{14}R^{15}$, $SO_2$—$C_{1-6}$ alkyl, SH, —O—$C_{1-6}$ alkyl, —S—$C_{1-6}$ alkyl, —OC(O)$NR^{14}R^{15}$, —$NR^{14}C(O)$—$C_{1-6}$ alkyl, —$NR^{14}C(O)_2R^{15}$, —$NR^{14}$—$C(O)NR^{15}R^{16}$, —$CO_2R^{14}$, and —$NR^{14}SO_2$—$C_{1-6}$ alkyl.

8. The compound of claim 7, or a pharmaceutically acceptable salt thereof, wherein A is selected from the group consisting of:

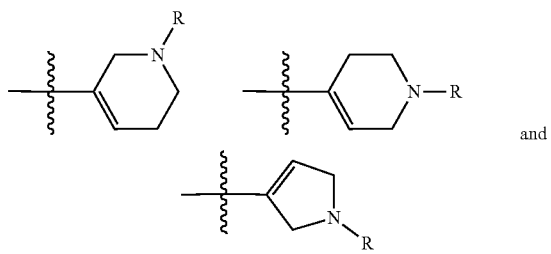

each of which is optionally substituted with 1 to 3 $R^x$ wherein each $R^x$ is independently —$C_{1-3}$ alkyl optionally substituted with —OH, —$OC_{1-3}$ alkyl, —CN, —$CO_2$—$C_{1-3}$ alkyl, and —$CONR^yR^z$ wherein $R^y$ and $R^z$ are each independently selected from $C_{1-3}$ alkyl and wherein $R^y$ and $R^z$ are optionally joined to form a 4 to 6 membered heterocyclic group optionally substituted with $NR^cR^d$, wherein $R^c$ and $R^d$ are each independently selected from the group consisting of H and $C_{1-3}$ alkyl.

9. The compound of claim 8, or a pharmaceutically acceptable salt thereof, wherein each $R^x$ is independently selected from the group consisting of Me, —$CH_2OH$, —$CH_2OMe$, —$CH_2CN$, —$CH_2CONMe_2$, —$CH_2CO_2Me$, —$CO_2Me$, and

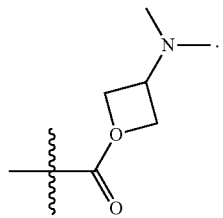

10. The compound of claim 7, or a pharmaceutically acceptable salt thereof, wherein R is selected from the group consisting of H, —$C_{1-6}$ alkyl, —$COR^1$, —$SO_2R^1$, —$CO_2R^2$, —$CONR^2R^3$, —$SO_2NR^2R^3$, a 3 to 7 membered cycloalkyl group, and a 4 to 7 membered heterocyclic group,
wherein the —$C_{1-6}$ alkyl is optionally substituted with 1 to 5 substituents independently selected from the group consisting of —$C_{1-6}$ alkyl, —$NR^2R^3$, —$CONR^2R^3$, —OH, —$SO_2NR^2R^3$, —$SO_2$—$C_{1-6}$ alkyl, —O—$C_{1-6}$ alkyl, —S—$C_{1-6}$ alkyl, —$NR^2C(O)$—$C_{1-6}$ alkyl, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —$C_{1-6}$ alkyl, and —OH, and wherein the aryl and heteroaryl are optionally substituted with 1 to 5 substituents independently selected from the group consisting of halogen, —CN, —$CO_2R^8$, —$CONR^8R^9$, OH, SH, $C_{1-6}$ alkyl, —O—$C_{1-6}$ alkyl, —S—$C_{1-6}$ alkyl, —$NR^8R^9$, —$OC(O)NR^8R^9$, —$NR^8C(O)$—$C_{1-6}$ alkyl, —$NR^8C(O)_2$—$C_{1-6}$ alkyl, —$NR^8$—$C(O)NR^9R^{10}$, —$OCO_2R^8$, —$C_{1-6}$ alkyl-$OR^8$, —$C_{1-6}$ alkyl-$NR^8R^9$, and —$C_{1-6}$ alkyl-$CO_2R^8$,
wherein each 3 to 7 membered cycloalkyl group and each 4 to 7 membered heterocyclic group is optionally substituted with 1 to 5 substituents independently selected from the group consisting of —$C_{1-6}$ alkyl, oxo, and —OH;
each $R^1$ is independently selected from the group consisting of aryl, a 4 to 7 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, and aryl; and
each $R^2$, $R^3$, $R^8$, $R^9$, $R^{10}$, $R^a$, and $R^b$ is independently selected from the group consisting of H and $C_{1-6}$ alkyl.

11. The compound of claim 10, or a pharmaceutically acceptable salt thereof, wherein R is selected from the group consisting of H, —$C_{1-6}$ alkyl, —$COR^1$, —$SO_2R^1$, —$CO_2R^2$, —$CONR^2R^3$, —$SO_2NR^2R^3$, a 4 to 6 membered cycloalkyl group, and a 4 to 6 membered heterocyclic group,
wherein the —$C_{1-6}$ alkyl is optionally substituted with 1 to 5 substituents independently selected from the group consisting of —$NR^2R^3$, —$CONR^2R^3$, —OH, —$SO_2NR^2R^3$, —$SO_2$—$C_{1-6}$ alkyl, —O—$C_{1-6}$ alkyl, —S—$C_{1-6}$ alkyl, —$NR^2C(O)$—$C_{1-6}$ alkyl, —$NR^2SO_2$—$C_{1-6}$ alkyl, phenyl, a 5 membered heteroaryl, a 4 to 6 membered cycloalkyl group, and a 4 to 6 membered heterocyclic group, wherein the 4 to 6 membered cycloalkyl group and the 4 to 6 membered heterocyclic group are optionally substituted with 1 to 5 substituents independently selected from the group consisting of oxo, and —OH,
wherein the 4 to 6 membered cycloalkyl group and the 4 to 6 membered heterocyclic group are optionally substituted with 1 to 5 substituents independently selected from the group consisting of —$C_{1-6}$ alkyl, oxo, and —OH;
each $R^1$ is independently selected from the group consisting of phenyl, a 4 to 6 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, and phenyl; and
each $R^2$, $R^3$, $R^a$, and $R^b$ is independently selected from the group consisting of H and $C_{1-6}$ alkyl.

12. The compound of claim 7, or a pharmaceutically acceptable salt thereof, wherein Y is H, A is selected from the group consisting of:

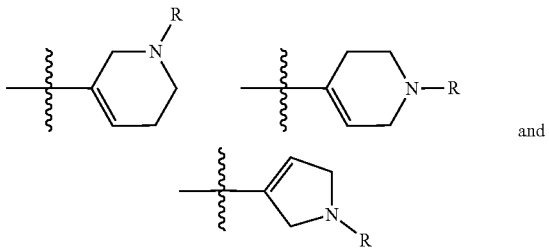

each of which is optionally substituted with 1 to 3 $R^x$ wherein each $R^x$ is independently —$C_{1-3}$ alkyl optionally substituted with —OH, —$OC_{1-3}$ alkyl, —CN, —$CO_2$—$C_{1-3}$ alkyl, and —$CONR^yR^z$ wherein $R^y$ and $R^z$ are each independently selected from $C_{1-3}$ alkyl and wherein $R^y$ and $R^z$ are optionally joined to form a 4 to 6 membered heterocyclic group optionally substituted with $NR^cR^d$, wherein $R^c$ and $R^d$ are each independently selected from the group consisting of H and $C_{1-3}$ alkyl;
R is selected from the group consisting of H, —$C_{1-6}$ alkyl, —$COR^1$, —$SO_2R^1$, —$CO_2R^2$, —$CONR^2R^3$, —$SO_2NR^2R^3$, a 3 to 7 membered cycloalkyl group, and a 4 to 7 membered heterocyclic group,
wherein the —$C_{1-6}$ alkyl is optionally substituted with 1 to 5 substituents independently selected from the group consisting of —$C_{1-6}$ alkyl, —$NR^2R^3$, —$CONR^2R^3$, —OH, —$SO_2NR^2R^3$, —$SO_2$—$C_{1-6}$ alkyl, —O—$C_{1-6}$ alkyl, —S—$C_{1-6}$ alkyl, —$NR^2C(O)$—$C_{1-6}$ alkyl, —$NR^2SO_2$—$C_{1-6}$ alkyl, aryl, heteroaryl, a 3 to 7 membered cycloalkyl group, and a 4 to 7 membered heterocyclic group, wherein the 3 to 7 membered cycloalkyl group and the 4 to 7 membered heterocyclic group are optionally substituted with 1 to 5 substituents independently selected from the group consisting of oxo, —$C_{1-6}$ alkyl, and —OH, and wherein the aryl and heteroaryl are optionally substituted with 1 to 5 substituents independently selected from the group consisting of halogen, —CN, —$CO_2R^8$, —$CONR^8R^9$, OH, SH, $C_{1-6}$ alkyl, —O—$C_{1-6}$ alkyl, —S—$C_{1-6}$ alkyl, —$NR^8R^9$, —$OC(O)NR^8R^9$, —$NR^8C(O)$—$C_{1-6}$ alkyl, —$NR^8C(O)_2$—$C_{1-6}$ alkyl, —$NR^8$—$C(O)NR^9R^{10}$, —$OCO_2R^8$, —$C_{1-6}$ alkyl-$OR^8$, —$C_{1-6}$ alkyl-$NR^8R^9$, and —$C_{1-6}$ alkyl-$CO_2R^8$, wherein the 3 to 7 membered cycloalkyl group and the 4 to 7 membered heterocyclic group are optionally substituted with 1 to 5 substituents independently selected from the group consisting of —$C_{1-6}$ alkyl, oxo, and —OH;

each $R^1$ is independently selected from the group consisting of aryl, a 4 to 7 membered heterocyclic group, and —$C_{1-6}$ alkyl wherein the —$C_{1-6}$ alkyl is optionally substituted with 1 to 5 substituents independently selected from the group consisting of —$NR^aR^b$, —OH, and aryl; and each $R^2$, $R^3$, $R^8$, $R^9$, $R^{10}$, $R^a$, and $R^b$ is independently selected from the group consisting of H and $C_{1-6}$ alkyl.

13. The compound of claim 7, or a pharmaceutically acceptable salt thereof, wherein Y is H, A is selected from the group consisting of:

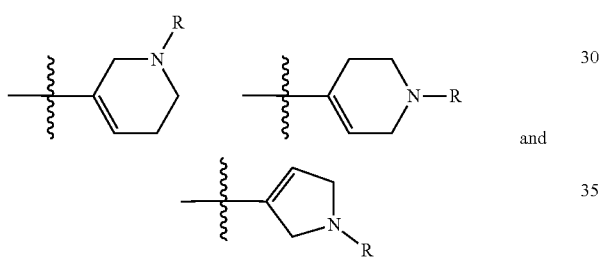

and

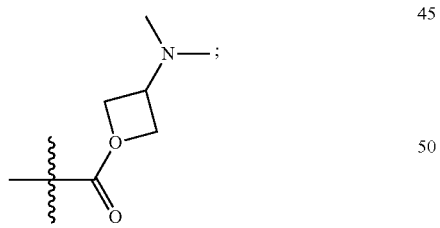

each of which is optionally substituted with 1 to 3 $R^x$ independently selected from the group consisting of Me, —$CH_2OH$, —$CH_2OMe$, —$CH_2CN$, —$CH_2CONMe_2$, —$CH_2CO_2Me$, —$CO_2Me$ and R is selected from the group consisting of H, —$C_{1-6}$ alkyl, —$COR^1$, —$SO_2R^1$, —$CO_2R^2$, —$CONR^2R^3$, —$SO_2NR^2R^3$, a 4 to 6 membered cycloalkyl group, and a 4 to 6 membered heterocyclic group, wherein the —$C_{1-6}$ alkyl is optionally substituted with 1 to 5 substituents independently selected from the group consisting of —$NR^2R^3$, —$CONR^2R^3$, —OH, —$SO_2NR^2R^3$, —$SO_2$—$C_{1-6}$ alkyl, —O—$C_{1-6}$ alkyl, —S—$C_{1-6}$ alkyl, —$NR^2C(O)$—$C_{1-6}$ alkyl, —$NR^2SO_2$—$C_{1-6}$ alkyl, phenyl, a 5 membered heteroaryl, a 4 to 6 membered cycloalkyl group, and a 4 to 6 membered heterocyclic group, wherein the 4 to 6 membered cycloalkyl group and the 4 to 6 membered heterocyclic group are optionally substituted with 1 to 5 substituents independently selected from the group consisting of oxo, and —OH, wherein the 4 to 6 membered cycloalkyl group and the 4 to 6 membered heterocyclic group are optionally substituted with 1 to 5 substituents independently selected from the group consisting of —$C_{1-6}$ alkyl, oxo, and —OH;

each $R^1$ is independently selected from the group consisting of phenyl, a 4 to 6 membered heterocyclic group, and —$C_{1-6}$alkyl wherein the —$C_{1-6}$alkyl is optionally substituted with 1 to 5 substituents independently selected from the group consisting of —$NR^aR^b$, —OH, and phenyl; and each $R^2$, $R^3$, $R^a$, and $R^b$ is independently selected from the group consisting of H and $C_{1-6}$ alkyl.

14. The compound of claim 1, which is:

a compound of formula 1:

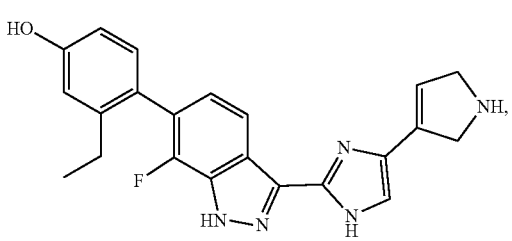

a compound of formula 2:

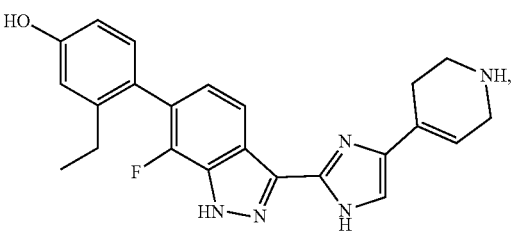

a compound of formula 3:

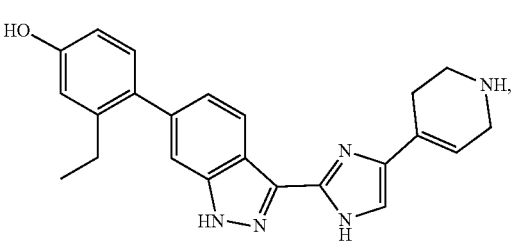

or a pharmaceutically acceptable salt thereof.

15. A compound selected from:
| Structure |
|---|
| 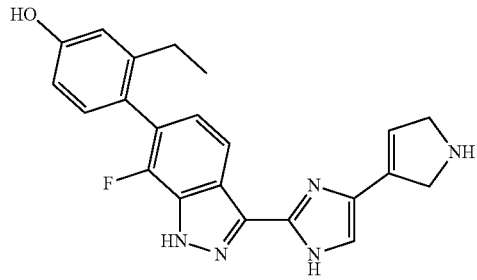 [SMILES: CCc1cc(O)ccc1-c1ccc2c(-c3nc(C4=CCNC4)c[nH]3)n[nH]c2c1F] |
| 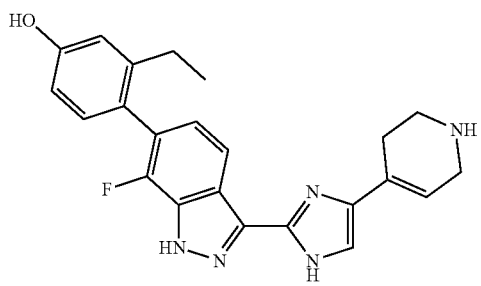 [SMILES: CCc1cc(O)ccc1-c1ccc2c(-c3nc(C4=CCNCC4)c[nH]3)n[nH]c2c1F] |
| 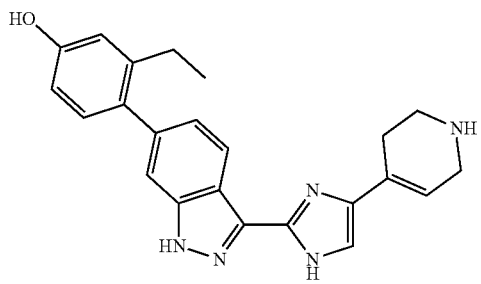 [SMILES: CCc1cc(O)ccc1-c1ccc2c(-c3nc(C4=CCNCC4)c[nH]3)n[nH]c2c1] |
| 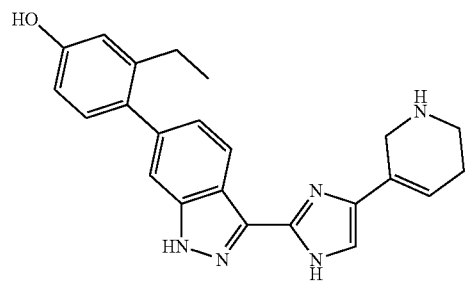 [SMILES: CCc1cc(O)ccc1-c1ccc2c(-c3nc(C4=CCCNC4)c[nH]3)n[nH]c2c1] |
| 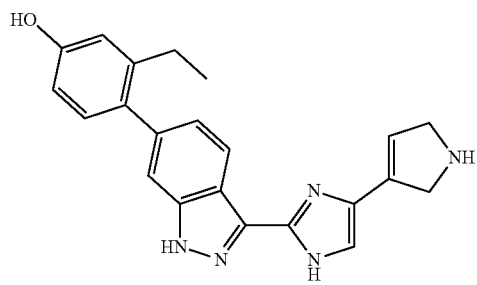 [SMILES: CCc1cc(O)ccc1-c1ccc2c(-c3nc(C4=CCNC4)c[nH]3)n[nH]c2c1] |

| Structure |
|---|
| 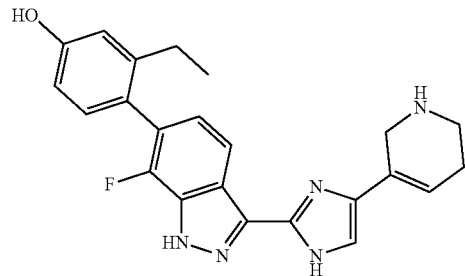 [SMILES: CCc1cc(O)ccc1-c1ccc2c(-c3nc(C4=CCCNC4)c[nH]3)n[nH]c2c1F] |
| 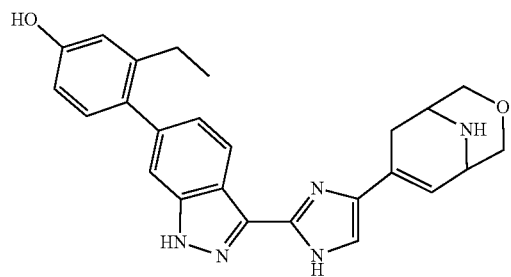 [SMILES: CCc1cc(O)ccc1-c1ccc2c(-c3nc(C4=CC5COCC(C4)N5)c[nH]3)n[nH]c2c1] |
| 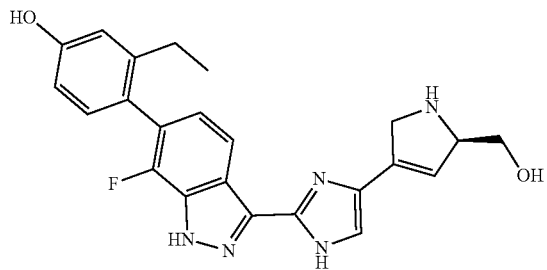 [SMILES: CCc1cc(O)ccc1-c1ccc2c(-c3nc(C4=C[C@H](CO)NC4)c[nH]3)n[nH]c2c1F] |
| 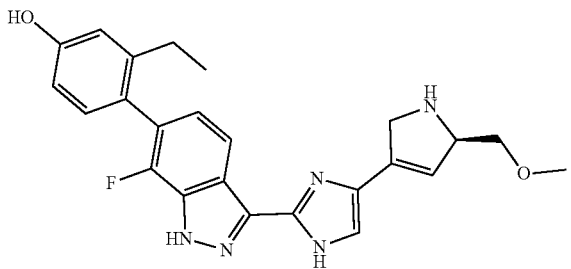 [SMILES: CCc1cc(O)ccc1-c1ccc2c(-c3nc(C4=C[C@H](COC)NC4)c[nH]3)n[nH]c2c1F] |
| 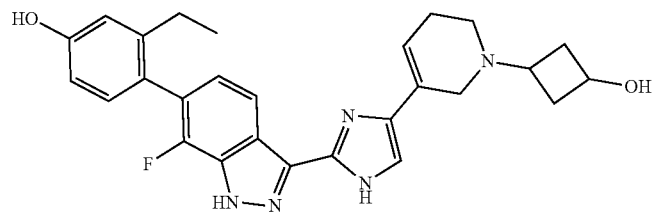 [SMILES: CCc1cc(O)ccc1-c1ccc2c(-c3nc(C4=CCCN(C5CC(O)C5)C4)c[nH]3)n[nH]c2c1F] |

-continued
| Structure |
|---|
| 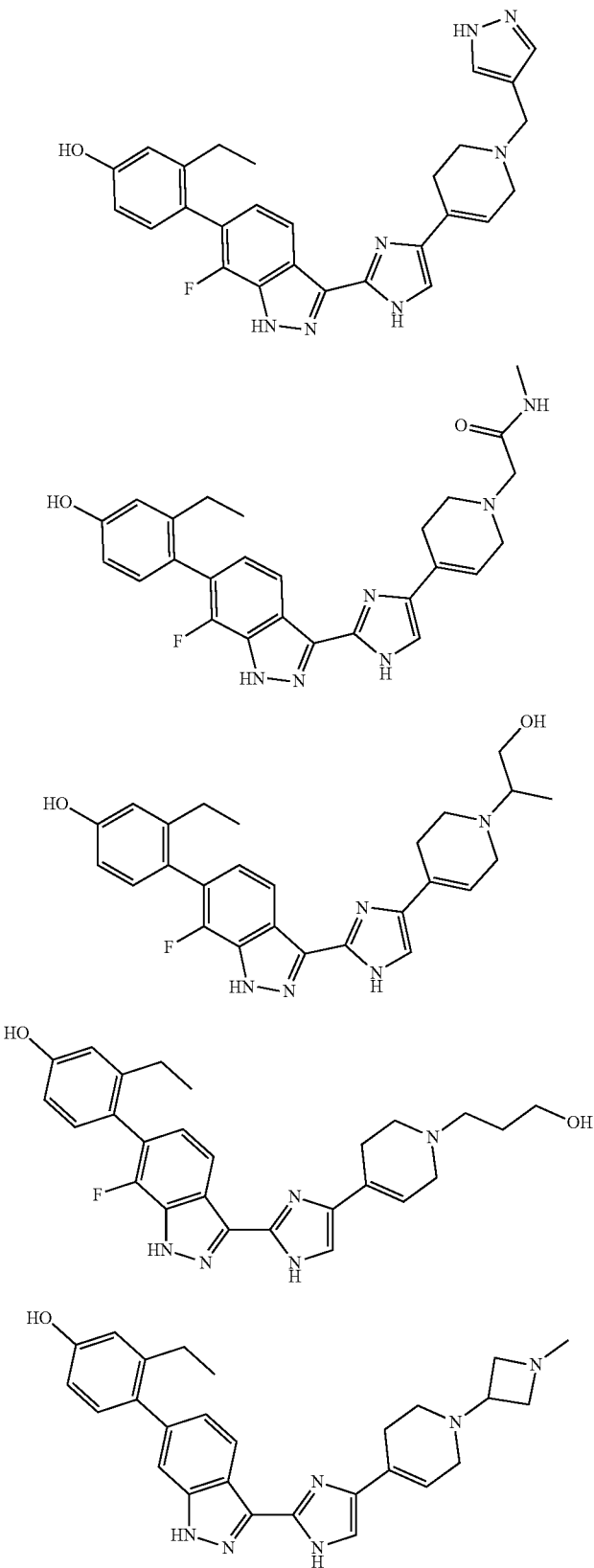 |

-continued
Structure
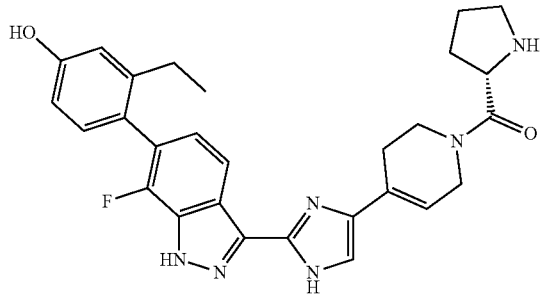 [SMILES: CCc1cc(O)ccc1-c1ccc2c(-c3nc(C4=CCN(C(=O)[C@@H]5CCCN5)CC4)c[nH]3)n[nH]c2c1F]
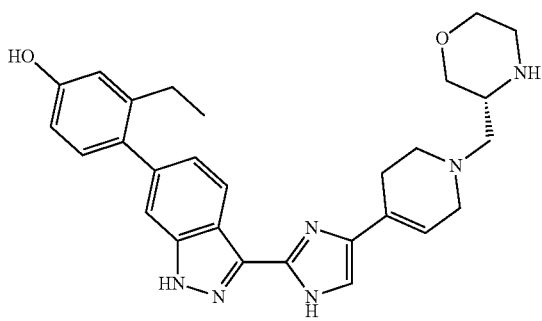 [SMILES: CCc1cc(O)ccc1-c1ccc2c(-c3nc(C4=CCN(C[C@@H]5COCCN5)CC4)c[nH]3)n[nH]c2c1]
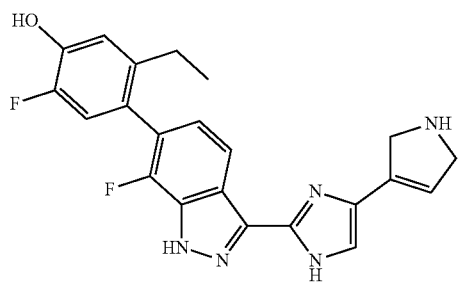 [SMILES: CCc1cc(O)c(F)cc1-c1ccc2c(-c3nc(C4=CCNC4)c[nH]3)n[nH]c2c1F]
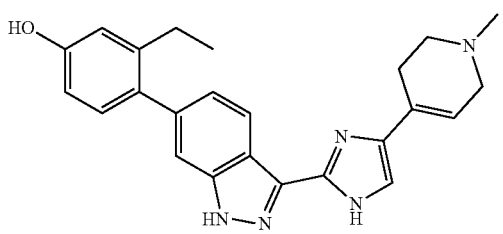 [SMILES: CCc1cc(O)ccc1-c1ccc2c(-c3nc(C4=CCN(C)CC4)c[nH]3)n[nH]c2c1]
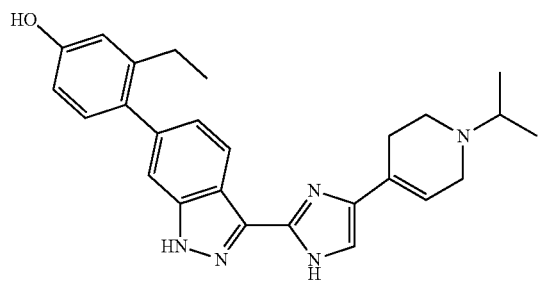 [SMILES: CCc1cc(O)ccc1-c1ccc2c(-c3nc(C4=CCN(C(C)C)CC4)c[nH]3)n[nH]c2c1]

| Structure |
|---|
| 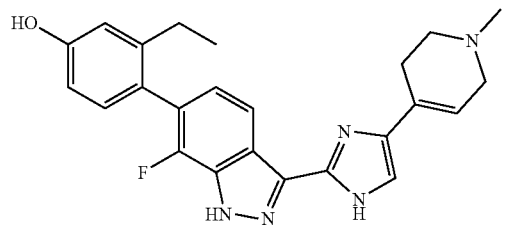 [SMILES: CCc1cc(O)ccc1-c1ccc2c(-c3nc(C4=CCN(C)CC4)c[nH]3)n[nH]c2c1F] |
| 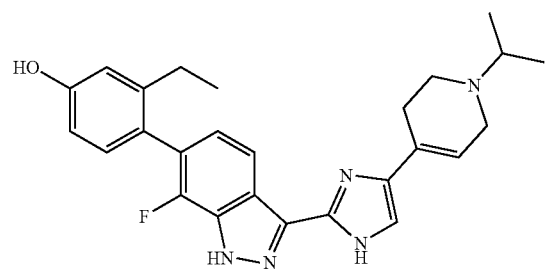 [SMILES: CCc1cc(O)ccc1-c1ccc2c(-c3nc(C4=CCN(C(C)C)CC4)c[nH]3)n[nH]c2c1F] |
| 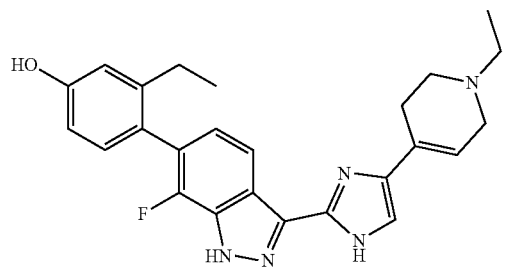 [SMILES: CCc1cc(O)ccc1-c1ccc2c(-c3nc(C4=CCN(CC)CC4)c[nH]3)n[nH]c2c1F] |
| 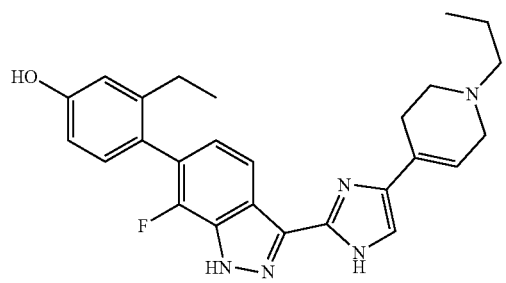 [SMILES: CCCN1CC=C(c2c[nH]c(-c3n[nH]c4c(F)c(-c5ccc(O)cc5CC)ccc34)n2)CC1] |
| 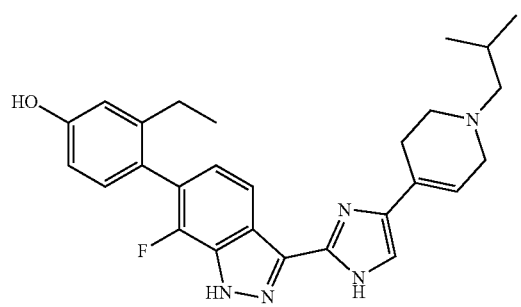 [SMILES: CCc1cc(O)ccc1-c1ccc2c(-c3nc(C4=CCN(CC(C)C)CC4)c[nH]3)n[nH]c2c1F] |

| Structure |
|---|
| 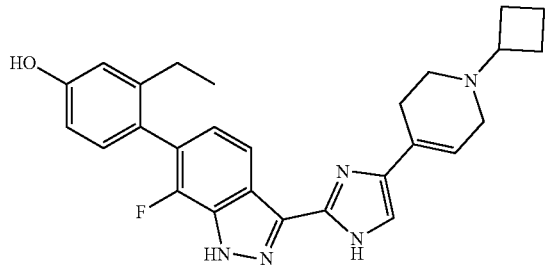 [SMILES: CCc1cc(O)ccc1-c1ccc2c(-c3nc(C4=CCN(C5CCC5)CC4)c[nH]3)n[nH]c2c1F] |
| 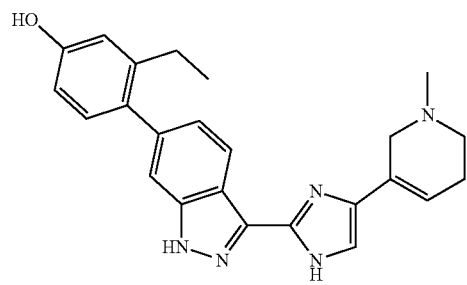 [SMILES: CCc1cc(O)ccc1-c1ccc2c(-c3nc(C4=CCCN(C)C4)c[nH]3)n[nH]c2c1] |
| 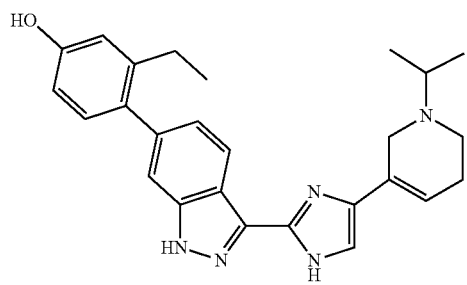 [SMILES: CCc1cc(O)ccc1-c1ccc2c(-c3nc(C4=CCCN(C(C)C)C4)c[nH]3)n[nH]c2c1] |
| 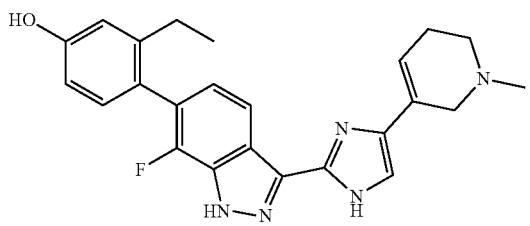 [SMILES: CCc1cc(O)ccc1-c1ccc2c(-c3nc(C4=CCCN(C)C4)c[nH]3)n[nH]c2c1F] |
| 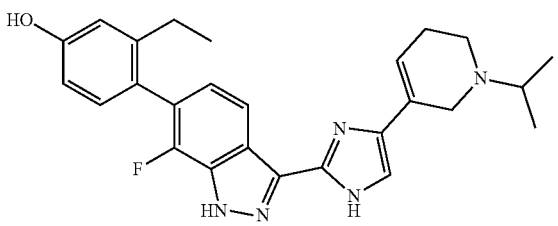 |
| 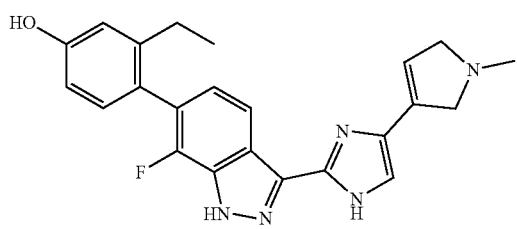 |

| Structure |
|---|
| 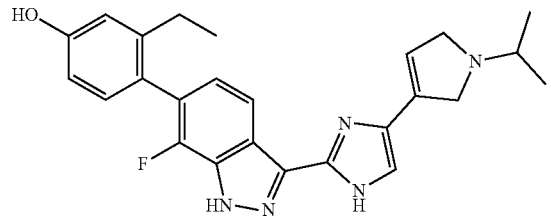 [SMILES: CCc1cc(O)ccc1-c1ccc2c(-c3nc(C4=CCN(C(C)C)C4)c[nH]3)n[nH]c2c1F] |
| 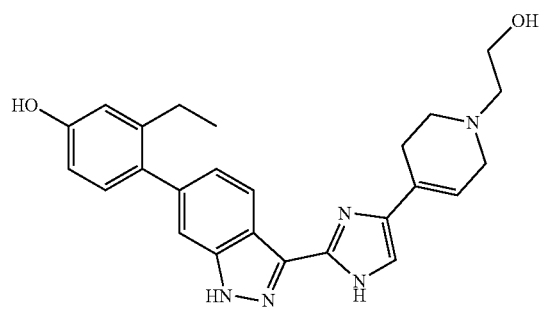 [SMILES: CCc1cc(O)ccc1-c1ccc2c(-c3nc(C4=CCN(CCO)CC4)c[nH]3)n[nH]c2c1] |
| 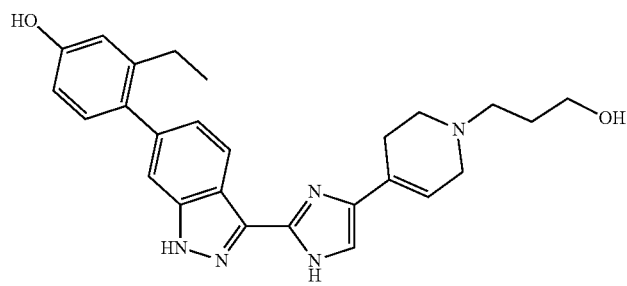 [SMILES: CCc1cc(O)ccc1-c1ccc2c(-c3nc(C4=CCN(CCCO)CC4)c[nH]3)n[nH]c2c1] |
| 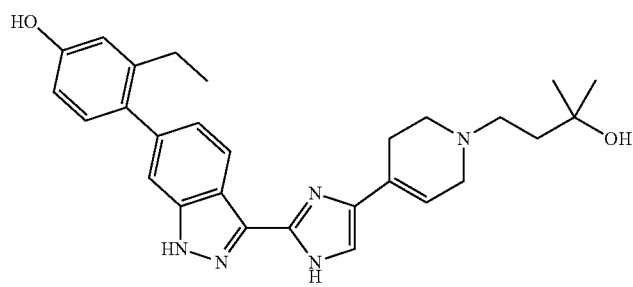 [SMILES: CCc1cc(O)ccc1-c1ccc2c(-c3nc(C4=CCN(CCC(C)(C)O)CC4)c[nH]3)n[nH]c2c1] |
| 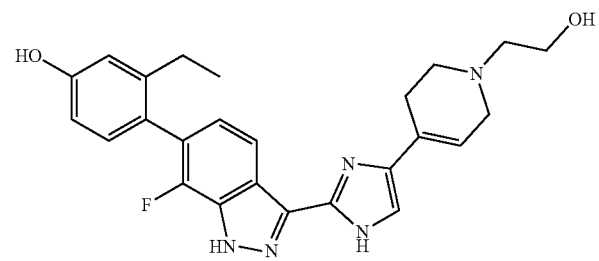 [SMILES: CCc1cc(O)ccc1-c1ccc2c(-c3nc(C4=CCN(CCO)CC4)c[nH]3)n[nH]c2c1F] |

| Structure |
|---|
| 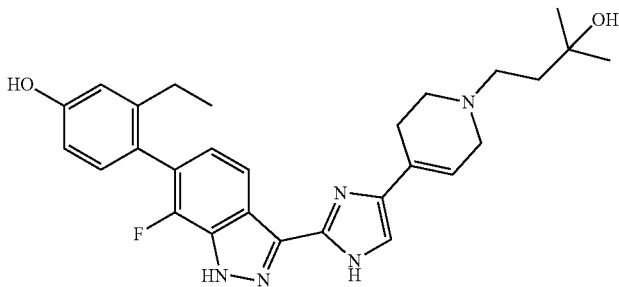 [SMILES: CCc1cc(O)ccc1-c1ccc2c(-c3nc(C4=CCN(CCC(C)(C)O)CC4)c[nH]3)n[nH]c2c1F] |
| 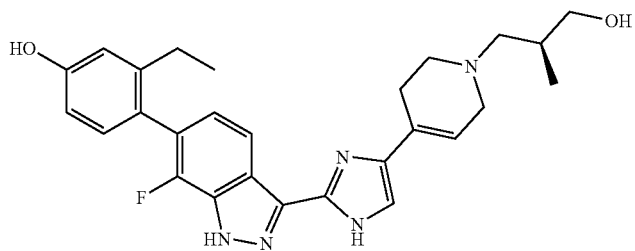 [SMILES: CCc1cc(O)ccc1-c1ccc2c(-c3nc(C4=CCN(C[C@H](C)CO)CC4)c[nH]3)n[nH]c2c1F] |
| 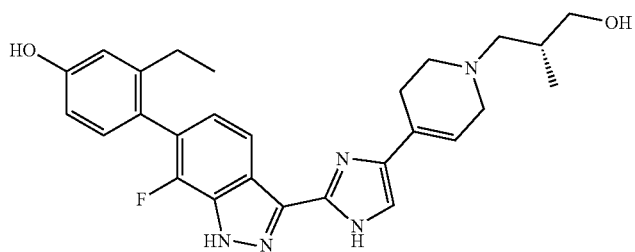 [SMILES: CCc1cc(O)ccc1-c1ccc2c(-c3nc(C4=CCN(C[C@@H](C)CO)CC4)c[nH]3)n[nH]c2c1F] |
| 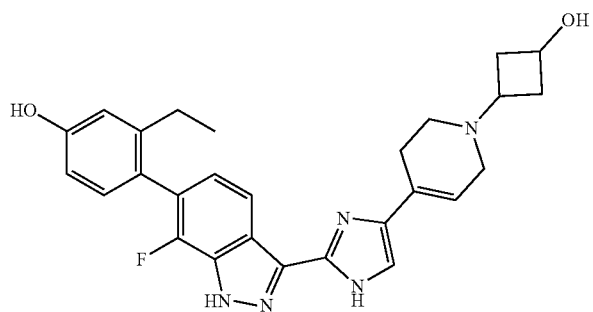 |
| 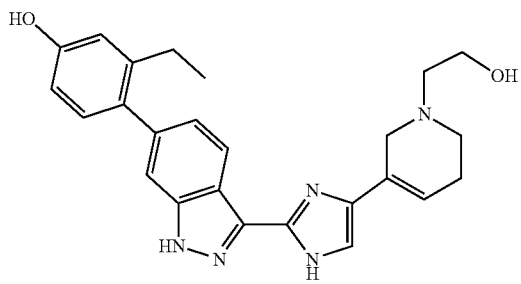 [SMILES: CCc1cc(O)ccc1-c1ccc2c(-c3nc(C4=CCCN(CCO)C4)c[nH]3)n[nH]c2c1] |

-continued
Structure
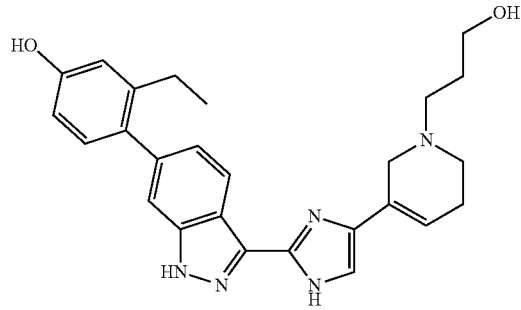 [SMILES: CCc1cc(O)ccc1-c1ccc2c(-c3nc(C4=CCCN(CCCO)C4)c[nH]3)n[nH]c2c1]
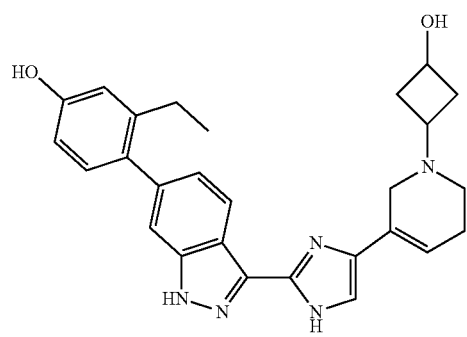 [SMILES: CCc1cc(O)ccc1-c1ccc2c(-c3nc(C4=CCCN(C5CC(O)C5)C4)c[nH]3)n[nH]c2c1]
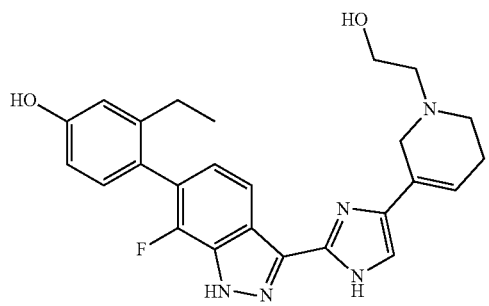 [SMILES: CCc1cc(O)ccc1-c1ccc2c(-c3nc(C4=CCCN(CCO)C4)c[nH]3)n[nH]c2c1F]
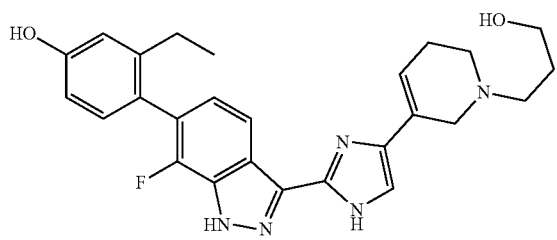 [SMILES: CCc1cc(O)ccc1-c1ccc2c(-c3nc(C4=CCCN(CCCO)C4)c[nH]3)n[nH]c2c1F]
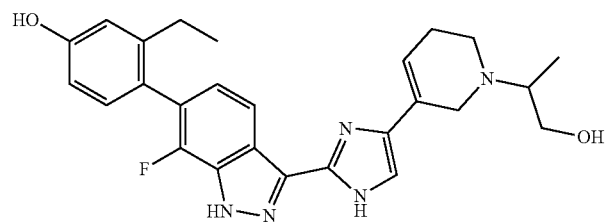 [SMILES: CCc1cc(O)ccc1-c1ccc2c(-c3nc(C4=CCCN(C(C)CO)C4)c[nH]3)n[nH]c2c1F]

| Structure |
|---|
| 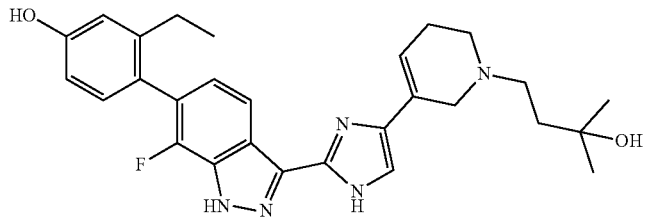 [SMILES: CCc1cc(O)ccc1-c1ccc2c(-c3nc(C4=CCCN(CCC(C)(C)O)C4)c[nH]3)n[nH]c2c1F] |
| 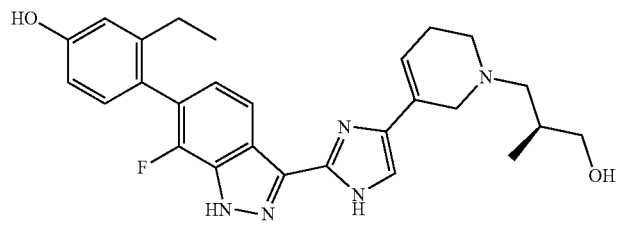 [SMILES: CCc1cc(O)ccc1-c1ccc2c(-c3nc(C4=CCCN(C[C@H](C)CO)C4)c[nH]3)n[nH]c2c1F] |
| 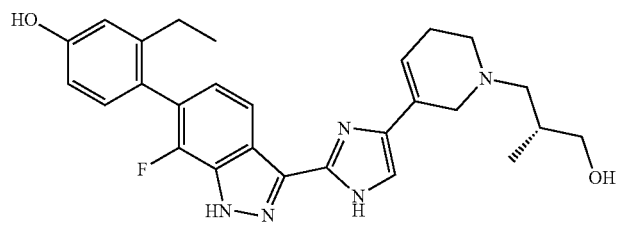 [SMILES: CCc1cc(O)ccc1-c1ccc2c(-c3nc(C4=CCCN(C[C@@H](C)CO)C4)c[nH]3)n[nH]c2c1F] |
| 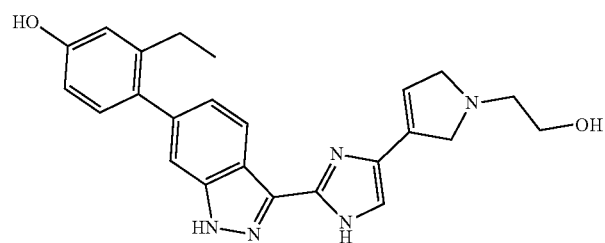 [SMILES: CCc1cc(O)ccc1-c1ccc2c(-c3nc(C4=CCN(CCO)C4)c[nH]3)n[nH]c2c1] |
| 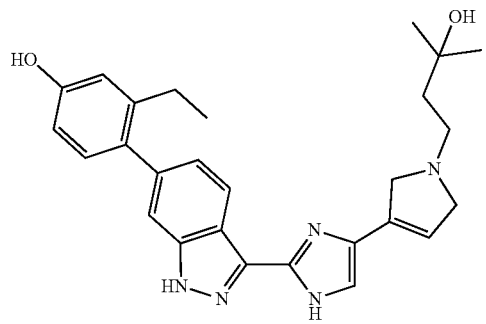 [SMILES: CCc1cc(O)ccc1-c1ccc2c(-c3nc(C4=CCN(CCC(C)(C)O)C4)c[nH]3)n[nH]c2c1] |
| 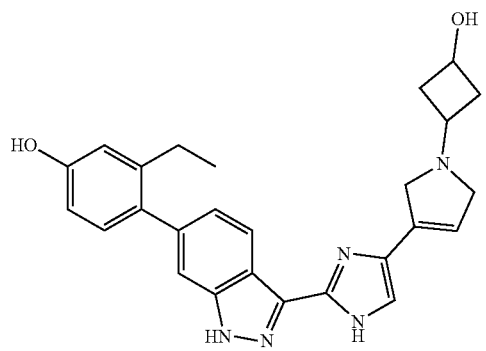 [SMILES: CCc1cc(O)ccc1-c1ccc2c(-c3nc(C4=CCN(C5CC(O)C5)C4)c[nH]3)n[nH]c2c1] |

-continued
Structure
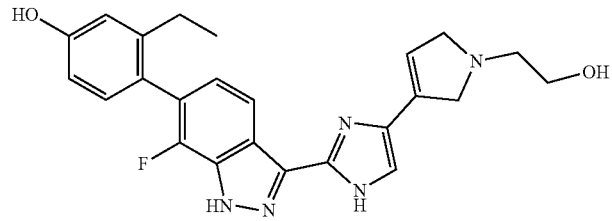 [SMILES: CCc1cc(O)ccc1-c1ccc2c(-c3nc(C4=CCN(CCO)C4)c[nH]3)n[nH]c2c1F]
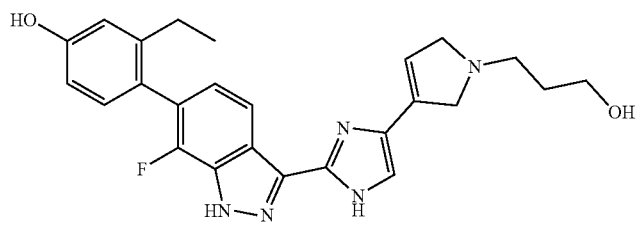 [SMILES: CCc1cc(O)ccc1-c1ccc2c(-c3nc(C4=CCN(CCCO)C4)c[nH]3)n[nH]c2c1F]
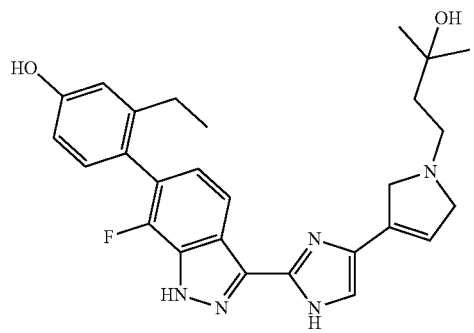 [SMILES: CCc1cc(O)ccc1-c1ccc2c(-c3nc(C4=CCN(CCC(C)(C)O)C4)c[nH]3)n[nH]c2c1F]
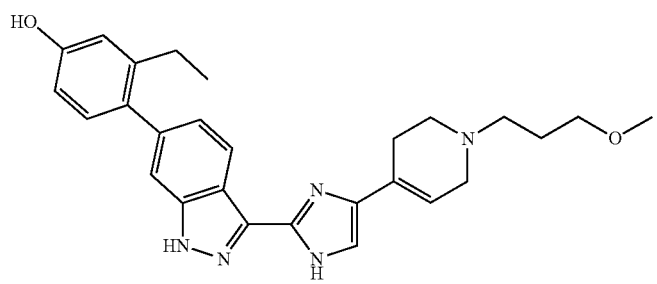 [SMILES: CCc1cc(O)ccc1-c1ccc2c(-c3nc(C4=CCN(CCCOC)CC4)c[nH]3)n[nH]c2c1]
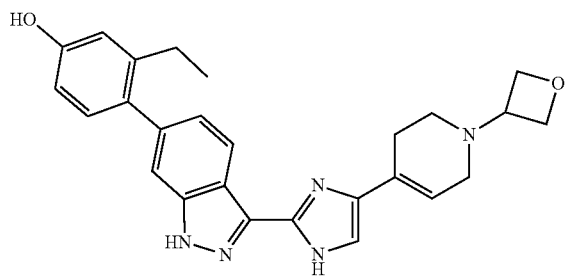 [SMILES: CCc1cc(O)ccc1-c1ccc2c(-c3nc(C4=CCN(C5COC5)CC4)c[nH]3)n[nH]c2c1]

-continued
Structure
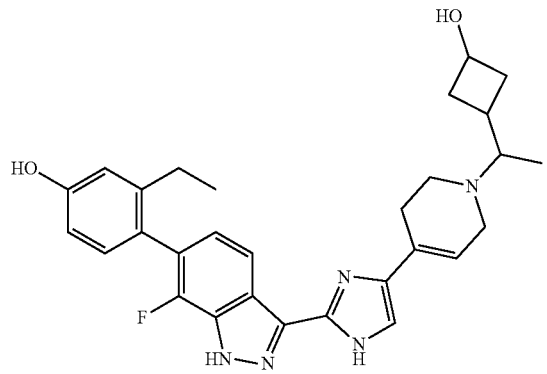 [SMILES: CCc1cc(O)ccc1-c1ccc2c(-c3nc(C4=CCN(C(C)C5CC(O)C5)CC4)c[nH]3)n[nH]c2c1F]
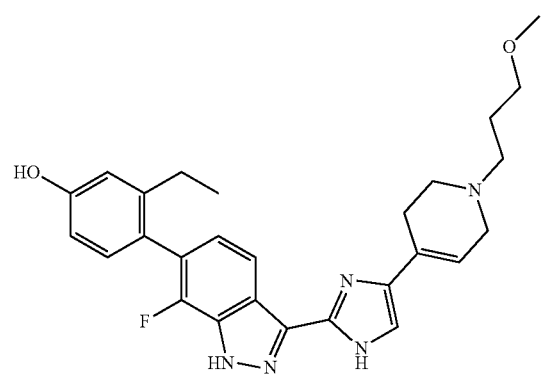 [SMILES: CCc1cc(O)ccc1-c1ccc2c(-c3nc(C4=CCN(CCCOC)CC4)c[nH]3)n[nH]c2c1F]
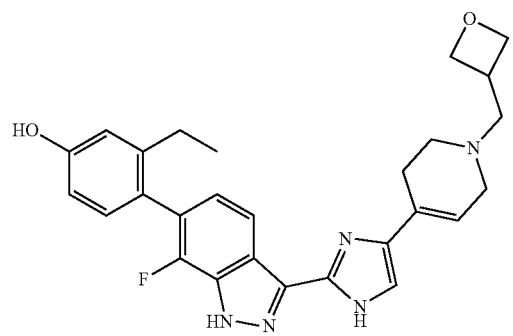 [SMILES: CCc1cc(O)ccc1-c1ccc2c(-c3nc(C4=CCN(CC5COC5)CC4)c[nH]3)n[nH]c2c1F]
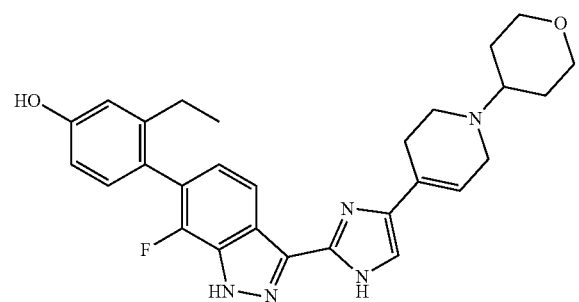 [SMILES: CCc1cc(O)ccc1-c1ccc2c(-c3nc(C4=CCN(C5CCOCC5)CC4)c[nH]3)n[nH]c2c1F]

-continued
| Structure |
|---|
| 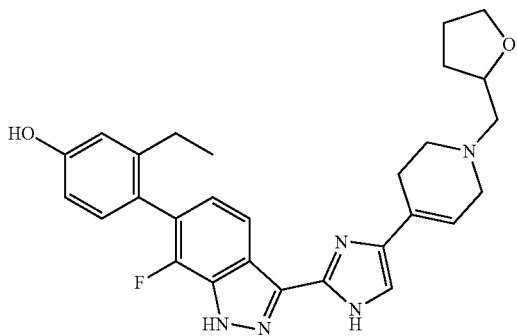 [SMILES: CCc1cc(O)ccc1-c1ccc2c(-c3nc(C4=CCN(CC5CCCO5)CC4)c[nH]3)n[nH]c2c1F] |
| 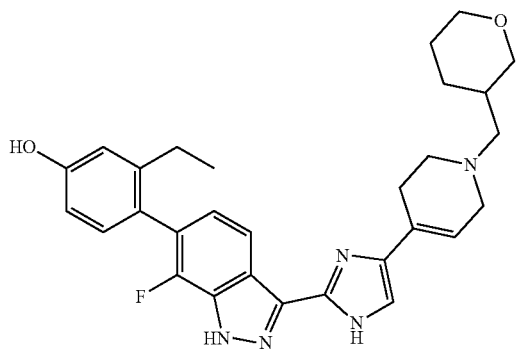 [SMILES: CCc1cc(O)ccc1-c1ccc2c(-c3nc(C4=CCN(CC5CCCOC5)CC4)c[nH]3)n[nH]c2c1F] |
| 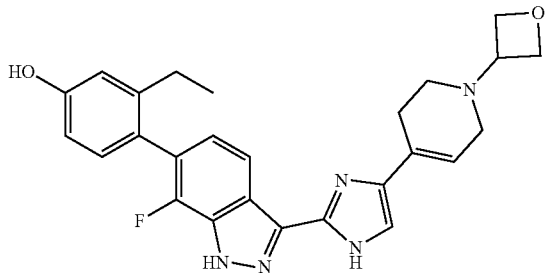 [SMILES: CCc1cc(O)ccc1-c1ccc2c(-c3nc(C4=CCN(C5COC5)CC4)c[nH]3)n[nH]c2c1F] |
| 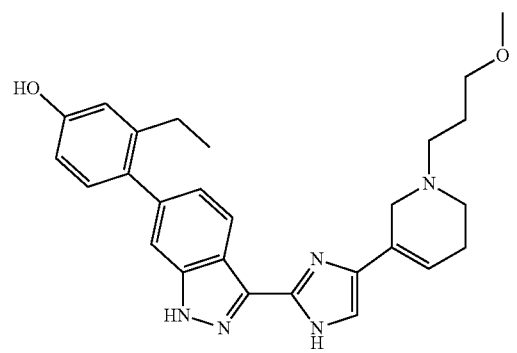 [SMILES: CCc1cc(O)ccc1-c1ccc2c(-c3nc(C4=CCCN(CCCOC)C4)c[nH]3)n[nH]c2c1] |
| 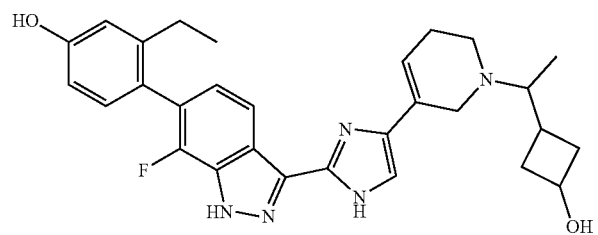 [SMILES: CCc1cc(O)ccc1-c1ccc2c(-c3nc(C4=CCCN(C(C)C5CC(O)C5)C4)c[nH]3)n[nH]c2c1F] |

-continued
| Structure |
|---|
| 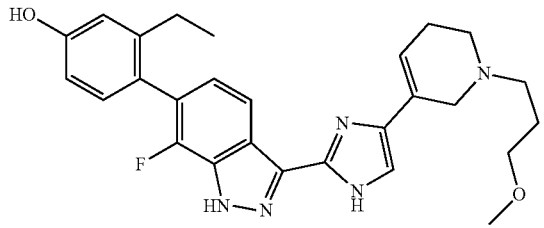 [SMILES: CCc1cc(O)ccc1-c1ccc2c(-c3nc(C4=CCCN(CCCOC)C4)c[nH]3)n[nH]c2c1F] |
| 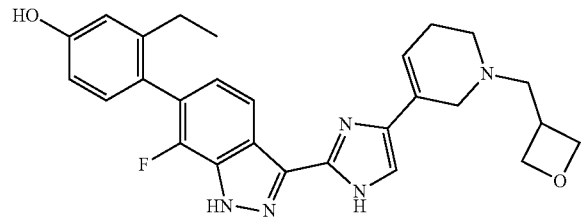 [SMILES: CCc1cc(O)ccc1-c1ccc2c(-c3nc(C4=CCCN(CC5COC5)C4)c[nH]3)n[nH]c2c1F] |
| 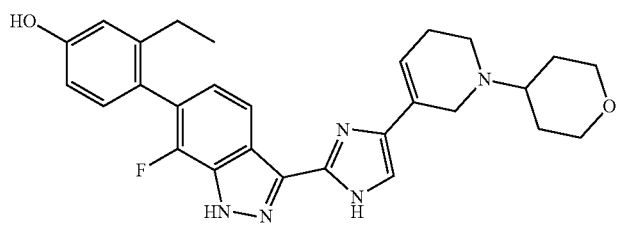 |
| 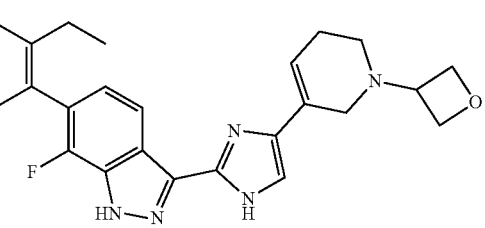 |
| 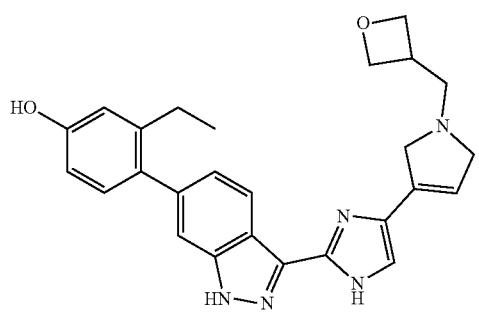 [SMILES: CCc1cc(O)ccc1-c1ccc2c(-c3nc(C4=CCN(CC5COC5)C4)c[nH]3)n[nH]c2c1] |
| 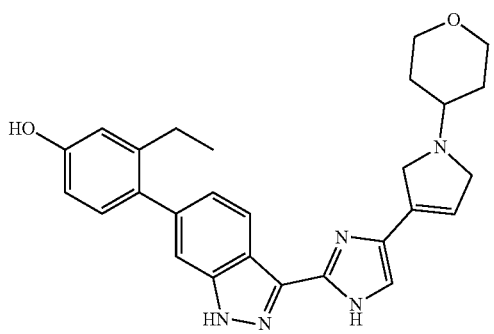 [SMILES: CCc1cc(O)ccc1-c1ccc2c(-c3nc(C4=CCN(C5CCOCC5)C4)c[nH]3)n[nH]c2c1] |

-continued
Structure
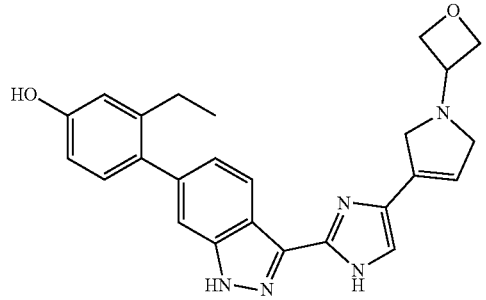 [SMILES: CCc1cc(O)ccc1-c1ccc2c(-c3nc(C4=CCN(C5COC5)C4)c[nH]3)n[nH]c2c1]
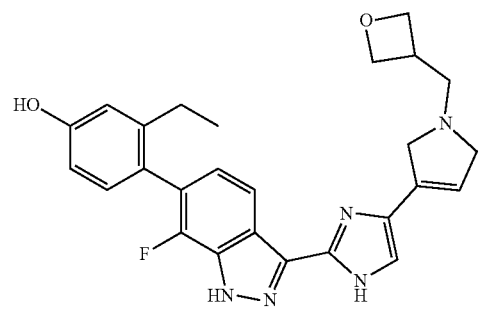 [SMILES: CCc1cc(O)ccc1-c1ccc2c(-c3nc(C4=CCN(CC5COC5)C4)c[nH]3)n[nH]c2c1F]
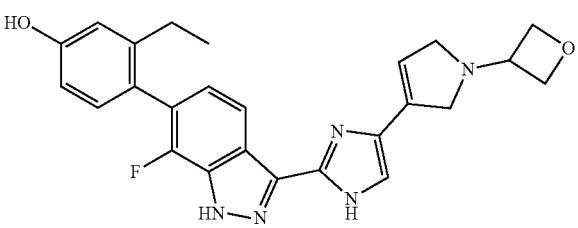
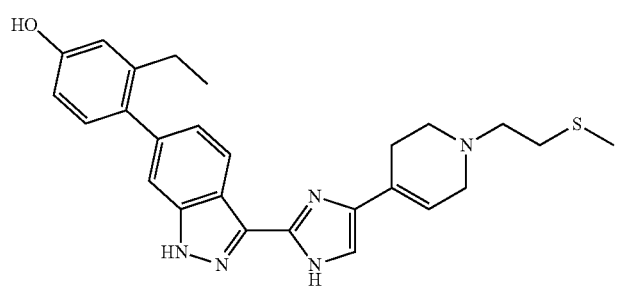 [SMILES: CCc1cc(O)ccc1-c1ccc2c(-c3nc(C4=CCN(CCSC)CC4)c[nH]3)n[nH]c2c1]
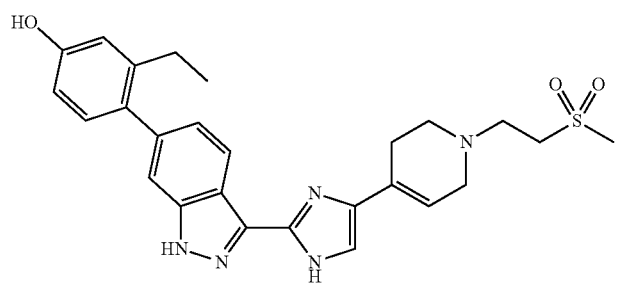 [SMILES: CCc1cc(O)ccc1-c1ccc2c(-c3nc(C4=CCN(CCS(C)(=O)=O)CC4)c[nH]3)n[nH]c2c1]

| Structure |
|---|
| 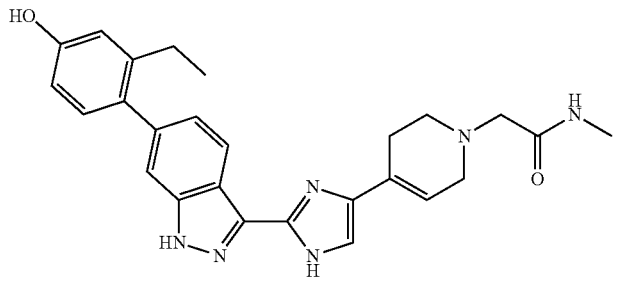 [SMILES: CCc1cc(O)ccc1-c1ccc2c(-c3nc(C4=CCN(CC(=O)NC)CC4)c[nH]3)n[nH]c2c1] |
| 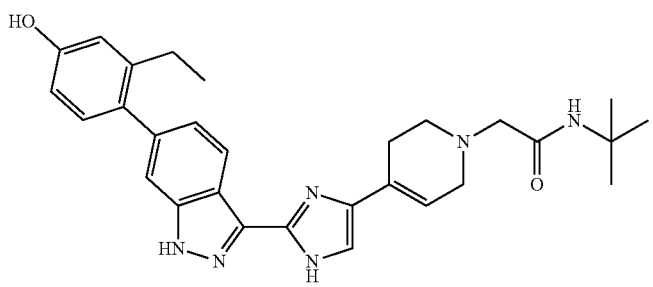 [SMILES: CCc1cc(O)ccc1-c1ccc2c(-c3nc(C4=CCN(CC(=O)NC(C)(C)C)CC4)c[nH]3)n[nH]c2c1] |
| 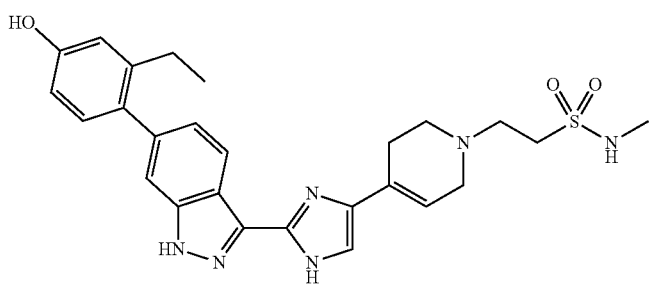 [SMILES: CCc1cc(O)ccc1-c1ccc2c(-c3nc(C4=CCN(CCS(=O)(=O)NC)CC4)c[nH]3)n[nH]c2c1] |
| 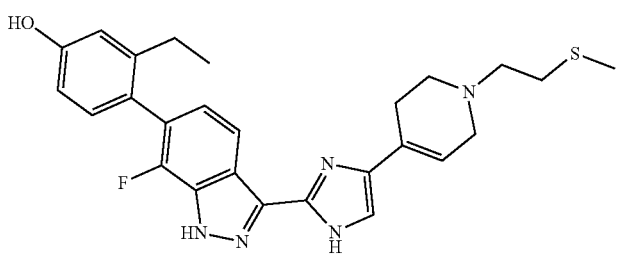 [SMILES: CCc1cc(O)ccc1-c1ccc2c(-c3nc(C4=CCN(CCSC)CC4)c[nH]3)n[nH]c2c1F] |
| 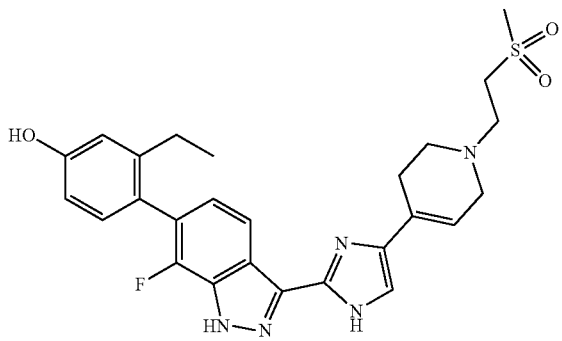 [SMILES: CCc1cc(O)ccc1-c1ccc2c(-c3nc(C4=CCN(CCS(C)(=O)=O)CC4)c[nH]3)n[nH]c2c1F] |

-continued
| Structure |
|---|
| 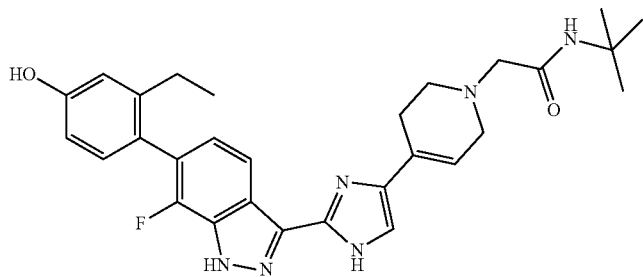 [SMILES: CCc1cc(O)ccc1-c1ccc2c(-c3nc(C4=CCN(CC(=O)NC(C)(C)C)CC4)c[nH]3)n[nH]c2c1F] |
| 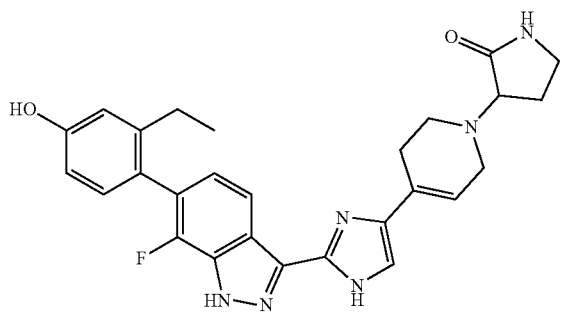 [SMILES: CCc1cc(O)ccc1-c1ccc2c(-c3nc(C4=CCN(C5CCNC5=O)CC4)c[nH]3)n[nH]c2c1F] |
| 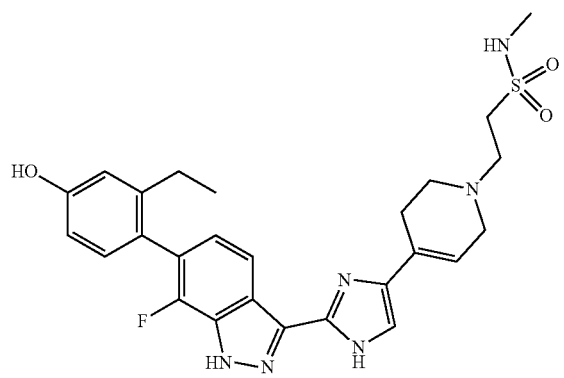 [SMILES: CCc1cc(O)ccc1-c1ccc2c(-c3nc(C4=CCN(CCS(=O)(=O)NC)CC4)c[nH]3)n[nH]c2c1F] |
| 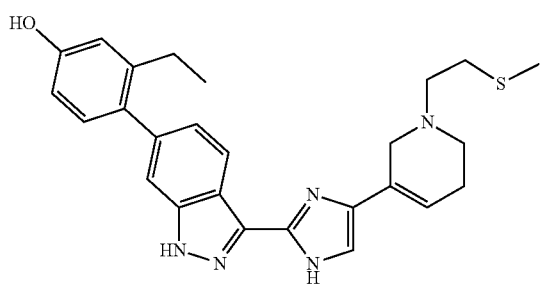 [SMILES: CCc1cc(O)ccc1-c1ccc2c(-c3nc(C4=CCCN(CCSC)C4)c[nH]3)n[nH]c2c1] |
| 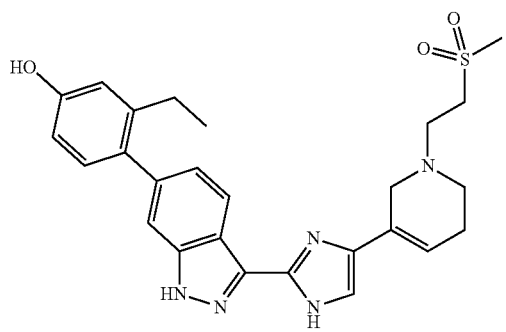 [SMILES: CCc1cc(O)ccc1-c1ccc2c(-c3nc(C4=CCCN(CCS(C)(=O)=O)C4)c[nH]3)n[nH]c2c1] |

| Structure |
|---|
| 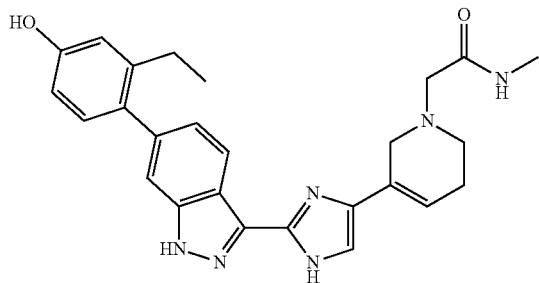 |
| 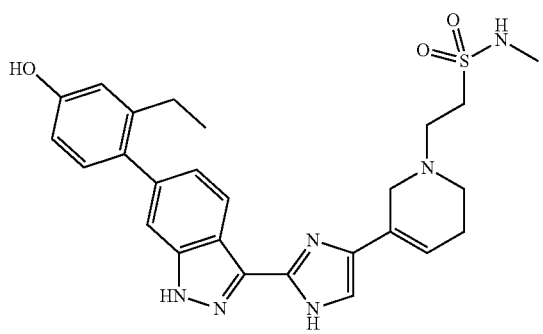 [SMILES: CCc1cc(O)ccc1-c1ccc2c(-c3nc(C4=CCCN(CCS(=O)(=O)NC)C4)c[nH]3)n[nH]c2c1] |
| 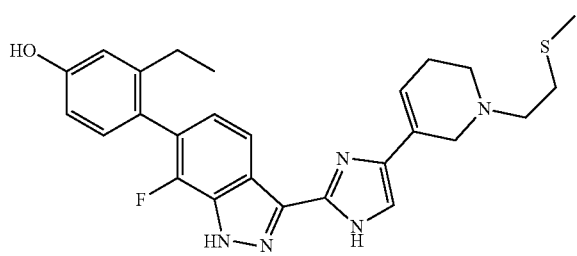 [SMILES: CCc1cc(O)ccc1-c1ccc2c(-c3nc(C4=CCCN(CCSC)C4)c[nH]3)n[nH]c2c1F] |
| 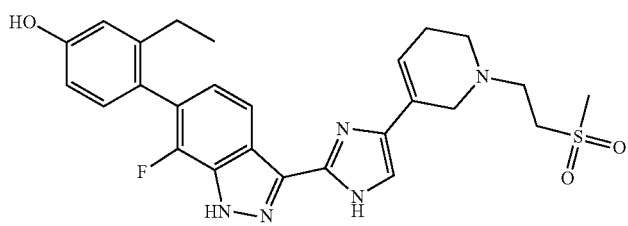 [SMILES: CCc1cc(O)ccc1-c1ccc2c(-c3nc(C4=CCCN(CCS(C)(=O)=O)C4)c[nH]3)n[nH]c2c1F] |
| 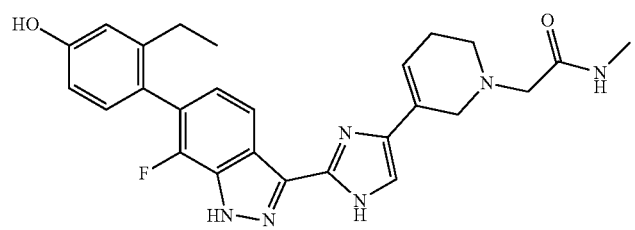 [SMILES: CCc1cc(O)ccc1-c1ccc2c(-c3nc(C4=CCCN(CC(=O)NC)C4)c[nH]3)n[nH]c2c1F] |

| Structure |
|---|
| 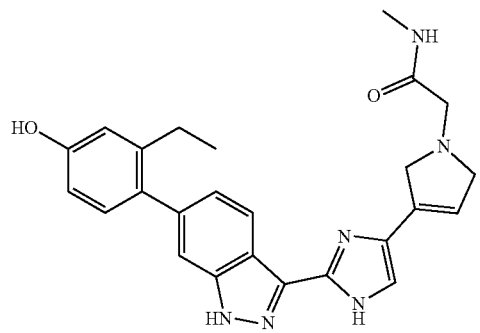 [SMILES: CCc1cc(O)ccc1-c1ccc2c(-c3nc(C4=CCN(CC(=O)NC)C4)c[nH]3)n[nH]c2c1] |
| 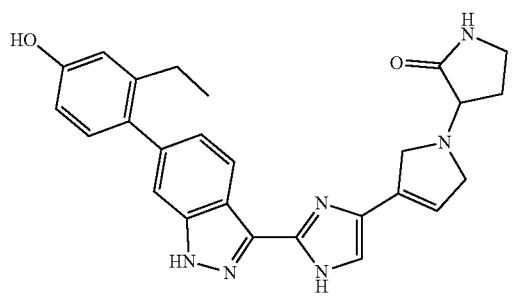 [SMILES: CCc1cc(O)ccc1-c1ccc2c(-c3nc(C4=CCN(C5CCNC5=O)C4)c[nH]3)n[nH]c2c1] |
| 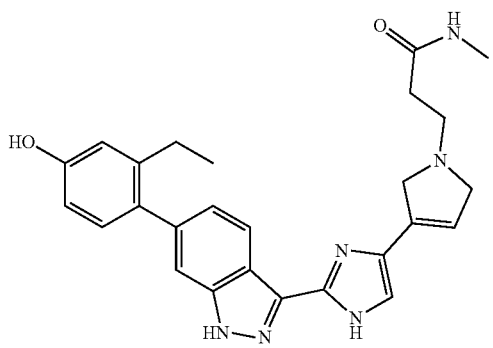 [SMILES: CCc1cc(O)ccc1-c1ccc2c(-c3nc(C4=CCN(CCC(=O)NC)C4)c[nH]3)n[nH]c2c1] |
| 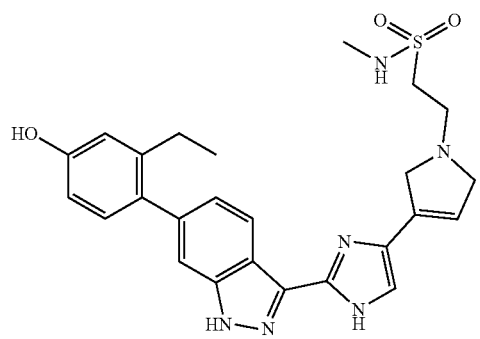 [SMILES: CCc1cc(O)ccc1-c1ccc2c(-c3nc(C4=CCN(CCS(=O)(=O)NC)C4)c[nH]3)n[nH]c2c1] |
| 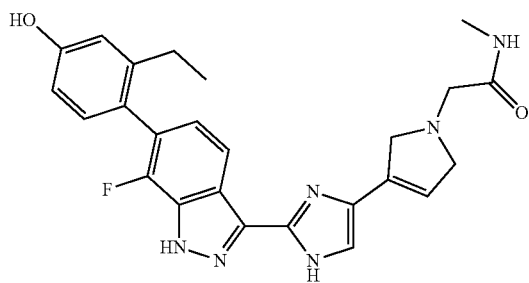 [SMILES: CCc1cc(O)ccc1-c1ccc2c(-c3nc(C4=CCN(CC(=O)NC)C4)c[nH]3)n[nH]c2c1F] |

-continued
Structure
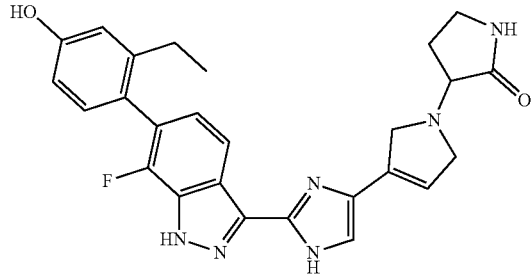 [SMILES: CCc1cc(O)ccc1-c1ccc2c(-c3nc(C4=CCN(C5CCNC5=O)C4)c[nH]3)n[nH]c2c1F]
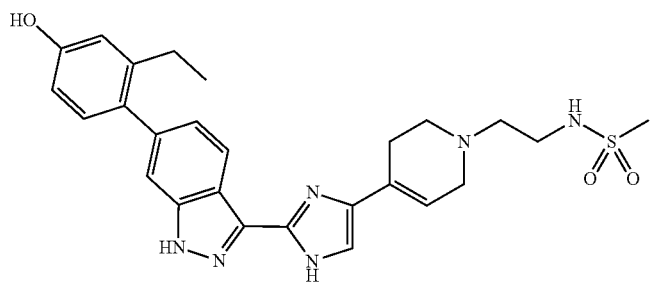 [SMILES: CCc1cc(O)ccc1-c1ccc2c(-c3nc(C4=CCN(CCNS(C)(=O)=O)CC4)c[nH]3)n[nH]c2c1]
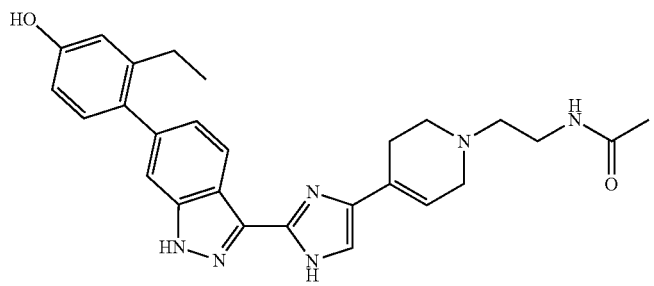 [SMILES: CCc1cc(O)ccc1-c1ccc2c(-c3nc(C4=CCN(CCNC(C)=O)CC4)c[nH]3)n[nH]c2c1]
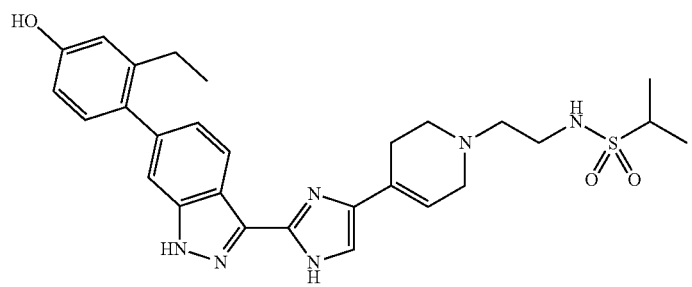 [SMILES: CCc1cc(O)ccc1-c1ccc2c(-c3nc(C4=CCN(CCNS(=O)(=O)C(C)C)CC4)c[nH]3)n[nH]c2c1]
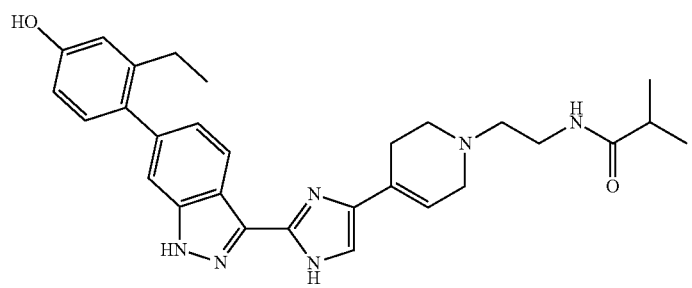 [SMILES: CCc1cc(O)ccc1-c1ccc2c(-c3nc(C4=CCN(CCNC(=O)C(C)C)CC4)c[nH]3)n[nH]c2c1]

-continued
| Structure |
|---|
| 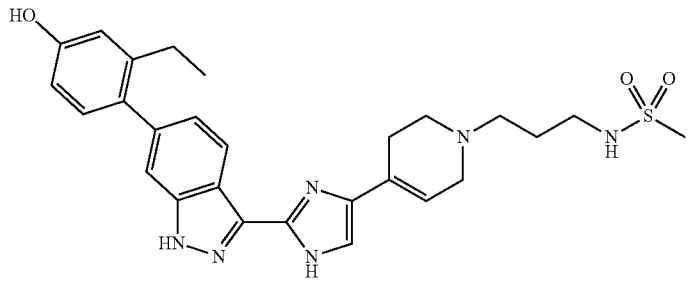 [SMILES: CCc1cc(O)ccc1-c1ccc2c(-c3nc(C4=CCN(CCCNS(C)(=O)=O)CC4)c[nH]3)n[nH]c2c1] |
| 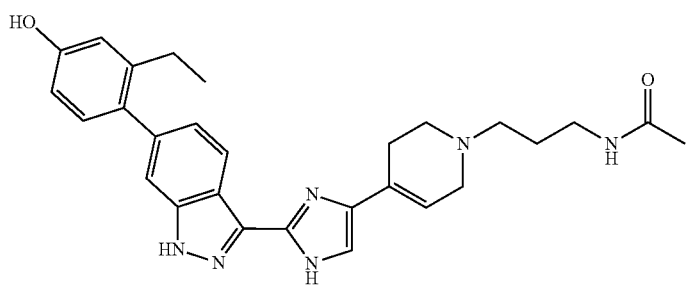 [SMILES: CCc1cc(O)ccc1-c1ccc2c(-c3nc(C4=CCN(CCCNC(C)=O)CC4)c[nH]3)n[nH]c2c1] |
| 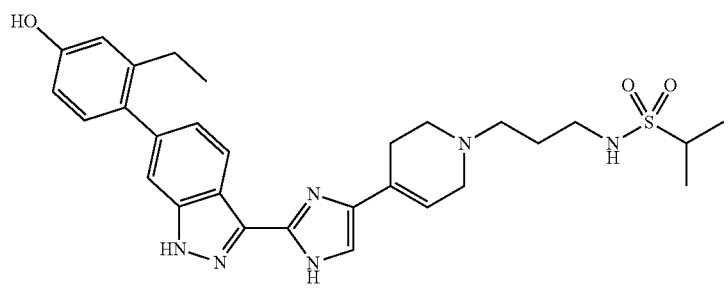 [SMILES: CCc1cc(O)ccc1-c1ccc2c(-c3nc(C4=CCN(CCCNS(=O)(=O)C(C)C)CC4)c[nH]3)n[nH]c2c1] |
| 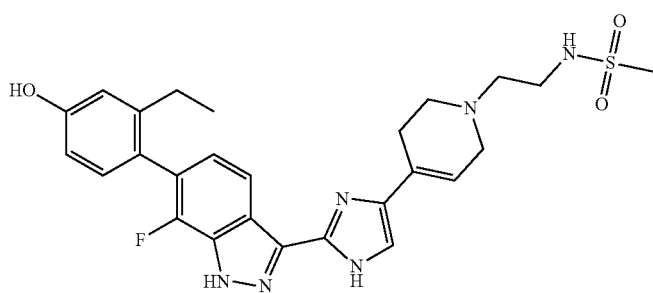 [SMILES: CCc1cc(O)ccc1-c1ccc2c(-c3nc(C4=CCN(CCNS(C)(=O)=O)CC4)c[nH]3)n[nH]c2c1F] |
| 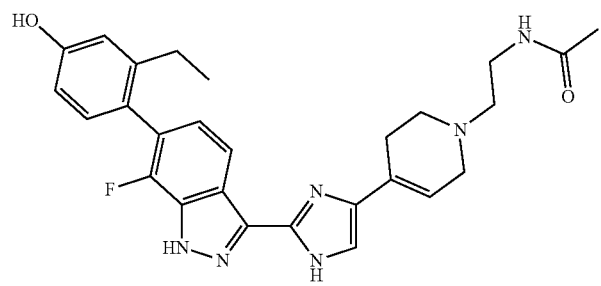 [SMILES: CCc1cc(O)ccc1-c1ccc2c(-c3nc(C4=CCN(CCNC(C)=O)CC4)c[nH]3)n[nH]c2c1F] |

| Structure |
|---|
| 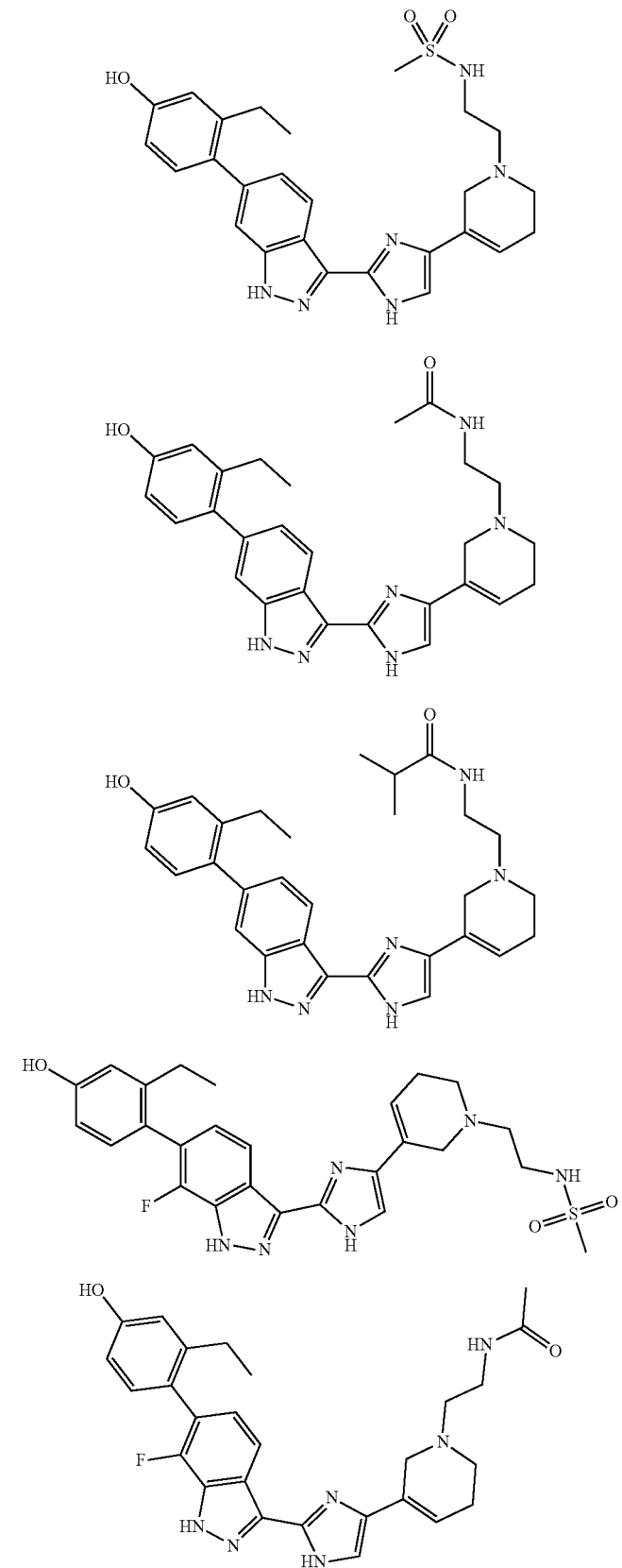 |

-continued
Structure
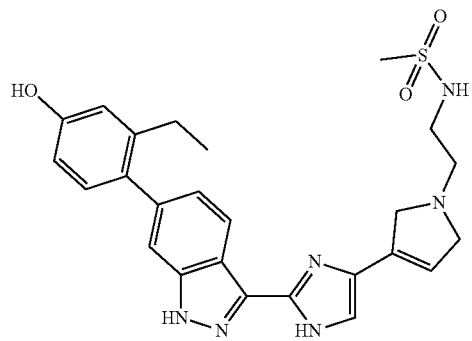 [SMILES: CCc1cc(O)ccc1-c1ccc2c(-c3nc(C4=CCN(CCNS(C)(=O)=O)C4)c[nH]3)n[nH]c2c1]
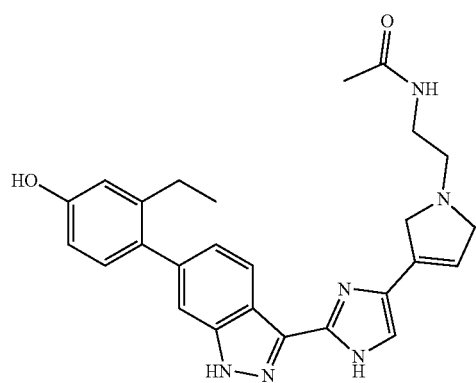 [SMILES: CCc1cc(O)ccc1-c1ccc2c(-c3nc(C4=CCN(CCNC(C)=O)C4)c[nH]3)n[nH]c2c1]
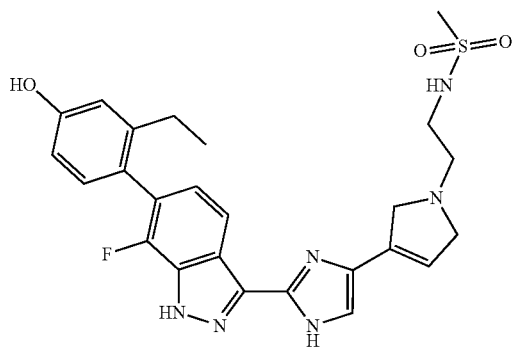 [SMILES: CCc1cc(O)ccc1-c1ccc2c(-c3nc(C4=CCN(CCNS(C)(=O)=O)C4)c[nH]3)n[nH]c2c1F]
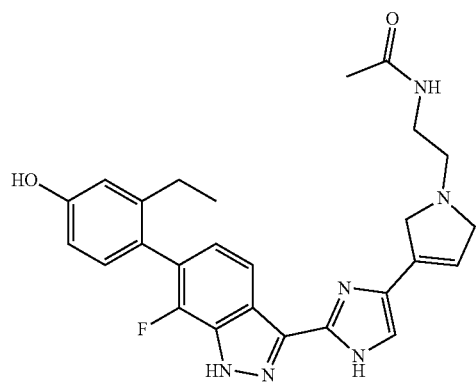 [SMILES: CCc1cc(O)ccc1-c1ccc2c(-c3nc(C4=CCN(CCNC(C)=O)C4)c[nH]3)n[nH]c2c1F]

-continued
| Structure |
|---|
| 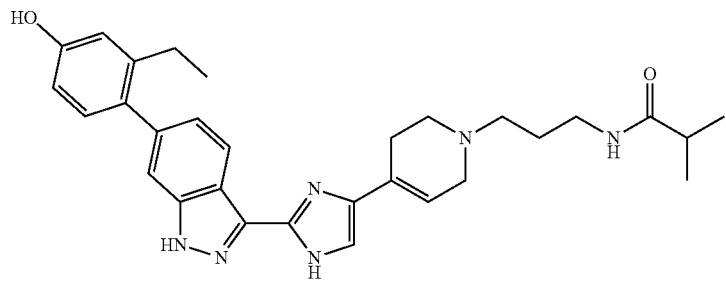 [SMILES: CCc1cc(O)ccc1-c1ccc2c(-c3nc(C4=CCN(CCCNC(=O)C(C)C)CC4)c[nH]3)n[nH]c2c1] |
| 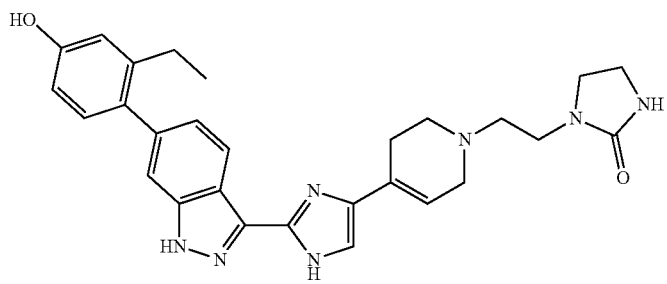 [SMILES: CCc1cc(O)ccc1-c1ccc2c(-c3nc(C4=CCN(CCN5CCNC5=O)CC4)c[nH]3)n[nH]c2c1] |
| 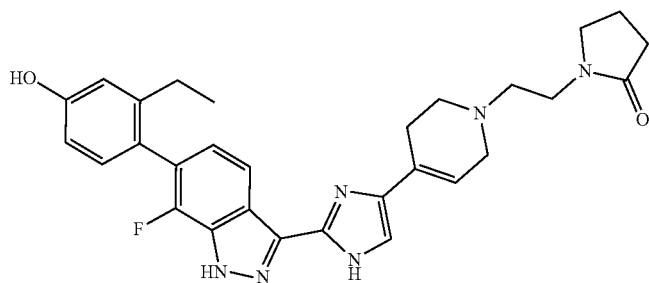 [SMILES: CCc1cc(O)ccc1-c1ccc2c(-c3nc(C4=CCN(CCN5CCCC5=O)CC4)c[nH]3)n[nH]c2c1F] |
| 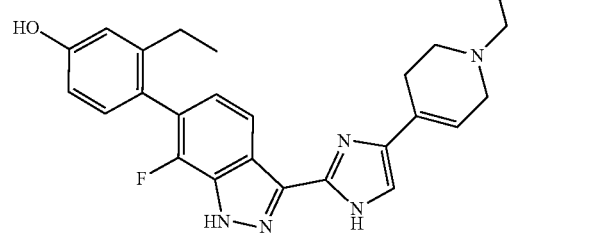 |
| 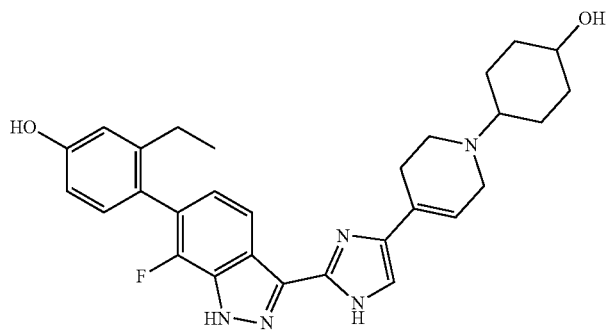 [SMILES: CCc1cc(O)ccc1-c1ccc2c(-c3nc(C4=CCN(C5CCC(O)CC5)CC4)c[nH]3)n[nH]c2c1F] |

| Structure |
| --- |
| 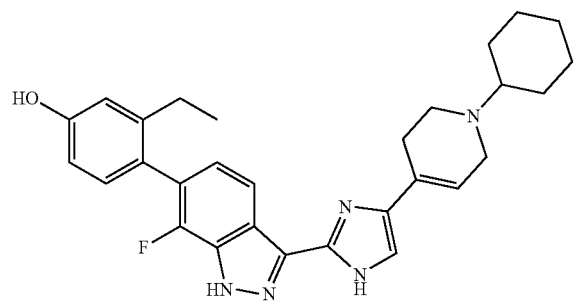 [SMILES: CCc1cc(O)ccc1-c1ccc2c(-c3nc(C4=CCN(C5CCCCC5)CC4)c[nH]3)n[nH]c2c1F] |
| 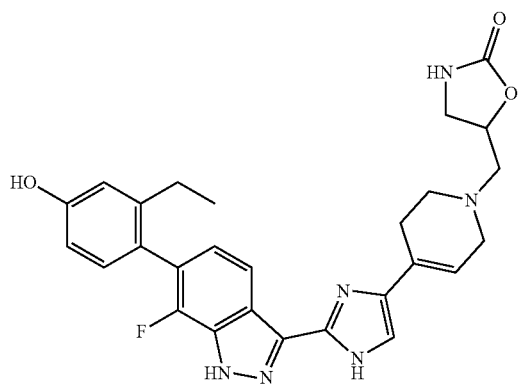 [SMILES: CCc1cc(O)ccc1-c1ccc2c(-c3nc(C4=CCN(CC5CNC(=O)O5)CC4)c[nH]3)n[nH]c2c1F] |
| 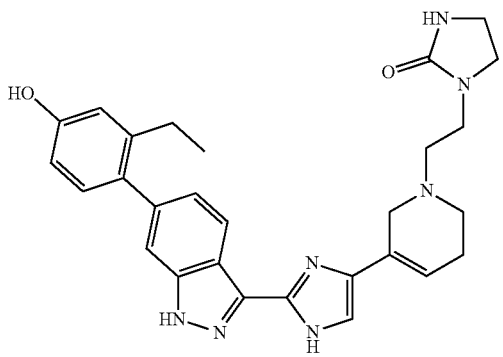 [SMILES: CCc1cc(O)ccc1-c1ccc2c(-c3nc(C4=CCCN(CCN5CCNC5=O)C4)c[nH]3)n[nH]c2c1] |
| 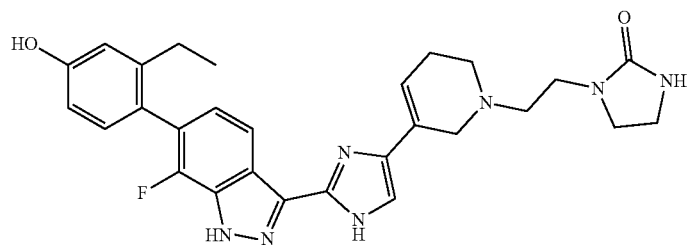 [SMILES: CCc1cc(O)ccc1-c1ccc2c(-c3nc(C4=CCCN(CCN5CCNC5=O)C4)c[nH]3)n[nH]c2c1F] |
| 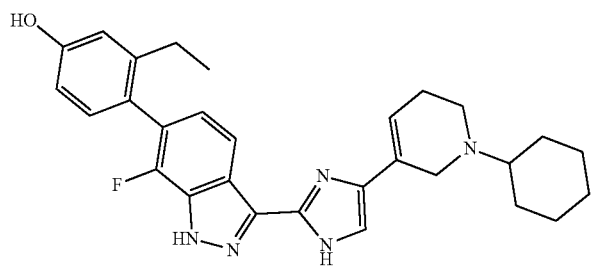 [SMILES: CCc1cc(O)ccc1-c1ccc2c(-c3nc(C4=CCCN(C5CCCCC5)C4)c[nH]3)n[nH]c2c1F] |

-continued
Structure
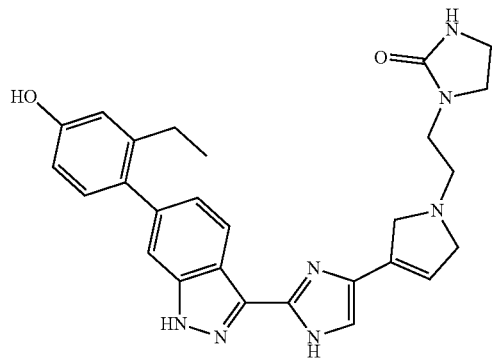 [SMILES: CCc1cc(O)ccc1-c1ccc2c(-c3nc(C4=CCN(CCN5CCNC5=O)C4)c[nH]3)n[nH]c2c1]
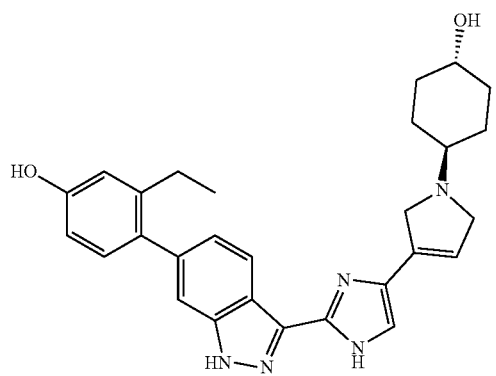 [SMILES: CCc1cc(O)ccc1-c1ccc2c(-c3nc(C4=CCN([C@H]5CC[C@H](O)CC5)C4)c[nH]3)n[nH]c2c1]
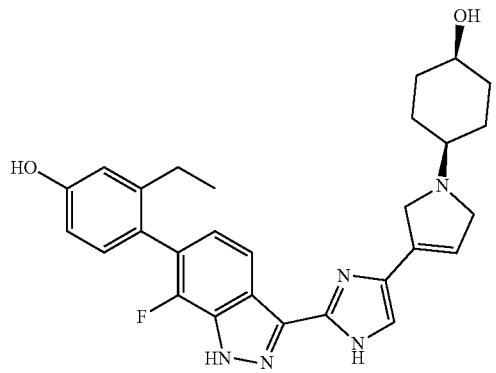 [SMILES: CCc1cc(O)ccc1-c1ccc2c(-c3nc(C4=CCN([C@H]5CC[C@@H](O)CC5)C4)c[nH]3)n[nH]c2c1F]
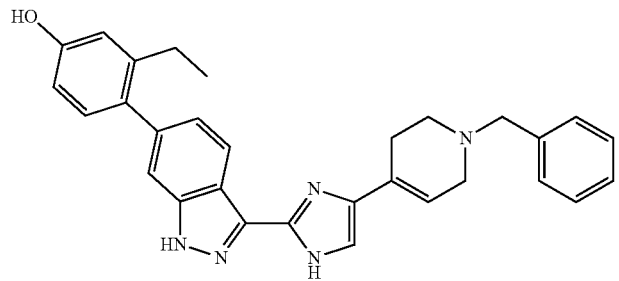 [SMILES: CCc1cc(O)ccc1-c1ccc2c(-c3nc(C4=CCN(Cc5ccccc5)CC4)c[nH]3)n[nH]c2c1]

-continued
| Structure |
|---|
| 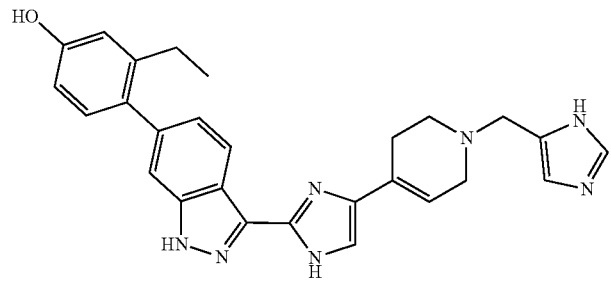 [SMILES: CCc1cc(O)ccc1-c1ccc2c(-c3nc(C4=CCN(Cc5cnc[nH]5)CC4)c[nH]3)n[nH]c2c1] |
| 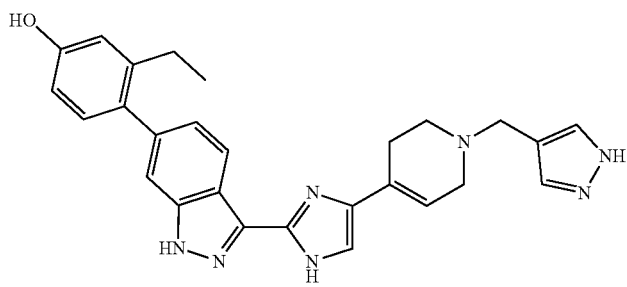 [SMILES: CCc1cc(O)ccc1-c1ccc2c(-c3nc(C4=CCN(Cc5cn[nH]c5)CC4)c[nH]3)n[nH]c2c1] |
| 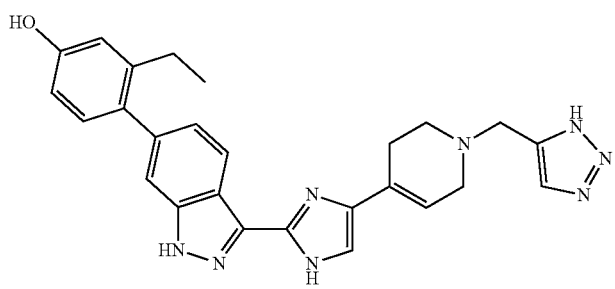 [SMILES: CCc1cc(O)ccc1-c1ccc2c(-c3nc(C4=CCN(Cc5cnn[nH]5)CC4)c[nH]3)n[nH]c2c1] |
| 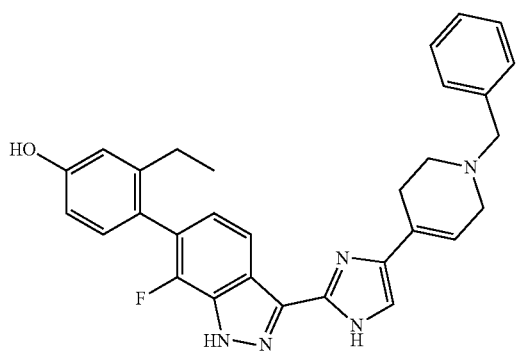 [SMILES: CCc1cc(O)ccc1-c1ccc2c(-c3nc(C4=CCN(Cc5ccccc5)CC4)c[nH]3)n[nH]c2c1F] |
| 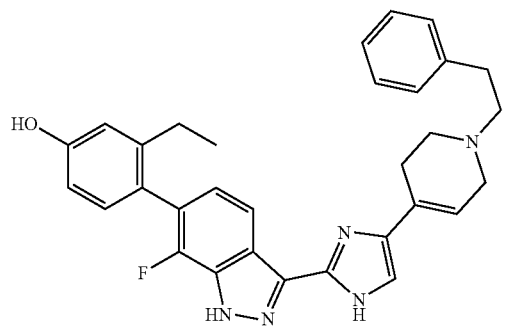 [SMILES: CCc1cc(O)ccc1-c1ccc2c(-c3nc(C4=CCN(CCc5ccccc5)CC4)c[nH]3)n[nH]c2c1F] |

-continued
| Structure |
|---|
| 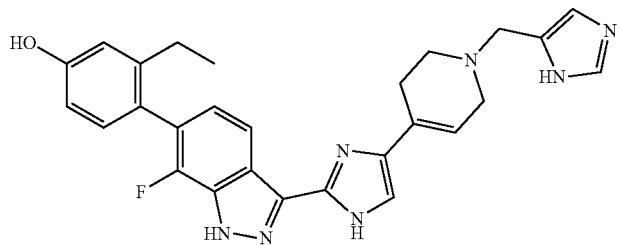 [SMILES: CCc1cc(O)ccc1-c1ccc2c(-c3nc(C4=CCN(Cc5cnc[nH]5)CC4)c[nH]3)n[nH]c2c1F] |
| 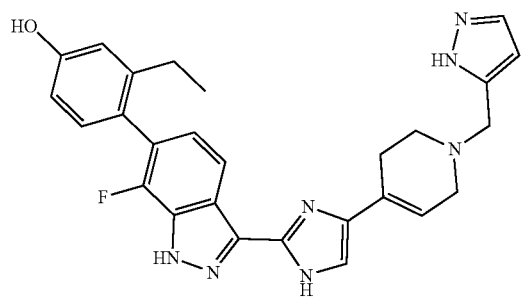 [SMILES: CCc1cc(O)ccc1-c1ccc2c(-c3nc(C4=CCN(Cc5ccn[nH]5)CC4)c[nH]3)n[nH]c2c1F] |
| 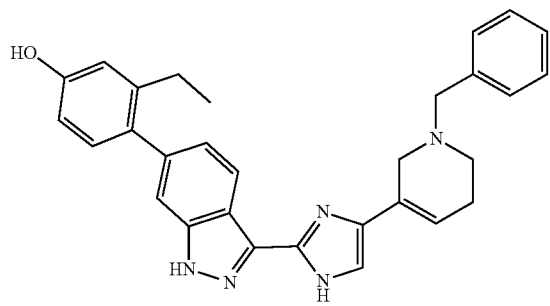 [SMILES: CCc1cc(O)ccc1-c1ccc2c(-c3nc(C4=CCCN(Cc5ccccc5)C4)c[nH]3)n[nH]c2c1] |
| 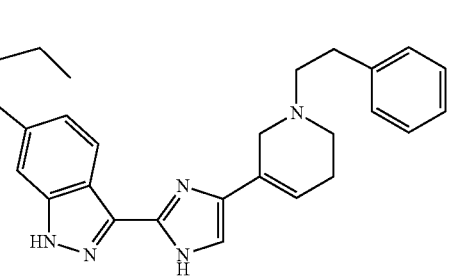 |
| 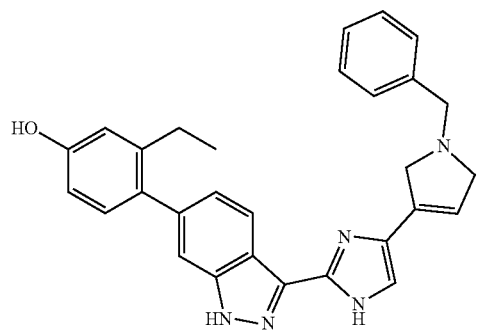 [SMILES: CCc1cc(O)ccc1-c1ccc2c(-c3nc(C4=CCN(Cc5ccccc5)C4)c[nH]3)n[nH]c2c1] |

-continued
| Structure |
|---|
| 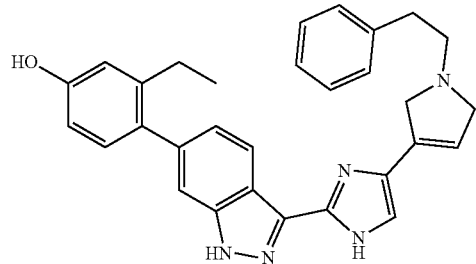 [SMILES: CCc1cc(O)ccc1-c1ccc2c(-c3nc(C4=CCN(CCc5ccccc5)C4)c[nH]3)n[nH]c2c1] |
| 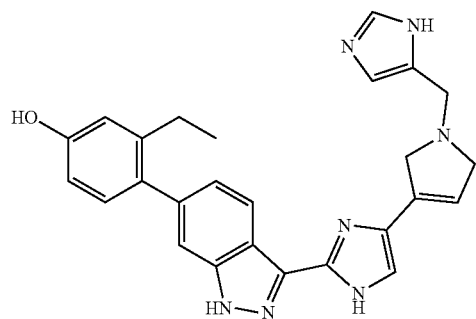 [SMILES: CCc1cc(O)ccc1-c1ccc2c(-c3nc(C4=CCN(Cc5cnc[nH]5)C4)c[nH]3)n[nH]c2c1] |
| 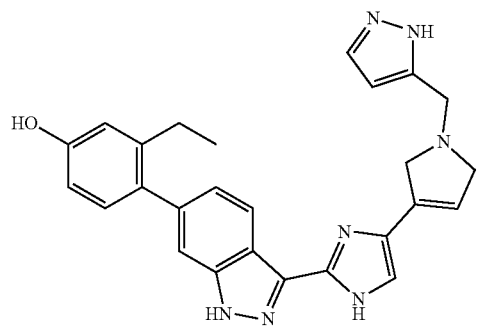 [SMILES: CCc1cc(O)ccc1-c1ccc2c(-c3nc(C4=CCN(Cc5ccn[nH]5)C4)c[nH]3)n[nH]c2c1] |
| 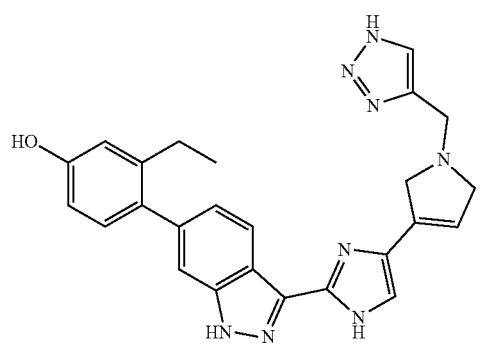 [SMILES: CCc1cc(O)ccc1-c1ccc2c(-c3nc(C4=CCN(Cc5c[nH]nn5)C4)c[nH]3)n[nH]c2c1] |
| 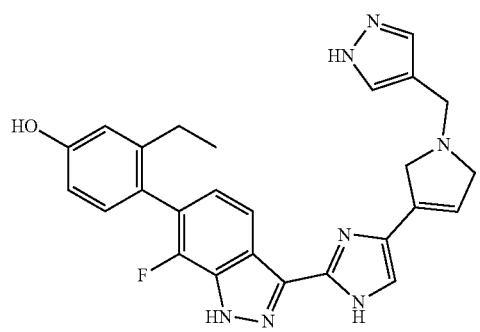 [SMILES: CCc1cc(O)ccc1-c1ccc2c(-c3nc(C4=CCN(Cc5cn[nH]c5)C4)c[nH]3)n[nH]c2c1F] |

| Structure |
|---|
| 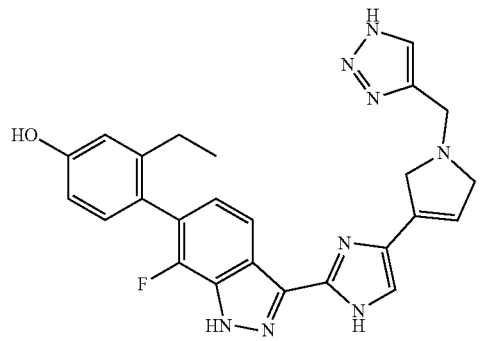 [SMILES: CCc1cc(O)ccc1-c1ccc2c(-c3nc(C4=CCN(Cc5c[nH]nn5)C4)c[nH]3)n[nH]c2c1F] |
| 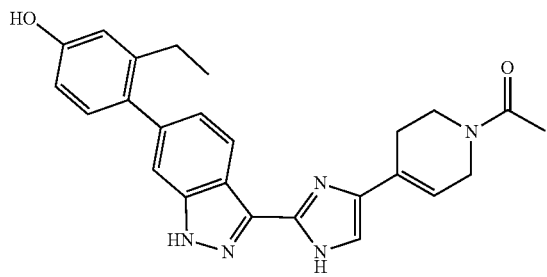 [SMILES: CCc1cc(O)ccc1-c1ccc2c(-c3nc(C4=CCN(C(C)=O)CC4)c[nH]3)n[nH]c2c1] |
| 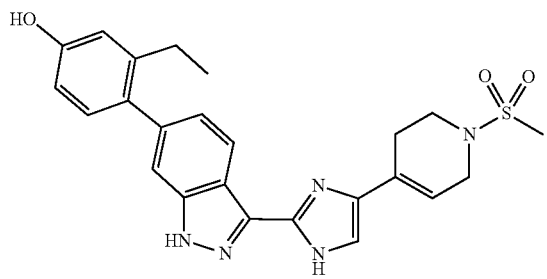 [SMILES: CCc1cc(O)ccc1-c1ccc2c(-c3nc(C4=CCN(S(C)(=O)=O)CC4)c[nH]3)n[nH]c2c1] |
| 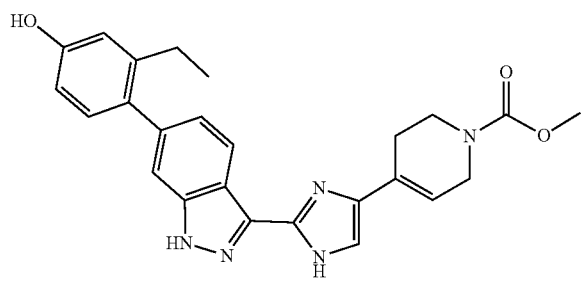 [SMILES: CCc1cc(O)ccc1-c1ccc2c(-c3nc(C4=CCN(C(=O)OC)CC4)c[nH]3)n[nH]c2c1] |
| 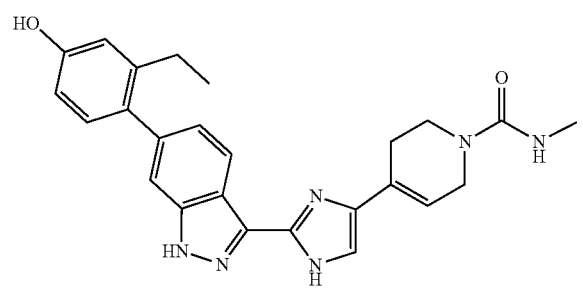 [SMILES: CCc1cc(O)ccc1-c1ccc2c(-c3nc(C4=CCN(C(=O)NC)CC4)c[nH]3)n[nH]c2c1] |

| Structure |
| --- |
| 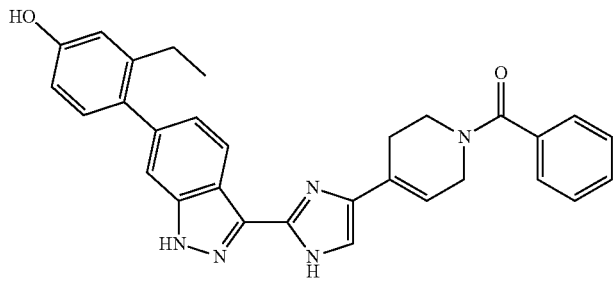 [SMILES: CCc1cc(O)ccc1-c1ccc2c(-c3nc(C4=CCN(C(=O)c5ccccc5)CC4)c[nH]3)n[nH]c2c1] |
| 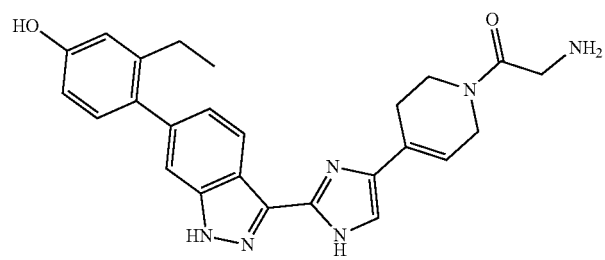 [SMILES: CCc1cc(O)ccc1-c1ccc2c(-c3nc(C4=CCN(C(=O)CN)CC4)c[nH]3)n[nH]c2c1] |
| 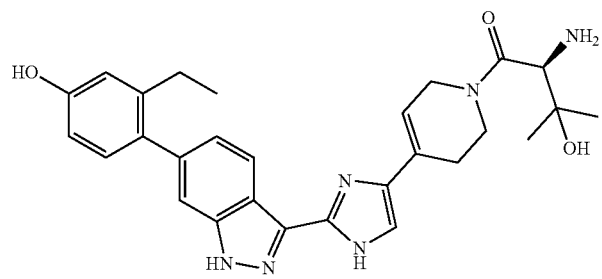 [SMILES: CCc1cc(O)ccc1-c1ccc2c(-c3nc(C4=CCN(C(=O)[C@@H](N)C(C)(C)O)CC4)c[nH]3)n[nH]c2c1] |
| 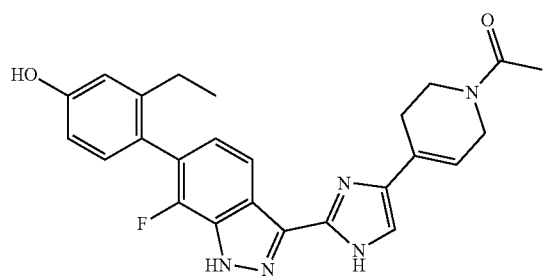 [SMILES: CCc1cc(O)ccc1-c1ccc2c(-c3nc(C4=CCN(C(C)=O)CC4)c[nH]3)n[nH]c2c1F] |
| 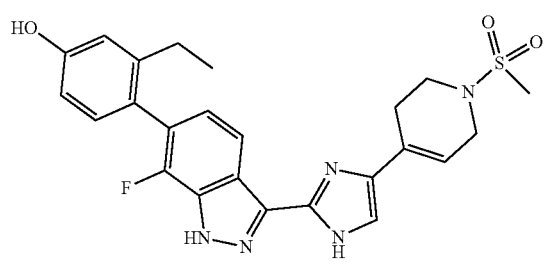 [SMILES: CCc1cc(O)ccc1-c1ccc2c(-c3nc(C4=CCN(S(C)(=O)=O)CC4)c[nH]3)n[nH]c2c1F] |

| Structure |
|---|
| 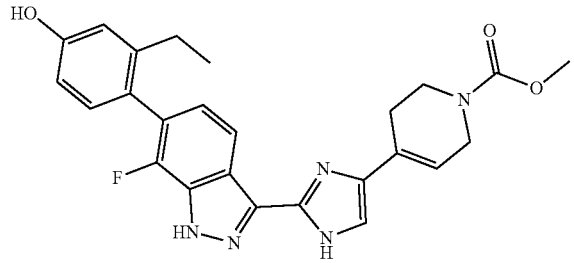 [SMILES: CCc1cc(O)ccc1-c1ccc2c(-c3nc(C4=CCN(C(=O)OC)CC4)c[nH]3)n[nH]c2c1F] |
| 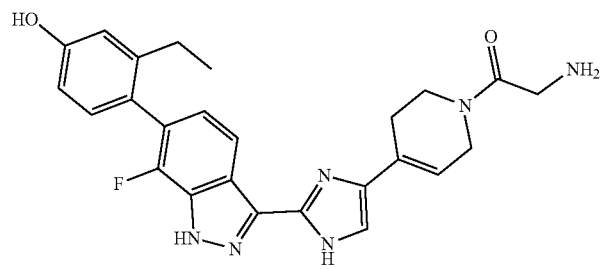 [SMILES: CCc1cc(O)ccc1-c1ccc2c(-c3nc(C4=CCN(C(=O)CN)CC4)c[nH]3)n[nH]c2c1F] |
| 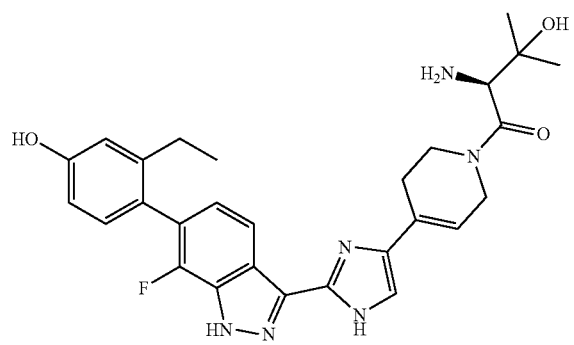 [SMILES: CCc1cc(O)ccc1-c1ccc2c(-c3nc(C4=CCN(C(=O)[C@@H](N)C(C)(C)O)CC4)c[nH]3)n[nH]c2c1F] |
| 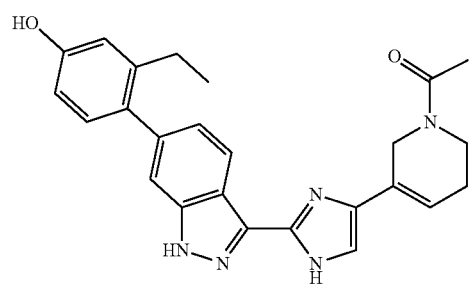 [SMILES: CCc1cc(O)ccc1-c1ccc2c(-c3nc(C4=CCCN(C(C)=O)C4)c[nH]3)n[nH]c2c1] |
| 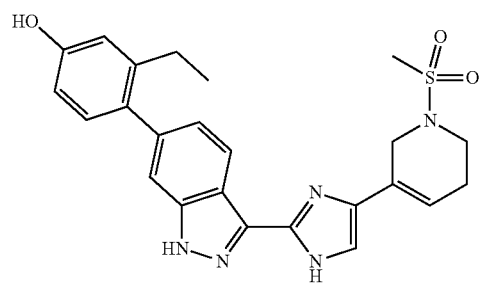 |

-continued
| Structure |
|---|
| 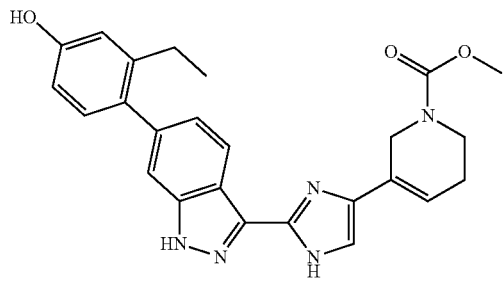 [SMILES: CCc1cc(O)ccc1-c1ccc2c(-c3nc(C4=CCCN(C(=O)OC)C4)c[nH]3)n[nH]c2c1] |
| 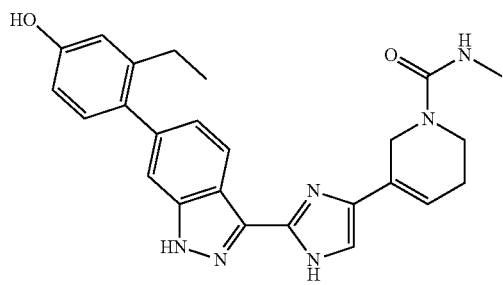 [SMILES: CCc1cc(O)ccc1-c1ccc2c(-c3nc(C4=CCCN(C(=O)NC)C4)c[nH]3)n[nH]c2c1] |
| 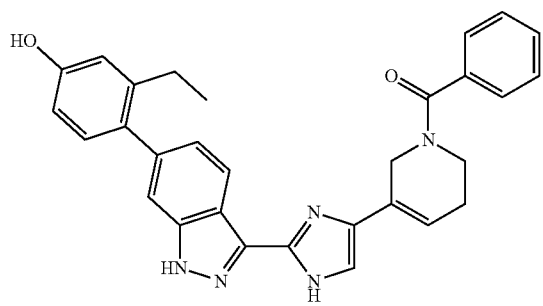 [SMILES: CCc1cc(O)ccc1-c1ccc2c(-c3nc(C4=CCCN(C(=O)c5ccccc5)C4)c[nH]3)n[nH]c2c1] |
| 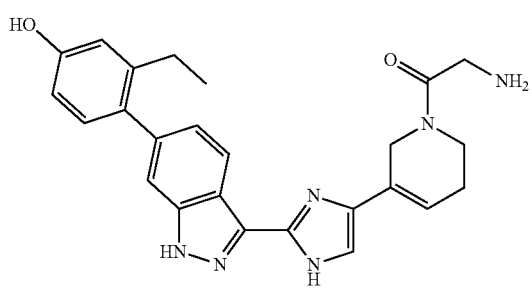 [SMILES: CCc1cc(O)ccc1-c1ccc2c(-c3nc(C4=CCCN(C(=O)CN)C4)c[nH]3)n[nH]c2c1] |
| 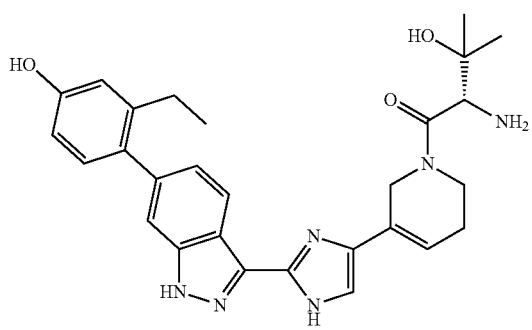 [SMILES: CCc1cc(O)ccc1-c1ccc2c(-c3nc(C4=CCCN(C(=O)[C@@H](N)C(C)(C)O)C4)c[nH]3)n[nH]c2c1] |

-continued
| Structure |
| --- |
| 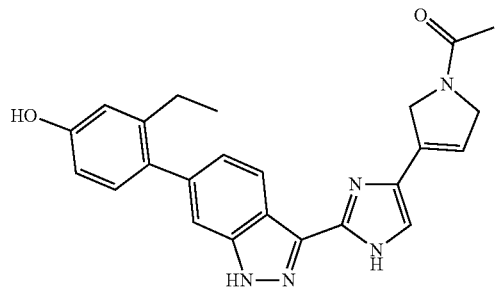 [SMILES: CCc1cc(O)ccc1-c1ccc2c(-c3nc(C4=CCN(C(C)=O)C4)c[nH]3)n[nH]c2c1] |
| 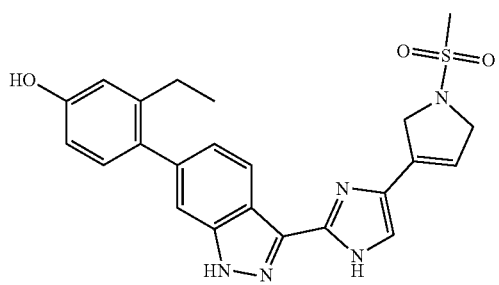 [SMILES: CCc1cc(O)ccc1-c1ccc2c(-c3nc(C4=CCN(S(C)(=O)=O)C4)c[nH]3)n[nH]c2c1] |
| 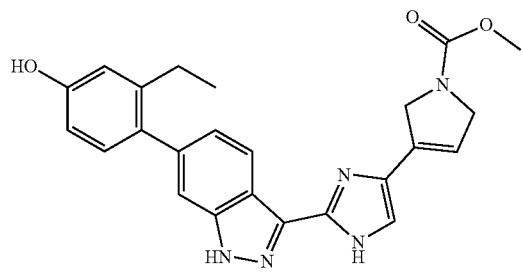 |
| 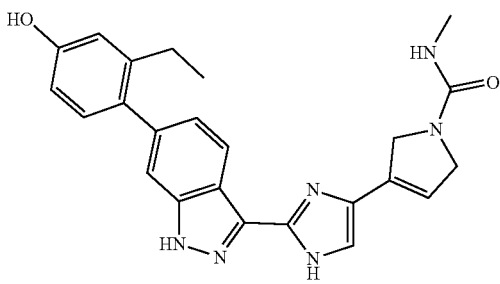 [SMILES: CCc1cc(O)ccc1-c1ccc2c(-c3nc(C4=CCN(C(=O)NC)C4)c[nH]3)n[nH]c2c1] |
| 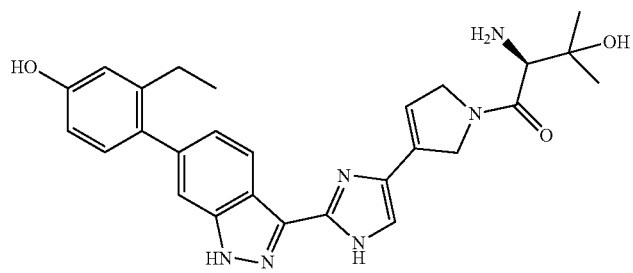 [SMILES: CCc1cc(O)ccc1-c1ccc2c(-c3nc(C4=CCN(C(=O)[C@@H](N)C(C)(C)O)C4)c[nH]3)n[nH]c2c1] |

-continued
Structure
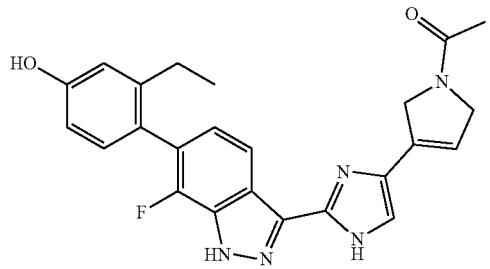
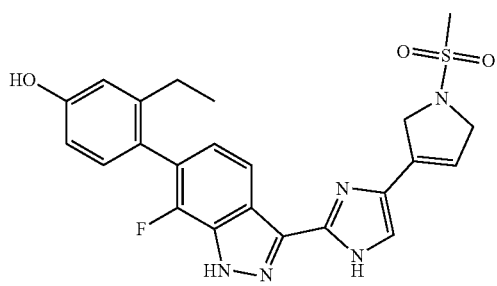 [SMILES: CCc1cc(O)ccc1-c1ccc2c(-c3nc(C4=CCN(S(C)(=O)=O)C4)c[nH]3)n[nH]c2c1F]
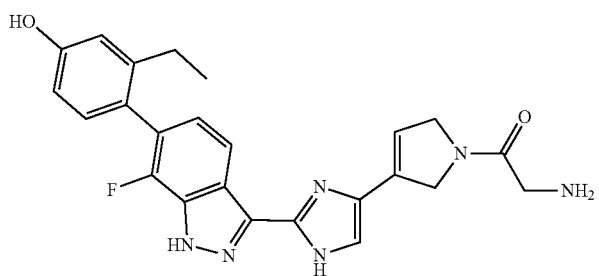 [SMILES: CCc1cc(O)ccc1-c1ccc2c(-c3nc(C4=CCN(C(=O)CN)C4)c[nH]3)n[nH]c2c1F]
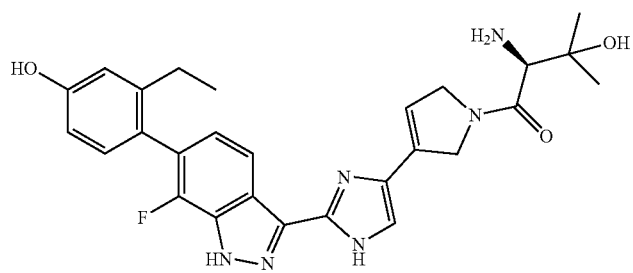 [SMILES: CCc1cc(O)ccc1-c1ccc2c(-c3nc(C4=CCN(C(=O)[C@@H](N)C(C)(C)O)C4)c[nH]3)n[nH]c2c1F]
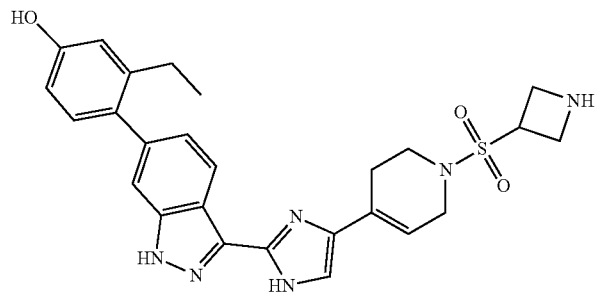 [SMILES: CCc1cc(O)ccc1-c1ccc2c(-c3nc(C4=CCN(S(=O)(=O)C5CNC5)CC4)c[nH]3)n[nH]c2c1]

-continued
Structure
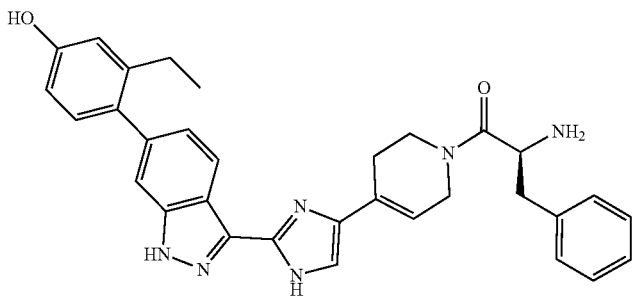 [SMILES: CCc1cc(O)ccc1-c1ccc2c(-c3nc(C4=CCN(C(=O)[C@@H](N)Cc5ccccc5)CC4)c[nH]3)n[nH]c2c1]
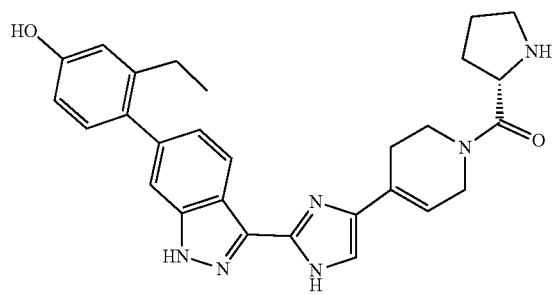 [SMILES: CCc1cc(O)ccc1-c1ccc2c(-c3nc(C4=CCN(C(=O)[C@@H]5CCCN5)CC4)c[nH]3)n[nH]c2c1]
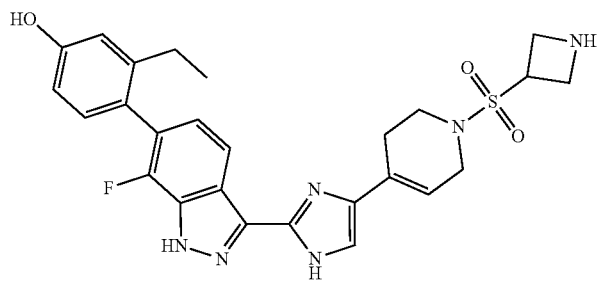 [SMILES: CCc1cc(O)ccc1-c1ccc2c(-c3nc(C4=CCN(S(=O)(=O)C5CNC5)CC4)c[nH]3)n[nH]c2c1F]
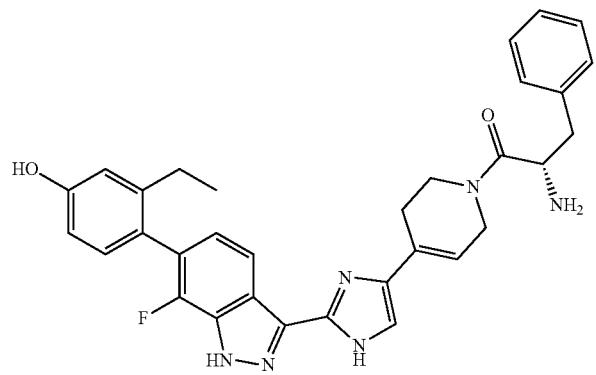 [SMILES: CCc1cc(O)ccc1-c1ccc2c(-c3nc(C4=CCN(C(=O)[C@@H](N)Cc5ccccc5)CC4)c[nH]3)n[nH]c2c1F]
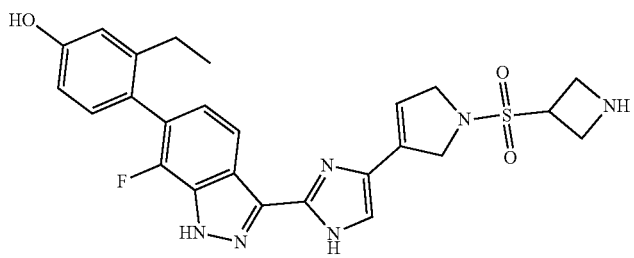 [SMILES: CCc1cc(O)ccc1-c1ccc2c(-c3nc(C4=CCN(S(=O)(=O)C5CNC5)C4)c[nH]3)n[nH]c2c1F]

-continued
Structure
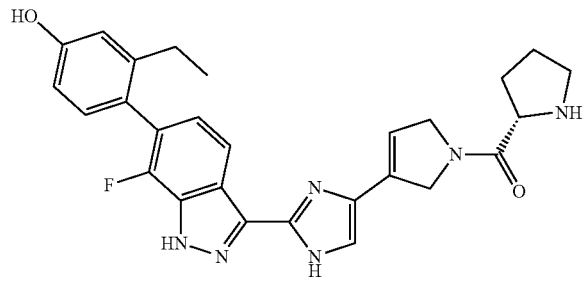 [SMILES: CCc1cc(O)ccc1-c1ccc2c(-c3nc(C4=CCN(C(=O)[C@@H]5CCCN5)C4)c[nH]3)n[nH]c2c1F]
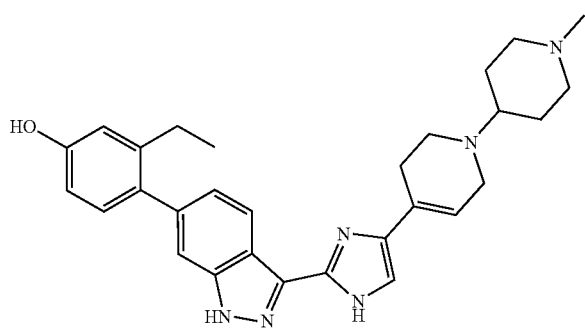 [SMILES: CCc1cc(O)ccc1-c1ccc2c(-c3nc(C4=CCN(C5CCN(C)CC5)CC4)c[nH]3)n[nH]c2c1]
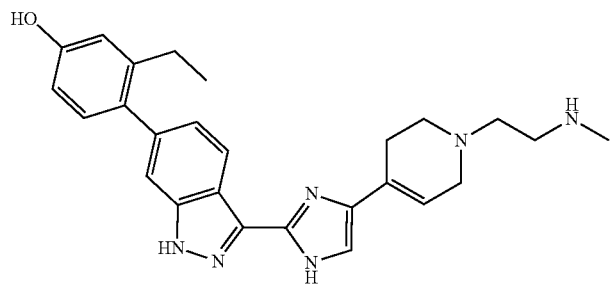 [SMILES: CCc1cc(O)ccc1-c1ccc2c(-c3nc(C4=CCN(CCNC)CC4)c[nH]3)n[nH]c2c1]
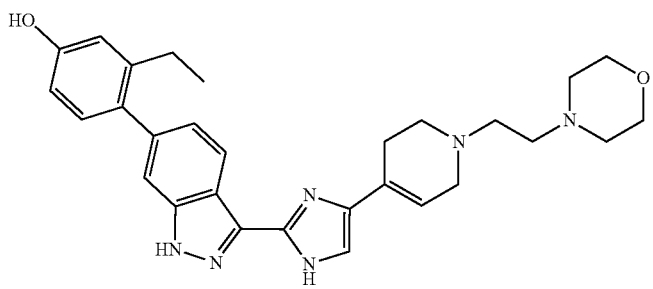 [SMILES: CCc1cc(O)ccc1-c1ccc2c(-c3nc(C4=CCN(CCN5CCOCC5)CC4)c[nH]3)n[nH]c2c1]
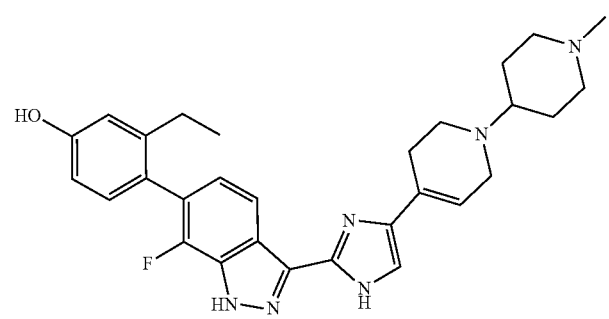 [SMILES: CCc1cc(O)ccc1-c1ccc2c(-c3nc(C4=CCN(C5CCN(C)CC5)CC4)c[nH]3)n[nH]c2c1F]

| Structure |
|---|
| 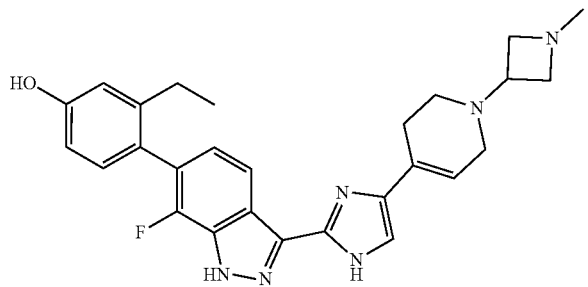 [SMILES: CCc1cc(O)ccc1-c1ccc2c(-c3nc(C4=CCN(C5CN(C)C5)CC4)c[nH]3)n[nH]c2c1F] |
| 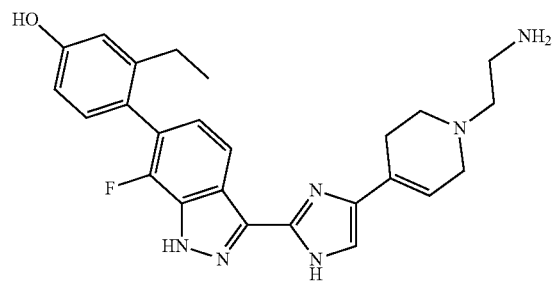 [SMILES: CCc1cc(O)ccc1-c1ccc2c(-c3nc(C4=CCN(CCN)CC4)c[nH]3)n[nH]c2c1F] |
| 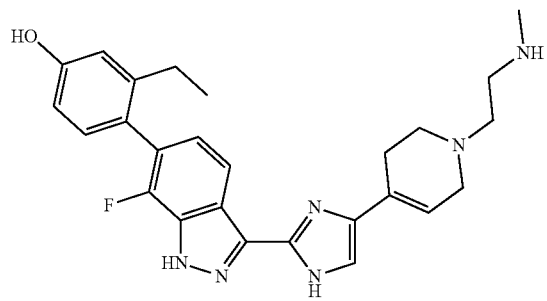 [SMILES: CCc1cc(O)ccc1-c1ccc2c(-c3nc(C4=CCN(CCNC)CC4)c[nH]3)n[nH]c2c1F] |
| 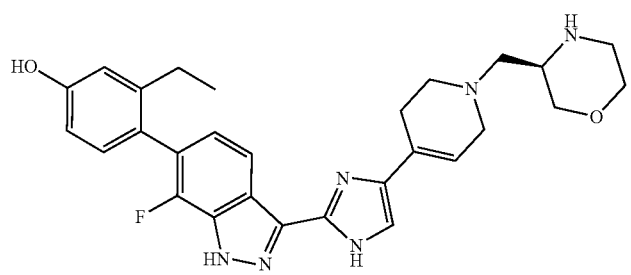 [SMILES: CCc1cc(O)ccc1-c1ccc2c(-c3nc(C4=CCN(C[C@@H]5COCCN5)CC4)c[nH]3)n[nH]c2c1F] |
| 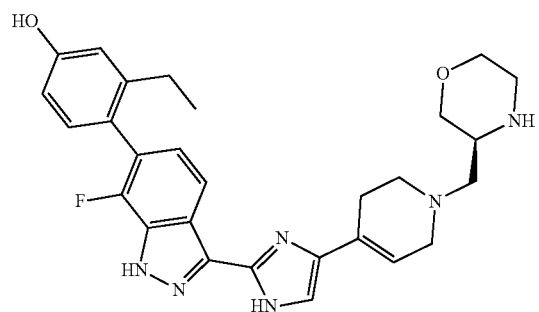 [SMILES: CCc1cc(O)ccc1-c1ccc2c(-c3nc(C4=CCN(C[C@H]5COCCN5)CC4)c[nH]3)n[nH]c2c1F] |

325
-continued
| Structure |
|---|
| 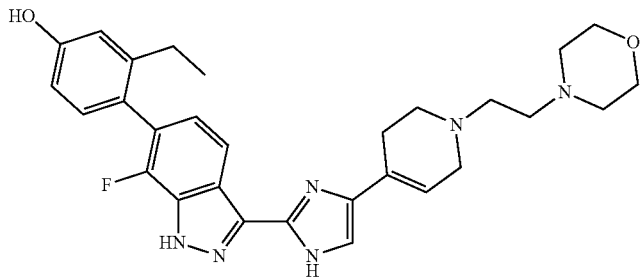 [SMILES: CCc1cc(O)ccc1-c1ccc2c(-c3nc(C4=CCN(CCN5CCOCC5)CC4)c[nH]3)n[nH]c2c1F] |
| 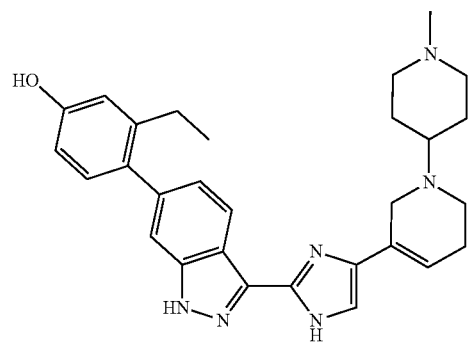 [SMILES: CCc1cc(O)ccc1-c1ccc2c(-c3nc(C4=CCCN(C5CCN(C)CC5)C4)c[nH]3)n[nH]c2c1] |
| 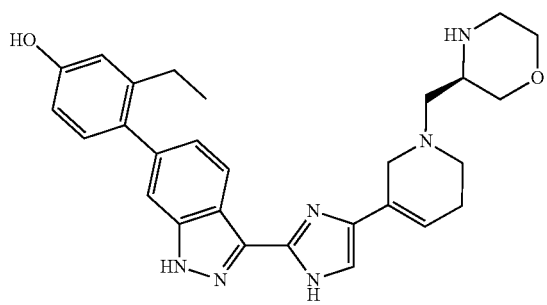 [SMILES: CCc1cc(O)ccc1-c1ccc2c(-c3nc(C4=CCCN(C[C@@H]5COCCN5)C4)c[nH]3)n[nH]c2c1] |
| 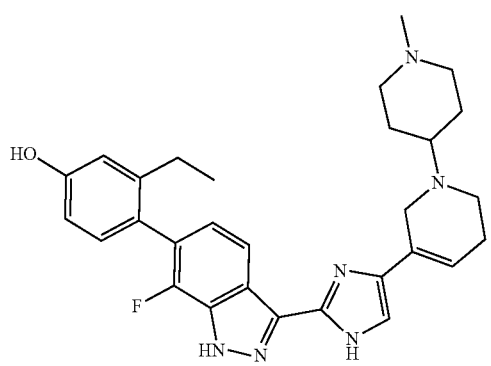 [SMILES: CCc1cc(O)ccc1-c1ccc2c(-c3nc(C4=CCCN(C5CCN(C)CC5)C4)c[nH]3)n[nH]c2c1F] |
| 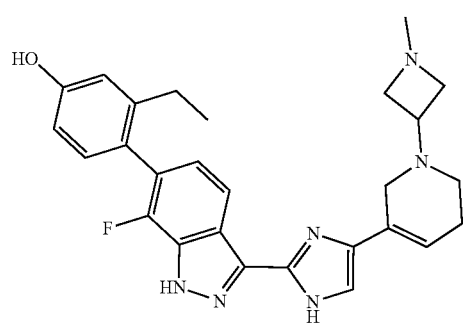 [SMILES: CCc1cc(O)ccc1-c1ccc2c(-c3nc(C4=CCCN(C5CN(C)C5)C4)c[nH]3)n[nH]c2c1F] |

-continued
| Structure |
|---|
| 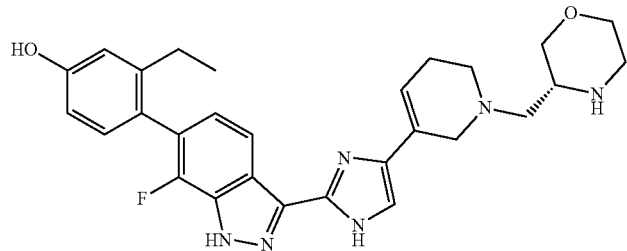 [SMILES: CCc1cc(O)ccc1-c1ccc2c(-c3nc(C4=CCCN(C[C@@H]5COCCN5)C4)c[nH]3)n[nH]c2c1F] |
| 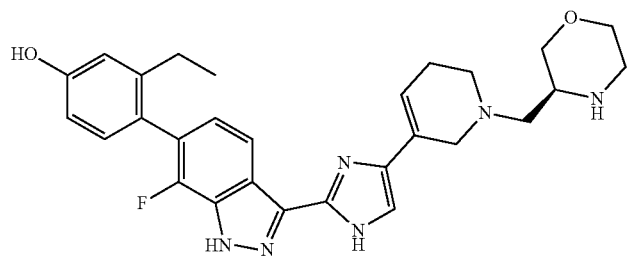 [SMILES: CCc1cc(O)ccc1-c1ccc2c(-c3nc(C4=CCCN(C[C@H]5COCCN5)C4)c[nH]3)n[nH]c2c1F] |
| 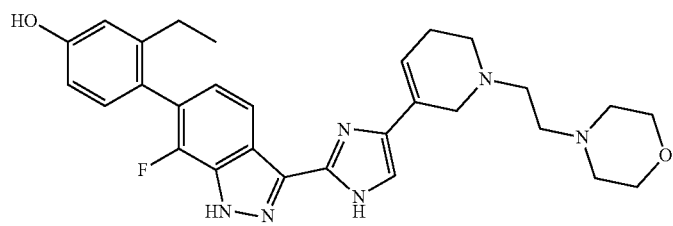 [SMILES: CCc1cc(O)ccc1-c1ccc2c(-c3nc(C4=CCCN(CCN5CCOCC5)C4)c[nH]3)n[nH]c2c1F] |
| 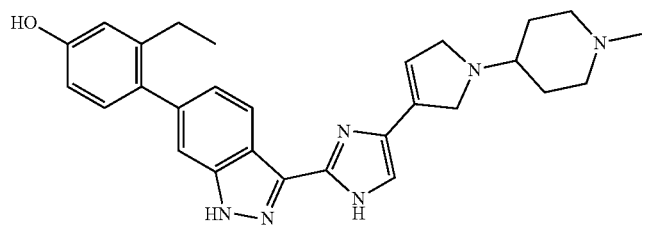 [SMILES: CCc1cc(O)ccc1-c1ccc2c(-c3nc(C4=CCN(C5CCN(C)CC5)C4)c[nH]3)n[nH]c2c1] |
| 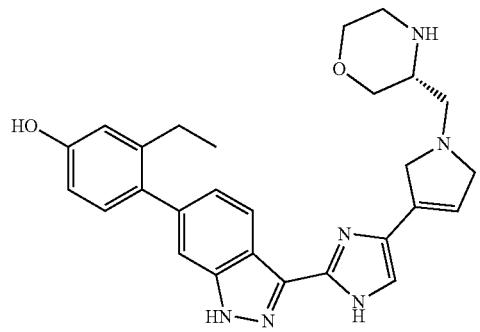 [SMILES: CCc1cc(O)ccc1-c1ccc2c(-c3nc(C4=CCN(C[C@@H]5COCCN5)C4)c[nH]3)n[nH]c2c1] |
| 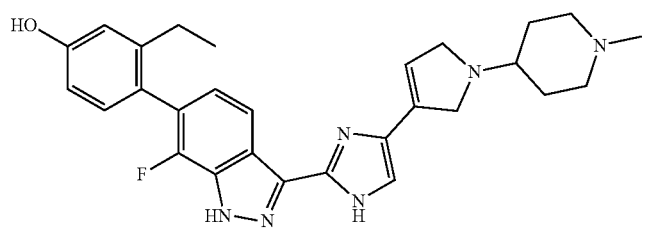 [SMILES: CCc1cc(O)ccc1-c1ccc2c(-c3nc(C4=CCN(C5CCN(C)CC5)C4)c[nH]3)n[nH]c2c1F] |

| Structure |
|---|
| 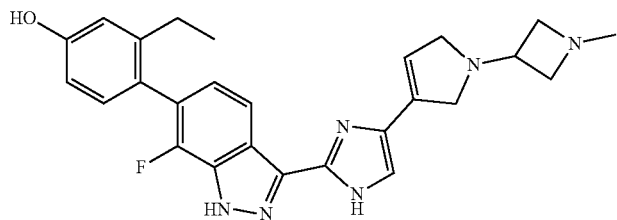 [SMILES: CCc1cc(O)ccc1-c1ccc2c(-c3nc(C4=CCN(C5CN(C)C5)C4)c[nH]3)n[nH]c2c1F] |
| 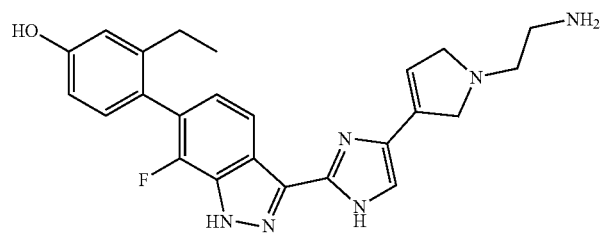 [SMILES: CCc1cc(O)ccc1-c1ccc2c(-c3nc(C4=CCN(CCN)C4)c[nH]3)n[nH]c2c1F] |
| 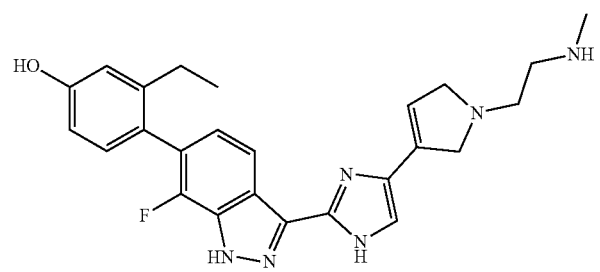 [SMILES: CCc1cc(O)ccc1-c1ccc2c(-c3nc(C4=CCN(CCNC)C4)c[nH]3)n[nH]c2c1F] |
| 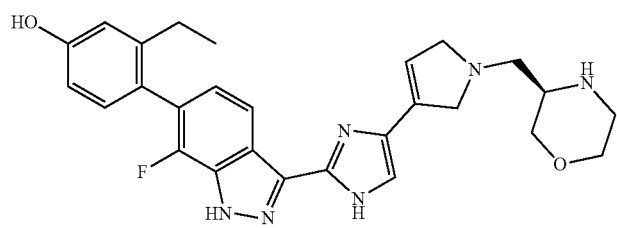 [SMILES: CCc1cc(O)ccc1-c1ccc2c(-c3nc(C4=CCN(C[C@@H]5COCCN5)C4)c[nH]3)n[nH]c2c1F] |
| 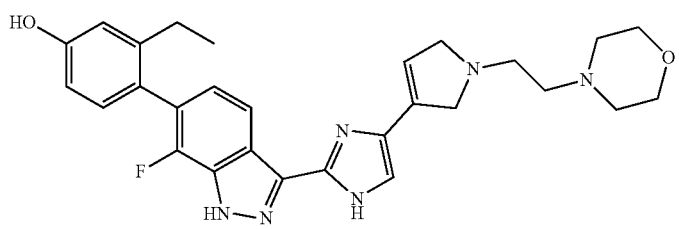 [SMILES: CCc1cc(O)ccc1-c1ccc2c(-c3nc(C4=CCN(CCN5CCOCC5)C4)c[nH]3)n[nH]c2c1F] |
| 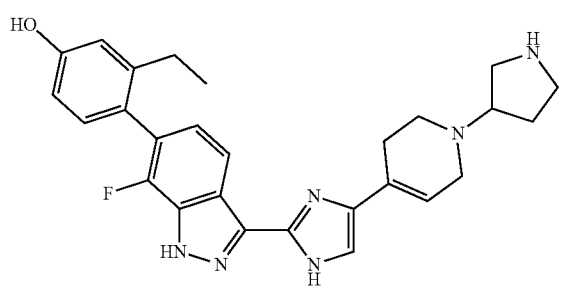 [SMILES: CCc1cc(O)ccc1-c1ccc2c(-c3nc(C4=CCN(C5CCNC5)CC4)c[nH]3)n[nH]c2c1F] |

-continued
| Structure |
| --- |
| 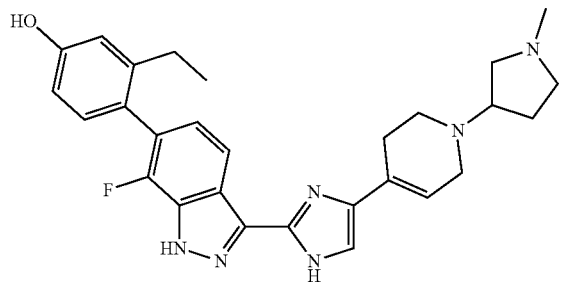 [SMILES: CCc1cc(O)ccc1-c1ccc2c(-c3nc(C4=CCN(C5CCN(C)C5)CC4)c[nH]3)n[nH]c2c1F] |
| 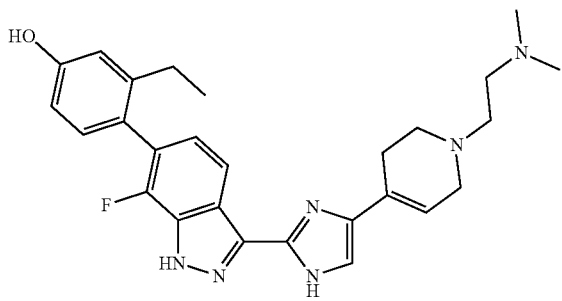 [SMILES: CCc1cc(O)ccc1-c1ccc2c(-c3nc(C4=CCN(CCN(C)C)CC4)c[nH]3)n[nH]c2c1F] |
| 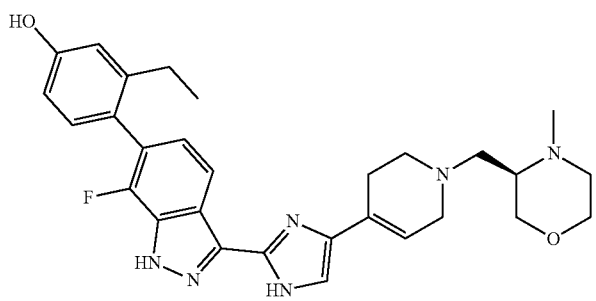 [SMILES: CCc1cc(O)ccc1-c1ccc2c(-c3nc(C4=CCN(C[C@@H]5COCCN5C)CC4)c[nH]3)n[nH]c2c1F] |
| 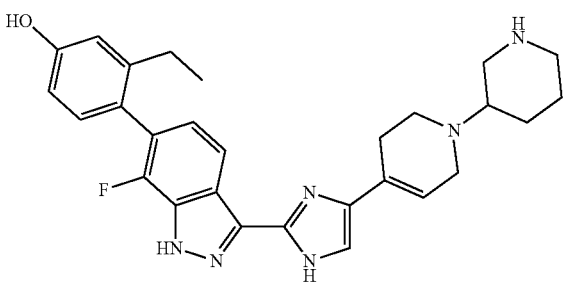 [SMILES: CCc1cc(O)ccc1-c1ccc2c(-c3nc(C4=CCN(C5CCCNC5)CC4)c[nH]3)n[nH]c2c1F] |
| 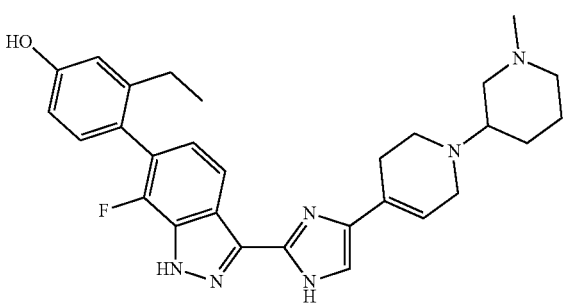 [SMILES: CCc1cc(O)ccc1-c1ccc2c(-c3nc(C4=CCN(C5CCCN(C)C5)CC4)c[nH]3)n[nH]c2c1F] |

| Structure |
|---|
| 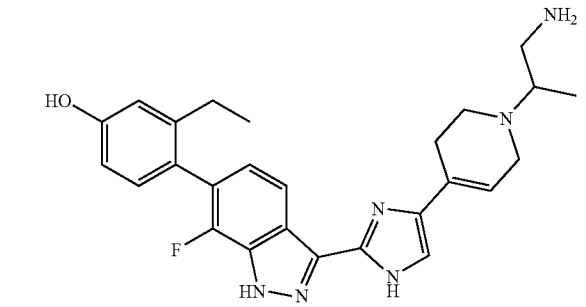 [SMILES: CCc1cc(O)ccc1-c1ccc2c(-c3nc(C4=CCN(C(C)CN)CC4)c[nH]3)n[nH]c2c1F] |
| 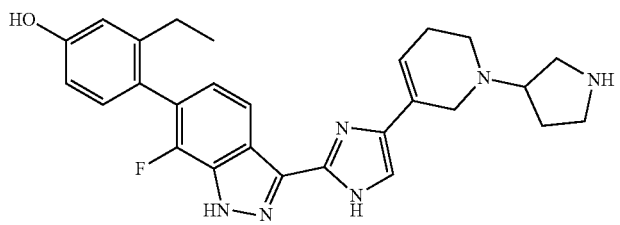 [SMILES: CCc1cc(O)ccc1-c1ccc2c(-c3nc(C4=CCCN(C5CCNC5)C4)c[nH]3)n[nH]c2c1F] |
| 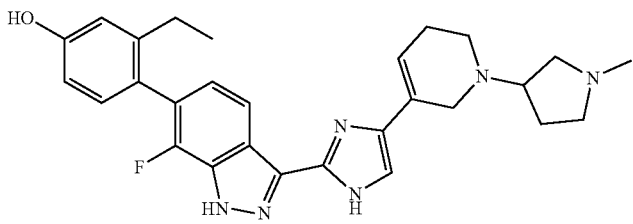 [SMILES: CCc1cc(O)ccc1-c1ccc2c(-c3nc(C4=CCCN(C5CCN(C)C5)C4)c[nH]3)n[nH]c2c1F] |
| 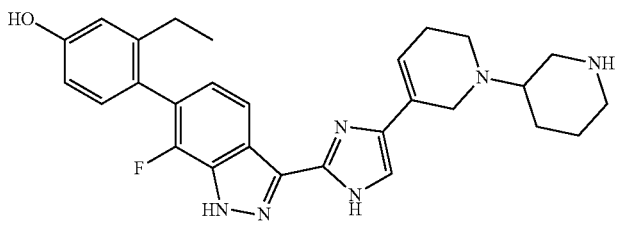 [SMILES: CCc1cc(O)ccc1-c1ccc2c(-c3nc(C4=CCCN(C5CCCNC5)C4)c[nH]3)n[nH]c2c1F] |
| 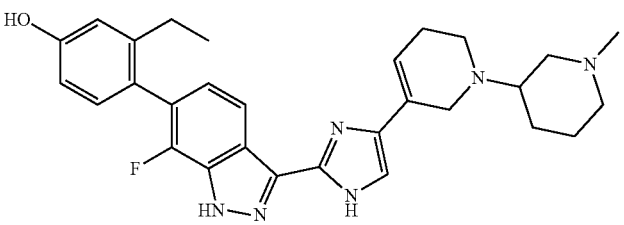 [SMILES: CCc1cc(O)ccc1-c1ccc2c(-c3nc(C4=CCCN(C5CCCN(C)C5)C4)c[nH]3)n[nH]c2c1F] |
| 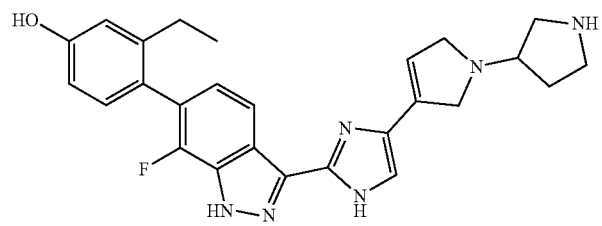 [SMILES: CCc1cc(O)ccc1-c1ccc2c(-c3nc(C4=CCN(C5CCNC5)C4)c[nH]3)n[nH]c2c1F] |

-continued
| Structure |
|---|
| 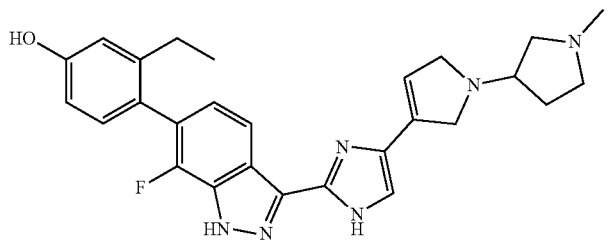 [SMILES: CCc1cc(O)ccc1-c1ccc2c(-c3nc(C4=CCN(C5CCN(C)C5)C4)c[nH]3)n[nH]c2c1F] |
| 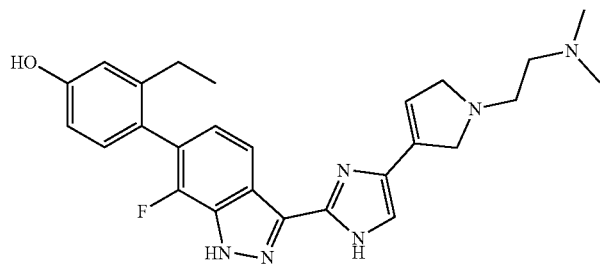 [SMILES: CCc1cc(O)ccc1-c1ccc2c(-c3nc(C4=CCN(CCN(C)C)C4)c[nH]3)n[nH]c2c1F] |
| 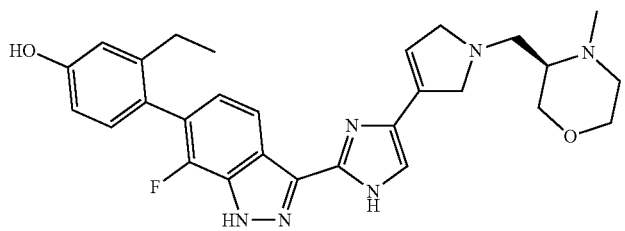 [SMILES: CCc1cc(O)ccc1-c1ccc2c(-c3nc(C4=CCN(C[C@@H]5COCCN5C)C4)c[nH]3)n[nH]c2c1F] |
| 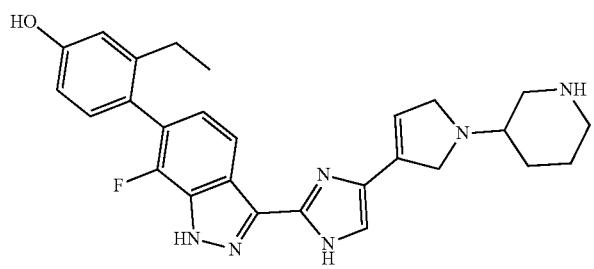 [SMILES: CCc1cc(O)ccc1-c1ccc2c(-c3nc(C4=CCN(C5CCCNC5)C4)c[nH]3)n[nH]c2c1F] |
| 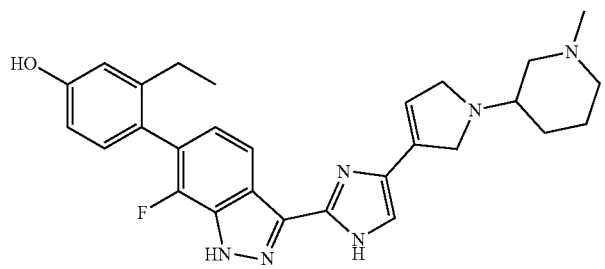 [SMILES: CCc1cc(O)ccc1-c1ccc2c(-c3nc(C4=CCN(C5CCCN(C)C5)C4)c[nH]3)n[nH]c2c1F] |
| 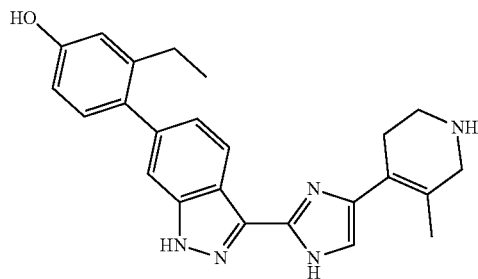 [SMILES: CCc1cc(O)ccc1-c1ccc2c(-c3nc(C4=C(C)CNCC4)c[nH]3)n[nH]c2c1] |

| Structure |
|---|
| 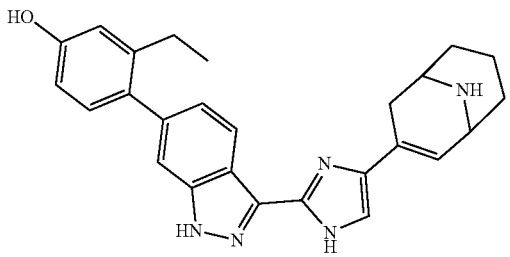 [SMILES: CCc1cc(O)ccc1-c1ccc2c(-c3nc(C4=CC5CCCC(C4)N5)c[nH]3)n[nH]c2c1] |
| 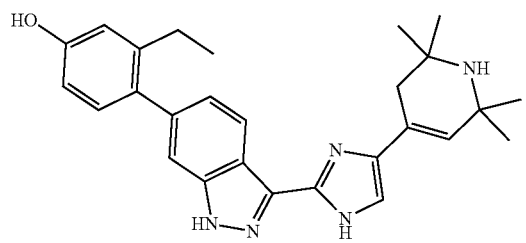 [SMILES: CCc1cc(O)ccc1-c1ccc2c(-c3nc(C4=CC(C)(C)NC(C)(C)C4)c[nH]3)n[nH]c2c1] |
| 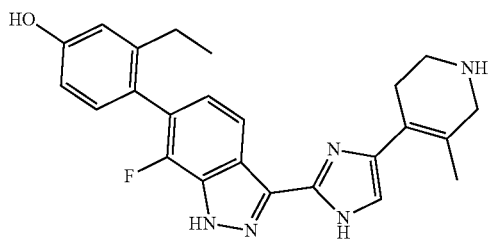 [SMILES: CCc1cc(O)ccc1-c1ccc2c(-c3nc(C4=C(C)CNCC4)c[nH]3)n[nH]c2c1F] |
| 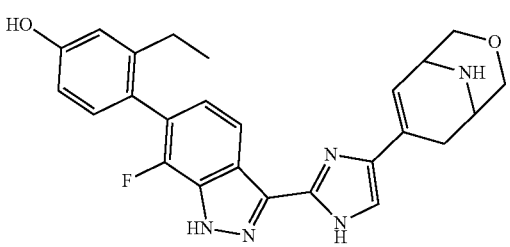 [SMILES: CCc1cc(O)ccc1-c1ccc2c(-c3nc(C4=CC5COCC(C4)N5)c[nH]3)n[nH]c2c1F] |
| 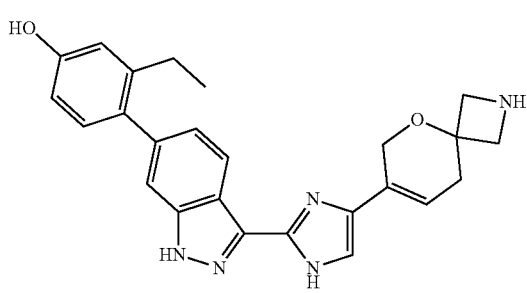 [SMILES: CCc1cc(O)ccc1-c1ccc2c(-c3nc(C4=CCC5(CNC5)OC4)c[nH]3)n[nH]c2c1] |
| 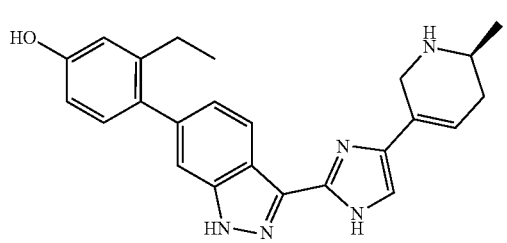 [SMILES: CCc1cc(O)ccc1-c1ccc2c(-c3nc(C4=CC[C@H](C)NC4)c[nH]3)n[nH]c2c1] |

-continued
| Structure |
|---|
| 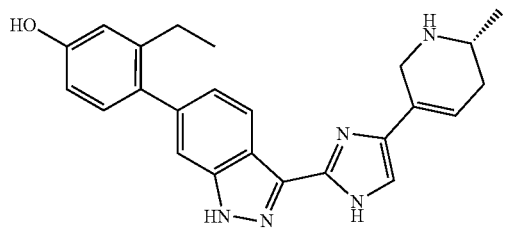 [SMILES: CCc1cc(O)ccc1-c1ccc2c(-c3nc(C4=CC[C@@H](C)NC4)c[nH]3)n[nH]c2c1] |
| 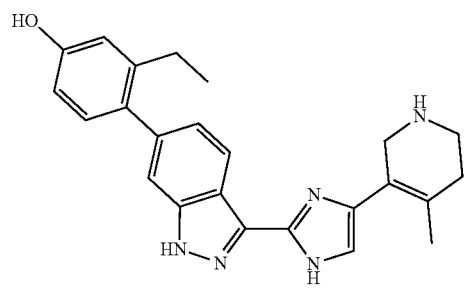 [SMILES: CCc1cc(O)ccc1-c1ccc2c(-c3nc(C4=C(C)CCNC4)c[nH]3)n[nH]c2c1] |
| 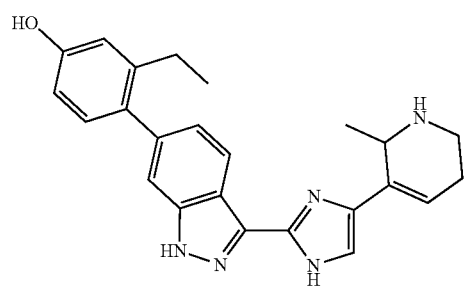 [SMILES: CCc1cc(O)ccc1-c1ccc2c(-c3nc(C4=CCCNC4C)c[nH]3)n[nH]c2c1] |
| 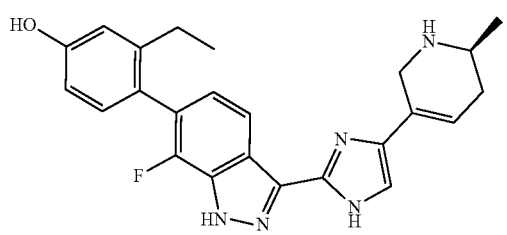 [SMILES: CCc1cc(O)ccc1-c1ccc2c(-c3nc(C4=CC[C@H](C)NC4)c[nH]3)n[nH]c2c1F] |
| 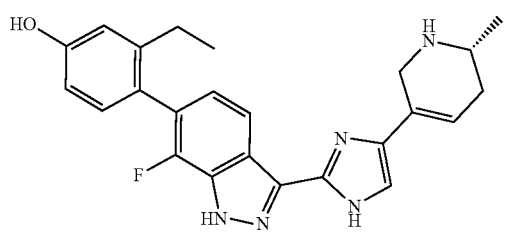 [SMILES: CCc1cc(O)ccc1-c1ccc2c(-c3nc(C4=CC[C@@H](C)NC4)c[nH]3)n[nH]c2c1F] |
| 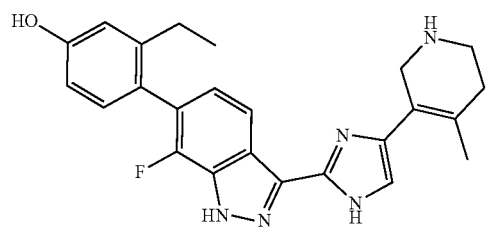 [SMILES: CCc1cc(O)ccc1-c1ccc2c(-c3nc(C4=C(C)CCNC4)c[nH]3)n[nH]c2c1F] |

-continued
| Structure |
|---|
| 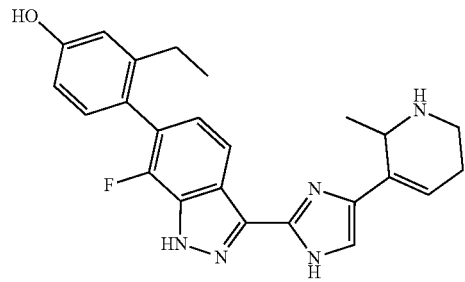 [SMILES: CCc1cc(O)ccc1-c1ccc2c(-c3nc(C4=CCCNC4C)c[nH]3)n[nH]c2c1F] |
| 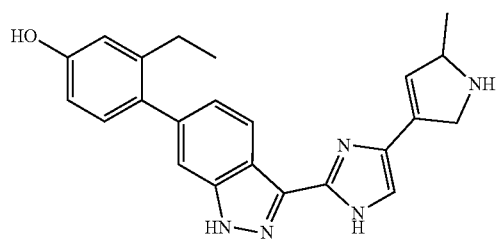 [SMILES: CCc1cc(O)ccc1-c1ccc2c(-c3nc(C4=CC(C)NC4)c[nH]3)n[nH]c2c1] |
| 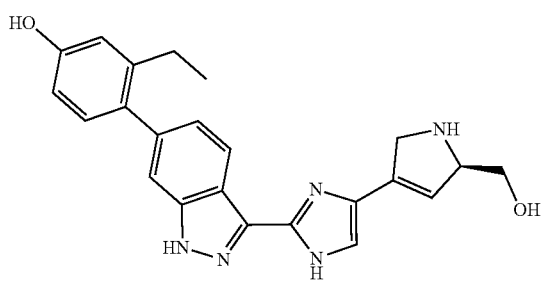 [SMILES: CCc1cc(O)ccc1-c1ccc2c(-c3nc(C4=C[C@H](CO)NC4)c[nH]3)n[nH]c2c1] |
| 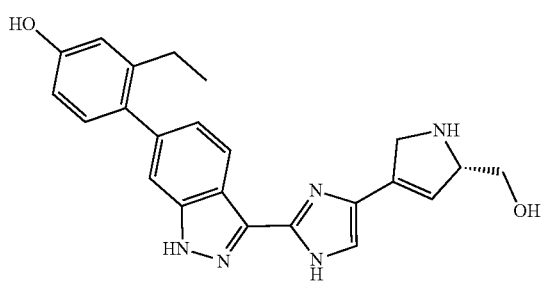 [SMILES: CCc1cc(O)ccc1-c1ccc2c(-c3nc(C4=C[C@@H](CO)NC4)c[nH]3)n[nH]c2c1] |
| 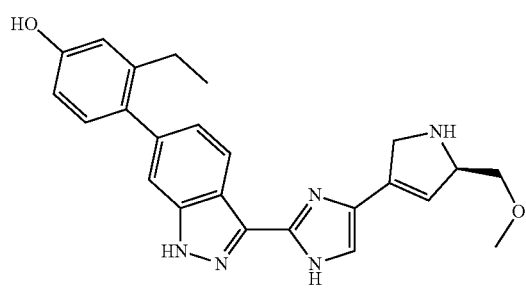 [SMILES: CCc1cc(O)ccc1-c1ccc2c(-c3nc(C4=C[C@H](COC)NC4)c[nH]3)n[nH]c2c1] |

-continued
| Structure |
|---|
| 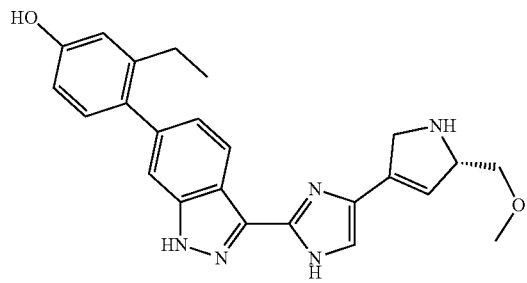 [SMILES: CCc1cc(O)ccc1-c1ccc2c(-c3nc(C4=C[C@@H](COC)NC4)c[nH]3)n[nH]c2c1] |
| 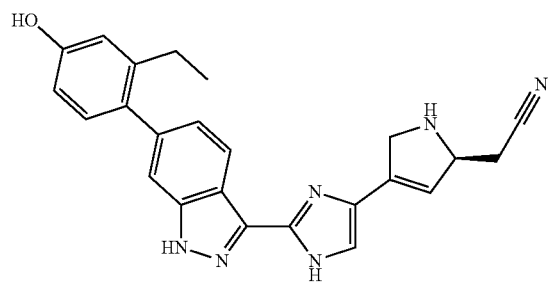 [SMILES: CCc1cc(O)ccc1-c1ccc2c(-c3nc(C4=C[C@H](CC#N)NC4)c[nH]3)n[nH]c2c1] |
| 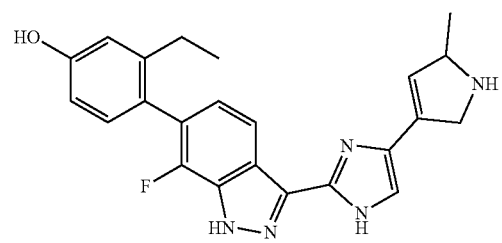 [SMILES: CCc1cc(O)ccc1-c1ccc2c(-c3nc(C4=CC(C)NC4)c[nH]3)n[nH]c2c1F] |
| 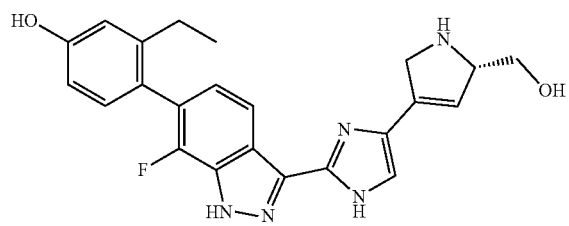 [SMILES: CCc1cc(O)ccc1-c1ccc2c(-c3nc(C4=C[C@@H](CO)NC4)c[nH]3)n[nH]c2c1F] |
| 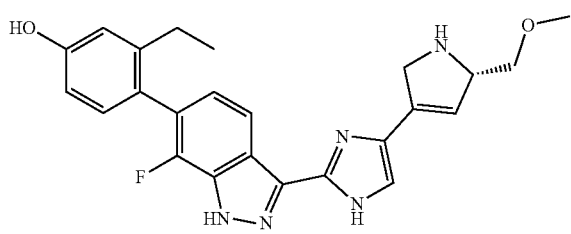 [SMILES: CCc1cc(O)ccc1-c1ccc2c(-c3nc(C4=C[C@@H](COC)NC4)c[nH]3)n[nH]c2c1F] |
| 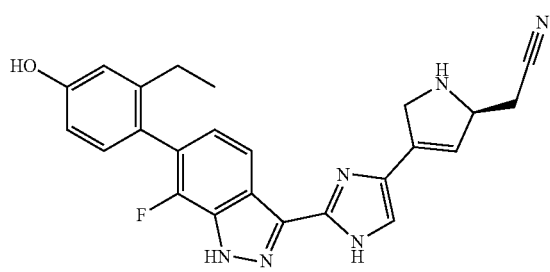 [SMILES: CCc1cc(O)ccc1-c1ccc2c(-c3nc(C4=C[C@H](CC#N)NC4)c[nH]3)n[nH]c2c1F] |

345
-continued
| Structure |
| --- |
| 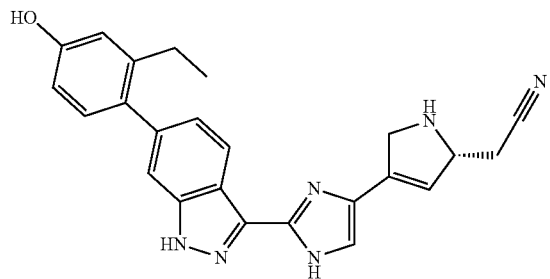 [SMILES: CCc1cc(O)ccc1-c1ccc2c(-c3nc(C4=C[C@@H](CC#N)NC4)c[nH]3)n[nH]c2c1] |
| 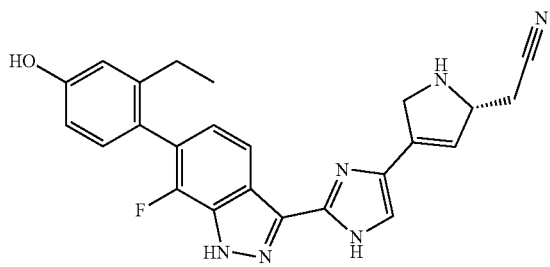 [SMILES: CCc1cc(O)ccc1-c1ccc2c(-c3nc(C4=C[C@@H](CC#N)NC4)c[nH]3)n[nH]c2c1F] |
| 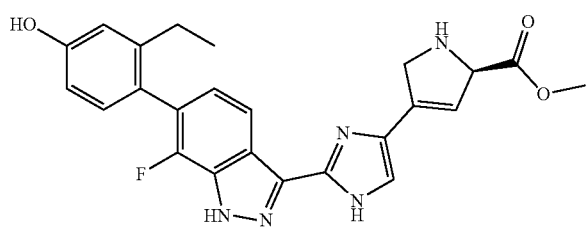 [SMILES: CCc1cc(O)ccc1-c1ccc2c(-c3nc(C4=C[C@H](C(=O)OC)NC4)c[nH]3)n[nH]c2c1F] |
| 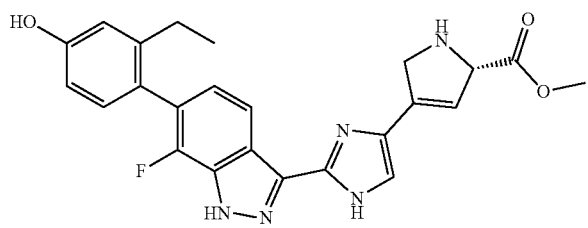 [SMILES: CCc1cc(O)ccc1-c1ccc2c(-c3nc(C4=C[C@@H](C(=O)OC)NC4)c[nH]3)n[nH]c2c1F] |
| 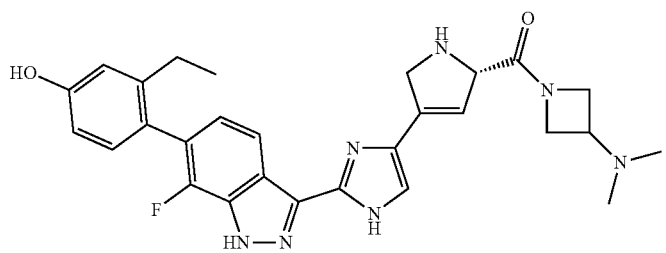 [SMILES: CCc1cc(O)ccc1-c1ccc2c(-c3nc(C4=C[C@@H](C(=O)N5CC(N(C)C)C5)NC4)c[nH]3)n[nH]c2c1F] |
| 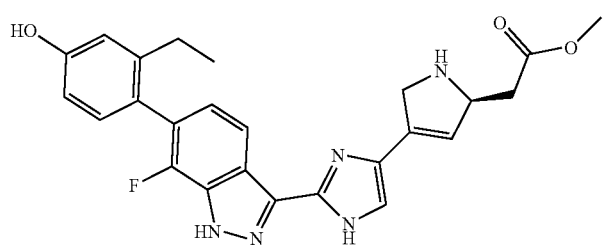 [SMILES: CCc1cc(O)ccc1-c1ccc2c(-c3nc(C4=C[C@H](CC(=O)OC)NC4)c[nH]3)n[nH]c2c1F] |

-continued
Structure
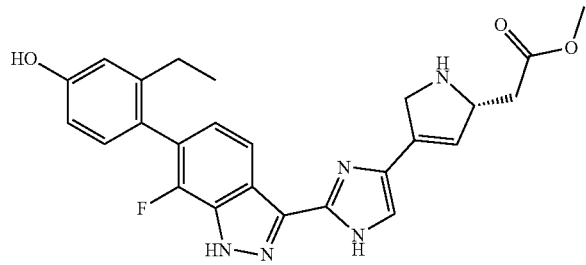 [SMILES: CCc1cc(O)ccc1-c1ccc2c(-c3nc(C4=C[C@@H](CC(=O)OC)NC4)c[nH]3)n[nH]c2c1F]
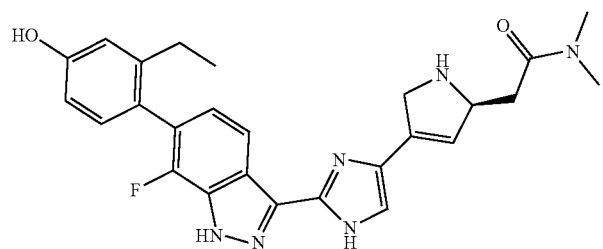 [SMILES: CCc1cc(O)ccc1-c1ccc2c(-c3nc(C4=C[C@H](CC(=O)N(C)C)NC4)c[nH]3)n[nH]c2c1F]
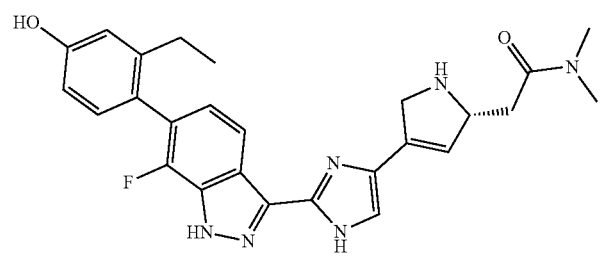 [SMILES: CCc1cc(O)ccc1-c1ccc2c(-c3nc(C4=C[C@@H](CC(=O)N(C)C)NC4)c[nH]3)n[nH]c2c1F]
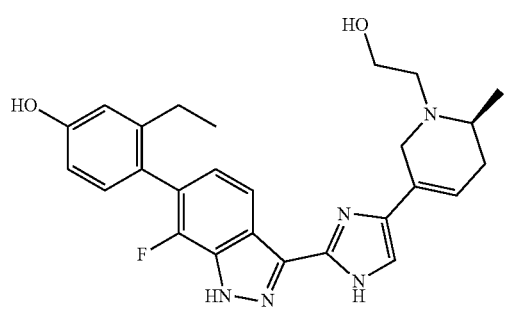 [SMILES: CCc1cc(O)ccc1-c1ccc2c(-c3nc(C4=CC[C@H](C)N(CCO)C4)c[nH]3)n[nH]c2c1F]
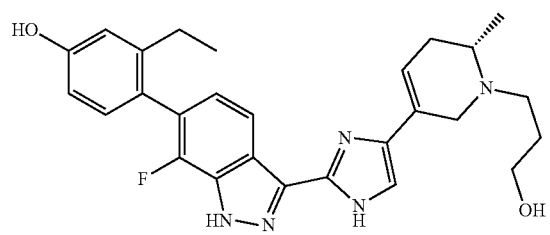 [SMILES: CCc1cc(O)ccc1-c1ccc2c(-c3nc(C4=CC[C@H](C)N(CCCO)C4)c[nH]3)n[nH]c2c1F]

| Structure |
| --- |
| 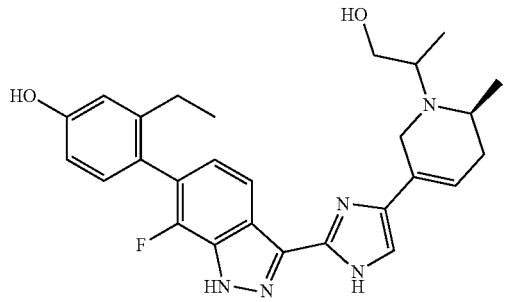 [SMILES: CCc1cc(O)ccc1-c1ccc2c(-c3nc(C4=CC[C@H](C)N(C(C)CO)C4)c[nH]3)n[nH]c2c1F] |
| 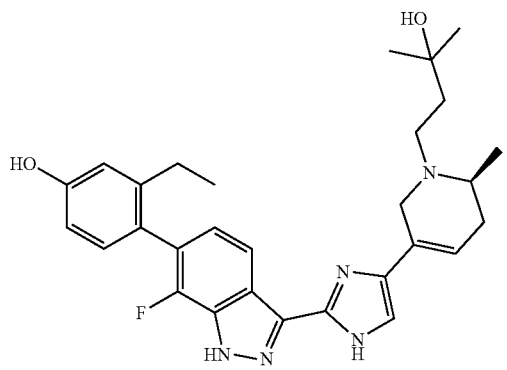 [SMILES: CCc1cc(O)ccc1-c1ccc2c(-c3nc(C4=CC[C@H](C)N(CCC(C)(C)O)C4)c[nH]3)n[nH]c2c1F] |
| 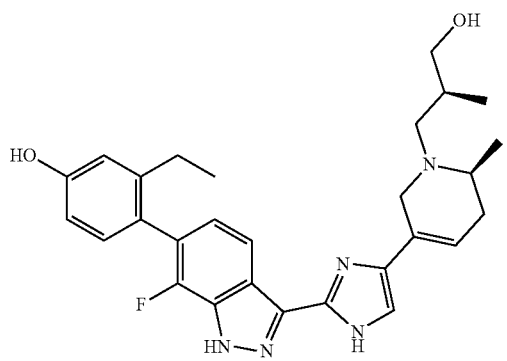 [SMILES: CCc1cc(O)ccc1-c1ccc2c(-c3nc(C4=CC[C@H](C)N(C[C@H](C)CO)C4)c[nH]3)n[nH]c2c1F] |
| 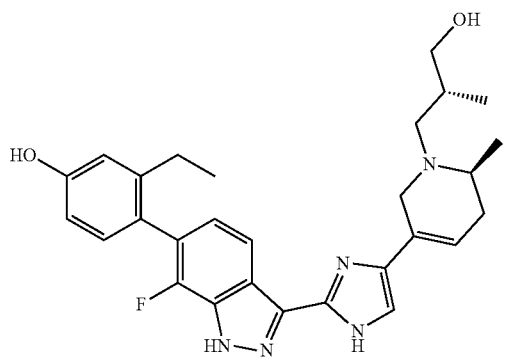 [SMILES: CCc1cc(O)ccc1-c1ccc2c(-c3nc(C4=CC[C@H](C)N(C[C@@H](C)CO)C4)c[nH]3)n[nH]c2c1F] |

-continued
Structure
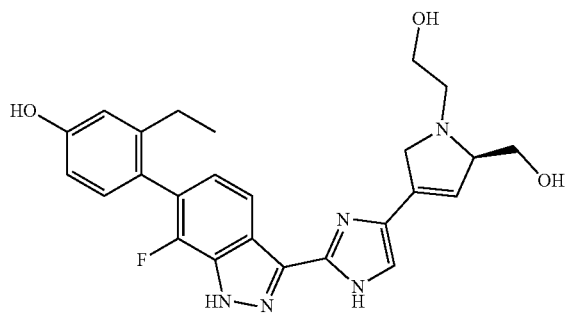 [SMILES: CCc1cc(O)ccc1-c1ccc2c(-c3nc(C4=C[C@H](CO)N(CCO)C4)c[nH]3)n[nH]c2c1F]
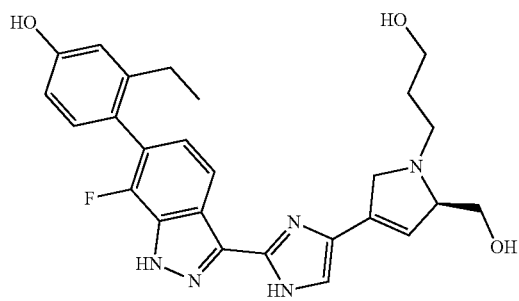 [SMILES: CCc1cc(O)ccc1-c1ccc2c(-c3nc(C4=C[C@H](CO)N(CCCO)C4)c[nH]3)n[nH]c2c1F]
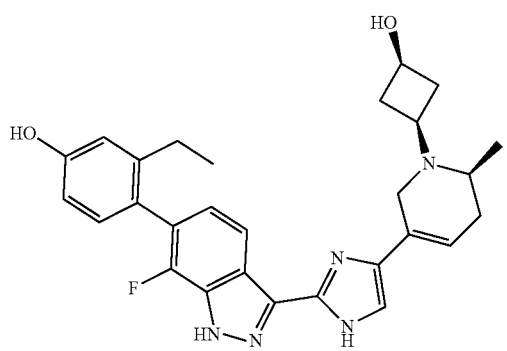 [SMILES: CCc1cc(O)ccc1-c1ccc2c(-c3nc(C4=CC[C@H](C)N([C@H]5C[C@@H](O)C5)C4)c[nH]3)n[nH]c2c1F]
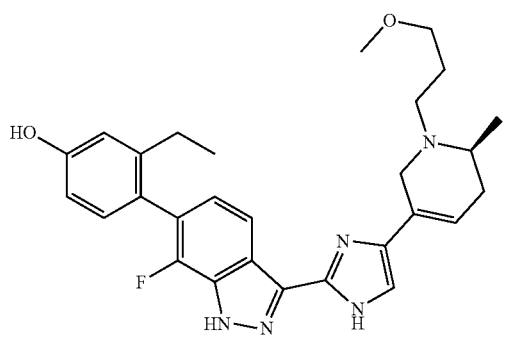 [SMILES: CCc1cc(O)ccc1-c1ccc2c(-c3nc(C4=CC[C@H](C)N(CCCOC)C4)c[nH]3)n[nH]c2c1F]
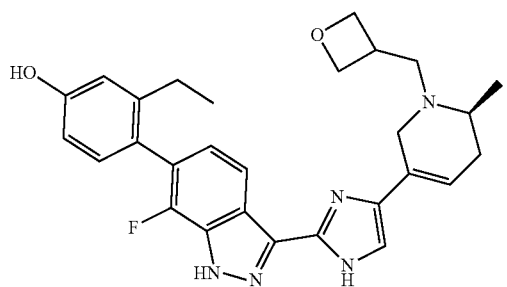 [SMILES: CCc1cc(O)ccc1-c1ccc2c(-c3nc(C4=CC[C@H](C)N(CC5COC5)C4)c[nH]3)n[nH]c2c1F]

-continued
Structure
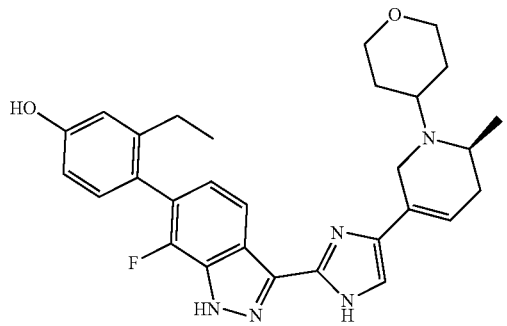 [SMILES: CCc1cc(O)ccc1-c1ccc2c(-c3nc(C4=CC[C@H](C)N(C5CCOCC5)C4)c[nH]3)n[nH]c2c1F]
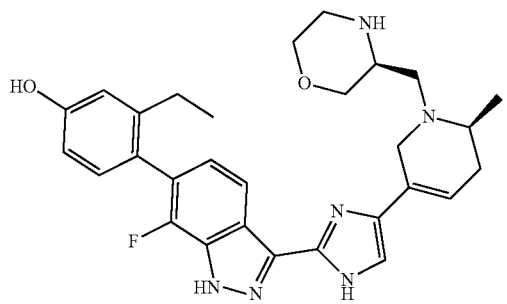 [SMILES: CCc1cc(O)ccc1-c1ccc2c(-c3nc(C4=CC[C@H](C)N(C[C@H]5COCCN5)C4)c[nH]3)n[nH]c2c1F]
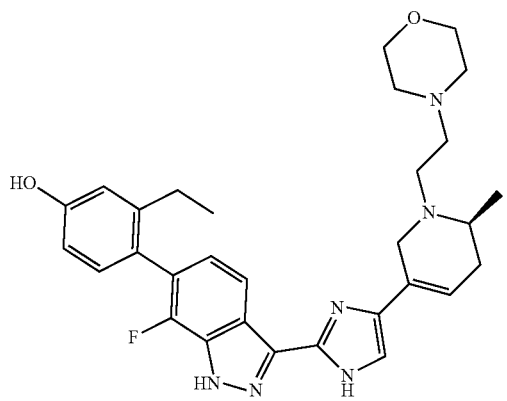 [SMILES: CCc1cc(O)ccc1-c1ccc2c(-c3nc(C4=CC[C@H](C)N(CCN5CCOCC5)C4)c[nH]3)n[nH]c2c1F]
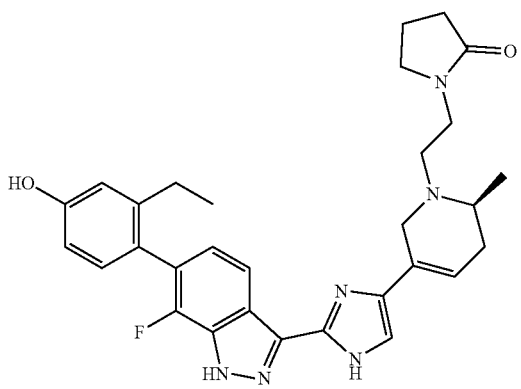 [SMILES: CCc1cc(O)ccc1-c1ccc2c(-c3nc(C4=CC[C@H](C)N(CCN5CCCC5=O)C4)c[nH]3)n[nH]c2c1F]

-continued
Structure
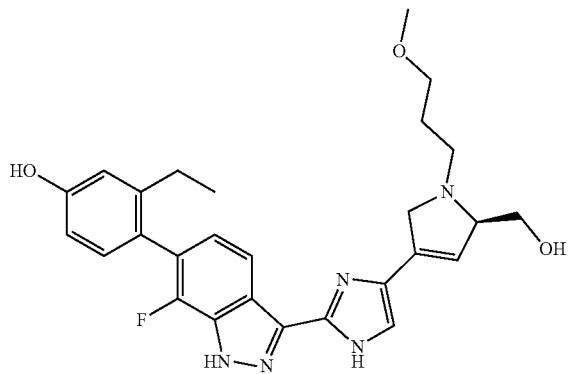 [SMILES: CCc1cc(O)ccc1-c1ccc2c(-c3nc(C4=C[C@H](CO)N(CCCOC)C4)c[nH]3)n[nH]c2c1F]
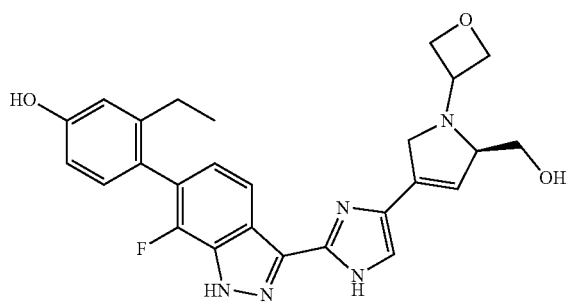 [SMILES: CCc1cc(O)ccc1-c1ccc2c(-c3nc(C4=C[C@H](CO)N(C5COC5)C4)c[nH]3)n[nH]c2c1F]
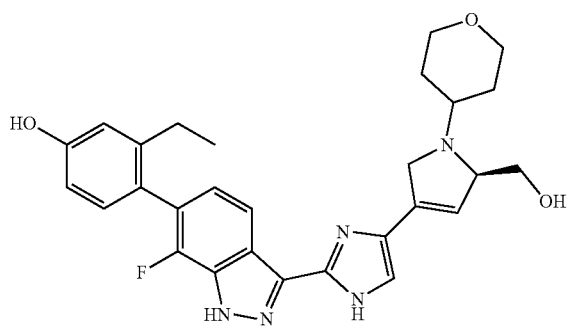 [SMILES: CCc1cc(O)ccc1-c1ccc2c(-c3nc(C4=C[C@H](CO)N(C5CCOCC5)C4)c[nH]3)n[nH]c2c1F]
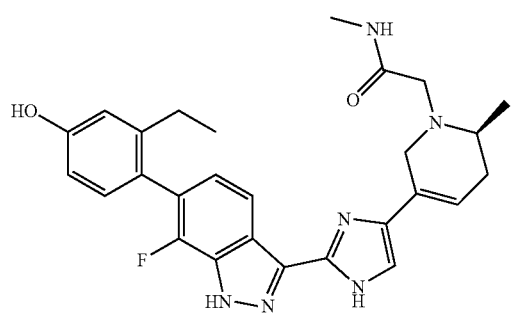 [SMILES: CCc1cc(O)ccc1-c1ccc2c(-c3nc(C4=CC[C@H](C)N(CC(=O)NC)C4)c[nH]3)n[nH]c2c1F]

| Structure |
|---|
| 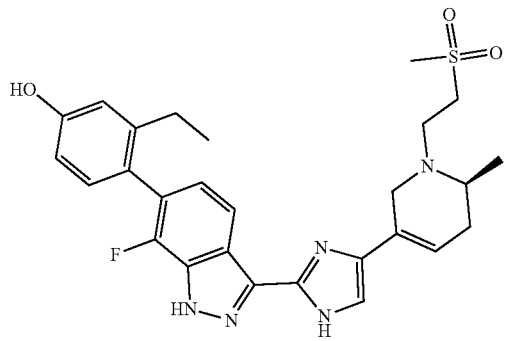 [SMILES: CCc1cc(O)ccc1-c1ccc2c(-c3nc(C4=CC[C@H](C)N(CCS(C)(=O)=O)C4)c[nH]3)n[nH]c2c1F] |
| 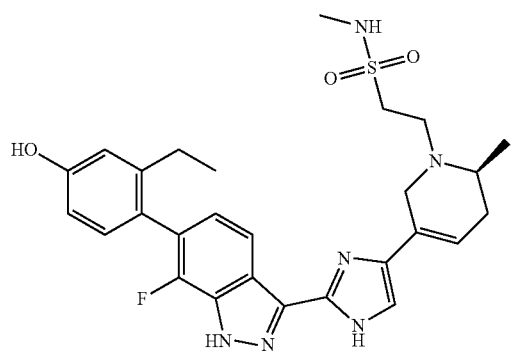 [SMILES: CCc1cc(O)ccc1-c1ccc2c(-c3nc(C4=CC[C@H](C)N(CCS(=O)(=O)NC)C4)c[nH]3)n[nH]c2c1F] |
| 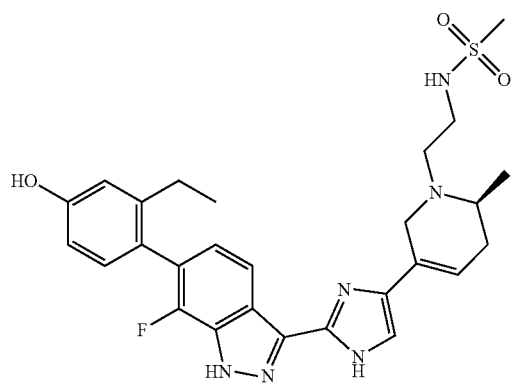 [SMILES: CCc1cc(O)ccc1-c1ccc2c(-c3nc(C4=CC[C@H](C)N(CCNS(C)(=O)=O)C4)c[nH]3)n[nH]c2c1F] |
| 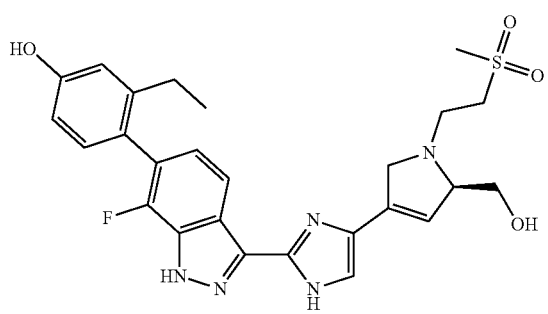 [SMILES: CCc1cc(O)ccc1-c1ccc2c(-c3nc(C4=C[C@H](CO)N(CCS(C)(=O)=O)C4)c[nH]3)n[nH]c2c1F] |

| Structure |
|---|
| 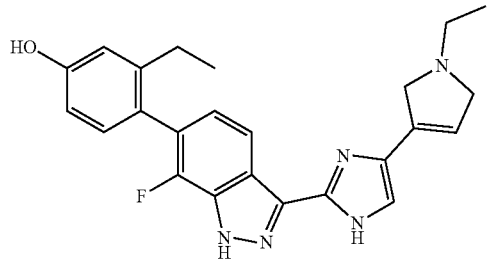 [SMILES: CCc1cc(O)ccc1-c1ccc2c(-c3nc(C4=CCN(CC)C4)c[nH]3)n[nH]c2c1F] |
| 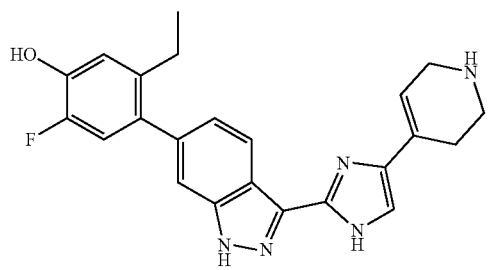 [SMILES: CCc1cc(O)c(F)cc1-c1ccc2c(-c3nc(C4=CCNCC4)c[nH]3)n[nH]c2c1] |
| 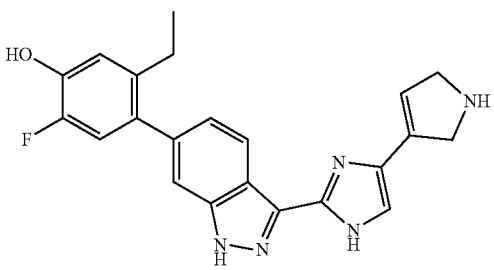 [SMILES: CCc1cc(O)c(F)cc1-c1ccc2c(-c3nc(C4=CCNC4)c[nH]3)n[nH]c2c1] |
| 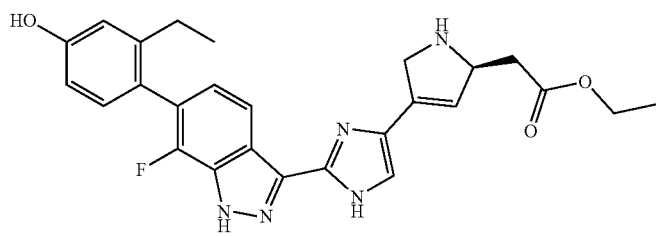 [SMILES: CCOC(=O)C[C@H]1C=C(c2c[nH]c(-c3n[nH]c4c(F)c(-c5ccc(O)cc5CC)ccc34)n2)CN1] |
| 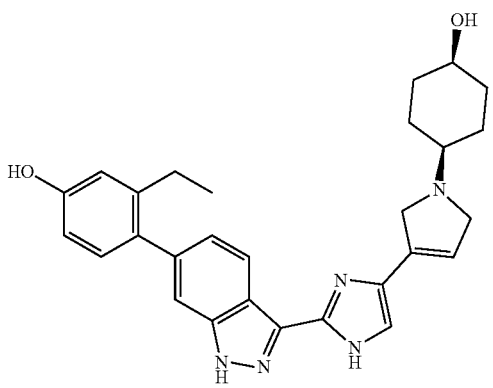 [SMILES: CCc1cc(O)ccc1-c1ccc2c(-c3nc(C4=CCN([C@H]5CC[C@@H](O)CC5)C4)c[nH]3)n[nH]c2c1] |

-continued
| Structure |
|---|
| 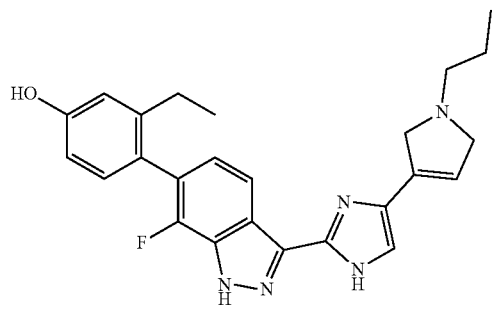 [SMILES: CCCN1CC=C(c2c[nH]c(-c3n[nH]c4c(F)c(-c5ccc(O)cc5CC)ccc34)n2)C1] |
| 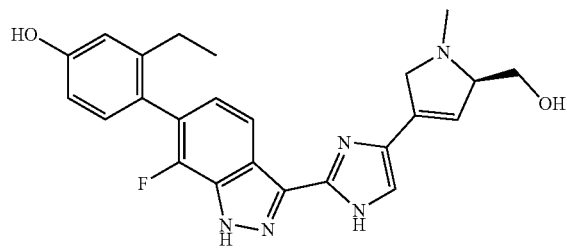 [SMILES: CCc1cc(O)ccc1-c1ccc2c(-c3nc(C4=C[C@H](CO)N(C)C4)c[nH]3)n[nH]c2c1F] |
| 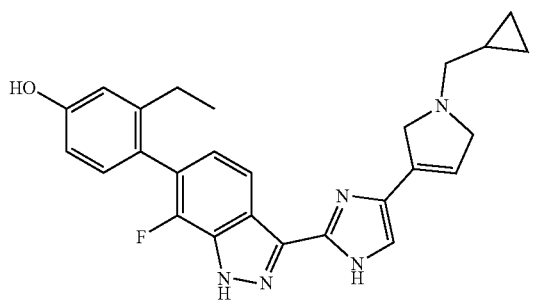 [SMILES: CCc1cc(O)ccc1-c1ccc2c(-c3nc(C4=CCN(CC5CC5)C4)c[nH]3)n[nH]c2c1F] |
| 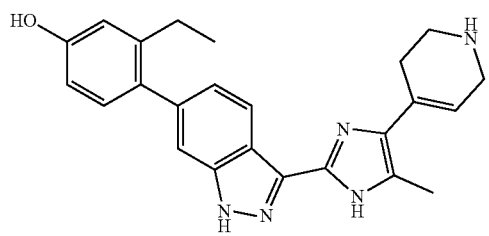 [SMILES: CCc1cc(O)ccc1-c1ccc2c(-c3nc(C4=CCNCC4)c(C)[nH]3)n[nH]c2c1] |
| 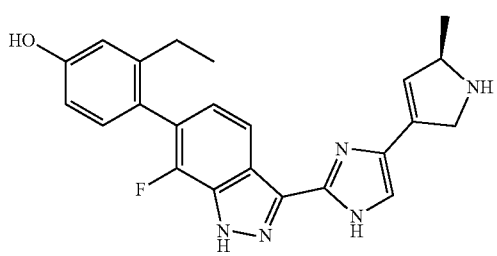 [SMILES: CCc1cc(O)ccc1-c1ccc2c(-c3nc(C4=C[C@@H](C)NC4)c[nH]3)n[nH]c2c1F] |
| 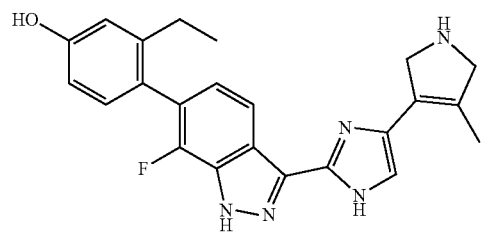 [SMILES: CCc1cc(O)ccc1-c1ccc2c(-c3nc(C4=C(C)CNC4)c[nH]3)n[nH]c2c1F] |

-continued
| Structure |
|---|
| 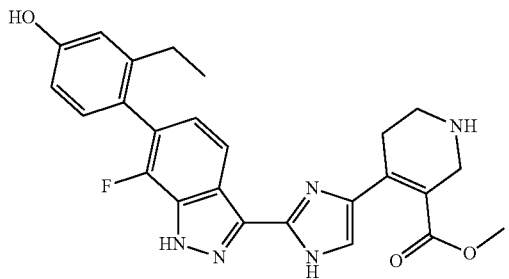 [SMILES: CCc1cc(O)ccc1-c1ccc2c(-c3nc(C4=C(C(=O)OC)CNCC4)c[nH]3)n[nH]c2c1F] |
| 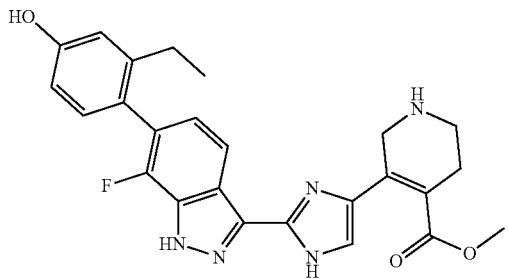 [SMILES: CCc1cc(O)ccc1-c1ccc2c(-c3nc(C4=C(C(=O)OC)CCNC4)c[nH]3)n[nH]c2c1F] |
| 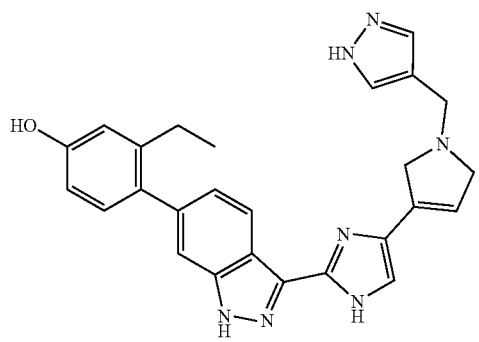 [SMILES: CCc1cc(O)ccc1-c1ccc2c(-c3nc(C4=CCN(Cc5cn[nH]c5)C4)c[nH]3)n[nH]c2c1] |
| 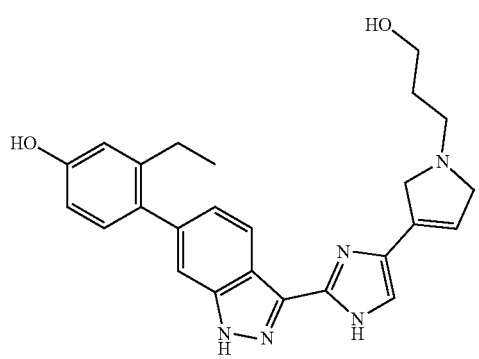 [SMILES: CCc1cc(O)ccc1-c1ccc2c(-c3nc(C4=CCN(CCCO)C4)c[nH]3)n[nH]c2c1] |
| 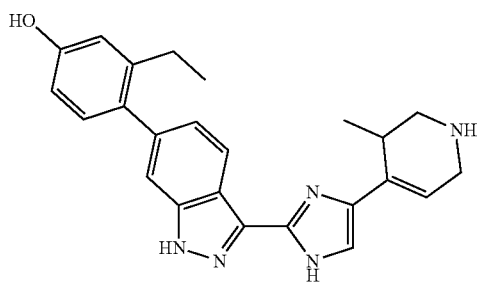 [SMILES: CCc1cc(O)ccc1-c1ccc2c(-c3nc(C4=CCNCC4C)c[nH]3)n[nH]c2c1] |

-continued
Structure
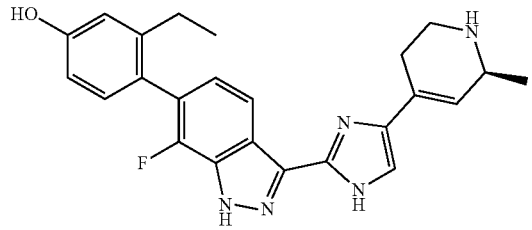 [SMILES: CCc1cc(O)ccc1-c1ccc2c(-c3nc(C4=C[C@H](C)NCC4)c[nH]3)n[nH]c2c1F]
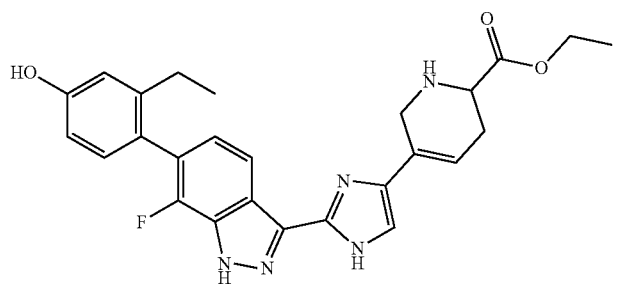 [SMILES: CCOC(=O)C1CC=C(c2c[nH]c(-c3n[nH]c4c(F)c(-c5ccc(O)cc5CC)ccc34)n2)CN1]
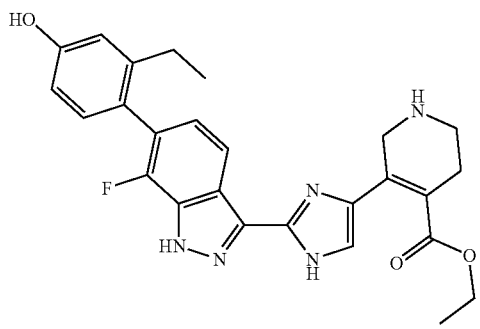 [SMILES: CCOC(=O)C1=C(c2c[nH]c(-c3n[nH]c4c(F)c(-c5ccc(O)cc5CC)ccc34)n2)CNCC1]
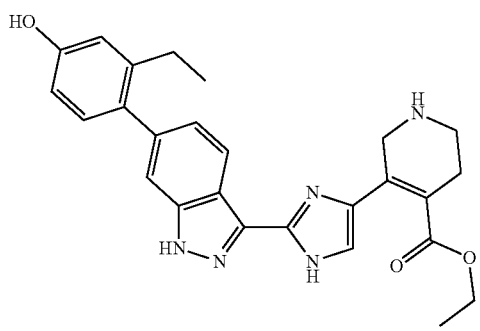 [SMILES: CCOC(=O)C1=C(c2c[nH]c(-c3n[nH]c4cc(-c5ccc(O)cc5CC)ccc34)n2)CNCC1]
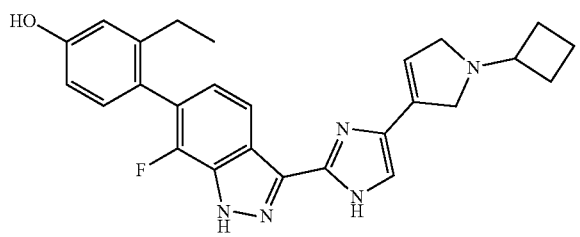 [SMILES: CCc1cc(O)ccc1-c1ccc2c(-c3nc(C4=CCN(C5CCC5)C4)c[nH]3)n[nH]c2c1F]

| Structure |
|---|
| 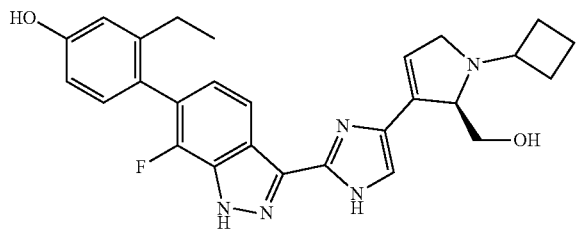 [SMILES: CCc1cc(O)ccc1-c1ccc2c(-c3nc(C4=CCN(C5CCC5)[C@H]4CO)c[nH]3)n[nH]c2c1F] |
| 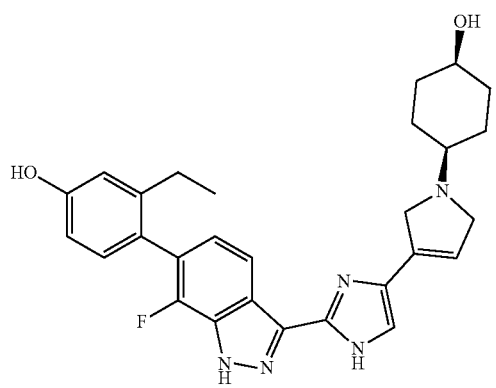 [SMILES: CCc1cc(O)ccc1-c1ccc2c(-c3nc(C4=CCN([C@H]5CC[C@@H](O)CC5)C4)c[nH]3)n[nH]c2c1F] |
| 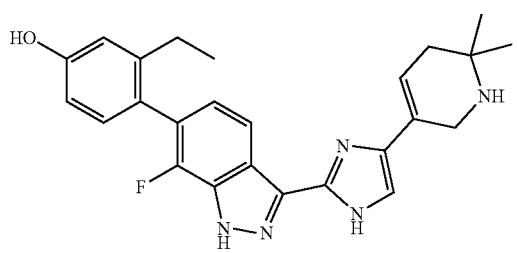 [SMILES: CCc1cc(O)ccc1-c1ccc2c(-c3nc(C4=CCC(C)(C)NC4)c[nH]3)n[nH]c2c1F] |
| 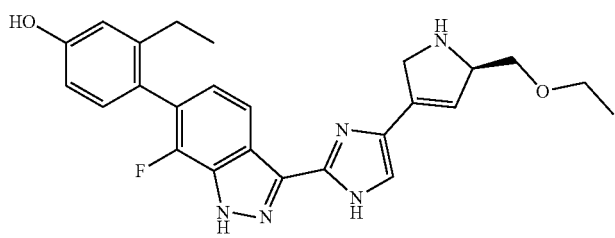 [SMILES: CCOC[C@H]1C=C(c2c[nH]c(-c3n[nH]c4c(F)c(-c5ccc(O)cc5CC)ccc34)n2)CN1] |
| 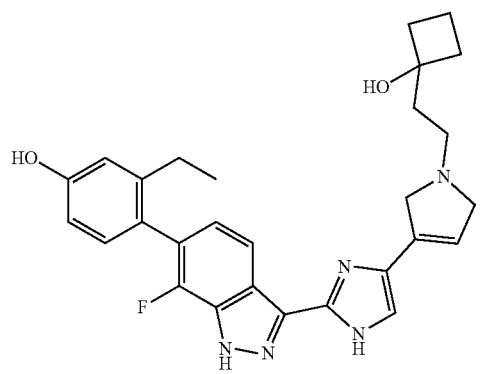 [SMILES: CCc1cc(O)ccc1-c1ccc2c(-c3nc(C4=CCN(CCC5(O)CCC5)C4)c[nH]3)n[nH]c2c1F] |

| Structure |
| --- |
| 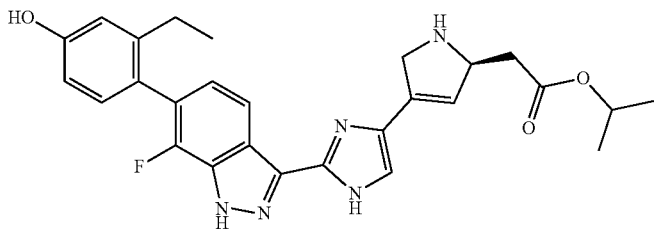 [SMILES: CCc1cc(O)ccc1-c1ccc2c(-c3nc(C4=C[C@H](CC(=O)OC(C)C)NC4)c[nH]3)n[nH]c2c1F] |
| 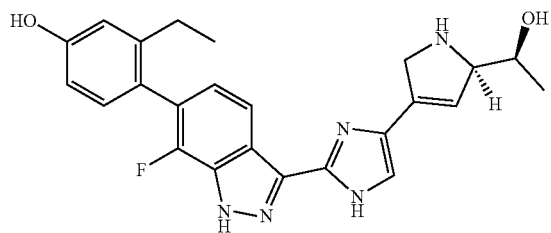 [SMILES: CCc1cc(O)ccc1-c1ccc2c(-c3nc(C4=C[C@H]([C@H](C)O)NC4)c[nH]3)n[nH]c2c1F] |
| 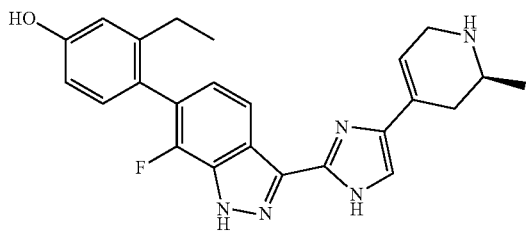 [SMILES: CCc1cc(O)ccc1-c1ccc2c(-c3nc(C4=CCN[C@@H](C)C4)c[nH]3)n[nH]c2c1F] |
| 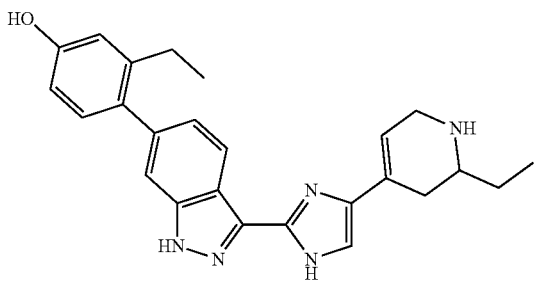 [SMILES: CCc1cc(O)ccc1-c1ccc2c(-c3nc(C4=CCNC(CC)C4)c[nH]3)n[nH]c2c1] |
| 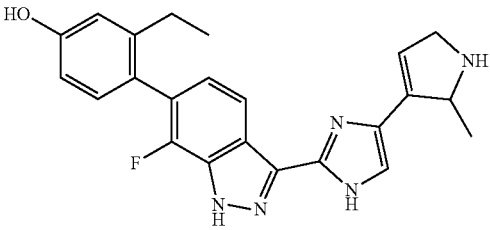 [SMILES: CCc1cc(O)ccc1-c1ccc2c(-c3nc(C4=CCNC4C)c[nH]3)n[nH]c2c1F] |
| 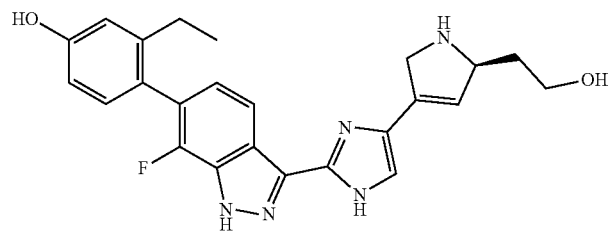 [SMILES: CCc1cc(O)ccc1-c1ccc2c(-c3nc(C4=C[C@H](CCO)NC4)c[nH]3)n[nH]c2c1F] |

| Structure |
|---|
| 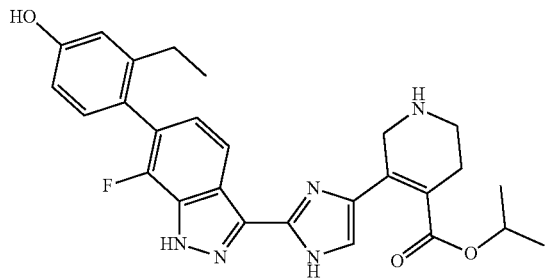 [SMILES: CCc1cc(O)ccc1-c1ccc2c(-c3nc(C4=C(C(=O)OC(C)C)CCNC4)c[nH]3)n[nH]c2c1F] |
| 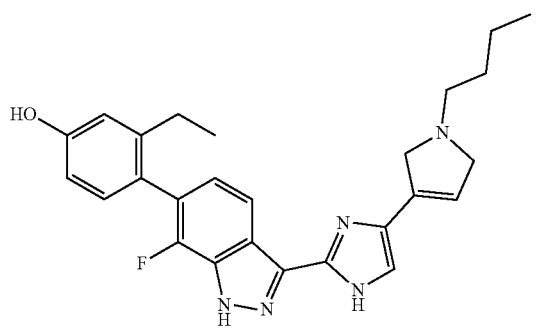 [SMILES: CCCCN1CC=C(c2c[nH]c(-c3n[nH]c4c(F)c(-c5ccc(O)cc5CC)ccc34)n2)C1] |
| 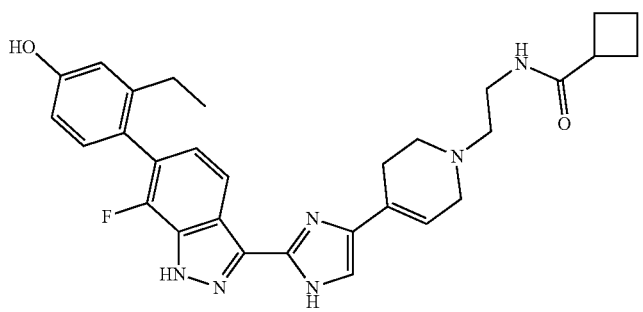 [SMILES: CCc1cc(O)ccc1-c1ccc2c(-c3nc(C4=CCN(CCNC(=O)C5CCC5)CC4)c[nH]3)n[nH]c2c1F] |
| 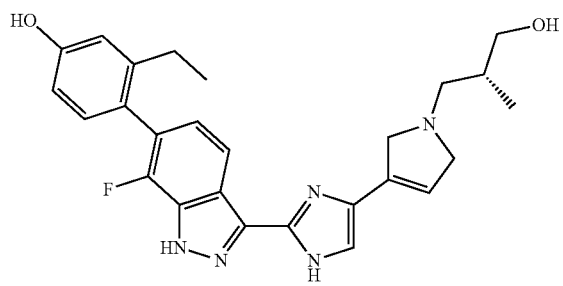 [SMILES: CCc1cc(O)ccc1-c1ccc2c(-c3nc(C4=CCN(C[C@@H](C)CO)C4)c[nH]3)n[nH]c2c1F] |
| 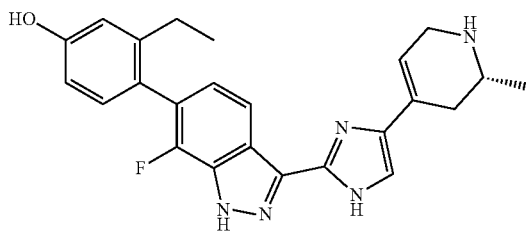 [SMILES: CCc1cc(O)ccc1-c1ccc2c(-c3nc(C4=CCN[C@H](C)C4)c[nH]3)n[nH]c2c1F] |

| Structure |
|---|
| 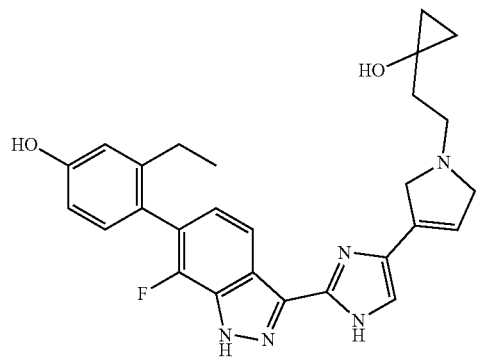 [SMILES: CCc1cc(O)ccc1-c1ccc2c(-c3nc(C4=CCN(CCC5(O)CC5)C4)c[nH]3)n[nH]c2c1F] |
| 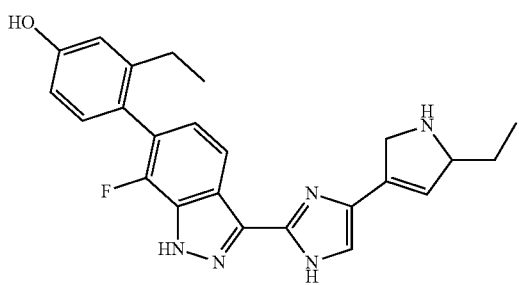 [SMILES: CCc1cc(O)ccc1-c1ccc2c(-c3nc(C4=CC(CC)NC4)c[nH]3)n[nH]c2c1F] |
| 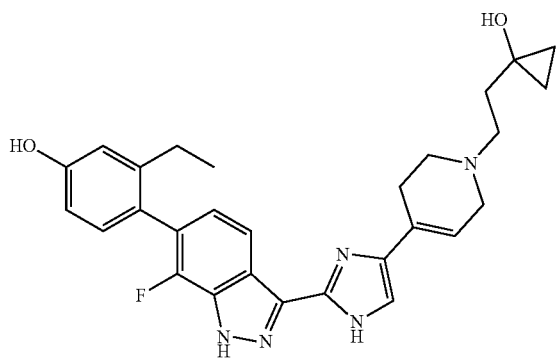 [SMILES: CCc1cc(O)ccc1-c1ccc2c(-c3nc(C4=CCN(CCC5(O)CC5)CC4)c[nH]3)n[nH]c2c1F] |
| 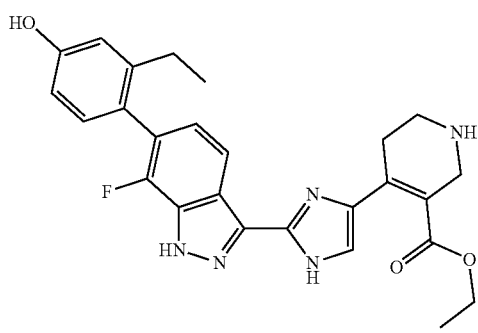 [SMILES: CCOC(=O)C1=C(c2c[nH]c(-c3n[nH]c4c(F)c(-c5ccc(O)cc5CC)ccc34)n2)CCNC1] |
| 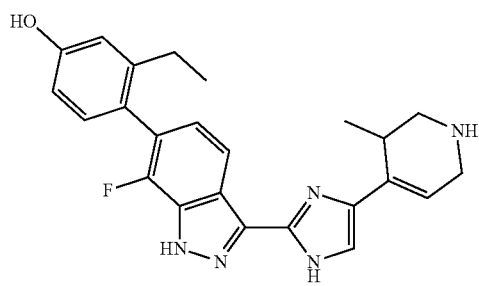 [SMILES: CCc1cc(O)ccc1-c1ccc2c(-c3nc(C4=CCNCC4C)c[nH]3)n[nH]c2c1F] |

| Structure |
|---|
| 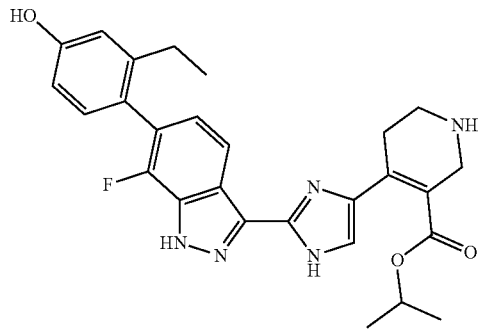 [SMILES: CCc1cc(O)ccc1-c1ccc2c(-c3nc(C4=C(C(=O)OC(C)C)CNCC4)c[nH]3)n[nH]c2c1F] |
| 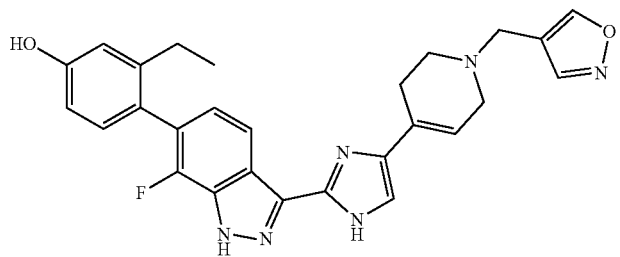 [SMILES: CCc1cc(O)ccc1-c1ccc2c(-c3nc(C4=CCN(Cc5cnoc5)CC4)c[nH]3)n[nH]c2c1F] |
| 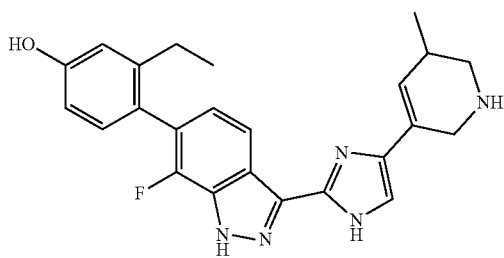 [SMILES: CCc1cc(O)ccc1-c1ccc2c(-c3nc(C4=CC(C)CNC4)c[nH]3)n[nH]c2c1F] |
| 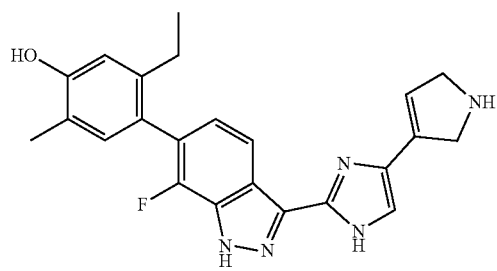 [SMILES: CCc1cc(O)c(C)cc1-c1ccc2c(-c3nc(C4=CCNC4)c[nH]3)n[nH]c2c1F] |
| 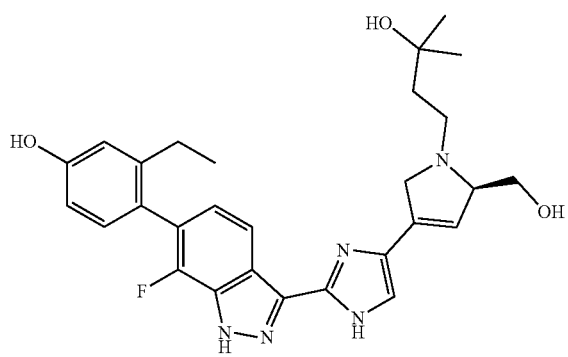 [SMILES: CCc1cc(O)ccc1-c1ccc2c(-c3nc(C4=C[C@H](CO)N(CCC(C)(C)O)C4)c[nH]3)n[nH]c2c1F] |

-continued
Structure
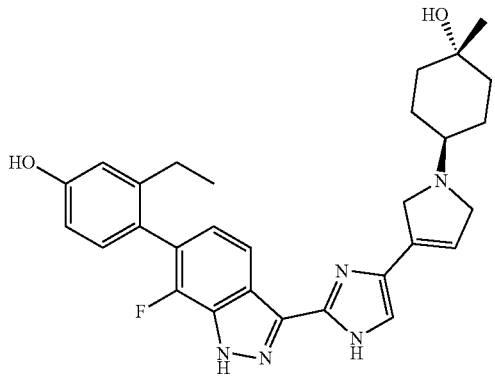 [SMILES: CCc1cc(O)ccc1-c1ccc2c(-c3nc(C4=CCN([C@H]5CC[C@](C)(O)CC5)C4)c[nH]3)n[nH]c2c1F]
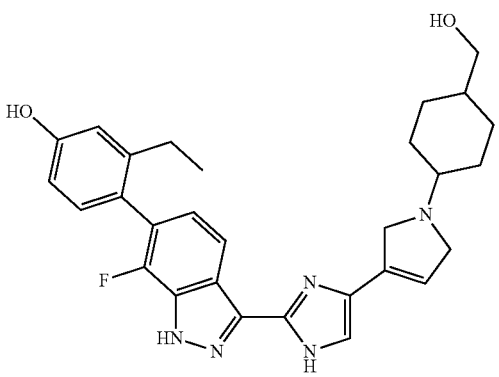 [SMILES: CCc1cc(O)ccc1-c1ccc2c(-c3nc(C4=CCN(C5CCC(CO)CC5)C4)c[nH]3)n[nH]c2c1F]
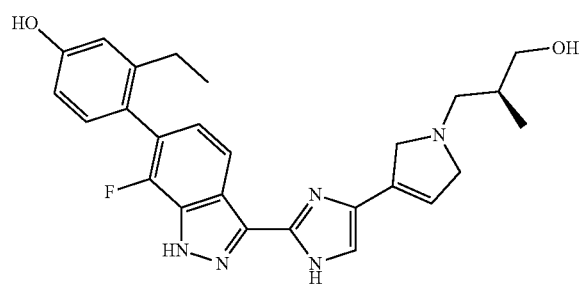 [SMILES: CCc1cc(O)ccc1-c1ccc2c(-c3nc(C4=CCN(C[C@H](C)CO)C4)c[nH]3)n[nH]c2c1F]
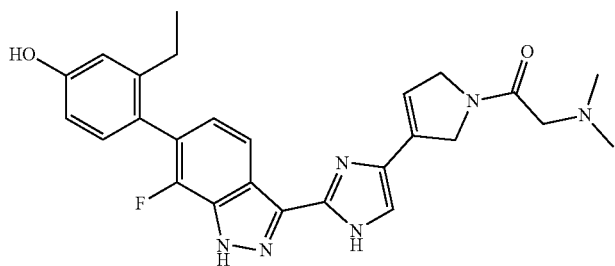 [SMILES: CCc1cc(O)ccc1-c1ccc2c(-c3nc(C4=CCN(C(=O)CN(C)C)C4)c[nH]3)n[nH]c2c1F]

| Structure |
| --- |
| 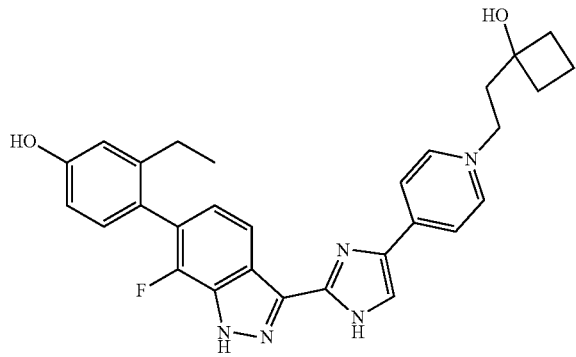 |
| 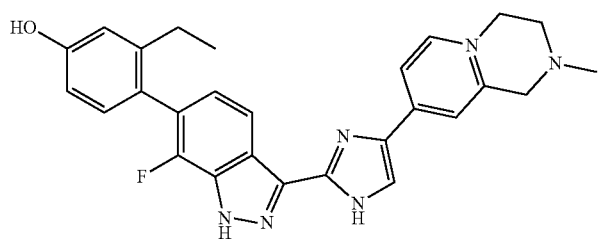 |
| 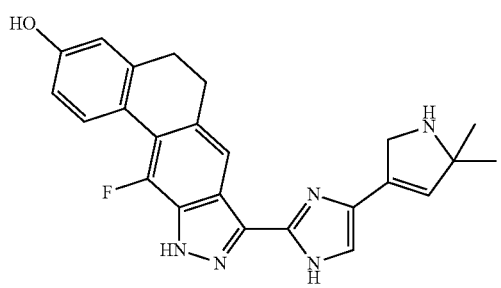 [SMILES: CC1(C)C=C(c2c[nH]c(-c3n[nH]c4c(F)c5c(cc34)CCc3cc(O)ccc3-5)n2)CN1] |
| 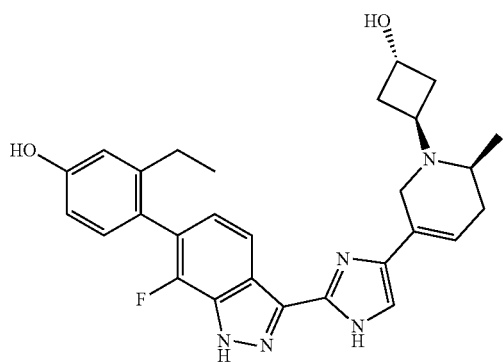 [SMILES: CCc1cc(O)ccc1-c1ccc2c(-c3nc(C4=CC[C@H](C)N([C@H]5C[C@H](O)C5)C4)c[nH]3)n[nH]c2c1F] |

-continued
| Structure |
| --- |
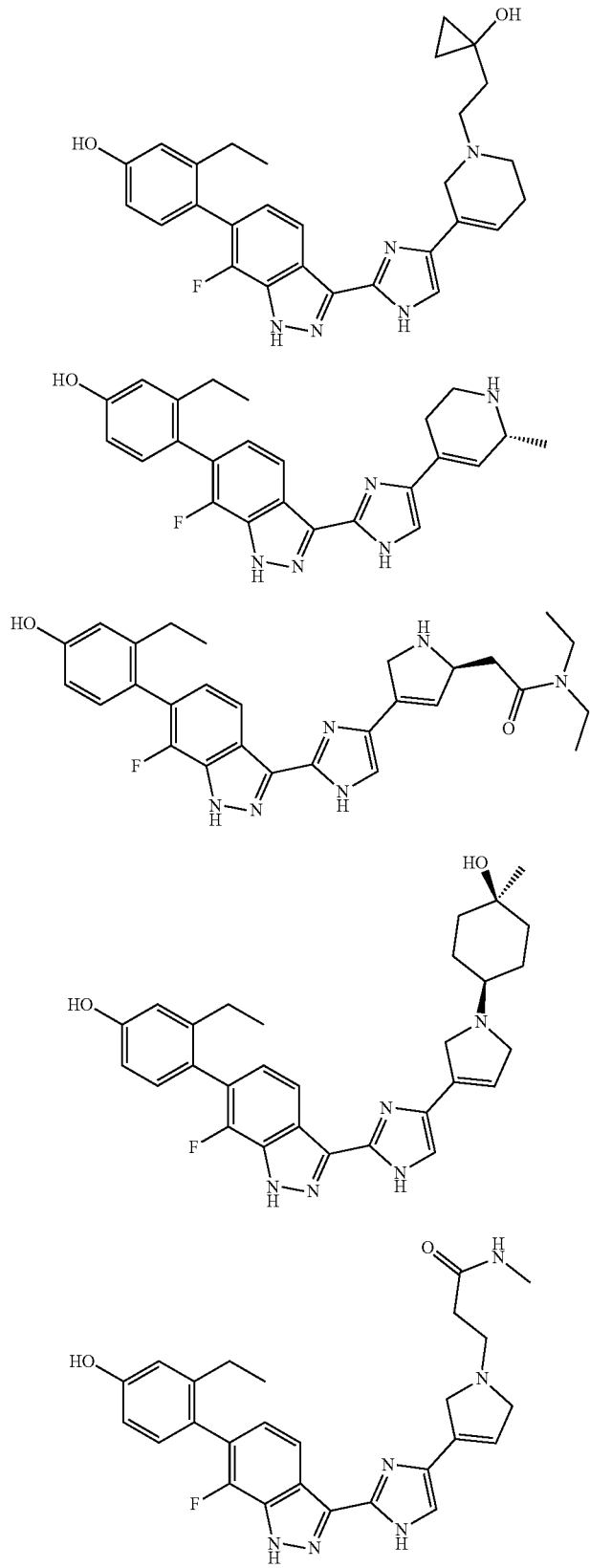

-continued
| Structure |
|---|
| 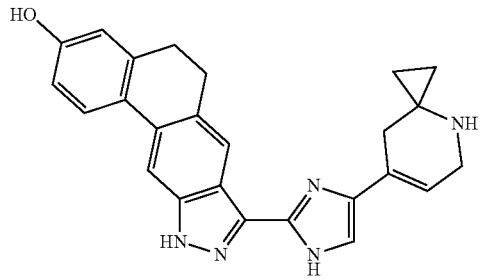 [SMILES: Oc1ccc2c(c1)CCc1cc3c(-c4nc(C5=CCNC6(CC6)C5)c[nH]4)n[nH]c3cc1-2] |
| 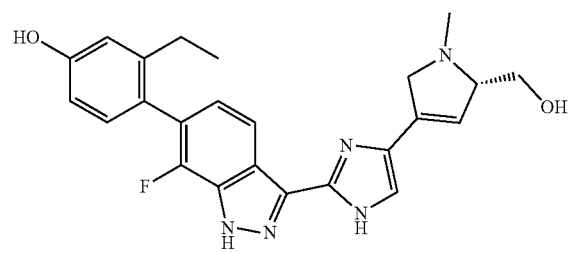 [SMILES: CCc1cc(O)ccc1-c1ccc2c(-c3nc(C4=C[C@@H](CO)N(C)C4)c[nH]3)n[nH]c2c1F] |
| 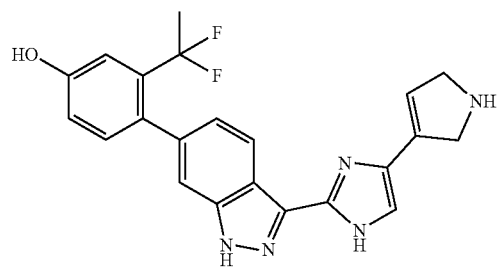 [SMILES: CC(F)(F)c1cc(O)ccc1-c1ccc2c(-c3nc(C4=CCNC4)c[nH]3)n[nH]c2c1] |
| 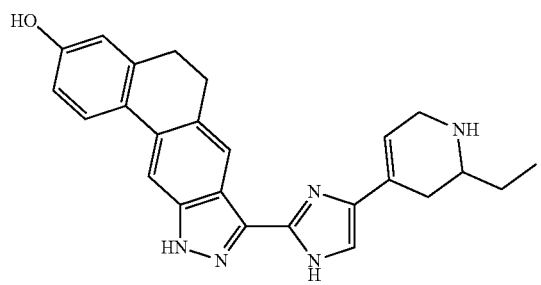 [SMILES: CCC1CC(c2c[nH]c(-c3n[nH]c4cc5c(cc34)CCc3cc(O)ccc3-5)n2)=CCN1] |
| 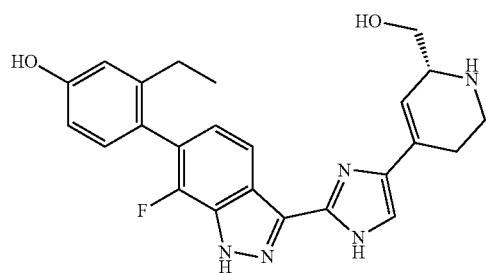 [SMILES: CCc1cc(O)ccc1-c1ccc2c(-c3nc(C4=C[C@H](CO)NCC4)c[nH]3)n[nH]c2c1F] |

| Structure |
|---|
| 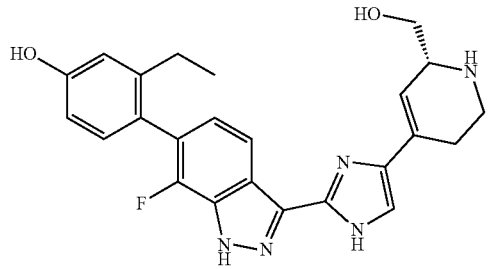 [SMILES: CCc1cc(O)ccc1-c1ccc2c(-c3nc(C4=C[C@H](CO)NCC4)c[nH]3)n[nH]c2c1F] |
| 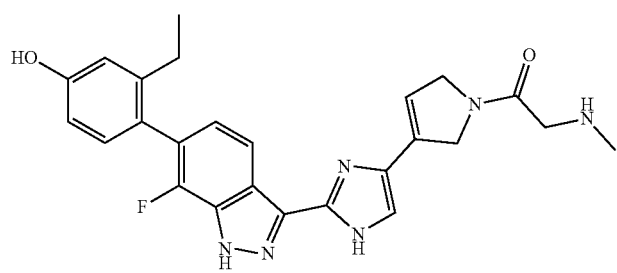 [SMILES: CCc1cc(O)ccc1-c1ccc2c(-c3nc(C4=CCN(C(=O)CNC)C4)c[nH]3)n[nH]c2c1F] |
| 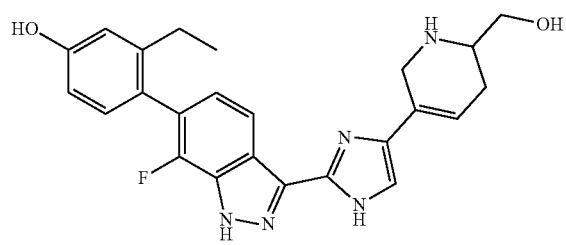 [SMILES: CCc1cc(O)ccc1-c1ccc2c(-c3nc(C4=CCC(CO)NC4)c[nH]3)n[nH]c2c1F] |
| 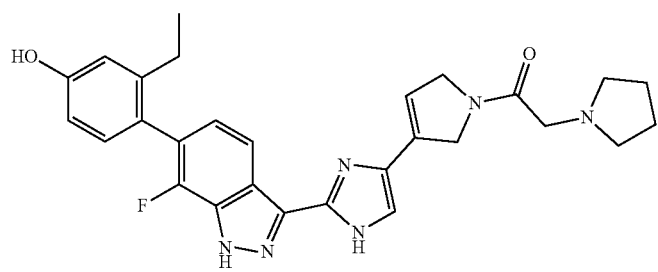 [SMILES: CCc1cc(O)ccc1-c1ccc2c(-c3nc(C4=CCN(C(=O)CN5CCCC5)C4)c[nH]3)n[nH]c2c1F] |
| 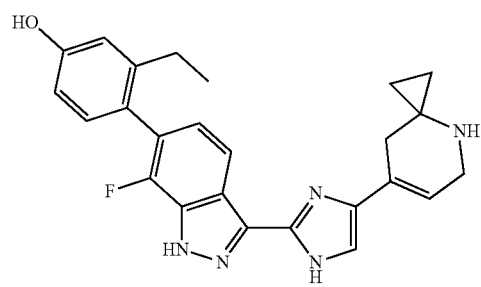 [SMILES: CCc1cc(O)ccc1-c1ccc2c(-c3nc(C4=CCNC5(CC5)C4)c[nH]3)n[nH]c2c1F] |

387
-continued
| Structure |
| --- |
| 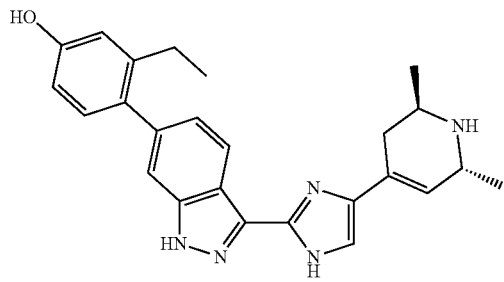<br>Mixture of enantiomers |
| 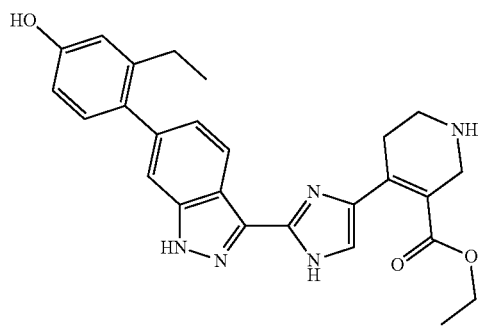 [SMILES: CCOC(=O)C1=C(c2c[nH]c(-c3n[nH]c4cc(-c5ccc(O)cc5CC)ccc34)n2)CCNC1] |
| 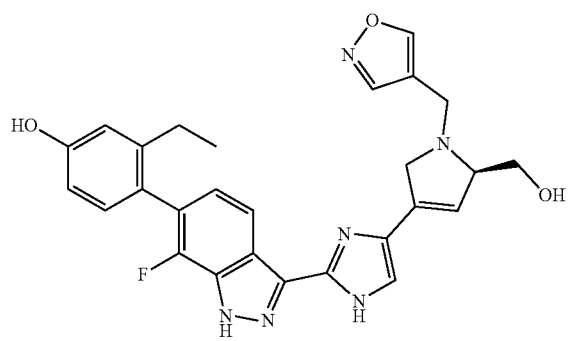 [SMILES: CCc1cc(O)ccc1-c1ccc2c(-c3nc(C4=C[C@H](CO)N(Cc5cnoc5)C4)c[nH]3)n[nH]c2c1F] |
| 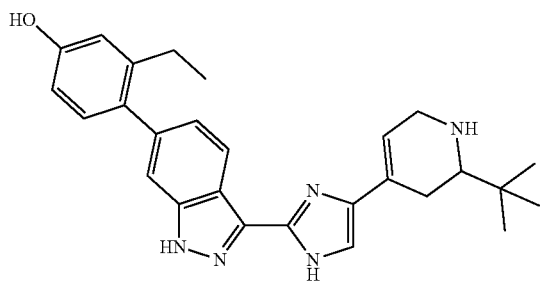 [SMILES: CCc1cc(O)ccc1-c1ccc2c(-c3nc(C4=CCNC(C(C)(C)C)C4)c[nH]3)n[nH]c2c1] |
| 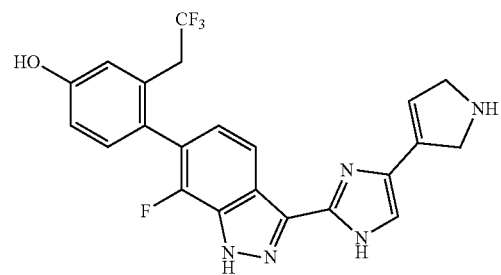 [SMILES: Oc1ccc(-c2ccc3c(-c4nc(C5=CCNC5)c[nH]4)n[nH]c3c2F)c(CC(F)(F)F)c1] |

-continued
Structure
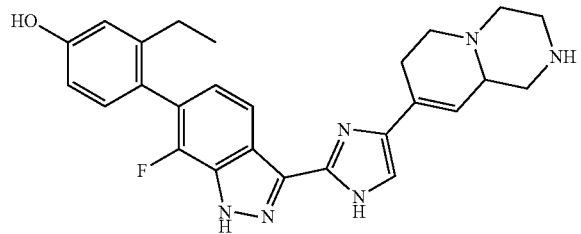 [SMILES: CCc1cc(O)ccc1-c1ccc2c(-c3nc(C4=CC5CNCCN5CC4)c[nH]3)n[nH]c2c1F]
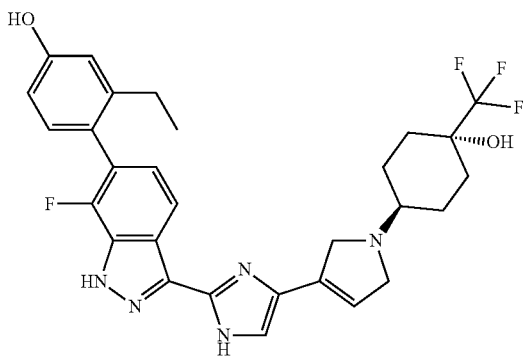 [SMILES: CCc1cc(O)ccc1-c1ccc2c(-c3nc(C4=CCN([C@H]5CC[C@@](O)(C(F)(F)F)CC5)C4)c[nH]3)n[nH]c2c1F]
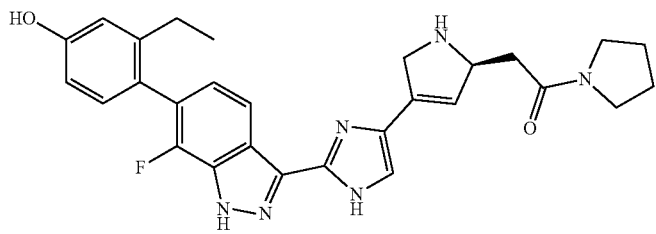 [SMILES: CCc1cc(O)ccc1-c1ccc2c(-c3nc(C4=C[C@H](CC(=O)N5CCCC5)NC4)c[nH]3)n[nH]c2c1F]
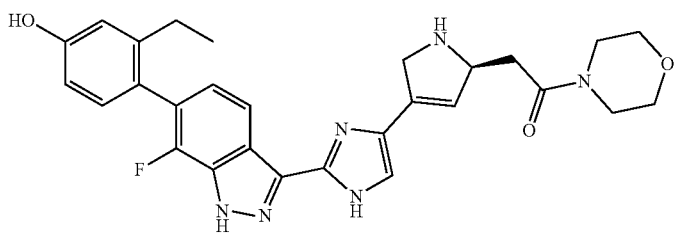 [SMILES: CCc1cc(O)ccc1-c1ccc2c(-c3nc(C4=C[C@H](CC(=O)N5CCOCC5)NC4)c[nH]3)n[nH]c2c1F]
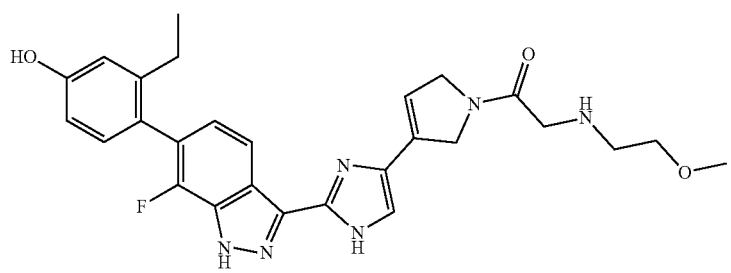 [SMILES: CCc1cc(O)ccc1-c1ccc2c(-c3nc(C4=CCN(C(=O)CNCCOC)C4)c[nH]3)n[nH]c2c1F]

-continued
Structure
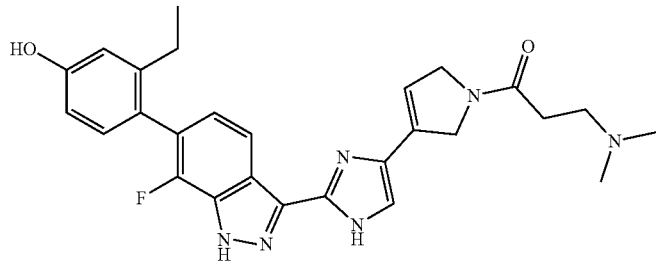 [SMILES: CCc1cc(O)ccc1-c1ccc2c(-c3nc(C4=CCN(C(=O)CCN(C)C)C4)c[nH]3)n[nH]c2c1F]
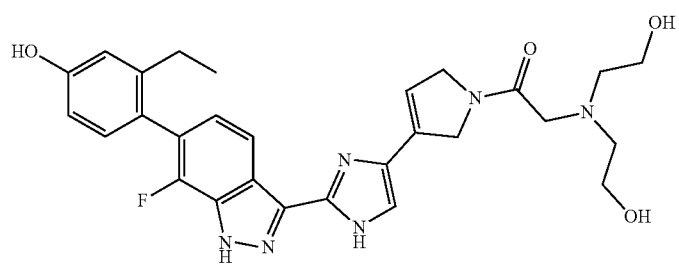 [SMILES: CCc1cc(O)ccc1-c1ccc2c(-c3nc(C4=CCN(C(=O)CN(CCO)CCO)C4)c[nH]3)n[nH]c2c1F]
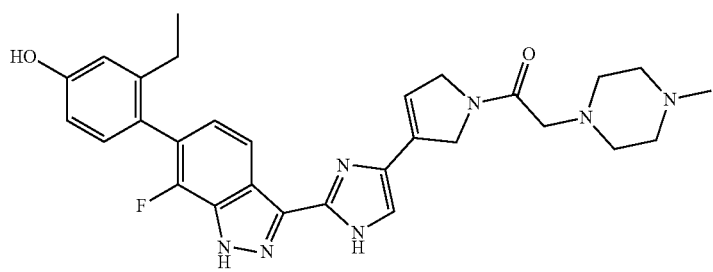 [SMILES: CCc1cc(O)ccc1-c1ccc2c(-c3nc(C4=CCN(C(=O)CN5CCN(C)CC5)C4)c[nH]3)n[nH]c2c1F]
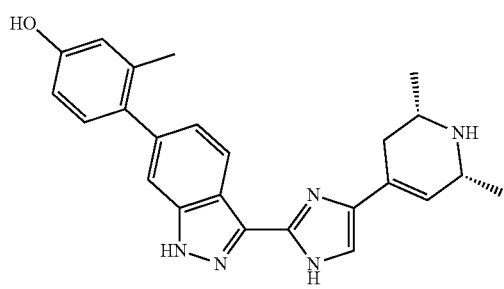 [SMILES: Cc1cc(O)ccc1-c1ccc2c(-c3nc(C4=C[C@@H](C)N[C@@H](C)C4)c[nH]3)n[nH]c2c1]
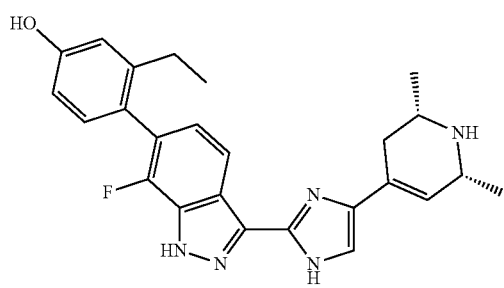 [SMILES: CCc1cc(O)ccc1-c1ccc2c(-c3nc(C4=C[C@@H](C)N[C@@H](C)C4)c[nH]3)n[nH]c2c1F]

| Structure |
|---|
| 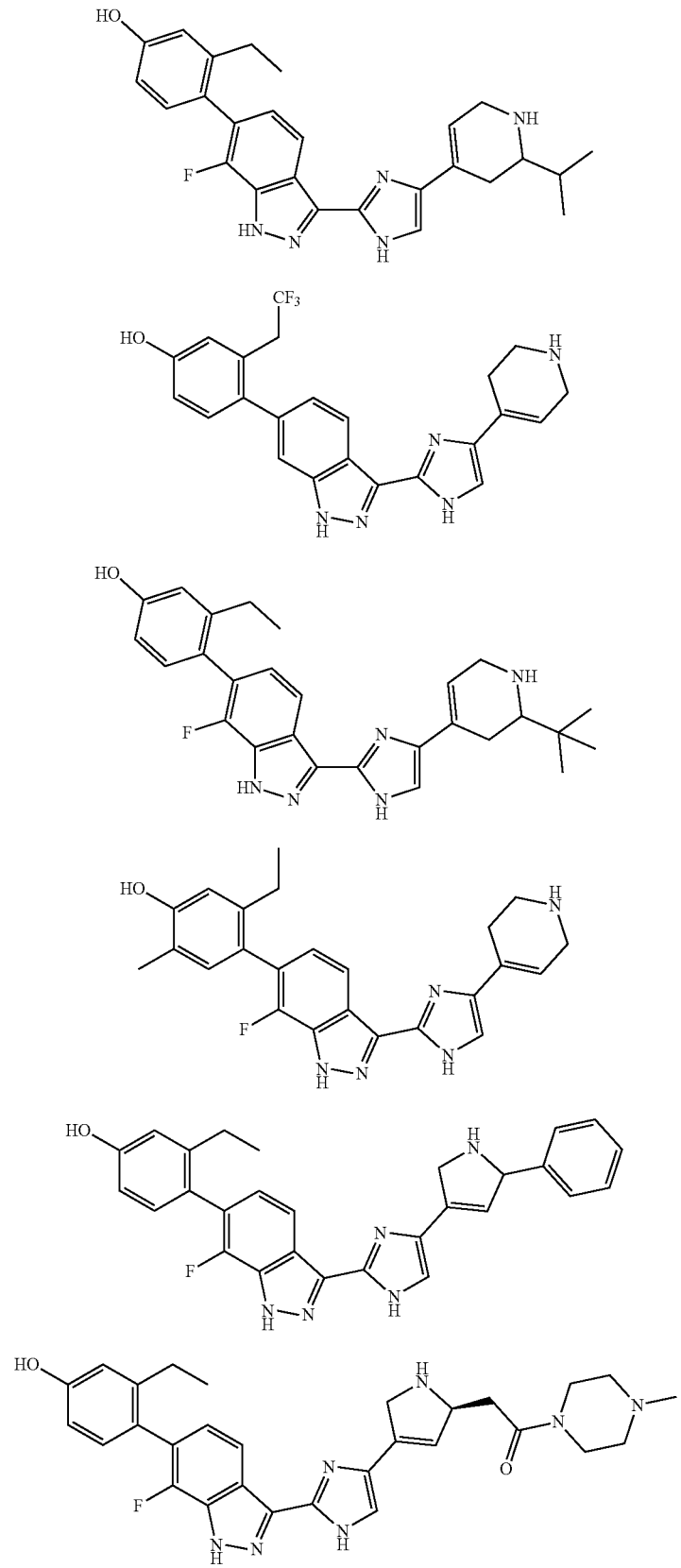 |

| Structure |
|---|
| 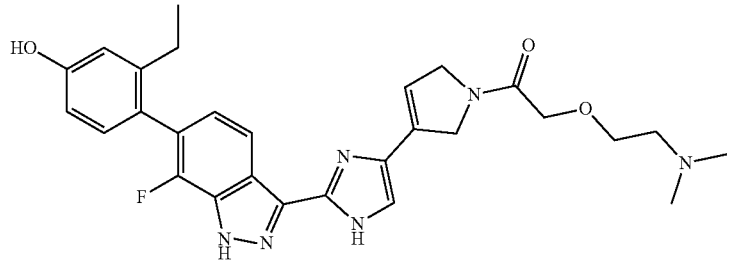 [SMILES: CCc1cc(O)ccc1-c1ccc2c(-c3nc(C4=CCN(C(=O)COCCN(C)C)C4)c[nH]3)n[nH]c2c1F] |
| 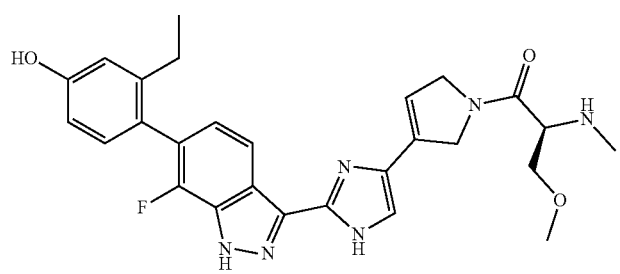 [SMILES: CCc1cc(O)ccc1-c1ccc2c(-c3nc(C4=CCN(C(=O)[C@H](COC)NC)C4)c[nH]3)n[nH]c2c1F] |
| 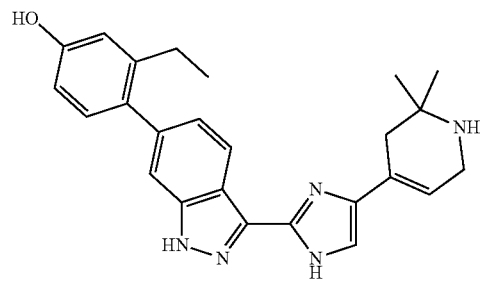 [SMILES: CCc1cc(O)ccc1-c1ccc2c(-c3nc(C4=CCNC(C)(C)C4)c[nH]3)n[nH]c2c1] |
| 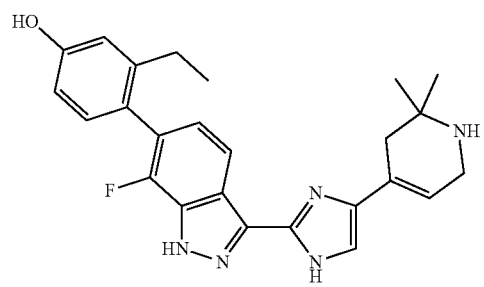 [SMILES: CCc1cc(O)ccc1-c1ccc2c(-c3nc(C4=CCNC(C)(C)C4)c[nH]3)n[nH]c2c1F] |
| 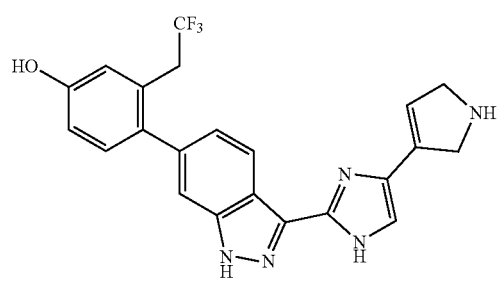 [SMILES: Oc1ccc(-c2ccc3c(-c4nc(C5=CCNC5)c[nH]4)n[nH]c3c2)c(CC(F)(F)F)c1] |

| Structure |
|---|
| 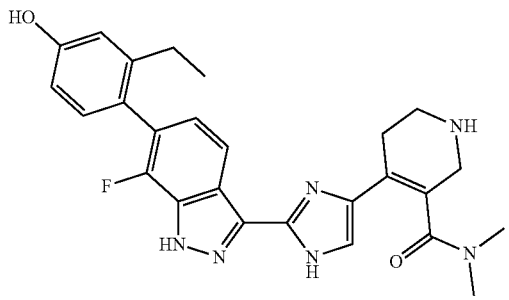 [SMILES: CCc1cc(O)ccc1-c1ccc2c(-c3nc(C4=C(C(=O)N(C)C)CNCC4)c[nH]3)n[nH]c2c1F] |
| 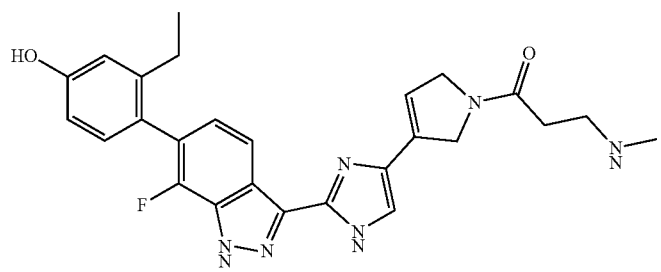 |
| 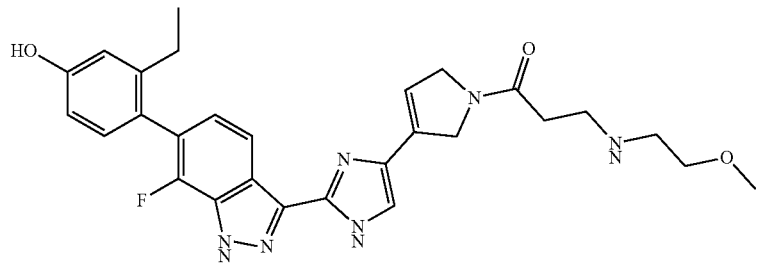 |
| 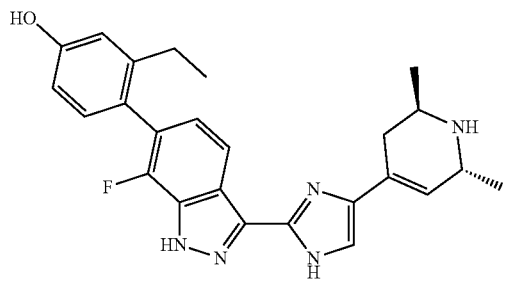<br>Mixture of enantiomers |
| 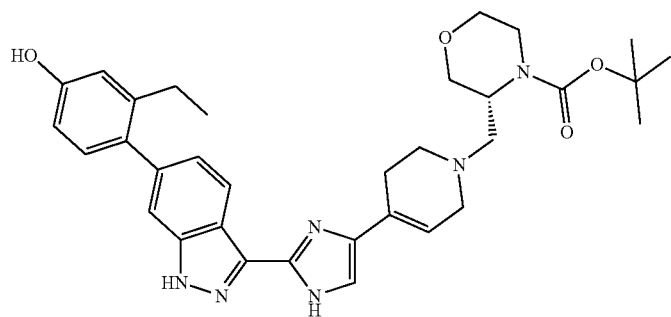 [SMILES: CCc1cc(O)ccc1-c1ccc2c(-c3nc(C4=CCN(C[C@@H]5COCCN5C(=O)OC(C)(C)C)CC4)c[nH]3)n[nH]c2c1] |

| Structure |
|---|
| 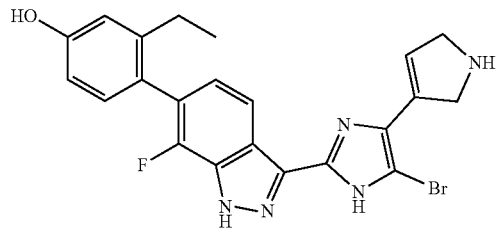 |
| 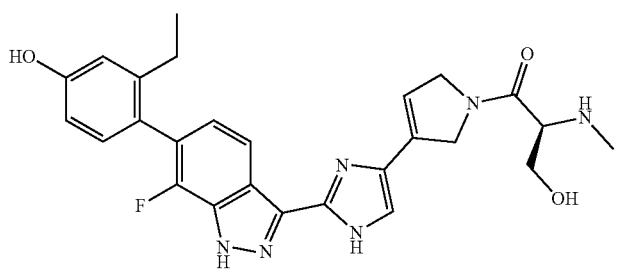 [SMILES: CCc1cc(O)ccc1-c1ccc2c(-c3nc(C4=CCN(C(=O)[C@H](CO)NC)C4)c[nH]3)n[nH]c2c1F] |
| 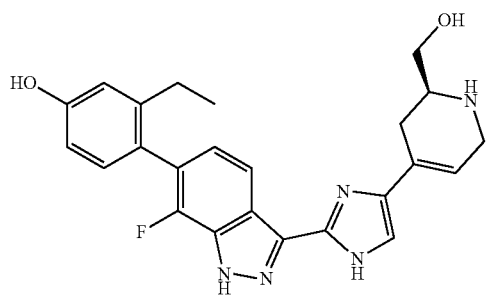 [SMILES: CCc1cc(O)ccc1-c1ccc2c(-c3nc(C4=CCN[C@H](CO)C4)c[nH]3)n[nH]c2c1F] |
| 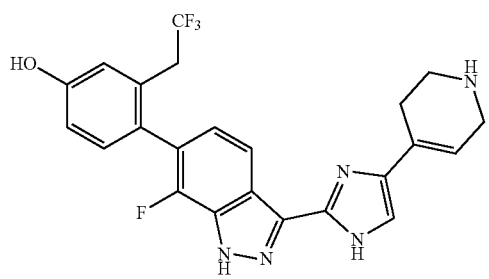 [SMILES: Oc1ccc(-c2ccc3c(-c4nc(C5=CCNCC5)c[nH]4)n[nH]c3c2F)c(CC(F)(F)F)c1] |
| 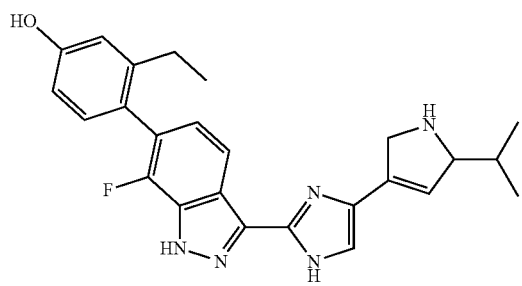 [SMILES: CCc1cc(O)ccc1-c1ccc2c(-c3nc(C4=CC(C(C)C)NC4)c[nH]3)n[nH]c2c1F] |

| Structure |
| --- |
| 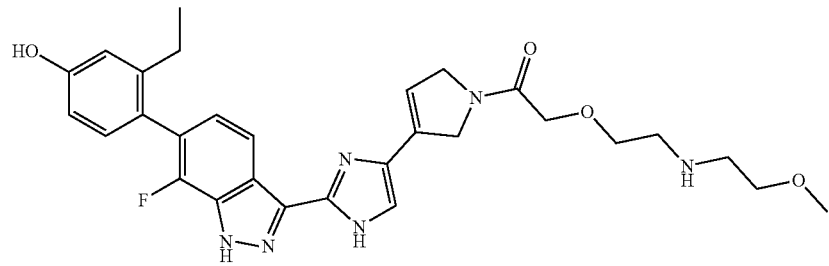 [SMILES: CCc1cc(O)ccc1-c1ccc2c(-c3nc(C4=CCN(C(=O)COCCNCCOC)C4)c[nH]3)n[nH]c2c1F] |
| 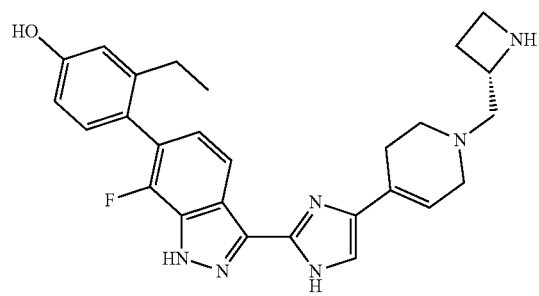 [SMILES: CCc1cc(O)ccc1-c1ccc2c(-c3nc(C4=CCN(C[C@@H]5CCN5)CC4)c[nH]3)n[nH]c2c1F] |
| 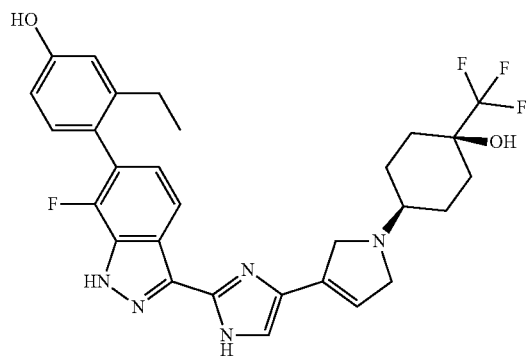 [SMILES: CCc1cc(O)ccc1-c1ccc2c(-c3nc(C4=CCN([C@H]5CC[C@](O)(C(F)(F)F)CC5)C4)c[nH]3)n[nH]c2c1F] |
| 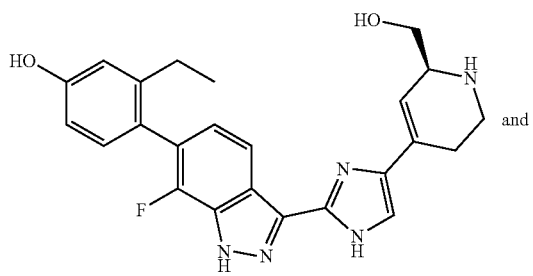 [SMILES: CCc1cc(O)ccc1-c1ccc2c(-c3nc(C4=C[C@@H](CO)NCC4)c[nH]3)n[nH]c2c1F] and |

| Structure |
|---|
| 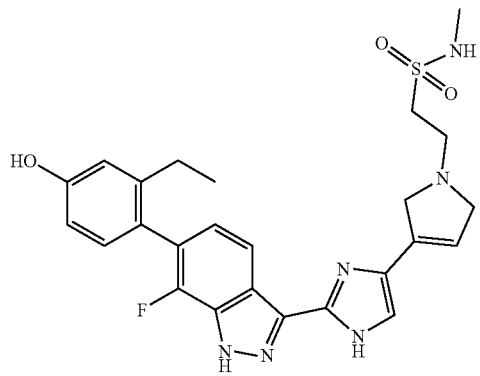 [SMILES: CCc1cc(O)ccc1-c1ccc2c(-c3nc(C4=CCN(CCS(=O)(=O)NC)C4)c[nH]3)n[nH]c2c1F] | or a pharmaceutically acceptable salt thereof.

16. A pharmaceutical composition comprising the compound of claim 1, or a pharmaceutically acceptable salt thereof, and a pharmaceutically acceptable carrier.

17. The pharmaceutical composition of claim 16, further comprising one or more other therapeutic agents.

18. A method for treating a respiratory disease modulated by a Janus kinase in a human in need thereof, the method comprising administering to the human the compound of claim 1, or a pharmaceutically acceptable salt thereof.

19. The method of claim 18, wherein the respiratory disease modulated by a Janus kinase is selected from the group consisting of asthma, chronic obstructive pulmonary disease, cystic fibrosis, pneumonitis, idiopathic pulmonary fibrosis, acute lung injury, acute respiratory distress syndrome, bronchitis, emphysema, bronchiolitis obliterans, sarcoidosis, an eosinophilic disease, a helminthic infection, pulmonary arterial hypertension, lymphangioleiomyomatosis, bronchiectasis, an infiltrative pulmonary disease, drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Löffler syndrome, bronchiolitis obliterans organizing pneumonia, lung graft-versus-host disease, COVID-19, SARS, MERS, chronic rhinosinusitis with or without nasal polyps, nasal polyposis, sinusitis with nasal polyps, rhinitis, and immune-checkpoint-inhibitor induced pneumonitis.

20. A method for treating lung transplant rejection modulated by a Janus kinase in a human in need thereof, the method comprising administering to the human the compound of claim 1, or a pharmaceutically acceptable salt thereof.

21. The method of claim 20, wherein the lung transplant rejection modulated by a Janus kinase is selected from the group consisting of primary graft dysfunction, organizing pneumonia, acute rejection, lymphocytic bronchiolitis, and chronic lung allograft dysfunction, bronchiolitis obliterans, restrictive chronic lung allograft dysfunction, and neutrophilic allograft dysfunction.

* * * * *